(12) United States Patent
Mita et al.

(10) Patent No.: US 8,053,452 B2
(45) Date of Patent: Nov. 8, 2011

(54) SUBSTITUTED ISOXAZOLINE OR ENONE OXIME COMPOUND, AND PEST CONTROL AGENT

(75) Inventors: Takeshi Mita, Funabashi (JP); Kenichi Toyama, Funabashi (JP); Yuki Furukawa, Funabashi (JP); Mitsuaki Komoda, Minamisaitama-gun (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 23 days.

(21) Appl. No.: 12/452,346

(22) PCT Filed: Jun. 27, 2008

(86) PCT No.: PCT/JP2008/061769
§ 371 (c)(1),
(2), (4) Date: Dec. 29, 2009

(87) PCT Pub. No.: WO2009/005015
PCT Pub. Date: Jan. 8, 2009

(65) Prior Publication Data
US 2010/0144808 A1    Jun. 10, 2010

(30) Foreign Application Priority Data

Jun. 29, 2007 (JP) ................. 2007-171805
Jul. 6, 2007 (JP) ................. 2007-178516
Sep. 12, 2007 (JP) ................. 2007-236231

(51) Int. Cl.
*A01N 43/80* (2006.01)
*A01N 37/18* (2006.01)
*C07D 261/04* (2006.01)
*C07C 237/28* (2006.01)

(52) U.S. Cl. ........ 514/378; 514/616; 514/620; 548/240; 564/157; 564/164

(58) Field of Classification Search .............. 514/378, 514/616, 620; 548/240; 564/157, 164
See application file for complete search history.

(56) References Cited

U.S. PATENT DOCUMENTS
2007/0066617 A1    3/2007  Mita et al.

FOREIGN PATENT DOCUMENTS

| | | |
|---|---|---|
| EP | 0 051 273 A1 | 5/1982 |
| GB | 2 161 802 A | 1/1986 |
| JP | A-5-125017 | 5/1993 |
| JP | A-10-130221 | 5/1998 |
| JP | A-2007-16017 | 1/2007 |
| JP | A-2007-91708 | 4/2007 |
| JP | A-2007-106756 | 4/2007 |
| JP | A-2007-308471 | 11/2007 |
| JP | A-2008-44880 | 2/2008 |
| WO | WO 01/32609 A1 | 5/2001 |
| WO | WO 02/062805 A1 | 8/2002 |
| WO | WO 2005/085216 A1 | 9/2005 |
| WO | WO 2007/026965 A1 | 3/2007 |
| WO | WO 2007/075459 A2 | 7/2007 |
| WO | WO 2007/105814 A1 | 9/2007 |
| WO | WO 2007/125984 A1 | 11/2007 |
| WO | WO 2008/108488 A1 | 9/2008 |
| WO | WO 2008/130651 A2 | 10/2008 |
| WO | WO 2010/020521 A1 | 2/2010 |
| WO | WO 2010/020522 A1 | 2/2010 |

OTHER PUBLICATIONS

Askri et al., "Spiroheterocycles from the Reaction of Arylnitrile Oxides with some (Z)-3-Arylidene-2(3H)-Benzofuranones. New Access to Orthohydroxyphenylisoxazoline Esters," *Heterocycles*, 2007, pp. 289-303, vol. 71—No. 2.
Gotthardt et al., "Zur Positions- und Regioselektivität neuer [3+2]-Cycloadditionen von Nitronen und einem Nitriloxid an Butatriene," *Chemisch Berichte*, (1986), pp. 563-574, vol. 119.
Weikert et al., "Synthesis and Anthelmintic Activity of 3'-Benzoylurea Derivatives of 6-Phenyl-2,3,5,6-tetrahydroimidazo[2,1-b]thiazole," *Journal of Medicinal Chemistry*, 1991, pp. 1630-1633, vol. 34.
Abraham et al., "Folate Analogues. 34. Synthesis and Antitumor Activity of Non-Polyglutamylatable Inhibitors of Dihydrofolate Reductase." *Journal of Medicinal Chemistry*, 1991, pp. 222-227, vol. 34.
Ibarra et al. "One-Pot Synthesis of β-Keto Sulfones and β-Keto Sulfoxides from Carboxylic Acids," *Journal of Organic Chemistry*, 1989, pp. 5620-5623, vol. 54.
Salomon et al., "Convenient Preparation of N,N-Dimethylacetamide Dimethyl Acetal," *Journal of Organic Chemistry*, 1984, pp. 3659-3660, vol. 49.

(Continued)

*Primary Examiner* — Kamal Saeed
*Assistant Examiner* — Kristin Bianchi
(74) *Attorney, Agent, or Firm* — Oliff & Berridge, PLC

(57) ABSTRACT

There is provided a novel pest control agent (pesticide), particularly insecticide or miticide. A substituted isoxazoline compound or a substituted enone oxime compound represented by Formula (1) or (2), and a pest control agent containing them:

wherein $A^1$, $A^2$, $A^3$ and $A^4$ are C or N, $G^1$ is a benzene ring, etc., $G^2$ is 1-trazolyl, etc., X and Y are halogen atom, etc., $R^3$ is haloalkyl, etc., $R^{3a}$ is halogen atom, etc., $R^{3b}$ and $R^{3c}$ are H, etc., is haloalkyl, etc., m is 0-5, n is 0-4.

14 Claims, No Drawings

OTHER PUBLICATIONS

Janza et al., "Stereoselective Cyclization Reactions of IBX-Generated Alkoxyamidyl Radicals," *Journal of Organic Chemistry*, 2005, pp. 6991-6994, vol. 70.
Shono et al., "A New [3+3]-Type Annelation Useful for the Formation of Piperidine Skeletons," *Journal of Organic Chemistry*, 1985, pp. 3243-3245, vol. 50.
Bodor et al., "A Convenient Synthesis of (Acyloxy)alkyl α-Ethers of Phenols," *Journal of Organic Chemistry*, 1983, pp. 5280-5284, vol. 48.
Andrus et al., "Synthesis of resveratrol using a direct decarbonylative Heck approach from resorcylic acid," *Tetrahedron Letters*, 2003, pp. 4819-4822, vol. 44.
Kotsuki et al., "A Facile New Method for Selective Deprotection of N-(*tert*-Butoxycarbonyl)-Protected Carboxamides with $Yb(OTf)_3$ Supported on Silica Gel," *Tetrahedron Letters*, 1998, pp. 4869-4870, vol. 39.
Ahmad et al., "A New Acylation Catalyst," *Journal of the Chemical Society*, 1987, pp. 114-115.
Tamura et al., "Monomethylation of Aromatic Rings by Friedel-Crafts Reaction with Chloromethyl Sulfide," *Chemical and Pharmaceutical Bulletin*, 1986, pp. 540-549, vol. 34.
Cabaret et al., "An Efficient Synthesis of Aryl Phenaceturates Using Acid Catalyzed Dicyclohexylcarbodiimide Esterification and Transient N-*tert*-Butoxycarbonylation," *Synthesis*, 1994, pp. 480-482.
Folkmann et al., "Acyloxymethyl Carbonochloridates, New Intermediates in Prodrug Synthesis," *Synthesis*, Dec. 1990, pp. 1159-1166.
Diaz et al., "Acid-Mediated Amine Exchange of N,N-Dimethylformamidines: Preparation of Electron-Rich Formamidines," *Synlett*, 2005, pp. 2214-2218, No. 14.
Loren et al., "*N*H-1,2,3-Triazoles from Azidomethyl Pivalate and Carbamates: Base-Labile N-Protecting Groups," *Synlett*, 2005, pp. 2847-2850, No. 18.
Lock et al., Studies of β-diketone complexes of rhenium, IX. The preparation and characterization of salts of the *trans*-dihalobis(pentane-2,4-dionato)rhenate(III) anion and an improved preparation of tris(pentane-2,4-dionato)rhenium (III), *Canadian Journal of Chemistry*, 1979, pp. 1252-1256, vol. 57.
Blicke et al., "Phenol-Halo-Phthaleins. Preliminary Paper," *Journal of the American Chemical Society*, Jun. 1929, pp. 1865-1875, vol. 51.
Paquette, "α-Halosulfones. IV. A Facile Conversion of Mercaptans to Homologous Terminal Olefins," *Journal of the American Chemical Society*, Oct. 20, 1964, pp. 4383-4385, vol. 86.
Erdos, "Erfahrungen in der Veresterung mit Chlorsulfonsäure," *Angewandte Chemie*, 1951, pp. 329-330, vol. 63—No. 14.
Pri-Bar et al., "$I_2$-Promoted Palladium-Catalyzed Carbonylation of Amines," *Journal of Organic Chemistry*, 1995, pp. 8124-8125, vol. 60.
Connor et al., "Benzyl Chloromethyl Ether," *Organic Synthesis*, 1988, pp. 101-103, Collective vol. 6.
Ichikawa et al., "Optically Active Antifungal Azoles. XII.[1)] Synthesis and Antifungal Activity of the Water-Soluble Prodrugs of 1-[(1R,2R)-2-(2,4-Difluorophenyl)-2-hydroxy-1-methyl-3-(1H-1,2,4-triazol-1-yl)propyl]-3-[4-(1H-1-tetrazolyl)phenyl]-2-imidazolidinone," *Chemical and Pharmaceutical Bulletin*, 2001, pp. 1102-1109, vol. 49—No. 9.
Sep. 9, 2008 Search Report issued in International Patent Application PCT/JP2008/061769 (with translation).

SUBSTITUTED ISOXAZOLINE OR ENONE OXIME COMPOUND, AND PEST CONTROL AGENT

TECHNICAL FIELD

The present invention relates to a novel substituted isoxazoline compound or substituted enone oxime compound and salts thereof, and a pest control agent containing the compounds as active ingredients. The pest control agent in the present invention means insect pest control agents aimed at harmful arthropods in the agriculture and horticulture field or in the livestock/sanitation field (internal or external parasites of mammals or birds as domestic animals or pet animals and sanitary insects and discomfort insects for domestic use and business use). In addition, the agricultural chemicals in the present invention mean insecticides and miticides, nematicides, herbicides, bactericides and the like in the agricultural and horticultural field.

BACKGROUND ART

Conventionally, with respect to substituted isoxazoline compounds, for example, a 5-haloalkyl-5-substituted aryl-3-substituted aryl-4,5-dihydroisoxazole compound is known to exhibit pest control activity, particularly insecticidal and miticidal activity (see Patent Documents 1 to 5). However, nothing is disclosed with respect to a 4-substituted-5-haloalkyl-5-substituted aryl-3-substituted aryl-4,5-dihydroisoxazole compound according to the present invention. In addition, with respect to a 3,5-bis substituted phenyl-4-substituted-5-substituted-4,5-dihydroisoxazole derivative, known is the synthesis of 5-alkoxycarbonyl-3,5-bis substituted phenyl-4-(substituted phenyl)-4,5-dihydroisoxazole derivative (for example, see Non-patent Document 1), 4-substituted alkylidene-3-substituted phenyl-5,5-bis phenyl-4,5-dihydroisoxazole derivative (for example, see Non-patent Document 2), and the like. However, nothing is disclosed with respect to a 4-substituted-5-haloalkyl-5-substituted aryl-3-substituted aryl-4,5-dihydroisoxazole compound according to the present invention.

[Patent Document 1]
International Publication No. WO 2005/085216 pamphlet
[Patent Document 2]
International Publication No. WO 2007/026965 pamphlet
[Patent Document 3]
International Publication No. WO 2007/105814 pamphlet
[Patent Document 4]
Japanese Patent Application Publication No. JP-A-2007-016017
[Patent Document 5]
Japanese Patent Application Publication No. JP-A-2007-106756
[Non-patent Document 1]
Heterocycles, vol. 71, p. 289 (2007)
[Non-patent Document 2]
Chemisch Berichte, vol. 119, p. 563 (1986)

DISCLOSURE OF THE INVENTION

Problems to be Solved by the Invention

The development of pest control agents for the purpose of controlling various pests such as agricultural and horticultural pests, forest pests or sanitary pests has been progressed and until today, various agents have been practically applied. However, due to the use of such agents for a long period, recently, pests have acquired drug resistance and there has been increased the number of situations in which the control with related art insecticides and bactericides which have been used becomes difficult. In addition, a part of the related art pest control agents has high toxicity or some of them remain in the environment for a long period to disturb the ecosystem, which is becoming a significant problem. Under such a situation, the development of a novel pest control agent having not only high pest control activity, but also low toxicity and a low residual property is constantly expected.

Means for Solving the Problems

As a result of assiduous research intended to overcome these disadvantages, the present inventors have found that a novel substituted isoxazoline compound and substituted enone oxime compound represented by the following General Formula (1) to General Formula (4) according to the present invention exhibit excellent pest control activity, particularly excellent insecticidal and miticidal activity and are extremely useful compounds having substantially no adverse effect on non-target organisms such as mammals, fish and beneficial insects to complete the present invention.

That is, the present invention relates to [1] to [14].

[1] A substituted isoxazoline compound or a substituted enone oxime compound represented by General Formula (1) or General Formula (2):

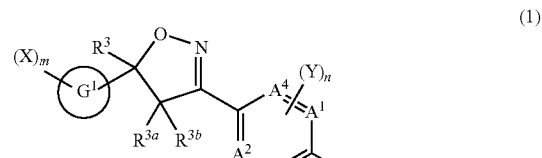

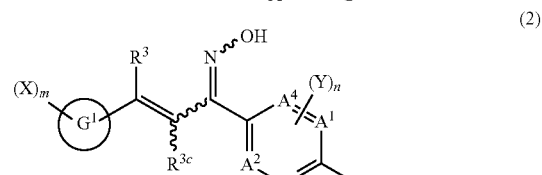

(where $A^1$, $A^2$, $A^3$ and $A^4$ independently represent a carbon atom or a nitrogen atom, $G^1$ represents a benzene ring, a nitrogen-containing 6-membered aromatic heterocyclic ring, a furan ring, a thiophene ring or a 5-membered aromatic heterocyclic ring containing two or more heteroatoms selected from an oxygen atom, a sulfur atom and a nitrogen atom, $G^2$ represents a structure represented by $G^2$-1 to $G^2$-11:

$G^2$-1:

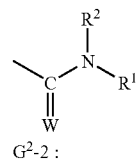

$G^2$-2:

-continued

G²-3:
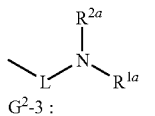

G²-4:
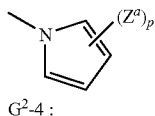

G²-5:
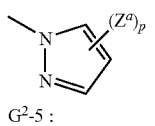

G²-6:
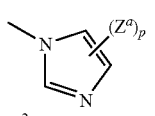

G²-7:
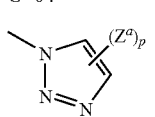

G²-8:
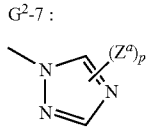

G²-9:
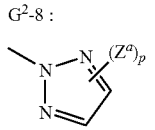

G²-10:
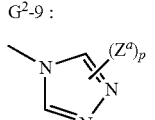

G²-11:
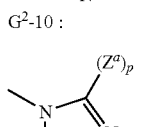

W represents an oxygen atom or a sulfur atom,

L represents —C($R^{4a}$)($R^{4b}$)—, —C($R^{4a}$)($R^{4b}$)$CH_2$—, —$CH_2$C($R^{4a}$)($R^{4b}$)—, —N($R^{4c}$)—, —C($R^{4a}$)($R^{4b}$)N($R^{4c}$)— or a single bond, X represents a halogen atom, a cyano, a nitro, an azide, —SCN, —$SF_5$, a $C_1$ to $C_6$ alkyl, a ($C_1$ to $C_6$) alkyl optionally substituted with $R^4$, a $C_3$ to $C_8$ cycloalkyl, a ($C_3$ to $C_8$) cycloalkyl optionally substituted with $R^4$, E1 to E19, a $C_2$ to $C_6$ alkenyl, a ($C_2$ to $C_6$) alkenyl optionally substituted with $R^4$, a $C_5$ to $C_{10}$ cycloalkenyl, a $C_5$ to $C_{10}$ halocycloalkenyl, a $C_2$ to $C_6$ alkynyl, a ($C_2$ to $C_6$) alkynyl optionally substituted with $R^4$, —OH, —$OR^5$, —OS(O)$_2R^5$, —SH, —S(O)$_rR^5$, —N($R^7$)$R^6$, —N=C($R^{7a}$)$R^{6a}$, —C(O)$R^8$, —C($R^8$)=NOH, —C($R^8$)=$NOR^9$, M3, M13, M30, —C(O)$OR^9$, —C(O)$SR^9$, —C(O)$NH_2$, —C(O)N($R^{10}$)$R^9$, —C(S)$OR^9$, —C(S)$SR^9$, —C(S)$NH_2$, —C(S)N($R^{10}$)$R^9$, M23 to M26, M28, M29, —S(O)$_2OR^9$, —S(O)$_2NH_2$, —S(O)$_2$N($R^{10}$)$R^9$, —Si($R^{11a}$)($R^{11b}$)$R^{11}$, a phenyl, a phenyl substituted with (Z)$_{p1}$ or D1 to D38, where when m represents an integer of 2 or more, Xs may be the same as or different from each other, and further, when two Xs are adjacent to each other, the two Xs adjacent to each other may form —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2$N($R^{12}$)—, —$CH_2$N($R^{12}$)$CH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$OCH_2CH_2S$—, —$CH_2CH$=CH—, —OCH=CH—, —SCH=CH—, —N($R^{12}$)CH=CH—, —OCH=N—, —SCH=N—, —N($R^{12}$)CH=N—, —N($R^{12}$)N=CH—, —CH=CHCH=CH—, —$OCH_2$CH=CH—, —N=CHCH=CH—, —N=CHCH=N— or —N=CHN=CH— to form together with carbon atoms to which each of the two Xs is bonded, a 5-membered ring or a 6-membered ring, and in this case, a hydrogen atom bonded to each carbon atom forming the ring may be optionally replaced by Z, and further when hydrogen atoms are replaced simultaneously by 2 or more Zs, Zs may be the same as or different from each other, Y represents a halogen atom, a cyano, a nitro, an azide, —SCN, —$SF_5$, a $C_1$ to $C_6$ alkyl, a ($C_1$ to $C_6$) alkyl optionally substituted with $R^4$, a $C_3$ to $C_8$ cycloalkyl, a ($C_3$ to $C_8$) cycloalkyl optionally substituted with $R^4$, E1 to E18, a $C_2$ to $C_6$ alkenyl, a ($C_2$ to $C_6$) alkenyl optionally substituted with $R^4$, a $C_2$ to $C_6$ alkynyl, a ($C_2$ to $C_6$) alkynyl optionally substituted with $R^4$, —OH, —$OR^5$, —OS(O)$_2R^5$, —SH, —S(O)$_rR^5$, —$NH_2$, —N($R^7$)$R^6$, —N($R^7$)C(O)$R^{8a}$, —N=C($R^{7a}$)$R^{6a}$, —C(O)$NH_2$, —C(O)N($R^{10}$)$R^9$, —C(S)$NH_2$, —C(S)N($R^{10}$)$R^9$, —Si($R^{11a}$)($R^{11b}$)$R^{11}$, a phenyl, a phenyl substituted with (Z)$_{p1}$ or D1 to D38, where when n represents an integer of 2 or more, Ys may be the same as or different from each other, and further, when two Ys are adjacent to each other, the two Ys adjacent to each other may form —$CH_2CH_2CH_2$—, —$CH_2CH_2O$—, —$CH_2OCH_2$—, —$OCH_2O$—, —$CH_2CH_2S$—, —$CH_2SCH_2$—, —$SCH_2S$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$OCH_2CH_2S$—, —$SCH_2CH_2S$—, —OCH=N—, —SCH=N—, —CH=CHCH=CH—, —CH=CHCH=N—, —CH=CHN=CH—, —CH=NCH=CH— or —N=CHCH=CH— to form together with carbon atoms to which each of the two Ys is bonded, a 5-membered ring or a 6-membered ring, and in this case, a hydrogen atom bonded to each carbon atom forming the ring may be optionally replaced by Z, further when hydrogen atoms are replaced simultaneously by 2 or more Zs, Zs may be the same as or different from each other, $Z^a$ represents a halogen atom, a cyano, a nitro, a $C_1$ to $C_6$ alkyl, a ($C_1$ to $C_6$) alkyl optionally substituted with $R^4$, —OH, —$OR^5$, —OS(O)$_2R^5$, —SH, —S(O)$_rR^5$, —$NH_2$, —N($R^7$)$R^6$, —C(O)$R^8$, —C($R^8$)=NOH, —C($R^8$)=$NOR^9$, M3, M13, M30, —C(O)$OR^9$, —C(O)$SR^9$, —C(O)N($R^2$)$R^1$, —C(S)$OR^9$, —C(S)$SR^9$, —C(S)N($R^2$)$R^1$, M23 to M26, M28, M29, —S(O)$_2OR^9$, —S(O)$_2NH_2$, —S(O)$_2$N($R^{10}$)$R^9$, —Si($R^{11a}$)($R^{11b}$)$R^{11}$, a phenyl or a phenyl substituted with (Z)$_{p1}$, where when p represents an integer of 2 or more, $Z^a$s may be the same as or different from each other, and further, when two $Z^a$s are adjacent to each other, the two $Z^a$ adjacent to each other may form —CH=CH—CH=CH— to form a fused ring, in this case, a hydrogen atom bonded to each carbon atom forming the ring may be optionally replaced by a halogen atom, a cyano group, a nitro group, a $C_1$ to $C_4$ alkyl group, a $C_1$ to $C_4$ haloalkyl group, a $C_1$ to $C_4$ alkoxy group or a $C_1$ to $C_4$ alkylthio group, $R^1$ represents a hydrogen atom, a cyano, a $C_1$ to $C_{12}$ alkyl, a ($C_1$ to $C_{12}$) alkyl optionally substituted with $R^{13}$, a $C_3$ to $C_{12}$ cycloalkyl, a ($C_3$ to $C_{12}$) cycloalkyl optionally substituted with $R^{13}$, E2 to E6, E9, E12 to E15, E18, a $C_2$ to $C_{12}$ alkenyl, a ($C_2$ to $C_{12}$) alkenyl optionally substituted with $R^{13}$, a $C_5$ to $C_{14}$ cycloalkenyl, a $C_5$ to $C_{14}$ halocycloalkenyl, a $C_3$ to $C_{12}$ alkynyl, a ($C_3$ to $C_{12}$) alkynyl optionally substituted with $R^{13}$, a $C_3$ to $C_{12}$ alkenyl, —C(O)$R^{14}$, —C($R^{14}$)=NOH, —C($R^{14}$)=NO$R^{15}$, M3, M13, M30, —C($R^{14}$)=NN($R^{17}$)$R^{16}$, —C(O)O$R^{15}$, —C(O)N($R^{17}$)$R^{16}$, —C(O)N($R^{17}$)O$R^{15}$, —C(O)N($R^{17}$)N($R^{17}$)$R^{16}$, —C(S)$R^{14}$, —C(S)O$R^{15}$, —C(S)S$R^{15}$, —C(S)N($R^{17}$)$R^{16}$, —C(=N$R^{16}$)O$R^{15}$, —C(=NO$R^{15}$)O$R^{15}$, M7, M17, M23, M26, —C(=N$R^{16}$)S$R^{15}$, M9, M19, M24, M28, —C(=N$R^{16}$)N($R^{17}$)$R^{16}$, —C(=NCN)N($R^{17}$)$R^{16}$, —C(=NO$R^{15}$)N($R^{17}$)$R^{16}$, —C(=NNO$_2$)N($R^{17}$)$R^{16}$, M11, M21, M25, M29, —O$R^{15}$, —S$R^{15}$, —S(O)$_2R^{15}$, —S(O)$_2$N($R^{17}$)$R^{16}$, —N($R^{17}$)$R^{16}$, —N=C($R^{17a}$)$R^{16a}$, —C(O)ON=C($R^{17a}$)$R^{16a}$, —SN($R^{19}$)$R^{18}$, a phenyl, a phenyl substituted with $(Z)_{p1}$, D1 to D25 or D27 to D38, $R^2$ represents a hydrogen atom, a cyano, a $C_1$ to $C_{12}$ alkyl, a ($C_1$ to $C_{12}$) alkyl optionally substituted with $R^{13a}$, a $C_3$ to $C_{12}$ cycloalkyl, a $C_3$ to $C_{12}$ alkenyl, a $C_3$ to $C_{12}$ haloalkenyl, a $C_5$ to $C_{14}$ cycloalkenyl, a $C_5$ to $C_{14}$ halocycloalkenyl, $C_3$ to $C_{12}$ alkynyl, a $C_3$ to $C_{12}$ haloalkynyl, —C(O)$R^{14a}$, —C(O)O$R^{15a}$, —C(O)S$R^{15a}$, —C(O)N($R^{17}$)$R^{16}$, —C(O)C(O)O$R^{15a}$, —C(S)O$R^{15a}$, —C(S)S$R^{15a}$, —C(S)N($R^{17}$)$R^{16}$, —O$R^{15}$, —S$R^{15}$, —N($R^{17}$)$R^{16}$, —N=C($R^{17a}$)$R^{16a}$, —S(O)$_2R^{15a}$, —S(O)$_2$N($R^{17}$)$R^{16}$, —SN($R^{19}$)$R^{18}$, a phenyl, a phenyl substituted with $(Z)_{p1}$, D1, D2 or D32 to D35, or $R^2$ together with $R^1$ may form =C($R^{2b}$)$R^{1b}$ or a $C_2$ to $C_7$ alkylene chain to form together with a nitrogen atom to which $R^1$ and $R^2$ are bonded, a 3- to 8-membered ring, and in this case, the alkylene chain may contain one oxygen atom, sulfur atom or nitrogen atom and may be optionally substituted with a halogen atom, a $C_1$ to $C_6$ alkyl group, a $C_1$ to $C_6$ haloalkyl group, a $C_1$ to $C_6$ alkoxy($C_1$ to $C_6$) alkyl group, a $C_1$ to $C_6$ alkoxy group, a —CHO group, a $C_1$ to $C_6$ alkylcarbonyl group, a $C_1$ to $C_6$ haloalkylcarbonyl group, a $C_1$ to $C_6$ alkoxycarbonyl group, a $C_1$ to $C_6$ haloalkoxycarbonyl group, a $C_1$ to $C_6$ alkylaminocarbonyl group, a $C_1$ to $C_6$ haloalkylaminocarbonyl group, a phenyl group, a phenyl substituted with $(Z)_{p1}$, a D32 group, a D33 group, a D34 group, a D35 group, an oxo group or a thioxo group, and further, when the substituent Y is present adjacent to $G^2$, $R^2$ together with Y may form —CH$_2$—, —CH$_2$CH$_2$—, —CH$_2$O—, —CH$_2$S—, —CH$_2$N($R^6$)—, —CH=CH— or —CH=N— to form together with atoms to which each of $R^2$ and Y is bonded, a 5-membered ring or a 6-membered ring, and in this case, a hydrogen atom bonded to each carbon atom forming the ring may be optionally replaced by a halogen atom, a $C_1$ to $C_6$ alkyl group, a $C_1$ to $C_6$ haloalkyl group, a $C_1$ to $C_6$ alkylidene group, a $C_1$ to $C_6$ haloalkylidene group, an oxo group or a thioxo group, $R^{1a}$ represents —C(O)$R^{14}$, —C(O)O$R^{15}$, —C(O)S$R^{15}$, —C(O)N($R^{17}$)$R^{16}$, —C(O)N($R^{17}$)O$R^{15}$, —C(O)N($R^{17}$)N($R^{17}$)$R^{16}$, —C(S)$R^{14}$, —C(S)O$R^{15}$, —C(S)S$R^{15}$, —C(S)N($R^{17}$)$R^{16}$, —C(S$R^{15}$)=NCN, —C(S$R^{15}$)=NNO$_2$, —S(O)$_2R^{15}$ or —S(O)$_2$N($R^{17}$)$R^{16}$, $R^{2a}$ represents a hydrogen atom, a cyano, a $C_1$ to $C_{12}$ alkyl, a ($C_1$ to $C_{12}$) alkyl optionally substituted with $R^{13a}$, a $C_3$ to $C_{12}$ cycloalkyl, a $C_3$ to $C_{12}$ alkenyl, a $C_3$ to $C_{12}$ haloalkenyl, a $C_3$ to $C_{12}$ alkynyl, a $C_3$ to $C_{12}$ haloalkynyl, —C(O)$R^{14a}$, —C(O)O$R^{15a}$, —C(O)S$R^{15a}$, —C(O)N($R^{17}$)$R^{16}$, —C(O)C(O)O$R^{15a}$, —C(S)O$R^{15a}$, —C(S)S$R^{15a}$, —C(S)N($R^{17}$)$R^{16}$, a $C_1$ to $C_{12}$ alkoxy, a $C_1$ to $C_{12}$ haloalkoxy, —S$R^{15}$, —S(O)$_2R^{15a}$, —SN($R^{19}$)$R^{18}$, a phenyl, a phenyl substituted with $(Z)_{p1}$, D1, D2 or D32 to D35, or $R^{2a}$ together with $R^{1a}$ may form a $C_3$ to $C_6$ alkylene chain to form together with a nitrogen atom to which $R^{1a}$ and $R^{2a}$ are bonded, a 4- to 7-membered ring, and in this case, the alkylene chain may contain one oxygen atom, sulfur atom or nitrogen atom and may be optionally substituted with a $C_1$ to $C_6$ alkyl group, a $C_1$ to $C_6$ alkylidene group, a —CHO group, a $C_1$ to $C_6$ alkylcarbonyl group, a $C_1$ to $C_6$ haloalkylcarbonyl group, a $C_1$ to $C_6$ alkoxycarbonyl group, a $C_1$ to $C_6$ haloalkoxycarbonyl group, a $C_1$ to $C_6$ alkylaminocarbonyl group, a $C_1$ to $C_6$ haloalkylaminocarbonyl group, a di($C_1$ to $C_6$ alkyl)aminocarbonyl group, a phenyl group, a D32 group, a D34 group, an oxo group or a thioxo group, $R^{1b}$ represents a hydrogen atom, $R^{14}$, —O$R^{15}$, —S$R^{15}$, —S(O)$_2R^{15}$ or —N($R^{17b}$)$R^{16b}$, $R^{2b}$ represents a $C_1$ to $C_6$ alkyl, —O$R^{15a}$, —S$R^{15a}$, —SC(O)$R^{14a}$, —SC(O)O$R^{15a}$ or —N($R^{17c}$)$R^{16c}$, or $R^{2b}$ together with $R^{1b}$ may form a $C_4$ to $C_5$ alkylene chain or a $C_4$ to $C_5$ alkenylene chain to form together with a carbon atom to which $R^{1b}$ and $R^{2b}$ are bonded, a 5- or 6-membered ring, and in this case, the alkylene chain or the alkenylene chain may contain one to three oxygen atom(s), sulfur atom(s) or nitrogen atom(s) and may be optionally substituted with a halogen atom, a cyano group, a nitro group, a $C_1$ to $C_6$ alkyl group, a $C_1$ to $C_6$ haloalkyl group, a $C_1$ to $C_6$ alkoxy group, a $C_1$ to $C_6$ haloalkoxy group, a $C_1$ to $C_6$ alkylthio group, a $C_1$ to $C_6$ haloalkylthio group or a $R^{17c}$ group, $R^3$ represents a halogen atom, a cyano, a $C_1$ to $C_6$ alkyl, a ($C_1$ to $C_6$) alkyl optionally substituted with $R^4$, a $C_3$ to $C_8$ cycloalkyl, a ($C_3$ to $C_8$) cycloalkyl optionally substituted with $R^4$, E1 to E19, a $C_3$ to $C_6$ alkenyl, a ($C_2$ to $C_6$) alkenyl optionally substituted with $R^4$, a $C_3$ to $C_6$ alkynyl, a ($C_2$ to $C_6$) alkynyl optionally substituted with $R^4$, —O$R^5$, —S(O)$_rR^5$, —N($R^{10}$)$R^9$, —C(O)$R^8$, —C($R^8$)=NOH, —C($R^8$)=NO$R^9$, M3, M13, M30, —C(O)O$R^9$, —C(O)S$R^9$, —C(O)NH$_2$, —C(O)N($R^{10}$)$R^9$, —C(S)O$R^9$, —C(S)S$R^9$, —C(S)NH$_2$, —C(S)N($R^{10}$)$R^9$, —Si($R^{11a}$)($R^{11b}$)$R^{11}$, —P(O)(O$R^{20}$)$_2$, a phenyl, a phenyl substituted with $(Z)_{p1}$ or D1 to D38, $R^{3a}$ represents a halogen atom, a cyano, a nitro, a $C_1$ to $C_6$ alkyl, a ($C_1$ to $C_6$) alkyl optionally substituted with $R^4$, a $C_3$ to $C_8$ cycloalkyl, a $C_2$ to $C_6$ alkenyl, a $C_2$ to $C_6$ alkynyl, —C(O)O$R^9$, —C(O)S$R^9$, —C(O)NH$_2$, —C(O)N($R^{10}$)$R^9$, —C(S)O$R^9$, —C(S)S$R^9$, —C(S)NH$_2$, —C(S)N($R^{10}$)$R^9$, a $C_1$ to $C_6$ alkylthio, a $C_1$ to $C_6$ haloalkylthio or a phenyl, $R^{3b}$ represents a hydrogen atom, a halogen atom, a $C_1$ to $C_6$ alkyl, a $C_3$ to $C_6$ haloalkyl, a $C_3$ to $C_6$ alkenyl or a $C_3$ to $C_6$ alkynyl, $R^{3c}$ represents a hydrogen atom or $R^{3a}$, D1 to D38 individually represent an aromatic heterocyclic ring represented by the following Structural Formulae:

D1

D2

-continued
D3 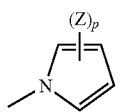
D4 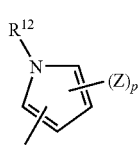
D5 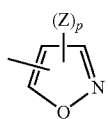
D6 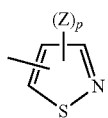
D7 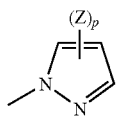
D8 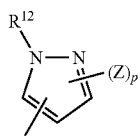
D9 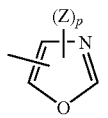
D10 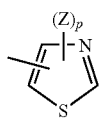
D11 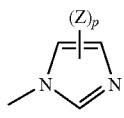
D12 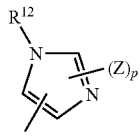
D13 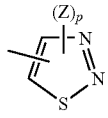
D14 
-continued
D15 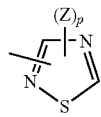
D16 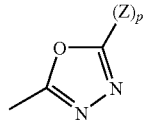
D17 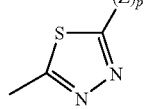
D18 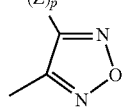
D19 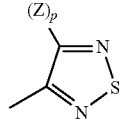
D20 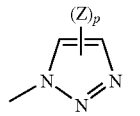
D21 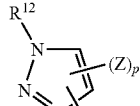
D22 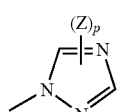
D23 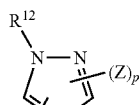
D24 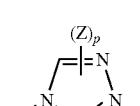
D25 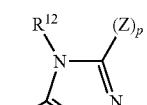
D26 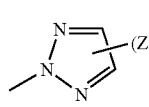

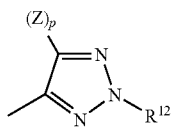
D27

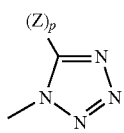
D28

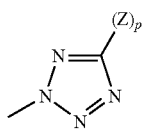
D29

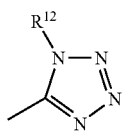
D30

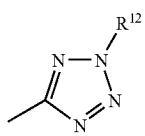
D31

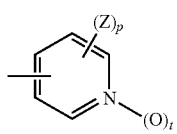
D32

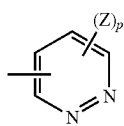
D33

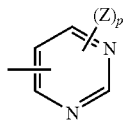
D34

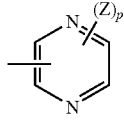
D35

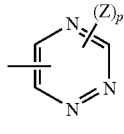
D36

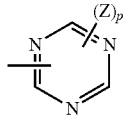
D37

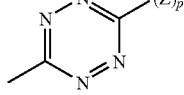
D38

Z represents a halogen atom, a cyano, a nitro, a $C_1$ to $C_6$ alkyl, a $C_1$ to $C_6$ haloalkyl, a $C_1$ to $C_4$ alkoxy($C_1$ to $C_4$) alkyl, a $C_1$ to $C_4$ haloalkoxy($C_1$ to $C_4$) alkyl, a $C_1$ to $C_4$ alkylthio($C_1$ to $C_4$) alkyl, a $C_1$ to $C_4$ haloalkylthio($C_1$ to $C_4$) alkyl, a $C_1$ to $C_4$ alkylsulfinyl($C_1$ to $C_4$) alkyl, a $C_1$ to $C_4$ haloalkylsulfinyl ($C_1$ to $C_4$) alkyl, a $C_1$ to $C_4$ alkylsulfonyl($C_1$ to $C_4$) alkyl, a $C_1$ to $C_4$ haloalkylsulfonyl($C_1$ to $C_4$) alkyl, a $C_3$ to $C_6$ cycloalkyl, a $C_3$ to $C_6$ halocycloalkyl, —OH, a $C_1$ to $C_6$ alkoxy, a $C_1$ to $C_6$ haloalkoxy, a $C_1$ to $C_6$ alkyl sulfonyloxy, a $C_1$ to $C_6$ haloalkylsulfonyloxy, a $C_1$ to $C_6$ alkylthio, a $C_1$ to $C_6$ haloalkylthio, a $C_1$ to $C_6$ alkylsulfinyl, a $C_1$ to $C_6$ haloalkylsulfinyl, a $C_1$ to $C_6$ alkylsulfonyl, a $C_1$ to $C_6$ haloalkylsulfonyl, —$NH_2$, a $C_1$ to $C_6$ alkylamino, a di($C_1$ to $C_6$ alkyl)amino, a $C_1$ to $C_6$ alkoxycarbonyl, a $C_1$ to $C_6$ haloalkoxycarbonyl, —C(O)$NH_2$, a $C_1$ to $C_6$ alkylaminocarbonyl, a $C_1$ to $C_6$ haloalkylaminocarbonyl, a di($C_1$ to $C_6$ alkyl)aminocarbonyl, —C(S)$NH_2$, —S(O)$_2NH_2$, a $C_1$ to $C_6$ alkylaminosulfonyl, a di($C_1$ to $C_6$ alkyl)aminosulfonyl, a phenyl or a phenyl optionally substituted with a halogen atom, where when p and p1 individually represent an integer of 2 or more, Zs may be the same as or different from each other, and further, when two Zs are adjacent to each other, the two Zs adjacent to each other may form —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$CH_2CH_2CH_2S$—, —$OCH_2CH_2S$— or —CH=CH—CH=CH— to form together with carbon atoms to which each of the two Zs is bonded, a 5-membered ring or a 6-membered ring, and in this case, a hydrogen atom bonded to each carbon atom forming the ring may be optionally replaced by a halogen atom, a cyano group, a nitro group, a $C_1$ to $C_4$ alkyl group, a $C_1$ to $C_4$ haloalkyl group, a $C_1$ to $C_4$ alkoxy group or a $C_1$ to $C_4$ alkylthio group, E1 to E19 individually represent a saturated heterocyclic ring represented by the following Structural Formulae:

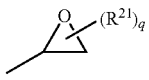
E1

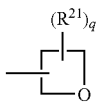
E2

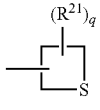
E3

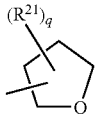
E4

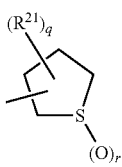
E5

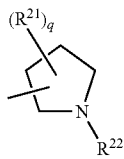
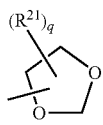
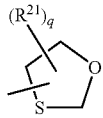
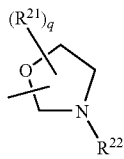
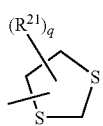
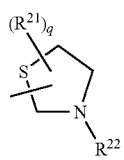
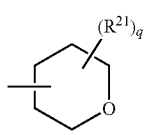
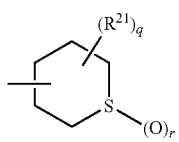
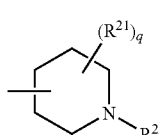
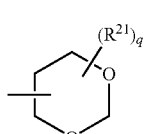
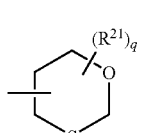

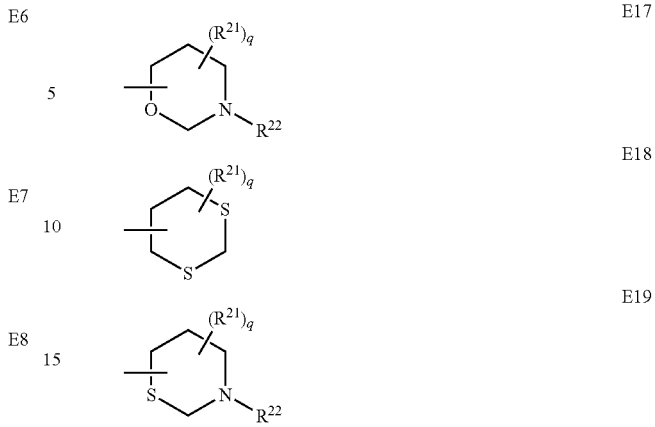

$R^4$ represents a halogen atom, a cyano, a $C_3$ to $C_8$ cycloalkyl, a $C_3$ to $C_8$ halocycloalkyl, E1 to E19, —OH, —OR$^5$, —SH, —S(O)$_r$R$^5$, —N(R$^7$)R$^6$, —N(R$^7$)C(O)R$^{8a}$, —C(O)OR$^9$, —C(O)N(R$^{10}$)R$^9$, —Si(R$^{11a}$)(R$^{11b}$)R$^{11}$, a phenyl, a phenyl substituted with $(Z)_{p1}$ or D1 to D38, $R^{4a}$ represents a hydrogen atom, a cyano, a $C_1$ to $C_6$ alkyl, a $C_1$ to $C_6$ haloalkyl, a $C_3$ to $C_6$ cycloalkyl, a $C_2$ to $C_6$ alkenyl, a $C_2$ to $C_4$ alkynyl, a $C_1$ to $C_6$ alkoxycarbonyl, —C(O)NH$_2$, —C(S)NH$_2$, a phenyl, a phenyl substituted with $(Z)_{p1}$, D1, D2, D9, D10 or D32, $R^{4b}$ represents a hydrogen atom or a $C_1$ to $C_6$ alkyl, or $R^{4b}$ together with $R^{4a}$ may form a $C_2$ to $C_5$ alkylene chain to form together with a carbon atom to which $R^{4a}$ and $R^{4b}$ are bonded, a 3- to 6-membered ring, and in this case, the alkylene chain may contain one oxygen atom, sulfur atom or nitrogen atom and may be optionally substituted with a $C_1$ to $C_6$ alkyl group, a —CHO group, a $C_1$ to $C_6$ alkylcarbonyl group, a $C_1$ to $C_6$ alkoxycarbonyl group, a $C_1$ to $C_6$ alkylaminocarbonyl group, a $C_1$ to $C_6$ haloalkylaminocarbonyl group or a phenyl group, $R^{4c}$ represents a hydrogen atom, a $C_1$ to $C_6$ alkyl, a $C_1$ to $C_6$ haloalkyl, a $C_1$ to $C_6$ alkylcarbonyl, a $C_1$ to $C_6$ haloalkylcarbonyl, a $C_3$ to $C_6$ cycloalkylcarbonyl, a $C_3$ to $C_6$ halocycloalkylcarbonyl, a $C_1$ to $C_6$ alkoxycarbonyl or a $C_1$ to $C_6$ haloalkoxycarbonyl, $R^5$ represents a $C_1$ to $C_6$ alkyl, a ($C_1$ to $C_6$) alkyl optionally substituted with $R^{23}$, a $C_3$ to $C_8$ cycloalkyl, a ($C_3$ to $C_8$) cycloalkyl optionally substituted with $R^{23}$, E2 to E6, E12 to E15, E18, a $C_2$ to $C_6$ alkenyl, a ($C_2$ to $C_6$) alkenyl optionally substituted with $R^{23}$, a $C_5$ to $C_{10}$ cycloalkenyl, a $C_5$ to $C_{10}$ halocycloalkenyl, a $C_3$ to $C_6$ alkynyl, a ($C_3$ to $C_6$) alkynyl optionally substituted with $R^{23}$, a $C_1$ to $C_6$ alkylcarbonyl, a $C_1$ to $C_6$ alkoxycarbonyl, a phenyl, a phenyl substituted with $(Z)_{p1}$, D1, D2, D4 to D6, D8 to D10, D12 to D19, D21, D23, D25, D27 or D30 to D38, $R^6$ represents a $C_1$ to $C_6$ alkyl, a ($C_1$ to $C_6$) alkyl optionally substituted with $R^{23}$, a $C_3$ to $C_8$ cycloalkyl, a $C_3$ to $C_8$ halocycloalkyl, a $C_3$ to $C_6$ alkenyl, a $C_3$ to $C_6$ haloalkenyl, a $C_3$ to $C_6$ alkynyl, a $C_3$ to $C_6$ haloalkynyl, —C(O)R$^8$, —C(O)OR$^9$, —C(O)SR$^9$, —C(O)NH$_2$, —C(O)N(R$^{19}$)R$^9$, —C(S)OR$^9$, —C(S)SR$^9$, —C(S)NH$_2$, —C(S)N(R$^{10}$)R$^9$, —C(O)C(O)R$^9$, —C(O)C(O)OR$^9$, —OH, —S(O)$_2$R$^9$, —S(O)$_2$N(R$^{10}$)R$^9$, —P(O)(OR$^{29}$)$_2$ or —P(S)(OR$^{20}$)$_2$, $R^7$ represents a hydrogen atom, a $C_1$ to $C_6$ alkyl, a ($C_1$ to $C_6$) alkyl optionally substituted with $R^{23}$, a $C_3$ to $C_8$ cycloalkyl, a $C_3$ to $C_6$ alkenyl, a $C_3$ to $C_6$ haloalkenyl, a $C_3$ to $C_6$ alkynyl, a $C_3$ to $C_6$ haloalkynyl, —CHO, a $C_1$ to $C_6$ alkylcarbonyl, a $C_1$ to $C_6$ haloalkylcarbonyl or a $C_1$ to $C_6$ alkoxycarbonyl, or $R^7$ together with $R^6$ may form a $C_2$ to $C_6$ alkylene chain to form together with a nitrogen atom to which $R^6$ and $R^7$ are bonded, a 3- to 7-membered ring, and in this case, the alkylene chain may contain one oxygen atom, sulfur atom or nitrogen atom and may be optionally substituted with a halogen atom, a $C_1$ to $C_6$ alkyl group, a $C_1$ to $C_6$ haloalkyl group, an oxo group or a thioxo group, $R^{6a}$ represents a $C_1$ to $C_6$ alkyl, a $C_1$ to $C_6$ alkoxy, a $C_1$ to $C_6$ haloalkoxy, a $C_3$ to $C_6$ alkenyloxy, a phenoxy or a phenoxy substituted with $(Z)_{p1}$, $R^{7a}$ represents a hydrogen atom, a $C_1$ to $C_6$ alkyl, a $C_1$ to $C_6$ haloalkyl, a $C_3$ to $C_6$ alkenyl, a phenyl or a phenyl substituted with $(Z)_{p1}$, or $R^{7a}$ together with $R^{6a}$ may form a $C_4$ to $C_6$ alkylene chain to form together with a carbon atom to which $R^{6a}$ and $R^{7a}$ are bonded, a 5- to 7-membered ring, and in this case, the alkylene chain may contain one oxygen atom or sulfur atom, $R^8$ represents a hydrogen atom, a $C_1$ to $C_6$ alkyl, a ($C_1$ to $C_6$) alkyl optionally substituted with $R^{23}$, a $C_3$ to $C_8$ cycloalkyl, a $C_3$ to $C_8$ halocycloalkyl, E4 to E6, E12 to E14, a $C_3$ to $C_6$ alkenyl, a $C_3$ to $C_6$ haloalkenyl, a $C_5$ to $C_{10}$ cycloalkenyl, a $C_5$ to $C_{10}$ halocycloalkenyl, a $C_3$ to $C_6$ alkynyl or a $C_3$ to $C_6$ haloalkynyl, $R^{8a}$ represents a phenyl, a phenyl substituted with $(Z)_{p1}$, or D1 to D38, $R^9$ represents a $C_1$ to $C_6$ alkyl, a ($C_1$ to $C_6$) alkyl optionally substituted with $R^{23}$, a $C_3$ to $C_8$ cycloalkyl, a $C_3$ to $C_8$ halocycloalkyl, E2 to E6, E12 to E19, a $C_3$ to $C_6$ alkenyl, a $C_3$ to $C_6$ haloalkenyl, a $C_3$ to $C_6$ alkynyl, a $C_3$ to $C_6$ haloalkynyl, a phenyl, a phenyl substituted with $(Z)_{p1}$, D1 to D25 or D27 to D38, $R^{10}$ represents a hydrogen atom, a $C_1$ to $C_6$ alkyl, a $C_1$ to $C_6$ haloalkyl, a $C_3$ to $C_6$ cycloalkyl($C_1$ to $C_4$) alkyl, a $C_1$ to $C_6$ alkoxy($C_1$ to $C_4$) alkyl, a $C_1$ to $C_6$ alkylthio($C_1$ to $C_4$) alkyl, a cyano($C_1$ to $C_6$) alkyl, a $C_3$ to $C_6$ alkenyl or a $C_3$ to $C_6$ alkynyl, or $R^{10}$ together with $R^9$ may form a $C_2$ to $C_6$ alkylene chain to form together with a nitrogen atom to which $R^9$ and $R^{10}$ are bonded, a 3- to 7-membered ring, and in this case, the alkylene chain may contain one oxygen atom, sulfur atom or nitrogen atom and may be optionally substituted with a halogen atom, a $C_1$ to $C_6$ alkyl group, a $C_1$ to $C_6$ alkoxy group, a —CHO group, a $C_1$ to $C_6$ alkylcarbonyl group or a $C_1$ to $C_6$ alkoxycarbonyl group, $R^{11}$ represents a $C_1$ to $C_6$ alkyl, a $C_1$ to $C_6$ haloalkyl, a $C_1$ to $C_6$ alkoxy, a phenyl or a phenyl substituted with $(Z)_{p1}$, $R^{11a}$ and $R^{11b}$ independently represent a $C_1$ to $C_6$ alkyl, a $C_1$ to $C_6$ haloalkyl or a $C_1$ to $C_6$ alkoxy, $R^{12}$ represents a hydrogen atom, a $C_1$ to $C_6$ alkyl, a $C_1$ to $C_6$ haloalkyl, a $C_1$ to $C_6$ alkoxycarbonyl($C_1$ to $C_4$) alkyl, a $C_1$ to $C_6$ haloalkoxycarbonyl($C_1$ to $C_4$) alkyl, a phenyl($C_1$ to $C_4$) alkyl, a phenyl($C_1$ to $C_4$) alkyl substituted with $(Z)_{p1}$, a $C_2$ to $C_6$ alkenyl, a $C_2$ to $C_6$ haloalkenyl, a $C_3$ to $C_6$ alkynyl, a $C_3$ to $C_6$ haloalkynyl, a $C_1$ to $C_6$ alkoxy, a $C_1$ to $C_6$ alkoxylcarbonyl, a $C_1$ to $C_6$ haloalkoxycarbonyl, a phenyl or a phenyl substituted with $(Z)_{p1}$, and further, when Z is present adjacent to $R^{12}$, $R^{12}$ and Z adjacent to each other may form —$CH_2CH_2CH_2CH_2$—, —CH=CH—CH=CH—, —N=CH—CH=CH—, —CH=N—CH=CH—, —CH=CH—N=CH— or —CH=CH—CH=N— to form together with atoms to which each of $R^{12}$ and Z is bonded, a 6-membered ring, and in this case, a hydrogen atom bonded to each carbon atom forming the ring may be optionally replaced by a halogen atom, a $C_1$ to $C_4$ alkyl group or a $C_1$ to $C_4$ haloalkyl group, $R^{13}$ and $R^{13a}$ independently represent a halogen atom, a cyano, a nitro, a $C_3$ to $C_8$ cycloalkyl, a $C_3$ to $C_8$ halocycloalkyl, a hydroxy($C_3$ to $C_8$) cycloalkyl, a $C_1$ to $C_4$ alkoxy($C_3$ to $C_8$) cycloalkyl, E1 to E19, a $C_5$ to $C_{10}$ cycloalkenyl, a $C_5$ to $C_{10}$ halocycloalkenyl, —$OR^{24}$, —$N(R^{25})R^{24}$, —SH, —$S(O)_rR^{26}$, —$C(O)R^{27}$, —$C(R^{27})$=NOH, —$C(R^{27})$=$NOR^{28}$, —C(O)OH, —$C(O)OR^{28}$, —$C(O)SR^{28}$, —$C(O)NH_2$, —$C(O)N(R^{29})R^{28}$, —$C(O)N(R^{29})OR^{28}$, —$C(O)N(R^{29})N(R^{29})R^{28}$, —$C(O)C(O)OR^{28}$, —$C(S)OR^{28}$, —$C(S)SR^{28}$, —$C(S)NH_2$, —$C(S)N(R^{29})R^{28}$, —$C(=NR^{29})OR^{28}$, —$C(=NR^{29})SR^{28}$, —$C(=NR^{29})N(R^{29})R^{28}$, —$C(=NOR^{28})N(R^{29})R^{28}$, —$S(O)_2OH$, —$S(O)_2NH_2$, —$S(O)_2N(R^{29})R^{28}$, —$Si(R^{11a})(R^{11b})R^{11}$, —$P(O)(OR^{20})_2$, —$P(S)(OR^{20})_2$, —$P(phenyl)_2$, —$P(O)(phenyl)_2$, M1 to M30, a phenyl, a phenyl substituted with $(Z)_{p1}$, a naphthyl or D1 to D38, M1 to M30 individually represent a partially saturated heterocyclic ring represented by the following Structural Formulae:

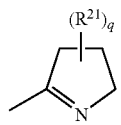

M1

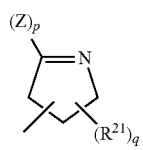

M2

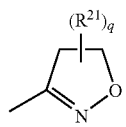

M3

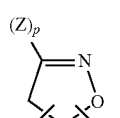

M4

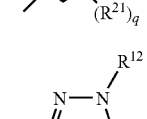

M5

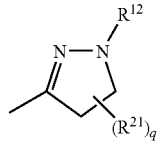

M6

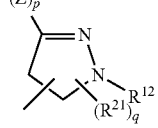

M7

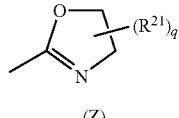

M8

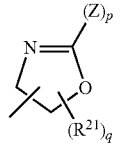

M9

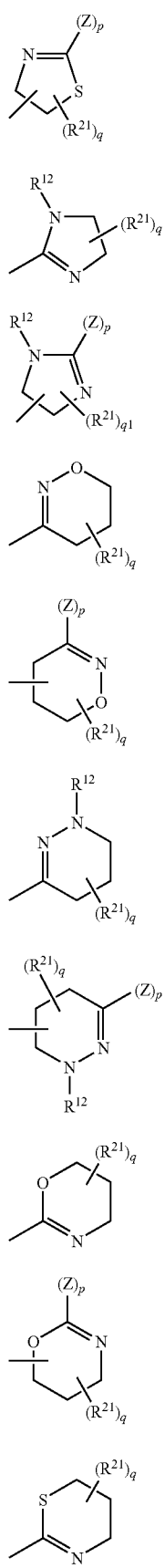
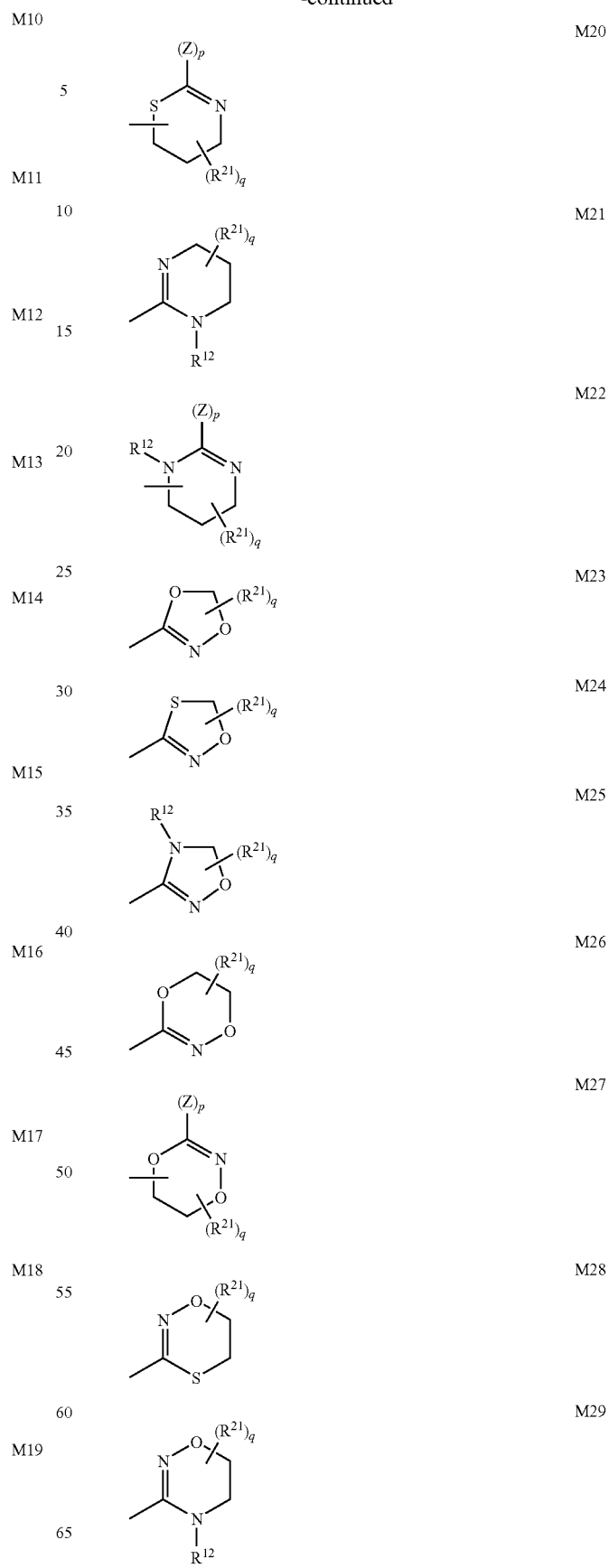

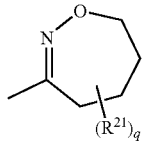
M30

$R^{14}$ and $R^{14a}$ independently represent a hydrogen atom, a $C_1$ to $C_{12}$ alkyl, a ($C_1$ to $C_{12}$) alkyl optionally substituted with $R^{30}$, a $C_3$ to $C_{12}$ cycloalkyl, a ($C_3$ to $C_{12}$) cycloalkyl optionally substituted with $R^{30}$, E1 to E19, a $C_2$ to $C_{12}$ alkenyl, a ($C_2$ to $C_{12}$) alkenyl optionally substituted with $R^{30}$, a $C_5$ to $C_{12}$ cycloalkenyl, a $C_5$ to $C_{12}$ halocycloalkenyl, a $C_2$ to $C_{12}$ alkynyl, a ($C_2$ to $C_{12}$) alkynyl optionally substituted with $R^{30}$—$C(R^{27})$=$NOR^{28}$, —$C(R^{27})$=$NN(R^{29})R^{28}$, —$C(O)OR^{28}$, —$C(O)N(R^{29})R^{28}$, M4, a phenyl, a phenyl substituted with $(Z)_{p1}$, a naphthyl or D1 to D38, $R^{15}$ and $R^{15a}$ independently represent a $C_1$ to $C_{12}$ alkyl, a ($C_1$ to $C_{12}$) alkyl optionally substituted with $R^{30}$, a $C_3$ to $C_{12}$ cycloalkyl, a ($C_3$ to $C_{12}$) cycloalkyl optionally substituted with $R^{30}$, E2 to E6, E12 to E19, a $C_2$ to $C_{12}$ alkenyl, a $C_2$ to $C_{12}$ haloalkenyl, a $C_5$ to $C_{10}$ cycloalkenyl, a $C_5$ to $C_{10}$ halocycloalkenyl, a $C_3$ to $C_{12}$ alkynyl, a $C_2$ to $C_{12}$ haloalkynyl, a phenyl, a phenyl substituted with $(Z)_{p1}$, D1, D2, D4 to D6, D8 to D10, D12 to D19, D21, D23, D25, D27 or D30 to D38, $R^{16}$ represents a hydrogen atom, a $C_1$ to $C_{12}$ alkyl, a ($C_1$ to $C_{12}$) alkyl optionally substituted with $R^{30}$, a $C_3$ to $C_{12}$ cycloalkyl, a ($C_3$ to $C_{12}$) cycloalkyl optionally substituted with $R^{30}$, E2 to E6, E12 to E19, a $C_2$ to $C_{12}$ alkenyl, a $C_2$ to $C_{12}$ haloalkenyl, a $C_5$ to $C_{10}$ cycloalkenyl, a $C_5$ to $C_{10}$ halocycloalkenyl, a $C_3$ to $C_{12}$ alkynyl, a $C_2$ to $C_{12}$ haloalkynyl, —$C(O)R^{27}$, —$C(O)OR^{28}$, —$C(O)SR^{28}$, —$C(O)NH_2$, —$C(O)N(R^{29})R^{28}$, —$C(S)R^{27}$, —$C(S)OR^{28}$, —$C(S)SR^{28}$, —$C(S)NH_2$, —$C(S)N(R^{29})R^{28}$, M7 M9, M17, M19, —$S(O)_2R^{28}$, —$S(O)_2NH_2$, —$S(O)_2N(R^{29})R^{28}$, —$P(O)(OR^{20})_2$, —$P(S)(OR^2)_2$, a phenyl, a phenyl substituted with $(Z)_{p1}$, D1 to D25 or D27 to D38, $R^{17}$ represents a hydrogen atom, a $C_1$ to $C_6$ alkyl, a $C_1$ to $C_6$ haloalkyl, a $C_3$ to $C_6$ cycloalkyl($C_1$ to $C_4$) alkyl, a $C_1$ to $C_4$ alkoxy($C_1$ to $C_4$) alkyl, a $C_1$ to $C_4$ haloalkoxy($C_1$ to $C_4$) alkyl, a $C_1$ to $C_4$ alkylthio($C_1$ to $C_4$) alkyl, a $C_1$ to $C_4$ haloalkylthio($C_1$ to $C_4$) alkyl, a $C_1$ to $C_4$ alkylsulfonyl($C_1$ to $C_4$) alkyl, a $C_1$ to $C_4$ haloalkylsulfonyl($C_1$ to $C_4$) alkyl, a cyano($C_1$ to $C_6$) alkyl, a $C_1$ to $C_4$ alkoxycarbonyl($C_1$ to $C_4$) alkyl, a phenyl($C_1$ to $C_4$) alkyl, a $C_2$ to $C_6$ alkenyl, a $C_2$ to $C_6$ haloalkenyl, a $C_3$ to $C_6$ alkynyl or a $C_3$ to $C_6$ haloalkynyl, or $R^{17}$ together with $R^{16}$ may form a $C_2$ to $C_6$ alkylene chain to form together with a nitrogen atom to which $R^{16}$ and $R^{17}$ are bonded, a 3- to 7-membered ring, and in this case, the alkylene chain may contain one oxygen atom, sulfur atom or nitrogen atom and may be optionally substituted with a halogen atom, a $C_1$ to $C_6$ alkyl group, a $C_1$ to $C_4$ alkoxy($C_1$ to $C_4$) alkyl group, a $C_1$ to $C_6$ alkoxy group, a —CHO group, a $C_1$ to $C_6$ alkylcarbonyl group, a $C_1$ to $C_6$ alkoxycarbonyl group, an oxo group or a thioxo group, $R^{16a}$ represents a hydrogen atom, a $C_1$ to $C_6$ alkyl, a $C_1$ to $C_6$ haloalkyl, a $C_1$ to $C_4$ alkoxy($C_1$ to $C_4$) alkyl, a $C_1$ to $C_4$ alkylthio($C_1$ to $C_4$) alkyl, a $C_1$ to $C_4$ alkylsulfonyl($C_1$ to $C_4$) alkyl, a $C_1$ to $C_4$ alkoxycarbonyl($C_1$ to $C_4$) alkyl, a phenyl($C_1$ to $C_4$) alkyl, a phenyl($C_1$ to $C_4$) alkyl substituted with $(Z)_{p1}$, a $C_3$ to $C_6$ cycloalkyl, E1 to E19, a phenyl($C_2$ to $C_4$) alkenyl, a di($C_1$ to $C_6$ alkyl)amino, a phenyl, a phenyl substituted with $(Z)_{p1}$ or D1 to D38, $R^{17a}$ represents a hydrogen atom, a $C_1$ to $C_6$ alkyl, a $C_1$ to $C_6$ alkoxy, a $C_1$ to $C_6$ alkylthio or a di($C_1$ to $C_6$ alkyl)amino, or $R^{17a}$ together with $R^{16a}$ may form a $C_3$ to $C_5$ alkylene chain to form together with a carbon atom to which $R^{16a}$ and $R^{17a}$ are bonded, a 4- to 6-membered ring, and in this case, the alkylene chain may contain one oxygen atom, sulfur atom or nitrogen atom and may be optionally substituted with a halogen atom, a $C_1$ to $C_6$ alkyl group, a $C_1$ to $C_6$ haloalkyl group, a —CHO group, a $C_1$ to $C_6$ alkylcarbonyl group or a $C_1$ to $C_6$ alkoxycarbonyl group, $R^{16b}$ represents a hydrogen atom, a cyano, a nitro, a $C_1$ to $C_6$ alkyl, a $C_1$ to $C_6$ haloalkyl or a $C_1$ to $C_6$ alkoxy, $R^{17b}$ represents a hydrogen atom or a $C_1$ to $C_6$ alkyl, or $R^{17b}$ together with $R^{16b}$ may form a $C_3$ to $C_5$ alkylene chain to form together with a nitrogen atom to which $R^{16b}$ and $R^{17b}$ are bonded, a 4- to 6-membered ring, and in this case, the alkylene chain may contain one oxygen atom, sulfur atom or nitrogen atom and may be optionally substituted with a $C_1$ to $C_6$ alkyl group, a —CHO group, a $C_1$ to $C_6$ alkylcarbonyl group or a $C_1$ to $C_6$ alkoxycarbonyl group, $R^{16c}$ represents a hydrogen atom, a $C_1$ to $C_6$ alkyl, a $C_1$ to $C_6$ haloalkyl, a $C_3$ to $C_6$ alkenyl, a $C_3$ to $C_6$ alkynyl, a $C_1$ to $C_6$ alkoxy, a $C_1$ to $C_6$ haloalkoxy, —$NH_2$, a $C_1$ to $C_6$ alkylamino, a di($C_1$ to $C_6$ alkyl)amino, —$NHC(O)R^{27}$, —$NHC(O)OR^{28}$, —$NHC(O)SR^{28}$, —$NHC(O)NH_2$, —$NHC(O)N(R^{29})R^{28}$, —$NHC(S)OR^{28}$, —$NHC(S)SR^{28}$, —$NHC(S)NH_2$, —$NHC(S)N(R^{29})R^{28}$, —$NHS(O)_2R^{28}$, —$NHS(O)_2NH_2$ or —$NHS(O)_2N(R^{29})R^{28}$, $R^{17c}$ represents a hydrogen atom or a $C_1$ to $C_6$ alkyl, or $R^{17c}$ together with $R^{16c}$ may form a $C_3$ to $C_5$ alkylene chain to form together with a nitrogen atom to which $R^{16c}$ and $R^{17c}$ are bonded, a 4- to 6-membered ring, and in this case, the alkylene chain may contain one oxygen atom, sulfur atom or nitrogen atom and may be optionally substituted with a $C_1$ to $C_6$ alkyl group, a —CHO group, a $C_1$ to $C_6$ alkylcarbonyl group or a $C_1$ to $C_6$ alkoxycarbonyl group, $R^{18}$ represents a $C_1$ to $C_{12}$ alkyl, a $C_1$ to $C_{12}$ haloalkyl, a $C_1$ to $C_{12}$ alkoxy($C_1$ to $C_{12}$) alkyl, a cyano($C_1$ to $C_{12}$) alkyl, a $C_1$ to $C_{12}$ alkoxycarbonyl($C_1$ to $C_{12}$) alkyl, a phenyl($C_1$ to $C_4$) alkyl, a phenyl($C_1$ to $C_4$) alkyl substituted with $(Z)_{p1}$, a $C_3$ to $C_{12}$ alkenyl, a $C_3$ to $C_{12}$ haloalkenyl, a $C_3$ to $C_{12}$ alkynyl, a $C_3$ to $C_{12}$ haloalkynyl, a $C_1$ to $C_{12}$ alkylcarbonyl, a $C_1$ to $C_{12}$ alkoxycarbonyl, —$C(O)ON$=$C(CH_3)SCH_3$, —$C(O)ON$=$C(SCH_3)C(O)N(CH_3)_2$, a phenyl or a phenyl substituted with $(Z)_{p1}$, $R^{19}$ represents a $C_1$ to $C_{12}$ alkyl, a $C_1$ to $C_{12}$ haloalkyl, a $C_1$ to $C_{12}$ alkoxy($C_1$ to $C_{12}$) alkyl, a cyano($C_1$ to $C_{12}$) alkyl, a $C_1$ to $C_{12}$ alkoxycarbonyl($C_1$ to $C_{12}$) alkyl, a phenyl($C_1$ to $C_4$)alkyl, a phenyl($C_1$ to $C_4$) alkyl substituted with $(Z)_{p1}$, a $C_3$ to $C_{12}$ alkenyl, a $C_3$ to $C_{12}$ haloalkenyl, a $C_3$ to $C_{12}$ alkynyl, a $C_3$ to $C_{12}$ haloalkynyl, a phenyl or a phenyl substituted with $(Z)_{p1}$, or $R^{19}$ together with $R^{18}$ may form a $C_4$ to $C_7$ alkylene chain to form together with a nitrogen atom to which $R^{18}$ and $R^{19}$ are bonded, a 5- to 8-membered ring, and in this case, the alkylene chain may contain one oxygen atom or sulfur atom and may be optionally substituted with a $C_1$ to $C_4$ alkyl group or a $C_1$ to $C_4$ alkoxy group, $R^{20}$ represents a $C_1$ to $C_6$ alkyl or a $C_1$ to $C_6$ haloalkyl, $R^{21}$ represents a halogen atom, a cyano, a $C_1$ to $C_6$ alkyl, a $C_1$ to $C_6$ haloalkyl, a hydroxy($C_1$ to $C_6$) alkyl, a $C_1$ to $C_4$ alkoxy($C_1$ to $C_4$) alkyl, a $C_1$ to $C_4$ alkoxycarbonyl($C_1$ to $C_4$)alkyl, a $C_1$ to $C_6$ alkoxy, a $C_1$ to $C_6$ alkylthio, a $C_1$ to $C_6$ alkylamino, a di($C_1$ to $C_4$ alkyl)amino, a $C_1$ to $C_6$ alkoxycarbonyl, a phenyl or a phenyl substituted with $(Z)_{p1}$, where when q represents an integer of 2 or more, $R^{21}$'s may be the same as or different from each other, and further when two $R^{21}$'s are replaced on the same carbon atom, the two $R^{21}$'s together with each other may form an oxo, a thioxo, an imino, a $C_1$ to $C_6$ alkylimino, a $C_1$ to $C_6$ alkoxyimino or a $C_1$ to $C_6$ alkylidene, $R^{22}$ represents a hydrogen atom, a $C_1$ to $C_6$ alkyl, a ($C_1$ to $C_6$) alkyl optionally substituted with $R^{30}$, a $C_3$ to $C_6$ cycloalkyl, a $C_3$ to $C_6$ alkenyl, a $C_3$ to $C_6$ haloalkenyl, a $C_3$ to $C_6$ alkynyl, —OH, a benzyloxy, —C(O)$R^{31}$, —C(O)O$R^{32}$, —C(O)S$R^{32}$, —C(O)N($R^{34}$)$R^{33}$, —C(S)N($R^{34}$)$R^{33}$, —S(O)$_2R^{32}$, —P(O)(O$R^{20}$)$_2$, —P(S)(O$R^{20}$)$_2$, a phenyl, a phenyl substituted with $(Z)_{p1}$ or D3, $R^{23}$ represents a halogen atom, a cyano, a $C_3$ to $C_8$ cycloalkyl, a $C_3$ to $C_8$ halocycloalkyl, E1 to E19, a $C_1$ to $C_6$ alkoxy, a $C_1$ to $C_6$ haloalkoxy, a $C_1$ to $C_6$ alkylthio, a $C_1$ to $C_6$ haloalkylthio, a $C_1$ to $C_6$ alkylsulfonyl, a $C_1$ to $C_6$ haloalkylsulfonyl, a $C_1$ to $C_6$ alkylamino, a di($C_1$ to $C_6$ alkyl)amino, —CHO, a $C_1$ to $C_6$ alkylcarbonyl, a $C_1$ to $C_6$ haloalkylcarbonyl, a $C_1$ to $C_6$ alkoxycarbonyl, a $C_1$ to $C_6$ haloalkoxycarbonyl, a $C_1$ to $C_6$ alkylaminocarbonyl, a di($C_1$ to $C_6$ alkyl) aminocarbonyl, a phenyl, a phenyl substituted with $(Z)_{p1}$ or D1 to D38, $R^{24}$ represents a hydrogen atom, a $C_1$ to $C_8$ alkyl, a ($C_1$ to $C_8$) alkyl optionally substituted with $R^{30}$, a $C_3$ to $C_8$ cycloalkyl, a ($C_3$ to $C_8$) cycloalkyl optionally substituted with $R^{30}$, E2 to E6, E12 to E19, a $C_3$ to $C_8$ alkenyl, a ($C_3$ to $C_8$) alkenyl optionally substituted with $R^{30}$, a $C_3$ to $C_8$ alkynyl, a ($C_3$ to $C_8$) alkynyl optionally substituted with $R^{30}$, —C(O)$R^{31}$, —C(O)O$R^{32}$, —C(O)S$R^{32}$, —C(O)N($R^{34}$)$R^{33}$, —C(O)C(O)$R^{32}$, —C(O)C(O)O$R^{32}$, —C(S)$R^{31}$, —C(S)O$R^{32}$, —C(S)S$R^{32}$, —C(S)N($R^{34}$)$R^{33}$, —S(O)$_2R^{32}$, S(O)$_2$N($R^{34}$)$R^{33}$, —Si($R^{11a}$)($R^{11b}$)$R^{11}$, —P(O)(O$R^{20}$)$_2$, —P(S)(O$R^{20}$)$_2$, a phenyl, a phenyl substituted with $(Z)_{p1}$, D1, D2, D4 to D6, D8 to D10, D12 to D19, D21, D23, D25, D27 or D30 to D38, $R^{25}$ represents a hydrogen atom, a $C_1$ to $C_6$ alkyl, a $C_1$ to $C_6$ haloalkyl, a $C_1$ to $C_4$ alkoxy($C_1$ to $C_4$) alkyl, a $C_1$ to $C_4$ alkylthio($C_1$ to $C_4$) alkyl, a $C_3$ to $C_6$ cycloalkyl, a $C_3$ to $C_6$ alkenyl, a $C_3$ to $C_6$ alkynyl, a $C_1$ to $C_6$ alkoxy, a phenyl or a phenyl substituted with $(Z)_{p1}$, or $R^{25}$ together with $R^{24}$ may form a $C_2$ to $C_5$ alkylene chain to form together with a nitrogen atom to which $R^{24}$ and $R^{25}$ are bonded, a 3- to 6-membered ring, and in this case, the alkylene chain may contain one oxygen atom, sulfur atom or nitrogen atom and may be substituted with a halogen atom, a $C_1$ to $C_6$ alkyl group, a $C_1$ to $C_6$ haloalkyl group, a $C_1$ to $C_6$ alkoxy group, a —CHO group, a $C_1$ to $C_6$ alkylcarbonyl group, a $C_1$ to $C_6$ alkoxycarbonyl group, a phenyl group, a phenyl group substituted with $(Z)_{p1}$, an oxo group or a thioxo group, $R^{26}$ represents a $C_1$ to $C_8$ alkyl, a ($C_1$ to $C_8$) alkyl optionally substituted with $R^{30}$, a $C_3$ to $C_8$ cycloalkyl, a ($C_3$ to $C_8$) cycloalkyl optionally substituted with $R^{30}$, E2 to E6, E12 to E19, a $C_3$ to $C_8$ alkenyl, a ($C_3$ to $C_8$) alkenyl optionally substituted with $R^{30}$, a $C_3$ to $C_8$ alkynyl, a ($C_3$ to $C_8$) alkynyl optionally substituted with $R^{30}$, —C(O)$R^{31}$, —C(O)O$R^{32}$, —C(O)S$R^{32}$, —C(O)N($R^{34}$)$R^{33}$, —C(O)C(O)$R^{32}$, —C(O)C(O)O$R^{32}$, —C(S)$R^{31}$, —C(S)O$R^{32}$, —C(S)S$R^{32}$, —C(S)N($R^{34}$)$R^{33}$, —SH, a $C_1$ to $C_6$ alkylthio, a $C_1$ to $C_6$ haloalkylthio, a phenylthio, a phenylthio substituted with $(Z)_{p1}$, —P(O)(O$R^{20}$)$_2$, —)P(S)(O$R^{20}$)$_2$, a phenyl, a phenyl substituted with $(Z)_{p1}$, D9, D10, D12, D14 to D17, D30, D32 or D34, $R^{27}$ represents a hydrogen atom, a $C_1$ to $C_6$ alkyl, a $C_1$ to $C_6$ haloalkyl, a $C_3$ to $C_6$ cycloalkyl($C_1$ to $C_4$) alkyl, a $C_1$ to $C_6$ alkoxy($C_1$ to $C_4$) alkyl, a $C_1$ to $C_6$ haloalkoxy($C_1$ to $C_4$) alkyl, a $C_1$ to $C_6$ alkylthio($C_1$ to $C_4$) alkyl, a $C_1$ to $C_6$ haloalkylthio ($C_1$ to $C_4$) alkyl, a $C_1$ to $C_6$ alkylsulfonyl($C_1$ to $C_4$) alkyl, a $C_1$ to $C_6$ haloalkylsulfonyl($C_1$ to $C_4$) alkyl, a phenyl($C_1$ to $C_4$) alkyl, a phenyl($C_1$ to $C_4$) alkyl substituted with $(Z)_{p1}$, a $C_3$ to $C_6$ cycloalkyl, a phenyl or a phenyl substituted with $(Z)_{p1}$, $R^{28}$ represents a $C_1$ to $C_8$ alkyl, a ($C_1$ to $C_8$) alkyl optionally substituted with $R^{30}$, a $C_3$ to $C_8$ cycloalkyl, a ($C_3$ to $C_8$) cycloalkyl optionally substituted with $R^{30}$, E1 to E7, E12 to E19, a $C_2$ to $C_8$ alkenyl, a ($C_2$ to $C_8$) alkenyl optionally substituted with $R^{30}$, a $C_3$ to $C_8$ alkynyl, a ($C_3$ to $C_8$) alkynyl optionally substituted with $R^{30}$, a phenyl, a phenyl substituted with $(Z)_{p1}$, D1 to D25 or D27 to D38, $R^{29}$ represents a hydrogen atom, a $C_1$ to $C_6$ alkyl, a ($C_1$ to $C_6$) alkyl optionally substituted with $R^{30}$, a $C_3$ to $C_6$ alkenyl, a $C_3$ to $C_6$ haloalkenyl, a $C_3$ to $C_6$ alkynyl, a $C_3$ to $C_6$ haloalkynyl, a phenyl or a phenyl substituted with $(Z)_{p1}$, or $R^{29}$ together with $R^{28}$ may form a $C_2$ to $C_5$ alkylene chain to form together with a nitrogen atom to which $R^{28}$ and $R^{29}$ are bonded, a 3- to 6-membered ring, and in this case, the alkylene chain may contain one oxygen atom, sulfur atom or nitrogen atom and may be optionally substituted with a halogen atom, a $C_1$ to $C_6$ alkyl group, a $C_1$ to $C_6$ alkoxy group, a —CHO group, a $C_1$ to $C_6$ alkylcarbonyl group, a $C_1$ to $C_6$ alkoxycarbonyl group, a phenyl group or a phenyl group substituted with $(Z)_{p1}$, $R^{30}$ represents a halogen atom, a cyano, a nitro, a $C_3$ to $C_8$ cycloalkyl, a $C_3$ to $C_8$ halocycloalkyl, E4, E5, E7, E8, E10, E12, E13, E15, E16, E18, a $C_2$ to $C_6$ alkenyl, a $C_2$ to $C_6$ haloalkenyl, a $C_5$ to $C_8$ cycloalkenyl, —OH, —O$R^{32}$, —OC(O)$R^{31}$, —OC(O)O$R^{32}$, —OC(O)N($R^{34}$)$R^{33}$, —OC(S)N($R^{34}$)$R^{33}$, —SH, —S(O)$_rR^{32}$, —S(=N$R^{33}$)$R^{32}$, —S($R^{32}$)=NC(O)$R^{31}$, —S(O)(=N$R^{33}$)$R^{32}$, —S(O)($R^{32}$)=NC(O)$R^{31}$, —SC(O)$R^{31}$, —SC(O)O$R^{32}$, —SC(O)N($R^{34}$)$R^{33}$, —SC(S)N($R^{34}$)$R^{33}$, —N($R^{34}$)$R^{33}$, —N($R^{34}$)C(O)$R^{31}$, —N($R^{34}$)C(O)O$R^{32}$, —N($R^{34}$)C(O)S$R^{32}$, —N($R^{34}$)C(O)N($R^{34}$)$R^{33}$, —N($R^{34}$)C(S)N($R^{34}$)$R^{33}$, —N($R^{34}$)S(O)$_2R^{32}$, —C(O)$R^{31}$, —C(O)OH, —C(O)O$R^{32}$, —C(O)S$R^{32}$, —C(O)N($R^{34}$)$R^{33}$, —C(O)C(O)O$R^{32}$, —P(O)(O$R^{20}$)$_2$, —P(S)(O$R^{20}$)$_2$, —P(phenyl)$_2$, —P(O)(phenyl)$_2$, a phenyl, a phenyl substituted with $(Z)_{p1}$ or D1 to D38, $R^{31}$ represents a hydrogen atom, a $C_1$ to $C_6$ alkyl, a $C_1$ to $C_6$ haloalkyl, a ($C_1$ to $C_4$) alkyl optionally substituted with $R^{35}$, a $C_3$ to $C_6$ cycloalkyl, a $C_3$ to $C_6$ halocycloalkyl, E4, E5, E12, E13, a $C_2$ to $C_8$ alkenyl, a $C_2$ to $C_8$ haloalkenyl, a $C_5$ to $C_{10}$ cycloalkenyl, a $C_5$ to $C_{10}$ halocycloalkenyl, a $C_2$ to $C_8$ alkynyl, a $C_2$ to $C_8$ haloalkynyl, a phenyl, a phenyl substituted with $(Z)_{p1}$ or D1 to D38, $R^{32}$ represents a $C_1$ to $C_6$ alkyl, a $C_1$ to $C_6$ haloalkyl, a ($C_1$ to $C_4$) alkyl optionally substituted with $R^{35}$, a ($C_1$ to $C_4$) haloalkyl optionally substituted with $R^{35}$, a $C_3$ to $C_6$ cycloalkyl, E4, E5, a $C_2$ to $C_8$ alkenyl, a $C_2$ to $C_8$ haloalkenyl, a $C_3$ to $C_8$ alkynyl, a $C_3$ to $C_8$ haloalkynyl, a phenyl, a phenyl substituted with $(Z)_{p1}$, D12, D32 or D34, $R^{33}$ represents a hydrogen atom, a cyano, a $C_1$ to $C_6$ alkyl, a $C_1$ to $C_6$ haloalkyl, a ($C_1$ to $C_4$) alkyl optionally substituted with $R^{35}$, a $C_3$ to $C_6$ cycloalkyl, E4, E5, E12, a $C_2$ to $C_8$ alkenyl, a $C_2$ to $C_8$ haloalkenyl, a $C_3$ to $C_8$ alkynyl, a phenyl, a phenyl substituted with $(Z)_{p1}$, D1 to D25 or D27 to D38, $R^{34}$ represents a hydrogen atom, a $C_1$ to $C_6$ alkyl, a $C_1$ to $C_6$ haloalkyl, a cyano($C_1$ to $C_6$) alkyl, a $C_3$ to $C_6$ cycloalkyl($C_1$ to $C_4$) alkyl, a $C_3$ to $C_8$ cycloalkyl, a $C_3$ to $C_6$ alkenyl or a $C_3$ to $C_6$ alkynyl, or $R^{34}$ together with $R^{33}$ may form a $C_2$ to $C_5$ alkylene chain to form together with a nitrogen atom to which $R^{33}$ and $R^{34}$ are bonded, a 3- to 6-membered ring, and in this case, the alkylene chain may contain one oxygen atom, sulfur atom or nitrogen atom and may be optionally substituted with a halogen atom, a $C_1$ to $C_4$ alkyl group, a $C_1$ to $C_4$ alkoxy group, a —CHO group, a $C_1$ to $C_4$ alkylcarbonyl group, a $C_1$ to $C_4$ alkoxycarbonyl group, a phenyl group or a phenyl group substituted with $(Z)_{p1}$, $R^{35}$ represents a cyano, a $C_3$ to $C_6$ cycloalkyl, a $C_3$ to $C_6$ halocycloalkyl, E4, E5, E12, E13, a $C_1$ to $C_4$ alkoxy, a $C_1$ to $C_4$ haloalkoxy, a phenoxy, a phenoxy substituted with $(Z)_{p1}$, a $C_1$ to $C_4$ alkylthio, a $C_1$ to $C_4$ haloalkylthio, a phenylthio, a phenylthio substituted with $(Z)_{p1}$, a $C_1$ to $C_4$ alkylsulfonyl, a $C_1$ to $C_4$ haloalkylsulfonyl, a phenylsulfonyl, a phenylsulfonyl substituted with $(Z)_{p1}$, —$N(R^{37})R^{36}$, a $C_1$ to $C_6$ alkylcarbonyl, a $C_1$ to $C_6$ haloalkylcarbonyl, a $C_1$ to $C_6$ alkoxycarbonyl, a $C_1$ to $C_6$ alkylaminocarbonyl, a di($C_1$ to $C_6$ alkyl) aminocarbonyl, a tri($C_1$ to $C_4$ alkyl) silyl, a phenyl, a phenyl substituted with $(Z)_{p1}$, a naphthyl or D1 to D38, $R^{36}$ represents a hydrogen atom, a $C_1$ to $C_6$ alkyl, a $C_1$ to $C_6$ alkylcarbonyl, a $C_1$ to $C_6$ haloalkylcarbonyl, a $C_1$ to $C_6$ alkoxycarbonyl, a phenylcarbonyl or a phenylcarbonyl substituted with $(Z)_{p1}$, $R^{37}$ represents a hydrogen atom or a $C_1$ to $C_6$ alkyl, m represents an integer of 0 to 5, n represents an integer of 0 to 4, p represents an integer of 0 to 4, p1 represents an integer of 1 to 5, q represents an integer of 0 to 8, r represents an integer of 0 to 2, and t represents an integer of 0 or 1), and a salt of the substituted isoxazoline compound or a salt of the substituted enone oxime compound.

[2] The substituted isoxazoline compound or the substituted enone oxime compound and the salt of the substituted isoxazoline compound or the salt of the substituted enone oxime compound according to [1], in which X represents a halogen atom, a cyano, a nitro, —$SF_5$, a $C_1$ to $C_6$ alkyl, a $C_1$ to $C_6$ haloalkyl, a hydroxy($C_1$ to $C_4$) haloalkyl, a $C_1$ to $C_4$ alkoxy($C_1$ to $C_4$) haloalkyl, —$OR^5$ or —$S(O)_rR^5$, where when m represents an integer of 2 or more, Xs may be the same as or different from each other, Y represents a halogen atom, a cyano, a nitro, a $C_1$ to $C_6$ alkyl, a $C_1$ to $C_6$ haloalkyl, a ($C_1$ to $C_4$) alkyl optionally substituted with $R^4$, a $C_2$ to $C_6$ alkenyl, a $C_2$ to $C_6$ alkynyl, —$OR^5$, —$S(O)_rR^5$, —$NH_2$, —$N(R^7)R^6$, —$C(S)NH_2$, D1 to D3, D7, D11 or D22, where when n represents an integer of 2 or more, Ys may be the same as or different from each other, $Z^a$ represents a halogen atom, a cyano, a nitro, a $C_1$ to $C_6$ alkyl, a $C_1$ to $C_6$ haloalkyl, a $C_1$ to $C_6$ alkoxy, a $C_1$ to $C_6$ haloalkoxy, a $C_1$ to $C_6$ alkylthio, a $C_1$ to $C_6$ haloalkylthio, a $C_1$ to $C_6$ alkylsulfinyl, a $C_1$ to $C_6$ haloalkylsulfinyl, a $C_1$ to $C_6$ alkylsulfonyl, a $C_1$ to $C_6$ haloalkylsulfonyl, —$NH_2$, —$C(O)N(R^2)R^1$ or —$C(S)N(R^2)R^1$, where when p represents an integer of 2 or more, $Z^a$s may be the same as or different from each other, $R^3$ represents a $C_1$ to $C_6$ haloalkyl or a $C_3$ to $C_8$ halocycloalkyl, $R^{3a}$ represents a halogen atom, a $C_1$ to $C_6$ alkyl or a $C_1$ to $C_6$ alkylthio, $R^{3b}$ represents a hydrogen atom or a halogen atom, $R^{3c}$ represents a hydrogen atom, a halogen atom or a $C_1$ to $C_6$ alkyl, $R^4$ represents —OH, a $C_1$ to $C_4$ alkoxy, a $C_1$ to $C_4$ haloalkoxy, a $C_1$ to $C_4$ alkylthio, a $C_1$ to $C_4$ haloalkylthio, a $C_1$ to $C_4$ alkylsulfinyl, a $C_1$ to $C_4$ haloalkylsulfinyl, a $C_1$ to $C_4$ alkylsulfonyl or a $C_1$ to $C_4$ haloalkylsulfonyl, $R^5$ represents a $C_1$ to $C_4$ alkyl, a $C_1$ to $C_4$ haloalkyl or a $C_1$ to $C_2$ haloalkoxy($C_1$ to $C_2$) haloalkyl, $R^6$ represents a $C_1$ to $C_4$ alkyl, —$C(O)R^8$, —$C(O)OR^9$, —$C(O)SR^9$, —$C(S)OR^9$, —$C(S)SR^9$ or —$S(O)_2R^9$, $R^7$ represents a hydrogen atom or a $C_1$ to $C_4$ alkyl, $R^8$ represents a hydrogen atom, a $C_1$ to $C_4$ alkyl, a $C_1$ to $C_4$ haloalkyl or a $C_3$ to $C_6$ cycloalkyl, and $R^9$ represents a $C_1$ to $C_4$ alkyl or a $C_1$ to $C_4$ haloalkyl.

[3] The substituted isoxazoline compound or the substituted enone oxime compound and the salt of the substituted isoxazoline compound or the salt of the substituted enone oxime compound according to [2], in which $A^1$ represents a carbon atom or a nitrogen atom, $A^2$, $A^3$ and $A^4$ individually represent a carbon atom, $G^1$ represents a benzene ring, $G^2$ represents a structure represented by $G^2$-1, $G^2$-2, $G^2$-4, $G^2$-6, $G^2$-7, $G^2$-9 or $G^2$-10, L represents —$C(R^{4a})(R^{4b})$—, X represents a halogen atom, a cyano, a nitro, —$SF_5$, a $C_1$ to $C_4$ alkyl, a $C_1$ to $C_4$ haloalkyl, a $C_1$ to $C_4$ alkoxy, a $C_1$ to $C_4$ haloalkoxy, a $C_1$ to $C_4$ alkylthio or a $C_1$ to $C_4$ haloalkylthio, where when m represents 2 or 3, Xs may be the same as or different from each other, Y represents a halogen atom, a cyano, a nitro, a $C_1$ to $C_4$ alkyl, a $C_1$ to $C_4$ haloalkyl, a $C_1$ to $C_2$ alkoxy($C_1$ to $C_2$) alkyl, a $C_2$ to $C_4$ alkynyl, a $C_1$ to $C_4$ alkoxy, a $C_1$ to $C_4$ haloalkoxy, a $C_1$ to $C_4$ alkylthio, a $C_1$ to $C_4$ haloalkylthio, —$N(R^7)R^6$ or —$C(S)NH_2$, $Z^a$ represents a halogen atom, a cyano, a nitro, a $C_1$ to $C_4$ alkyl, —$NH_2$, —$C(O)N(R^2)R^1$ or —$C(S)N(R^2)R^1$, where when p represents an integer of 2 or more, $Z^a$s may be the same as or different from each other, $R^1$ represents a hydrogen atom, a $C_1$ to $C_6$ alkyl, a ($C_1$ to $C_6$) alkyl optionally substituted with $R^{13}$, a $C_3$ to $C_6$ cycloalkyl, a ($C_3$ to $C_6$) cycloalkyl optionally substituted with $R^{13}$, E4, E5, E12, a $C_3$ to $C_6$ alkenyl, a $C_3$ to $C_6$ haloalkenyl, a $C_3$ to $C_6$ alkynyl, a $C_1$ to $C_6$ alkylcarbonyl, —CH=$NOR^{15}$, —$C(O)OR^{15}$, —$C(O)N(R^{17})R^{16}$, —$C(S)OR^{15}$, —$C(S)N(R^{17})R^{16}$, —$C(OR^{15})$=$NOR^{15}$, —$C(NH_2)$=NCN, —$C(NH_2)$=$NOR^{15}$, —$C(NH_2)$=$NNO_2$, —$N(R^{17})R^{16}$, a phenyl substituted with $(Z)_{p1}$, D1, D5 to D8, D10, D17 or D32 to D35, $R^2$ represents a hydrogen atom, a $C_1$ to $C_6$ alkyl, a ($C_1$ to $C_4$) alkyl substituted with $R^{13a}$, a $C_3$ to $C_6$ cycloalkyl, a $C_3$ to $C_6$ alkenyl, a $C_3$ to $C_6$ alkynyl, —$C(O)R^{14a}$, —$C(O)OR^{15a}$, —$C(O)C(O)OR^{15a}$ or a $C_1$ to $C_6$ haloalkylthio, or $R^2$ together with $R^1$ may form =$C(R^{2b})R^{1b}$, $R^{1a}$ represents —$C(O)R^{14}$, —$C(O)OR^{15}$, —$C(O)SR^{15}$, —$C(O)N(R^{17})R^{16}$, —$C(O)N(R^{17})N(R^{17})R^{16}$ or —$C(S)R^{14}$, $R^{2a}$ represents a hydrogen atom, a $C_1$ to $C_6$ alkyl, a ($C_1$ to $C_4$) alkyl substituted with $R^{13a}$, a $C_3$ to $C_6$ alkenyl or a $C_3$ to $C_6$ alkynyl, $R^{1b}$ represents a $C_1$ to $C_6$ alkyl, a $C_1$ to $C_6$ alkoxy, a $C_1$ to $C_6$ haloalkoxy, a $C_1$ to $C_6$ alkylthio or —$N(R^{17b})R^{16b}$, $R^{2b}$ represents a $C_1$ to $C_6$ alkylthio or —$N(R^{17c})R^{16c}$, or $R^{2b}$ together with $R^{1b}$ may form —$N(R^{17c})CH$=CHS— to form together with a carbon atom to which $R^{1b}$ and $R^{2b}$ are bonded, a 5-membered ring, $R^3$ represents a $C_1$ to $C_4$ haloalkyl, $R^{3a}$ represents a halogen atom or a $C_1$ to $C_2$ alkyl, $R^{3b}$ represents a hydrogen atom, $R^{3c}$ represents a hydrogen atom, a halogen atom or a $C_1$ to $C_2$ alkyl, Z represents a halogen atom, a cyano, a nitro, a $C_1$ to $C_4$ alkyl, a $C_1$ to $C_4$ haloalkyl, a $C_1$ to $C_4$ alkoxy, a $C_1$ to $C_4$ alkylsulfonyloxy or a $C_1$ to $C_4$ alkylthio, where when p and p1 individually represent an integer of 2 or more, Zs may be the same as or different from each other, $R^{4a}$ represents a hydrogen atom, a cyano, a $C_1$ to $C_2$ alkyl, a $C_1$ to $C_2$ haloalkyl, a $C_2$ to $C_4$ alkynyl or —$C(S)NH_2$, $R^{4b}$ represents a hydrogen atom, $R^6$ represents a hydrogen atom, a $C_1$ to $C_4$ alkyl, —CHO, a $C_1$ to $C_4$ alkylcarbonyl, a $C_1$ to $C_4$ haloalkylcarbonyl, a $C_1$ to $C_4$ alkoxycarbonyl, a $C_1$ to $C_4$ alkylthiocarbonyl, a $C_1$ to $C_4$ alkoxythiocarbonyl or a $C_1$ to $C_4$ alkyldithiocarbonyl, $R^7$ represents a hydrogen atom or a $C_1$ to $C_4$ alkyl, $R^{12}$ represents a $C_1$ to $C_4$ alkyl, $R^{13}$ represents a halogen atom, a cyano, a $C_3$ to $C_4$ cycloalkyl, E4, E7, —$OR^{24}$, —$N(R^{25})R^{24}$, —$S(O)_r R^{26}$, a $C_1$ to $C_4$ alkylcarbonyl, —$C(R^{27})$=$NOR^{28}$, —$C(O)N(R^{29})R^{28}$, —$C(S)NH_2$, a phenyl, a phenyl substituted with $(Z)_{p1}$, D1, D5, D7, D8, D10, D13, D16, D17, D22, D32 or D34, $R^{13a}$ represents a cyano, a $C_3$ to $C_4$ cycloalkyl, —$OR^{24}$, —$S(O)_r R^{26}$, a $C_1$ to $C_4$ alkoxycarbonyl or D32, $R^{14}$ represents a $C_1$ to $C_6$ alkyl, a ($C_1$ to $C_6$) alkyl optionally substituted with $R^{30}$, a $C_3$ to $C_6$ cycloalkyl, E4, E5, E10, a $C_2$ to $C_6$ alkenyl, a $C_2$ to $C_6$ haloalkenyl, a $C_2$ to $C_6$ alkynyl, a phenyl substituted with $(Z)_{p1}$ or D32, $R^{14a}$ represents a $C_1$ to $C_6$ alkyl, a $C_1$ to $C_6$ haloalkyl, a $C_1$ to $C_4$ alkoxy($C_1$ to $C_4$) alkyl, a $C_1$ to $C_4$ alkylthio($C_1$ to $C_4$) alkyl, a $C_1$ to $C_4$ alkylsulfinyl($C_1$ to $C_4$) alkyl, a $C_1$ to $C_4$ alkylsulfonyl($C_1$ to $C_4$) alkyl, a $C_3$ to $C_6$ cycloalkyl, a $C_2$ to $C_6$ alkenyl, a $C_2$ to $C_6$ alkynyl, a phenyl, a phenyl substituted with $(Z)_{p1}$ or D32, $R^{15}$ represents a $C_1$ to $C_6$ alkyl, a $C_1$ to $C_6$ haloalkyl, a $C_3$ to $C_4$ cycloalkyl($C_1$ to $C_4$) alkyl, a $C_1$ to $C_4$ alkoxycarbonyl($C_1$ to $C_4$) alkyl or a $C_3$ to $C_6$ alkenyl, $R^{15a}$ represents a $C_1$ to $C_6$ alkyl, a $C_1$ to $C_6$ haloalkyl, a $C_1$ to $C_4$ alkoxy($C_1$ to $C_4$) alkyl, a $C_3$ to $C_6$ alkenyl, a $C_3$ to $C_6$ alkynyl or a phenyl, $R^{16}$ represents a hydrogen atom, a $C_1$ to $C_6$ alkyl, a ($C_1$ to $C_6$) alkyl optionally substituted with $R^{30}$, a $C_3$ to $C_6$ cycloalkyl, a $C_3$ to $C_6$ alkenyl, a $C_3$ to $C_6$ alkynyl, a $C_1$ to $C_6$ alkylcarbonyl, a $C_1$ to $C_6$ haloalkylcarbonyl, a $C_1$ to $C_6$ alkoxycarbonyl, a phenyl, a phenyl substituted with $(Z)_{p1}$, D32 or D34, $R^{17}$ represents a hydrogen atom, a $C_1$ to $C_6$ alkyl, a $C_3$ to $C_6$ alkenyl or a $C_3$ to $C_6$ alkynyl, or $R^{17}$ together with $R^{16}$ may form a $C_3$ to $C_5$ alkylene chain to form together with a nitrogen atom to which $R^{16}$ and $R^{17}$ are bonded, a 4- to 6-membered ring, and in this case, the alkylene chain may contain one sulfur atom, $R^{16b}$ represents a cyano, a nitro or a $C_1$ to $C_6$ alkoxy, $R^{17b}$ represents a hydrogen atom or a $C_1$ to $C_6$ alkyl, $R^{16c}$ represents a hydrogen atom, a $C_1$ to $C_6$ alkyl, a $C_1$ to $C_6$ haloalkyl or a $C_1$ to $C_6$ alkoxy, $R^{17c}$ represents a hydrogen atom or a $C_1$ to $C_6$ alkyl, $R^{21}$ represents a $C_1$ to $C_2$ alkyl, $R^{24}$ represents a hydrogen atom, a $C_1$ to $C_4$ alkyl, a $C_1$ to $C_4$ haloalkyl, —$C(O)R^{31}$ or —$C(O)OR^{32}$, $R^{25}$ represents a hydrogen atom or a $C_1$ to $C_4$ haloalkyl, $R^{26}$ represents a $C_1$ to $C_4$ alkyl, $R^{27}$ represents a hydrogen atom or a $C_1$ to $C_4$ alkyl, $R^{28}$ represents a $C_1$ to $C_4$ alkyl, a $C_1$ to $C_4$ haloalkyl, a hydroxy($C_1$ to $C_4$) haloalkyl, a $C_3$ to $C_4$ cycloalkyl, a $C_3$ to $C_4$ alkenyl or a $C_3$ to $C_4$ alkynyl, $R^{29}$ represents a hydrogen atom or a $C_1$ to $C_4$ alkyl, $R^{30}$ represents a halogen atom, a $C_3$ to $C_6$ cycloalkyl, a $C_1$ to $C_4$ alkoxy, a $C_1$ to $C_4$ haloalkoxy, —$S(O)_r R^{32}$, —$S(R^{32})$=$NC(O)R^{31}$, —$S(O)(R^{32})$=NH, —$N(R^{34})R^{33}$, —$N(R^{34})C(O)R^{31}$, —$N(R^{34})C(O)OR^{32}$, —$C(O)N(R^{34})R^{33}$, a phenyl substituted with $(Z)_{p1}$ or D32, $R^{31}$ represents a $C_1$ to $C_4$ alkyl, a $C_1$ to $C_4$ haloalkyl or a $C_3$ to $C_6$ cycloalkyl, $R^{32}$ represents a $C_1$ to $C_4$ alkyl, a $C_1$ to $C_4$ haloalkyl or a cyano($C_1$ to $C_2$) alkyl, $R^{33}$ represents a hydrogen atom, a $C_1$ to $C_4$ alkyl or a cyano($C_1$ to $C_2$) alkyl, $R^{34}$ represents a hydrogen atom or a cyano($C_1$ to $C_2$) alkyl, m represents an integer of 1 to 3, n represents an integer of 0 or 1, p represents an integer of 0 to 2, p1 represents an integer of 1 to 3, q represents an integer of 0 or 1, and t represents 0.

[4] The substituted isoxazoline compound or the substituted enone oxime compound and the salt of the substituted isoxazoline compound or the salt of the substituted enone oxime compound according to [3], in which $G^2$ represents a structure represented by $G^2$-1, $G^2$-2, $G^2$-7 or $G^2$-10, X represents a halogen atom, a cyano, —$SF_5$, a $C_1$ to $C_2$ haloalkyl, a $C_1$ to $C_2$ haloalkoxy or a $C_1$ to $C_2$ haloalkylthio, where when m represents 2 or 3, Xs may be the same as or different from each other, Y represents a halogen atom, a cyano, a nitro, a $C_1$ to $C_2$ alkyl, a $C_1$ to $C_2$ haloalkyl, a $C_1$ to $C_2$ alkoxymethyl, a $C_2$ to $C_3$ alkynyl, a $C_1$ to $C_2$ haloalkoxy, a $C_1$ to $C_2$ haloalkylthio, —$N(R^7)R^6$ or —$C(S)NH_2$, $Z^a$ represents a halogen atom, a nitro, a methyl or —$NH_2$, $R^1$ represents a $C_1$ to $C_4$ alkyl, a ($C_1$ to $C_4$) alkyl optionally substituted with $R^{13}$, a $C_3$ to $C_4$ cycloalkyl, a cyclopropyl substituted with $R^{13}$, E4, E5, a $C_3$ to $C_4$ alkenyl, a $C_3$ to $C_4$ haloalkenyl, —CH=$NOR^{15}$, —$C(O)OR^{15}$, —$C(O)NHR^{16}$, —$C(S)OR^{15}$, —$N(R^{17})R^{16}$, D34 or D35, $R^2$ represents a hydrogen atom, a $C_1$ to $C_4$ alkyl, a ($C_1$ to $C_2$) alkyl substituted with $R^{13a}$, a $C_3$ to $C_4$ alkynyl, —$C(O)R^{14a}$, —$C(O)OR^{15a}$ or a $C_1$ to $C_4$ haloalkylthio, or $R^2$ together with $R^1$ may form =$C(R^{2b})R^{1b}$, $R^{1a}$ represents —$C(O)R^{14}$, —$C(O)N(R^{17})R^{16}$ or —$C(S)R^{14}$, $R^{2a}$ represents a hydrogen atom, a $C_1$ to $C_4$ alkyl, a ($C_1$ to $C_2$) alkyl substituted with $R^{13a}$, a $C_3$ to $C_4$ alkenyl or a $C_3$ to $C_4$ alkynyl, $R^{1b}$ represents a $C_1$ to $C_4$ alkoxy or a $C_1$ to $C_4$ alkylthio, $R^{2b}$ represents —$NHR^{16c}$, $R^3$ represents a $C_1$ to $C_2$ haloalkyl, $R^{3a}$ represents a halogen atom or a methyl, $R^{3c}$ represents a hydrogen atom, Z represents a halogen atom, a cyano or a nitro, $R^{4a}$ represents a hydrogen atom, a cyano, a methyl or —$C(S)NH_2$, $R^6$ represents a hydrogen atom, a $C_1$ to $C_2$ alkyl or a $C_1$ to $C_2$ alkylcarbonyl, $R^7$ represents a hydrogen atom or a $C_1$ to $C_2$ alkyl, $R^{13}$ represents a halogen atom, a cyano, a $C_3$ to $C_4$ cycloalkyl, E4, E7, —$OR^{24}$, —$NHR^{24}$, —$C(R^{27})$=$NOR^{28}$, —$C(O)N(R^{29})R^{28}$, a phenyl, a phenyl substituted with $(Z)_{p1}$, D8, D10, D13, D16, D22, D32 or D34, $R^{12}$ represents a methyl, $R^{13a}$ represents a cyano, a $C_3$ to $C_4$ cycloalkyl, —$OR^{24}$ or a $C_1$ to $C_4$ alkylthio, $R^{14}$ represents a $C_1$ to $C_4$ alkyl, a ($C_1$ to $C_4$) alkyl optionally substituted with $R^{30}$, a $C_3$ to $C_4$ cycloalkyl, E4, E5, a $C_2$ to $C_4$ alkenyl, a $C_2$ to $C_4$ alkynyl or a phenyl substituted with $(Z)_{p1}$, $R^{14a}$ represents a $C_1$ to $C_4$ alkyl, a $C_1$ to $C_2$ alkoxy($C_1$ to $C_2$) alkyl, a $C_3$ to $C_4$ cycloalkyl or a $C_2$ to $C_4$ alkenyl, $R^{15}$ represents a $C_1$ to $C_4$ alkyl, $R^{15a}$ represents a $C_1$ to $C_4$ alkyl, a $C_1$ to $C_4$ haloalkyl or a $C_1$ to $C_2$ alkoxy($C_1$ to $C_2$) alkyl, $R^{16}$ represents a hydrogen atom, a $C_1$ to $C_4$ alkyl, a $C_1$ to $C_4$ haloalkyl, a $C_3$ to $C_4$ cycloalkyl, a $C_3$ to $C_4$ alkynyl, a phenyl, D32 or D34, $R^{17}$ represents a hydrogen atom, a $C_1$ to $C_4$ alkyl, a $C_3$ to $C_4$ alkenyl or a $C_3$ to $C_4$ alkynyl, $R^{16c}$ represents a hydrogen atom or a $C_1$ to $C_4$ alkyl, $R^{21}$ represents a methyl, $R^{24}$ represents a $C_1$ to $C_4$ alkyl, a $C_1$ to $C_4$ haloalkyl, a $C_1$ to $C_4$ alkylcarbonyl or a $C_1$ to $C_4$ alkoxycarbonyl, $R^{27}$ represents a hydrogen atom or a $C_1$ to $C_2$ alkyl, $R^{28}$ represents a $C_1$ to $C_4$ alkyl, a $C_1$ to $C_4$ haloalkyl, a $C_3$ to $C_4$ alkenyl or a $C_3$ to $C_4$ alkynyl, $R^{29}$ represents a hydrogen atom or a $C_1$ to $C_2$ alkyl,
$R^{30}$ represents a halogen atom, a $C_3$ to $C_4$ cycloalkyl, —S(O)$_r R^{32}$, —N(R$^{34}$)R$^{33}$ or —C(O)N(R$^{34}$)R$^{33}$,
$R^{32}$ represents a $C_1$ to $C_4$ alkyl or a $C_1$ to $C_4$ haloalkyl,
$R^{33}$ represents a $C_1$ to $C_4$ alkyl or a cyano($C_1$ to $C_2$) alkyl, and
$R^{34}$ represents a hydrogen atom.

[5] The substituted isoxazoline compound or the substituted enone oxime compound and the salt of the substituted isoxazoline compound or the salt of the substituted enone oxime compound according to [4], in which
$A^1$ represents a carbon atom,
$G^2$ represents a structure represented by $G^2$-1,
W represents an oxygen atom,
X represents a halogen atom or a trifluoromethyl, where when m represents 2 or 3, Xs may be the same as or different from each other,
Y represents a halogen atom, a methyl, an ethyl or a trifluoromethyl,
$R^1$ represents a ($C_1$ to $C_2$) alkyl substituted with $R^{13}$, E4, —CH=NOR$^{15}$, —C(O)OR$^{15}$, —C(O)NH$_2$, —N(R$^{17}$)R$^{16}$, D34 or D35,
$R^2$ represents a hydrogen atom, a ($C_1$ to $C_2$) alkyl substituted with $R^{13a}$, a $C_1$ to $C_3$ alkylcarbonyl, a cyclopropylcarbonyl or a $C_1$ to $C_3$ alkoxycarbonyl,
$R^3$ represents a trifluoromethyl or a chlorodifluoromethyl,
Z represents a halogen atom or a cyano,
$R^{13}$ represents a halogen atom, a $C_1$ to $C_3$ alkoxy, a $C_1$ to $C_2$ haloalkoxy, —C(O)NHR$^{28}$, D10 or D32,
$R^{13a}$ represents —OR$^{24}$,
$R^{15}$ represents a $C_1$ to $C_2$ alkyl,
$R^{16}$ represents a phenyl or D34,
$R^{17}$ represents a $C_1$ to $C_2$ alkyl,
$R^{24}$ represents a $C_1$ to $C_2$ alkyl or a $C_1$ to $C_2$ alkylcarbonyl,
$R^{28}$ represents a $C_1$ to $C_2$ haloalkyl,
p represents an integer of 0 or 1, and
q represents 0.

[6] The substituted isoxazoline compound or the substituted enone oxime compound and the salt of the substituted isoxazoline compound or the salt of the substituted enone oxime compound according to [4], in which
$A^1$ represents a carbon atom,
$G^2$ represents a structure represented by $G^2$-2,
X represents a halogen atom or a trifluoromethyl, where when m represents 2 or 3, Xs may be the same as or different from each other,
Y represents a halogen atom, a nitro or a methyl,
$R^{1a}$ represents —C(O)R$^{14}$ or —C(O)NHR$^{16}$,
$R^{2a}$ represents a hydrogen atom, a $C_1$ to $C_2$ alkyl, a ($C_1$ to $C_2$) alkyl substituted with $R^{13a}$ or a propargyl,
$R^3$ represents a trifluoromethyl or a chlorodifluoromethyl,
$R^{4a}$ represents a hydrogen atom, a cyano or a methyl,
$R^{13a}$ represents a cyano, a cyclopropyl or a $C_1$ to $C_2$ alkoxy,
$R^{14}$ represents a $C_1$ to $C_4$ alkyl, a $C_1$ to $C_4$ haloalkyl, a ($C_1$ to $C_2$) alkyl substituted with $R^{30}$, a $C_3$ to $C_4$ cycloalkyl or E4,
$R^{16}$ represents a $C_1$ to $C_2$ alkyl, a cyclopropyl or a propargyl,
$R^{30}$ represents a cyclopropyl, a $C_1$ to $C_2$ alkylthio, a $C_1$ to $C_2$ alkylsulfinyl or a $C_1$ to $C_2$ alkylsulfonyl, and
q represents 0.

[7] The substituted isoxazoline compound or the substituted enone oxime compound and the salt of the substituted isoxazoline compound or the salt of the substituted enone oxime compound according to [4], in which
$A^1$ represents a carbon atom,
$G^2$ represents a structure represented by $G^2$-7 or $G^2$-10, X represents a halogen atom or a trifluoromethyl, where when m represents 2 or 3, Xs may be the same as or different from each other,
Y represents a cyano or a nitro,
$R^3$ represents a trifluoromethyl or a chlorodifluoromethyl, and
p represents 0.

[8] A substituted isoxazoline compound or a substituted enone oxime compound represented by General Formula (3) or General Formula (4):

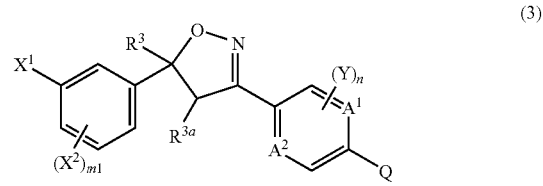

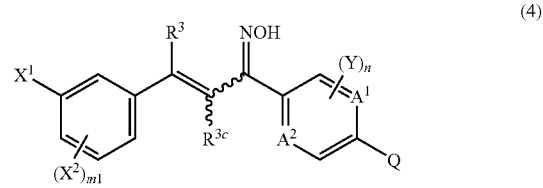

(where $A^1$ and $A^2$ independently represent a carbon atom or a nitrogen atom,
Q represents a halogen atom, a cyano, a nitro, —CH(R$^{4a}$)—R$^a$, —OH, a $C_1$ to $C_4$ alkoxy, a $C_1$ to $C_4$ haloalkoxy, a halosulfonyloxy, a $C_1$ to $C_4$ alkylsulfonyloxy, a $C_1$ to $C_4$ haloalkylsulfonyloxy, a phenylsulfonyloxy, a phenylsulfonyloxy substituted with $(Z)_{p1}$, a $C_1$ to $C_4$ alkylthio, a $C_1$ to $C_4$ alkylsulfinyl, a $C_1$ to $C_4$ alkylsulfonyl, a $C_1$ to $C_4$ haloalkylthio, a $C_1$ to $C_4$ haloalkylsulfinyl, a $C_1$ to $C_4$ haloalkylsulfonyl, —NH$_2$ or —C(O)R$^b$,
$X^1$ represents a halogen atom, —SF$_5$, a $C_1$ to $C_4$ haloalkyl, a $C_1$ to $C_4$ haloalkoxy or a $C_1$ to $C_4$ haloalkylthio,
$X^2$ represents a halogen atom, a cyano, a nitro, a $C_1$ to $C_4$ alkyl, a $C_1$ to $C_4$ haloalkyl, a $C_1$ to $C_4$ alkoxy, a $C_1$ to $C_4$ haloalkoxy, a $C_1$ to $C_4$ alkylthio or a $C_1$ to $C_4$ haloalkylthio, where when m1 represents 2, $X^2$s may be the same as or different from each other,
Y represents a halogen atom, a cyano, a nitro, a $C_1$ to $C_4$ alkyl, a $C_1$ to $C_4$ haloalkyl, a $C_1$ to $C_2$ alkoxy($C_1$ to $C_2$) alkyl, a $C_2$ to $C_4$ alkynyl, a $C_1$ to $C_4$ alkoxy, a $C_1$ to $C_4$ haloalkoxy, a $C_1$ to $C_4$ alkylthio, a $C_1$ to $C_4$ haloalkylthio, —N(R$^7$)R$^6$ or —C(S)NH$_2$,
Z represents a halogen atom or a methyl, where when p1 represents an integer of 2 or more, Zs may be the same as or different from each other,
$R^a$ represents a hydrogen atom, a halogen atom, —OH, a $C_1$ to $C_2$ alkylcarbonyloxy, a $C_1$ to $C_2$ alkylsulfonyloxy, a $C_1$ to $C_2$ haloalkylsulfonyloxy or —NH$_2$,
$R^b$ represents a hydrogen atom, a halogen atom, a $C_1$ to $C_2$ alkyl, a $C_1$ to $C_2$ haloalkyl, —OH, a $C_1$ to $C_4$ alkoxy, a 1-pyrazolyl, a 1-imidazolyl or a 1-triazolyl,
$R^3$ represents a $C_1$ to $C_4$ haloalkyl,
$R^{3a}$ represents a halogen atom or a $C_1$ to $C_2$ alkyl,
$R^{3c}$ represents a hydrogen atom, a halogen atom or a $C_1$ to $C_2$ alkyl,
$R^{4a}$ represents a hydrogen atom, a $C_1$ to $C_2$ alkyl or a $C_1$ to $C_2$ haloalkyl,
$R^6$ represents a hydrogen atom, a $C_1$ to $C_4$ alkyl, —CHO, a $C_1$ to $C_4$ alkylcarbonyl, a $C_1$ to a $C_4$ haloalkylcarbonyl, a $C_1$ to $C_4$ alkoxycarbonyl, a $C_1$ to $C_4$ alkylthiocarbonyl, a $C_1$ to $C_4$ alkoxythiocarbonyl or a $C_1$ to $C_4$ alkyldithiocarbonyl, $R^7$ represents a hydrogen atom or a $C_1$ to $C_4$ alkyl, m1 represents an integer of 0 to 2, n represents an integer of 0 or 1, and p1 represents an integer of 1 to 5), and a salt of the substituted isoxazoline compound or a salt of the substituted enone oxime compound.

[9] The substituted isoxazoline compound or the substituted enone oxime compound and the salt of the substituted isoxazoline compound or the salt of the substituted enone oxime compound according to [8], in which Q represents a halogen atom, a cyano, a nitro, a $C_1$ to $C_2$ alkyl, a $C_1$ to $C_2$ haloalkyl, a hydroxy($C_1$ to $C_2$) alkyl, —OH, a $C_1$ to $C_2$ alkoxy, a $C_1$ to $C_2$ haloalkoxy, a $C_1$ to $C_2$ alkylsulfonyloxy, a $C_1$ to $C_2$ haloalkylsulfonyloxy, a $C_1$ to $C_2$ alkylthio, a $C_1$ to $C_2$ alkylsulfinyl, a $C_1$ to $C_2$ alkylsulfonyl, —NH$_2$ or —C(O)R$^b$, $X^1$ represents a halogen atom, —SF$_5$, a $C_1$ to $C_2$ haloalkyl, a $C_1$ to $C_2$ haloalkoxy or a $C_1$ to $C_2$ haloalkylthio, $X^2$ represents a halogen atom, a cyano, a $C_1$ to $C_2$ haloalkyl, a $C_1$ to $C_2$ haloalkoxy or a $C_1$ to $C_2$ haloalkylthio, where when m1 represents 2, $X^2$s may be the same as or different from each other, Y represents a halogen atom, a cyano, a nitro, a $C_1$ to $C_2$ alkyl, a $C_1$ to $C_2$ haloalkyl, a $C_1$ to $C_2$ alkoxymethyl, a $C_2$ to $C_3$ alkynyl, a $C_1$ to $C_2$ haloalkoxy, a $C_1$ to $C_2$ haloalkylthio, —N(R$^7$)R$^6$ or —C(S)NH$_2$, $R^b$ represents a hydrogen atom, a halogen atom, a methyl, —OH or a $C_1$ to $C_2$ alkoxy, $R^3$ represents a $C_1$ to $C_2$ haloalkyl, $R^{3a}$ represents a halogen atom or a methyl, $R^6$ represents a hydrogen atom, a $C_1$ to $C_2$ alkyl or a $C_1$ to $C_2$ alkylcarbonyl, and $R^7$ represents a hydrogen atom or a $C_1$ to $C_2$ alkyl.

[10] The substituted isoxazoline compound or the substituted enone oxime compound and the salt of the substituted isoxazoline compound or the salt of the substituted enone oxime compound according to [9], in which $A^1$ represents a carbon atom or a nitrogen atom, $A^2$ represents a carbon atom, Q represents a halogen atom, a cyano, a nitro, a methylthio, a methylsulfinyl or a methylsulfonyl, $X^1$ and $X^2$ independently represent a halogen atom or a trifluoromethyl, where when m1 represents 2, $X^2$s may be the same as or different from each other, Y represents a halogen atom, a cyano, a nitro, a methyl, an ethyl or a trifluoromethyl, $R^3$ represents a trifluoromethyl or a chlorodifluoromethyl, and $R^{3a}$ represents a halogen atom or a methyl.

[11] A pest control agent containing one type or two or more types selected from the substituted isoxazoline compound or the substituted enone oxime compound and the salt of the substituted isoxazoline compound or the salt of the substituted enone oxime compound as described in [1] to [10], as active ingredient(s).

[12] An agricultural chemical containing one type or two or more types selected from the substituted isoxazoline compound or the substituted enone oxime compound and the salt of the substituted isoxazoline compound or the salt of the substituted enone oxime compound as described in [1] to [10], as active ingredient(s).

[13] A control agent against internal or external parasites of mammals or birds containing one type or two or more types selected from the substituted isoxazoline compound or the substituted enone oxime compound and the salt of the substituted isoxazoline compound or the salt of the substituted enone oxime compound as described in [1] to [10], as active ingredient(s).

[14] An insecticide or a miticide containing one type or two or more types selected from the substituted isoxazoline compound or the substituted enone oxime compound and the salt of the substituted isoxazoline compound or the salt of the substituted enone oxime compound as described in [1] to [10], as active ingredient(s).

Effects of the Invention

The compound of the present invention has excellent insecticidal and miticidal activity with respect to a number of agricultural insect pests, spider mites and internal or external parasites of mammals or birds, and also exerts satisfactory control effect on insect pests which have acquired resistance to related art pesticides. Furthermore, the compound has substantially no adverse effect on mammals, fish and beneficial insects, and has a low residual property to have a light burden on the environment.

Accordingly, the present invention can provide a useful novel pest control agent.

BEST MODES FOR CARRYING OUT THE INVENTION

In the compounds included in the present invention, although geometric isomers of an E-form and a Z-form may exist depending on a substituent type, the present invention includes the E-form, the Z-form or a mixture containing the E-form and the Z-form at any ratio. Furthermore, although the compounds included in the present invention include optically active substances due to the presence of one or more asymmetric carbon atom(s), the present invention includes all of the optically active compounds or racemic bodies.

Among the compounds included in the present invention, compounds capable of being converted into acid addition salts by a common method may be converted into, for example, salts of hydrohalic acids such as hydrofluoric acid, hydrochloric acid, hydrobromic acid and hydriodic acid; salts of inorganic acids such as nitric acid, sulfuric acid, phosphoric acid, chloric acid and perchloric acid; salts of sulfonic acids such as methanesulfonic acid, ethanesulfonic acid, trifluoromethanesulfonic acid, benzenesulfonic acid and p-toluenesulfonic acid; salts of carboxylic acids such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid and citric acid; or salts of amino acids such as glutamic acid and aspartic acid.

In addition, among the compounds included in the present invention, compounds capable of being converted into metal salts by a common method may be converted into, for example, salts of alkali metals such as lithium, sodium and potassium; salts of alkaline earth metals such as calcium, barium and magnesium; or salts of aluminum.

Next, specific examples of each substituent shown in the present specification are shown below. Here, n-, s- and tert- mean normal, iso, secondary and tertiary, respectively, and Ph means phenyl.

Examples of halogen atoms in the compound of the present invention include a fluorine atom, a chlorine atom, a bromine atom and an iodine atom. Here, the expression "halo" in the present specification also represents these halogen atoms.

The expression "$C_a$ to $C_b$ alkyl" in the present specification represents a straight chain or branched chain hydrocarbon group having a to b pieces of carbon atoms. Specific examples of the "$C_a$ to $C_b$ alkyl" include a methyl group, an ethyl group, an n-propyl group, an i-propyl group, an n-butyl group, an i-butyl group, an s-butyl group, a tert-butyl group, an n-pentyl group, a 1,1-dimethylpropyl group and an n-hexyl group, and each of the alkyl groups is selected from within the range of the specified number of carbon atoms.

The expression "$C_a$ to $C_b$ haloalkyl" in the present specification represents a straight chain or branched chain hydrocarbon group having a to b pieces of carbon atoms in which a hydrogen atom bonded to a carbon atom is optionally substituted with a halogen atom. In this case, when hydrogen atoms are substituted with two or more halogen atoms, these halogen atoms may be the same as or different from each other. Specific examples of the "$C_a$ to $C_b$ haloalkyl" include a fluoromethyl group, a chloromethyl group, a bromomethyl group, an iodomethyl group, a difluoromethyl group, a dichloromethyl group, a trifluoromethyl group, a chlorodifluoromethyl group, a trichloromethyl group, a bromodifluoromethyl group, a 2-fluoroethyl group, a 2-chloroethyl group, a 2-bromoethyl group, a 2,2-difluoroethyl group, a 2,2,2-trifluoroethyl group, a 2-chloro-2,2-difluoroethyl group, a 2,2,2-trichloroethyl group, a 1,1,2,2-tetrafluoroethyl group, a 2-chloro-1,1,2-trifluoroethyl group, a pentafluoroethyl group, a 3,3,3-trifluoropropyl group, a 2,2,3,3,3-pentafluoropropyl group, a 1,1,2,3,3,3-hexafluoropropyl group, a heptafluoropropyl group, a 2,2,2-trifluoro-1-(trifluoromethyl)ethyl group, a 1,2,2,2-tetrafluoro-1-(trifluoromethyl)ethyl group, a 2,2,3,3,4,4,4-heptafluorobutyl group and a nonafluorobutyl group. Each of the haloalkyl groups is selected from within the range of the specified number of carbon atoms.

The expression "$C_a$ to $C_b$ cycloalkyl" in the present specification represents a cyclic hydrocarbon group having a to b pieces of carbon atoms, and the "$C_a$ to $C_b$ cycloalkyl" can form a monocyclic or composite ring structure having a 3-membered ring to a 6-membered ring. Furthermore, each ring may be optionally substituted with an alkyl group within the range of the specified number of carbon atoms. Specific examples of the "$C_a$ to $C_b$ cycloalkyl" include a cyclopropyl group, a 1-methylcyclopropyl group, a 2-methylcyclopropyl group, a 2,2-dimethylcyclopropyl group, a cyclobutyl group, a cyclopentyl group and a cyclohexyl group, and each of the cycloalkyl groups is selected from within the range of the specified number of carbon atoms.

The expression "$C_a$ to $C_b$ halocycloalkyl" in the present specification represents a cyclic hydrocarbon group having a to b pieces of carbon atoms in which a hydrogen atom bonded to a carbon atom is optionally substituted with a halogen atom, and the "$C_a$ to $C_b$ halocycloalkyl" can form a monocyclic or composite ring structure having a 3-membered ring to a 6-membered ring. Furthermore, each ring may be optionally substituted with an alkyl group within the range of the specified number of carbon atoms, the substitution of a halogen atom may be on the ring structure part, the side chain part or both of them. Furthermore, when hydrogen atoms are substituted with two or more halogen atoms, these halogen atoms may be the same as or different from each other. Specific examples of the "$C_a$ to $C_b$ halocycloalkyl" include a 2,2-difluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group and a 2,2,3,3-tetrafluorocyclobutyl group, and each of the halocycloalkyl groups is selected from within the range of the specified number of carbon atoms.

The expression "$C_a$ to $C_b$ alkenyl" in the present specification represents a straight chain or branched chain unsaturated hydrocarbon group having a to b pieces of carbon atoms and one or more double bond(s) in the molecule. Specific examples of the "$C_a$ to $C_b$ alkenyl" include a vinyl group, a 1-propenyl group, a 2-propenyl group, a 1-methylethenyl group, a 2-butenyl group, a 2-methyl-2-propenyl group, a 2-methyl-2-butenyl group, a 3-methyl-2-butenyl group and a 1,1-dimethyl-2-propenyl group, and each of the alkenyl groups is selected from within the range of the specified number of carbon atoms.

The expression "$C_a$ to $C_b$ haloalkenyl" in the present specification represents a straight chain or branched chain unsaturated hydrocarbon group having a to b pieces of carbon atoms and one or more double bond(s) in the molecule in which a hydrogen atom bonded to a carbon atom is optionally substituted with a halogen atom. In this case, when hydrogen atoms are substituted with two or more halogen atoms, these halogen atoms may be the same as or different from each other. Specific examples of the "$C_a$ to $C_b$ haloalkenyl" include a 2,2-dichlorovinyl group, a 2-fluoro-2-propenyl group, a 2-chloro-2-propenyl group, a 3-chloro-2-propenyl group, a 2-bromo-2-propenyl group, a 3,3-difluoro-2-propenyl group, a 2,3-dichloro-2-propenyl group, a 3,3-dichloro-2-propenyl group, a 2,3,3-trifluoro-2-propenyl group, a 2,3,3-trichloro-2-propenyl group, a 1-(trifluoromethyl)ethenyl group, a 4,4-difluoro-3-butenyl group, a 3,4,4-trifluoro-3-butenyl group and a 3-chloro-4,4,4-trifluoro-2-butenyl group, and each of the haloalkenyl groups is selected from within the range of the specified number of carbon atoms.

The expression "$C_a$ to $C_b$ cycloalkenyl" in the present specification represents a cyclic unsaturated hydrocarbon group having a to b pieces of carbon atoms and one or more double bond(s), and the "$C_a$ to $C_b$ cycloalkenyl" can form a monocyclic or composite ring structure having a 3-membered ring to a 6-membered ring. Furthermore, each ring may be optionally substituted with an alkyl group within the range of the specified number of carbon atoms, and moreover, the double bond may be either an endo- or exo-type. Specific examples of the "$C_a$ to $C_b$ cycloalkenyl group" include a 1-cyclopenten-1-yl group, a 2-cyclopenten-1-yl group, a 1-cyclohexen-1-yl group and a 2-cyclohexen-1-yl group, and each of the cycloalkenyl groups is selected from within the range of the specified number of carbon atoms.

The expression "$C_a$ to $C_b$ halocycloalkenyl" in the present specification represents a cyclic unsaturated hydrocarbon group having a to b pieces of carbon atoms and one or more double bond(s) in which a hydrogen atom bonded to a carbon atom is optionally substituted with a halogen atom, and the "$C_a$ to $C_b$ halocycloalkenyl" can form a monocyclic or composite ring structure having a 3-membered ring to a 6-membered ring. Furthermore, each ring may be optionally substituted with an alkyl group within the range of a specified number of carbon atoms, and moreover, the double bond may be either an endo- or exo-type. In addition, the substitution of a halogen atom may be on the ring structure part, the side chain part or both of them, and when hydrogen atoms are substituted with two or more halogen atoms, these halogen atoms may be the same as or different from each other. Specific examples of the "$C_a$ to $C_b$ halocycloalkenyl" include a 2-fluoro-1-cyclopentenyl group, a 2-chloro-1-cyclopentenyl group, a 3-chloro-2-cyclopentenyl group and a 2-fluoro-1-cyclohexenyl group, and each of the halocycloalkenyl groups is selected from within the range of the specified number of carbon atoms.

The expression "$C_a$ to $C_b$ alkylidene" in the present specification represents a straight chain or branched chain hydrocarbon group having a to b pieces of carbon atoms and bonded through its double bond. Specific examples of the "$C_a$ to $C_b$ alkylidene" include a methylidene group, an ethylidene group, a propylidene group and a 1-methylethylidene group, and each of the alkylidene groups is selected from within the range of the specified number of carbon atoms.

The expression "$C_a$ to $C_b$ haloalkylidene" in the present specification represents a straight chain or branched chain unsaturated hydrocarbon group having a to b pieces of carbon atoms and one or more double bond(s) in the molecule and bonded through the double bond(s), in which a hydrogen atom bonded to a carbon atom is optionally substituted with a halogen atom. In this case, when hydrogen atoms are substituted with two or more halogen atoms, these halogen atoms may be the same as or different from each other. Specific examples of the "$C_a$ to $C_b$, haloalkylidene" include a difluoromethylidene group, a dichloromethylidene group and a 2,2,2-trifluoroethylidene group, and each of the haloalkylidene groups is selected from within the range of the specified number of carbon atoms.

The expression "$C_a$ to $C_b$ alkynyl" in the present specification represents a straight chain or branched chain unsaturated hydrocarbon group having a to b pieces of carbon atoms and one or more triple bond(s) in the molecule. Specific examples of the "$C_a$ to $C_b$ alkynyl" include an ethynyl group, a 1-propynyl group, a 2-propynyl group, a 1-butynyl group, a 2-butynyl group, a 3-butynyl group and a 1,1-dimethyl-2-propynyl group, and each of the alkynyl groups is selected from within the range of the specified number of carbon atoms.

The expression "$C_a$ to $C_b$ haloalkynyl" in the present specification represents a straight chain or branched chain unsaturated hydrocarbon group having a to b pieces of carbon atoms and one or more triple bond(s) in the molecule in which a hydrogen atom bonded to a carbon atom is optionally substituted with a halogen atom. In this case, when hydrogen atoms are substituted with two or more halogen atoms, these halogen atoms may be the same as or different from each other. Specific examples of the "$C_a$ to $C_b$, haloalkynyl" include a 2-chloroethynyl group, a 2-bromoethynyl group, a 2-iodoethynyl group, a 3-chloro-2-propynyl group, a 3-bromo-2-propynyl group and a 3-iodo-2-propynyl group, and each of the haloalkynyl groups is selected from within the range of the specified number of carbon atoms.

The expression "$C_a$ to $C_b$, alkoxy" in the present specification represents an alkyl-O— group as defined above having a to b pieces of carbon atoms. Specific examples of the "$C_a$ to $C_b$, alkoxy" include a methoxy group, an ethoxy group, an n-propyloxy group, an i-propyloxy group, an n-butyloxy group, an i-butyloxy group, an s-butyloxy group and a tert-butyloxy group, and each of the alkoxy groups is selected from within the range of the specified number of carbon atoms.

The expression "$C_a$ to $C_b$, haloalkoxy" in the present specification represents a haloalkyl-O— group as defined above having a to b pieces of carbon atoms. Specific examples of the "$C_a$ to $C_b$ haloalkoxy" include a difluoromethoxy group, a trifluoromethoxy group, a chlorodifluoromethoxy group, a bromodifluoromethoxy group, a 2-fluoroethoxy group, a 2-chloroethoxy group, a 2,2,2-trifluoroethoxy group, a 1,1,2,2-tetrafluoroethoxy group, a 2-chloro-1,1,2-trifluoroethoxy group and a 1,1,2,3,3,3-hexafluoropropyloxy group, and each of the haloalkoxy groups is selected from within the range of the specified number of carbon atoms.

The expression "$C_a$ to $C_b$ alkenyloxy" in the present specification represents an alkenyl-O— group as defined above having a to b pieces of carbon atoms. Specific examples of the "$C_a$ to $C_b$ alkenyloxy" include a 2-propenyloxy group, a 2-butenyloxy group, a 2-methyl-2-propenyloxy group and a 3-methyl-2-butenyloxy group, and each of the alkenyloxy groups is selected from within the range of the specified number of carbon atoms.

The expression "$C_a$ to $C_b$ alkylthio" in the present specification represents an alkyl-S— group as defined above having a to b pieces of carbon atoms. Specific examples of the "$C_a$ to $C_b$ alkylthio" include a methylthio group, an ethylthio group, an n-propylthio group, an i-propylthio group, an n-butylthio group, an i-butylthio group, an s-butylthio group and a tert-butylthio group, and each of the alkylthio groups is selected from within the range of the specified number of carbon atoms.

The expression "$C_a$ to $C_b$ haloalkylthio" in the present specification represents a haloalkyl-S— group as defined above having a to b pieces of carbon atoms. Specific examples of the "$C_a$ to $C_b$ haloalkylthio" include a difluoromethylthio group, a trifluoromethylthio group, a chlorodifluoromethylthio group, a bromodifluoromethylthio group, a 2,2,2-trifluoroethylthio group, a 1,1,2,2-tetrafluoroethylthio group, a 2-chloro-1,1,2-trifluoroethylthio group, a pentafluoroethylthio group, a 1,1,2,3,3,3-hexafluoropropylthio group, a heptafluoropropylthio group, a 1,2,2,2-tetrafluoro-1-(trifluoromethyl)ethylthio group and a nonafluorobutylthio group, and each of the haloalkylthio groups is selected from within the range of the specified number of carbon atoms.

The expression "$C_a$ to $C_b$ alkylsulfinyl" in the present specification represents an alkyl-S(O)— group as defined above having a to b pieces of carbon atoms. Specific examples of the "$C_a$ to $C_b$ alkylsulfinyl" include a methylsulfinyl group, an ethylsulfinyl group, an n-propylsulfinyl group, an i-propylsulfinyl group, an n-butylsulfinyl group, an i-butylsulfinyl group, an s-butylsulfinyl group and a tert-butylsulfinyl group, and each of the alkylsulfinyl groups is selected from within the range of the specified number of carbon atoms.

The expression "$C_a$ to $C_b$ haloalkylsulfinyl" in the present specification represents a haloalkyl-S(O)— group as defined above having a to b pieces of carbon atoms. Specific examples of the "$C_a$ to $C_b$ haloalkylsulfinyl" include a difluoromethylsulfinyl group, a trifluoromethylsulfinyl group, a chlorodifluoromethylsulfinyl group, a bromodifluoromethylsulfinyl group, a 2,2,2-trifluoroethylsulfinyl group, a 1,2,2,2-tetrafluoro-1-(trifluoromethyl)ethylsulfinyl group and a nonafluorobutylsulfinyl group, and each of the haloalkylsulfinyl groups is selected from within the range of the specified number of carbon atoms.

The expression "$C_a$ to $C_b$ alkylsulfonyl" in the present specification represents an alkyl-$SO_2$— group as defined above having a to b pieces of carbon atoms. Specific examples of the "$C_a$ to $C_b$ alkylsulfonyl" include a methylsulfonyl group, an ethylsulfonyl group, an n-propylsulfonyl group, an i-propylsulfonyl group, an n-butylsulfonyl group, an i-butylsulfonyl group, an s-butylsulfonyl group and a tert-butylsulfonyl group, and each of the alkylsulfonyl groups is selected from within the range of the specified number of carbon atoms.

The expression "$C_a$ to $C_b$ haloalkylsulfonyl" in the present specification represents a haloalkyl-$SO_2$— group as defined above having a to b pieces of carbon atoms. Specific examples of the "$C_a$ to $C_b$ haloalkylsulfonyl" include a difluoromethylsulfonyl group, a trifluoromethylsulfonyl group, a chlorodifluoromethylsulfonyl group, a bromodifluoromethylsulfonyl group, a 2,2,2-trifluoroethylsulfonyl group, a 1,1,2,2-tetrafluoroethylsulfonyl group and a 2-chloro-1,1,2-trifluoroethylsulfonyl group, and each of the haloalkylsulfonyl groups is selected from within the range of the specified number of carbon atoms.

The expression "$C_a$ to $C_b$ alkylamino" in the present specification represents an amino group in which one of the hydrogen atoms is substituted with an alkyl group as defined above having a to b pieces of carbon atoms. Specific examples of the "$C_a$ to $C_b$ alkylamino" include a methylamino group, an ethylamino group, an n-propylamino group, an i-propylamino group, an n-butylamino group, an i-butylamino group and a tert-butylamino group, and each of the alkylamino groups is selected from within the range of the specified number of carbon atoms.

The expression "di($C_a$ to $C_b$ alkyl)amino" in the present specification represents an amino group in which both of the hydrogen atoms are substituted with alkyl groups as defined above having a to b pieces of carbon atoms and the alkyl groups may be the same as or different from each other. Specific examples of the "di($C_a$ to $C_b$ alkyl)amino" include a dimethylamino group, an ethyl(methyl)amino group, a diethylamino group, an n-propyl(methyl)amino group, an i-propyl(methyl)amino group, a di(n-propyl)amino group and a di(n-butyl)amino group, and each of the dialkylamino groups is selected from within the range of the specified number of carbon atoms.

The expression "$C_a$ to $C_b$ alkylimino" in the present specification represents an alkyl-N= group as defined above having a to b pieces of carbon atoms. Specific examples of the "$C_a$ to $C_b$ alkylimino" include a methylimino group, an ethylimino group, an n-propylimino group, an i-propylimino group, an n-butylimino group, an i-butylimino group and an s-butylimino group, and each of the alkylimino groups is selected from within the range of the specified number of carbon atoms.

The expression "$C_a$ to $C_b$ alkoxyimino" in the present specification represents an alkoxy-N= group as defined above having a to b pieces of carbon atoms. Specific examples of the "$C_a$ to $C_b$ alkoxyimino" include a methoxyimino group, an ethoxyimino group, an n-propyloxyimino group, an i-propyloxyimino group and an n-butyloxyimino group, and each of the alkoxyimino groups is selected from within the range of the specified number of carbon atoms.

The expression "$C_a$ to $C_b$ alkylcarbonyl" in the present specification represents an alkyl-C(O)— group as defined above having a to b pieces of carbon atoms. Specific examples of the "$C_a$ to $C_b$ alkylcarbonyl" include an acetyl group, a propionyl group, a butyryl group, an isobutyryl group, a valeryl group, an isovaleryl group, a 2-methylbutanoyl group, a pivaloyl group, a hexanoyl group and a heptanoyl group, and each of the alkylcarbonyl groups is selected from within the range of the specified number of carbon atoms.

The expression "$C_a$ to $C_b$ haloalkylcarbonyl" in the present specification represents a haloalkyl-C(O)— group as defined above having a to b pieces of carbon atoms. Specific examples of the "$C_a$ to $C_b$ haloalkylcarbonyl" include a fluoroacetyl group, a chloroacetyl group, a difluoroacetyl group, a dichloroacetyl group, a trifluoroacetyl group, a chlorodifluoroacetyl group, a bromodifluoroacetyl group, a trichloroacetyl group, a pentafluoropropionyl group, a heptafluorobutanoyl group and a 3-chloro-2,2-dimethylpropanoyl group, and each of the haloalkylcarbonyl groups is selected from within the range of the specified number of carbon atoms.

The expression "$C_a$ to $C_b$ cycloalkylcarbonyl" in the present specification represents a cycloalkyl-C(O)— group as defined above having a to b pieces of carbon atoms. Specific examples of the "$C_a$ to $C_b$ cycloalkylcarbonyl" include a cyclopropylcarbonyl group, a 2-methylcyclopropylcarbonyl group and a cyclobutylcarbonyl group, and each of the cycloalkylcarbonyl groups is selected from within the range of the specified number of carbon atoms.

The expression "$C_a$ to $C_b$ halocycloalkylcarbonyl" in the present specification represents a halocycloalkyl-C(O)— group as defined above having a to b pieces of carbon atoms. Specific examples of the "$C_a$ to $C_b$ halocycloalkylcarbonyl" include a 2,2-dichlorocyclopropylcarbonyl group and a 2,2-dichloro-1-methylcyclopropylcarbonyl group, and each of the halocycloalkylcarbonyl groups is selected from within the range of the specified number of carbon atoms.

The expression "$C_a$ to $C_b$ alkoxycarbonyl" in the present specification represents an alkyl-O—C(O)— group as defined above having a to b pieces of carbon atoms. Specific examples of the "$C_a$ to $C_b$ alkoxycarbonyl" include a methoxycarbonyl group, an ethoxycarbonyl group, an n-propyloxycarbonyl group, an i-propyloxycarbonyl group, an n-butoxycarbonyl group, an i-butoxycarbonyl group and a tert-butoxycarbonyl group, and each of the alkoxycarbonyl groups is selected from within the range of the specified number of carbon atoms.

The expression "$C_a$ to $C_b$ haloalkoxycarbonyl" in the present specification represents a haloalkyl-O—C(O)— group as defined above having a to b pieces of carbon atoms. Specific examples of the "$C_a$ to $C_b$ haloalkoxycarbonyl" include a chloromethoxycarbonyl group, a 2-chloroethoxycarbonyl group, a 2,2-difluoroethoxycarbonyl group, a 2,2,2-trifluoroethoxycarbonyl group and a 2,2,2-trichloroethoxycarbonyl group, and each of the haloalkoxycarbonyl groups is selected from within the range of the specified number of carbon atoms.

The expression "$C_a$ to $C_b$ alkylthiocarbonyl" in the present specification represents an alkyl-S—C(O)— group as defined above having a to b pieces of carbon atoms. Specific examples of the "$C_a$ to $C_b$ alkylthiocarbonyl" include a methylthio-C(O)— group, an ethylthio-C(O)— group, an n-propylthio-C(O)— group, an i-propylthio-C(O)— group, an n-butylthio-C(O)— group, an i-butylthio-C(O)— group and a tert-butylthio-C(O)— group, and each of the alkylthiocarbonyl groups is selected from within the range of the specified number of carbon atoms.

The expression "$C_a$ to $C_b$ alkoxythiocarbonyl" in the present specification represents an alkyl-O—C(S)— group as defined above having a to b pieces of carbon atoms. Specific examples of the "$C_a$ to $C_b$ alkoxythiocarbonyl" include a methoxy-C(S)— group, an ethoxy-C(S)— group, an n-propyloxy-C(S)— group and an i-propyloxy-C(S)— group, and each of the alkoxythiocarbonyl groups is selected from within the range of the specified number of carbon atoms.

The expression "$C_a$ to $C_b$ alkyldithiocarbonyl" in the present specification represents an alkyl-S—C(S)— group as defined above having a to b pieces of carbon atoms. Specific examples of the "$C_a$ to $C_b$ alkyldithiocarbonyl" include a methylthio-C(S)— group, an ethylthio-C(S)— group, an n-propylthio-C(S)— group and an i-propylthio-C(S)— group, and each of the alkyldithiocarbonyl groups is selected from within the range of the specified number of carbon atoms.

The expression "$C_a$ to $C_b$ alkylaminocarbonyl" in the present specification represents a carbamoyl group in which one of the hydrogen atoms is substituted with an alkyl group as defined above having a to b pieces of carbon atoms. Specific examples of the "$C_a$ to $C_b$ alkylaminocarbonyl" include a methylcarbamoyl group, an ethylcarbamoyl group, an n-propylcarbamoyl group, an i-propylcarbamoyl group, an n-butylcarbamoyl group, an i-butylcarbamoyl group, an s-butylcarbamoyl group and a tert-butylcarbamoyl group, and each of the alkylaminocarbonyl groups is selected from within the range of the specified number of carbon atoms.

The expression "$C_a$ to $C_b$ haloalkylaminocarbonyl" in the present specification represents a carbamoyl group in which one of the hydrogen atoms is substituted with a haloalkyl group as defined above having a to b pieces of carbon atoms. Specific examples of the "$C_a$ to $C_b$ haloalkylaminocarbonyl" include a 2-fluoroethylcarbamoyl group, a 2-chloroethylcarbamoyl group, a 2,2-difluoroethylcarbamoyl group and a 2,2,2-trifluoroethylcarbamoyl group, and each of the haloalkylaminocarbonyl groups is selected from within the range of the specified number of carbon atoms.

The expression "di($C_a$ to $C_b$ alkyl)aminocarbonyl" in the present specification represents a carbamoyl group in which both of the hydrogen atoms are substituted with alkyl groups as defined above having a to b pieces of carbon atoms and the alkyl groups may be the same as or different from each other. Specific examples of the "di($C_a$ to $C_b$ alkyl)aminocarbonyl" include an N,N-dimethylcarbamoyl group, an N-ethyl-N-methylcarbamoyl group, an N,N-diethylcarbamoyl group, an N,N-di(n-propyl)carbamoyl group and an N,N-di(n-butyl) carbamoyl group, and each of the dialkylaminocarbonyl groups is selected from within the range of the specified number of carbon atoms.

The expression "$C_a$ to $C_b$ alkylaminosulfonyl" in the present specification represents a sulfamoyl group in which one of the hydrogen atoms is substituted with an alkyl group as defined above having a to b pieces of carbon atoms. Specific examples of the "$C_a$ to $C_b$ alkylaminosulfonyl" include a methylsulfamoyl group, an ethylsulfamoyl group, an n-propylsulfamoyl group, an i-propylsulfamoyl group, an n-butylsulfamoyl group, an i-butylsulfamoyl group, an s-butylsulfamoyl group and a tert-butylsulfamoyl group, and each of the alkylaminosulfonyl groups is selected from within the range of the specified number of carbon atoms.

The expression "di($C_a$ to $C_b$ alkyl)aminosulfonyl" in the present specification represents a sulfamoyl group in which both of the hydrogen atoms are substituted with alkyl groups as defined above having a to b pieces of carbon atoms and the alkyl groups may be the same as or different from each other. Specific examples of the "di($C_a$ to $C_b$, alkyl)aminosulfonyl" include an N,N-dimethylsulfamoyl group, an N-ethyl-N-methylsulfamoyl group, an N,N-diethylsulfamoyl group, an N,N-di(n-propyl)sulfamoyl group and an N,N-di(n-butyl) sulfamoyl group, and each of the dialkylaminosulfonyl groups is selected from within the range of the specified number of carbon atoms.

The expression "tri($C_a$ to $C_b$ alkyl)silyl" in the present specification represents a silyl group which is substituted with alkyl groups as defined above having a to b pieces of carbon atoms and the alkyl groups may be the same as or different from each other. Specific examples of the "tri($C_a$ to $C_b$ alkyl)silyl" include a trimethylsilyl group, a triethylsilyl group, a tri(n-propyl)silyl group, an ethyldimethylsilyl group, an n-propyldimethylsilyl group, an n-butyldimethylsilyl group, an i-butyldimethylsilyl group and a tert-butyldimethylsilyl group, and each of the trialkylsilyl groups is selected from within the range of the specified number of carbon atoms.

The expression "$C_a$ to $C_b$ alkylcarbonyloxy" in the present specification represents an alkylcarbonyl-O— group as defined above having a to b pieces of carbon atoms. Specific examples of the "$C_a$ to $C_b$ alkylcarbonyloxy" include an acetoxy group, and each of the alkylcarbonyloxy groups is selected from within the range of the specified number of carbon atoms.

The expression "$C_a$ to $C_b$ alkylsulfonyloxy" in the present specification represents an alkylsulfonyl-O— group as defined above having a to b pieces of carbon atoms. Specific examples of the "$C_a$ to $C_b$ alkylsulfonyloxy" include a methylsulfonyloxy group, an ethylsulfonyloxy group, an n-propylsulfonyloxy group and an i-propylsulfonyloxy group, and each of the alkylsulfonyloxy groups is selected from within the range of the specified number of carbon atoms.

The expression "$C_a$ to $C_b$ haloalkylsulfonyloxy" in the present specification represents a haloalkylsulfonyl-O— group as defined above having a to b pieces of carbon atoms. Specific examples of the "$C_a$ to $C_b$, haloalkylsulfonyloxy" include a difluoromethylsulfonyloxy group, a trifluoromethylsulfonyloxy group, a chlorodifluoromethylsulfonyloxy group and a bromodifluoromethylsulfonyloxy group, and each of the haloalkylsulfonyloxy groups is selected from within the range of the specified number of carbon atoms.

Each expression "$C_a$ to $C_b$ cycloalkyl($C_d$ to $C_e$) alkyl", "hydroxy($C_d$ to $C_e$) alkyl", "$C_a$ to $C_b$ alkoxy($C_d$ to $C_e$) alkyl", "$C_a$ to $C_b$ haloalkoxy($C_d$ to $C_e$) alkyl", "$C_a$ to $C_b$ alkylthio($C_d$ to $C_e$) alkyl", "$C_a$ to $C_b$ haloalkylthio($C_d$ to $C_e$) alkyl", "$C_a$ to $C_b$ alkylsulfinyl($C_d$ to $C_e$) alkyl", "$C_a$ to $C_b$ haloalkylsulfinyl ($C_d$ to $C_e$) alkyl", "$C_a$ to $C_b$ alkylsulfonyl($C_d$ to $C_e$) alkyl", "$C_a$ to $C_b$ haloalkylsulfonyl($C_d$ to $C_e$)alkyl", "cyano($C_d$ to $C_e$) alkyl", "$C_a$ to $C_b$ alkoxycarbonyl($C_d$ to $C_e$) alkyl", "$C_a$ to $C_b$ haloalkoxycarbonyl($C_d$ to $C_e$) alkyl", "phenyl($C_d$ to $C_e$) alkyl", "phenyl($C_d$ to $C_e$) alkyl substituted with $(Z)_{p1}$" or the like in the present specification represents an alkyl group as defined above having d to e pieces of carbon atoms in which a hydrogen atom bonded to a carbon atom is substituted with any of a $C_a$ to $C_b$ cycloalkyl group, a $C_a$ to $C_b$ alkoxy group, a $C_a$ to $C_b$ haloalkoxy group, a $C_a$ to $C_b$ alkylthio group, a $C_a$ to $C_b$ haloalkylthio group, a $C_a$ to $C_b$ alkylsulfinyl group, a $C_a$ to $C_b$ haloalkylsulfinyl group, a $C_a$ to $C_b$ alkylsulfonyl group, a $C_a$ to $C_b$ haloalkylsulfonyl group, a $C_a$ to $C_b$ alkoxycarbonyl group, a $C_a$ to $C_b$ haloalkoxycarbonyl group, a hydroxy group, a cyano group, a phenyl group or a phenyl group substituted with $(Z)_{p1}$, all of which are as defined above. Each of the alkyl groups is selected from within the range of the specified number of carbon atoms.

Each expression "($C_a$ to $C_b$) alkyl optionally substituted with $R^4$", "($C_a$ to $C_b$) alkyl optionally substituted with $R^{13}$", "($C_a$ to $C_b$) alkyl optionally substituted with $R^{13a}$", "($C_a$ to $C_b$) alkyl optionally substituted with $R^{23}$", "($C_a$ to $C_b$) alkyl optionally substituted with $R^{30}$", "($C_a$ to $C_b$) alkyl optionally substituted with $R^{35}$" or the like in the present specification represents an alkyl group as defined above having a to b pieces of carbon atoms in which a hydrogen atom bonded to a carbon atom is Each of the alkyl groups is selected from within the range of the specified number of carbon atoms. In this case, when the number of substituents $R^4$, $R^{13}$, $R^{13a}$, $R^{23}$, $R^{30}$ or $R^{35}$ on each ($C_a$ to $C_b$) alkyl group is two or more, $R^4$, $R^{13}$, $R^{13a}$, $R^{23}$, $R^{30}$s or $R^{35}$s may be the same as or different from each other.

Each expression "hydroxy($C_d$ to $C_e$) haloalkyl, "$C_a$ to $C_b$ alkoxy($C_d$ to $C_e$) haloalkyl" or "$C_a$ to $C_b$ haloalkoxy($C_d$ to $C_e$) haloalkyl" in the present specification represents a haloalkyl group as defined above having d to e pieces of carbon atoms in which a hydrogen atom or a halogen atom bonded to a carbon atom is substituted with any of a $C_a$ to $C_b$ alkoxy group, a $C_a$ to $C_b$ haloalkoxy group or a hydroxy group, all of which are as defined above. Each of the haloalkyl groups is selected from within the range of the specified number of carbon atoms.

The expression "($C_a$ to $C_b$) haloalkyl optionally substituted with $R^{35}$" in the present specification represents a haloalkyl group as defined above having a to b pieces of carbon atoms in which a hydrogen atom or a halogen atom bonded to a carbon atom is optionally substituted with any of $R^{35}$, and each of the haloalkyl groups is selected from within the range of the specified number of carbon atoms. In this case, when the number of substituents $R^{35}$ on the ($C_a$ to $C_b$) haloalkyl group is two or more, $R^{35}$s may be the same as or different from each other.

Each expression "hydroxy($C_d$ to $C_e$)cycloalkyl", "$C_a$ to $C_b$ alkoxy($C_d$ to $C_e$)cycloalkyl" or the like in the present specification represents a cycloalkyl group as defined above having d to e pieces of carbon atoms in which a hydrogen atom bonded to a carbon atom is optionally substituted with any of a $C_a$ to $C_b$ alkoxy group or a hydroxy group, both of which are as defined above, and each of the cycloalkyl groups is selected from within the range of the specified number of carbon atoms.

Each expression "($C_a$ to $C_b$) cycloalkyl optionally substituted with $R^{4}$", "($C_a$ to $C_b$) cycloalkyl optionally substituted with $R^{13}$", "($C_a$ to $C_b$) cycloalkyl optionally substituted with $R^{23}$", "($C_a$ to $C_b$) cycloalkyl optionally substituted with $R^{30}$" or the like in the present specification represents a cycloalkyl group as defined above having a to b pieces of carbon atoms in which a hydrogen atom bonded to a carbon atom is optionally substituted with any of $R^{4}$, $R^{13}$, $R^{23}$ or $R^{30}$, and each of the cycloalkyl groups is selected from within the range of the specified number of carbon atoms. In this case, the substitution of $R^{4}$, $R^{13}$, $R^{23}$ or $R^{30}$ may be on the ring structure part, the side chain part or both of them. Furthermore, when the number of substituents $R^{4}$, $R^{13}$, $R^{23}$ or $R^{30}$ on each ($C_a$ to $C_b$) cycloalkyl group is two or more, $R^{4}$s, $R^{13}$s, $R^{23}$s or $R^{30}$s may be the same as or different from each other.

The expression "phenyl($C_a$ to $C_b$) alkenyl" in the present specification represents an alkenyl group as defined above having a to b pieces of carbon atoms in which a hydrogen atom bonded to a carbon atom is optionally substituted with a phenyl group, and each of the alkenyl groups is selected from within the range of the specified number of carbon atoms.

Each expression "($C_a$ to $C_b$) alkenyl optionally substituted with $R^{4}$", "($C_a$ to $C_b$) alkenyl optionally substituted with $R^{13}$", "($C_a$ to $C_b$) alkenyl optionally substituted with $R^{23}$" or "($C_a$ to $C_b$) alkenyl optionally substituted with $R^{30}$" in the present specification represents an alkenyl group as defined above having a to b pieces of carbon atoms in which a hydrogen atom bonded to a carbon atom is optionally substituted with any of $R^{4}$, $R^{13}$, $R^{23}$ or $R^{30}$, and each of the alkenyl groups is selected from within the range of the specified number of carbon atoms. In this case, when the number of substituents $R^{4}$, $R^{13}$, $R^{23}$ or $R^{30}$ on each ($C_a$ to $C_b$) alkenyl group is two or more, $R^{4}$s, $R^{13}$s, $R^{23}$s or $R^{30}$s may be the same as or different from each other.

Each expression "($C_a$ to $C_b$) alkynyl optionally substituted with $R^{4}$", "($C_a$ to $C_b$) alkynyl optionally substituted with $R^{13}$", "($C_a$ to $C_b$) alkynyl optionally substituted with $R^{23}$" or "($C_a$ to $C_b$) alkynyl optionally substituted with $R^{30}$" in the present specification represents an alkynyl group as defined above having a to b pieces of carbon atoms in which a hydrogen atom bonded to a carbon atom is optionally substituted with any of $R^{4}$, $R^{13}$, $R^{23}$ or $R^{30}$, and each of the alkynyl groups is selected from within the range of the specified number of carbon atoms. In this case, when the number of substituents $R^{4}$, $R^{13}$, $R^{23}$ or $R^{30}$ on each ($C_a$ to $C_b$) alkynyl group is two or more, $R^{4}$s, $R^{13}$s, $R^{23}$s or $R^{30}$s may be the same as or different from each other.

Specific examples of the expressions in the present specification of ($R^{2}$ together with $R^{1}$ may form a $C_2$ to $C_7$ alkylene chain to form together with a nitrogen atom to which $R^{1}$ and $R^{2}$ are bonded, a 3- to 8-membered ring, and in this case, the alkylene chain may contain one oxygen atom, sulfur atom or nitrogen atom and may be optionally substituted with an oxo group or a thioxo group), ($R^{7}$ together with $R^{6}$ may form a $C_2$ to $C_6$ alkylene chain to form together with a nitrogen atom to which $R^{6}$ and $R^{7}$ are bonded, a 3- to 7-membered ring, and in this case, the alkylene chain may contain one oxygen atom, sulfur atom or nitrogen atom and may be optionally substituted with an oxo group or a thioxo group), ($R^{17}$ together with $R^{16}$ may form a $C_a$ to $C_b$ alkylene chain to form together with a nitrogen atom to which $R^{16}$ and $R^{17}$ are bonded, a d- to e-membered ring, and in this case, the alkylene chain may contain one oxygen atom, sulfur atom or nitrogen atom and may be optionally substituted with an oxo group or a thioxo group), ($R^{25}$ together with $R^{24}$ may form a $C_2$ to $C_5$ alkylene chain to form together with a nitrogen atom to which $R^{24}$ and $R^{25}$ are bonded, a 3- to 6-membered ring, and in this case, the alkylene chain may contain one oxygen atom, sulfur atom or nitrogen atom and may be optionally substituted with an oxo group or a thioxo group) and the like include an aziridine, an azetidine, an azetidin-2-one, a pyrrolidine, a pyrrolidin-2-one, an oxazolidine, an oxazolidin-2-one, an oxazolidine-2-thione, a thiazolidine, a thiazolidin-2-one, a thiazolidine-2-thione, an imidazolidine, an imidazolidin-2-one, an imidazolidine-2-thione, a piperidine, a piperidin-2-one, a piperidine-2-thione, a 2H-3,4,5,6-tetrahydro-1,3-oxazin-2-one, a 2H-3,4,5,6-tetrahydro-1,3-oxazine-2-thione, a morpholine, a 2H-3,4,5,6-tetrahydro-1,3-thiazin-2-one, a 2H-3,4,5,6-tetrahydro-1,3-thiazine-2-thione, a thiomorpholine, a perhydropyrimidin-2-one, a piperazine, a homopiperidine, a homopiperidin-2-one and a heptamethyleneimine. Each of the rings is selected from within the range of the specified number of carbon atoms.

Specific examples of the expression in the present specification of ($R^{2a}$ together with $R^{1a}$ may form a $C_3$ to $C_6$ alkylene chain to form together with a nitrogen atom to which $R^{1a}$ and $R^{2a}$ are bonded, a 4- to 7-membered ring, and in this case, the alkylene chain may contain one oxygen atom, sulfur atom or nitrogen atom and may be optionally substituted with an oxo group or a thioxo group) include an azetidin-2-one, a pyrrolidin-2-one, a pyrrolidine-2,5-dione, an oxazolidin-2-one, an oxazolidine-2-thione, an oxazolidine-2,4-dione, a thiazolidin-2-one, a thiazolidine-2-thione, a thiazolidine-2,4-dione, an imidazolidin-2-one, an imidazolidine-2-thione, an imidazolidine-2,4-dione, a piperidin-2-one, a piperidine-2-thione, a piperidine-2,6-dione, a 2H-3,4,5,6-tetrahydro-1,3-oxazin-2-one, a 2H-3,4,5,6-tetrahydro-1,3-oxazine-2-thione, a 2H-3,4,5,6-tetrahydro-1,3-thiazin-2-one, a 2H-3,4,5,6-tetrahydro-1,3-thiazine-2-thione, a perhydropyrimidin-2-one and a homopiperidin-2-one. Each of the rings is selected from within the range of the specified number of carbon atoms.

Specific examples of the expression in the present specification of ($R^{2b}$ together with $R^{1b}$ may form a $C_4$ to $C_5$ alkylene chain or a $C_4$ to $C_5$ alkenylene chain to form together with a carbon atom to which $R^{1b}$ and $R^{2b}$ are bonded, a 5- to 6-membered ring, and in this case, the alkylene chain or the alkenylene chain may contain one to three oxygen atom(s), sulfur atom(s) or nitrogen atom(s)) include a thiazolidin-2-ylidene, a 2,3-dihydrothiazol-2-ylidene, an imidazolidin-2-ylidene, a 2,3-dihydroimidazol-2-ylidene, a 2,3-dihydro-1,3,4-thiadiazol-2-ylidene, a 1,2-dihydropyridin-2-ylidene, a 2,3-dihydropyridazin-3-ylidene, a 1,2-dihydropyrazin-2-ylidene, a 1,2-dihydropyrimidin-2-ylidene and a 6H-2,3-dihydro-1,3,4-thiadiazin-2-ylidene. Each of the rings is selected from within the range of the specified number of carbon atoms.

Specific examples of the expression in the present specification of ($R^{4b}$ together with $R^{4a}$ may form a $C_2$ to $C_5$ alkylene chain to form together with a carbon atom to which $R^{4a}$ and $R^{4b}$ are bonded, a 3- to 6-membered ring, and in this case, the alkylene chain may contain one oxygen atom, sulfur atom or nitrogen atom) include a cyclopropane ring, a cyclobutane ring, a cyclopentane ring, a tetrahydrofuran ring, a tetrahydrothiophene ring, a pyrrolidine ring, a cyclohexane ring, a tetrahydropyran ring, a tetrahydrothiopyran ring, a piperidine ring, a cycloheptane ring, an oxepane ring, a thiepane ring and an azepane ring. Each of the rings is selected from within the range of the specified number of carbon atoms.

Specific examples of the expressions in the present specification of ($R^{7a}$ together with $R^{6a}$ may form a $C_4$ to $C_6$ alkylene chain to form together with a carbon atom to which $R^{6a}$ and $R^{7a}$ are bonded, a 5- to 7-membered ring, and in this case, the alkylene chain may contain one oxygen atom or sulfur atom), ($R^{17a}$ together with $R^{16a}$ may form a $C_3$ to $C_5$ alkylene chain to form together with a carbon atom to which $R^{16a}$ and $R^{17a}$ are bonded, a 4- to 6-membered ring, and in this case, the alkylene chain may contain one oxygen atom, sulfur atom or nitrogen atom) and the like include a cyclopentylidene, a tetrahydrofuran-3-ylidene, a tetrahydrothiophen-3-ylidene, a cyclohexylidene, a tetrahydropyran-3-ylidene, a tetrahydropyran-4-ylidene, a tetrahydrothiopyran-3-ylidene and a tetrahydrothiopyran-4-ylidene. Each of the rings is selected from within the range of the specified number of carbon atoms.

Specific examples of the expressions in the present specification of ($R^{10}$ together with $R^9$ may form a $C_2$ to $C_6$ alkylene chain to form together with a nitrogen atom to which $R^9$ and $R^{10}$ are bonded, a 3- to 7-membered ring, and in this case, the alkylene chain may contain one oxygen atom, sulfur atom or nitrogen atom), ($R^{17b}$ together with $R^{16b}$ may form a $C_3$ to $C_5$ alkylene chain to form together with a nitrogen atom to which $R^{16b}$ and $R^{17b}$ are bonded, a 4- to 6-membered ring, and in this case, the alkylene chain may contain one oxygen atom, sulfur atom or nitrogen atom), ($R^{17c}$ together with $R^{16c}$ may form a $C_3$ to $C_5$ alkylene chain to form together with a nitrogen atom to which $R^{16c}$ and $R^{17c}$ are bonded, a 4- to 6-membered ring, and in this case, the alkylene chain may contain one oxygen atom, sulfur atom or nitrogen atom), ($R^{19}$ together with $R^{18}$ may form a $C_4$ to $C_7$ alkylene chain to form together with a nitrogen atom to which $R^{18}$ and $R^{19}$ are bonded, a 5- to 8-membered ring, and in this case, the alkylene chain may contain one oxygen atom or sulfur atom), ($R^{29}$ together with $R^{28}$ may form a $C_2$ to $C_5$ alkylene chain to form together with a nitrogen atom to which $R^{28}$ and $R^{29}$ are bonded, a 3- to 6-membered ring, and in this case, the alkylene chain may contain one oxygen atom, sulfur atom or nitrogen atom), ($R^{34}$ together with $R^{33}$ may form a $C_2$ to $C_5$ alkylene chain to form together with a nitrogen atom to which $R^{33}$ and $R^{34}$ are bonded, a 3- to 6-membered ring, and in this case, the alkylene chain may contain one oxygen atom, sulfur atom or nitrogen atom) and the like include an aziridine, an azetidine, a pyrrolidine, an oxazolidine, a thiazolidine, an imidazolidine, a piperidine, a morpholine, a thiomorpholine, a piperazine, a homopiperidine and a heptamethyleneimine. Each of the rings is selected from within the range of the specified number of carbon atoms.

In the compounds included in the present invention, examples of the combination of atoms represented by $A^1$, $A^2$, $A^3$ and $A^4$ include the following groups:

That is, A-I: $A^1$, $A^2$, $A^3$ and $A^4$ are carbon atoms,

A-II: $A^1$ is a nitrogen atom and $A^2$, $A^3$ and $A^4$ are carbon atoms,

A-III: $A^2$ is a nitrogen atom and $A^1$, $A^3$ and $A^4$ are carbon atoms,

A-IV: $A^1$ and $A^3$ are nitrogen atoms and $A^2$ and $A^4$ are carbon atoms,

A-V: $A^1$ and $A^2$ are nitrogen atoms and $A^3$ and $A^4$ are carbon atoms,

A-VI: $A^2$ and $A^3$ are nitrogen atoms and $A^1$ and $A^4$ are carbon atoms,

A-VII: $A^2$ and $A^4$ are nitrogen atoms and $A^1$ and $A^3$ are carbon atoms.

Among them, preferred combinations of atoms represented by $A^1$, $A^2$, $A^3$ and $A^4$ are A-I, A-II and A-III, and specifically preferred is A-I.

In the compounds included in the present invention, examples of the substituent represented by $G^1$ include aromatic 6-membered rings such as a phenyl, a pyridyl, a pyridazinyl, a pyrimidinyl and a pyrazinyl, and aromatic 5-membered rings such as a furyl, a thienyl, an isoxazolyl, an isothiazolyl, a pyrazolyl, an oxazolyl, a thiazolyl and an imidazolyl. Among them, preferred are a phenyl, a pyridyl, a thienyl, a pyrazolyl and a thiazolyl, and specifically preferred is a phenyl.

In the compounds included in the present invention, examples of the substituent represented by $G^2$ include $G^2$-1 (for example, substituted carbamoyl groups), $G^2$-2 (for example, substituted aminoalkyl groups) and $G^2$-3 to $G^2$-11 (for example, substituted azole groups). Among them, preferred are $G^2$-1, $G^2$-2, $G^2$-4, $G^2$-6, $G^2$-7, $G^2$-9 and $G^2$-10, and specifically preferred are $G^2$-1, $G^2$-2, $G^2$-7 and $G^2$-10.

In the compounds included in the present invention, when $G^2$ represents the structure represented by $G^2$-1, examples of the substituent represented by W include an oxygen atom or a sulfur atom.

In the compounds included in the present invention, when $G^2$ represents the structure represented by $G^2$-2, examples of the structure represented by L include —C($R^{4a}$)($R^{4b}$)—, —C($R^{4a}$)($R^{4b}$)CH$_2$—, —CH$_2$C($R^{4a}$)($R^{4b}$)—, —N($R^{4c}$)—, —C($R^{4a}$)($R^{4b}$)N($R^{4c}$)— or a single bond. Among them, specifically preferred is —C($R^{4a}$)($R^{4b}$)—.

In the compounds included in the present invention, examples of the preferred range of the substituent represented by X include the following groups. In this case, in each of the following cases, when m represents an integer of two or more, Xs may be the same as or different from each other.

That is, X-I: a halogen atom and a trifluoromethyl.

X-II: a halogen atom, a cyano, —SF$_5$, a $C_1$ to $C_2$ haloalkyl, a $C_1$ to $C_2$ haloalkoxy and a $C_1$ to $C_2$ haloalkylthio.

X-III: a halogen atom, a cyano, a nitro, —SF$_5$, a $C_1$ to $C_4$ alkyl, a $C_1$ to $C_4$ haloalkyl, a $C_1$ to $C_4$ alkoxy, a $C_1$ to $C_4$ haloalkoxy, a $C_1$ to $C_4$ alkylthio and a $C_1$ to $C_4$ haloalkylthio.

X-IV: a halogen atom, a cyano, a nitro, —SF$_5$, a $C_1$ to $C_6$ alkyl, a $C_1$ to $C_6$ haloalkyl, a hydroxy($C_1$ to $C_4$) haloalkyl, a $C_1$ to $C_4$ alkoxy($C_1$ to $C_4$) haloalkyl, —OR$^5$ and —S(O)$_r$R$^5$ (where R$^5$ represents a $C_1$ to $C_4$ alkyl, a $C_1$ to $C_4$ haloalkyl or a $C_1$ to $C_2$ haloalkoxy($C_1$ to $C_2$) haloalkyl, and r represents an integer of 0 to 2).

In the compounds included in the present invention, examples of m representing the number of substituents represented by X include integers of 0 to 5, and among them, m is preferably 1, 2 and 3.

In the compounds included in the present invention, examples of the preferred range of the substituent represented by Y include the following groups. In this case, in each of the following cases, when n represents an integer of two or more, Ys may be the same as or different from each other.

That is, Y-I: a halogen atom, a methyl, an ethyl and a trifluoromethyl.

Y-II: a halogen atom, a nitro and a methyl.

Y-III: a cyano and a nitro.

Y-IV: a halogen atom, a cyano, a nitro, a $C_1$ to $C_2$ alkyl, a $C_1$ to $C_2$ haloalkyl, a $C_1$ to $C_2$ alkoxymethyl, a $C_2$ to $C_3$ alkynyl, a $C_1$ to $C_2$ haloalkoxy, a $C_1$ to $C_2$ haloalkylthio, —N(R$^7$)R$^6$ (where R$^6$ represents a hydrogen atom, a $C_1$ to $C_2$ alkyl or a $C_1$ to $C_2$ alkylcarbonyl, and $R^7$ represents a hydrogen atom or a $C_1$ to $C_2$ alkyl) and —C(S)NH$_2$.

Y-V: a halogen atom, a cyano, a nitro, a $C_1$ to $C_4$ alkyl, a $C_1$ to $C_4$ haloalkyl, a $C_1$ to $C_2$ alkoxy($C_1$ to $C_2$) alkyl, a $C_2$ to $C_4$ alkynyl, a $C_1$ to $C_4$ alkoxy, a $C_1$ to $C_4$ haloalkoxy, a $C_1$ to $C_4$ alkylthio, a $C_1$ to $C_4$ haloalkylthio, —N($R^7$)$R^6$ (where $R^6$ represents a hydrogen atom, a $C_1$ to $C_4$ alkyl, —CHO, a $C_1$ to $C_4$ alkylcarbonyl, a $C_1$ to $C_4$ haloalkylcarbonyl, a $C_1$ to $C_4$ alkoxycarbonyl, a $C_1$ to $C_4$ alkylthiocarbonyl, a $C_1$ to $C_4$ alkoxythiocarbonyl or a $C_1$ to $C_4$ alkyldithiocarbonyl, and $R^7$ represents a hydrogen atom or a $C_1$ to $C_4$ alkyl) and —C(S)NH$_2$.

Y-VI: a halogen atom, a cyano, a nitro, a $C_1$ to $C_6$ alkyl, a $C_1$ to $C_6$ haloalkyl, a ($C_1$ to $C_4$) alkyl optionally substituted with $R^4$ (where $R^4$ represents —OH, a $C_1$ to $C_4$ alkoxy, a $C_1$ to $C_4$ haloalkoxy, a $C_1$ to $C_4$ alkylthio, a $C_1$ to $C_4$ haloalkylthio, a $C_1$ to $C_4$ alkylsulfinyl, a $C_1$ to $C_4$ haloalkylsulfinyl, a $C_1$ to $C_4$ alkylsulfonyl or a $C_1$ to $C_4$ haloalkylsulfonyl), a $C_2$ to $C_6$ alkenyl, a $C_2$ to $C_6$ alkynyl, —OR$^5$, —S(O)$_r$R$^5$ (where $R^5$ represents a $C_1$ to $C_4$ alkyl or a $C_1$ to $C_4$ haloalkyl, and r represents an integer of 0 to 2), —NH$_2$, —N($R^7$)$R^6$ (where $R^6$ represents a $C_1$ to $C_4$ alkyl, —C(O)$R^8$, —C(O)O$R^9$, —C(O)S$R^9$, —C(S)O$R^9$, —C(S)S$R^9$ or —S(O)$_2$$R^9$, $R^7$ represents a hydrogen atom or a $C_1$ to $C_4$ alkyl, $R^8$ represents a hydrogen atom, a $C_1$ to $C_4$ alkyl, a $C_1$ to $C_4$ haloalkyl or a $C_3$ to $C_6$ cycloalkyl, and $R^9$ represents a $C_1$ to $C_4$ alkyl or a $C_1$ to $C_4$ haloalkyl), —C(S)NH$_2$, D1 to D3, D7, D11 and D22 (where p represents 0).

In the compounds included in the present invention, examples of n representing the number of substituents represented by Y include integers of 0 to 4, and among them, n is preferably 0 and 1.

In the compounds included in the present invention, when $G^2$ represents the structure represented by $G^2$-1, examples of the preferred range of the substituent represented by $R^1$ include the following groups.

That is, $R^1$-I: a ($C_1$ to $C_2$) alkyl substituted with $R^{13}$ (where $R^{13}$ represents a halogen atom, a $C_1$ to $C_3$ alkoxy, a $C_1$ to $C_2$ haloalkoxy, —C(O)NHR$^{28}$, D10 or D32, p represents 0, and t represents 0), E4 (where q represents 0) and —N($R^{17}$)$R^{16}$ (where $R^{16}$ represents a phenyl or D34, $R^{17}$ represents a $C_1$ to $C_2$ alkyl, and p represents 0).

$R^1$-II: —CH=NOR$^{15}$ (where $R^{15}$ represents a $C_1$ to $C_2$ alkyl).

$R^1$-III: —C(O)OR$^{15}$ (where $R^{15}$ represents a $C_1$ to $C_2$ alkyl).

$R^1$-IV: —C(O)NH$_2$.

$R^1$-V: D34 and D35 (where Z represents a halogen atom or a cyano, and p represents an integer of 0 or 1).

$R^1$-VI: a $C_1$ to $C_4$ alkyl, a ($C_1$ to $C_4$) alkyl optionally substituted with $R^{13}$ (where $R^{13}$ represents a halogen atom, a cyano, a $C_3$ to $C_4$ cycloalkyl, E4, E7, —OR$^{24}$, —NHR$^{24}$, —C($R^2$)=NOR$^{28}$, —C(O)N($R^{29}$)$R^{28}$, a phenyl, a phenyl substituted with $(Z)_{p1}$, D8, D10, D13, D16, D22, D32 or D34, $R^{12}$ represents a methyl, $R^{21}$ represents a methyl, $R^{24}$ represents a $C_1$ to $C_4$ alkyl, a $C_1$ to $C_4$ haloalkyl, a $C_1$ to $C_4$ alkylcarbonyl or a $C_1$ to $C_4$ alkoxycarbonyl, $R^{27}$ represents a hydrogen atom or a $C_1$ to $C_2$ alkyl, $R^{28}$ represents a $C_1$ to $C_4$ alkyl, a $C_1$ to $C_4$ haloalkyl, a $C_3$ to $C_4$ alkenyl or a $C_3$ to $C_4$ alkynyl, $R^{29}$ represents a hydrogen atom or a $C_1$ to $C_2$ alkyl, Z represents a halogen atom, a cyano or a nitro, p represents an integer of 0 or 1, p1 represents 1, q represents an integer of 0 or 1, and t represents 0), a $C_3$ to $C_4$ cycloalkyl, a cyclopropyl substituted with $R^{13}$ (where $R^{13}$ represents —C(O)N($R^{29}$)$R^{28}$, D10 or D32, $R^{28}$ represents a $C_1$ to $C_4$ haloalkyl, $R^{29}$ represents a hydrogen atom, p represents 0, and t represents 0), E4, E5 (where q represents 0, and r represents an integer of 0 to 2), a $C_3$ to $C_4$ alkenyl, a $C_3$ to $C_4$ haloalkenyl and —N($R^{17}$)$R^{16}$ (where $R^{16}$ represents a phenyl, D32 or D34, $R^{17}$ represents a hydrogen atom, a $C_1$ to $C_2$ alkyl, a $C_3$ to $C_4$ alkenyl or a $C_3$ to $C_4$ alkynyl, p represents 0, and t represents 0).

$R^1$-VII: —CH=NOR$^{15}$ (where $R^{15}$ represents a $C_1$ to $C_4$ alkyl).

$R^1$-VIII: —C(O)OR$^{15}$ and —C(S)OR$^{15}$ (where $R^{15}$ represents a $C_1$ to $C_4$ alkyl).

$R^1$-IX: —C(O)NHR$^{16}$ (where $R^{16}$ represents a hydrogen atom, a $C_1$ to $C_4$ alkyl or a $C_1$ to $C_4$ haloalkyl).

$R^1$-X: $R^1$ together with $R^2$ forms =C($R^{2b}$)$R^{1b}$ (where $R^{1b}$ represents a $C_1$ to $C_4$ alkoxy or a $C_1$ to $C_4$ alkylthio, $R^{2b}$ represents —NHR$^{16c}$, and $R^{16c}$ represents a hydrogen atom or a $C_1$ to $C_4$ alkyl).

$R^1$-XI: a hydrogen atom, a $C_1$ to $C_6$ alkyl, a ($C_1$ to $C_6$) alkyl optionally substituted with $R^{13}$ (where $R^{13}$ represents a halogen atom, a cyano, a $C_3$ to $C_4$ cycloalkyl, E4, E7, —OR$^{24}$, —N($R^{25}$)$R^{24}$, —S(O)$_r$$R^{26}$, a $C_1$ to $C_4$ alkylcarbonyl, —C($R^{27}$)=NOR$^{28}$, —C(O)N($R^{29}$)$R^{28}$, —C(S)NH$_2$, a phenyl, a phenyl substituted with $(Z)_{p1}$, D1, D5, D7, D8, D10, D13, D16, D17, D22, D32 or D34, $R^{12}$ represents a $C_1$ to $C_4$ alkyl, $R^{21}$ represents a $C_1$ to $C_2$ alkyl, $R^{24}$ represents a hydrogen atom, a $C_1$ to $C_4$ alkyl, a $C_1$ to $C_4$ haloalkyl, —C(O)$R^{31}$ or —C(O)OR$^{32}$, $R^{25}$ represents a hydrogen atom or a $C_1$ to $C_4$ haloalkyl, $R^{26}$ represents a $C_1$ to $C_4$ alkyl, $R^{27}$ represents a hydrogen atom or a $C_1$ to $C_4$ alkyl, $R^{28}$ represents a $C_1$ to $C_4$ alkyl, a $C_1$ to $C_4$ haloalkyl, a hydroxy($C_1$ to $C_4$) haloalkyl, a $C_3$ to $C_4$ cycloalkyl, a $C_3$ to $C_4$ alkenyl or a $C_3$ to $C_4$ alkynyl, $R^{29}$ represents a hydrogen atom or a $C_1$ to $C_4$ alkyl, $R^{31}$ represents a $C_1$ to $C_4$ alkyl, a $C_1$ to $C_4$ haloalkyl or a $C_3$ to $C_6$ cycloalkyl, $R^{32}$ represents a $C_1$ to $C_4$ alkyl or a $C_1$ to $C_4$ haloalkyl, Z represents a halogen atom, a cyano, a nitro, a $C_1$ to $C_4$ alkyl, a $C_1$ to $C_4$ haloalkyl or a $C_1$ to $C_4$ alkoxy, p represents an integer of 0 or 1, p1 represents 1, q represents an integer of 0 or 1, r represents an integer of 0 to 2, and t represents 0), a $C_3$ to $C_6$ cycloalkyl, a ($C_3$ to $C_6$) cycloalkyl optionally substituted with $R^{13}$ (where $R^{13}$ represents a halogen atom, a cyano, —C(O)N($R^{29}$)$R^{28}$, D10 or D32, $R^{28}$ represents a $C_1$ to $C_4$ haloalkyl, $R^{29}$ represents a hydrogen atom, p represents 0, and t represents 0), E4, E5, E12 (where q represents 0, and r represents an integer of 0 to 2), a $C_3$ to $C_6$ alkenyl, a $C_3$ to $C_6$ haloalkenyl and a $C_3$ to $C_6$ alkynyl.

$R^1$-XII: a $C_1$ to $C_6$ alkylcarbonyl, —C(OR$^{15}$)=NOR$^{15}$, —C(NH$_2$)=NCN, —C(NH$_2$)=NOR$^{15}$ (where $R^{15}$ represents a $C_1$ to $C_6$ alkyl) and —C(NH$_2$)=NNO$_2$.

$R^1$-XIII: —CH=NOR$^{15}$ (where $R^{15}$ represents a $C_1$ to $C_6$ alkyl, a $C_1$ to $C_6$ haloalkyl or a $C_3$ to $C_6$ alkenyl).

$R^1$-XIV: —C(O)OR$^{15}$ and —C(S)OR$^{15}$ (where $R^{15}$ represents a $C_1$ to $C_6$ alkyl, a $C_1$ to $C_6$ haloalkyl, a $C_3$ to $C_4$ cycloalkyl($C_1$ to $C_4$) alkyl or a $C_1$ to $C_4$ alkoxycarbonyl($C_1$ to $C_4$) alkyl).

$R^1$-XV: —C(O)N($R^{17}$)$R^{16}$ and —C(S)N($R^{17}$)$R^{16}$ (where $R^{16}$ represents a hydrogen atom, a $C_1$ to $C_6$ alkyl, a ($C_1$ to $C_6$) alkyl optionally substituted with $R^{30}$, a $C_3$ to $C_6$ alkenyl, a $C_1$ to $C_6$ alkylcarbonyl, a $C_1$ to $C_6$ haloalkylcarbonyl or a $C_1$ to $C_6$ alkoxycarbonyl, $R^{17}$ represents a hydrogen atom or a $C_1$ to $C_6$ alkyl, $R^{30}$ represents a halogen atom, a phenyl substituted with $(Z)_{p1}$ or D32, Z represents a halogen atom, p represents 0, p1 represents 1, and t represents 0).

$R^1$-XVI: —N($R^{17}$)$R^{16}$ (where $R^{16}$ represents a $C_1$ to $C_6$ haloalkyl, a $C_1$ to $C_6$ alkylcarbonyl, a $C_1$ to $C_6$ alkoxycarbonyl, a phenyl, a phenyl substituted with $(Z)_{p1}$, D32 or D34, $R^{17}$ represents a hydrogen atom, a $C_1$ to $C_6$ alkyl, a $C_3$ to $C_6$ alkenyl or a $C_3$ to $C_6$ alkynyl, Z represents a halogen atom, a cyano or a nitro, p represents 0, p1 represents 1, and t represents 0).

R$^1$-XVI: a phenyl substituted with $(Z)_{p1}$, D1, D5 to D8, D10, D17 and D32 to D35 (where R$^{12}$ represents a C$_1$ to C$_4$ alkyl, Z represents a halogen atom, a cyano, a nitro, a C$_1$ to C$_4$ alkyl, a C$_1$ to C$_4$ haloalkyl or a C$_1$ to C$_4$ alkylsulfonyloxy, p represents an integer of 0 or 1, p1 represents an integer of 1 to 3, and t represents 0).

R$^1$-XVII: R$^1$ together with R$^2$ forms =C(R$^{2b}$)R$^{1b}$ (where R$^{1b}$ represents a C$_1$ to C$_6$ alkyl, a C$_1$ to C$_6$ alkoxy, a C$_1$ to C$_6$ haloalkoxy, a C$_1$ to C$_6$ alkylthio or —N(R$^{17b}$)R$^{16b}$, R$^{2b}$ represents a C$_1$ to C$_6$ alkylthio or —N(R$^{17c}$)R$^{16c}$, or R$^{2b}$ together with R$^{1b}$ may form —N(R$^{17c}$)CH=CHS— to form together with a carbon atom to which R$^{1b}$ and R$^{2b}$ are bonded, a 5-membered ring, R$^{16b}$ represents a cyano, a nitro or a C$_1$ to C$_6$ alkoxy, R$^{17b}$ represents a hydrogen atom or a C$_1$ to C$_6$ alkyl, R$^{16c}$ represents a hydrogen atom, a C$_1$ to C$_6$ alkyl, a C$_1$ to C$_6$ haloalkyl or a C$_1$ to C$_6$ alkoxy, and R$^{17c}$ represents a hydrogen atom or a C$_1$ to C$_6$ alkyl).

In the compounds included in the present invention, when G$^2$ represents the structure represented by G$^2$-2, examples of the preferred range of the substituent represented by R$^{1a}$ include the following groups.

That is, R$^{1a}$-I: —C(O)R$^{14}$ (where R$^{14}$ represents a C$_1$ to C$_4$ alkyl, a C$_1$ to C$_4$ haloalkyl, a (C$_1$ to C$_2$) alkyl substituted with R$^{30}$, a C$_3$ to C$_4$ cycloalkyl or E4, R$^{30}$ represents a cyclopropyl, a C$_1$ to C$_2$ alkylthio, a C$_1$ to C$_2$ alkylsulfinyl or a C$_1$ to C$_2$ alkylsulfonyl), p represents 0, and q represents 0).

R$^{1a}$-II: —C(O)NHR$^{16}$ (where R$^{16}$ represents a C$_1$ to C$_2$ alkyl, a cyclopropyl or a propargyl).

R$^{1a}$-III: —C(O)R$^{14}$ (where R$^{14}$ represents a (C$_1$ to C$_4$) alkyl optionally substituted with R$^{30}$, R$^{30}$ represents —N(R$^{34}$)R$^{33}$ or —C(O)N(R$^{34}$)R$^{33}$, R$^{33}$ represents a C$_1$ to C$_4$ alkyl or a cyano(C$_1$ to C$_2$) alkyl, and R$^{34}$ represents a hydrogen atom).

R$^{1a}$-IV: —C(O)R$^{14}$ and —C(S)R$^{14}$ (where R$^{14}$ represents a C$_1$ to C$_4$ alkyl, a (C$_1$ to C$_4$) alkyl optionally substituted with R$^{30}$, a C$_3$ to C$_4$ cycloalkyl, a C$_2$ to C$_4$ alkenyl, a C$_2$ to C$_4$ alkynyl or a phenyl substituted with $(Z)_{p1}$, R$^{30}$ represents a halogen atom or a C$_3$ to C$_4$ cycloalkyl, Z represents a halogen atom or a cyano, when p1 represents an integer of two or more, Zs may be the same as or different form each other, and p1 represents an integer of 1 to 3).

R$^{1a}$-V: —C(O)R$^{14}$ and —C(S)R$^{14}$ (where R$^{14}$ represents a (C$_1$ to C$_4$) alkyl optionally substituted with R$^{30}$, E4 or E5, R$^{30}$ represents a halogen atom or —S(O)$_r$R$^{32}$, R$^{32}$ represents a C$_1$ to C$_4$ alkyl or a C$_1$ to C$_4$ haloalkyl, q represents 0, and r represents an integer of 0 to 2).

R$^{1a}$-VI: —C(O)N(R$^{17}$)R$^{16}$) (where R$^{16}$ represents a C$_1$ to C$_4$ alkyl, a C$_1$ to C$_4$ haloalkyl, a C$_3$ to C$_4$ cycloalkyl or a C$_3$ to C$_4$ alkynyl, and R$^{17}$ represents a hydrogen atom or a C$_1$ to C$_4$ alkyl).

R$^{1a}$-VII: —C(O)R$^{14}$ (where R$^{14}$ represents a (C$_1$ to C$_4$) alkyl optionally substituted with R$^{30}$, R$^{30}$ represents —N(R$^{34}$)R$^{33}$, —N(R$^{34}$)C(O)R$^{31}$, —N(R$^{34}$)C(O)OR$^{32}$ or —C(O)N(R$^{34}$)R$^{33}$, R$^{31}$ represents a C$_1$ to C$_4$ haloalkyl, R$^{32}$ represents a C$_1$ to C$_4$ alkyl, R$^{33}$ represents a C$_1$ to C$_4$ alkyl or a cyano(C$_1$ to C$_2$) alkyl, and R$^{34}$ represents a hydrogen atom or a cyano(C$_1$ to C$_2$) alkyl).

R$^{1a}$-VIII: —C(O)R$^{14}$ and —C(S)R$^{14}$ (where R$^{14}$ represents a C$_1$ to C$_6$ alkyl, a C$_1$ to C$_6$ alkyl optionally substituted with R$^{30}$, a C$_3$ to C$_6$ cycloalkyl, a C$_2$ to C$_6$ alkenyl, a C$_2$ to C$_6$ haloalkenyl, a C$_2$ to C$_6$ alkynyl, a phenyl substituted with $(Z)_{p1}$ or D32, R$^{30}$ represents a halogen atom or a C$_3$ to C$_6$ cycloalkyl, Z represents a halogen atom, a cyano, a nitro or a C$_1$ to C$_4$ alkylthio, when p1 represents an integer of two or more, Zs may be the same as or different form each other, p represents an integer of 0 or 1, p1 represents an integer of 1 to 3, and t represents 0).

R$^{1a}$-IX: —C(O)R$^{14}$ and —C(S)R$^{14}$ (where R$^{14}$ represents a (C$_1$ to C$_4$) alkyl optionally substituted with R$^{30}$, E4, E5 or E10, R$^{30}$ represents a halogen atom, a C$_1$ to C$_4$ alkoxy, a C$_1$ to C$_4$ haloalkoxy, —S(O)$_r$R$^{32}$, —S(R$^{32}$)=NC(O)R$^{31}$ or —S(O)(R$^{32}$)=NH, R$^{31}$ represents a C$_1$ to C$_4$ haloalkyl, R$^{32}$ represents a C$_1$ to C$_4$ alkyl, a C$_1$ to C$_4$ haloalkyl or a cyano(C$_1$ to C$_2$) alkyl, q represents 0, and r represents an integer of 0 to 2).

R$^{1a}$-X: —C(O)OR$^{15}$ and —C(O)SR$^{15}$ (where R$^{15}$ represents a C$_1$ to C$_6$ haloalkyl).

R$^{1a}$-XI: —C(O)N(R$^{17}$)R$^{16}$ and —C(O)N(R$^{17}$)N(R$^{17}$)R$^{16}$ (where R$^{16}$ represents a C$_1$ to C$_6$ alkyl, a C$_1$ to C$_6$ haloalkyl, a C$_3$ to C$_6$ cycloalkyl or a C$_3$ to C$_6$ alkynyl, R$^{17}$ represents a hydrogen atom or a C$_1$ to C$_6$ alkyl, or R$^{17}$ together with R$^{16}$ may form a C$_3$ to C$_5$ alkylene chain to form together with a nitrogen atom to which R$^{16}$ and R$^{17}$ are bonded, a 4- to 6-membered ring, and in this case, the alkylene chain may contain one sulfur atom).

In the compounds included in the present invention, when G$^2$ represents the structure represented by G$^2$-1, examples of the preferred range of the substituent represented by R$^2$ include the following groups.

That is, R$^2$-I: a hydrogen atom.

R$^2$-II: a (C$_1$ to C$_2$) alkyl substituted with R$^{13a}$ (where R$^{13a}$ represents —OR$^{24}$, and R$^{24}$ represents a C$_1$ to C$_2$ alkyl or a C$_1$ to C$_2$ alkylcarbonyl).

R$^2$-III: a C$_1$ to C$_3$ alkylcarbonyl, a cyclopropylcarbonyl and a C$_1$ to C$_3$ alkoxycarbonyl.

R$^2$-IV: a C$_1$ to C$_4$ alkyl, a (C$_1$ to C$_2$) alkyl substituted with R$^{13a}$ (where R$^{13a}$ represents a cyano, —OR$^{24}$ or a C$_1$ to C$_4$ alkylthio, and R$^{24}$ represents a C$_1$ to C$_4$ alkyl, a C$_1$ to C$_4$ haloalkyl, a C$_1$ to C$_4$ alkylcarbonyl or a C$_1$ to C$_4$ alkoxycarbonyl), and a C$_3$ to C$_4$ alkynyl.

R$^2$-V: —C(O)R$^{14a}$ (where R$^{14a}$ represents a C$_1$ to C$_4$ alkyl, a C$_1$ to C$_2$ alkoxy(C$_1$ to C$_2$) alkyl, a C$_3$ to C$_4$ cycloalkyl or a C$_2$ to C$_4$ alkenyl).

R$^2$-VI: —C(O)OR$^{15a}$ (where R$^{15a}$ represents a C$_1$ to C$_4$ alkyl, a C$_1$ to C$_4$ haloalkyl or a C$_1$ to C$_2$ alkoxy(C$_1$ to C$_2$) alkyl).

R$^2$-VII: a C$_1$ to C$_6$ alkyl, a (C$_1$ to C$_4$) alkyl substituted with R$^{13a}$ (where R$^{13a}$ represents a cyano, a C$_3$ to C$_4$ cycloalkyl, —OR$^{24}$, —S(O)$_r$R$^{26}$ or D32, R$^{24}$ represents a C$_1$ to C$_4$ alkyl, a C$_1$ to C$_4$ haloalkyl, —C(O)R$^{31}$ or a C$_1$ to C$_4$ alkoxycarbonyl, R$^{26}$ represents a C$_1$ to C$_4$ alkyl, R$^{31}$ represents a C$_1$ to C$_4$ alkyl, a C$_1$ to C$_4$ haloalkyl or a C$_3$ to C$_6$ cycloalkyl, p represents 0, r represents an integer of 0 to 2, and t represents 0), a C$_3$ to C$_6$ cycloalkyl, a C$_3$ to C$_6$ alkenyl and a C$_3$ to C$_6$ alkynyl.

R$^2$-VIII: —C(O)R$^{14a}$ (where R$^{14a}$ represents a C$_1$ to C$_6$ alkyl, a C$_1$ to C$_6$ haloalkyl, a C$_1$ to C$_4$ alkoxy(C$_1$ to C$_4$) alkyl, a C$_1$ to C$_4$ alkylthio(C$_1$ to C$_4$) alkyl, a C$_1$ to C$_4$ alkylsulfinyl(C$_1$ to C$_4$) alkyl, a C$_1$ to C$_4$ alkylsulfonyl(C$_1$ to C$_4$) alkyl, a C$_3$ to C$_6$ cycloalkyl, a C$_2$ to C$_6$ alkenyl, a C$_2$ to C$_6$ alkynyl, a phenyl, a phenyl substituted with $(Z)_{p1}$ or D32, Z represents a halogen atom, a cyano, a nitro, a C$_1$ to C$_6$ alkyl or C$_1$ to C$_6$ alkoxy, p represents 0, p1 represents 1, and t represents 0) and —C(O)C(O)OR$^{15a}$ (where R$^{15a}$ represents a C$_1$ to C$_6$ alkyl).

R$^2$-IX: —C(O)OR$^{15a}$ (where R$^{15a}$ represents a C$_1$ to C$_6$ alkyl, a C$_1$ to C$_6$ haloalkyl, a C$_1$ to C$_4$ alkoxy(C$_1$ to C$_4$) alkyl, a C$_3$ to C$_6$ alkenyl, a C$_3$ to C$_6$ alkynyl or a phenyl).

R$^2$-X: a C$_1$ to C$_6$ haloalkylthio.

In the compounds included in the present invention, when G$^2$ represents the structure represented by G$^2$-2, examples of the preferred range of the substituent represented by R$^{2a}$ include the following groups.

That is, R$^{2a}$-I: a hydrogen atom.

R$^{2a}$-II: a C$_1$ to C$_2$ alkyl, a (C$_1$ to C$_2$) alkyl substituted with R$^{13a}$ (where R$^{13a}$ represents a cyano, a cyclopropyl or a C$_1$ to C$_2$ alkoxy) and a propargyl.

$R^{2a}$-III: a $C_1$ to $C_4$ alkyl, a ($C_1$ to $C_2$) alkyl substituted with $R^{13a}$ (where $R^{13a}$ represents a cyano, a $C_3$ to $C_4$ cycloalkyl or a $C_1$ to $C_2$ alkoxy), a $C_3$ to $C_4$ alkenyl and a $C_3$ to $C_4$ alkynyl.

$R^{2a}$-IV: a $C_1$ to $C_6$ alkyl, a ($C_1$ to $C_4$) alkyl substituted with $R^{13a}$ (where $R^{13a}$ represents a cyano, a $C_3$ to $C_4$ cycloalkyl, a $C_1$ to $C_4$ alkoxy, a $C_1$ to $C_4$ alkylthio or a $C_1$ to $C_4$ alkoxycarbonyl), a $C_3$ to $C_6$ alkenyl and a $C_3$ to $C_6$ alkynyl.

In the compounds included in the present invention, examples of the preferred range of the substituent represented by $R^3$ include the following groups.

That is, $R^3$-I: a trifluoromethyl and a chlorodifluoromethyl.

$R^3$-II: a difluoromethyl, a trifluoromethyl, a chlorodifluoromethyl, a bromodifluoromethyl, a 1,1,2,2-tetrafluoroethyl and a pentafluoroethyl.

$R^3$-III: a $C_1$ to $C_2$ haloalkyl.

$R^3$-IV: a $C_1$ to $C_4$ haloalkyl optionally substituted with two or more of any halogen atoms.

$R^3$-V: a $C_1$ to $C_4$ haloalkyl.

$R^3$-VI: a $C_1$ to $C_6$ haloalkyl and a $C_3$ to $C_8$ halocycloalkyl.

In the compounds included in the present invention, examples of the preferred range of the substituent represented by $R^{3a}$ include the following groups.

That is, $R^{3a}$-I: a halogen atom and a methyl.

$R^{3a}$-II: a halogen atom and a $C_1$ to $C_2$ alkyl.

$R^{3a}$-III: a halogen atom, a $C_1$ to $C_6$ alkyl and a $C_1$ to $C_6$ alkylthio.

In the compounds included in the present invention, examples of the preferred range of the substituent represented by $R^{3b}$ include the following groups.

That is, $R^{3b}$-I: a hydrogen atom.

$R^{3b}$-II: a hydrogen atom and a halogen atom.

In the compounds included in the present invention, examples of the preferred range of the substituent represented by $R^{3c}$ include the following groups.

That is, $R^{3c}$-I: a hydrogen atom.

$R^{3a}$-II: a hydrogen atom, a halogen atom and a $C_1$ to $C_2$ alkyl.

In the compounds included in the present invention, examples of the preferred range of the substituent represented by $R^{4a}$ include the following groups.

That is, $R^{4a}$-I: a hydrogen atom, a cyano and a methyl.

$R^{4a}$-II: a hydrogen atom, a cyano, a methyl and —C(S)NH$_2$.

$R^{4a}$-III: a hydrogen atom, a cyano, a $C_1$ to $C_2$ alkyl, a $C_1$ to $C_2$ haloalkyl, a $C_2$ to $C_4$ alkynyl and —C(S)NH$_2$.

In the compounds included in the present invention, a preferred substituent represented by $R^{4b}$ is a hydrogen atom.

These groups representing the preferred range of each substituent of the compounds included in the present invention may be optionally combined, each of which represents the range of the preferred compound of the present invention.

When $G^2$ represents the structure represented by $G^2$-1, examples of the combination of X, Y, $R^1$ and $R^2$ in the preferred range include combinations shown in Table 1. However, the combinations in Table 1 are only for exemplification and the present invention is not limited to these combinations.

In Table, the expression "-" represents unsubstituted.

TABLE 1

| X | Y | $R^1$ | $R^2$ |
|---|---|---|---|
| X-I | — | $R^1$-I | $R^2$-I |
| X-I | — | $R^1$-I | $R^2$-II |
| X-I | — | $R^1$-I | $R^2$-III |
| X-I | — | $R^1$-I | $R^2$-VI |
| X-I | — | $R^1$-II | $R^2$-I |

TABLE 1-continued

| X | Y | $R^1$ | $R^2$ |
|---|---|---|---|
| X-I | — | $R^1$-II | $R^2$-II |
| X-I | — | $R^1$-II | $R^2$-III |
| X-I | — | $R^1$-III | $R^2$-I |
| X-I | — | $R^1$-III | $R^2$-III |
| X-I | — | $R^1$-IV | $R^2$-I |
| X-I | — | $R^1$-V | $R^2$-I |
| X-I | — | $R^1$-V | $R^2$-II |
| X-I | — | $R^1$-V | $R^2$-III |
| X-I | — | $R^1$-V | $R^2$-IV |
| X-I | — | $R^1$-V | $R^2$-V |
| X-I | — | $R^1$-V | $R^2$-VI |
| X-I | Y-I | $R^1$-I | $R^2$-I |
| X-I | Y-I | $R^1$-I | $R^2$-II |
| X-I | Y-I | $R^1$-I | $R^2$-III |
| X-I | Y-I | $R^1$-I | $R^2$-IV |
| X-I | Y-I | $R^1$-I | $R^2$-V |
| X-I | Y-I | $R^1$-I | $R^2$-VI |
| X-I | Y-I | $R^1$-I | $R^2$-VII |
| X-I | Y-I | $R^1$-I | $R^2$-VIII |
| X-I | Y-I | $R^1$-I | $R^2$-IX |
| X-I | Y-I | $R^1$-I | $R^2$-X |
| X-I | Y-I | $R^1$-II | $R^2$-I |
| X-I | Y-I | $R^1$-II | $R^2$-II |
| X-I | Y-I | $R^1$-II | $R^2$-III |
| X-I | Y-I | $R^1$-II | $R^2$-IV |
| X-I | Y-I | $R^1$-II | $R^2$-VI |
| X-I | Y-I | $R^1$-II | $R^2$-VII |
| X-I | Y-I | $R^1$-II | $R^2$-IX |
| X-I | Y-I | $R^1$-III | $R^2$-I |
| X-I | Y-I | $R^1$-III | $R^2$-III |
| X-I | Y-I | $R^1$-III | $R^2$-V |
| X-I | Y-I | $R^1$-III | $R^2$-VI |
| X-I | Y-I | $R^1$-III | $R^2$-VIII |
| X-I | Y-I | $R^1$-III | $R^2$-IX |
| X-I | Y-I | $R^1$-III | $R^2$-X |
| X-I | Y-I | $R^1$-IV | $R^2$-I |
| X-I | Y-I | $R^1$-IV | $R^2$-II |
| X-I | Y-I | $R^1$-IV | $R^2$-III |
| X-I | Y-I | $R^1$-IV | $R^2$-IV |
| X-I | Y-I | $R^1$-IV | $R^2$-VI |
| X-I | Y-I | $R^1$-IV | $R^2$-VII |
| X-I | Y-I | $R^1$-IV | $R^2$-IX |
| X-I | Y-I | $R^1$-V | $R^2$-I |
| X-I | Y-I | $R^1$-V | $R^2$-II |
| X-I | Y-I | $R^1$-V | $R^2$-III |
| X-I | Y-I | $R^1$-V | $R^2$-IV |
| X-I | Y-I | $R^1$-V | $R^2$-V |
| X-I | Y-I | $R^1$-V | $R^2$-VI |
| X-I | Y-I | $R^1$-V | $R^2$-VII |
| X-I | Y-I | $R^1$-V | $R^2$-VIII |
| X-I | Y-I | $R^1$-V | $R^2$-IX |
| X-I | Y-I | $R^1$-V | $R^2$-X |
| X-I | Y-I | $R^1$-VI | $R^2$-I |
| X-I | Y-I | $R^1$-VI | $R^2$-II |
| X-I | Y-I | $R^1$-VI | $R^2$-III |
| X-I | Y-I | $R^1$-VI | $R^2$-IV |
| X-I | Y-I | $R^1$-VI | $R^2$-V |
| X-I | Y-I | $R^1$-VI | $R^2$-VI |
| X-I | Y-I | $R^1$-VII | $R^2$-I |
| X-I | Y-I | $R^1$-VII | $R^2$-II |
| X-I | Y-I | $R^1$-VII | $R^2$-III |
| X-I | Y-I | $R^1$-VII | $R^2$-IV |
| X-I | Y-I | $R^1$-VII | $R^2$-VI |
| X-I | Y-I | $R^1$-VIII | $R^2$-I |
| X-I | Y-I | $R^1$-VIII | $R^2$-III |
| X-I | Y-I | $R^1$-VIII | $R^2$-V |
| X-I | Y-I | $R^1$-VIII | $R^2$-VI |
| X-I | Y-I | $R^1$-IX | $R^2$-I |
| X-I | Y-I | $R^1$-IX | $R^2$-II |
| X-I | Y-I | $R^1$-IX | $R^2$-III |
| X-I | Y-I | $R^1$-IX | $R^2$-IV |
| X-I | Y-I | $R^1$-IX | $R^2$-VI |
| X-I | Y-I | $R^1$-X | — |
| X-I | Y-I | $R^1$-XI | $R^2$-I |
| X-I | Y-I | $R^1$-XI | $R^2$-II |
| X-I | Y-I | $R^1$-XI | $R^2$-III |
| X-I | Y-I | $R^1$-XII | $R^2$-I |
| X-I | Y-I | $R^1$-XIII | $R^2$-I |

TABLE 1-continued

| X | Y | R¹ | R² |
|---|---|---|---|
| X-I | Y-I | R¹-XIII | R²-II |
| X-I | Y-I | R¹-XIII | R²-III |
| X-I | Y-I | R¹-XIV | R²-I |
| X-I | Y-I | R¹-XIV | R²-III |
| X-I | Y-I | R¹-XV | R²-I |
| X-I | Y-I | R¹-XV | R²-II |
| X-I | Y-I | R¹-XV | R²-III |
| X-I | Y-I | R¹-XVI | R²-I |
| X-I | Y-I | R¹-XVI | R²-II |
| X-I | Y-I | R¹-XVI | R²-III |
| X-I | Y-I | R¹-XVII | R²-I |
| X-I | Y-I | R¹-XVII | R²-II |
| X-I | Y-I | R¹-XVII | R²-III |
| X-I | Y-I | R¹-XVIII | — |
| X-I | Y-IV | R¹-I | R²-I |
| X-I | Y-IV | R¹-I | R²-II |
| X-I | Y-IV | R¹-I | R²-III |
| X-I | Y-IV | R¹-I | R²-IV |
| X-I | Y-IV | R¹-I | R²-V |
| X-I | Y-IV | R¹-I | R²-VI |
| X-I | Y-IV | R¹-II | R²-I |
| X-I | Y-IV | R¹-II | R²-II |
| X-I | Y-IV | R¹-II | R²-III |
| X-I | Y-IV | R¹-II | R²-IV |
| X-I | Y-IV | R¹-II | R²-VI |
| X-I | Y-IV | R¹-III | R²-I |
| X-I | Y-IV | R¹-III | R²-III |
| X-I | Y-IV | R¹-III | R²-V |
| X-I | Y-IV | R¹-III | R²-VI |
| X-I | Y-IV | R¹-IV | R²-I |
| X-I | Y-IV | R¹-IV | R²-II |
| X-I | Y-IV | R¹-IV | R²-III |
| X-I | Y-IV | R¹-IV | R²-IV |
| X-I | Y-IV | R¹-IV | R²-VI |
| X-I | Y-IV | R¹-V | R²-I |
| X-I | Y-IV | R¹-V | R²-II |
| X-I | Y-IV | R¹-V | R²-III |
| X-I | Y-IV | R¹-V | R²-IV |
| X-I | Y-IV | R¹-V | R²-V |
| X-I | Y-IV | R¹-V | R²-VI |
| X-I | Y-IV | R¹-VI | R²-I |
| X-I | Y-IV | R¹-VI | R²-II |
| X-I | Y-IV | R¹-VI | R²-III |
| X-I | Y-IV | R¹-VII | R²-I |
| X-I | Y-IV | R¹-VII | R²-II |
| X-I | Y-IV | R¹-VII | R²-III |
| X-I | Y-IV | R¹-VIII | R²-I |
| X-I | Y-IV | R¹-VIII | R²-III |
| X-I | Y-IV | R¹-IX | R²-I |
| X-I | Y-IV | R¹-IX | R²-II |
| X-I | Y-IV | R¹-IX | R²-III |
| X-I | Y-IV | R¹-X | — |
| X-I | Y-IV | R¹-XI | R²-I |
| X-I | Y-IV | R¹-XII | R²-I |
| X-I | Y-IV | R¹-XIII | R²-I |
| X-I | Y-IV | R¹-XIV | R²-I |
| X-I | Y-IV | R¹-XV | R²-I |
| X-I | Y-IV | R¹-XVI | R²-I |
| X-I | Y-IV | R¹-XVII | R²-I |
| X-I | Y-IV | R¹-XVII | R²-III |
| X-I | Y-IV | R¹-XVIII | — |
| X-I | Y-V | R¹-I | R²-I |
| X-I | Y-V | R¹-I | R²-II |
| X-I | Y-V | R¹-I | R²-III |
| X-I | Y-V | R¹-II | R²-I |
| X-I | Y-V | R¹-II | R²-II |
| X-I | Y-V | R¹-II | R²-III |
| X-I | Y-V | R¹-III | R²-I |
| X-I | Y-V | R¹-III | R²-II |
| X-I | Y-V | R¹-IV | R²-I |
| X-I | Y-V | R¹-IV | R²-II |
| X-I | Y-V | R¹-IV | R²-III |
| X-I | Y-V | R¹-V | R²-I |
| X-I | Y-V | R¹-V | R²-II |
| X-I | Y-V | R¹-V | R²-III |
| X-I | Y-V | R¹-VI | R²-I |
| X-I | Y-V | R¹-VII | R²-I |
| X-I | Y-V | R¹-VIII | R²-I |
| X-I | Y-V | R¹-IX | R²-I |
| X-I | Y-V | R¹-X | — |
| X-I | Y-VI | R¹-I | R²-I |
| X-I | Y-VI | R¹-I | R²-III |
| X-I | Y-VI | R¹-II | R²-I |
| X-I | Y-VI | R¹-III | R²-I |
| X-I | Y-VI | R¹-IV | R²-I |
| X-I | Y-VI | R¹-V | R²-I |
| X-I | Y-VI | R¹-V | R²-III |
| X-II | Y-I | R¹-I | R²-I |
| X-II | Y-I | R¹-I | R²-II |
| X-II | Y-I | R¹-I | R²-III |
| X-II | Y-I | R¹-I | R²-IV |
| X-II | Y-I | R¹-I | R²-V |
| X-II | Y-I | R¹-I | R²-VI |
| X-II | Y-I | R¹-II | R²-I |
| X-II | Y-I | R¹-II | R²-II |
| X-II | Y-I | R¹-II | R²-III |
| X-II | Y-I | R¹-II | R²-IV |
| X-II | Y-I | R¹-II | R²-VI |
| X-II | Y-I | R¹-III | R²-I |
| X-II | Y-I | R¹-III | R²-III |
| X-II | Y-I | R¹-III | R²-V |
| X-II | Y-I | R¹-III | R²-VI |
| X-II | Y-I | R¹-IV | R²-I |
| X-II | Y-I | R¹-IV | R²-II |
| X-II | Y-I | R¹-IV | R²-III |
| X-II | Y-I | R¹-IV | R²-IV |
| X-II | Y-I | R¹-IV | R²-VI |
| X-II | Y-I | R¹-V | R²-I |
| X-II | Y-I | R¹-V | R²-II |
| X-II | Y-I | R¹-V | R²-III |
| X-II | Y-I | R¹-V | R²-IV |
| X-II | Y-I | R¹-V | R²-V |
| X-II | Y-I | R¹-V | R²-VI |
| X-II | Y-I | R¹-VI | R²-I |
| X-II | Y-I | R¹-VI | R²-II |
| X-II | Y-I | R¹-VI | R²-III |
| X-II | Y-I | R¹-VII | R²-I |
| X-II | Y-I | R¹-VII | R²-II |
| X-II | Y-I | R¹-VII | R²-III |
| X-II | Y-I | R¹-VIII | R²-I |
| X-II | Y-I | R¹-VIII | R²-III |
| X-II | Y-I | R¹-IX | R²-I |
| X-II | Y-I | R¹-IX | R²-II |
| X-II | Y-I | R¹-IX | R²-III |
| X-II | Y-I | R¹-X | — |
| X-II | Y-I | R¹-XI | R²-I |
| X-II | Y-I | R¹-XII | R²-I |
| X-II | Y-I | R¹-XIII | R²-I |
| X-II | Y-I | R¹-XIV | R²-I |
| X-II | Y-I | R¹-XV | R²-I |
| X-II | Y-I | R¹-XVI | R²-I |
| X-II | Y-I | R¹-XVII | R²-I |
| X-II | Y-I | R¹-XVII | R²-III |
| X-II | Y-I | R¹-XVIII | — |
| X-II | Y-IV | R¹-I | R²-I |
| X-II | Y-IV | R¹-I | R²-II |
| X-II | Y-IV | R¹-I | R²-III |
| X-II | Y-IV | R¹-II | R²-I |
| X-II | Y-IV | R¹-II | R²-II |
| X-II | Y-IV | R¹-II | R²-III |
| X-II | Y-IV | R¹-III | R²-I |
| X-II | Y-IV | R¹-III | R²-III |
| X-II | Y-IV | R¹-IV | R²-I |
| X-II | Y-IV | R¹-IV | R²-II |
| X-II | Y-IV | R¹-IV | R²-III |
| X-II | Y-IV | R¹-V | R²-I |
| X-II | Y-IV | R¹-V | R²-II |
| X-II | Y-IV | R¹-V | R²-III |
| X-II | Y-IV | R¹-VI | R²-I |
| X-II | Y-IV | R¹-VII | R²-I |
| X-II | Y-IV | R¹-VIII | R²-I |
| X-II | Y-IV | R¹-IX | R²-I |
| X-II | Y-IV | R¹-X | — |
| X-II | Y-V | R¹-I | R²-I |
| X-II | Y-V | R¹-I | R²-III |
| X-II | Y-V | R¹-II | R²-I |

TABLE 1-continued

| X | Y | R¹ | R² |
|---|---|---|---|
| X-II | Y-V | R¹-III | R²-I |
| X-II | Y-V | R¹-IV | R²-I |
| X-II | Y-V | R¹-V | R²-I |
| X-II | Y-V | R¹-V | R²-III |
| X-II | Y-VI | R¹-I | R²-I |
| X-II | Y-VI | R¹-I | R²-III |
| X-II | Y-VI | R¹-II | R²-I |
| X-II | Y-VI | R¹-V | R²-III |
| X-III | Y-I | R¹-I | R²-I |
| X-III | Y-I | R¹-I | R²-II |
| X-III | Y-I | R¹-I | R²-III |
| X-III | Y-I | R¹-II | R²-I |
| X-III | Y-I | R¹-II | R²-II |
| X-III | Y-I | R¹-II | R²-III |
| X-III | Y-I | R¹-III | R²-I |
| X-III | Y-I | R¹-III | R²-III |
| X-III | Y-I | R¹-IV | R²-I |
| X-III | Y-I | R¹-IV | R²-II |
| X-III | Y-I | R¹-IV | R²-III |
| X-III | Y-I | R¹-V | R²-I |
| X-III | Y-I | R¹-V | R²-II |
| X-III | Y-I | R¹-V | R²-III |
| X-III | Y-I | R¹-VI | R²-I |
| X-III | Y-I | R¹-VII | R²-I |
| X-III | Y-I | R¹-VIII | R²-I |
| X-III | Y-I | R¹-IX | R²-I |
| X-III | Y-I | R¹-X | — |
| X-III | Y-IV | R¹-I | R²-I |
| X-III | Y-IV | R¹-I | R²-III |
| X-III | Y-IV | R¹-II | R²-I |
| X-III | Y-IV | R¹-III | R²-I |
| X-III | Y-IV | R¹-IV | R²-I |
| X-III | Y-IV | R¹-V | R²-I |
| X-III | Y-IV | R¹-V | R²-III |
| X-III | Y-V | R¹-I | R²-I |
| X-III | Y-V | R¹-I | R²-III |
| X-III | Y-V | R¹-II | R²-I |
| X-III | Y-V | R¹-V | R²-III |
| X-III | Y-VI | R¹-I | R²-I |
| X-III | Y-VI | R¹-II | R²-I |
| X-IV | Y-I | R¹-I | R²-I |
| X-IV | Y-I | R¹-I | R²-III |
| X-IV | Y-I | R¹-II | R²-I |
| X-IV | Y-I | R¹-III | R²-I |
| X-IV | Y-I | R¹-IV | R²-I |
| X-IV | Y-I | R¹-V | R²-I |
| X-IV | Y-I | R¹-V | R²-III |
| X-IV | Y-IV | R¹-I | R²-I |
| X-IV | Y-IV | R¹-I | R²-III |
| X-IV | Y-IV | R¹-II | R²-I |
| X-IV | Y-IV | R¹-V | R²-III |
| X-IV | Y-V | R¹-I | R²-I |
| X-IV | Y-V | R¹-II | R²-I |
| X-IV | Y-VI | R¹-I | R²-I |
| X-IV | Y-VI | R¹-II | R²-I |

When $G^2$ represents the structure represented by $G^2$-2, examples of the preferred range of the combination of X, Y, $R^1$ and $R^2$ include combinations shown in Table 2. However, the combinations in Table 2 are only for exemplification and the present invention is not limited to these combinations.

In Table, the expression "-" represents unsubstituted.

TABLE 2

| X | Y | R¹ᵃ | R²ᵃ |
|---|---|---|---|
| X-I | — | R¹ᵃ-I | R²ᵃ-I |
| X-I | — | R¹ᵃ-I | R²ᵃ-II |
| X-I | — | R¹ᵃ-I | R²ᵃ-III |
| X-I | — | R¹ᵃ-I | R²ᵃ-IV |
| X-I | — | R¹ᵃ-II | R²ᵃ-I |
| X-I | — | R¹ᵃ-II | R²ᵃ-II |
| X-I | — | R¹ᵃ-III | R²ᵃ-I |
| X-I | — | R¹ᵃ-IV | R²ᵃ-I |
| X-I | — | R¹ᵃ-IV | R²ᵃ-II |
| X-I | — | R¹ᵃ-IV | R²ᵃ-III |
| X-I | — | R¹ᵃ-V | R²ᵃ-I |
| X-I | — | R¹ᵃ-V | R²ᵃ-II |
| X-I | — | R¹ᵃ-V | R²ᵃ-III |
| X-I | — | R¹ᵃ-VI | R²ᵃ-I |
| X-I | — | R¹ᵃ-VII | R²ᵃ-I |
| X-I | — | R¹ᵃ-VIII | R²ᵃ-I |
| X-I | — | R¹ᵃ-VIII | R²ᵃ-II |
| X-I | — | R¹ᵃ-IX | R²ᵃ-I |
| X-I | — | R¹ᵃ-IX | R²ᵃ-II |
| X-I | — | R¹ᵃ-X | R²ᵃ-I |
| X-I | — | R¹ᵃ-XI | R²ᵃ-I |
| X-I | Y-II | R¹ᵃ-I | R²ᵃ-I |
| X-I | Y-II | R¹ᵃ-I | R²ᵃ-II |
| X-I | Y-II | R¹ᵃ-I | R²ᵃ-III |
| X-I | Y-II | R¹ᵃ-I | R²ᵃ-IV |
| X-I | Y-II | R¹ᵃ-II | R²ᵃ-I |
| X-I | Y-II | R¹ᵃ-II | R²ᵃ-II |
| X-I | Y-II | R¹ᵃ-III | R²ᵃ-I |
| X-I | Y-II | R¹ᵃ-IV | R²ᵃ-I |
| X-I | Y-II | R¹ᵃ-IV | R²ᵃ-II |
| X-I | Y-II | R¹ᵃ-IV | R²ᵃ-III |
| X-I | Y-II | R¹ᵃ-V | R²ᵃ-I |
| X-I | Y-II | R¹ᵃ-V | R²ᵃ-II |
| X-I | Y-II | R¹ᵃ-V | R²ᵃ-III |
| X-I | Y-II | R¹ᵃ-VI | R²ᵃ-I |
| X-I | Y-II | R¹ᵃ-VII | R²ᵃ-I |
| X-I | Y-II | R¹ᵃ-VIII | R²ᵃ-I |
| X-I | Y-II | R¹ᵃ-VIII | R²ᵃ-II |
| X-I | Y-II | R¹ᵃ-IX | R²ᵃ-I |
| X-I | Y-II | R¹ᵃ-IX | R²ᵃ-II |
| X-I | Y-II | R¹ᵃ-X | R²ᵃ-I |
| X-I | Y-II | R¹ᵃ-XI | R²ᵃ-I |
| X-I | Y-IV | R¹ᵃ-I | R²ᵃ-I |
| X-I | Y-IV | R¹ᵃ-I | R²ᵃ-II |
| X-I | Y-IV | R¹ᵃ-I | R²ᵃ-III |
| X-I | Y-IV | R¹ᵃ-II | R²ᵃ-I |
| X-I | Y-IV | R¹ᵃ-III | R²ᵃ-I |
| X-I | Y-IV | R¹ᵃ-IV | R²ᵃ-I |
| X-I | Y-IV | R¹ᵃ-IV | R²ᵃ-II |
| X-I | Y-IV | R¹ᵃ-V | R²ᵃ-I |
| X-I | Y-IV | R¹ᵃ-V | R²ᵃ-II |
| X-I | Y-IV | R¹ᵃ-VI | R²ᵃ-I |
| X-I | Y-IV | R¹ᵃ-VII | R²ᵃ-I |
| X-I | Y-IV | R¹ᵃ-VIII | R²ᵃ-I |
| X-I | Y-IV | R¹ᵃ-IX | R²ᵃ-I |
| X-I | Y-IV | R¹ᵃ-X | R²ᵃ-I |
| X-I | Y-IV | R¹ᵃ-XI | R²ᵃ-I |
| X-I | Y-V | R¹ᵃ-I | R²ᵃ-I |
| X-I | Y-V | R¹ᵃ-I | R²ᵃ-II |
| X-I | Y-V | R¹ᵃ-II | R²ᵃ-I |
| X-I | Y-V | R¹ᵃ-III | R²ᵃ-I |
| X-I | Y-V | R¹ᵃ-IV | R²ᵃ-I |
| X-I | Y-V | R¹ᵃ-V | R²ᵃ-I |
| X-I | Y-V | R¹ᵃ-VI | R²ᵃ-I |
| X-I | Y-VI | R¹ᵃ-I | R²ᵃ-I |
| X-I | Y-VI | R¹ᵃ-II | R²ᵃ-I |
| X-II | Y-II | R¹ᵃ-I | R²ᵃ-I |
| X-II | Y-II | R¹ᵃ-I | R²ᵃ-II |
| X-II | Y-II | R¹ᵃ-I | R²ᵃ-III |
| X-II | Y-II | R¹ᵃ-II | R²ᵃ-I |
| X-II | Y-II | R¹ᵃ-III | R²ᵃ-I |
| X-II | Y-II | R¹ᵃ-IV | R²ᵃ-I |
| X-II | Y-II | R¹ᵃ-IV | R²ᵃ-II |
| X-II | Y-II | R¹ᵃ-V | R²ᵃ-I |
| X-II | Y-II | R¹ᵃ-V | R²ᵃ-II |
| X-II | Y-II | R¹ᵃ-VI | R²ᵃ-I |
| X-II | Y-II | R¹ᵃ-VII | R²ᵃ-I |
| X-II | Y-II | R¹ᵃ-VIII | R²ᵃ-I |
| X-II | Y-II | R¹ᵃ-IX | R²ᵃ-I |
| X-II | Y-II | R¹ᵃ-X | R²ᵃ-I |
| X-II | Y-II | R¹ᵃ-XI | R²ᵃ-I |
| X-II | Y-IV | R¹ᵃ-I | R²ᵃ-I |
| X-II | Y-IV | R¹ᵃ-I | R²ᵃ-II |
| X-II | Y-IV | R¹ᵃ-II | R²ᵃ-I |
| X-II | Y-IV | R¹ᵃ-III | R²ᵃ-I |
| X-II | Y-IV | R¹ᵃ-IV | R²ᵃ-I |

TABLE 2-continued

| X | Y | $R^{1a}$ | $R^{2a}$ |
|---|---|---|---|
| X-II | Y-IV | $R^{1a}$-V | $R^{2a}$-I |
| X-II | Y-IV | $R^{1a}$-VI | $R^{2a}$-I |
| X-II | Y-IV | $R^{1a}$-VII | $R^{2a}$-I |
| X-II | Y-IV | $R^{1a}$-VIII | $R^{2a}$-I |
| X-II | Y-IV | $R^{1a}$-IX | $R^{2a}$-I |
| X-II | Y-IV | $R^{1a}$-X | $R^{2a}$-I |
| X-II | Y-IV | $R^{1a}$-XI | $R^{2a}$-I |
| X-II | Y-V | $R^{1a}$-I | $R^{2a}$-I |
| X-II | Y-V | $R^{1a}$-II | $R^{2a}$-I |
| X-II | Y-VI | $R^{1a}$-I | $R^{2a}$-I |
| X-II | Y-VI | $R^{1a}$-II | $R^{2a}$-I |
| X-III | Y-II | $R^{1a}$-I | $R^{2a}$-I |
| X-III | Y-II | $R^{1a}$-I | $R^{2a}$-II |
| X-III | Y-II | $R^{1a}$-II | $R^{2a}$-I |
| X-III | Y-II | $R^{1a}$-III | $R^{2a}$-I |
| X-III | Y-II | $R^{1a}$-IV | $R^{2a}$-I |
| X-III | Y-II | $R^{1a}$-V | $R^{2a}$-I |
| X-III | Y-II | $R^{1a}$-VI | $R^{2a}$-I |
| X-III | Y-IV | $R^{1a}$-I | $R^{2a}$-I |
| X-III | Y-IV | $R^{1a}$-II | $R^{2a}$-I |
| X-III | Y-V | $R^{1a}$-I | $R^{2a}$-I |
| X-III | Y-V | $R^{1a}$-II | $R^{2a}$-I |
| X-III | Y-VI | $R^{1a}$-I | $R^{2a}$-I |
| X-III | Y-VI | $R^{1a}$-II | $R^{2a}$-I |
| X-IV | Y-II | $R^{1a}$-I | $R^{2a}$-I |
| X-IV | Y-II | $R^{1a}$-II | $R^{2a}$-I |
| X-IV | Y-IV | $R^{1a}$-I | $R^{2a}$-I |
| X-IV | Y-IV | $R^{1a}$-II | $R^{2a}$-I |
| X-IV | Y-V | $R^{1a}$-I | $R^{2a}$-I |
| X-IV | Y-V | $R^{1a}$-II | $R^{2a}$-I |
| X-IV | Y-VI | $R^{1a}$-I | $R^{2a}$-I |
| X-IV | Y-VI | $R^{1a}$-II | $R^{2a}$-I |

The compounds of the present invention can be produced, for example, by the following methods.

a $C_1$ to $C_4$ alkylcarbonyloxy group (for example, a pivaloyloxy group), a $C_1$ to $C_4$ alkoxycarbonyloxy group (for example, an isobutyloxycarbonyloxy group) or an azolyl group (for example, an imidazol-1-yl group)) which can be synthesized from a compound represented by General Formula (5) (where $A^1$, $A^2$, $A^3$, $A^4$, $G^1$, X, Y, $R^3$, $R^{3a}$, $R^{3b}$, m and n represent the same as the respective definitions in the above) by using methods known in the literature, for example, a method of reacting with a halogenating agent such as thionyl chloride, phosphorus pentachloride or oxalyl chloride according to the method described in Journal of Medicinal Chemistry (J. Med. Chem.), vol. 34, p. 1630 (1991) and the like, a method of reacting with a halogenated organic acid such as pivaloyl chloride or isobutyl chloroformate, if necessary in the presence of a base, according to the methods described in Tetrahedron Letters (Tetrahedron Lett.), vol. 44, p. 4819 (2003), Journal of Medicinal Chemistry (J. Med. Chem.), vol. 34, p. 222 (1991) and the like, or a method of reacting with carbonyldiimidazole, sulfonyldiimidazole or the like according to The Journal of Organic Chemistry (J. Org. Chem.), vol. 54, p. 5620 (1989), and 1 to 10 equivalent(s) of a compound represented by General Formula (7) (where $R^1$ and $R^2$ represent the same as the respective definitions in the above), if necessary using a solvent such as dichloromethane, chloroform, diethyl ether, tetrahydrofuran, 1,4-dioxane, ethyl acetate or acetonitrile, if necessary in the presence of 1 to 2 equivalent(s) of a base such as potassium carbonate, triethylamine, pyridine or 4-(dimethylamino)pyridine with respect to 1 equivalent of the compound represented by General Formula (6), at a temperature ranging from 0° C. to a reflux temperature of the solvent for 10 minutes to 24 hours, a compound of the present invention represented by General Production Method A

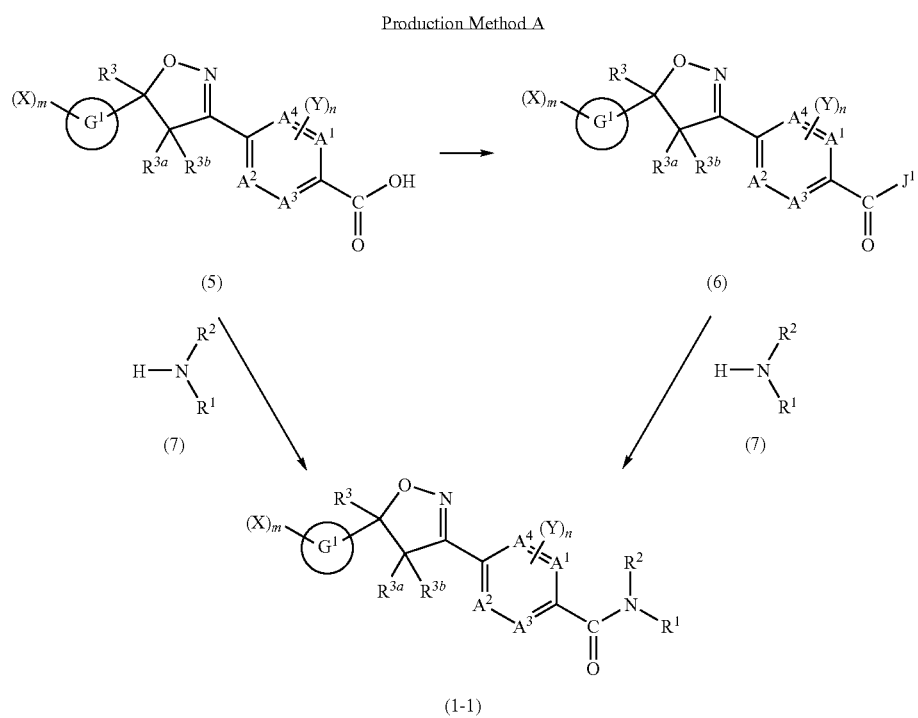

By reacting 1 equivalent of a compound represented by General Formula (6) (where $A^1$, $A^2$, $A^3$, $A^4$, $G^1$, X, Y, $R^3$, $R^{3a}$, $R^{3b}$, m, n represent the same as the respective definitions in the above and $J^1$ represents a chlorine atom, a bromine atom, Formula (1-1) (where $A^1$, $A^2$, $A^3$, $A^4$, $G^1$, Y, $R^1$, $R^2$, $R^3$, $R^{3a}$, $R^{3b}$, m and n represent the same as the respective definitions in the above) corresponding to General Formula (1) in which $G^2$ is $G^2$-1 and W is an oxygen atom can be synthesized.

Furthermore, by reacting 1 equivalent of the compound represented by General Formula (5) and 1 to 20 equivalent(s) of the compound represented by General Formula (7), if necessary using a solvent such as dichloromethane, chloroform, diethyl ether, tetrahydrofuran or 1,4-dioxane, if necessary in the presence of 1 to 4 equivalent(s) of a base such as potassium carbonate, triethylamine, pyridine or 4-(dimethylamino)pyridine with respect to 1 equivalent of the compound represented by General Formula (5), using 1 to 4 equivalent(s) of a condensing agent such as WSC (1-ethyl-3-(3-dimethylaminopropyl)-carbodiimide hydrochloride) or CDI (carbonyldiimidazole) with respect to 1 equivalent of the compound represented by General Formula (5) at a temperature ranging from 0° C. to a reflux temperature of the solvent for 10 minutes to 24 hours, the compound of the present invention represented by General Formula (1-1) can be also obtained.

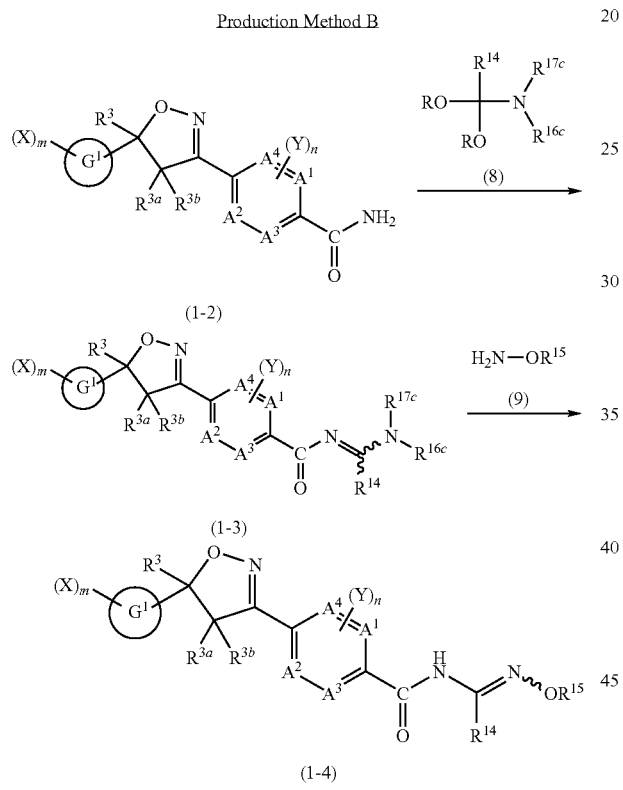

By reacting 1 equivalent of a compound of the present invention represented by General Formula (1-2) (where $A^1$, $A^2$, $A^3$, $A^4$, $G^1$, X, Y, $R^3$, $R^{3a}$, $R^{3b}$, m and n represent the same as the respective definitions in the above) corresponding to General Formula (1) in which $G^2$ is $G^2$-1, W is an oxygen atom, and $R^1$ and $R^2$ are hydrogen atoms, and 2 to 10 equivalents of a compound represented by General Formula (8) (where $R^{14}$, $R^{16c}$ and $R^{17c}$ represent the same as the respective definitions in the above and R represents a $C_1$ to $C_6$ alkyl), if necessary under an atmosphere of an inert gas such as nitrogen or argon, without solvent or with a solvent such as benzene or toluene at a temperature ranging from room temperature to a reflux temperature of the solvent for 1 hour to 24 hours, a compound of the present invention represented by General Formula (1-3) (where $A^1$, $A^2$, $A^3$, $A^4$, $G^1$, X, Y, $R^3$, $R^{3a}$, $R^{3b}$, $R^{14}$, $R^{16c}$, $R^{17c}$, m and n represent the same as the respective definitions in the above) corresponding to General Formula (1) in which $G^2$ is $G^2$-1, W is an oxygen atom, and $R^2$ together with $R^1$ forms $=C(R^{14})N(R^{17c})R^{16c}$ can be obtained.

The compounds represented by General Formula (8) used here are known compounds and some of them are commercially available. The others can be easily synthesized by methods known in the literature, for example, The Journal of Organic Chemistry (J. Org. Chem.), vol. 49, p. 3659 (1984).

By reacting 1 equivalent of the compound of the present invention represented by General Formula (1-3) obtained in such a manner and 1 to 5 equivalent(s) of alkoxyamines represented by General Formula (9) (where $R^{15}$ represents the same as the definition in the above) or salts thereof, if necessary using a solvent such as methanol, ethanol, diethyl ether, tetrahydrofuran or 1,4-dioxane, furthermore, when the compound represented by General Formula (9) is a salt, if necessary with the addition of 1 to 4 equivalent(s) of a base such as triethylamine or 1,8-diazabicyclo(5,4,0)-7-undecene, at a temperature ranging from room temperature to a reflux temperature of the solvent for 10 minutes to 24 hours, a compound of the present invention represented by General Formula (1-4) (where $A^1$, $A^2$, $A^3$, $A^4$, $G^1$, X, Y, $R^3$, $R^{3a}$, $R^{3b}$, $R^{14}$, $R^{15}$, m and n represent the same as the respective definitions in the above) corresponding to General Formula (1) in which $G^2$ is $G^2$-1, W is an oxygen atom, $R^1$ is $-C(R^{14})=NOR^{15}$, and $R^2$ is a hydrogen atom can be obtained.

The compounds represented by General Formula (9) used here are known compounds and some of them are commercially available. The others can be easily synthesized according to methods known in the literature, for example, The Journal of Organic Chemistry (J. Org. Chem.), vol. 70, p. 6991 (2005).

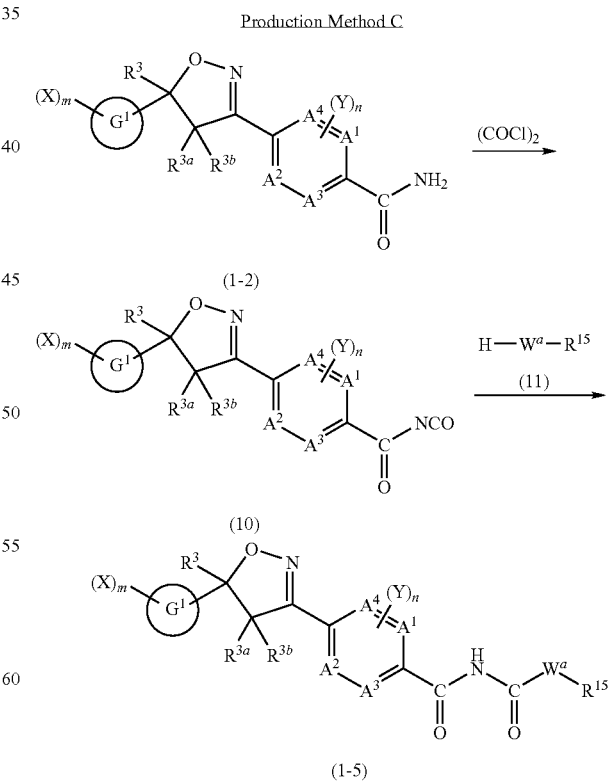

To a compound of the present invention represented by General Formula (1-2) (where $A^1$, $A^2$, $A^3$, $A^4$, $G^1$, X, Y, $R^3$, $R^{3a}$, $R^{3b}$, m and n represent the same as the respective definitions in the above) corresponding to General Formula (1) in which $G^2$ is $G^2$-1, W is an oxygen atom, and $R^1$ and $R^2$ are hydrogen atoms, under an atmosphere of an inert gas such as nitrogen or argon, if necessary using a solvent such as toluene, dichloromethane or 1,2-dichloroethane, 1 to 1.5 equivalent(s) of oxalyl chloride with respect to 1 equivalent of the compound of the present invention represented by General Formula (1-2) is added at a temperature ranging from 0° C. to room temperature. Subsequently, by reacting the mixture at a temperature ranging from room temperature to a reflux temperature of the solvent for 1 hour to 24 hours, a substituted acyl isocyanate represented by General Formula (10) (where $A^1$, $A^2$, $A^3$, $A^4$, $G^1$, X, Y, $R^3$, $R^{3a}$, $R^{3b}$, m and n represent the same as the respective definitions in the above) can be obtained.

By reacting 1 equivalent of the substituted acyl isocyanate represented by General Formula (10) obtained in such a manner and 1 to 20 equivalent(s) of an alcohol or a thiol represented by General Formula (11) (where $W^a$ represents an oxygen atom or a sulfur atom, and $R^{15}$ represents the same as the definition in the above), if necessary in the presence of 1 to 4 equivalent(s) of a base such as potassium carbonate, triethylamine, pyridine or 4-(dimethylamino)pyridine, if necessary using a solvent such as benzene, toluene, dichloromethane, chloroform, diethyl ether, tetrahydrofuran or 1,4-dioxane, at a temperature ranging from 0° C. to a reflux temperature of the solvent for 10 minutes to 24 hours, a compound of the present invention represented by General Formula (1-5) (where $A^1$, $A^2$, $A^3$, $A^4$, $G^1$, X, Y, $R^3$, $R^{3a}$, $R^{3b}$, $R^{15}$, m and n represent the same as the respective definitions in the above, and $W^a$ represents an oxygen atom or a sulfur atom) corresponding to General Formula (1) in which $G^2$ is $G^2$-1, W is an oxygen atom, $R^1$ is —C(O)—$W^a$—$R^{15}$, and $R^2$ is a hydrogen atom can be obtained.

The compounds represented by General Formula (11) used here are known compounds and some of them are commercially available. The others can be easily synthesized according to general synthetic methods for alcohols and thiols described in the literature.

Production Method D

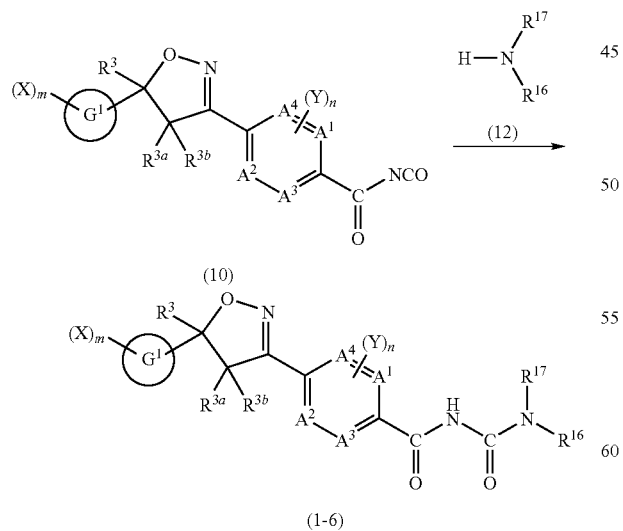

By reacting 1 equivalent of the substituted acyl isocyanate represented by General Formula (10) (where $A^1$, $A^2$, $A^3$, $A^4$, $G^1$, X, Y, $R^3$, $R^{3a}$, $R^{3b}$, m and n represent the same as the respective definitions in the above) used in Production Method C and 1 to 20 equivalent(s) of a primary or secondary amine represented by General Formula (12) (where $R^{16}$ and $R^{17}$ represent the same as the respective definitions in the above), if necessary using a solvent such as benzene, toluene, dichloromethane, chloroform, diethyl ether, tetrahydrofuran or 1,4-dioxane, at a temperature ranging from 0° C. to a reflux temperature of the solvent for 10 minutes to 24 hours, a compound of the present invention represented by General Formula (1-6) (where $A^1$, $A^2$, $A^3$, $A^4$, $G^1$, X, Y, $R^3$, $R^{3a}$, $R^{3b}$, $R^{16}$, $R^{17}$, m and n represent the same as the respective definitions in the above) corresponding to General Formula (1) in which $G^2$ is $G^2$-1, W is an oxygen atom, $R^1$ is —C(O)N($R^{17}$)$R^{16}$, and $R^2$ is a hydrogen atom can be obtained.

Production Method E

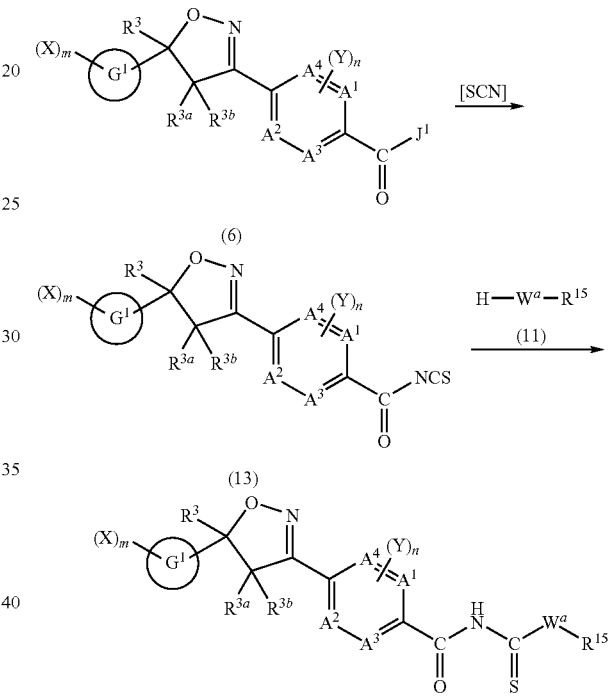

To the compound represented by General Formula (6) (where $A^1$, $A^2$, $A^3$, $A^4$, $G^1$, X, Y, $R^3$, $R^{3a}$, $R^{3b}$, m, n and $J^1$ represent the same as the respective definitions in the above) used in Production Method A, for example, under an atmosphere of an inert gas such as nitrogen or argon, if necessary using a solvent such as benzene, toluene, dichloromethane, acetone or acetonitrile, 1 to 1.5 equivalent(s) of potassium thiocyanate, sodium thiocyanate or ammonium thiocyanate with respect to 1 equivalent of the compound represented by General Formula (6) is added at a temperature ranging from 0° C. to room temperature. Subsequently, by reacting the mixture at a temperature ranging from room temperature to a reflux temperature of the solvent for 10 minutes to 24 hours, a substituted acyl isothiocyanate represented by General Formula (13) (where $A^1$, $A^2$, $A^3$, $A^4$, $G^1$, X, Y, $R^3$, $R^{3a}$, $R^{3b}$, m and n represent the same as the respective definitions in the above) can be obtained.

By reacting the substituted acyl isothiocyanate represented by General Formula (13) obtained in such a manner and an alcohol or a thiol represented by General Formula (11) (where $W^a$ and $R^{15}$ represent the same as the respective definitions in the above) under substantially the same condition as that in Production Method C, a compound of the present invention represented by General Formula (1-7) (where $A^1, A^2, A^3, A^4, G^1, W^a, Y, R^3, R^{3a}, R^{3b}, R^{15}$, m and n represent the same as the respective definitions in the above) corresponding to General Formula (1) in which $G^2$ is $G^2$-1, W is an oxygen atom, $R^1$ is $-C(S)-W^a-R^{15}$, and $R^2$ is a hydrogen atom can be obtained.

Production Method F

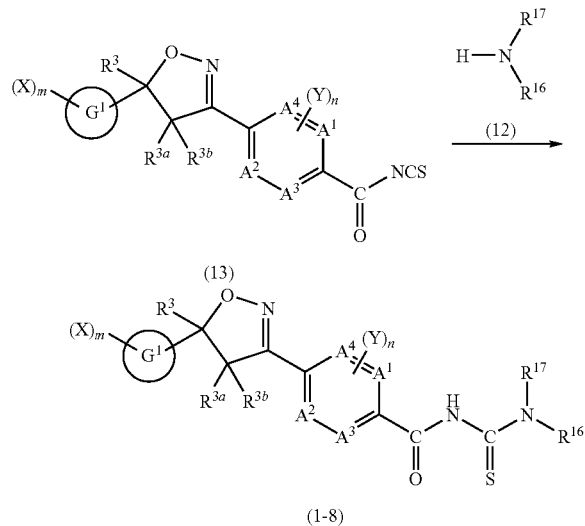

By reacting the substituted acyl isothiocyanate represented by General Formula (13) (where $A^1, A^2, A^3, A^4, G^1, X, Y, R^3, R^{3a}, R^{3b}$, m and n represent the same as the respective definitions in the above) used in Production Method E and a primary or secondary amine represented by General Formula (12) (where $R^{16}$ and $R^{17}$ represent the same as the respective definitions in the above) under substantially the same condition as that in Production Method D, a compound of the present invention represented by General Formula (1-8) (where $A^1, A^2, A^3, A^4, G^1, X, Y, R^3, R^{3a}, R^{3b}, R^{16}, R^{17}$, m and n represent the same as the respective definitions in the above) corresponding to General Formula (1) in which $G^2$ is $G^2$-1, W is an oxygen atom, $R^1$ is $-C(S)N(R^{17})R^{16}$, and $R^2$ is a hydrogen atom can be obtained.

Production Method G

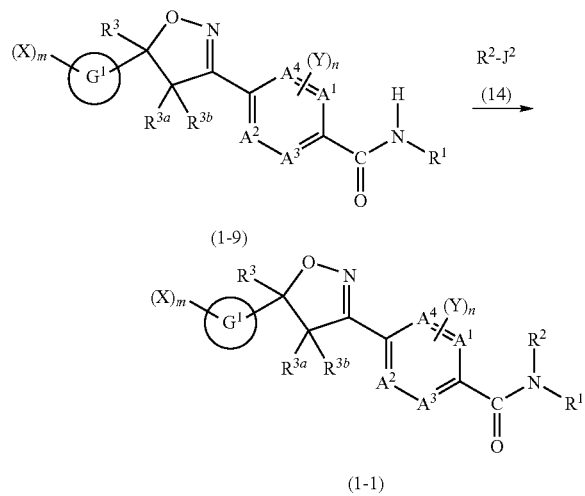

By reacting 1 equivalent of a compound of the present invention represented by General Formula (1-9) (where $A^1, A^2, A^3, A^4, G^1, X, Y, R^1, R^3, R^{3a}, R^{3b}$, m and n represent the same as the respective definitions in the above) corresponding to General Formula (1) in which $G^2$ is $G^2$-1, W is an oxygen atom, and $R^2$ is a hydrogen atom and 1 to 10 equivalent(s) of a compound represented by General Formula (14) (where $R^2$ is the same definition in the above except a hydrogen atom, $J^2$ represents a favorable leaving group such as a chlorine atom, a bromine atom, an iodine atom, a $C_1$ to $C_4$ alkylcarbonyloxy group (for example, a pivaloyloxy group), a $C_1$ to $C_4$ alkyl sulfonate group (for example, a methanesulfonyloxy group), a $C_1$ to $C_4$ haloalkyl sulfonate group (for example, a trifluoromethanesulfonyloxy group), an aryl sulfonate group (for example, a benzenesulfonyloxy group and a p-toluenesulfonyloxy group) or an azolyl group (for example, an imidazol-1-yl group)), if necessary in the presence of 1 to 3 equivalent(s) of a base such as sodium hydride, potassium tertiary butoxide, potassium hydroxide, potassium carbonate, triethylamine or pyridine with respect to 1 equivalent of the compound of the present invention represented by General Formula (1-9), if necessary using a polar solvent such as tetrahydrofuran, 1,4-dioxane, acetonitrile or N,N-dimethylformamide, at a temperature ranging from 0 to 90° C. for 10 minutes to 24 hours, a compound of the present invention represented by General Formula (1-1) (where $A^1, A^2, A^3, A^4, G^1, X, Y, R^1, R^3, R^{3a}, R^{3b}$, m and n represent the same as the respective definitions in the above, and $R^2$ is the same definition in the above except a hydrogen atom) corresponding to General Formula (1) in which $G^2$ is $G^2$-1, and W is an oxygen atom can be obtained.

Production Method H

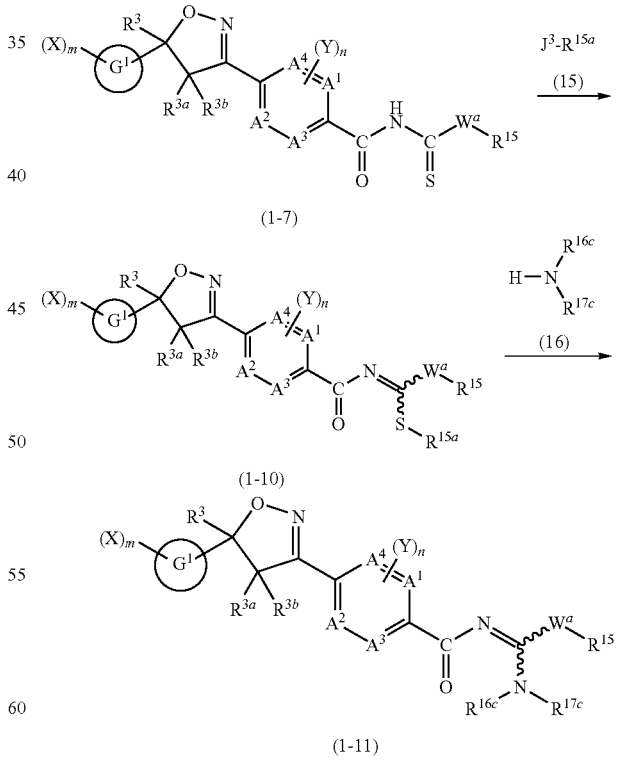

By reacting the compound of the present invention represented by General Formula (1-7) (where $A^1, A^2, A^3, A^4, G^1, W^a, X, Y, R^3, R^{3a}, R^{3b}, R^{15}$, m and n represent the same as the respective definitions in the above) corresponding to General Formula (1) in which $G^2$ is $G^2$-1, W is an oxygen atom, $R^1$ is —C(S)—$W^a$—$R^{15}$, and $R^2$ is a hydrogen atom and a compound represented by General Formula (15) (where $R^{15a}$ represents the same as the definition in the above, and $J^3$ represents a chlorine atom, a bromine atom, an iodine atom or the like) under substantially the same condition as that in Production Method G, a compound of the present invention represented by General Formula (1-10) (where $A^1, A^2, A^3, A^4, G^1, W^a, X, Y, R^3, R^{3a}, R^{3b}, R^{15}, R^{15a}$, m and n represent the same as the respective definitions in the above) corresponding to General Formula (1) in which $G^2$ is $G^2$-1, W is an oxygen atom, $R^2$ together with $R^1$ forms =C($SR^{15a}$)—$W^a$—$R^{15}$ can be obtained.

By reacting 1 equivalent of the compound of the present invention represented by General Formula (1-10) obtained in such a manner and 1 to 50 equivalent(s) of a primary or secondary amine represented by General Formula (16) (where $R^{16c}$ and $R^{17c}$ represent the same as the respective definitions in the above) or a salt thereof, if necessary in the presence of 1 to 20 equivalent(s) of a base such as potassium carbonate, sodium hydrogen carbonate, triethylamine, diisopropylethylamine or pyridine with respect to 1 equivalent of the compound of the present invention represented by General Formula (1-10), if necessary using toluene, dichloromethane, chloroform, methanol, ethanol, diethyl ether, tetrahydrofuran, 1,4-dioxane, ethyl acetate, N,N-dimethylformamide, acetic acid, acetonitrile, water or the like or a mixture thereof at any ratio as solvent, at a temperature ranging from 0° C. to a reflux temperature of the solvent for 5 minutes to 24 hours, a compound of the present invention represented by General Formula (1-11) (where $A^1, A^2, A^3, A^4, G^1, W^a, X, Y, R^3, R^{3a}, R^{3b}, R^{15}, R^{16c}, R^{17c}$, m and n represent the same as the respective definitions in the above) corresponding to General Formula (1) in which $G^2$ is $G^2$-1, W is an oxygen atom, $R^2$ together with $R^1$ forms =C(N($R^{17c}$)$R^{16c}$)—$W^a$—$R^{15}$ can be obtained.

Production Method I

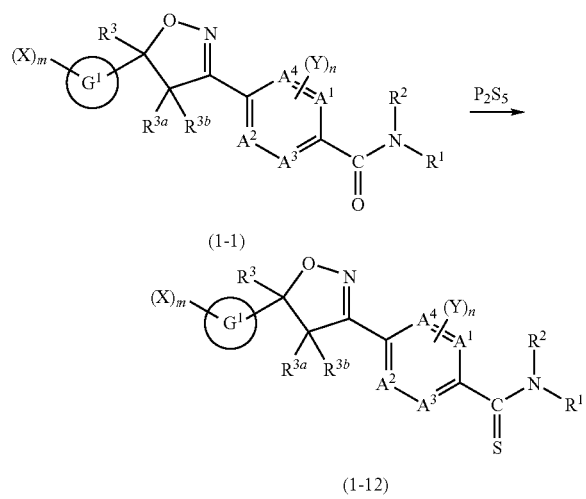

(1-1)

(1-12)

By reacting 1 equivalent of a compound of the present invention represented by General Formula (1-1) (where $A^1, A^2, A^3, A^4, G^1, X, Y, R^1, R^2, R^3, R^{3a}, R^{3b}$, m and n represent the same as the respective definitions in the above) corresponding to General Formula (1) in which $G^2$ is $G^2$-1 and W is an oxygen atom and 1 to 10 equivalent(s) of a sulfurizing agent such as diphosphorus pentasulfide, diphosphorus pentasulfide-HMDO (hexamethyldisiloxane) or Lawesson's Reagent (2,4-bis(4-methoxyphenyl)-1,3,2,4-dithiadiphosphetane 2,4-disulfide), if necessary in the presence of 1 to 4 equivalent(s) of a base such as sodium hydrogen carbonate, triethylamine or pyridine with respect to 1 equivalent of the compound of the present invention represented by General Formula (1-1), if necessary using a solvent such as benzene, toluene, chlorobenzene, dichloromethane, chloroform, 1,2-dimethoxyethane, tetrahydrofuran, 1,4-dioxane or HMPA, at a temperature ranging from room temperature to a reflux temperature of the reaction mixture for 10 minutes to 50 hours, or in pyridine as solvent at a temperature ranging from 80° C. to a reflux temperature the reaction mixture for 1 to 3 hours, a compound of the present invention represented by General Formula (1-12) (where $A^1, A^2, A^3, A^4, G^1, X, Y, R^1, R^2, R^3, R^{3a}, R^{3b}$, m and n represent the same as the respective definitions in the above) corresponding to General Formula (1) in which $G^2$ is $G^2$-1 and W is a sulfur atom can be obtained.

Production Method J

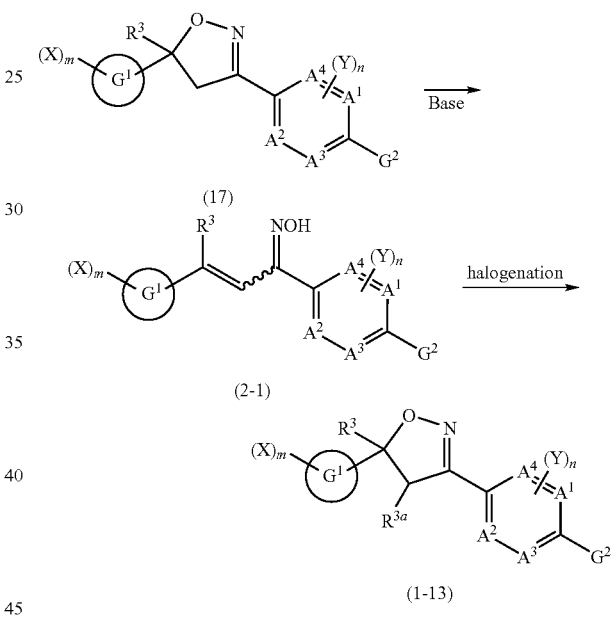

(17)

(2-1)

(1-13)

By reacting a compound represented by General Formula (17) (where $A^1, A^2, A^3, A^4, G^1, G^2, X, Y, R^3$, m and n represent the same as the respective definitions in the above), if necessary using a solvent such as diethyl ether, tetrahydrofuran or tetrahydrofuran-hexane, with 1 to 3 equivalent(s) of a strong base such as lithium aluminium hydride, lithium diisopropylamide or lithium hexamethyldisilazane with respect to 1 equivalent of the compound represented by General Formula (17) at a temperature ranging from −20° C. to room temperature for 1 minute to 1 hour, a compound of the present invention represented by General Formula (2-1) (where $A^1, A^2, A^3, A^4, G^1, G^2, X, Y, R^3$, m and n represent the same as the respective definitions in the above) corresponding to General Formula (2) in which $R^{3c}$ is a hydrogen atom can be obtained.

By reacting the compound of the present invention represented by General Formula (2-1) obtained in such a manner, if necessary using a solvent such as benzene, toluene, t-butyl methyl ether or tetrahydrofuran, with 1 to 2 equivalent(s) of a halogenating agent such as N-chlorosuccinimide, N-bromosuccinimide or bromine with respect to 1 equivalent of the compound of the present invention represented by General Formula (2-1) at a temperature ranging from 0 to 50° C. for 15 minutes to 24 hours, a compound of the present invention represented by General Formula (1-13) (where $A^1, A^2, A^3, A^4, G^1, G^2, X, Y, R^3$, m and n represent the same as the respective definitions in the above and $R^{3a}$ represents a chlorine atom, bromine atom or iodine atom) corresponding to General Formula (1) in which $R^{3b}$ is a hydrogen atom can be obtained.

Production Method K

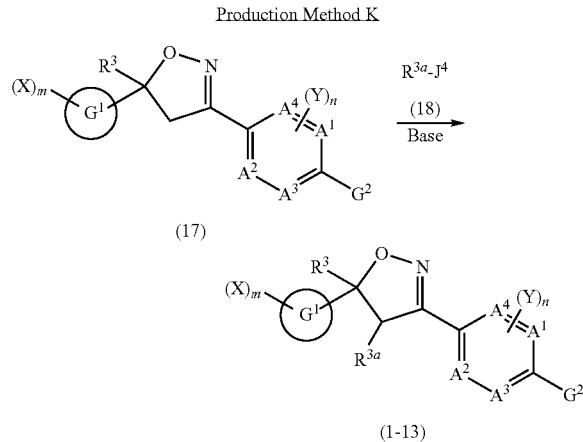

(17)

(1-13)

To a compound represented by General Formula (17) (where $A^1, A^2, A^3, A^4, G^1, G^2, X, Y, R^3$, m and n represent the same as the respective definitions in the above) in a solvent such as tetrahydrofuran or tetrahydrofuran-hexane, 1 to 2 equivalent(s) of a base such as lithium diisopropylamide or lithium hexamethyldisilazane with respect to 1 equivalent of the compound represented by General Formula (17) is added at a temperature ranging from −78° C. to −20° C. Subsequently, by reacting the mixture with 1 to 10 equivalent(s) of a compound represented by General Formula (18) (where $R^{3a}$ represents a halogen atom, a $C_1$ to $C_6$ alkyl group, a $C_1$ to $C_6$ haloalkyl group, a $C_3$ to $C_6$ alkenyl group, a $C_3$ to $C_6$ alkynyl group or the like, and $J^4$ represents a chlorine atom, a bromine atom, an iodine atom, a $C_1$ to $C_4$ alkyl sulfonate group (for example, a methanesulfonyloxy group), a $C_1$ to $C_4$ haloalkyl sulfonate group (for example, a trifluoromethanesulfonyloxy group), a succinimide group or the like) with respect to 1 equivalent of the compound represented by General Formula (17) at a temperature ranging from −78° C. to −20° C. for 15 minutes to 5 hours, a compound of the present invention represented by General Formula (1-13) (where $A^1, A^2, A^3, A^4, G^1, G^2, X, Y, R^3$, m and n represent the same as the respective definitions in the above, and $R^{3a}$ represents a halogen atom, a $C_1$ to $C_6$ alkyl group, a $C_1$ to $C_6$ haloalkyl group, a $C_3$ to $C_6$ alkenyl group, a $C_3$ to $C_6$ alkynyl group or the like) corresponding to General Formula (1) in which $R^{3b}$ is a hydrogen atom can be obtained.

Production Method L

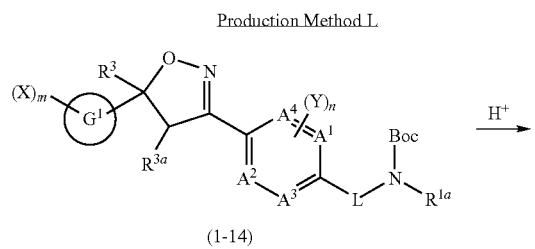

(1-14)

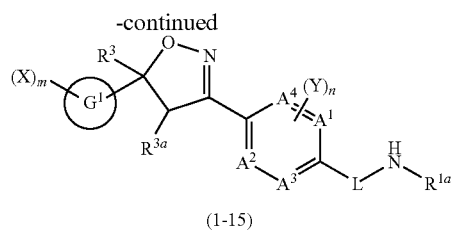

(1-15)

By reacting a compound of the present invention represented by General Formula (1-14) (where $A^1, A^2, A^3, A^4, G^1, L, X, Y, R^{1a}, R^3, R^{3a}$, m and n represent the same as the respective definitions in the above) corresponding to General Formula (1) in which $G^2$ is $G^2$-2, $R^{3b}$ is a hydrogen atom, and $R^{2a}$ is a tert-butoxycarbonyl group under a common condition of elimination reaction of a tert-butoxycarbonyl group according to methods known in the literature, for example, Synthesis, p. 480 (1994) and Tetrahedron Letters (Tetrahedron Lett.), vol. 39, p. 4869 (1998), a compound of the present invention represented by General Formula (1-15) (where $A^1, A^2, A^3, A^4, G^1, L, X, Y, R^{1a}, R^3, R^{3a}$, m and n represent the same as the respective definitions in the above) corresponding to General Formula (1) in which $G^2$ is $G^2$-2, and $R^{2a}$ and $R^{3b}$ are hydrogen atoms can be synthesized.

Production Method M

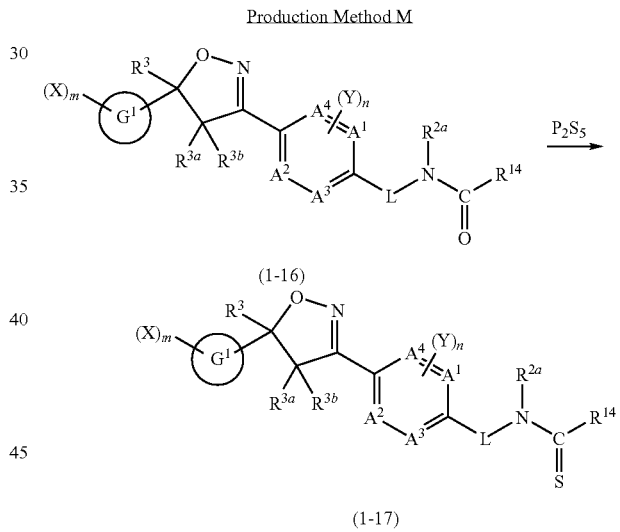

(1-16)

(1-17)

By reacting a compound of the present invention represented by General Formula (1-16) (where $A^1, A^2, A^3, A^4, G^1, L, X, Y, R^{2a}, R^3, R^{3a}, R^{3b}, R^{14}$, m and n represent the same as the respective definitions in the above) corresponding to General Formula (1) in which $G^2$ is $G^2$-2 and $R^{1a}$ is —C(O)$R^{14}$, and a sulfurizing agent such as diphosphorus pentasulfide, diphosphorus pentasulfide-hexamethyldisiloxane (HMDO) or Lawesson's Reagent (2,4-bis(4-methoxyphenyl)-1,3,2,4-dithiadiphosphetane 2,4-disulfide) under substantially the same condition as that in Production Method I, a compound of the present invention represented by General Formula (1-17) (where $A^1, A^2, A^3, A^4, G^1, L, X, Y, R^{2a}, R^3, R^{3a}, R^{3b}, R^{14}$, m and n represent the same as the respective definitions in the above) corresponding to General Formula (1) in which $G^2$ is $G^2$-2 and $R^{1a}$ is —C(S)$R^{14}$ can be obtained.

In Production Method A to Production Method M, the objective compounds of the present invention can be obtained by subjecting the reaction mixture after the completion of the reaction to a common after treatment: for example, the reaction mixture is directly concentrated; or dissolved in an organic solvent, washed with water, and then concentrated; or poured into ice water, extracted with an organic solvent, and then concentrated. Furthermore, when purification is required, the objective compound can be separated and purified by any purification method such as recrystallization, column chromatography, thin layer chromatography or preparative liquid chromatography.

The compound represented by General Formula (5) used in Production Method A can be synthesized, for example, according to Reaction Formula 1 and Reaction Formula 2 below.

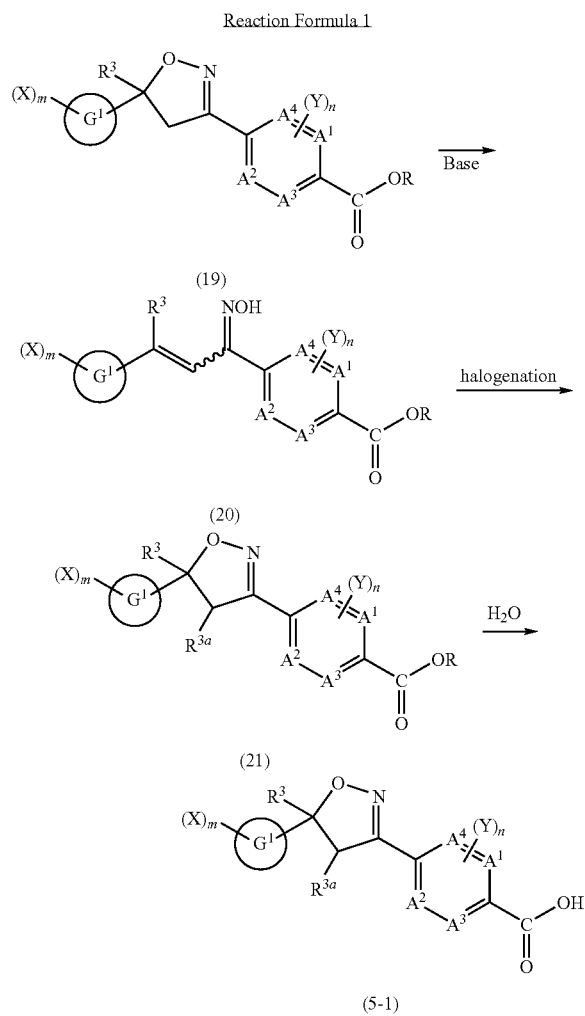

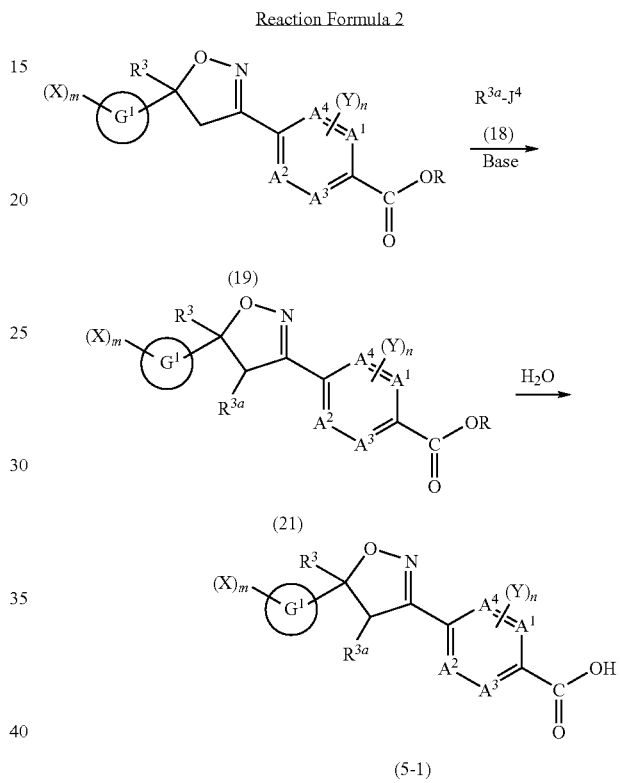

By hydrolyzing a compound represented by General Formula (21) (where $A^1$, $A^2$, $A^3$, $A^4$, $G^1$, X, Y, $R^3$, m, n and R represent the same as the respective definitions in the above, and $R^{3a}$ represents a chlorine atom, a bromine atom or an iodine atom), which is obtained by reacting a known compound represented by General Formula (19) (where $A^1$, $A^2$, $A^3$, $A^4$, $G^1$, X, Y, $R^3$, m and n represent the same as the respective definitions in the above, and R represents a $C_1$ to $C_6$ alkyl group) described in International Patent Application Publication (WO 2005/085216), Japanese Patent Application Publication (JP 2007/308471) and the like under substantially the same condition as that in Production Method J, according to a common condition for ester hydrolysis known in the literature, for example, the reaction condition described in Angewandte Chemie (Angew. Chem.), vol. 63, p. 329 (1951) or Journal of the American Chemical Society (J. Am. Chem. Soc.), vol. 51, p. 1865 (1929), a compound represented by General Formula (5-1) (where $A^1$, $A^2$, $A^3$, $A^4$, $G^1$, X, Y, $R^3$, m and n represent the same as the respective definitions in the above, and $R^{3a}$ represents a chlorine atom, a bromine atom or an iodine atom) corresponding to General Formula (5) in which $R^{3b}$ is a hydrogen atom can be obtained.

By hydrolyzing a compound represented by General Formula (21) (where $A^1$, $A^2$, $A^3$, $A^4$, $G^1$, X, Y, $R^3$, m, n and R represent the same as the respective definitions in the above, and $R^{3a}$ represents a halogen atom, a $C_1$ to $C_6$ alkyl group, a $C_1$ to $C_6$ haloalkyl group, a $C_3$ to $C_6$ alkenyl group, a $C_3$ to $C_6$ alkynyl group or the like), which is obtained by reacting a known compound represented by General Formula (19) (where $A^1$, $A^2$, $A^3$, $A^4$, $G^1$, X, Y, $R^3$, m and n represent the same as the respective definitions in the above, and R represents a $C_1$ to $C_6$ alkyl group) described in International Patent Application Publication (WO 2005/085216), Japanese Patent Application Publication (JP 2007/308471) and the like under substantially the same condition as that in Production Method K, according to a common condition for an ester hydrolysis reaction known in the literature similar to Reaction Formula 1, a compound represented by General Formula (5-1) (where $A^1$, $A^2$, $A^3$, $A^4$, $G^1$, X, Y, $R^3$, m and n represent the same as the respective definitions in the above, and $R^{3a}$ represents a halogen atom, a $C_1$ to $C_6$ alkyl group, a $C_1$ to $C_6$ haloalkyl group, a $C_3$ to $C_6$ alkenyl group, a $C_3$ to $C_6$ alkynyl group or the like) corresponding to General Formula (5) in which $R^{3b}$ is a hydrogen atom can be obtained.

Some of the compounds represented by General Formula (7) used in Production Method A, the compounds represented by General Formula (12) used in Production Method D and Production Method F and the compounds represented by General Formula (16) used in Production Method H are known compounds and some of them are commercially available. The others can be easily synthesized according to known methods described in the literature, for example, Canadian Journal of Chemistry (Can. J. Chem.), vol. 57, p. 1253 (1979), Journal of the Chemical Society, Chemical Communications (J. Chem. Soc., Chem. Commun.), p. 114 (1987), The Journal of Organic Chemistry (J. Org. Chem.), vol. 50, p. 3243 (1985) and vol. 60, p. 8124 (1995), Synlett, p. 2214, (2005), International Patent Application Publication (WO 2002/062805) and Japanese Patent Application Publication (JP 10/130,221).

Some of the compounds represented by General Formula (14) used in Production Method G, the compounds represented by General Formula (15) used in Production Method H and the compounds represented by General Formula (18) used in Production Method K are known compounds and some of them are commercially available. The others can be easily synthesized according to general synthetic methods described in the literature, for example, methods described in Chemical and Pharmaceutical Bulletin (Chem. Pharm. Bull.), vol. 34, p. 540 (1986) and vol. 49, p. 1102 (2001), Journal of the American Chemical Society (J. Am. Chem. Soc.), vol. 86, p. 4383 (1964), The Journal of Organic Chemistry (J. Org. Chem.), vol. 48, p. 5280 (1983), Organic Synthesis (Org. Synth.), Collective vol. 6, p. 101 (1988), Synlett, p. 2847, (2005), Synthesis, p. 1159, (1990), Japanese Patent Application Publication (JP 05/125017), European Patent Publication (EP 0,051,273) and UK Patent Publication (GB 2,161, 802).

The compounds represented by General Formula (17) used in Production Method J and Production Method K are known compounds described in International Patent Application Publication (WO 2005/085216), International Patent Application Publication (WO 2007/026965), International Patent Application Publication (WO 2007/105814), Japanese Patent Application Publication (JP 2007/016017), Japanese Patent Application Publication (JP 2007/106756), Japanese Patent Application Publication (JP 2007/308471) and the like.

In each of the reactions, each of the production intermediates to be the starting materials of Production Method A to Production Method K can be obtained by common after treatment after the completion of the reaction.

Furthermore, each of the production intermediates produced by these methods may be used as it is without isolation and purification in a reaction of the next process.

Specific examples of the active compounds represented by Structure Formulae [1]-1 to [1]-110 and [2]-1 to [2]-75 included in the present invention include compounds shown in Table 3 to Table 5. However, the compounds in Table 3 to Table 5 are only for exemplification and the present invention is not limited to these compounds.

TABLE 3

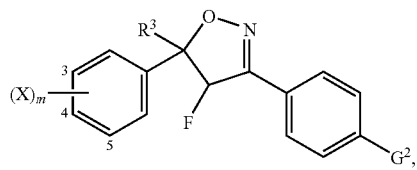

[1] - 1

TABLE 3-continued

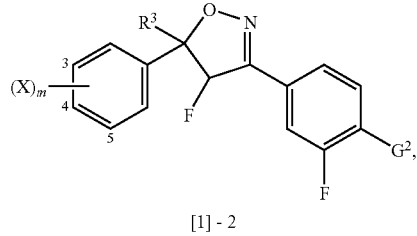

[1] - 2

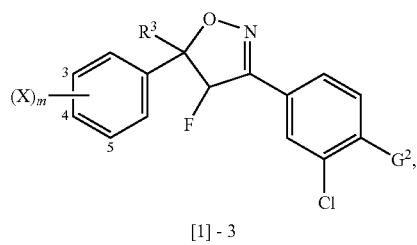

[1] - 3

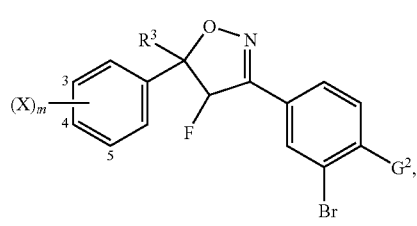

[1] - 4

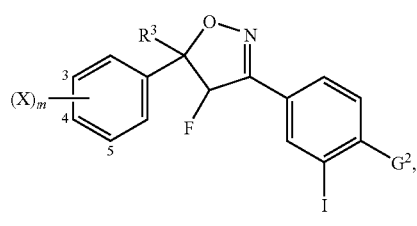

[1] - 5

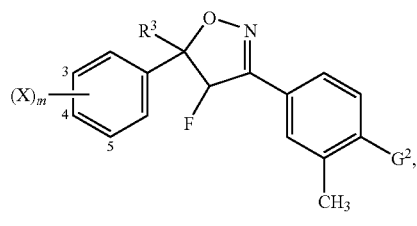

[1] - 6

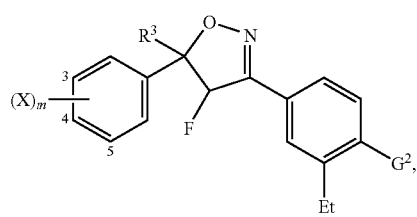

[1] - 7

TABLE 3-continued
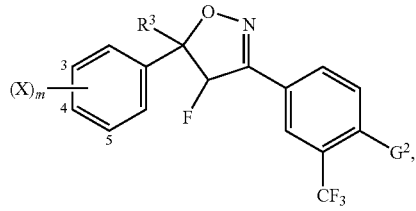
[1] - 8
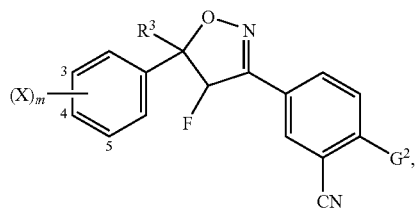
[1] - 9
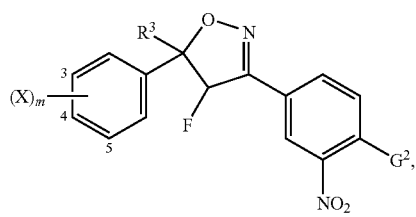
[1] - 10
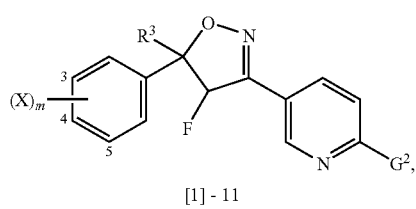
[1] - 11
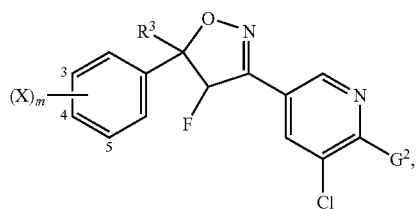
[1] - 12
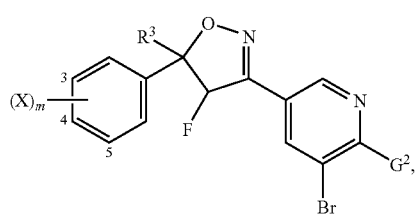
[1] - 13
TABLE 3-continued
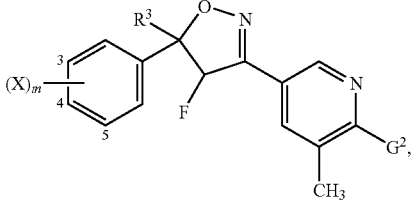
[1] - 14
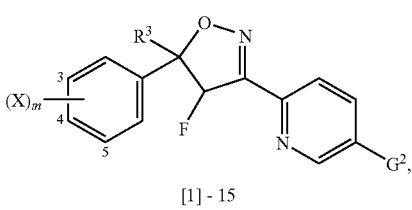
[1] - 15
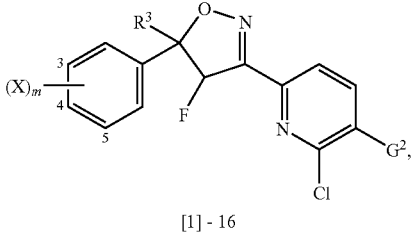
[1] - 16
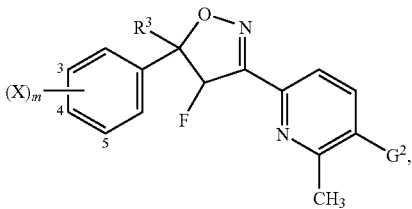
[1] - 17
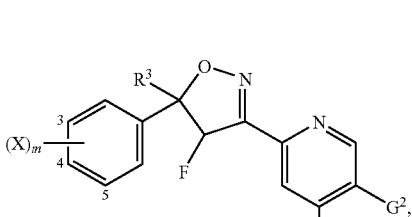
[1] - 18
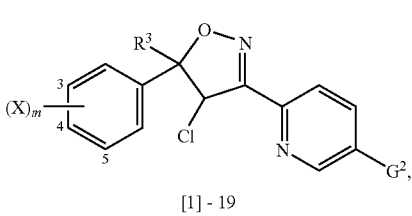
[1] - 19

TABLE 3-continued
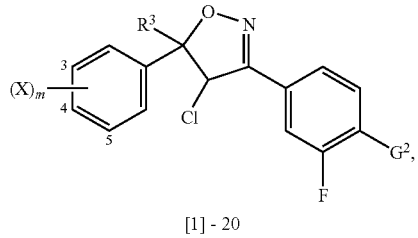
[1] - 20
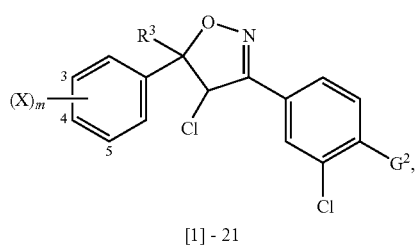
[1] - 21
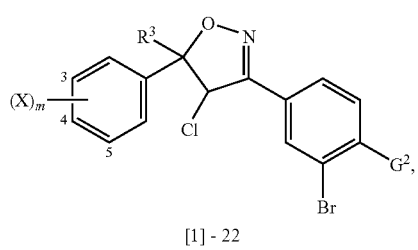
[1] - 22
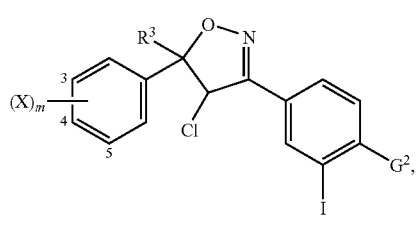
[1] - 23
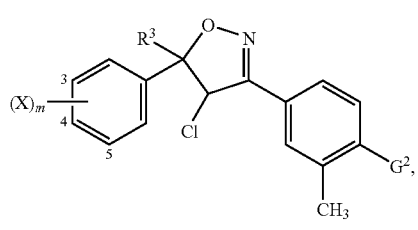
[1] - 24
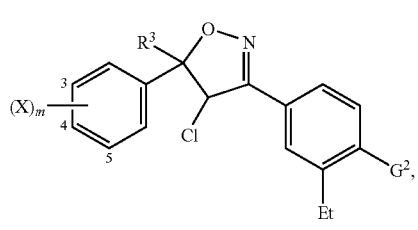
[1] - 25
TABLE 3-continued
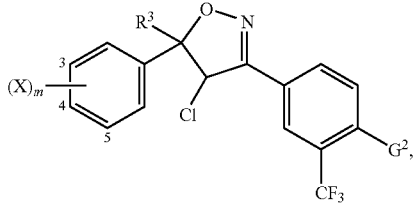
[1] - 26
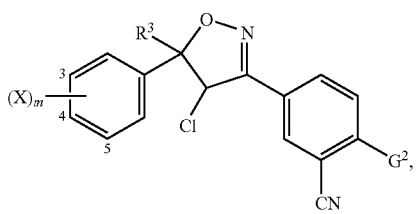
[1] - 27
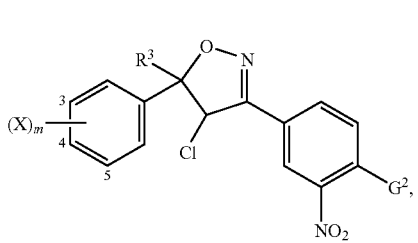
[1] - 28
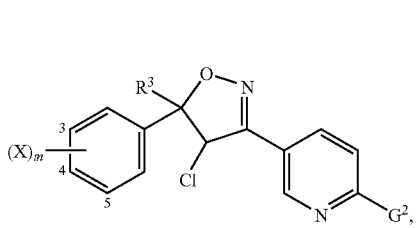
[1] - 29
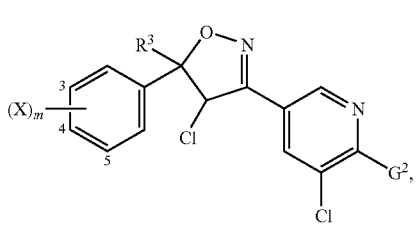
[1] - 30
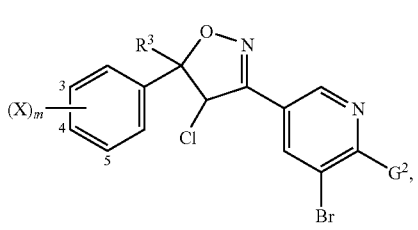
[1] - 31

TABLE 3-continued
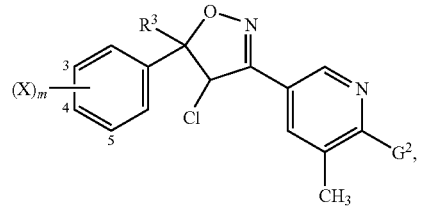
[1] - 32
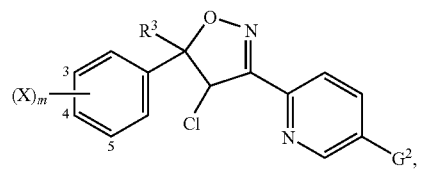
[1] - 33
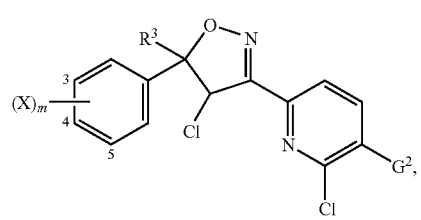
[1] - 34
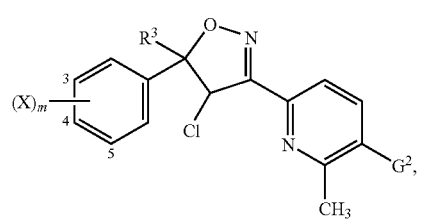
[1] - 35
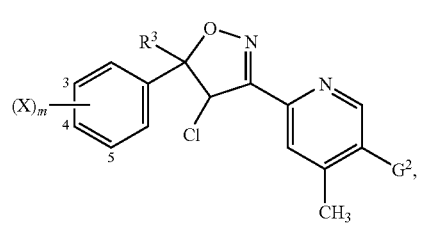
[1] - 36
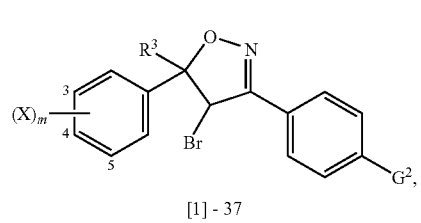
[1] - 37
TABLE 3-continued
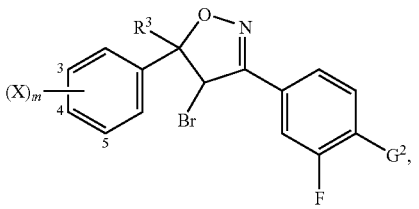
[1] - 38
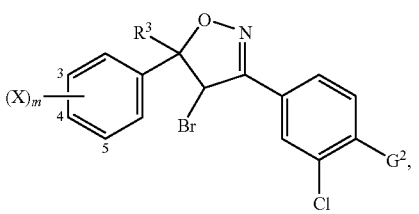
[1] - 39
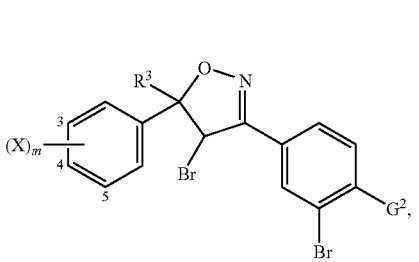
[1] - 40
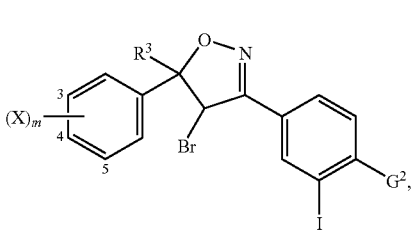
[1] - 41
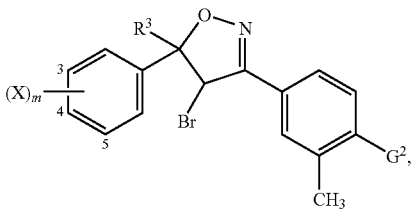
[1] - 42
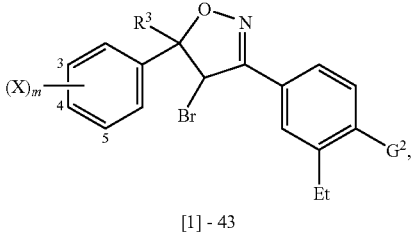
[1] - 43

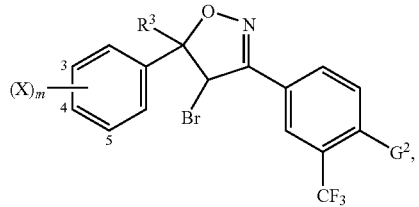
[1]-44
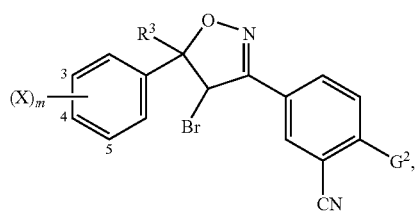
[1]-45
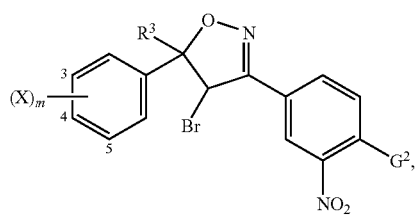
[1]-46
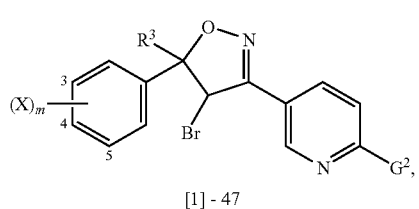
[1]-47
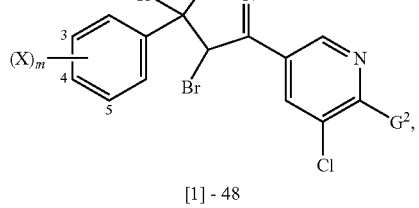
[1]-48
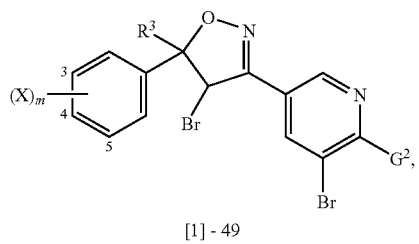
[1]-49
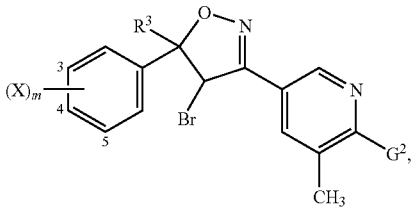
[1]-50
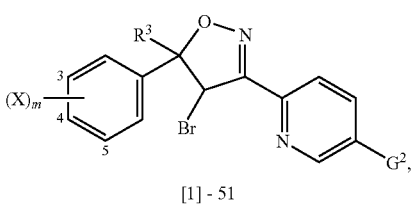
[1]-51
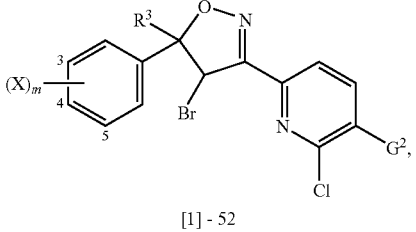
[1]-52
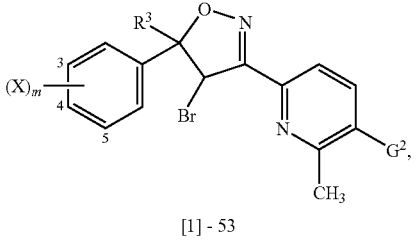
[1]-53
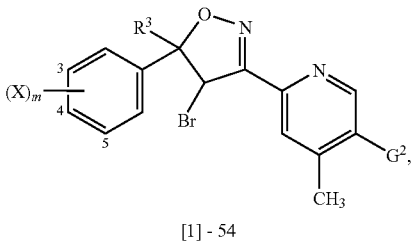
[1]-54
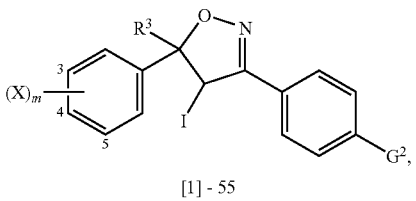
[1]-55

TABLE 3-continued
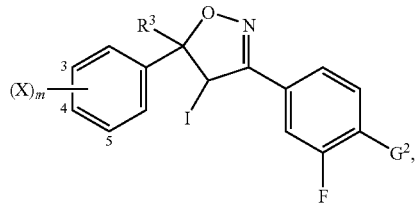
[1] - 56
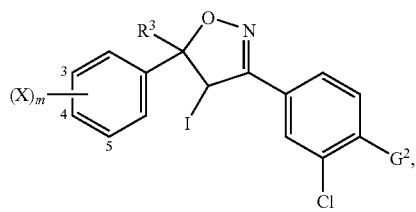
[1] - 57
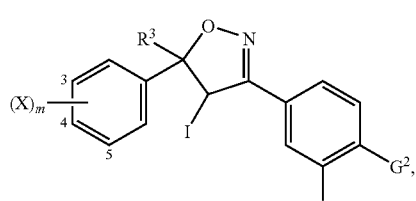
[1] - 58
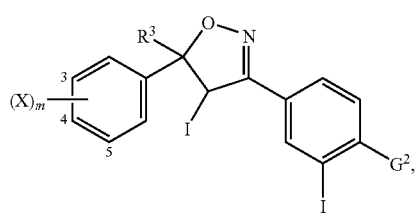
[1] - 59
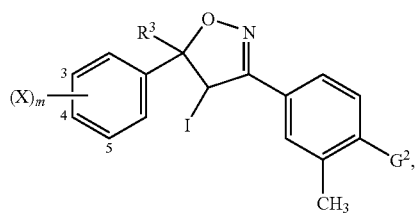
[1] - 60
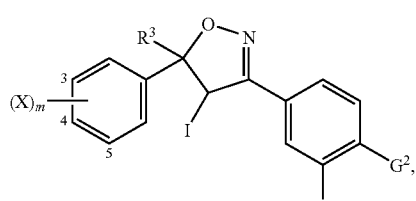
[1] - 61
TABLE 3-continued
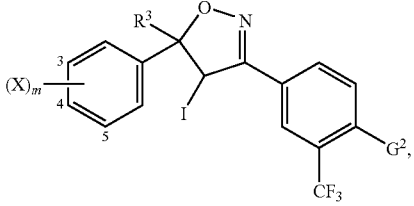
[1] - 62
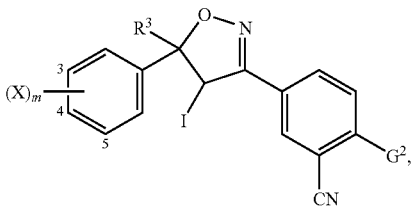
[1] - 63
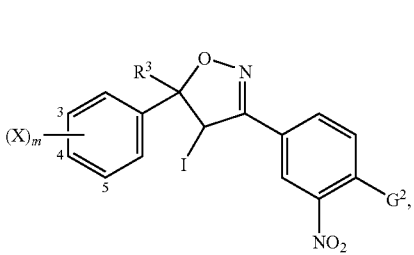
[1] - 64
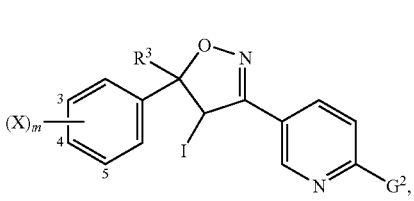
[1] - 65
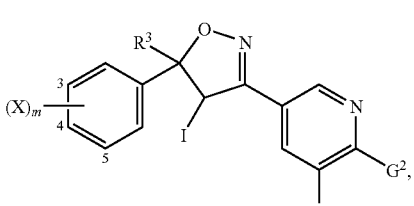
[1] - 66
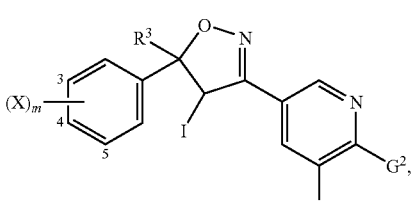
[1] - 67

TABLE 3-continued
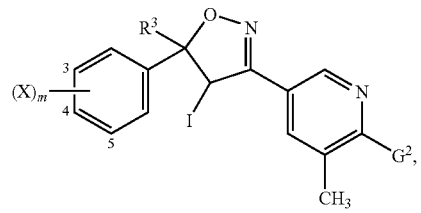
[1] - 68
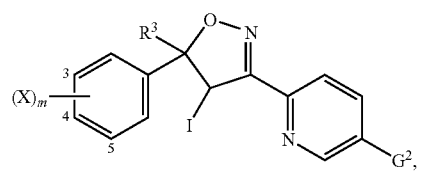
[1] - 69
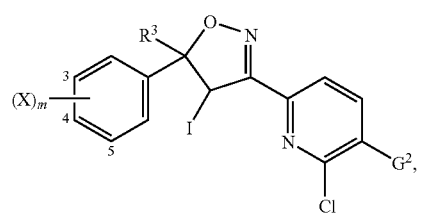
[1] - 70
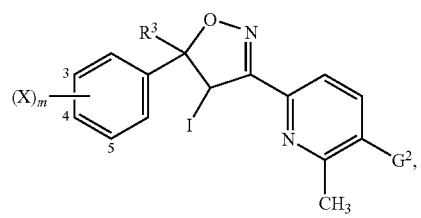
[1] - 71
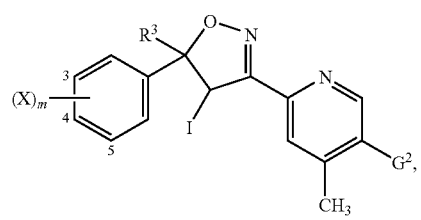
[1] - 72
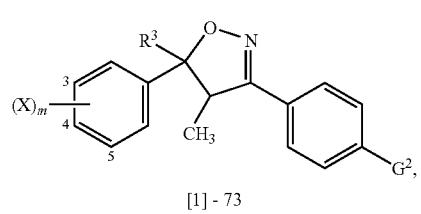
[1] - 73
TABLE 3-continued
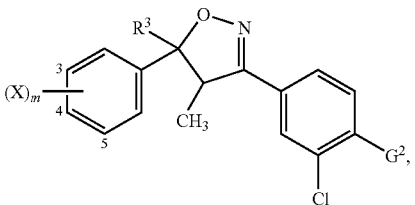
[1] - 74
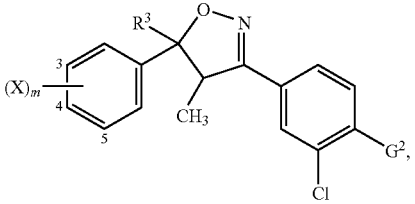
[1] - 75
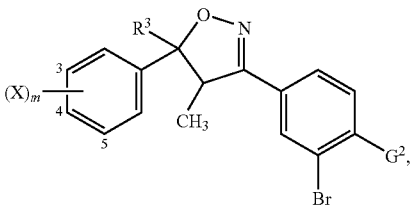
[1] - 76
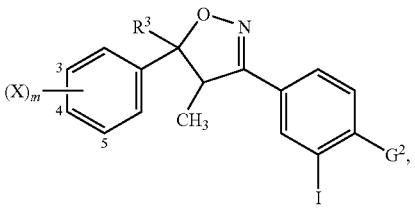
[1] - 77
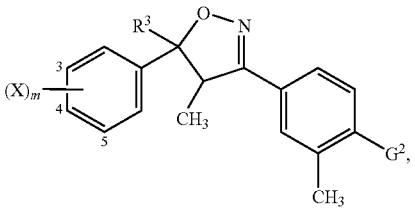
[1] - 78
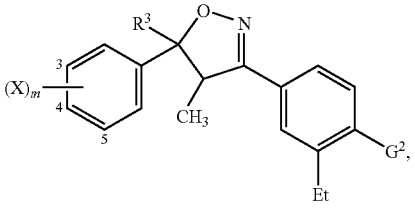
[1] - 79

TABLE 3-continued
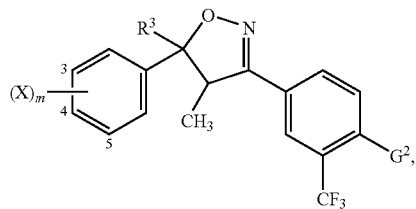
[1] - 80
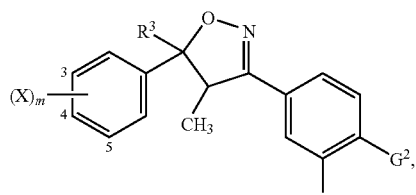
[1] - 81
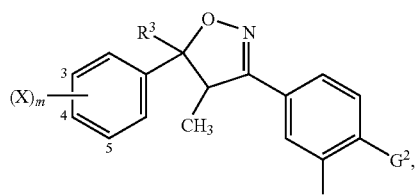
[1] - 82
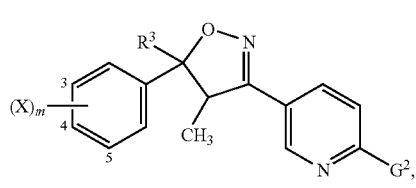
[1] - 83
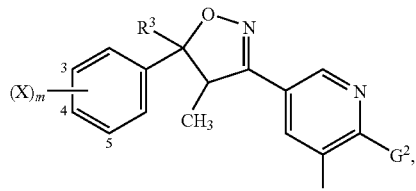
[1] - 84
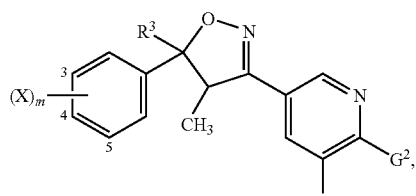
[1] - 85
TABLE 3-continued
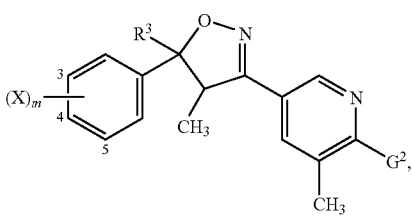
[1] - 86
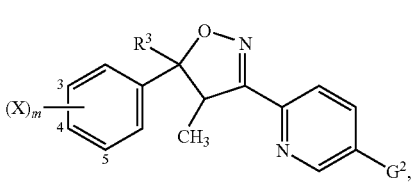
[1] - 87
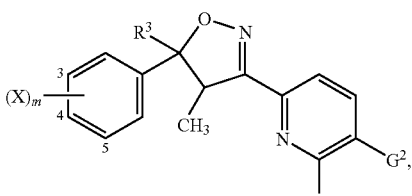
[1] - 88
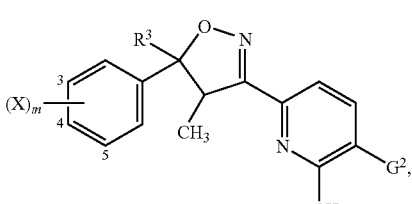
[1] - 89
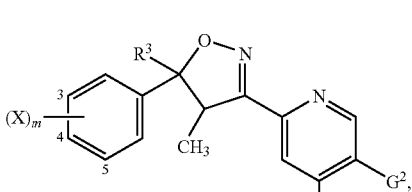
[1] - 90
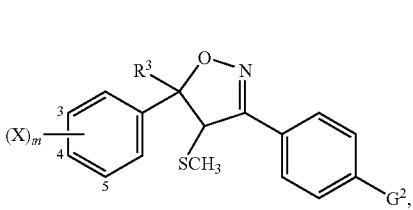
[1] - 91

TABLE 3-continued
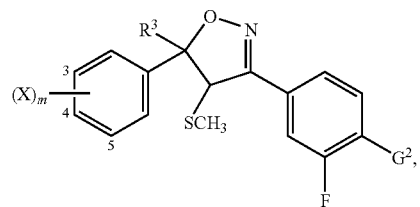
[1] - 92
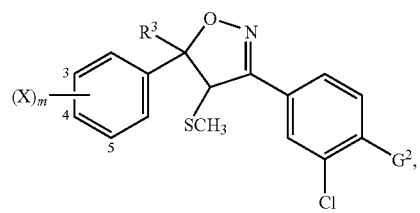
[1] - 93
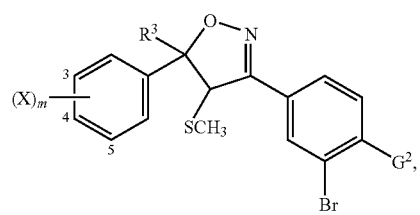
[1] - 94
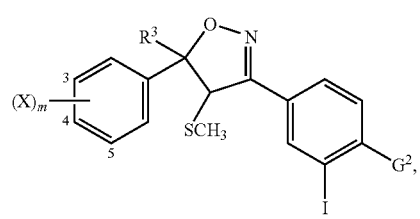
[1] - 95
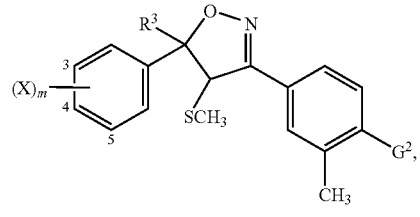
[1] - 96
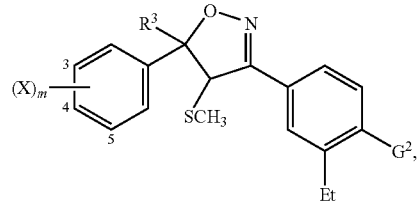
[1] - 97
TABLE 3-continued
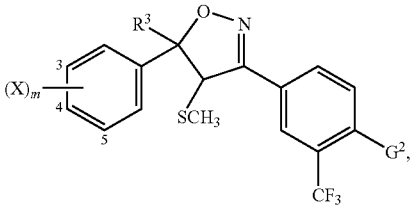
[1] - 98
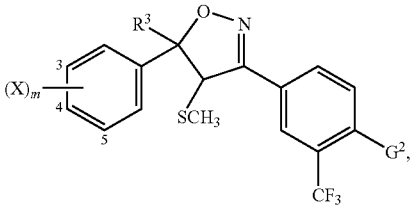
[1] - 99
[1] - 100
[1] - 101
[1] - 102
[1] - 103

TABLE 3-continued
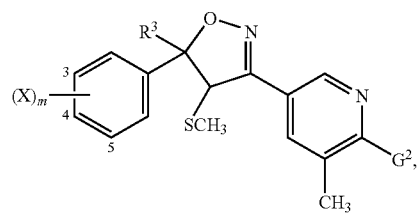
[1] - 104
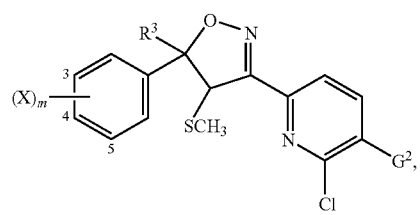
[1] - 105
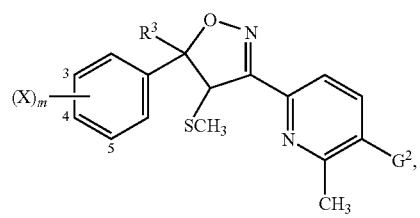
[1] - 106
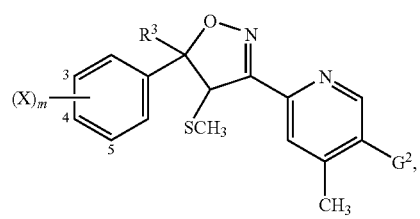
[1] - 107
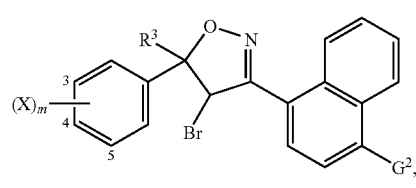
[1] - 108
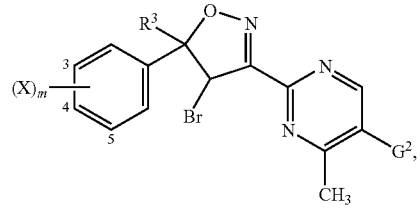
[1] - 109
TABLE 3-continued
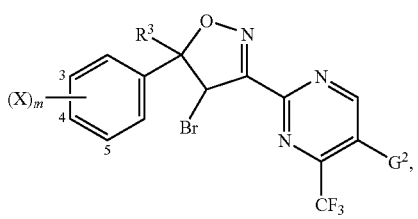
[1] - 110
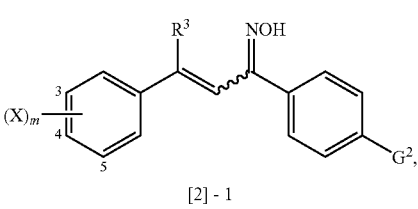
[2] - 1
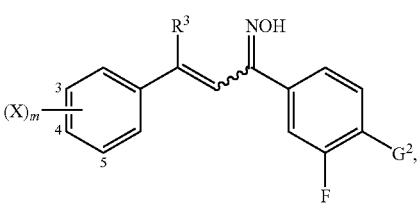
[2] - 2
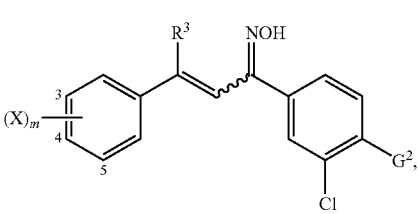
[2] - 3
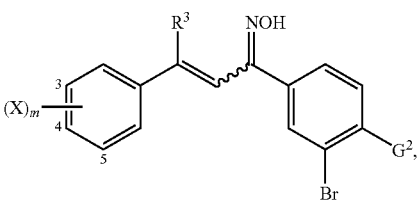
[2] - 4
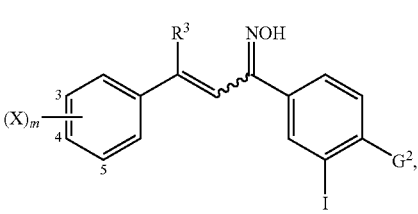
[2] - 5

TABLE 3-continued
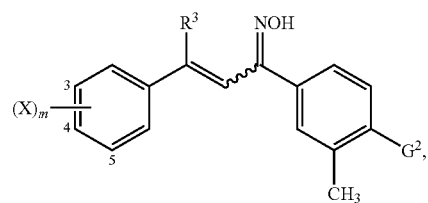
[2] - 6
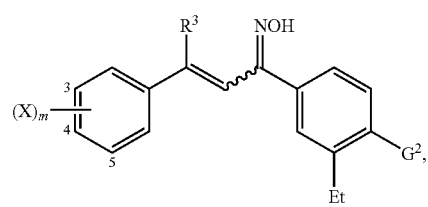
[2] - 7
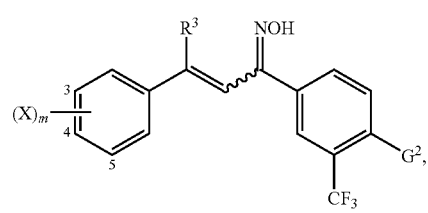
[2] - 8
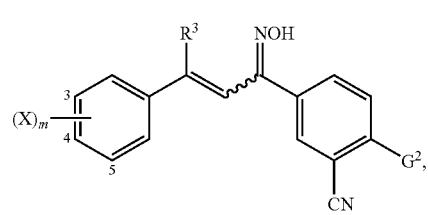
[2] - 9
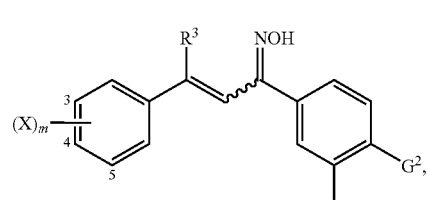
[2] - 10
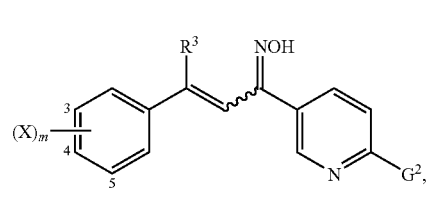
[2] - 11
TABLE 3-continued
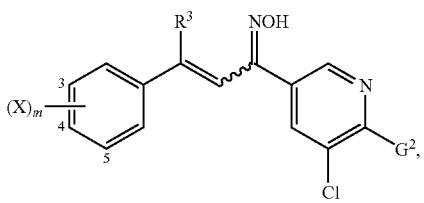
[2] - 12
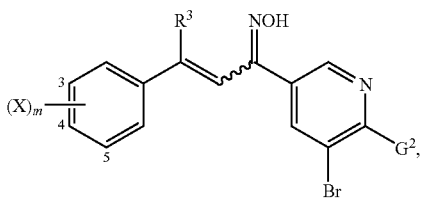
[2] - 13
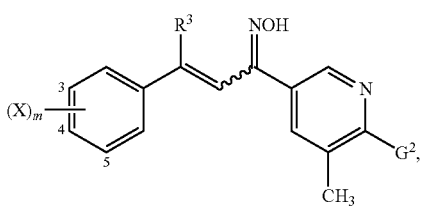
[2] - 14
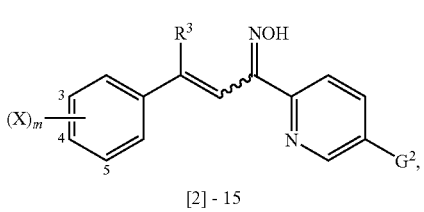
[2] - 15
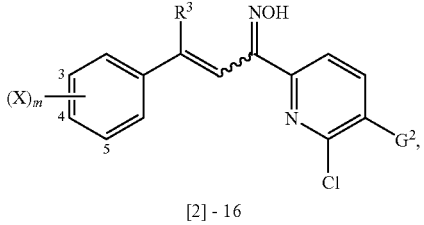
[2] - 16
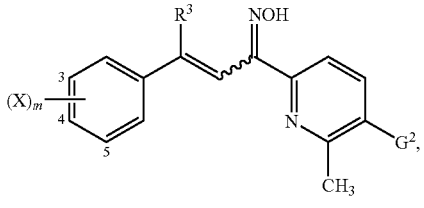
[2] - 17

TABLE 3-continued
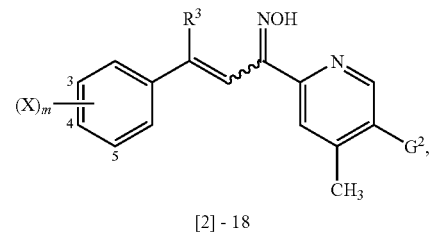
[2] - 18
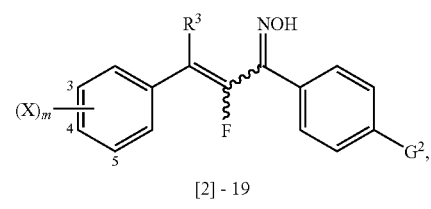
[2] - 19
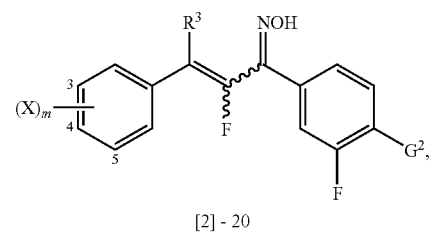
[2] - 20
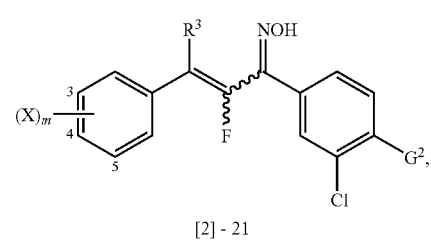
[2] - 21
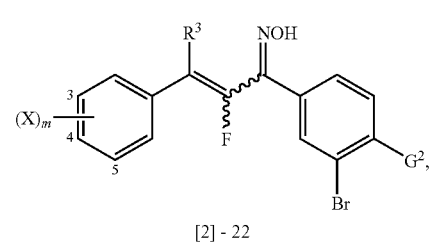
[2] - 22
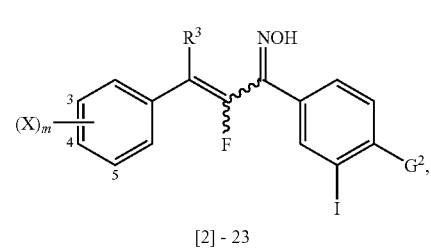
[2] - 23
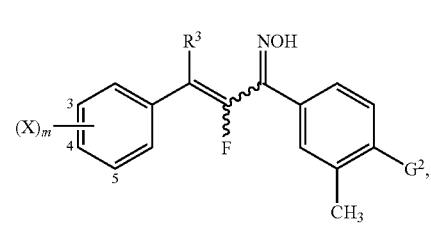
[2] - 24
TABLE 3-continued
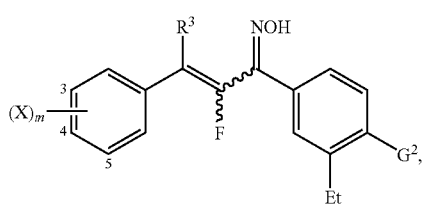
[2] - 25
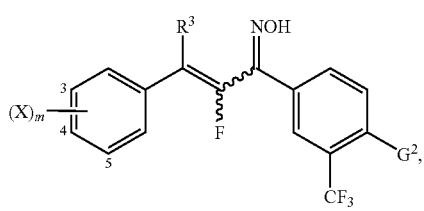
[2] - 26
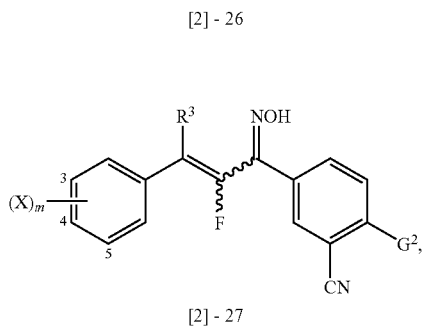
[2] - 27
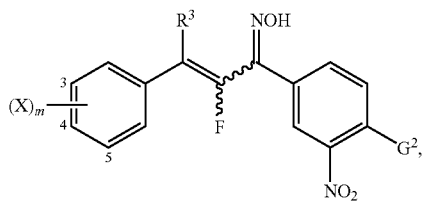
[2] - 28
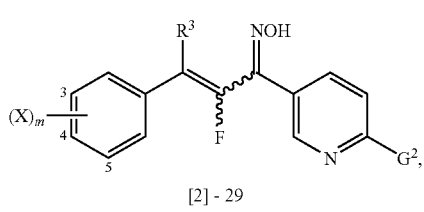
[2] - 29
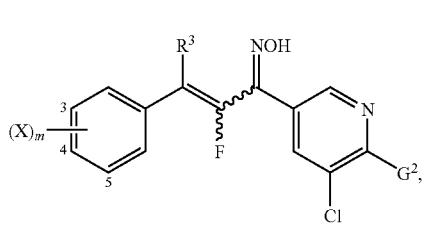
[2] - 30

TABLE 3-continued
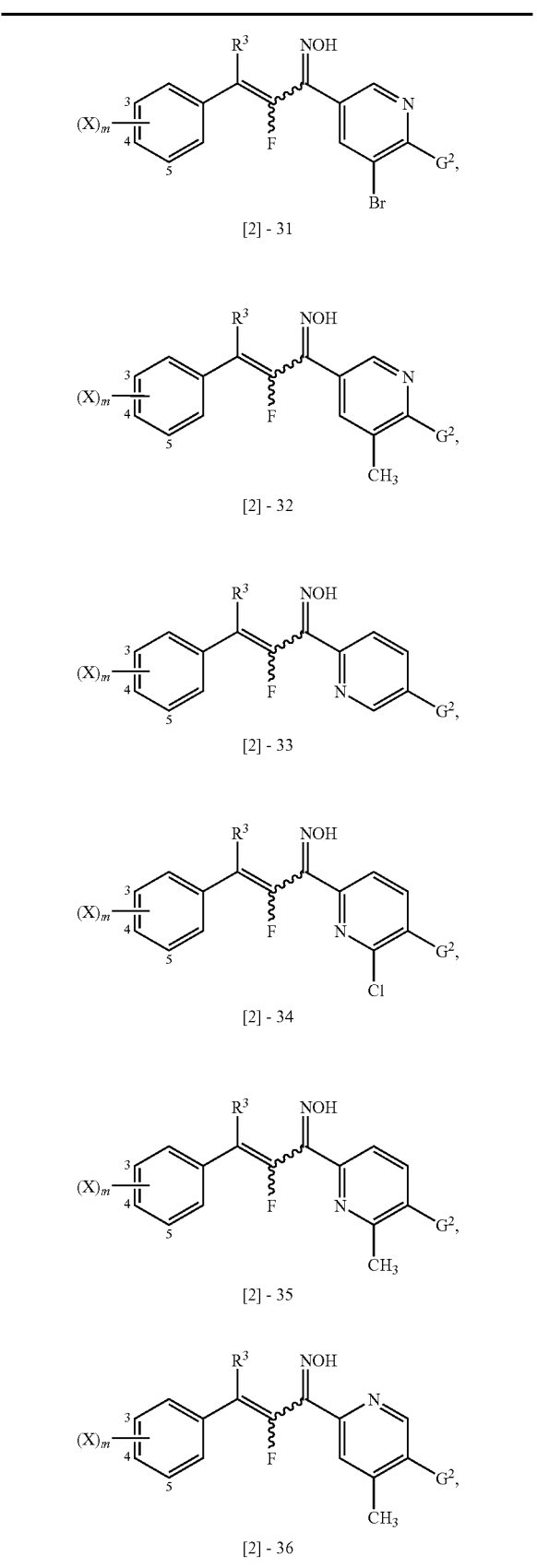
[2] - 31
[2] - 32
[2] - 33
[2] - 34
[2] - 35
[2] - 36
TABLE 3-continued
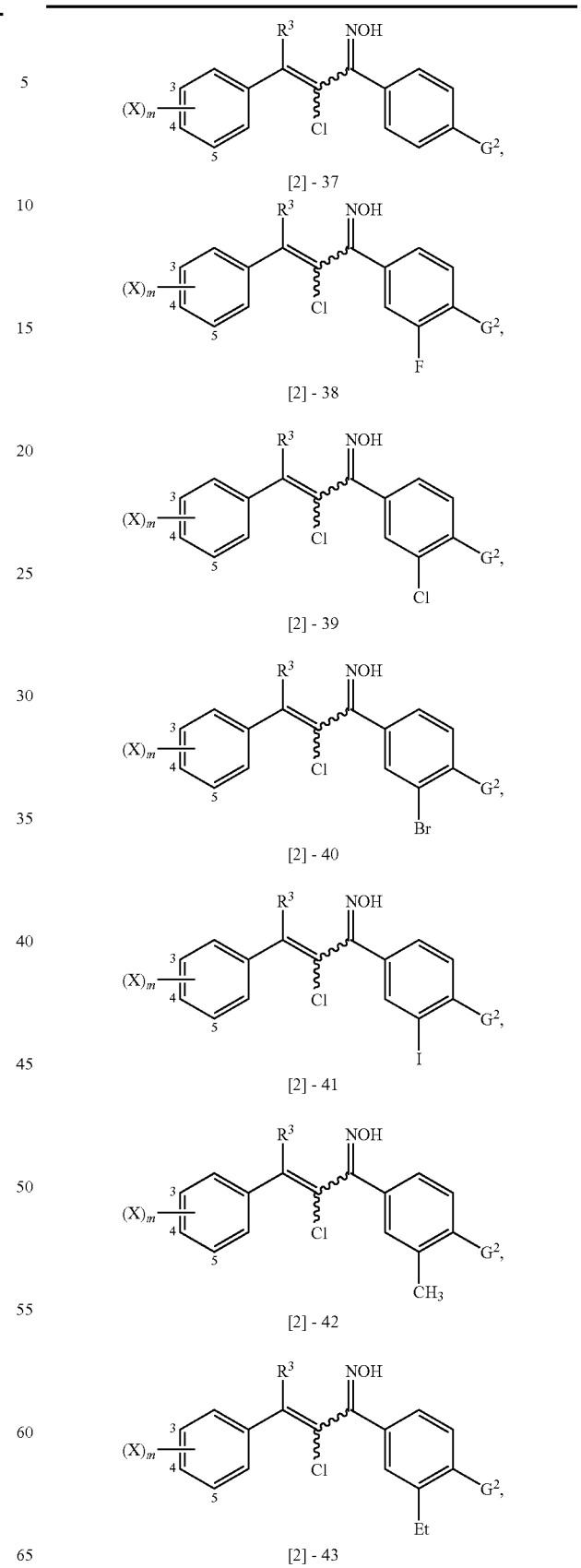
[2] - 37
[2] - 38
[2] - 39
[2] - 40
[2] - 41
[2] - 42
[2] - 43

TABLE 3-continued
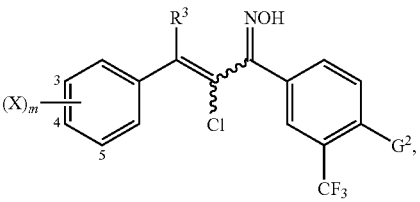
[2] - 44
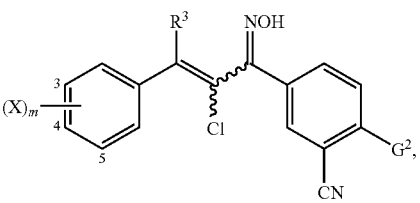
[2] - 45
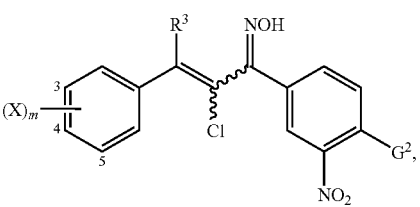
[2] - 46
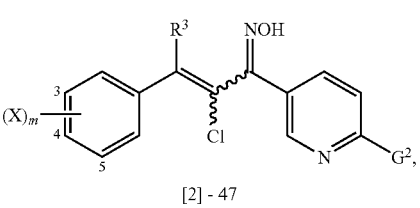
[2] - 47
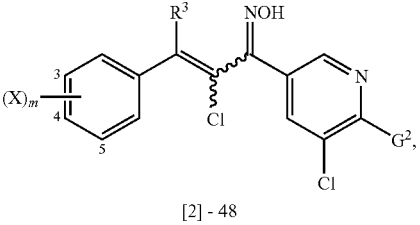
[2] - 48
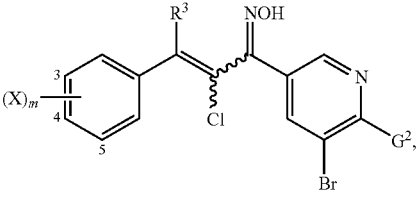
[2] - 49
TABLE 3-continued
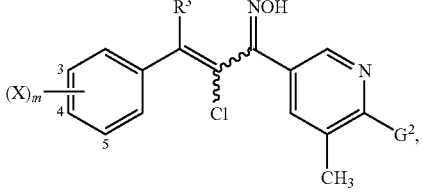
[2] - 50
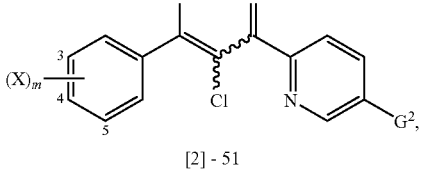
[2] - 51
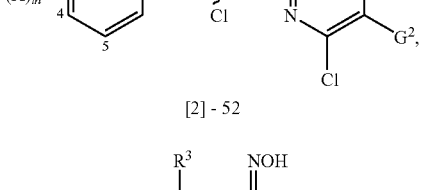
[2] - 52
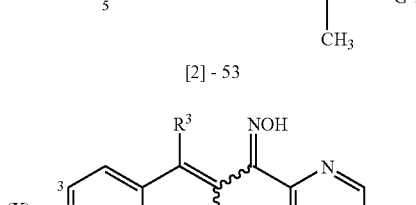
[2] - 53
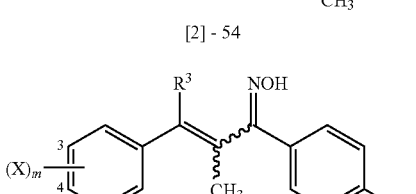
[2] - 54
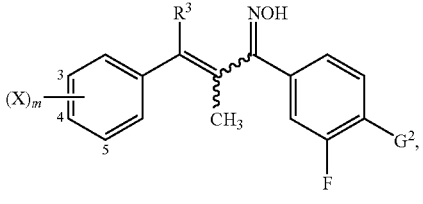
[2] - 55
[2] - 56

TABLE 3-continued
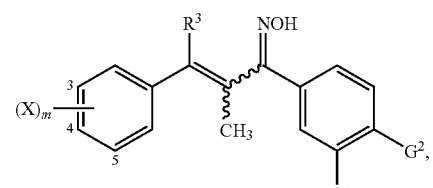
[2] - 57
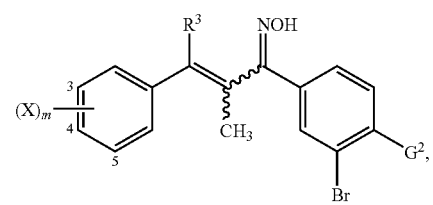
[2] - 58
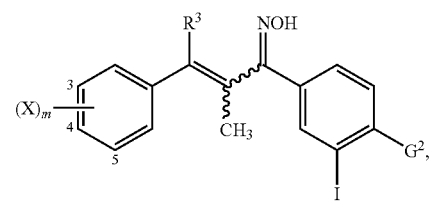
[2] - 59
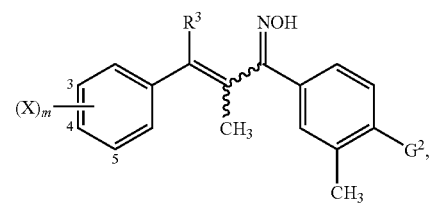
[2] - 60
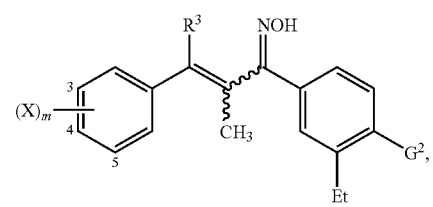
[2] - 61
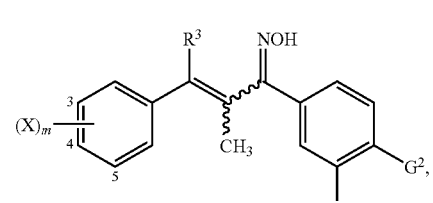
[2] - 62
TABLE 3-continued
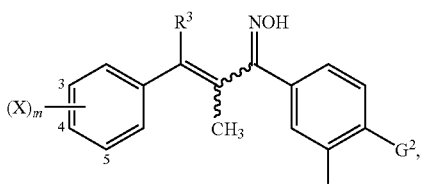
[2] - 63
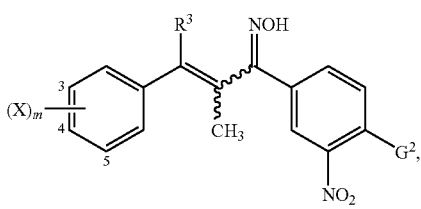
[2] - 64
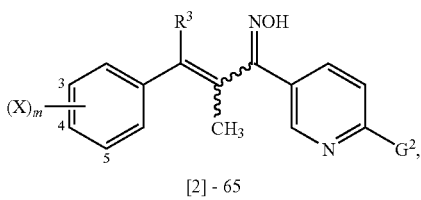
[2] - 65
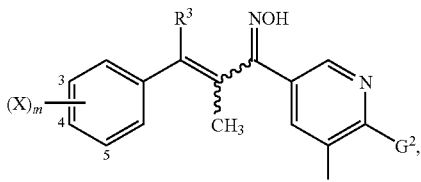
[2] - 66
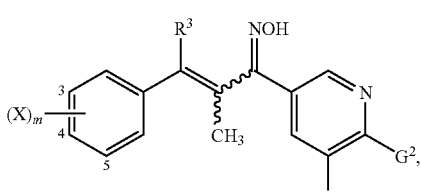
[2] - 67
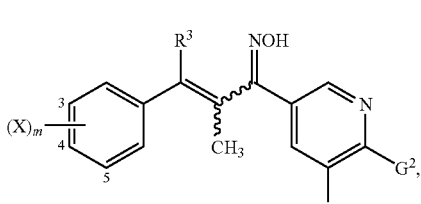
[2] - 68
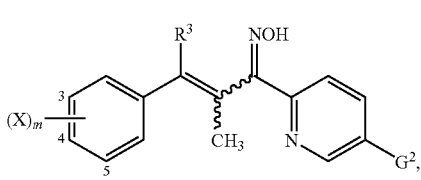
[2] - 69

TABLE 3-continued

[2] - 70, [2] - 71, [2] - 72, [2] - 73, [2] - 74, [2] - 75

Compounds represented by Structure Formulae [1]-1 to [1]-110 and [2]-1 to [2]-75 having structures in which $G^2$ is represented by $G^2$-1-a or $G^2$-1-b.

$G^2$-1-a:

$G^2$-1-b:

In Table, the number representing the substitution site of a substituent $(X)_m$ corresponds to the site indicated by the number in each of Structure Formulae [1]-1 to [1]-110 and [2]-1 to [2]-75.

Furthermore, in Table, aromatic heterocyclic rings represented by D8-1a to D35-1c represent the following structures, D8-1a:

D8-2b:

D8-2c:

D8-3a:

D8-3b:

D10-1a:

D10-2a:

-continued

D13-1a:
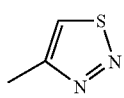

D16-1a:
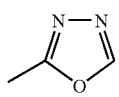

D22-1a:
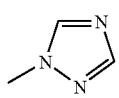

D32-1a:
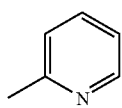

D34-1a:
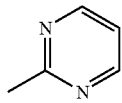

D34-1c:
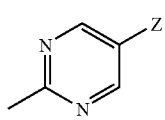

D34-3a:
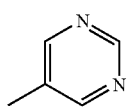

D35-1a:
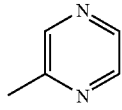

D35-1c:
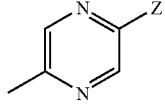

for example, the expression (CH$_2$(D8-3b)Cl) represents a 3-chloro-1-methylpyrazol-5-ylmethyl group and the expression ((D34-1c)Cl) represents a 5-chloropyrimidin-2-yl group, in Table, aliphatic heterocyclic rings represented by E4-1a to E7-1b represent the following structures, E4-1a:
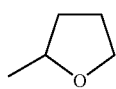

E4-2a:
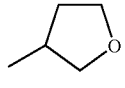

E5-2a:
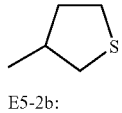

E5-2b:
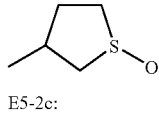

E5-2c:
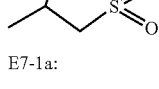

E7-1a:
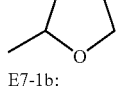

E7-1b:
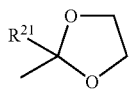

for example, the expression (CH$_2$(E7-1a)) represents a 1,3-dioxolan-2-ylmethyl group and the expression (CH$_2$(E7-1b)CH$_3$) represents a 2-methyl-1,3-dioxolan-2-ylmethyl group.

Furthermore, in Table, T-2 and T-3 represent the following structures,

T-2:
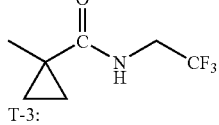

T-3:
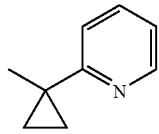

in Table, the description of Et represents an ethyl group and, in the same manner, n-Pr and Pr-n represent normal propyl groups, i-Pr and Pr-i represent isopropyl groups, c-Pr and Pr-c represent cyclopropyl groups, t-Bu and Bu-t represent tertiary butyl groups, c-Bu and Bu-c represent cyclobutyl groups, and Ph represents a phenyl group.

TABLE 4

| $(X)_m$ | $R^3$ | $R^2$ | $R^1$ |
|---|---|---|---|
| 3-Cl | $CF_3$ | H | $CH_2C(O)NHCH_2CF_3$ |
| 3-Cl | $CF_3$ | H | $CH(CH_3)C(O)NHCH_2CF_3$(D) |
| 3-Cl | $CF_3$ | H | $CH_2$(D10-2a) |
| 3-Cl | $CF_3$ | H | CH=NOCH$_3$(Z) |
| 3-Cl | $CF_3$ | H | CH=NOEt(Z) |
| 3-Br | $CF_3$ | $C(O)OCH_3$ | $CH_2OEt$ |
| 3-Br | $CF_3$ | H | $CH_2OCH_2CF_3$ |
| 3-Br | $CF_3$ | H | E4-1a |
| 3-Br | $CF_3$ | H | $CH_2C(O)NHCH_2CF_3$ |
| 3-Br | $CF_3$ | H | $CH(CH_3)C(O)NHCH_2CF_3$(D) |
| 3-Br | $CF_3$ | H | $CH_2$(D10-2a) |
| 3-Br | $CF_3$ | H | CH=NOCH$_3$(Z) |
| 3-Br | $CF_3$ | H | CH=NOEt(Z) |
| 3-Br | $CF_3$ | C(O)Et | $C(O)OCH_3$ |
| 3-Br | $CF_3$ | H | (D34-1c)CN |
| 3-I | $CF_3$ | $C(O)OCH_3$ | $CH_2OEt$ |
| 3-I | $CF_3$ | H | $CH_2OCH_2CF_3$ |
| 3-I | $CF_3$ | $C(O)OCH_3$ | $CH_2OCH_2CF_3$ |
| 3-I | $CF_3$ | H | E4-1a |
| 3-I | $CF_3$ | H | $CH_2C(O)NHCH_2CF_3$ |
| 3-I | $CF_3$ | H | $CH(CH_3)C(O)NHCH_2CF_3$ |
| 3-I | $CF_3$ | H | $CH(CH_3)C(O)NHCH_2CF_3$(D) |
| 3-I | $CF_3$ | H | $CH_2$(D10-2a) |
| 3-I | $CF_3$ | H | $CH_2$(D32-1a) |
| 3-I | $CF_3$ | $C(O)CH_3$ | $CH_2$(D32-1a) |
| 3-I | $CF_3$ | $C(O)OCH_3$ | $CH_2$(D32-1a) |
| 3-I | $CF_3$ | H | CH=NOCH$_3$(Z) |
| 3-I | $CF_3$ | H | CH=NOEt(Z) |
| 3-I | $CF_3$ | C(O)Et | $C(O)OCH_3$ |
| 3-I | $CF_3$ | $C(O)CH_3$ | (D34-1c)Cl |
| 3-I | $CF_3$ | $C(O)OCH_3$ | (D34-1c)Cl |
| 3-I | $CF_3$ | H | (D34-1c)CN |
| 3-I | $CF_3$ | $CH_3$ | (D34-1c)CN |
| 3-I | $CF_3$ | $CH_2OC(O)CH_3$ | (D34-1c)CN |
| 3-I | $CF_3$ | C(O)Pr-i | (D34-1c)CN |
| 3-I | $CF_2Cl$ | H | $CH_2C(O)NHCH_2CF_3$ |
| 3-I | $CF_2Cl$ | H | $CH(CH_3)C(O)NHCH_2CF_3$(D) |
| 3-I | $CF_2Cl$ | H | $CH_2$(D10-2a) |
| 3-I | $CF_2Cl$ | H | CH=NOCH$_3$(Z) |
| 3-I | $CF_2Cl$ | H | CH=NOEt(Z) |
| 3-$CF_3$ | $CF_3$ | $C(O)OCH_3$ | $CH_2OEt$ |
| 3-$CF_3$ | $CF_3$ | H | $CH_2OCH_2CF_3$ |
| 3-$CF_3$ | $CF_3$ | $C(O)OCH_3$ | $CH_2OCH_2CF_3$ |
| 3-$CF_3$ | $CF_3$ | H | E4-1a |
| 3-$CF_3$ | $CF_3$ | H | $CH_2C(O)NHCH_2CF_3$ |
| 3-$CF_3$ | $CF_3$ | H | $CH(CH_3)C(O)NHCH_2CF_3$ |
| 3-$CF_3$ | $CF_3$ | H | $CH(CH_3)C(O)NHCH_2CF_3$(D) |
| 3-$CF_3$ | $CF_3$ | H | $CH_2$(D10-2a) |
| 3-$CF_3$ | $CF_3$ | H | $CH_2$(D32-1a) |
| 3-$CF_3$ | $CF_3$ | $C(O)CH_3$ | $CH_2$(D32-1a) |
| 3-$CF_3$ | $CF_3$ | $C(O)OCH_3$ | $CH_2$(D32-1a) |
| 3-$CF_3$ | $CF_3$ | H | CH=NOCH$_3$(Z) |
| 3-$CF_3$ | $CF_3$ | H | CH=NOEt(Z) |
| 3-$CF_3$ | $CF_3$ | C(O)Et | $C(O)OCH_3$ |
| 3-$CF_3$ | $CF_3$ | $C(O)CH_3$ | (D34-1c)Cl |
| 3-$CF_3$ | $CF_3$ | $C(O)OCH_3$ | (D34-1c)Cl |
| 3-$CF_3$ | $CF_3$ | H | (D34-1c)CN |
| 3-$CF_3$ | $CF_3$ | $CH_3$ | (D34-1c)CN |
| 3-$CF_3$ | $CF_3$ | $CH_2OC(O)CH_3$ | (D34-1c)CN |
| 3-$CF_3$ | $CF_3$ | C(O)Pr-i | (D34-1c)CN |
| 3-$CF_3$ | $CF_2Cl$ | H | $CH_2C(O)NHCH_2CF_3$ |
| 3-$CF_3$ | $CF_2Cl$ | H | $CH(CH_3)C(O)NHCH_2CF_3$(D) |
| 3-$CF_3$ | $CF_2Cl$ | H | $CH_2$(D10-2a) |
| 3-$CF_3$ | $CF_2Cl$ | H | CH=NOCH$_3$(Z) |
| 3-$CF_3$ | $CF_2Cl$ | H | CH=NOEt(Z) |
| 3-$CF_2CF_3$ | $CF_3$ | $C(O)OCH_3$ | $CH_2OEt$ |
| 3-$CF_2CF_3$ | $CF_3$ | H | $CH_2OCH_2CF_3$ |
| 3-$CF_2CF_3$ | $CF_3$ | H | E4-1a |
| 3-$CF_2CF_3$ | $CF_3$ | H | $CH_2C(O)NHCH_2CF_3$ |
| 3-$CF_2CF_3$ | $CF_3$ | H | $CH(CH_3)C(O)NHCH_2CF_3$(D) |
| 3-$CF_2CF_3$ | $CF_3$ | H | $CH_2$(D10-2a) |
| 3-$CF_2CF_3$ | $CF_3$ | H | CH=NOCH$_3$(Z) |
| 3-$CF_2CF_3$ | $CF_3$ | H | CH=NOEt(Z) |
| 3-$CF_2CF_3$ | $CF_3$ | C(O)Et | $C(O)OCH_3$ |
| 3-$CF_2CF_3$ | $CF_3$ | H | (D34-1c)CN |
| 3-$CF_2CF_2CF_3$ | $CF_3$ | H | $CH_2C(O)NHCH_2CF_3$ |
| 3-$CF_2CF_2CF_3$ | $CF_3$ | H | $CH(CH_3)C(O)NHCH_2CF_3$(D) |
| 3-$CF_2CF_2CF_3$ | $CF_3$ | H | $CH_2$(D10-2a) |

TABLE 4-continued

| (X)$_m$ | R$^3$ | R$^2$ | R$^1$ |
|---|---|---|---|
| 3-CF$_2$CF$_2$CF$_3$ | CF$_3$ | H | CH=NOCH$_3$(Z) |
| 3-CF$_2$CF$_2$CF$_3$ | CF$_3$ | H | CH=NOEt(Z) |
| 3-CF(CF$_3$)$_2$ | CF$_3$ | H | CH$_2$C(O)NHCH$_2$CF$_3$ |
| 3-CF(CF$_3$)$_2$ | CF$_3$ | H | CH(CH$_3$)C(O)NHCH$_2$CF$_3$(D) |
| 3-CF(CF$_3$)$_2$ | CF$_3$ | H | CH$_2$(D10-2a) |
| 3-CF(CF$_3$)$_2$ | CF$_3$ | H | CH=NOCH$_3$(Z) |
| 3-CF(CF$_3$)$_2$ | CF$_3$ | H | CH=NOEt(Z) |
| 3-OCF$_3$ | CF$_3$ | C(O)OCH$_3$ | CH$_2$OEt |
| 3-OCF$_3$ | CF$_3$ | H | CH$_2$OCH$_2$CF$_3$ |
| 3-OCF$_3$ | CF$_3$ | H | E4-1a |
| 3-OCF$_3$ | CF$_3$ | H | CH$_2$C(O)NHCH$_2$CF$_3$ |
| 3-OCF$_3$ | CF$_3$ | H | CH(CH$_3$)C(O)NHCH$_2$CF$_3$(D) |
| 3-OCF$_3$ | CF$_3$ | H | CH$_2$(D10-2a) |
| 3-OCF$_3$ | CF$_3$ | H | CH=NOCH$_3$(Z) |
| 3-OCF$_3$ | CF$_3$ | H | CH=NOEt(Z) |
| 3-OCF$_3$ | CF$_3$ | C(O)Et | C(O)OCH$_3$ |
| 3-OCF$_3$ | CF$_3$ | H | (D34-1c)CN |
| 3-OCF$_2$Br | CF$_3$ | H | CH$_2$C(O)NHCH$_2$CF$_3$ |
| 3-OCF$_2$Br | CF$_3$ | H | CH(CH$_3$)C(O)NHCH$_2$CF$_3$(D) |
| 3-OCF$_2$Br | CF$_3$ | H | CH$_2$(D10-2a) |
| 3-OCF$_2$Br | CF$_3$ | H | CH=NOCH$_3$(Z) |
| 3-OCF$_2$Br | CF$_3$ | H | CH=NOEt(Z) |
| 3-SCF$_3$ | CF$_3$ | C(O)OCH$_3$ | CH$_2$OEt |
| 3-SCF$_3$ | CF$_3$ | H | CH$_2$OCH$_2$CF$_3$ |
| 3-SCF$_3$ | CF$_3$ | H | E4-1a |
| 3-SCF$_3$ | CF$_3$ | H | CH$_2$C(O)NHCH$_2$CF$_3$ |
| 3-SCF$_3$ | CF$_3$ | H | CH(CH$_3$)C(O)NHCH$_2$CF$_3$(D) |
| 3-SCF$_3$ | CF$_3$ | H | CH$_2$(D10-2a) |
| 3-SCF$_3$ | CF$_3$ | H | CH=NOCH$_3$(Z) |
| 3-SCF$_3$ | CF$_3$ | H | CH=NOEt(Z) |
| 3-SCF$_3$ | CF$_3$ | C(O)Et | C(O)OCH$_3$ |
| 3-SCF$_3$ | CF$_3$ | H | (D34-1c)CN |
| 3-SCF$_2$Cl | CF$_3$ | H | CH$_2$C(O)NHCH$_2$CF$_3$ |
| 3-SCF$_2$Cl | CF$_3$ | H | CH(CH$_3$)C(O)NHCH$_2$CF$_3$(D) |
| 3-SCF$_2$Cl | CF$_3$ | H | CH$_2$(D10-2a) |
| 3-SCF$_2$Cl | CF$_3$ | H | CH=NOCH$_3$(Z) |
| 3-SCF$_2$Cl | CF$_3$ | H | CH=NOEt(Z) |
| 3-SCF$_2$Br | CF$_3$ | H | CH$_2$C(O)NHCH$_2$CF$_3$ |
| 3-SCF$_2$Br | CF$_3$ | H | CH(CH$_3$)C(O)NHCH$_2$CF$_3$(D) |
| 3-SCF$_2$Br | CF$_3$ | H | CH$_2$(D10-2a) |
| 3-SCF$_2$Br | CF$_3$ | H | CH=NOCH$_3$(Z) |
| 3-SCF$_2$Br | CF$_3$ | H | CH=NOEt(Z) |
| 3-SF$_5$ | CF$_3$ | C(O)OCH$_3$ | CH$_2$OEt |
| 3-SF$_5$ | CF$_3$ | H | CH$_2$OCH$_2$CF$_3$ |
| 3-SF$_5$ | CF$_3$ | H | E4-1a |
| 3-SF$_5$ | CF$_3$ | H | CH$_2$C(O)NHCH$_2$CF$_3$ |
| 3-SF$_5$ | CF$_3$ | H | CH(CH$_3$)C(O)NHCH$_2$CF$_3$(D) |
| 3-SF$_5$ | CF$_3$ | H | CH$_2$(D10-2a) |
| 3-SF$_5$ | CF$_3$ | H | CH=NOCH$_3$(Z) |
| 3-SF$_5$ | CF$_3$ | H | CH=NOEt(Z) |
| 3-SF$_5$ | CF$_3$ | C(O)Et | C(O)OCH$_3$ |
| 3-SF$_5$ | CF$_3$ | H | (D34-1c)CN |
| 3-Cl-4-F | CF$_3$ | C(O)OCH$_3$ | CH$_2$OEt |
| 3-Cl-4-F | CF$_3$ | H | CH$_2$OCH$_2$CF$_3$ |
| 3-Cl-4-F | CF$_3$ | C(O)OCH$_3$ | CH$_2$OCH$_2$CF$_3$ |
| 3-Cl-4-F | CF$_3$ | H | E4-1a |
| 3-Cl-4-F | CF$_3$ | H | CH$_2$C(O)NHCH$_2$CF$_3$ |
| 3-Cl-4-F | CF$_3$ | H | CH(CH$_3$)C(O)NHCH$_2$CF$_3$ |
| 3-Cl-4-F | CF$_3$ | H | CH(CH$_3$)C(O)NHCH$_2$CF$_3$(D) |
| 3-Cl-4-F | CF$_3$ | H | CH$_2$(D10-2a) |
| 3-Cl-4-F | CF$_3$ | H | CH$_2$(D32-1a) |
| 3-Cl-4-F | CF$_3$ | C(O)CH$_3$ | CH$_2$(D32-1a) |
| 3-Cl-4-F | CF$_3$ | C(O)OCH$_3$ | CH$_2$(D32-1a) |
| 3-Cl-4-F | CF$_3$ | H | CH=NOCH$_3$(Z) |
| 3-Cl-4-F | CF$_3$ | H | CH=NOEt(Z) |
| 3-Cl-4-F | CF$_3$ | C(O)Et | C(O)OCH$_3$ |
| 3-Cl-4-F | CF$_3$ | C(O)CH$_3$ | (D34-1c)Cl |
| 3-Cl-4-F | CF$_3$ | C(O)OCH$_3$ | (D34-1c)Cl |
| 3-Cl-4-F | CF$_3$ | H | (D34-1c)CN |
| 3-Cl-4-F | CF$_3$ | CH$_3$ | (D34-1c)CN |
| 3-Cl-4-F | CF$_3$ | CH$_2$OC(O)OH$_3$ | (D34-1c)CN |
| 3-Cl-4-F | CF$_3$ | C(O)Pr-i | (D34-1c)CN |
| 3-Cl-4-F | CF$_2$Cl | H | CH$_2$C(O)NHCH$_2$CF$_3$ |
| 3-Cl-4-F | CF$_2$Cl | H | CH(CH$_3$)C(O)NHCH$_2$CF$_3$(D) |
| 3-Cl-4-F | CF$_2$Cl | H | CH$_2$(D10-2a) |
| 3-Cl-4-F | CF$_2$Cl | H | CH=NOCH$_3$(Z) |
| 3-Cl-4-F | CF$_2$Cl | H | CH=NOEt(Z) |
| 3-F-5-Cl | CF$_3$ | C(O)OCH$_3$ | CH$_2$OEt |

TABLE 4-continued

| $(X)_m$ | $R^3$ | $R^2$ | $R^1$ |
|---|---|---|---|
| 3-F-5-Cl | $CF_3$ | H | $CH_2OCH_2CF_3$ |
| 3-F-5-Cl | $CF_3$ | $C(O)OCH_3$ | $CH_2OCH_2CF_3$ |
| 3-F-5-Cl | $CF_3$ | H | E4-1a |
| 3-F-5-Cl | $CF_3$ | H | $CH_2C(O)NHCH_2CF_3$ |
| 3-F-5-Cl | $CF_3$ | H | $CH(CH_3)C(O)NHCH_2CF_3$ |
| 3-F-5-Cl | $CF_3$ | H | $CH(CH_3)C(O)NHCH_2CF_3(D)$ |
| 3-F-5-Cl | $CF_3$ | H | $CH_2(D10\text{-}2a)$ |
| 3-F-5-Cl | $CF_3$ | H | $CH_2(D32\text{-}1a)$ |
| 3-F-5-Cl | $CF_3$ | $C(O)CH_3$ | $CH_2(D32\text{-}1a)$ |
| 3-F-5-Cl | $CF_3$ | $C(O)OCH_3$ | $CH_2(D32\text{-}1a)$ |
| 3-F-5-Cl | $CF_3$ | H | $CH=NOCH_3(Z)$ |
| 3-F-5-Cl | $CF_3$ | H | $CH=NOEt(Z)$ |
| 3-F-5-Cl | $CF_3$ | $C(O)Et$ | $C(O)OCH_3$ |
| 3-F-5-Cl | $CF_3$ | $C(O)CH_3$ | $(D34\text{-}1c)Cl$ |
| 3-F-5-Cl | $CF_3$ | $C(O)OCH_3$ | $(D34\text{-}1c)Cl$ |
| 3-F-5-Cl | $CF_3$ | H | $(D34\text{-}1c)CN$ |
| 3-F-5-Cl | $CF_3$ | $CH_3$ | $(D34\text{-}1c)CN$ |
| 3-F-5-Cl | $CF_3$ | $CH_2OC(O)CH_3$ | $(D34\text{-}1c)CN$ |
| 3-F-5-Cl | $CF_3$ | $C(O)Pr\text{-}i$ | $(D34\text{-}1c)CN$ |
| 3-F-5-Cl | $CF_2Cl$ | H | $CH_2C(O)NHCH_2CF_3$ |
| 3-F-5-Cl | $CF_2Cl$ | H | $CH(CH_3)C(O)NHCH_2CF_3(D)$ |
| 3-F-5-Cl | $CF_2Cl$ | H | $CH_2(D10\text{-}2a)$ |
| 3-F-5-Cl | $CF_2Cl$ | H | $CH=NOCH_3(Z)$ |
| 3-F-5-Cl | $CF_2Cl$ | H | $CH=NOEt(Z)$ |
| $3,4\text{-}Cl_2$ | $CF_3$ | $C(O)OCH_3$ | $CH_2OEt$ |
| $3,4\text{-}Cl_2$ | $CF_3$ | H | $CH_2OCH_2CF_3$ |
| $3,4\text{-}Cl_2$ | $CF_3$ | $C(O)OCH_3$ | $CH_2OCH_2CF_3$ |
| $3,4\text{-}Cl_2$ | $CF_3$ | H | E4-1a |
| $3,4\text{-}Cl_2$ | $CF_3$ | H | $CH_2C(O)NHCH_2CF_3$ |
| $3,4\text{-}Cl_2$ | $CF_3$ | H | $CH(CH_3)C(O)NHCH_2CF_3$ |
| $3,4\text{-}Cl_2$ | $CF_3$ | H | $CH(CH_3)C(O)NHCH_2CF_3(D)$ |
| $3,4\text{-}Cl_2$ | $CF_3$ | H | $CH_2(D10\text{-}2a)$ |
| $3,4\text{-}Cl_2$ | $CF_3$ | H | $CH_2(D32\text{-}1a)$ |
| $3,4\text{-}Cl_2$ | $CF_3$ | $C(O)CH_3$ | $CH_3(D32\text{-}1a)$ |
| $3,4\text{-}Cl_2$ | $CF_3$ | $C(O)OCH_3$ | $CH_2(D32\text{-}1a)$ |
| $3,4\text{-}Cl_2$ | $CF_3$ | H | $CH=NOCH_3(Z)$ |
| $3,4\text{-}Cl_2$ | $CF_3$ | H | $CH=NOEt(Z)$ |
| $3,4\text{-}Cl_2$ | $CF_3$ | $C(O)Et$ | $C(O)OCH_3$ |
| $3,4\text{-}Cl_2$ | $CF_3$ | $C(O)CH_3$ | $(D34\text{-}1c)Cl$ |
| $3,4\text{-}Cl_2$ | $CF_3$ | $C(O)OCH_3$ | $(D34\text{-}1c)Cl$ |
| $3,4\text{-}Cl_2$ | $CF_3$ | H | $(D34\text{-}1c)CN$ |
| $3,4\text{-}Cl_2$ | $CF_3$ | $CH_3$ | $(D34\text{-}1c)CN$ |
| $3,4\text{-}Cl_2$ | $CF_3$ | $CH_2OC(O)CH_3$ | $(D34\text{-}1c)CN$ |
| $3,4\text{-}Cl_2$ | $CF_3$ | $C(O)Pr\text{-}i$ | $(D34\text{-}1c)CN$ |
| $3,4\text{-}Cl_2$ | $CF_2Cl$ | H | $CH_2C(O)NHCH_2CF_3$ |
| $3,4\text{-}Cl_2$ | $CF_2Cl$ | H | $CH(CH_3)C(O)NHCH_2CF_3(D)$ |
| $3,4\text{-}Cl_2$ | $CF_2Cl$ | H | $CH_2(D10\text{-}2a)$ |
| $3,4\text{-}Cl_2$ | $CF_2Cl$ | H | $CH=NOCH_3(Z)$ |
| $3,4\text{-}Cl_2$ | $CF_2Cl$ | H | $CH=NOEt(Z)$ |
| $3,5\text{-}Cl_2$ | $CF_3$ | $C(O)CH_3$ | $CH_2CF_3$ |
| $3,5\text{-}Cl_2$ | $CF_3$ | $C(O)OCH_3$ | $CH_2OCH_3$ |
| $3,5\text{-}Cl_2$ | $CF_3$ | $C(O)OCH_3$ | $CH_2OEt$ |
| $3,5\text{-}Cl_2$ | $CF_3$ | $C(O)OCH_3$ | $CH_2OPr\text{-}i$ |
| $3,5\text{-}Cl_2$ | $CF_3$ | H | $CH_2OCH_2CF_3$ |
| $3,5\text{-}Cl_2$ | $CF_3$ | $C(O)OCH_3$ | $CH_2OCH_2CF_3$ |
| $3,5\text{-}Cl_2$ | $CF_3$ | H | E4-1a |
| $3,5\text{-}Cl_2$ | $CF_3$ | H | $CH_2C(O)NHCH_2CH_2Cl$ |
| $3,5\text{-}Cl_2$ | $CF_3$ | H | $CH_2C(O)NHCH_2CF_3$ |
| $3,5\text{-}Cl_2$ | $CF_3$ | H | $CH(CH_3)C(O)NHCH_2CH_2Cl$ |
| $3,5\text{-}Cl_2$ | $CF_3$ | H | $CH(CH_3)C(O)NHCH_2CF_3$ |
| $3,5\text{-}Cl_2$ | $CF_3$ | H | $CH(CH_3)C(O)NHCH_2CF_3(D)$ |
| $3,5\text{-}Cl_2$ | $CF_3$ | H | $CH_2(D10\text{-}2a)$ |
| $3,5\text{-}Cl_2$ | $CF_3$ | $C(O)CH_3$ | $CH_2(D10\text{-}2a)$ |
| $3,5\text{-}Cl_2$ | $CF_3$ | $C(O)Et$ | $CH_2(D10\text{-}2a)$ |
| $3,5\text{-}Cl_2$ | $CF_3$ | H | $CH_2(D32\text{-}1a)$ |
| $3,5\text{-}Cl_2$ | $CF_3$ | $C(O)CH_3$ | $CH_2(D32\text{-}1a)$ |
| $3,5\text{-}Cl_2$ | $CF_3$ | $C(O)Et$ | $CH_2(D32\text{-}1a)$ |
| $3,5\text{-}Cl_2$ | $CF_3$ | $C(O)OCH_3$ | $CH_2(D32\text{-}1a)$ |
| $3,5\text{-}Cl_2$ | $CF_3$ | H | $CH=NOCH_3(Z)$ |
| $3,5\text{-}Cl_2$ | $CF_3$ | $CH_2OCH_3$ | $CH=NOCH_3$ |
| $3,5\text{-}Cl_2$ | $CF_3$ | $CH_2OC(O)CH_3$ | $CH=NOCH_3$ |
| $3,5\text{-}Cl_2$ | $CF_3$ | H | $CH=NOEt(Z)$ |
| $3,5\text{-}Cl_2$ | $CF_3$ | $C(O)Et$ | $C(O)OCH_3$ |
| $3,5\text{-}Cl_2$ | $CF_3$ | $CH_3$ | $(D34\text{-}1c)Cl$ |
| $3,5\text{-}Cl_2$ | $CF_3$ | $CH_2OC(O)CH_3$ | $(D34\text{-}1c)Cl$ |
| $3,5\text{-}Cl_2$ | $CF_3$ | $C(O)CH_3$ | $(D34\text{-}1c)Cl$ |
| $3,5\text{-}Cl_2$ | $CF_3$ | $C(O)Pr\text{-}c$ | $(D34\text{-}1c)Cl$ |
| $3,5\text{-}Cl_2$ | $CF_3$ | $C(O)CH_2OCH_3$ | $(D34\text{-}1c)Cl$ |

TABLE 4-continued

| (X)$_m$ | R$^3$ | R$^2$ | R$^1$ |
|---|---|---|---|
| 3,5-Cl$_2$ | CF$_3$ | C(O)OCH$_3$ | (D34-1c)Cl |
| 3,5-Cl$_2$ | CF$_3$ | C(O)OCH$_2$Cl | (D34-1c)Cl |
| 3,5-Cl$_2$ | CF$_3$ | C(O)OCH$_2$CH$_2$OCH$_3$ | (D34-1c)Cl |
| 3,5-Cl$_2$ | CF$_3$ | H | (D34-1c)CN |
| 3,5-Cl$_2$ | CF$_3$ | CH$_3$ | (D34-1c)CN |
| 3,5-Cl$_2$ | CF$_3$ | CH$_2$OCH$_3$ | (D34-1c)CN |
| 3,5-Cl$_2$ | CF$_3$ | CH$_2$OC(O)CH$_3$ | (D34-1c)CN |
| 3,5-Cl$_2$ | CF$_3$ | C(O)CH$_3$ | (D34-1c)CN |
| 3,5-Cl$_2$ | CF$_3$ | C(O)Pr-i | (D34-1c)CN |
| 3,5-Cl$_2$ | CF$_3$ | C(O)OCH$_3$ | (D34-1c)CN |
| 3,5-Cl$_2$ | CF$_3$ | H | D34-3a |
| 3,5-Cl$_2$ | CF$_3$ | CH$_3$ | D34-3a |
| 3,5-Cl$_2$ | CF$_3$ | CH$_2$OCH$_3$ | D34-3a |
| 3,5-Cl$_2$ | CF$_3$ | C(O)Et | D34-3a |
| 3,5-Cl$_2$ | CF$_3$ | C(O)Pr-i | D34-3a |
| 3,5-Cl$_2$ | CF$_3$ | C(O)OCH$_3$ | (D35-1c)Cl |
| 3,5-Cl$_2$ | CF$_3$ | H | N(CH$_3$)Ph |
| 3,5-Cl$_2$ | CF$_3$ | H | N(CH$_3$)(D34-1a) |
| 3,5-Cl$_2$ | CF$_2$Cl | C(O)OCH$_3$ | CH$_2$OEt |
| 3,5-Cl$_2$ | CF$_2$Cl | H | CH$_2$OCH$_2$CF$_3$ |
| 3,5-Cl$_2$ | CF$_2$Cl | H | E4-1a |
| 3,5-Cl$_2$ | CF$_2$Cl | H | CH$_2$C(O)NHCH$_2$CF$_3$ |
| 3,5-Cl$_2$ | CF$_2$Cl | H | CH(CH$_3$)C(O)NHCH$_2$CF$_3$(D) |
| 3,5-Cl$_2$ | CF$_2$Cl | H | CH$_2$(D10-2a) |
| 3,5-Cl$_2$ | CF$_2$Cl | H | CH=NOCH$_3$(Z) |
| 3,5-Cl$_2$ | CF$_2$Cl | H | CH=NOEt(Z) |
| 3,5-Cl$_2$ | CF$_2$Cl | C(O)Et | C(O)OCH$_3$ |
| 3,5-Cl$_2$ | CF$_2$Cl | H | (D34-1c)CN |
| 3-Br-4-F | CF$_3$ | C(O)OCH$_3$ | CH$_2$OEt |
| 3-Br-4-F | CF$_3$ | H | CH$_2$OCH$_2$CF$_3$ |
| 3-Br-4-F | CF$_3$ | C(O)OCH$_3$ | CH$_2$OCH$_2$CF$_3$ |
| 3-Br-4-F | CF$_3$ | H | E4-1a |
| 3-Br-4-F | CF$_3$ | H | CH$_2$C(O)NHCH$_2$CF$_3$ |
| 3-Br-4-F | CF$_3$ | H | CH(CH$_3$)C(O)NHCH$_2$CF$_3$ |
| 3-Br-4-F | CF$_3$ | H | CH(CH$_3$)C(O)NHCH$_2$CF$_3$(D) |
| 3-Br-4-F | CF$_3$ | H | CH$_2$(D10-2a) |
| 3-Br-4-F | CF$_3$ | H | CH$_2$(D32-1a) |
| 3-Br-4-F | CF$_3$ | C(O)CH$_3$ | CH$_2$(D32-1a) |
| 3-Br-4-F | CF$_3$ | C(O)OCH$_3$ | CH$_2$(D32-1a) |
| 3-Br-4-F | CF$_3$ | H | CH=NOCH$_3$(Z) |
| 3-Br-4-F | CF$_3$ | H | CH=NOEt(Z) |
| 3-Br-4-F | CF$_3$ | C(O)Et | C(O)OCH$_3$ |
| 3-Br-4-F | CF$_3$ | C(O)CH$_3$ | (D34-1c)Cl |
| 3-Br-4-F | CF$_3$ | C(O)OCH$_3$ | (D34-1c)Cl |
| 3-Br-4-F | CF$_3$ | H | (D34-1c)CN |
| 3-Br-4-F | CF$_3$ | CH$_3$ | (D34-1c)CN |
| 3-Br-4-F | CF$_3$ | CH$_2$OC(O)CH$_3$ | (D34-1c)CN |
| 3-Br-4-F | CF$_3$ | C(O)Pr-i | (D34-1c)CN |
| 3-Br-4-F | CF$_2$Cl | H | CH$_2$C(O)NHCH$_2$CF$_3$ |
| 3-Br-4-F | CF$_2$Cl | H | CH(CH$_3$)C(O)NHCH$_2$CF$_3$(D) |
| 3-Br-4-F | CF$_2$Cl | H | CH$_2$(D10-2a) |
| 3-Br-4-F | CF$_2$Cl | H | CH=NOCH$_3$(Z) |
| 3-Br-4-F | CF$_2$Cl | H | CH=NOEt(Z) |
| 3-F-5-Br | CF$_3$ | C(O)OCH$_3$ | CH$_2$OEt |
| 3-F-5-Br | CF$_3$ | H | CH$_2$OCH$_2$CF$_3$ |
| 3-F-5-Br | CF$_3$ | C(O)OCH$_3$ | CH$_2$OCH$_2$CF$_3$ |
| 3-F-5-Br | CF$_3$ | H | E4-1a |
| 3-F-5-Br | CF$_3$ | H | CH$_2$C(O)NHCH$_2$CF$_3$ |
| 3-F-5-Br | CF$_3$ | H | CH(CH$_3$)C(O)NHCH$_2$CF$_3$ |
| 3-F-5-Br | CF$_3$ | H | CH(CH$_3$)C(O)NHCH$_2$CF$_3$(D) |
| 3-F-5-Br | CF$_3$ | H | CH$_2$(D10-2a) |
| 3-F-5-Br | CF$_3$ | H | CH$_2$(D32-1a) |
| 3-F-5-Br | CF$_3$ | C(O)CH$_3$ | CH$_2$(D32-1a) |
| 3-F-5-Br | CF$_3$ | C(O)OCH$_3$ | CH$_2$(D32-1a) |
| 3-F-5-Br | CF$_3$ | H | CH=NOCH$_3$(Z) |
| 3-F-5-Br | CF$_3$ | H | CH=NOEt(Z) |
| 3-F-5-Br | CF$_3$ | C(O)Et | C(O)OCH$_3$ |
| 3-F-5-Br | CF$_3$ | C(O)CH$_3$ | (D34-1c)Cl |
| 3-F-5-Br | CF$_3$ | C(O)OCH$_3$ | (D34-1c)Cl |
| 3-F-5-Br | CF$_3$ | H | (D34-1c)CN |
| 3-F-5-Br | CF$_3$ | CH$_3$ | (D34-1c)CN |
| 3-F-5-Br | CF$_3$ | CH$_2$OC(O)CH$_3$ | (D34-1c)CN |
| 3-F-5-Br | CF$_3$ | C(O)Pr-i | (D34-1c)CN |
| 3-F-5-Br | CF$_2$Cl | H | CH$_2$C(O)NHCH$_2$CF$_3$ |
| 3-F-5-Br | CF$_2$Cl | H | CH(CH$_3$)C(O)NHCH$_2$CF$_3$(D) |
| 3-F-5-Br | CF$_2$Cl | H | CH$_2$(D10-2a) |
| 3-F-5-Br | CF$_2$Cl | H | CH=NOCH$_3$(Z) |
| 3-F-5-Br | CF$_2$Cl | H | CH=NOEt(Z) |

TABLE 4-continued

| (X)$_m$ | R$^3$ | R$^2$ | R$^1$ |
|---|---|---|---|
| 3-Br-4-Cl | CF$_3$ | C(O)OCH$_3$ | CH$_2$OEt |
| 3-Br-4-Cl | CF$_3$ | H | CH$_2$OCH$_2$CF$_3$ |
| 3-Br-4-Cl | CF$_3$ | H | E4-1a |
| 3-Br-4-Cl | CF$_3$ | H | CH$_2$C(O)NHCH$_2$CF$_3$ |
| 3-Br-4-Cl | CF$_3$ | H | CH(CH$_3$)C(O)NHCH$_2$CF$_3$(D) |
| 3-Br-4-Cl | CF$_3$ | H | CH$_2$(D10-2a) |
| 3-Br-4-Cl | CF$_3$ | H | CH=NOCH$_3$(Z) |
| 3-Br-4-Cl | CF$_3$ | H | CH=NOEt(Z) |
| 3-Br-4-Cl | CF$_3$ | C(O)Et | C(O)OCH$_3$ |
| 3-Br-4-Cl | CF$_3$ | H | (D34-1c)CN |
| 3-Cl-4-Br | CF$_3$ | C(O)OCH$_3$ | CH$_2$OEt |
| 3-Cl-4-Br | CF$_3$ | H | CH$_2$OCH$_2$CF$_3$ |
| 3-Cl-4-Br | CF$_3$ | H | E4-1a |
| 3-Cl-4-Br | CF$_3$ | H | CH$_2$C(O)NHCH$_2$CF$_3$ |
| 3-Cl-4-Br | CF$_3$ | H | CH(CH$_3$)C(O)NHCH$_2$CF$_3$(D) |
| 3-Cl-4-Br | CF$_3$ | H | CH$_2$(D10-2a) |
| 3-Cl-4-Br | CF$_3$ | H | CH=NOCH$_3$(Z) |
| 3-Cl-4-Br | CF$_3$ | H | CH=NOEt(Z) |
| 3-Cl-4-Br | CF$_3$ | C(O)Et | C(O)OCH$_3$ |
| 3-Cl-4-Br | CF$_3$ | H | (D34-1c)CN |
| 3-Cl-5-Br | CF$_3$ | C(O)CH$_3$ | CH$_2$CF$_3$ |
| 3-Cl-5-Br | CF$_3$ | C(O)OCH$_3$ | CH$_2$OCH$_3$ |
| 3-Cl-5-Br | CF$_3$ | C(O)OCH$_3$ | CH$_2$OEt |
| 3-Cl-5-Br | CF$_3$ | C(O)OCH$_3$ | CH$_2$OPr-i |
| 3-Cl-5-Br | CF$_3$ | H | CH$_2$OCH$_2$CF$_3$ |
| 3-Cl-5-Br | CF$_3$ | C(O)OCH$_3$ | CH$_2$OCH$_2$CF$_3$ |
| 3-Cl-5-Br | CF$_3$ | H | E4-1a |
| 3-Cl-5-Br | CF$_3$ | H | CH$_2$C(O)NHCH$_2$Cl |
| 3-Cl-5-Br | CF$_3$ | H | CH$_2$C(O)NHCH$_2$CF$_3$ |
| 3-Cl-5-Br | CF$_3$ | H | CH(CH$_3$)C(O)NHCH$_2$Cl |
| 3-Cl-5-Br | CF$_3$ | H | CH(CH$_3$)C(O)NHCH$_2$CF$_3$ |
| 3-Cl-5-Br | CF$_3$ | H | CH(CH$_3$)C(O)NHCH$_2$CF$_3$(D) |
| 3-Cl-5-Br | CF$_3$ | H | CH$_2$(D10-2a) |
| 3-Cl-5-Br | CF$_3$ | C(O)CH$_3$ | CH$_2$(D10-2a) |
| 3-Cl-5-Br | CF$_3$ | C(O)Et | CH$_2$(D10-2a) |
| 3-Cl-5-Br | CF$_3$ | H | CH$_2$(D32-1a) |
| 3-Cl-5-Br | CF$_3$ | C(O)CH$_3$ | CH$_2$(D32-1a) |
| 3-Cl-5-Br | CF$_3$ | C(O)Et | CH$_2$(D32-1a) |
| 3-Cl-5-Br | CF$_3$ | C(O)OCH$_3$ | CH$_2$(D32-1a) |
| 3-Cl-5-Br | CF$_3$ | H | CH=NOCH$_3$(Z) |
| 3-Cl-5-Br | CF$_3$ | CH$_2$OCH$_3$ | CH=NOCH$_3$ |
| 3-Cl-5-Br | CF$_3$ | CH$_2$OC(O)CH$_3$ | CH=NOCH$_3$ |
| 3-Cl-5-Br | CF$_3$ | H | CH=NOEt(Z) |
| 3-Cl-5-Br | CF$_3$ | C(O)Et | C(O)OCH$_3$ |
| 3-Cl-5-Br | CF$_3$ | CH$_2$OC(O)CH$_3$ | (D34-1c)Cl |
| 3-Cl-5-Br | CF$_3$ | C(O)CH$_3$ | (D34-1c)Cl |
| 3-Cl-5-Br | CF$_3$ | C(O)Pr-c | (D34-1c)Cl |
| 3-Cl-5-Br | CF$_3$ | C(O)OCH$_3$ | (D34-1c)Cl |
| 3-Cl-5-Br | CF$_3$ | H | (D34-1c)CN |
| 3-Cl-5-Br | CF$_3$ | CH$_3$ | (D34-1c)CN |
| 3-Cl-5-Br | CF$_3$ | CH$_2$OCH$_3$ | (D34-1c)CN |
| 3-Cl-5-Br | CF$_3$ | CH$_2$OC(O)CH$_3$ | (D34-1c)CN |
| 3-Cl-5-Br | CF$_3$ | C(O)Pr-i | (D34-1c)CN |
| 3-Cl-5-Br | CF$_3$ | C(O)OCH$_3$ | (D34-1c)CN |
| 3-Cl-5-Br | CF$_3$ | CH$_2$OCH$_3$ | D34-3a |
| 3-Cl-5-Br | CF$_3$ | C(O)Et | D34-3a |
| 3-Cl-5-Br | CF$_3$ | C(O)Pr-i | D34-3a |
| 3-Cl-5-Br | CF$_3$ | C(O)OCH$_3$ | (D35-1c)Cl |
| 3-Cl-5-Br | CF$_3$ | H | N(CH$_3$)Ph |
| 3-Cl-5-Br | CF$_3$ | H | N(CH$_3$)(D34-1a) |
| 3-Cl-5-Br | CF$_2$Cl | C(O)OCH$_3$ | CH$_2$OEt |
| 3-Cl-5-Br | CF$_2$Cl | H | CH$_2$OCH$_2$CF$_3$ |
| 3-Cl-5-Br | CF$_2$Cl | H | E4-1a |
| 3-Cl-5-Br | CF$_2$Cl | H | CH$_2$C(O)NHCH$_2$CF$_3$ |
| 3-Cl-5-Br | CF$_2$Cl | H | CH(CH$_3$)C(O)NHCH$_2$CF$_3$(D) |
| 3-Cl-5-Br | CF$_2$Cl | H | CH$_2$(D10-2a) |
| 3-Cl-5-Br | CF$_2$Cl | H | CH=NOCH$_3$(Z) |
| 3-Cl-5-Br | CF$_2$Cl | H | CH=NOEt(Z) |
| 3-Cl-5-Br | CF$_2$Cl | C(O)Et | C(O)OCH$_3$ |
| 3-Cl-5-Br | CF$_2$Cl | H | (D34-1c)CN |
| 3,4-Br$_2$ | CF$_3$ | C(O)OCH$_3$ | CH$_2$OEt |
| 3,4-Br$_2$ | CF$_3$ | H | CH$_2$OCH$_2$CF$_3$ |
| 3,4-Br$_2$ | CF$_3$ | H | E4-1a |
| 3,4-Br$_2$ | CF$_3$ | H | CH$_2$C(O)NHCH$_2$CF$_3$ |
| 3,4-Br$_2$ | CF$_3$ | H | CH(CH$_3$)C(O)NHCH$_2$CF$_3$(D) |
| 3,4-Br$_2$ | CF$_3$ | H | CH$_2$(D10-2a) |
| 3,4-Br$_2$ | CF$_3$ | H | CH=NOCH$_3$(Z) |
| 3,4-Br$_2$ | CF$_3$ | H | CH=NOEt(Z) |

TABLE 4-continued

| $(X)_m$ | $R^3$ | $R^2$ | $R^1$ |
|---|---|---|---|
| 3,4-Br$_2$ | CF$_3$ | C(O)Et | C(O)OCH$_3$ |
| 3,4-Br$_2$ | CF$_3$ | H | (D34-1c)CN |
| 3,5-Br$_2$ | CF$_3$ | C(O)CH$_3$ | CH$_2$CF$_3$ |
| 3,5-Br$_2$ | CF$_3$ | C(O)OCH$_3$ | CH$_2$OCH$_3$ |
| 3,5-Br$_2$ | CF$_3$ | C(O)OCH$_3$ | CH$_2$OEt |
| 3,5-Br$_2$ | CF$_3$ | C(O)OCH$_3$ | CH$_2$OPr-i |
| 3,5-Br$_2$ | CF$_3$ | H | CH$_2$OCH$_2$CF$_3$ |
| 3,5-Br$_2$ | CF$_3$ | C(O)OCH$_3$ | CH$_2$OCH$_2$CF$_3$ |
| 3,5-Br$_2$ | CF$_3$ | H | E4-1a |
| 3,5-Br$_2$ | CF$_3$ | H | CH$_2$C(O)NHCH$_2$CH$_2$Cl |
| 3,5-Br$_2$ | CF$_3$ | H | CH$_2$C(O)NHCH$_2$CF$_3$ |
| 3,5-Br$_2$ | CF$_3$ | H | CH(CH$_3$)C(O)NHCH$_2$CH$_2$Cl |
| 3,5-Br$_2$ | CF$_3$ | H | CH(CH$_3$)C(O)NHCH$_2$CF$_3$ |
| 3,5-Br$_2$ | CF$_3$ | H | CH(CH$_3$)C(O)NHCH$_2$CF$_3$(D) |
| 3,5-Br$_2$ | CF$_3$ | H | CH$_2$(D10-2a) |
| 3,5-Br$_2$ | CF$_3$ | C(O)CH$_3$ | CH$_2$(D10-2a) |
| 3,5-Br$_2$ | CF$_3$ | C(O)Et | CH$_2$(D10-2a) |
| 3,5-Br$_2$ | CF$_3$ | H | CH$_2$(D32-1a) |
| 3,5-Br$_2$ | CF$_3$ | C(O)CH$_3$ | CH$_3$(D32-1a) |
| 3,5-Br$_2$ | CF$_3$ | C(O)Et | CH$_2$(D32-1a) |
| 3,5-Br$_2$ | CF$_3$ | C(O)OCH$_3$ | CH$_2$(D32-1a) |
| 3,5-Br$_2$ | CF$_3$ | H | CH=NOCH$_3$(Z) |
| 3,5-Br$_2$ | CF$_3$ | CH$_2$OCH$_3$ | CH=NOCH$_3$ |
| 3,5-Br$_2$ | CF$_3$ | CH$_2$OC(O)CH$_3$ | CH=NOCH$_3$ |
| 3,5-Br$_2$ | CF$_3$ | H | CH=NOEt(Z) |
| 3,5-Br$_2$ | CF$_3$ | C(O)Et | C(O)OCH$_3$ |
| 3,5-Br$_2$ | CF$_3$ | CH$_2$OC(O)CH$_3$ | (D34-1c)Cl |
| 3,5-Br$_2$ | CF$_3$ | C(O)CH$_3$ | (D34-1c)Cl |
| 3,5-Br$_2$ | CF$_3$ | C(O)Pr-c | (D34-1c)Cl |
| 3,5-Br$_2$ | CF$_3$ | C(O)OCH$_3$ | (D34-1c)Cl |
| 3,5-Br$_2$ | CF$_3$ | H | (D34-1c)CN |
| 3,5-Br$_2$ | CF$_3$ | CH$_3$ | (D34-1c)CN |
| 3,5-Br$_2$ | CF$_3$ | CH$_2$OCH$_3$ | (D34-1c)CN |
| 3,5-Br$_2$ | CF$_3$ | CH$_2$OC(O)CH$_3$ | (D34-1c)CN |
| 3,5-Br$_2$ | CF$_3$ | C(O)Pr-i | (D34-1c)CN |
| 3,5-Br$_2$ | CF$_3$ | C(O)OCH$_3$ | (D34-1c)CN |
| 3,5-Br$_2$ | CF$_3$ | CH$_2$OCH$_3$ | D34-3a |
| 3,5-Br$_2$ | CF$_3$ | C(O)Et | D34-3a |
| 3,5-Br$_2$ | CF$_3$ | C(O)Pr-i | D34-3a |
| 3,5-Br$_2$ | CF$_3$ | C(O)OCH$_3$ | (D35-1c)Cl |
| 3,5-Br$_2$ | CF$_3$ | H | N(CH$_3$)Ph |
| 3,5-Br$_2$ | CF$_3$ | H | N(CH$_3$)(D34-1a) |
| 3,5-Br$_2$ | CF$_2$Cl | C(O)OCH$_3$ | CH$_2$OEt |
| 3,5-Br$_2$ | CF$_2$Cl | H | CH$_2$OCH$_2$CF$_3$ |
| 3,5-Br$_2$ | CF$_2$Cl | H | E4-1a |
| 3,5-Br$_2$ | CF$_2$Cl | H | CH$_2$C(O)NHCH$_2$CF$_3$ |
| 3,5-Br$_2$ | CF$_2$Cl | H | CH(CH$_3$)C(O)NHCH$_2$CF$_3$(D) |
| 3,5-Br$_2$ | CF$_2$Cl | H | CH$_2$(D10-2a) |
| 3,5-Br$_2$ | CF$_2$Cl | H | CH=NOCH$_3$(Z) |
| 3,5-Br$_2$ | CF$_2$Cl | H | CH=NOEt(Z) |
| 3,5-Br$_2$ | CF$_2$Cl | C(O)Et | C(O)OCH$_3$ |
| 3,5-Br$_2$ | CF$_2$Cl | H | (D34-1c)CN |
| 3-I-4-F | CF$_3$ | C(O)OCH$_3$ | CH$_2$OEt |
| 3-I-4-F | CF$_3$ | H | CH$_2$OCH$_2$CF$_3$ |
| 3-I-4-F | CF$_3$ | H | E4-1a |
| 3-I-4-F | CF$_3$ | H | CH$_2$C(O)NHCH$_2$CF$_3$ |
| 3-I-4-F | CF$_3$ | H | CH(CH$_3$)C(O)NHCH$_2$CF$_3$(D) |
| 3-I-4-F | CF$_3$ | H | CH$_2$(D10-2a) |
| 3-I-4-F | CF$_3$ | H | CH=NOCH$_3$(Z) |
| 3-I-4-F | CF$_3$ | H | CH=NOEt(Z) |
| 3-I-4-F | CF$_3$ | C(O)Et | C(O)OCH$_3$ |
| 3-I-4-F | CF$_3$ | H | (D34-1c)CN |
| 3-F-5-I | CF$_3$ | C(O)OCH$_3$ | CH$_2$OEt |
| 3-F-5-I | CF$_3$ | H | CH$_2$OCH$_2$CF$_3$ |
| 3-F-5-I | CF$_3$ | H | E4-1a |
| 3-F-5-I | CF$_3$ | H | CH$_2$C(O)NHCH$_2$CF$_3$ |
| 3-F-5-I | CF$_3$ | H | CH(CH$_3$)C(O)NHCH$_2$CF$_3$(D) |
| 3-F-5-I | CF$_3$ | H | CH$_2$(D10-2a) |
| 3-F-5-I | CF$_3$ | H | CH=NOCH$_3$(Z) |
| 3-F-5-I | CF$_3$ | H | CH=NOEt(Z) |
| 3-F-5-I | CF$_3$ | C(O)Et | C(O)OCH$_3$ |
| 3-F-5-I | CF$_3$ | H | (D34-1c)CN |
| 3-Cl-5-I | CF$_3$ | C(O)OCH$_3$ | CH$_2$OEt |
| 3-Cl-5-I | CF$_3$ | H | CH$_2$OCH$_2$CF$_3$ |
| 3-Cl-5-I | CF$_3$ | C(O)OCH$_3$ | CH$_2$OCH$_2$CF$_3$ |
| 3-Cl-5-I | CF$_3$ | H | E4-1a |
| 3-Cl-5-I | CF$_3$ | H | CH$_2$C(O)NHCH$_2$CF$_3$ |
| 3-Cl-5-I | CF$_3$ | H | CH(CH$_3$)C(O)NHCH$_2$CF$_3$ |

TABLE 4-continued

| $(X)_m$ | $R^3$ | $R^2$ | $R^1$ |
|---|---|---|---|
| 3-Cl-5-I | $CF_3$ | H | $CH(CH_3)C(O)NHCH_2CF_3(D)$ |
| 3-Cl-5-I | $CF_3$ | H | $CH_2(D10-2a)$ |
| 3-Cl-5-I | $CF_3$ | H | $CH_2(D32-1a)$ |
| 3-Cl-5-I | $CF_3$ | $C(O)CH_3$ | $CH_2(D32-1a)$ |
| 3-Cl-5-I | $CF_3$ | $C(O)OCH_3$ | $CH_2(D32-1a)$ |
| 3-Cl-5-I | $CF_3$ | H | $CH=NOCH_3(Z)$ |
| 3-Cl-5-I | $CF_3$ | H | $CH=NOEt(Z)$ |
| 3-Cl-5-I | $CF_3$ | $C(O)Et$ | $C(O)OCH_3$ |
| 3-Cl-5-I | $CF_3$ | $C(O)CH_3$ | $(D34-1c)Cl$ |
| 3-Cl-5-I | $CF_3$ | $C(O)OCH_3$ | $(D34-1c)Cl$ |
| 3-Cl-5-I | $CF_3$ | H | $(D34-1c)CN$ |
| 3-Cl-5-I | $CF_3$ | $CH_3$ | $(D34-1c)CN$ |
| 3-Cl-5-I | $CF_3$ | $CH_2OC(O)CH_3$ | $(D34-1c)CN$ |
| 3-Cl-5-I | $CF_3$ | $C(O)Pr-i$ | $(D34-1c)CN$ |
| 3-Cl-5-I | $CF_2Cl$ | H | $CH_2C(O)NHCH_2CF_3$ |
| 3-Cl-5-I | $CF_2Cl$ | H | $CH(CH_3)C(O)NHCH_2CF_3(D)$ |
| 3-Cl-5-I | $CF_2Cl$ | H | $CH_2(D10-2a)$ |
| 3-Cl-5-I | $CF_2Cl$ | H | $CH=NOCH_3(Z)$ |
| 3-Cl-5-I | $CF_2Cl$ | H | $CH=NOEt(Z)$ |
| 3-Cl-5-$CH_3$ | $CF_3$ | H | $CH_2C(O)NHCH_2CF_3$ |
| 3-Cl-5-$CH_3$ | $CF_3$ | H | $CH(CH_3)C(O)NHCH_2CF_3(D)$ |
| 3-Cl-5-$CH_3$ | $CF_3$ | H | $CH_2(D10-2a)$ |
| 3-Cl-5-$CH_3$ | $CF_3$ | H | $CH=NOCH_3(Z)$ |
| 3-Cl-5-$CH_3$ | $CF_3$ | H | $CH=NOEt(Z)$ |
| 3-Br-5-$CH_3$ | $CF_3$ | H | $CH_2C(O)NHCH_2CF_3$ |
| 3-Br-5-$CH_3$ | $CF_3$ | H | $CH(CH_3)C(O)NHCH_2CF_3(D)$ |
| 3-Br-5-$CH_3$ | $CF_3$ | H | $CH_2(D10-2a)$ |
| 3-Br-5-$CH_3$ | $CF_3$ | H | $CH=NOCH_3(Z)$ |
| 3-Br-5-$CH_3$ | $CF_3$ | H | $CH=NOEt(Z)$ |
| 3-$CF_3$-4-F | $CF_3$ | $C(O)OCH_3$ | $CH_2OEt$ |
| 3-$CF_3$-4-F | $CF_3$ | H | $CH_2OCH_2CF_3$ |
| 3-$CF_3$-4-F | $CF_3$ | $C(O)OCH_3$ | $CH_2OCH_2CF_3$ |
| 3-$CF_3$-4-F | $CF_3$ | H | E4-1a |
| 3-$CF_3$-4-F | $CF_3$ | H | $CH_2C(O)NHCH_2CF_3$ |
| 3-$CF_3$-4-F | $CF_3$ | H | $CH(CH_3)C(O)NHCH_2CF_3$ |
| 3-$CF_3$-4-F | $CF_3$ | H | $CH(CH_3)C(O)NHCH_2CF_3(D)$ |
| 3-$CF_3$-4-F | $CF_3$ | H | $CH_2(D10-2a)$ |
| 3-$CF_3$-4-F | $CF_3$ | H | $CH_2(D32-1a)$ |
| 3-$CF_3$-4-F | $CF_3$ | $C(O)CH_3$ | $CH_2(D32-1a)$ |
| 3-$CF_3$-4-F | $CF_3$ | $C(O)OCH_3$ | $CH_2(D32-1a)$ |
| 3-$CF_3$-4-F | $CF_3$ | H | $CH=NOCH_3(Z)$ |
| 3-$CF_3$-4-F | $CF_3$ | H | $CH=NOEt(Z)$ |
| 3-$CF_3$-4-F | $CF_3$ | $C(O)Et$ | $C(O)OCH_3$ |
| 3-$CF_3$-4-F | $CF_3$ | $C(O)CH_3$ | $(D34-1c)Cl$ |
| 3-$CF_3$-4-F | $CF_3$ | $C(O)OCH_3$ | $(D34-1c)Cl$ |
| 3-$CF_3$-4-F | $CF_3$ | H | $(D34-1c)CN$ |
| 3-$CF_3$-4-F | $CF_3$ | $CH_3$ | $(D34-1c)CN$ |
| 3-$CF_3$-4-F | $CF_3$ | $CH_2OC(O)CH_3$ | $(D34-1c)CN$ |
| 3-$CF_3$-4-F | $CF_3$ | $C(O)Pr-i$ | $(D34-1c)CN$ |
| 3-$CF_3$-4-F | $CF_2Cl$ | H | $CH_2C(O)NHCH_2CF_3$ |
| 3-$CF_3$-4-F | $CF_2Cl$ | H | $CH(CH_3)C(O)NHCH_2CF_3(D)$ |
| 3-$CF_3$-4-F | $CF_2Cl$ | H | $CH_2(D10-2a)$ |
| 3-$CF_3$-4-F | $CF_2Cl$ | H | $CH=NOCH_3(Z)$ |
| 3-$CF_3$-4-F | $CF_2Cl$ | H | $CH=NOEt(Z)$ |
| 3-F-5-$CF_3$ | $CF_3$ | $C(O)OCH_3$ | $CH_2OEt$ |
| 3-F-5-$CF_3$ | $CF_3$ | H | $CH_2OCH_2CF_3$ |
| 3-F-5-$CF_3$ | $CF_3$ | $C(O)OCH_3$ | $CH_2OCH_2CF_3$ |
| 3-F-5-$CF_3$ | $CF_3$ | H | E4-1a |
| 3-F-5-$CF_3$ | $CF_3$ | H | $CH_2C(O)NHCH_2CF_3$ |
| 3-F-5-$CF_3$ | $CF_3$ | H | $CH(CH_3)C(O)NHCH_2CF_3$ |
| 3-F-5-$CF_3$ | $CF_3$ | H | $CH(CH_3)C(O)NHCH_2CF_3(D)$ |
| 3-F-5-$CF_3$ | $CF_3$ | H | $CH_2(D10-2a)$ |
| 3-F-5-$CF_3$ | $CF_3$ | H | $CH_2(D32-1a)$ |
| 3-F-5-$CF_3$ | $CF_3$ | $C(O)CH_3$ | $CH_2(D32-1a)$ |
| 3-F-5-$CF_3$ | $CF_3$ | $C(O)OCH_3$ | $CH_2(D32-1a)$ |
| 3-F-5-$CF_3$ | $CF_3$ | H | $CH=NOCH_3(Z)$ |
| 3-F-5-$CF_3$ | $CF_3$ | H | $CH=NOEt(Z)$ |
| 3-F-5-$CF_3$ | $CF_3$ | $C(O)Et$ | $C(O)OCH_3$ |
| 3-F-5-$CF_3$ | $CF_3$ | $C(O)CH_3$ | $(D34-1c)Cl$ |
| 3-F-5-$CF_3$ | $CF_3$ | $C(O)OCH_3$ | $(D34-1c)Cl$ |
| 3-F-5-$CF_3$ | $CF_3$ | H | $(D34-1c)CN$ |
| 3-F-5-$CF_3$ | $CF_3$ | $CH_3$ | $(D34-1c)CN$ |
| 3-F-5-$CF_3$ | $CF_3$ | $CH_2OC(O)CH_3$ | $(D34-1c)CN$ |
| 3-F-5-$CF_3$ | $CF_3$ | $C(O)Pr-i$ | $(D34-1c)CN$ |
| 3-F-5-$CF_3$ | $CF_2Cl$ | H | $CH_2C(O)NHCH_2CF_3$ |
| 3-F-5-$CF_3$ | $CF_2Cl$ | H | $CH(CH_3)C(O)NHCH_2CF_3(D)$ |
| 3-F-5-$CF_3$ | $CF_2Cl$ | H | $CH_2(D10-2a)$ |
| 3-F-5-$CF_3$ | $CF_2Cl$ | H | $CH=NOCH_3(Z)$ |

TABLE 4-continued

| (X)$_m$ | R$^3$ | R$^2$ | R$^1$ |
|---|---|---|---|
| 3-F-5-CF$_3$ | CF$_2$Cl | H | CH=NOEt(Z) |
| 3-CF$_3$-4-Cl | CF$_3$ | C(O)OCH$_3$ | CH$_2$OEt |
| 3-CF$_3$-4-Cl | CF$_3$ | H | CH$_2$OCH$_2$CF$_3$ |
| 3-CF$_3$-4-Cl | CF$_3$ | C(O)OCH$_3$ | CH$_2$OCH$_2$CF$_3$ |
| 3-CF$_3$-4-Cl | CF$_3$ | H | E4-1a |
| 3-CF$_3$-4-Cl | CF$_3$ | H | CH$_2$C(O)NHCH$_2$CF$_3$ |
| 3-CF$_3$-4-Cl | CF$_3$ | H | CH(CH$_3$)C(O)NHCH$_2$CF$_3$ |
| 3-CF$_3$-4-Cl | CF$_3$ | H | CH(CH$_3$)C(O)NHCH$_2$CF$_3$(D) |
| 3-CF$_3$-4-Cl | CF$_3$ | H | CH$_2$(D10-2a) |
| 3-CF$_3$-4-Cl | CF$_3$ | H | CH$_2$(D32-1a) |
| 3-CF$_3$-4-Cl | CF$_3$ | C(O)CH$_3$ | CH$_2$(D32-1a) |
| 3-CF$_3$-4-Cl | CF$_3$ | C(O)OCH$_3$ | CH$_2$(D32-1a) |
| 3-CF$_3$-4-Cl | CF$_3$ | H | CH=NOCH$_3$(Z) |
| 3-CF$_3$-4-Cl | CF$_3$ | H | CH=NOEt(Z) |
| 3-CF$_3$-4-Cl | CF$_3$ | C(O)Et | C(O)OCH$_3$ |
| 3-CF$_3$-4-Cl | CF$_3$ | C(O)CH$_3$ | (D34-1c)Cl |
| 3-CF$_3$-4-Cl | CF$_3$ | C(O)OCH$_3$ | (D34-1c)Cl |
| 3-CF$_3$-4-Cl | CF$_3$ | H | (D34-1c)CN |
| 3-CF$_3$-4-Cl | CF$_3$ | CH$_3$ | (D34-1c)CN |
| 3-CF$_3$-4-Cl | CF$_3$ | CH$_2$OC(O)CH$_3$ | (D34-1c)CN |
| 3-CF$_3$-4-Cl | CF$_3$ | C(O)Pr-i | (D34-1c)CN |
| 3-CF$_3$-4-Cl | CF$_2$Cl | H | CH$_2$C(O)NHCH$_2$CF$_3$ |
| 3-CF$_3$-4-Cl | CF$_2$Cl | H | CH(CH$_3$)C(O)NHCH$_2$CF$_3$(D) |
| 3-CF$_3$-4-Cl | CF$_2$Cl | H | CH$_2$(D10-2a) |
| 3-CF$_3$-4-Cl | CF$_2$Cl | H | CH=NOCH$_3$(Z) |
| 3-CF$_3$-4-Cl | CF$_2$Cl | H | CH=NOEt(Z) |
| 3-Cl-5-CF$_3$ | CF$_3$ | C(O)CH$_3$ | CH$_2$CF$_3$ |
| 3-Cl-5-CF$_3$ | CF$_3$ | C(O)OCH$_3$ | CH$_2$OCH$_3$ |
| 3-Cl-5-CF$_3$ | CF$_3$ | C(O)OCH$_3$ | CH$_2$OEt |
| 3-Cl-5-CF$_3$ | CF$_3$ | C(O)OCH$_3$ | CH$_2$OPr-i |
| 3-Cl-5-CF$_3$ | CF$_3$ | H | CH$_2$OCH$_2$CF$_3$ |
| 3-Cl-5-CF$_3$ | CF$_3$ | C(O)OCH$_3$ | CH$_2$OCH$_2$CF$_3$ |
| 3-Cl-5-CF$_3$ | CF$_3$ | H | E4-1a |
| 3-Cl-5-CF$_3$ | CF$_3$ | H | CH$_2$C(O)NHCH$_2$CH$_2$Cl |
| 3-Cl-5-CF$_3$ | CF$_3$ | H | CH$_2$C(O)NHCH$_2$CF$_3$ |
| 3-Cl-5-CF$_3$ | CF$_3$ | H | CH(CH$_3$)C(O)NHCH$_2$CH$_2$Cl |
| 3-Cl-5-CF$_3$ | CF$_3$ | H | CH(CH$_3$)C(O)NHCH$_2$CF$_3$ |
| 3-Cl-5-CF$_3$ | CF$_3$ | H | CH(CH$_3$)C(O)NHCH$_2$CF$_3$(D) |
| 3-Cl-5-CF$_3$ | CF$_3$ | H | CH$_2$(D10-2a) |
| 3-Cl-5-CF$_3$ | CF$_3$ | C(O)CH$_3$ | CH$_2$(D10-2a) |
| 3-Cl-5-CF$_3$ | CF$_3$ | C(O)Et | CH$_2$(D10-2a) |
| 3-Cl-5-CF$_3$ | CF$_3$ | H | CH$_2$(D32-1a) |
| 3-Cl-5-CF$_3$ | CF$_3$ | C(O)CH$_3$ | CH$_2$(D32-1a) |
| 3-Cl-5-CF$_3$ | CF$_3$ | C(O)Et | CH$_2$(D32-1a) |
| 3-Cl-5-CF$_3$ | CF$_3$ | C(O)OCH$_3$ | CH$_2$(D32-1a) |
| 3-Cl-5-CF$_3$ | CF$_3$ | H | CH=NOCH$_3$(Z) |
| 3-Cl-5-CF$_3$ | CF$_3$ | CH$_2$OCH$_3$ | CH=NOCH$_3$ |
| 3-Cl-5-CF$_3$ | CF$_3$ | CH$_2$OC(O)CH$_3$ | CH=NOCH$_3$ |
| 3-Cl-5-CF$_3$ | CF$_3$ | H | CH=NOEt(Z) |
| 3-Cl-5-CF$_3$ | CF$_3$ | C(O)Et | C(O)OCH$_3$ |
| 3-Cl-5-CF$_3$ | CF$_3$ | CH$_2$OC(O)CH$_3$ | (D34-1c)Cl |
| 3-Cl-5-CF$_3$ | CF$_3$ | C(O)CH$_3$ | (D34-1c)Cl |
| 3-Cl-5-CF$_3$ | CF$_3$ | C(O)Pr-c | (D34-1c)Cl |
| 3-Cl-5-CF$_3$ | CF$_3$ | C(O)OCH$_3$ | (D34-1c)Cl |
| 3-Cl-5-CF$_3$ | CF$_3$ | H | (D34-1c)CN |
| 3-Cl-5-CF$_3$ | CF$_3$ | CH$_3$ | (D34-1c)CN |
| 3-Cl-5-CF$_3$ | CF$_3$ | CH$_2$OCH$_3$ | (D34-1c)CN |
| 3-Cl-5-CF$_3$ | CF$_3$ | CH$_2$OC(O)CH$_3$ | (D34-1c)CN |
| 3-Cl-5-CF$_3$ | CF$_3$ | C(O)Pr-i | (D34-1c)CN |
| 3-Cl-5-CF$_3$ | CF$_3$ | C(O)OCH$_3$ | (D34-1c)CN |
| 3-Cl-5-CF$_3$ | CF$_3$ | CH$_2$OCH$_3$ | D34-3a |
| 3-Cl-5-CF$_3$ | CF$_3$ | C(O)Et | D34-3a |
| 3-Cl-5-CF$_3$ | CF$_3$ | C(O)Pr-i | D34-3a |
| 3-Cl-5-CF$_3$ | CF$_3$ | C(O)OCH$_3$ | (D35-1c)Cl |
| 3-Cl-5-CF$_3$ | CF$_3$ | H | N(CH$_3$)Ph |
| 3-Cl-5-CF$_3$ | CF$_3$ | H | N(CH$_3$)(D34-1a) |
| 3-Cl-5-CF$_3$ | CF$_2$Cl | C(O)OCH$_3$ | CH$_2$OEt |
| 3-Cl-5-CF$_3$ | CF$_2$Cl | H | CH$_2$OCH$_2$CF$_3$ |
| 3-Cl-5-CF$_3$ | CF$_2$Cl | H | E4-1a |
| 3-Cl-5-CF$_3$ | CF$_2$Cl | H | CH$_2$C(O)NHCH$_2$CF$_3$ |
| 3-Cl-5-CF$_3$ | CF$_2$Cl | H | CH(CH$_3$)C(O)NHCH$_2$CF$_3$(D) |
| 3-Cl-5-CF$_3$ | CF$_2$Cl | H | CH$_2$(D10-2a) |
| 3-Cl-5-CF$_3$ | CF$_2$Cl | H | CH=NOCH$_3$(Z) |
| 3-Cl-5-CF$_3$ | CF$_2$Cl | H | CH=NOEt(Z) |
| 3-Cl-5-CF$_3$ | CF$_2$Cl | C(O)Et | C(O)OCH$_3$ |
| 3-Cl-5-CF$_3$ | CF$_2$Cl | H | (D34-1c)CN |
| 3-Br-5-CF$_3$ | CF$_3$ | C(O)CH$_3$ | CH$_2$CF$_3$ |
| 3-Br-5-CF$_3$ | CF$_3$ | C(O)OCH$_3$ | CH$_2$OCH$_3$ |

TABLE 4-continued

| $(X)_m$ | $R^3$ | $R^2$ | $R^1$ |
|---|---|---|---|
| 3-Br-5-CF$_3$ | CF$_3$ | C(O)OCH$_3$ | CH$_2$OEt |
| 3-Br-5-CF$_3$ | CF$_3$ | C(O)OCH$_3$ | CH$_2$OPr-i |
| 3-Br-5-CF$_3$ | CF$_3$ | H | CH$_2$OCH$_2$CF$_3$ |
| 3-Br-5-CF$_3$ | CF$_3$ | C(O)OCH$_3$ | CH$_2$OCH$_2$CF$_3$ |
| 3-Br-5-CF$_3$ | CF$_3$ | H | E4-1a |
| 3-Br-5-CF$_3$ | CF$_3$ | H | CH$_2$C(O)NHCH$_2$CH$_2$Cl |
| 3-Br-5-CF$_3$ | CF$_3$ | H | CH$_2$C(O)NHCH$_2$CF$_3$ |
| 3-Br-5-CF$_3$ | CF$_3$ | H | CH(CH$_3$)C(O)NHCH$_2$CH$_2$Cl |
| 3-Br-5-CF$_3$ | CF$_3$ | H | CH(CH$_3$)C(O)NHCH$_2$CF$_3$ |
| 3-Br-5-CF$_3$ | CF$_3$ | H | CH(CH$_3$)C(O)NHCH$_2$CF$_3$(D) |
| 3-Br-5-CF$_3$ | CF$_3$ | H | CH$_2$(D10-2a) |
| 3-Br-5-CF$_3$ | CF$_3$ | C(O)CH$_3$ | CH$_2$(D10-2a) |
| 3-Br-5-CF$_3$ | CF$_3$ | C(O)Et | CH$_2$(D10-2a) |
| 3-Br-5-CF$_3$ | CF$_3$ | H | CH$_2$(D32-1a) |
| 3-Br-5-CF$_3$ | CF$_3$ | C(O)CH$_3$ | CH$_2$(D32-1a) |
| 3-Br-5-CF$_3$ | CF$_3$ | C(O)Et | CH$_2$(D32-1a) |
| 3-Br-5-CF$_3$ | CF$_3$ | C(O)OCH$_3$ | CH$_2$(D32-1a) |
| 3-Br-5-CF$_3$ | CF$_3$ | H | CH=NOCH$_3$(Z) |
| 3-Br-5-CF$_3$ | CF$_3$ | CH$_2$OCH$_3$ | CH=NOCH$_3$ |
| 3-Br-5-CF$_3$ | CF$_3$ | CH$_2$OC(O)CH$_3$ | CH=NOCH$_3$ |
| 3-Br-5-CF$_3$ | CF$_3$ | H | CH=NOEt(Z) |
| 3-Br-5-CF$_3$ | CF$_3$ | C(O)Et | C(O)OCH$_3$ |
| 3-Br-5-CF$_3$ | CF$_3$ | CH$_2$OC(O)CH$_3$ | (D34-1c)Cl |
| 3-Br-5-CF$_3$ | CF$_3$ | C(O)CH$_3$ | (D34-1c)Cl |
| 3-Br-5-CF$_3$ | CF$_3$ | C(O)Pr-c | (D34-1c)Cl |
| 3-Br-5-CF$_3$ | CF$_3$ | C(O)OCH$_3$ | (D34-1c)Cl |
| 3-Br-5-CF$_3$ | CF$_3$ | H | (D34-1c)CN |
| 3-Br-5-CF$_3$ | CF$_3$ | CH$_3$ | (D34-1c)CN |
| 3-Br-5-CF$_3$ | CF$_3$ | CH$_2$OCH$_3$ | (D34-1c)CN |
| 3-Br-5-CF$_3$ | CF$_3$ | CH$_2$OC(O)CH$_3$ | (D34-1c)CN |
| 3-Br-5-CF$_3$ | CF$_3$ | C(O)Pr-i | (D34-1c)CN |
| 3-Br-5-CF$_3$ | CF$_3$ | C(O)OCH$_3$ | (D34-1c)CN |
| 3-Br-5-CF$_3$ | CF$_3$ | CH$_2$OCH$_3$ | D34-3a |
| 3-Br-5-CF$_3$ | CF$_3$ | C(O)Et | D34-3a |
| 3-Br-5-CF$_3$ | CF$_3$ | C(O)Pr-i | D34-3a |
| 3-Br-5-CF$_3$ | CF$_3$ | C(O)OCH$_3$ | (D35-1c)Cl |
| 3-Br-5-CF$_3$ | CF$_3$ | H | N(CH$_3$)Ph |
| 3-Br-5-CF$_3$ | CF$_3$ | H | N(CH$_3$)(D34-1a) |
| 3-Br-5-CF$_3$ | CF$_2$Cl | C(O)OCH$_3$ | CH$_2$OEt |
| 3-Br-5-CF$_3$ | CF$_2$Cl | H | CH$_2$OCH$_2$CF$_3$ |
| 3-Br-5-CF$_3$ | CF$_2$Cl | H | E4-1a |
| 3-Br-5-CF$_3$ | CF$_2$Cl | H | CH$_2$C(O)NHCH$_2$CF$_3$ |
| 3-Br-5-CF$_3$ | CF$_2$Cl | H | CH(CH$_3$)C(O)NHCH$_2$CF$_3$(D) |
| 3-Br-5-CF$_3$ | CF$_2$Cl | H | CH$_2$(D10-2a) |
| 3-Br-5-CF$_3$ | CF$_2$Cl | H | CH=NOCH$_3$(Z) |
| 3-Br-5-CF$_3$ | CF$_2$Cl | H | CH=NOEt(Z) |
| 3-Br-5-CF$_3$ | CF$_2$Cl | C(O)Et | C(O)OCH$_3$ |
| 3-Br-5-CF$_3$ | CF$_2$Cl | H | (D34-1c)CN |
| 3-CH$_3$-5-CF$_3$ | CF$_3$ | H | CH$_2$C(O)NHCH$_2$CF$_3$ |
| 3-CH$_3$-5-CF$_3$ | CF$_3$ | H | CH(CH$_3$)C(O)NHCH$_2$CF$_3$(D) |
| 3-CH$_3$-5-CF$_3$ | CF$_3$ | H | CH$_2$(D10-2a) |
| 3-CH$_3$-5-CF$_3$ | CF$_3$ | H | CH=NOCH$_3$(Z) |
| 3-CH$_3$-5-CF$_3$ | CF$_3$ | H | CH=NOEt(Z) |
| 3,5-(CF$_3$)$_2$ | CHF$_2$ | H | CH$_2$C(O)NHCH$_2$CF$_3$ |
| 3,5-(CF$_3$)$_2$ | CHF$_2$ | H | CH(CH$_3$)C(O)NHCH$_2$CF$_3$(D) |
| 3,5-(CF$_3$)$_2$ | CHF$_2$ | H | CH$_2$(D10-2a) |
| 3,5-(CF$_3$)$_2$ | CHF$_2$ | H | CH=NOCH$_3$(Z) |
| 3,5-(CF$_3$)$_2$ | CHF$_2$ | H | CH=NOEt(Z) |
| 3,5-(CF$_3$)$_2$ | CF$_3$ | C(O)OCH$_3$ | CH$_3$ |
| 3,5-(CF$_3$)$_2$ | CF$_3$ | C(O)OEt | CH$_3$ |
| 3,5-(CF$_3$)$_2$ | CF$_3$ | H | c-Pr |
| 3,5-(CF$_3$)$_2$ | CF$_3$ | H | CH$_2$Pr-c |
| 3,5-(CF$_3$)$_2$ | CF$_3$ | H | c-Bu |
| 3,5-(CF$_3$)$_2$ | CF$_3$ | H | CH$_2$CF$_3$ |
| 3,5-(CF$_3$)$_2$ | CF$_3$ | C(O)CH$_3$ | CH$_2$CF$_3$ |
| 3,5-(CF$_3$)$_2$ | CF$_3$ | H | CH$_2$CH$_2$CF$_3$ |
| 3,5-(CF$_3$)$_2$ | CF$_3$ | C(O)OCH$_3$ | CH$_2$OCH$_3$ |
| 3,5-(CF$_3$)$_2$ | CF$_3$ | C(O)OPr-i | CH$_2$OCH$_3$ |
| 3,5-(CF$_3$)$_2$ | CF$_3$ | H | CH$_2$OEt |
| 3,5-(CF$_3$)$_2$ | CF$_3$ | C(O)CH$_3$ | CH$_2$OEt |
| 3,5-(CF$_3$)$_2$ | CF$_3$ | C(O)OCH$_3$ | CH$_2$OEt |
| 3,5-(CF$_3$)$_2$ | CF$_3$ | C(O)OEt | CH$_2$OEt |
| 3,5-(CF$_3$)$_2$ | CF$_3$ | C(O)OCH$_3$ | CH$_2$OPr-i |
| 3,5-(CF$_3$)$_2$ | CF$_3$ | H | CH$_2$OCH$_2$CF$_3$ |
| 3,5-(CF$_3$)$_2$ | CF$_3$ | C(O)CH$_3$ | CH$_2$OCH$_2$CF$_3$ |
| 3,5-(CF$_3$)$_2$ | CF$_3$ | C(O)OCH$_3$ | CH$_2$OCH$_2$CF$_3$ |
| 3,5-(CF$_3$)$_2$ | CF$_3$ | C(O)OCH$_3$ | CH$_2$OC(O)CH$_3$ |
| 3,5-(CF$_3$)$_2$ | CF$_3$ | C(O)OCH$_3$ | CH$_2$OC(O)OCH$_3$ |

TABLE 4-continued

| (X)$_m$ | R$^3$ | R$^2$ | R$^1$ |
|---|---|---|---|
| 3,5-(CF$_3$)$_2$ | CF$_3$ | H | CH(CH$_3$)OCH$_2$CF$_3$ |
| 3,5-(CF$_3$)$_2$ | CF$_3$ | H | E4-1a |
| 3,5-(CF$_3$)$_2$ | CF$_3$ | C(O)Et | E4-1a |
| 3,5-(CF$_3$)$_2$ | CF$_3$ | C(O)OCH$_3$ | E4-1a |
| 3,5-(CF$_3$)$_2$ | CF$_3$ | H | CH$_2$CH$_2$OCH$_3$ |
| 3,5-(CF$_3$)$_2$ | CF$_3$ | H | CH$_2$(E4-1a) |
| 3,5-(CF$_3$)$_2$ | CF$_3$ | H | E4-2a(R) |
| 3,5-(CF$_3$)$_2$ | CF$_3$ | H | CH$_2$CH(OCH$_3$)$_2$ |
| 3,5-(CF$_3$)$_2$ | CF$_3$ | H | CH$_2$(E7-1a) |
| 3,5-(CF$_3$)$_2$ | CF$_3$ | H | CH$_2$(E7-1b)CH$_3$ |
| 3,5-(CF$_3$)$_2$ | CF$_3$ | H | CH$_2$(E4-2a) |
| 3,5-(CF$_3$)$_2$ | CF$_3$ | H | E5-2a |
| 3,5-(CF$_3$)$_2$ | CF$_3$ | H | E5-2b |
| 3,5-(CF$_3$)$_2$ | CF$_3$ | H | E5-2c |
| 3,5-(CF$_3$)$_2$ | CF$_3$ | H | CH$_2$CH=NOCH$_3$ |
| 3,5-(CF$_3$)$_2$ | CF$_3$ | H | CH$_2$C(CH$_3$)=NOCH$_3$ |
| 3,5-(CF$_3$)$_2$ | CF$_3$ | C(O)OPr-i | CH$_2$CN |
| 3,5-(CF$_3$)$_2$ | CF$_3$ | H | CH$_2$C(O)NHCH$_3$ |
| 3,5-(CF$_3$)$_2$ | CF$_3$ | H | CH$_2$C(O)N(CH$_3$)$_2$ |
| 3,5-(CF$_3$)$_2$ | CF$_3$ | H | CH$_2$C(O)NHEt |
| 3,5-(CF$_3$)$_2$ | CF$_3$ | H | CH$_2$C(O)NHPr-n |
| 3,5-(CF$_3$)$_2$ | CF$_3$ | H | CH$_2$C(O)NHPr-i |
| 3,5-(CF$_3$)$_2$ | CF$_3$ | H | CH$_2$C(O)NHCH$_2$F |
| 3,5-(CF$_3$)$_2$ | CF$_3$ | H | CH$_2$C(O)NHCH$_2$Cl |
| 3,5-(CF$_3$)$_2$ | CF$_3$ | H | CH$_2$C(O)NHCH$_2$CF$_3$ |
| 3,5-(CF$_3$)$_2$ | CF$_3$ | H | CH$_2$C(O)NHCH$_2$CH=CH$_2$ |
| 3,5-(CF$_3$)$_2$ | CF$_3$ | H | CH$_2$C(O)NHCH$_2$C≡CH |
| 3,5-(CF$_3$)$_2$ | CF$_3$ | H | CH(CH$_3$)C(O)NHCH$_2$CH$_2$Cl |
| 3,5-(CF$_3$)$_2$ | CF$_3$ | H | CH(CH$_3$)C(O)NHCH$_2$CH$_2$Cl(D) |
| 3,5-(CF$_3$)$_2$ | CF$_3$ | H | CH(CH$_3$)C(O)NHCH$_2$CF$_3$ |
| 3,5-(CF$_3$)$_2$ | CF$_3$ | H | CH(CH$_3$)C(O)NHCH$_2$CF$_3$(D) |
| 3,5-(CF$_3$)$_2$ | CF$_3$ | H | T-2 |
| 3,5-(CF$_3$)$_2$ | CF$_3$ | H | CH$_2$CH=CH$_2$ |
| 3,5-(CF$_3$)$_2$ | CF$_3$ | H | CH$_2$(Ph-4-NO$_2$) |
| 3,5-(CF$_3$)$_2$ | CF$_3$ | H | CH$_2$(Ph-4-CN) |
| 3,5-(CF$_3$)$_2$ | CF$_3$ | H | CH(CH$_3$)Ph(R) |
| 3,5-(CF$_3$)$_2$ | CF$_3$ | H | CH$_2$(D8-1a)CH$_3$ |
| 3,5-(CF$_3$)$_2$ | CF$_3$ | H | CH$_2$(D8-2b)Cl |
| 3,5-(CF$_3$)$_2$ | CF$_3$ | H | CH$_2$(D8-2c)Cl |
| 3,5-(CF$_3$)$_2$ | CF$_3$ | H | CH$_2$(D8-3a)CH$_3$ |
| 3,5-(CF$_3$)$_2$ | CF$_3$ | H | CH$_2$(D8-3b)Cl |
| 3,5-(CF$_3$)$_2$ | CF$_3$ | H | CH$_2$(D10-1a) |
| 3,5-(CF$_3$)$_2$ | CF$_3$ | H | CH$_2$(D10-2a) |
| 3,5-(CF$_3$)$_2$ | CF$_3$ | C(O)CH$_3$ | CH$_2$(D10-2a) |
| 3,5-(CF$_3$)$_2$ | CF$_3$ | C(O)Et | CH$_2$(D10-2a) |
| 3,5-(CF$_3$)$_2$ | CF$_3$ | H | CH$_2$(D13-1a) |
| 3,5-(CF$_3$)$_2$ | CF$_3$ | H | CH$_2$(D16-1a) |
| 3,5-(CF$_3$)$_2$ | CF$_3$ | H | CH$_2$(D22-1a) |
| 3,5-(CF$_3$)$_2$ | CF$_3$ | H | CH$_2$(D32-1a) |
| 3,5-(CF$_3$)$_2$ | CF$_3$ | Et | CH$_2$(D32-1a) |
| 3,5-(CF$_3$)$_2$ | CF$_3$ | CH$_2$OCH$_3$ | CH$_2$(D32-1a) |
| 3,5-(CF$_3$)$_2$ | CF$_3$ | CH$_2$CN | CH$_2$(D32-1a) |
| 3,5-(CF$_3$)$_2$ | CF$_3$ | CH$_2$C≡CH | CH$_2$(D32-1a) |
| 3,5-(CF$_3$)$_2$ | CF$_3$ | C(O)CH$_3$ | CH$_2$(D32-1a) |
| 3,5-(CF$_3$)$_2$ | CF$_3$ | C(O)Et | CH$_2$(D32-1a) |
| 3,5-(CF$_3$)$_2$ | CF$_3$ | C(O)Pr-c | CH$_2$(D32-1a) |
| 3,5-(CF$_3$)$_2$ | CF$_3$ | C(O)Bu-t | CH$_2$(D32-1a) |
| 3,5-(CF$_3$)$_2$ | CF$_3$ | C(O)CH$_2$OCH$_3$ | CH$_2$(D32-1a) |
| 3,5-(CF$_3$)$_2$ | CF$_3$ | C(O)CH=CH$_2$ | CH$_2$(D32-1a) |
| 3,5-(CF$_3$)$_2$ | CF$_3$ | C(O)OCH$_3$ | CH$_2$(D32-1a) |
| 3,5-(CF$_3$)$_2$ | CF$_3$ | H | CH$_2$(D32-1a) |
| 3,5-(CF$_3$)$_2$ | CF$_3$ | H | CH(CH$_3$)(D32-1a) |
| 3,5-(CF$_3$)$_2$ | CF$_3$ | H | T-3 |
| 3,5-(CF$_3$)$_2$ | CF$_3$ | H | CH=NOCH$_3$ |
| 3,5-(CF$_3$)$_2$ | CF$_3$ | H | CH=NOCH$_3$(Z) |
| 3,5-(CF$_3$)$_2$ | CF$_3$ | CH$_2$OCH$_3$ | CH=NOCH$_3$ |
| 3,5-(CF$_3$)$_2$ | CF$_3$ | CH$_2$OEt | CH=NOCH$_3$ |
| 3,5-(CF$_3$)$_2$ | CF$_3$ | CH$_2$OC(O)CH$_3$ | CH=NOCH$_3$ |
| 3,5-(CF$_3$)$_2$ | CF$_3$ | CH$_2$CN | CH=NOCH$_3$ |
| 3,5-(CF$_3$)$_2$ | CF$_3$ | H | CH=NOEt |
| 3,5-(CF$_3$)$_2$ | CF$_3$ | H | CH=NOEt(Z) |
| 3,5-(CF$_3$)$_2$ | CF$_3$ | C(O)Et | C(O)OCH$_3$ |
| 3,5-(CF$_3$)$_2$ | CF$_3$ | H | C(O)OEt |
| 3,5-(CF$_3$)$_2$ | CF$_3$ | H | C(O)OPr-i |
| 3,5-(CF$_3$)$_2$ | CF$_3$ | C(O)CH$_3$ | C(O)OPr-i |
| 3,5-(CF$_3$)$_2$ | CF$_3$ | C(O)Et | C(O)OPr-i |
| 3,5-(CF$_3$)$_2$ | CF$_3$ | C(O)Bu-t | C(O)OPr-i |
| 3,5-(CF$_3$)$_2$ | CF$_3$ | C(O)CH$_2$OCH$_3$ | C(O)OPr-i |

TABLE 4-continued

| (X)$_m$ | R$^3$ | R$^2$ | R$^1$ |
|---|---|---|---|
| 3,5-(CF$_3$)$_2$ | CF$_3$ | C(O)OCH$_3$ | C(O)OPr-i |
| 3,5-(CF$_3$)$_2$ | CF$_3$ | C(O)OEt | C(O)OPr-i |
| 3,5-(CF$_3$)$_2$ | CF$_3$ | H | C(O)NH$_2$ |
| 3,5-(CF$_3$)$_2$ | CF$_3$ | CH$_3$ | C(O)NH$_2$ |
| 3,5-(CF$_3$)$_2$ | CF$_3$ | H | C(O)NHEt |
| 3,5-(CF$_3$)$_2$ | CF$_3$ | H | C(O)NHCH$_2$CF$_3$ |
| 3,5-(CF$_3$)$_2$ | CF$_3$ | —C(NH$_2$)(OCH$_3$)— | |
| 3,5-(CF$_3$)$_2$ | CF$_3$ | —C(NH$_2$)(OEt)— | |
| 3,5-(CF$_3$)$_2$ | CF$_3$ | —C(NHCH$_3$)(OCH$_3$)— | |
| 3,5-(CF$_3$)$_2$ | CF$_3$ | H | C(S)OPr-i |
| 3,5-(CF$_3$)$_2$ | CF$_3$ | CH$_2$OC(O)CH$_3$ | (D34-1c)Cl |
| 3,5-(CF$_3$)$_2$ | CF$_3$ | C(O)CH$_3$ | (D34-1c)Cl |
| 3,5-(CF$_3$)$_2$ | CF$_3$ | C(O)Pr-c | (D34-1c)Cl |
| 3,5-(CF$_3$)$_2$ | CF$_3$ | C(O)OCH$_3$ | (D34-1c)Cl |
| 3,5-(CF$_3$)$_2$ | CF$_3$ | H | (D34-1c)CN |
| 3,5-(CF$_3$)$_2$ | CF$_3$ | CH$_3$ | (D34-1c)CN |
| 3,5-(CF$_3$)$_2$ | CF$_3$ | CH$_2$OCH$_3$ | (D34-1c)CN |
| 3,5-(CF$_3$)$_2$ | CF$_3$ | CH$_2$OC(O)CH$_3$ | (D34-1c)CN |
| 3,5-(CF$_3$)$_2$ | CF$_3$ | C(O)Pr-i | (D34-1c)CN |
| 3,5-(CF$_3$)$_2$ | CF$_3$ | C(O)OCH$_3$ | (D34-1c)CN |
| 3,5-(CF$_3$)$_2$ | CF$_3$ | CH$_2$OCH$_3$ | D34-3a |
| 3,5-(CF$_3$)$_2$ | CF$_3$ | CH$_2$CN | D34-3a |
| 3,5-(CF$_3$)$_2$ | CF$_3$ | C(O)Et | D34-3a |
| 3,5-(CF$_3$)$_2$ | CF$_3$ | C(O)Pr-i | D34-3a |
| 3,5-(CF$_3$)$_2$ | CF$_3$ | CH$_3$ | D35-1a |
| 3,5-(CF$_3$)$_2$ | CF$_3$ | C(O)OCH$_3$ | (D35-1c)Cl |
| 3,5-(CF$_3$)$_2$ | CF$_3$ | H | N(CH$_3$)Ph |
| 3,5-(CF$_3$)$_2$ | CF$_3$ | H | N(CH$_2$CH=CH$_2$)Ph |
| 3,5-(CF$_3$)$_2$ | CF$_3$ | H | N(CH$_2$C≡CH)Ph |
| 3,5-(CF$_3$)$_2$ | CF$_3$ | H | N(CH$_3$)(D32-1a) |
| 3,5-(CF$_3$)$_2$ | CF$_3$ | H | NH(D34-1a) |
| 3,5-(CF$_3$)$_2$ | CF$_3$ | CH$_3$ | NH(D34-1a) |
| 3,5-(CF$_3$)$_2$ | CF$_3$ | H | N(CH$_3$)(D34-1a) |
| 3,5-(CF$_3$)$_2$ | CF$_3$ | H | N(Et)(D34-1a) |
| 3,5-(CF$_3$)$_2$ | CF$_2$Cl | C(O)OCH$_3$ | CH$_2$OEt |
| 3,5-(CF$_3$)$_2$ | CF$_2$Cl | H | CH$_2$OCH$_2$CF$_3$ |
| 3,5-(CF$_3$)$_2$ | CF$_2$Cl | C(O)OCH$_3$ | CH$_2$OCH$_2$CF$_3$ |
| 3,5-(CF$_3$)$_2$ | CF$_2$Cl | H | E4-1a |
| 3,5-(CF$_3$)$_2$ | CF$_2$Cl | H | CH$_2$C(O)NHCH$_2$CF$_3$ |
| 3,5-(CF$_3$)$_2$ | CF$_2$Cl | H | CH(CH$_3$)C(O)NHCH$_2$CF$_3$ |
| 3,5-(CF$_3$)$_2$ | CF$_2$Cl | H | CH(CH$_3$)C(O)NHCH$_2$CF$_3$(D) |
| 3,5-(CF$_3$)$_2$ | CF$_2$Cl | H | CH$_2$(D10-2a) |
| 3,5-(CF$_3$)$_2$ | CF$_2$Cl | H | CH$_2$(D32-1a) |
| 3,5-(CF$_3$)$_2$ | CF$_2$Cl | C(O)CH$_3$ | CH$_2$(D32-1a) |
| 3,5-(CF$_3$)$_2$ | CF$_2$Cl | C(O)OCH$_3$ | CH$_2$(D32-1a) |
| 3,5-(CF$_3$)$_2$ | CF$_2$Cl | H | CH=NOCH$_3$(Z) |
| 3,5-(CF$_3$)$_2$ | CF$_2$Cl | H | CH=NOEt(Z) |
| 3,5-(CF$_3$)$_2$ | CF$_2$Cl | C(O)Et | C(O)OCH$_3$ |
| 3,5-(CF$_3$)$_2$ | CF$_2$Cl | C(O)CH$_3$ | (D34-1c)Cl |
| 3,5-(CF$_3$)$_2$ | CF$_2$Cl | C(O)OCH$_3$ | (D34-1c)Cl |
| 3,5-(CF$_3$)$_2$ | CF$_2$Cl | H | (D34-1c)CN |
| 3,5-(CF$_3$)$_2$ | CF$_2$Cl | CH$_3$ | (D34-1c)CN |
| 3,5-(CF$_3$)$_2$ | CF$_2$Cl | CH$_2$OC(O)CH$_3$ | (D34-1c)CN |
| 3,5-(CF$_3$)$_2$ | CF$_2$Cl | C(O)Pr-i | (D34-1c)CN |
| 3,5-(CF$_3$)$_2$ | CF$_2$Br | H | CH$_2$C(O)NHCH$_2$CF$_3$ |
| 3,5-(CF$_3$)$_2$ | CF$_2$Br | H | CH(CH$_3$)C(O)NHCH$_2$CF$_3$(D) |
| 3,5-(CF$_3$)$_2$ | CF$_2$Br | H | CH$_2$(D10-2a) |
| 3,5-(CF$_3$)$_2$ | CF$_2$Br | H | CH=NOCH$_3$(Z) |
| 3,5-(CF$_3$)$_2$ | CF$_2$Br | H | CH=NOEt(Z) |
| 3,5-(CF$_3$)$_2$ | CF$_2$CHF$_2$ | H | CH$_2$C(O)NHCH$_2$CF$_3$ |
| 3,5-(CF$_3$)$_2$ | CF$_2$CHF$_2$ | H | CH(CH$_3$)C(O)NHCH$_2$CF$_3$(D) |
| 3,5-(CF$_3$)$_2$ | CF$_2$CHF$_2$ | H | CH$_2$(D10-2a) |
| 3,5-(CF$_3$)$_2$ | CF$_2$CHF$_2$ | H | CH=NOCH$_3$(Z) |
| 3,5-(CF$_3$)$_2$ | CF$_2$CHF$_2$ | H | CH=NOEt(Z) |
| 3-CF$_3$-5-OCH$_3$ | CF$_3$ | H | CH$_2$C(O)NHCH$_2$CF$_3$ |
| 3-CF$_3$-5-OCH$_3$ | CF$_3$ | H | CH(CH$_3$)C(O)NHCH$_2$CF$_3$(D) |
| 3-CF$_3$-5-OCH$_3$ | CF$_3$ | H | CH$_2$(D10-2a) |
| 3-CF$_3$-5-OCH$_3$ | CF$_3$ | H | CH=NOCH$_3$(Z) |
| 3-CF$_3$-5-OCH$_3$ | CF$_3$ | H | CH=NOEt(Z) |
| 3-Cl-5-OCHF$_2$ | CF$_3$ | C(O)OCH$_3$ | CH$_2$OEt |
| 3-Cl-5-OCHF$_2$ | CF$_3$ | H | CH$_2$OCH$_2$CF$_3$ |
| 3-Cl-5-OCHF$_2$ | CF$_3$ | C(O)OCH$_3$ | CH$_2$OCH$_2$CF |
| 3-Cl-5-OCHF$_2$ | CF$_3$ | H | E4-1a |
| 3-Cl-5-OCHF$_2$ | CF$_3$ | H | CH$_2$C(O)NHCH$_2$CF$_3$ |
| 3-Cl-5-OCHF$_2$ | CF$_3$ | H | CH(CH$_3$)C(O)NHCH$_2$CF$_3$ |
| 3-Cl-5-OCHF$_2$ | CF$_3$ | H | CH(CH$_3$)C(O)NHCH$_2$CF$_3$(D) |
| 3-Cl-5-OCHF$_2$ | CF$_3$ | H | CH$_2$(D10-2a) |
| 3-Cl-5-OCHF$_2$ | CF$_3$ | H | CH$_2$(D32-1a) |

TABLE 4-continued

| (X)$_m$ | R$^3$ | R$^2$ | R$^1$ |
|---|---|---|---|
| 3-Cl-5-OCHF$_2$ | CF$_3$ | C(O)CH$_3$ | CH$_2$(D32-1a) |
| 3-Cl-5-OCHF$_2$ | CF$_3$ | C(O)OCH$_3$ | CH$_2$(D32-1a) |
| 3-Cl-5-OCHF$_2$ | CF$_3$ | H | CH=NOCH$_3$(Z) |
| 3-Cl-5-OCHF$_2$ | CF$_3$ | H | CH=NOEt(Z) |
| 3-Cl-5-OCHF$_2$ | CF$_3$ | C(O)Et | C(O)OCH$_3$ |
| 3-Cl-5-OCHF$_2$ | CF$_3$ | C(O)CH$_3$ | (D34-1c)Cl |
| 3-Cl-5-OCHF$_2$ | CF$_3$ | C(O)OCH$_3$ | (D34-1c)Cl |
| 3-Cl-5-OCHF$_2$ | CF$_3$ | H | (D34-1c)CN |
| 3-Cl-5-OCHF$_2$ | CF$_3$ | CH$_3$ | (D34-1c)CN |
| 3-Cl-5-OCHF$_2$ | CF$_3$ | CH$_2$OC(O)CH$_3$ | (D34-1c)CN |
| 3-Cl-5-OCHF$_2$ | CF$_3$ | C(O)Pr-i | (D34-1c)CN |
| 3-Cl-5-OCHF$_2$ | CF$_2$Cl | H | CH$_2$C(O)NHCH$_2$CF$_3$ |
| 3-Cl-5-OCHF$_2$ | CF$_2$Cl | H | CH(CH$_3$)C(O)NHCH$_2$CF$_3$(D) |
| 3-Cl-5-OCHF$_2$ | CF$_2$Cl | H | CH$_2$(D10-2a) |
| 3-Cl-5-OCHF$_2$ | CF$_2$Cl | H | CH=NOCH$_3$(Z) |
| 3-Cl-5-OCHF$_2$ | CF$_2$Cl | H | CH=NOEt(Z) |
| 3-Br-5-OCHF$_2$ | CF$_3$ | C(O)OCH$_3$ | CH$_2$OEt |
| 3-Br-5-OCHF$_2$ | CF$_3$ | H | CH$_2$OCH$_2$CF$_3$ |
| 3-Br-5-OCHF$_2$ | CF$_3$ | H | E4-1a |
| 3-Br-5-OCHF$_2$ | CF$_3$ | H | CH$_2$C(O)NHCH$_2$CF$_3$ |
| 3-Br-5-OCHF$_2$ | CF$_3$ | H | CH(CH$_3$)C(O)NHCH$_2$CF$_3$(D) |
| 3-Br-5-OCHF$_2$ | CF$_3$ | H | CH$_2$(D10-2a) |
| 3-Br-5-OCHF$_2$ | CF$_3$ | H | CH=NOCH$_3$(Z) |
| 3-Br-5-OCHF$_2$ | CF$_3$ | H | CH=NOEt(Z) |
| 3-Br-5-OCHF$_2$ | CF$_3$ | C(O)Et | C(O)OCH$_3$ |
| 3-Br-5-OCHF$_2$ | CF$_3$ | H | (D34-1c)CN |
| 3-CF$_3$-5-OCHF$_2$ | CF$_3$ | C(O)OCH$_3$ | CH$_2$OEt |
| 3-CF$_3$-5-OCHF$_2$ | CF$_3$ | H | CH$_2$OCH$_2$CF$_3$ |
| 3-CF$_3$-5-OCHF$_2$ | CF$_3$ | H | E4-1a |
| 3-CF$_3$-5-OCHF$_2$ | CF$_3$ | H | CH$_2$C(O)NHCH$_2$CF$_3$ |
| 3-CF$_3$-5-OCHF$_2$ | CF$_3$ | H | CH(CH$_3$)C(O)NHCH$_2$CF$_3$(D) |
| 3-CF$_3$-5-OCHF$_2$ | CF$_3$ | H | CH$_2$(D10-2a) |
| 3-CF$_3$-5-OCHF$_2$ | CF$_3$ | H | CH=NOCH$_3$(Z) |
| 3-CF$_3$-5-OCHF$_2$ | CF$_3$ | H | CH=NOEt(Z) |
| 3-CF$_3$-5-OCHF$_2$ | CF$_3$ | C(O)Et | C(O)OCH$_3$ |
| 3-CF$_3$-5-OCHF$_2$ | CF$_3$ | H | (D34-1c)CN |
| 3-Cl-5-OCF$_3$ | CF$_3$ | C(O)OCH$_3$ | CH$_2$OEt |
| 3-Cl-5-OCF$_3$ | CF$_3$ | H | CH$_2$OCH$_2$CF$_3$ |
| 3-Cl-5-OCF$_3$ | CF$_3$ | C(O)OCH$_3$ | CH$_2$OCH$_2$CF$_3$ |
| 3-Cl-5-OCF$_3$ | CF$_3$ | H | E4-1a |
| 3-Cl-5-OCF$_3$ | CF$_3$ | H | CH$_2$C(O)NHCH$_2$CF$_3$ |
| 3-Cl-5-OCF$_3$ | CF$_3$ | H | CH(CH$_3$)C(O)NHCH$_2$CF$_3$ |
| 3-Cl-5-OCF$_3$ | CF$_3$ | H | CH(CH$_3$)C(O)NHCH$_2$CF$_3$(D) |
| 3-Cl-5-OCF$_3$ | CF$_3$ | H | CH$_2$(D10-2a) |
| 3-Cl-5-OCF$_3$ | CF$_3$ | H | CH$_2$(D32-1a) |
| 3-Cl-5-OCF$_3$ | CF$_3$ | C(O)CH$_3$ | CH$_2$(D32-1a) |
| 3-Cl-5-OCF$_3$ | CF$_3$ | C(O)OCH$_3$ | CH$_2$(D32-1a) |
| 3-Cl-5-OCF$_3$ | CF$_3$ | H | CH=NOCH$_3$(Z) |
| 3-Cl-5-OCF$_3$ | CF$_3$ | H | CH=NOEt(Z) |
| 3-Cl-5-OCF$_3$ | CF$_3$ | C(O)Et | C(O)OCH$_3$ |
| 3-Cl-5-OCF$_3$ | CF$_3$ | C(O)CH$_3$ | (D34-1c)Cl |
| 3-Cl-5-OCF$_3$ | CF$_3$ | C(O)OCH$_3$ | (D34-1c)Cl |
| 3-Cl-5-OCF$_3$ | CF$_3$ | H | (D34-1c)CN |
| 3-Cl-5-OCF$_3$ | CF$_3$ | CH$_3$ | (D34-1c)CN |
| 3-Cl-5-OCF$_3$ | CF$_3$ | CH$_2$OC(O)CH$_3$ | (D34-1c)CN |
| 3-Cl-5-OCF$_3$ | CF$_3$ | C(O)Pr-i | (D34-1c)CN |
| 3-Cl-5-OCF$_3$ | CF$_2$Cl | H | CH$_2$C(O)NHCH$_2$CF$_3$ |
| 3-Cl-5-OCF$_3$ | CF$_2$Cl | H | CH(CH$_3$)C(O)NHCH$_2$CF$_3$(D) |
| 3-Cl-5-OCF$_3$ | CF$_2$Cl | H | CH$_2$(D10-2a) |
| 3-Cl-5-OCF$_3$ | CF$_2$Cl | H | CH=NOCH$_3$(Z) |
| 3-Cl-5-OCF$_3$ | CF$_2$Cl | H | CH=NOEt(Z) |
| 3-Br-5-OCF$_3$ | CF$_3$ | C(O)OCH$_3$ | CH$_2$OEt |
| 3-Br-5-OCF$_3$ | CF$_3$ | H | CH$_2$OCH$_2$CF$_3$ |
| 3-Br-5-OCF$_3$ | CF$_3$ | H | E4-1a |
| 3-Br-5-OCF$_3$ | CF$_3$ | H | CH$_2$C(O)NHCH$_2$CF$_3$ |
| 3-Br-5-OCF$_3$ | CF$_3$ | H | CH(CH$_3$)C(O)NHCH$_2$CF$_3$(D) |
| 3-Br-5-OCF$_3$ | CF$_3$ | H | CH$_2$(D10-2a) |
| 3-Br-5-OCF$_3$ | CF$_3$ | H | CH=NOCH$_3$(Z) |
| 3-Br-5-OCF$_3$ | CF$_3$ | H | CH=NOEt(Z) |
| 3-Br-5-OCF$_3$ | CF$_3$ | C(O)Et | C(O)OCH$_3$ |
| 3-Br-5-OCF$_3$ | CF$_3$ | H | (D34-1c)CN |
| 3-CF$_3$-5-OCF$_3$ | CF$_3$ | C(O)OCH$_3$ | CH$_2$OEt |
| 3-CF$_3$-5-OCF$_3$ | CF$_3$ | H | CH$_2$OCH$_2$CF$_3$ |
| 3-CF$_3$-5-OCF$_3$ | CF$_3$ | H | E4-1a |
| 3-CF$_3$-5-OCF$_3$ | CF$_3$ | H | CH$_2$C(O)NHCH$_2$CF$_3$ |
| 3-CF$_3$-5-OCF$_3$ | CF$_3$ | H | CH(CH$_3$)C(O)NHCH$_2$CF$_3$(D) |
| 3-CF$_3$-5-OCF$_3$ | CF$_3$ | H | CH$_2$(D10-2a) |
| 3-CF$_3$-5-OCF$_3$ | CF$_3$ | H | CH=NOCH$_3$(Z) |

TABLE 4-continued

| (X)$_m$ | R$^3$ | R$^2$ | R$^1$ |
|---|---|---|---|
| 3-CF$_3$-5-OCF$_3$ | CF$_3$ | H | CH=NOEt(Z) |
| 3-CF$_3$-5-OCF$_3$ | CF$_3$ | C(O)Et | C(O)OCH$_3$ |
| 3-CF$_3$-5-OCF$_3$ | CF$_3$ | H | (D34-1c)CN |
| 3-Cl-5-SCF$_3$ | CF$_3$ | C(O)OCH$_3$ | CH$_2$OEt |
| 3-Cl-5-SCF$_3$ | CF$_3$ | H | CH$_2$OCH$_2$CF$_3$ |
| 3-Cl-5-SCF$_3$ | CF$_3$ | C(O)OCH$_3$ | CH$_2$OCH$_2$CF$_3$ |
| 3-Cl-5-SCF$_3$ | CF$_3$ | H | E4-1a |
| 3-Cl-5-SCF$_3$ | CF$_3$ | H | CH$_2$C(O)NHCH$_2$F$_3$ |
| 3-Cl-5-SCF$_3$ | CF$_3$ | H | CH(CH$_3$)C(O)NHCH$_2$CF$_3$ |
| 3-Cl-5-SCF$_3$ | CF$_3$ | H | CH(CH$_3$)C(O)NHCH$_2$CF$_3$(D) |
| 3-Cl-5-SCF$_3$ | CF$_3$ | H | CH$_2$(D10-2a) |
| 3-Cl-5-SCF$_3$ | CF$_3$ | H | CH$_2$(D32-1a) |
| 3-Cl-5-SCF$_3$ | CF$_3$ | C(O)CH$_3$ | CH$_2$(D32-1a) |
| 3-Cl-5-SCF$_3$ | CF$_3$ | C(O)OCH$_3$ | CH$_2$(D32-1a) |
| 3-Cl-5-SCF$_3$ | CF$_3$ | H | CH=NOCH$_3$(Z) |
| 3-Cl-5-SCF$_3$ | CF$_3$ | H | CH=NOEt(Z) |
| 3-Cl-5-SCF$_3$ | CF$_3$ | C(O)Et | C(O)OCH$_3$ |
| 3-Cl-5-SCF$_3$ | CF$_3$ | C(O)CH$_3$ | (D34-1c)Cl |
| 3-Cl-5-SCF$_3$ | CF$_3$ | C(O)OCH$_3$ | (D34-1c)Cl |
| 3-Cl-5-SCF$_3$ | CF$_3$ | H | (D34-1c)CN |
| 3-Cl-5-SCF$_3$ | CF$_3$ | CH$_3$ | (D34-1c)CN |
| 3-Cl-5-SCF$_3$ | CF$_3$ | CH$_2$OC(O)CH$_3$ | (D34-1c)CN |
| 3-Cl-5-SCF$_3$ | CF$_3$ | C(O)Pr-i | (D34-1c)CN |
| 3-Cl-5-SCF$_3$ | CF$_2$Cl | H | CH$_2$C(O)NHCH$_2$CF$_3$ |
| 3-Cl-5-SCF$_3$ | CF$_2$Cl | H | CH(CH$_3$)C(O)NHCH$_2$CF$_3$(D) |
| 3-Cl-5-SCF$_3$ | CF$_2$Cl | H | CH$_2$(D10-2a) |
| 3-Cl-5-SCF$_3$ | CF$_2$Cl | H | CH=NOCH$_3$(Z) |
| 3-Cl-5-SCF$_3$ | CF$_2$Cl | H | CH=NOEt(Z) |
| 3-Br-5-SCF$_3$ | CF$_3$ | C(O)OCH$_3$ | CH$_2$OEt |
| 3-Br-5-SCF$_3$ | CF$_3$ | H | CH$_2$OCH$_2$CF$_3$ |
| 3-Br-5-SCF$_3$ | CF$_3$ | H | E4-1a |
| 3-Br-5-SCF$_3$ | CF$_3$ | H | CH$_2$C(O)NHCH$_2$CF$_3$ |
| 3-Br-5-SCF$_3$ | CF$_3$ | H | CH(CH$_3$)C(O)NHCH$_2$CF$_3$(D) |
| 3-Br-5-SCF$_3$ | CF$_3$ | H | CH$_2$(D10-2a) |
| 3-Br-5-SCF$_3$ | CF$_3$ | H | CH=NOCH$_3$(Z) |
| 3-Br-5-SCF$_3$ | CF$_3$ | H | CH=NOEt(Z) |
| 3-Br-5-SCF$_3$ | CF$_3$ | C(O)Et | C(O)OCH$_3$ |
| 3-Br-5-SCF$_3$ | CF$_3$ | H | (D34-1c)CN |
| 3-CF$_3$-5-NO$_2$ | CF$_3$ | H | CH$_2$C(O)NHCH$_2$CF$_3$ |
| 3-CF$_3$-5-NO$_2$ | CF$_3$ | H | CH(CH$_3$)C(O)NHCH$_2$CF$_3$(D) |
| 3-CF$_3$-5-NO$_2$ | CF$_3$ | H | CH$_2$(D10-2a) |
| 3-CF$_3$-5-NO$_2$ | CF$_3$ | H | CH=NOCH$_3$(Z) |
| 3-CF$_3$-5-NO$_2$ | CF$_3$ | H | CH=NOEt(Z) |
| 3-Cl-5-CN | CF$_3$ | H | CH$_2$C(O)NHCH$_2$CF$_3$ |
| 3-Cl-5-CN | CF$_3$ | H | CH(CH$_3$)C(O)NHCH$_2$CF$_3$(D) |
| 3-Cl-5-CN | CF$_3$ | H | CH$_2$(D10-2a) |
| 3-Cl-5-CN | CF$_3$ | H | CH=NOCH$_3$(Z) |
| 3-Cl-5-CN | CF$_3$ | H | CH=NOEt(Z) |
| 3-Br-5-CN | CF$_3$ | H | CH$_2$C(O)NHCH$_2$CF$_3$ |
| 3-Br-5-CN | CF$_3$ | H | CH(CH$_3$)C(O)NHCH$_2$CF$_3$(D) |
| 3-Br-5-CN | CF$_3$ | H | CH$_2$(D10-2a) |
| 3-Br-5-CN | CF$_3$ | H | CH=NOCH$_3$(Z) |
| 3-Br-5-CN | CF$_3$ | H | CH=NOEt(Z) |
| 3-CF$_3$-5-CN | CF$_3$ | C(O)OCH$_3$ | CH$_2$OEt |
| 3-CF$_3$-5-CN | CF$_3$ | H | CH$_2$OCH$_2$CF$_3$ |
| 3-CF$_3$-5-CN | CF$_3$ | H | E4-1a |
| 3-CF$_3$-5-CN | CF$_3$ | H | CH$_2$C(O)NHCH$_2$CF$_3$ |
| 3-CF$_3$-5-CN | CF$_3$ | H | CH(CH$_3$)C(O)NHCH$_2$CF$_3$(D) |
| 3-CF$_3$-5-CN | CF$_3$ | H | CH$_2$(D10-2a) |
| 3-CF$_3$-5-CN | CF$_3$ | H | CH=NOCH$_3$(Z) |
| 3-CF$_3$-5-CN | CF$_3$ | H | CH=NOEt(Z) |
| 3-CF$_3$-5-CN | CF$_3$ | C(O)Et | C(O)OCH$_3$ |
| 3-CF$_3$-5-CN | CF$_3$ | H | (D34-1c)CN |
| 3,4,5-F$_3$ | CF$_3$ | C(O)OCH$_3$ | CH$_2$OEt |
| 3,4,5-F$_3$ | CF$_3$ | H | CH$_2$OCH$_2$CF$_3$ |
| 3,4,5-F$_3$ | CF$_3$ | H | E4-1a |
| 3,4,5-F$_3$ | CF$_3$ | H | CH$_2$C(O)NHCH$_2$CF$_3$ |
| 3,4,5-F$_3$ | CF$_3$ | H | CH(CH$_3$)C(O)NHCH$_2$CF$_3$(D) |
| 3,4,5-F$_3$ | CF$_3$ | H | CH$_2$(D10-2a) |
| 3,4,5-F$_3$ | CF$_3$ | H | CH=NOCH$_3$(Z) |
| 3,4,5-F$_3$ | CF$_3$ | H | CH=NOEt(Z) |
| 3,4,5-F$_3$ | CF$_3$ | C(O)Et | C(O)OCH$_3$ |
| 3,4,5-F$_3$ | CF$_3$ | H | (D34-1c)CN |
| 3,5-Cl$_2$-4-F | CF$_3$ | C(O)CH$_3$ | CH$_2$CF$_3$ |
| 3,5-Cl$_2$-4-F | CF$_3$ | C(O)OCH$_3$ | CH$_2$OCH$_3$ |
| 3,5-Cl$_2$-4-F | CF$_3$ | C(O)OCH$_3$ | CH$_2$OEt |
| 3,5-Cl$_2$-4-F | CF$_3$ | C(O)OCH$_3$ | CH$_2$OPr-i |
| 3,5-Cl$_2$-4-F | CF$_3$ | H | CH$_2$OCH$_2$CF$_3$ |

TABLE 4-continued

| $(X)_m$ | $R^3$ | $R^2$ | $R^1$ |
|---|---|---|---|
| 3,5-Cl$_2$-4-F | CF$_3$ | C(O)OCH$_3$ | CH$_2$OCH$_2$CF$_3$ |
| 3,5-Cl$_2$-4-F | CF$_3$ | H | E4-1a |
| 3,5-Cl$_2$-4-F | CF$_3$ | H | CH$_2$C(O)NHCH$_2$CH$_2$Cl |
| 3,5-Cl$_2$-4-F | CF$_3$ | H | CH$_2$C(O)NHCH$_2$CF$_3$ |
| 3,5-Cl$_2$-4-F | CF$_3$ | H | CH(CH$_3$)C(O)NHCH$_2$CH$_2$Cl |
| 3,5-Cl$_2$-4-F | CF$_3$ | H | CH(CH$_3$)C(O)NHCH$_2$CF$_3$ |
| 3,5-Cl$_2$-4-F | CF$_3$ | H | CH(CH$_3$)C(O)NHCH$_2$CF$_3$(D) |
| 3,5-Cl$_2$-4-F | CF$_3$ | H | CH$_2$(D10-2a) |
| 3,5-Cl$_2$-4-F | CF$_3$ | C(O)CH$_3$ | CH$_2$(D10-2a) |
| 3,5-Cl$_2$-4-F | CF$_3$ | C(O)Et | CH$_2$(D10-2a) |
| 3,5-Cl$_2$-4-F | CF$_3$ | H | CH$_2$(D32-1a) |
| 3,5-Cl$_2$-4-F | CF$_3$ | C(O)CH$_3$ | CH$_2$(D32-1a) |
| 3,5-Cl$_2$-4-F | CF$_3$ | C(O)Et | CH$_2$(D32-1a) |
| 3,5-Cl$_2$-4-F | CF$_3$ | C(O)OCH$_3$ | CH$_2$(D32-1a) |
| 3,5-Cl$_2$-4-F | CF$_3$ | H | CH=NOCH$_3$(Z) |
| 3,5-Cl$_2$-4-F | CF$_3$ | CH$_2$OCH$_3$ | CH=NOCH$_3$ |
| 3,5-Cl$_2$-4-F | CF$_3$ | CH$_2$OC(O)CH$_3$ | CH=NOCH$_3$ |
| 3,5-Cl$_2$-4-F | CF$_3$ | H | CH=NOEt(Z) |
| 3,5-Cl$_2$-4-F | CF$_3$ | C(O)Et | C(O)OCH$_3$ |
| 3,5-Cl$_2$-4-F | CF$_3$ | CH$_2$OC(O)CH$_3$ | (D34-1c)Cl |
| 3,5-Cl$_2$-4-F | CF$_3$ | C(O)CH$_3$ | (D34-1c)Cl |
| 3,5-Cl$_2$-4-F | CF$_3$ | C(O)Pr-c | (D34-1c)Cl |
| 3,5-Cl$_2$-4-F | CF$_3$ | C(O)OCH$_3$ | (D34-1c)Cl |
| 3,5-Cl$_2$-4-F | CF$_3$ | H | (D34-1c)CN |
| 3,5-Cl$_2$-4-F | CF$_3$ | CH$_3$ | (D34-1c)CN |
| 3,5-Cl$_2$-4-F | CF$_3$ | CH$_2$OCH$_3$ | (D34-1c)CN |
| 3,5-Cl$_2$-4-F | CF$_3$ | CH$_2$OC(O)CH$_3$ | (D34-1c)CN |
| 3,5-Cl$_2$-4-F | CF$_3$ | C(O)Pr-i | (D34-1c)CN |
| 3,5-Cl$_2$-4-F | CF$_3$ | C(O)OCH$_3$ | (D34-1c)CN |
| 3,5-Cl$_2$-4-F | CF$_3$ | CH$_2$OCH$_3$ | D34-3a |
| 3,5-Cl$_2$-4-F | CF$_3$ | C(O)Et | D34-3a |
| 3,5-Cl$_2$-4-F | CF$_3$ | C(O)Pr-i | D34-3a |
| 3,5-Cl$_2$-4-F | CF$_3$ | C(O)OCH$_3$ | (D35-1c)Cl |
| 3,5-Cl$_2$-4-F | CF$_3$ | H | N(CH$_3$)Ph |
| 3,5-Cl$_2$-4-F | CF$_3$ | H | N(CH$_3$)(D34-1a) |
| 3,5-Cl$_2$-4-F | CF$_2$Cl | C(O)OCH$_3$ | CH$_2$OEt |
| 3,5-Cl$_2$-4-F | CF$_2$Cl | H | CH$_2$OCH$_2$CF$_3$ |
| 3,5-Cl$_2$-4-F | CF$_2$Cl | H | E4-1a |
| 3,5-Cl$_2$-4-F | CF$_2$Cl | H | CH$_2$C(O)NHCH$_2$CF$_3$ |
| 3,5-Cl$_2$-4-F | CF$_2$Cl | H | CH(CH$_3$)C(O)NHCH$_2$CF$_3$(D) |
| 3,5-Cl$_2$-4-F | CF$_2$Cl | H | CH$_2$(D10-2a) |
| 3,5-Cl$_2$-4-F | CF$_2$Cl | H | CH=NOCH$_3$(Z) |
| 3,5-Cl$_2$-4-F | CF$_2$Cl | H | CH=NOEt(Z) |
| 3,5-Cl$_2$-4-F | CF$_2$Cl | C(O)Et | C(O)OCH$_3$ |
| 3,5-Cl$_2$-4-F | CF$_2$Cl | H | (D34-1c)CN |
| 3,4,5-Cl$_3$ | CF$_3$ | C(O)CH$_3$ | CH$_2$CF$_3$ |
| 3,4,5-Cl$_3$ | CF$_3$ | C(O)OCH$_3$ | CH$_2$OCH$_3$ |
| 3,4,5-Cl$_3$ | CF$_3$ | C(O)OCH$_3$ | CH$_2$OEt |
| 3,4,5-Cl$_3$ | CF$_3$ | C(O)OCH$_3$ | CH$_2$OPr-i |
| 3,4,5-Cl$_3$ | CF$_3$ | H | CH$_2$OCH$_2$CF$_3$ |
| 3,4,5-Cl$_3$ | CF$_3$ | C(O)OCH$_3$ | CH$_2$OCH$_2$CF$_3$ |
| 3,4,5-Cl$_3$ | CF$_3$ | H | E4-1a |
| 3,4,5-Cl$_3$ | CF$_3$ | H | CH$_2$C(O)NHCH$_2$CH$_2$Cl |
| 3,4,5-Cl$_3$ | CF$_3$ | H | CH$_2$C(O)NHCH$_2$CF$_3$ |
| 3,4,5-Cl$_3$ | CF$_3$ | H | CH(CH$_3$)C(O)NHCH$_2$CH$_2$Cl |
| 3,4,5-Cl$_3$ | CF$_3$ | H | CH(CH$_3$)C(O)NHCH$_2$CF$_3$ |
| 3,4,5-Cl$_3$ | CF$_3$ | H | CH(CH$_3$)C(O)NHCH$_2$CF$_3$(D) |
| 3,4,5-Cl$_3$ | CF$_3$ | H | CH$_2$(D10-2a) |
| 3,4,5-Cl$_3$ | CF$_3$ | C(O)CH$_3$ | CH$_2$(D10-2a) |
| 3,4,5-Cl$_3$ | CF$_3$ | C(O)Et | CH$_2$(D10-2a) |
| 3,4,5-Cl$_3$ | CF$_3$ | H | CH$_2$(D32-1a) |
| 3,4,5-Cl$_3$ | CF$_3$ | C(O)CH$_3$ | CH$_2$(D32-1a) |
| 3,4,5-Cl$_3$ | CF$_3$ | C(O)Et | CH$_2$(D32-1a) |
| 3,4,5-Cl$_3$ | CF$_3$ | C(O)OCH$_3$ | CH$_2$(D32-1a) |
| 3,4,5-Cl$_3$ | CF$_3$ | H | CH=NOCH$_3$(Z) |
| 3,4,5-Cl$_3$ | CF$_3$ | CH$_2$OCH$_3$ | CH=NOCH$_3$ |
| 3,4,5-Cl$_3$ | CF$_3$ | CH$_2$OC(O)CH$_3$ | CH=NOCH$_3$ |
| 3,4,5-Cl$_3$ | CF$_3$ | H | CH=NOEt(Z) |
| 3,4,5-Cl$_3$ | CF$_3$ | C(O)Et | C(O)OCH$_3$ |
| 3,4,5-Cl$_3$ | CF$_3$ | CH$_2$OC(O)CH$_3$ | (D34-1c)Cl |
| 3,4,5-Cl$_3$ | CF$_3$ | C(O)CH$_3$ | (D34-1c)Cl |
| 3,4,5-Cl$_3$ | CF$_3$ | C(O)Pr-c | (D34-1c)Cl |
| 3,4,5-Cl$_3$ | CF$_3$ | C(O)OCH$_3$ | (D34-1c)Cl |
| 3,4,5-Cl$_3$ | CF$_3$ | H | (D34-1c)CN |
| 3,4,5-Cl$_3$ | CF$_3$ | CH$_3$ | (D34-1c)CN |
| 3,4,5-Cl$_3$ | CF$_3$ | CH$_2$OCH$_3$ | (D34-1c)CN |
| 3,4,5-Cl$_3$ | CF$_3$ | CH$_2$OC(O)CH$_3$ | (D34-1c)CN |
| 3,4,5-Cl$_3$ | CF$_3$ | C(O)Pr-i | (D34-1c)CN |

TABLE 4-continued

| $(X)_m$ | $R^3$ | $R^2$ | $R^1$ |
|---|---|---|---|
| 3,4,5-Cl$_3$ | CF$_3$ | C(O)OCH$_3$ | (D34-1c)CN |
| 3,4,5-Cl$_3$ | CF$_3$ | CH$_2$OCH$_3$ | D34-3a |
| 3,4,5-Cl$_3$ | CF$_3$ | C(O)Et | D34-3a |
| 3,4,5-Cl$_3$ | CF$_3$ | C(O)Pr-i | D34-3a |
| 3,4,5-Cl$_3$ | CF$_3$ | C(O)OCH$_3$ | (D35-1c)Cl |
| 3,4,5-Cl$_3$ | CF$_3$ | H | N(CH$_3$)Ph |
| 3,4,5-Cl$_3$ | CF$_3$ | H | N(CH$_3$)(D34-1a) |
| 3,4,5-Cl$_3$ | CF$_2$Cl | C(O)OCH$_3$ | CH$_2$OEt |
| 3,4,5-Cl$_3$ | CF$_2$Cl | H | CH$_2$OCH$_2$CF$_3$ |
| 3,4,5-Cl$_3$ | CF$_2$Cl | H | E4-1a |
| 3,4,5-Cl$_3$ | CF$_2$Cl | H | CH$_2$C(O)NHCH$_2$CF$_3$ |
| 3,4,5-Cl$_3$ | CF$_2$Cl | H | CH(CH$_3$)C(O)NHCH$_2$CF$_3$(D) |
| 3,4,5-Cl$_3$ | CF$_2$Cl | H | CH$_2$(D10-2a) |
| 3,4,5-Cl$_3$ | CF$_2$Cl | H | CH=NOCH$_3$(Z) |
| 3,4,5-Cl$_3$ | CF$_2$Cl | H | CH=NOEt(Z) |
| 3,4,5-Cl$_3$ | CF$_2$Cl | C(O)Et | C(O)OCH$_3$ |
| 3,4,5-Cl$_3$ | CF$_2$Cl | H | (D34-1c)CN |
| 3,5-Br$_2$-4-F | CF$_3$ | C(O)CH$_3$ | CH$_2$CF$_3$ |
| 3,5-Br$_2$-4-F | CF$_3$ | C(O)OCH$_3$ | CH$_2$OCH$_3$ |
| 3,5-Br$_2$-4-F | CF$_3$ | C(O)OCH$_3$ | CH$_2$OEt |
| 3,5-Br$_2$-4-F | CF$_3$ | C(O)OCH$_3$ | CH$_2$OPr-i |
| 3,5-Br$_2$-4-F | CF$_3$ | H | CH$_2$OCH$_2$CF$_3$ |
| 3,5-Br$_2$-4-F | CF$_3$ | C(O)OCH$_3$ | CH$_2$OCH$_2$CF$_3$ |
| 3,5-Br$_2$-4-F | CF$_3$ | H | E4-1a |
| 3,5-Br$_2$-4-F | CF$_3$ | H | CH$_2$C(O)NHCH$_2$CH$_2$Cl |
| 3,5-Br$_2$-4-F | CF$_3$ | H | CH$_2$C(O)NHCH$_2$CF$_3$ |
| 3,5-Br$_2$-4-F | CF$_3$ | H | CH(CH$_3$)C(O)NHCH$_2$CH$_2$Cl |
| 3,5-Br$_2$-4-F | CF$_3$ | H | CH(CH$_3$)C(O)NHCH$_2$CF$_3$ |
| 3,5-Br$_2$-4-F | CF$_3$ | H | CH(CH$_3$)C(O)NHCH$_2$CF$_3$(D) |
| 3,5-Br$_2$-4-F | CF$_3$ | H | CH$_2$(D10-2a) |
| 3,5-Br$_2$-4-F | CF$_3$ | C(O)CH$_3$ | CH$_2$(D10-2a) |
| 3,5-Br$_2$-4-F | CF$_3$ | C(O)Et | CH$_2$(D10-2a) |
| 3,5-Br$_2$-4-F | CF$_3$ | H | CH$_2$(D32-1a) |
| 3,5-Br$_2$-4-F | CF$_3$ | C(O)CH$_3$ | CH$_2$(D32-1a) |
| 3,5-Br$_2$-4-F | CF$_3$ | C(O)Et | CH$_2$(D32-1a) |
| 3,5-Br$_2$-4-F | CF$_3$ | C(O)OCH$_3$ | CH$_2$(D32-1a) |
| 3,5-Br$_2$-4-F | CF$_3$ | H | CH=NOCH$_3$(Z) |
| 3,5-Br$_2$-4-F | CF$_3$ | CH$_2$OCH$_3$ | CH=NOCH$_3$ |
| 3,5-Br$_2$-4-F | CF$_3$ | CH$_2$OC(O)CH$_3$ | CH=NOCH$_3$ |
| 3,5-Br$_2$-4-F | CF$_3$ | H | CH=NOEt(Z) |
| 3,5-Br$_2$-4-F | CF$_3$ | C(O)Et | C(O)OCH$_3$ |
| 3,5-Br$_2$-4-F | CF$_3$ | CH$_2$OC(O)CH$_3$ | (D34-1c)Cl |
| 3,5-Br$_2$-4-F | CF$_3$ | C(O)CH$_3$ | (D34-1c)Cl |
| 3,5-Br$_2$-4-F | CF$_3$ | C(O)Pr-c | (D34-1c)Cl |
| 3,5-Br$_2$-4-F | CF$_3$ | C(O)OCH$_3$ | (D34-1c)Cl |
| 3,5-Br$_2$-4-F | CF$_3$ | H | (D34-1c)CN |
| 3,5-Br$_2$-4-F | CF$_3$ | CH$_3$ | (D34-1c)CN |
| 3,5-Br$_2$-4-F | CF$_3$ | CH$_2$OCH$_3$ | (D34-1c)CN |
| 3,5-Br$_2$-4-F | CF$_3$ | CH$_2$OC(O)CH$_3$ | (D34-1c)CN |
| 3,5-Br$_2$-4-F | CF$_3$ | C(O)Pr-i | (D34-1c)CN |
| 3,5-Br$_2$-4-F | CF$_3$ | C(O)OCH$_3$ | (D34-1c)CN |
| 3,5-Br$_2$-4-F | CF$_3$ | CH$_2$OCH$_3$ | D34-3a |
| 3,5-Br$_2$-4-F | CF$_3$ | C(O)Et | D34-3a |
| 3,5-Br$_2$-4-F | CF$_3$ | C(O)Pr-i | D34-3a |
| 3,5-Br$_2$-4-F | CF$_3$ | C(O)OCH$_3$ | (D35-1c)Cl |
| 3,5-Br$_2$-4-F | CF$_3$ | H | N(CH$_3$)Ph |
| 3,5-Br$_2$-4-F | CF$_2$Cl | H | N(CH$_3$)(D34-1a) |
| 3,5-Br$_2$-4-F | CF$_2$Cl | C(O)OCH$_3$ | CH$_2$OEt |
| 3,5-Br$_2$-4-F | CF$_2$Cl | H | CH$_2$OCH$_2$CF$_3$ |
| 3,5-Br$_2$-4-F | CF$_2$Cl | H | E4-1a |
| 3,5-Br$_2$-4-F | CF$_2$Cl | H | CH$_2$C(O)NHCH$_2$CF$_3$ |
| 3,5-Br$_2$-4-F | CF$_2$Cl | H | CH(CH$_3$)C(O)NHCH$_2$CF$_3$(D) |
| 3,5-Br$_2$-4-F | CF$_2$Cl | H | CH$_2$(D10-2a) |
| 3,5-Br$_2$-4-F | CF$_2$Cl | H | CH=NOCH$_3$(Z) |
| 3,5-Br$_2$-4-F | CF$_2$Cl | H | CH=NOEt(Z) |
| 3,5-Br$_2$-4-F | CF$_2$Cl | C(O)Et | C(O)OCH$_3$ |
| 3,4,5-Br$_3$ | CF$_3$ | H | (D34-1c)CN |
| 3,4,5-Br$_3$ | CF$_3$ | C(O)OCH$_3$ | CH$_2$OEt |
| 3,4,5-Br$_3$ | CF$_3$ | H | CH$_2$OCH$_2$CF$_3$ |
| 3,4,5-Br$_3$ | CF$_3$ | H | E4-1a |
| 3,4,5-Br$_3$ | CF$_3$ | H | CH$_2$C(O)NHCH$_2$CF$_3$ |
| 3,4,5-Br$_3$ | CF$_3$ | H | CH(CH$_3$)C(O)NHCH$_2$CF$_3$(D) |
| 3,4,5-Br$_3$ | CF$_3$ | H | CH$_2$(D10-2a) |
| 3,4,5-Br$_3$ | CF$_3$ | H | CH=NOCH$_3$(Z) |
| 3,4,5-Br$_3$ | CF$_3$ | H | CH=NOEt(Z) |
| 3,4,5-Br$_3$ | CF$_3$ | C(O)Et | C(O)OCH$_3$ |
| 3,4,5-Br$_3$ | CF$_3$ | H | (D34-1c)CN |
| 3,4-Cl$_2$-5-CH$_3$ | CF$_3$ | H | CH$_2$C(O)NHCH$_2$CF$_3$ |

TABLE 4-continued

| $(X)_m$ | $R^3$ | $R^2$ | $R^1$ |
|---|---|---|---|
| 3,4-Cl$_2$-5-CH$_3$ | CF$_3$ | H | CH(CH$_3$)C(O)NHCH$_2$CF$_3$(D) |
| 3,4-Cl$_2$-5-CH$_3$ | CF$_3$ | H | CH$_2$(D10-2a) |
| 3,4-Cl$_2$-5-CH$_3$ | CF$_3$ | H | CH=NOCH$_3$(Z) |
| 3,4-Cl$_2$-5-CH$_3$ | CF$_3$ | H | CH=NOEt(Z) |
| 3,4-F$_2$-5-CF$_3$ | CF$_3$ | C(O)CH$_3$ | CH$_2$CF$_3$ |
| 3,4-F$_2$-5-CF$_3$ | CF$_3$ | C(O)OCH$_3$ | CH$_2$OCH$_3$ |
| 3,4-F$_2$-5-CF$_3$ | CF$_3$ | C(O)OCH$_3$ | CH$_2$OEt |
| 3,4-F$_2$-5-CF$_3$ | CF$_3$ | H | CH$_2$OCH$_2$CF$_3$ |
| 3,4-F$_2$-5-CF$_3$ | CF$_3$ | C(O)OCH$_3$ | CH$_2$OCH$_2$CF$_3$ |
| 3,4-F$_2$-5-CF$_3$ | CF$_3$ | H | E4-1a |
| 3,4-F$_2$-5-CF$_3$ | CF$_3$ | H | CH$_2$C(O)NHCH$_2$CF$_3$ |
| 3,4-F$_2$-5-CF$_3$ | CF$_3$ | H | CH(CH$_3$)C(O)NHCH$_2$CH$_2$Cl |
| 3,4-F$_2$-5-CF$_3$ | CF$_3$ | H | CH(CH$_3$)C(O)NHCH$_2$CF$_3$ |
| 3,4-F$_2$-5-CF$_3$ | CF$_3$ | H | CH(CH$_3$)C(O)NHCH$_2$CF$_3$(D) |
| 3,4-F$_2$-5-CF$_3$ | CF$_3$ | H | CH$_2$(D10-2a) |
| 3,4-F$_2$-5-CF$_3$ | CF$_3$ | H | CH$_2$(D32-1a) |
| 3,4-F$_2$-5-CF$_3$ | CF$_3$ | C(O)CH$_3$ | CH$_2$(D32-1a) |
| 3,4-F$_2$-5-CF$_3$ | CF$_3$ | C(O)Et | CH$_2$(D32-1a) |
| 3,4-F$_2$-5-CF$_3$ | CF$_3$ | C(O)OCH$_3$ | CH$_2$(D32-1a) |
| 3,4-F$_2$-5-CF$_3$ | CF$_3$ | H | CH=NOCH$_3$(Z) |
| 3,4-F$_2$-5-CF$_3$ | CF$_3$ | CH$_2$OCH$_3$ | CH=NOCH$_3$ |
| 3,4-F$_2$-5-CF$_3$ | CF$_3$ | H | CH=NOEt(Z) |
| 3,4-F$_2$-5-CF$_3$ | CF$_3$ | C(O)OCH$_3$ | C(O)OCH$_3$ |
| 3,4-F$_2$-5-CF$_3$ | CF$_3$ | CH$_2$OC(O)CH$_3$ | (D34-1c)Cl |
| 3,4-F$_2$-5-CF$_3$ | CF$_3$ | C(O)CH$_3$ | (D34-1c)Cl |
| 3,4-F$_2$-5-CF$_3$ | CF$_3$ | C(O)Pr-c | (D34-1c)Cl |
| 3,4-F$_2$-5-CF$_3$ | CF$_3$ | CH(O)OCH$_3$ | (D34-1c)Cl |
| 3,4-F$_2$-5-CF$_3$ | CF$_3$ | H | (D34-1c)CN |
| 3,4-F$_2$-5-CF$_3$ | CF$_3$ | CH$_3$ | (D34-1c)CN |
| 3,4-F$_2$-5-CF$_3$ | CF$_3$ | CH$_2$OC(O)CH$_3$ | (D34-1c)CN |
| 3,4-F$_2$-5-CF$_3$ | CF$_3$ | C(O)Pr-i | (D34-1c)CN |
| 3,4-F$_2$-5-CF$_3$ | CF$_3$ | CH(O)OCH$_3$ | (D34-1c)CN |
| 3,4-F$_2$-5-CF$_3$ | CF$_3$ | C(O)Et | D34-3a |
| 3,4-F$_2$-5-CF$_3$ | CF$_3$ | C(O)Pr-i | D34-3a |
| 3,4-F$_2$-5-CF$_3$ | CF$_2$Cl | CH(O)OCH$_3$ | CH$_2$OEt |
| 3,4-F$_2$-5-CF$_3$ | CF$_2$Cl | H | CH$_2$OCH$_2$CF$_3$ |
| 3,4-F$_2$-5-CF$_3$ | CF$_2$Cl | H | E4-1a |
| 3,4-F$_2$-5-CF$_3$ | CF$_2$Cl | H | CH$_2$C(O)NHCH$_2$CF$_3$ |
| 3,4-F$_2$-5-CF$_3$ | CF$_2$Cl | H | CH(CH$_3$)C(O)NHCH$_2$CF$_3$(D) |
| 3,4-F$_2$-5-CF$_3$ | CF$_2$Cl | H | CH$_2$(D10-2a) |
| 3,4-F$_2$-5-CF$_3$ | CF$_2$Cl | H | CH=NOCH$_3$(Z) |
| 3,4-F$_2$-5-CF$_3$ | CF$_2$Cl | H | CH=NOEt(Z) |
| 3,4-F$_2$-5-CF$_3$ | CF$_2$Cl | C(O)Et | C(O)OCH$_3$ |
| 3,4-F$_2$-5-CF$_3$ | CF$_2$Cl | H | (D34-1c)CN |
| 3-Cl-4-F-5-CF$_3$ | CF$_3$ | C(O)CH$_3$ | CH$_2$CF$_3$ |
| 3-Cl-4-F-5-CF$_3$ | CF$_3$ | C(O)OCH$_3$ | CH$_2$OCH$_3$ |
| 3-Cl-4-F-5-CF$_3$ | CF$_3$ | C(O)OCH$_3$ | CH$_2$OEt |
| 3-Cl-4-F-5-CF$_3$ | CF$_3$ | H | CH$_2$OCH$_2$CF$_3$ |
| 3-Cl-4-F-5-CF$_3$ | CF$_3$ | C(O)OCH$_3$ | CH$_2$OCH$_2$CF$_3$ |
| 3-Cl-4-F-5-CF$_3$ | CF$_3$ | H | E4-1a |
| 3-Cl-4-F-5-CF$_3$ | CF$_3$ | H | CH$_2$C(O)NHCH$_2$CF$_3$ |
| 3-Cl-4-F-5-CF$_3$ | CF$_3$ | H | CH(CH$_3$)C(O)NHCH$_2$CH$_2$Cl |
| 3-Cl-4-F-5-CF$_3$ | CF$_3$ | H | CH(CH$_3$)C(O)NHCH$_2$CF$_3$ |
| 3-Cl-4-F-5-CF$_3$ | CF$_3$ | H | CH(CH$_3$)C(O)NHCH$_2$CF$_3$(D) |
| 3-Cl-4-F-5-CF$_3$ | CF$_3$ | H | CH$_2$(D10-2a) |
| 3-Cl-4-F-5-CF$_3$ | CF$_3$ | H | CH$_2$(D32-1a) |
| 3-Cl-4-F-5-CF$_3$ | CF$_3$ | C(O)CH$_3$ | CH$_2$(D32-1a) |
| 3-Cl-4-F-5-CF$_3$ | CF$_3$ | C(O)Et | CH$_2$(D32-1a) |
| 3-Cl-4-F-5-CF$_3$ | CF$_3$ | C(O)OCH$_3$ | CH$_2$(D32-1a) |
| 3-Cl-4-F-5-CF$_3$ | CF$_3$ | H | CH=NOCH$_3$(Z) |
| 3-Cl-4-F-5-CF$_3$ | CF$_3$ | CH$_2$OCH$_3$ | CH=NOCH$_3$ |
| 3-Cl-4-F-5-CF$_3$ | CF$_3$ | H | CH=NOEt(Z) |
| 3-Cl-4-F-5-CF$_3$ | CF$_3$ | C(O)Et | C(O)OCH$_3$ |
| 3-Cl-4-F-5-CF$_3$ | CF$_3$ | CH$_2$OC(O)CH$_3$ | (D34-1c)Cl |
| 3-Cl-4-F-5-CF$_3$ | CF$_3$ | C(O)CH$_3$ | (D34-1c)Cl |
| 3-Cl-4-F-5-CF$_3$ | CF$_3$ | C(O)Pr-c | (D34-1c)Cl |
| 3-Cl-4-F-5-CF$_3$ | CF$_3$ | C(O)OCH$_3$ | (D34-1c)Cl |
| 3-Cl-4-F-5-CF$_3$ | CF$_3$ | H | (D34-1c)CN |
| 3-Cl-4-F-5-CF$_3$ | CF$_3$ | CH$_3$ | (D34-1c)CN |
| 3-Cl-4-F-5-CF$_3$ | CF$_3$ | CH$_2$OC(O)CH$_3$ | (D34-1c)CN |
| 3-Cl-4-F-5-CF$_3$ | CF$_3$ | C(O)Pr-i | (D34-1c)CN |
| 3-Cl-4-F-5-CF$_3$ | CF$_3$ | C(O)OCH$_3$ | (D34-1c)CN |
| 3-Cl-4-F-5-CF$_3$ | CF$_3$ | C(O)Et | D34-3a |
| 3-Cl-4-F-5-CF$_3$ | CF$_3$ | C(O)Pr-i | D34-3a |
| 3-Cl-4-F-5-CF$_3$ | CF$_2$Cl | C(O)OCH$_3$ | CH$_2$OEt |
| 3-Cl-4-F-5-CF$_3$ | CF$_2$Cl | H | CH$_2$OCH$_2$CF$_3$ |
| 3-Cl-4-F-5-CF$_3$ | CF$_2$Cl | H | E4-1a |
| 3-Cl-4-F-5-CF$_3$ | CF$_2$Cl | H | CH$_2$C(O)NHCH$_2$CF$_3$ |

TABLE 4-continued

| (X)$_m$ | R$^3$ | R$^2$ | R$^1$ |
|---|---|---|---|
| 3-Cl-4-F-5-CF$_3$ | CF$_2$Cl | H | CH(CH$_3$)C(O)NHCH$_2$CF$_3$(D) |
| 3-Cl-4-F-5-CF$_3$ | CF$_2$Cl | H | CH$_2$(D10-2a) |
| 3-Cl-4-F-5-CF$_3$ | CF$_2$Cl | H | CH=NOCH$_3$(Z) |
| 3-Cl-4-F-5-CF$_3$ | CF$_2$Cl | H | CH=NOEt(Z) |
| 3-Cl-4-F-5-CF$_3$ | CF$_2$Cl | C(O)Et | C(O)OCH$_3$ |
| 3-Cl-4-F-5-CF$_3$ | CF$_2$Cl | H | (D34-1c)CN |
| 3,4-Cl$_2$-5-CF$_3$ | CF$_3$ | C(O)CH$_3$ | CH$_2$CF$_3$ |
| 3,4-Cl$_2$-5-CF$_3$ | CF$_3$ | C(O)OCH$_3$ | CH$_2$OCH$_3$ |
| 3,4-Cl$_2$-5-CF$_3$ | CF$_3$ | C(O)OCH$_3$ | CH$_2$OEt |
| 3,4-Cl$_2$-5-CF$_3$ | CF$_3$ | H | CH$_2$OCH$_2$CF$_3$ |
| 3,4-Cl$_2$-5-CF$_3$ | CF$_3$ | C(O)OCH$_3$ | CH$_2$OCH$_2$CF$_3$ |
| 3,4-Cl$_2$-5-CF$_3$ | CF$_3$ | H | E4-1a |
| 3,4-Cl$_2$-5-CF$_3$ | CF$_3$ | H | CH$_2$C(O)NHCH$_2$CF$_3$ |
| 3,4-Cl$_2$-5-CF$_3$ | CF$_3$ | H | CH(CH$_3$)C(O)NHCH$_2$CH$_2$Cl |
| 3,4-Cl$_2$-5-CF$_3$ | CF$_3$ | H | CH(CH$_3$)C(O)NHCH$_2$CF$_3$ |
| 3,4-Cl$_2$-5-CF$_3$ | CF$_3$ | H | CH(CH$_3$)C(O)NHCH$_2$CF$_3$(D) |
| 3,4-Cl$_2$-5-CF$_3$ | CF$_3$ | H | CH$_2$(D10-2a) |
| 3,4-Cl$_2$-5-CF$_3$ | CF$_3$ | H | CH$_2$(D32-1a) |
| 3,4-Cl$_2$-5-CF$_3$ | CF$_3$ | C(O)CH$_3$ | CH$_2$(D32-1a) |
| 3,4-Cl$_2$-5-CF$_3$ | CF$_3$ | C(O)Et | CH$_2$(D32-1a) |
| 3,4-Cl$_2$-5-CF$_3$ | CF$_3$ | C(O)OCH$_3$ | CH$_2$(D32-1a) |
| 3,4-Cl$_2$-5-CF$_3$ | CF$_3$ | H | CH=NOCH$_3$(Z) |
| 3,4-Cl$_2$-5-CF$_3$ | CF$_3$ | CH$_2$OCH$_3$ | CH=NOCH$_3$ |
| 3,4-Cl$_2$-5-CF$_3$ | CF$_3$ | H | CH=NOEt(Z) |
| 3,4-Cl$_2$-5-CF$_3$ | CF$_3$ | C(O)Et | C(O)OCH$_3$ |
| 3,4-Cl$_2$-5-CF$_3$ | CF$_3$ | CH$_2$OC(O)CH$_3$ | (D34-1c)Cl |
| 3,4-Cl$_2$-5-CF$_3$ | CF$_3$ | C(O)CH$_3$ | (D34-1c)Cl |
| 3,4-Cl$_2$-5-CF$_3$ | CF$_3$ | C(O)Pr-c | (D34-1c)Cl |
| 3,4-Cl$_2$-5-CF$_3$ | CF$_3$ | C(O)OCH$_3$ | (D34-1c)Cl |
| 3,4-Cl$_2$-5-CF$_3$ | CF$_3$ | H | (D34-1c)CN |
| 3,4-Cl$_2$-5-CF$_3$ | CF$_3$ | CH$_3$ | (D34-1c)CN |
| 3,4-Cl$_2$-5-CF$_3$ | CF$_3$ | CH$_2$OC(O)CH$_3$ | (D34-1c)CN |
| 3,4-Cl$_2$-5-CF$_3$ | CF$_3$ | C(O)Pr-i | (D34-1c)CN |
| 3,4-Cl$_2$-5-CF$_3$ | CF$_3$ | C(O)OCH$_3$ | (D34-1c)CN |
| 3,4-Cl$_2$-5-CF$_3$ | CF$_3$ | C(O)Et | D34-3a |
| 3,4-Cl$_2$-5-CF$_3$ | CF$_3$ | C(O)Pr-i | D34-3a |
| 3,4-Cl$_2$-5-CF$_3$ | CF$_2$Cl | C(O)OCH$_3$ | CH$_2$OEt |
| 3,4-Cl$_2$-5-CF$_3$ | CF$_2$Cl | H | CH$_2$OCH$_2$CF$_3$ |
| 3,4-Cl$_2$-5-CF$_3$ | CF$_2$Cl | H | E4-1a |
| 3,4-Cl$_2$-5-CF$_3$ | CF$_2$Cl | H | CH$_2$C(O)NHCH$_2$CF$_3$ |
| 3,4-Cl$_2$-5-CF$_3$ | CF$_2$Cl | H | CH(CH$_3$)C(O)NHCH$_2$CF$_3$(D) |
| 3,4-Cl$_2$-5-CF$_3$ | CF$_2$Cl | H | CH$_2$(D10-2a) |
| 3,4-Cl$_2$-5-CF$_3$ | CF$_2$Cl | H | CH=NOCH$_3$(Z) |
| 3,4-Cl$_2$-5-CF$_3$ | CF$_2$Cl | H | CH=NOEt(Z) |
| 3,4-Cl$_2$-5-CF$_3$ | CF$_2$Cl | C(O)Et | C(O)OCH$_3$ |
| 3,4-Cl$_2$-5-CF$_3$ | CF$_2$Cl | H | (D34-1c)CN |
| 3,5-(CF$_3$)$_2$-4-Cl | CF$_3$ | C(O)CH$_3$ | CH$_2$CF$_3$ |
| 3,5-(CF$_3$)$_2$-4-Cl | CF$_3$ | C(O)OCH$_3$ | CH$_2$OCH$_3$ |
| 3,5-(CF$_3$)$_2$-4-Cl | CF$_3$ | C(O)OCH$_3$ | CH$_2$OEt |
| 3,5-(CF$_3$)$_2$-4-Cl | CF$_3$ | H | CH$_2$OCH$_2$CF$_3$ |
| 3,5-(CF$_3$)$_2$-4-Cl | CF$_3$ | C(O)OCH$_3$ | CH$_2$OCH$_2$CF$_3$ |
| 3,5-(CF$_3$)$_2$-4-Cl | CF$_3$ | H | E4-1a |
| 3,5-(CF$_3$)$_2$-4-Cl | CF$_3$ | H | CH$_2$C(O)NHCH$_2$CF$_3$ |
| 3,5-(CF$_3$)$_2$-4-Cl | CF$_3$ | H | CH(CH$_3$)C(O)NHCH$_2$CH$_2$Cl |
| 3,5-(CF$_3$)$_2$-4-Cl | CF$_3$ | H | CH(CH$_3$)C(O)NHCH$_2$CF$_3$ |
| 3,5-(CF$_3$)$_2$-4-Cl | CF$_3$ | H | CH(CH$_3$)C(O)NHCH$_2$CF$_3$(D) |
| 3,5-(CF$_3$)$_2$-4-Cl | CF$_3$ | H | CH$_2$(D10-2a) |
| 3,5-(CF$_3$)$_2$-4-Cl | CF$_3$ | H | CH$_2$(D32-1a) |
| 3,5-(CF$_3$)$_2$-4-Cl | CF$_3$ | C(O)CH$_3$ | CH$_2$(D32-1a) |
| 3,5-(CF$_3$)$_2$-4-Cl | CF$_3$ | C(O)Et | CH$_2$(D32-1a) |
| 3,5-(CF$_3$)$_2$-4-Cl | CF$_3$ | C(O)OCH$_3$ | CH$_2$(D32-1a) |
| 3,5-(CF$_3$)$_2$-4-Cl | CF$_3$ | H | CH=NOCH$_3$(Z) |
| 3,5-(CF$_3$)$_2$-4-Cl | CF$_3$ | CH$_2$OCH$_3$ | CH=NOCH$_3$ |
| 3,5-(CF$_3$)$_2$-4-Cl | CF$_3$ | H | CH=NOEt(Z) |
| 3,5-(CF$_3$)$_2$-4-Cl | CF$_3$ | C(O)Et | C(O)OCH$_3$ |
| 3,5-(CF$_3$)$_2$-4-Cl | CF$_3$ | CH$_2$OC(O)CH$_3$ | (D34-1c)Cl |
| 3,5-(CF$_3$)$_2$-4-Cl | CF$_3$ | C(O)CH$_3$ | (D34-1c)Cl |
| 3,5-(CF$_3$)$_2$-4-Cl | CF$_3$ | C(O)Pr-c | (D34-1c)Cl |
| 3,5-(CF$_3$)$_2$-4-Cl | CF$_3$ | C(O)OCH$_3$ | (D34-1c)Cl |
| 3,5-(CF$_3$)$_2$-4-Cl | CF$_3$ | H | (D34-1c)CN |
| 3,5-(CF$_3$)$_2$-4-Cl | CF$_3$ | CH$_3$ | (D34-1c)CN |
| 3,5-(CF$_3$)$_2$-4-Cl | CF$_3$ | CH$_2$OC(O)CH$_3$ | (D34-1c)CN |
| 3,5-(CF$_3$)$_2$-4-Cl | CF$_3$ | C(O)Pr-i | (D34-1c)CN |
| 3,5-(CF$_3$)$_2$-4-Cl | CF$_3$ | C(O)OCH$_3$ | (D34-1c)CN |
| 3,5-(CF$_3$)$_2$-4-Cl | CF$_3$ | C(O)Et | D34-3a |
| 3,5-(CF$_3$)$_2$-4-Cl | CF$_3$ | C(O)Pr-i | D34-3a |
| 3,5-(CF$_3$)$_2$-4-Cl | CF$_2$Cl | C(O)OCH$_3$ | CH$_2$OEt |
| 3,5-(CF$_3$)$_2$-4-Cl | CF$_2$Cl | H | CH$_2$OCH$_2$CF$_3$ |

TABLE 4-continued

| (X)$_m$ | R$^3$ | R$^2$ | R$^1$ |
|---|---|---|---|
| 3,5-(CF$_3$)$_2$-4-Cl | CF$_2$Cl | H | E4-1a |
| 3,5-(CF$_3$)$_2$-4-Cl | CF$_2$Cl | H | CH$_2$C(O)NHCH$_2$CF$_3$ |
| 3,5-(CF$_3$)$_2$-4-Cl | CF$_2$Cl | H | CH(CH$_3$)C(O)NHCH$_2$CF$_3$(D) |
| 3,5-(CF$_3$)$_2$-4-Cl | CF$_2$Cl | H | CH$_2$(D10-2a) |
| 3,5-(CF$_3$)$_2$-4-Cl | CF$_2$Cl | H | CH=NOCH$_3$(Z) |
| 3,5-(CF$_3$)$_2$-4-Cl | CF$_2$Cl | H | CH=NOEt(Z) |
| 3,5-(CF$_3$)$_2$-4-Cl | CF$_2$Cl | C(O)Et | C(O)OCH$_3$ |
| 3,5-(CF$_3$)$_2$-4-Cl | CF$_2$Cl | H | (D34-1c)CN |
| 3,5-Cl$_2$-4-OCHF$_2$ | CF$_3$ | C(O)OCH$_3$ | CH$_2$OEt |
| 3,5-Cl$_2$-4-OCHF$_2$ | CF$_3$ | H | CH$_2$OCH$_2$CF$_3$ |
| 3,5-Cl$_2$-4-OCHF$_2$ | CF$_3$ | H | E4-1a |
| 3,5-Cl$_2$-4-OCHF$_2$ | CF$_3$ | H | CH$_2$C(O)NHCH$_2$CF$_3$ |
| 3,5-Cl$_2$-4-OCHF$_2$ | CF$_3$ | H | CH(CH$_3$)C(O)NHCH$_2$CF$_3$(D) |
| 3,5-Cl$_2$-4-OCHF$_2$ | CF$_3$ | H | CH$_2$(D10-2a) |
| 3,5-Cl$_2$-4-OCHF$_2$ | CF$_3$ | H | CH=NOCH$_3$(Z) |
| 3,5-Cl$_2$-4-OCHF$_2$ | CF$_3$ | H | CH=NOEt(Z) |
| 3,5-Cl$_2$-4-OCHF$_2$ | CF$_3$ | C(O)Et | C(O)OCH$_3$ |
| 3,5-Cl$_2$-4-OCHF$_2$ | CF$_3$ | H | (D34-1c)CN |
| 3,5-Br$_2$-4-OCHF$_2$ | CF$_3$ | C(O)OCH$_3$ | CH$_2$OEt |
| 3,5-Br$_2$-4-OCHF$_2$ | CF$_3$ | H | CH$_2$OCH$_2$CF$_3$ |
| 3,5-Br$_2$-4-OCHF$_2$ | CF$_3$ | H | E4-1a |
| 3,5-Br$_2$-4-OCHF$_2$ | CF$_3$ | H | CH$_2$C(O)NHCH$_2$CF$_3$ |
| 3,5-Br$_2$-4-OCHF$_2$ | CF$_3$ | H | CH(CH$_3$)C(O)NHCH$_2$CF$_3$(D) |
| 3,5-Br$_2$-4-OCHF$_2$ | CF$_3$ | H | CH$_2$(D10-2a) |
| 3,5-Br$_2$-4-OCHF$_2$ | CF$_3$ | H | CH=NOCH$_3$(Z) |
| 3,5-Br$_2$-4-OCHF$_2$ | CF$_3$ | H | CH=NOEt(Z) |
| 3,5-Br$_2$-4-OCHF$_2$ | CF$_3$ | C(O)Et | C(O)OCH$_3$ |
| 3,5-Br$_2$-4-OCHF$_2$ | CF$_3$ | H | (D34-1c)CN |

Compounds represented by Structure Formulae [1]-1 to [1]-110 and [2]-1 to [2]-75 having structures in which G$^2$ is represented by G$^2$-2-a.

G$^2$-2-a:

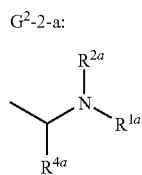

In Table, the number representing the substitution site of the substituent (X)$_m$ corresponds to the site indicated by the number in each of Structure Formulae [1]-1 to [1]-110 and [2]-1 to [2]-75.

Furthermore, in Table, aliphatic heterocyclic rings represented by E4-2a to E5-2c represent the following structures, E4-2a:

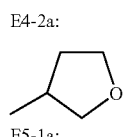

E5-1a:

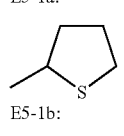

E5-1b:

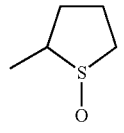

E5-1c:

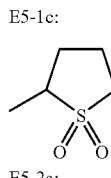

E5-2a:

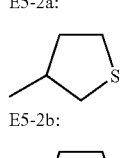

E5-2b:

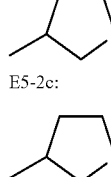

E5-2c:

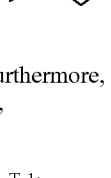

furthermore, in Table, T-1 represents the following structure,

T-1:

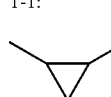

in Table, the description of Et represents an ethyl group and, in the same manner, n-Pr and Pr-n represent normal propyl groups, i-Pr and Pr-i represent isopropyl groups, c-Pr and Pr-c represent cyclopropyl groups, i-Bu and Bu-i represent isobutyl groups, c-Bu and Bu-c represent cyclobutyl groups, and Ph represents a phenyl group.

TABLE 5

| (X)$_m$ | R$^3$ | R$^{4a}$ | R$^{2a}$ | R$^{1a}$ |
|---|---|---|---|---|
| 3-Br | CF$_3$ | H | H | C(O)Pr-c |
| 3-Br | CF$_3$ | H | H | C(O)CH$_2$Pr-c |
| 3-Br | CF$_3$ | H | H | C(O)CH$_2$CF$_3$ |
| 3-Br | CF$_3$ | CH$_3$ | H | C(O)(E4-2a) |
| 3-Br | CF$_3$ | H | H | C(O)CH$_2$SCH$_3$ |
| 3-Br | CF$_3$ | H | H | C(O)CH$_2$S(O)CH$_3$ |
| 3-Br | CF$_3$ | H | H | C(O)CH$_2$SO$_2$CH$_3$ |
| 3-Br | CF$_3$ | H | H | C(O)CH$_2$SEt |
| 3-Br | CF$_3$ | H | H | C(O)CH$_2$S(O)Et |
| 3-Br | CF$_3$ | H | H | C(O)CH$_2$SO$_2$Et |
| 3-I | CF$_3$ | H | H | C(O)Et |
| 3-I | CF$_3$ | H | H | C(O)Pr-n |
| 3-I | CF$_3$ | H | H | C(O)Pr-i |
| 3-I | CF$_3$ | H | H | C(O)Pr-c |
| 3-I | CF$_3$ | CH$_3$ | H | C(O)Pr-c |
| 3-I | CF$_3$ | H | H | C(O)Bu-i |
| 3-I | CF$_3$ | H | H | C(O)CH$_2$Pr-c |
| 3-I | CF$_3$ | CH$_3$ | H | C(O)CH$_2$Pr-c |
| 3-I | CF$_3$ | H | H | C(O)CH$_2$CF$_3$ |
| 3-I | CF$_3$ | CH$_3$ | H | C(O)CH$_2$CF$_3$ |
| 3-I | CF$_3$ | CH$_3$ | H | C(O)(E4-2a) |
| 3-I | CF$_3$ | H | H | C(O)CH$_2$SCH$_3$ |
| 3-I | CF$_3$ | H | H | C(O)CH$_2$S(O)CH$_3$ |
| 3-I | CF$_3$ | H | H | C(O)CH$_2$SO$_2$CH$_3$ |
| 3-I | CF$_3$ | H | H | C(O)CH$_2$SEt |
| 3-I | CF$_3$ | H | H | C(O)CH$_2$S(O)Et |
| 3-I | CF$_3$ | H | H | C(O)CH$_2$SO$_2$Et |
| 3-I | CF$_3$ | H | H | C(O)NHEt |
| 3-I | CF$_3$ | H | H | C(O)NHPr-c |
| 3-I | CF$_3$ | CH$_3$ | H | C(O)NHPr-c |
| 3-CF$_3$ | CF$_3$ | H | H | C(O)Et |
| 3-CF$_3$ | CF$_3$ | H | H | C(O)Pr-n |
| 3-CF$_3$ | CF$_3$ | H | H | C(O)Pr-i |
| 3-CF$_3$ | CF$_3$ | H | H | C(O)Pr-c |
| 3-CF$_3$ | CF$_3$ | CH$_3$ | H | C(O)Pr-c |
| 3-CF$_3$ | CF$_3$ | H | H | C(O)Bu-i |
| 3-CF$_3$ | CF$_3$ | H | H | C(O)CH$_2$Pr-c |
| 3-CF$_3$ | CF$_3$ | CH$_3$ | H | C(O)CH$_2$Pr-c |
| 3-CF$_3$ | CF$_3$ | H | H | C(O)CH$_2$CF$_3$ |
| 3-CF$_3$ | CF$_3$ | CH$_3$ | H | C(O)CH$_2$CF$_3$ |
| 3-CF$_3$ | CF$_3$ | CH$_3$ | H | C(O)(E4-2a) |
| 3-CF$_3$ | CF$_3$ | H | H | C(O)CH$_2$SCH$_3$ |
| 3-CF$_3$ | CF$_3$ | H | H | C(O)CH$_2$S(O)CH$_3$ |
| 3-CF$_3$ | CF$_3$ | H | H | C(O)CH$_2$SO$_2$CH$_3$ |
| 3-CF$_3$ | CF$_3$ | H | H | C(O)CH$_2$SEt |
| 3-CF$_3$ | CF$_3$ | H | H | C(O)CH$_2$S(O)Et |
| 3-CF$_3$ | CF$_3$ | H | H | C(O)CH$_2$SO$_2$Et |
| 3-CF$_3$ | CF$_3$ | H | H | C(O)NHEt |
| 3-CF$_3$ | CF$_3$ | H | H | C(O)NHPr-c |
| 3-CF$_3$ | CF$_3$ | CH$_3$ | H | C(O)NHPr-c |
| 3-CF$_2$CF$_3$ | CF$_3$ | H | H | C(O)Pr-c |
| 3-CF$_2$CF$_3$ | CF$_3$ | H | H | C(O)CH$_2$Pr-c |
| 3-CF$_2$CF$_3$ | CF$_3$ | H | H | C(O)CH$_2$CF$_3$ |
| 3-CF$_2$CF$_3$ | CF$_3$ | CH$_3$ | H | C(O)(E4-2a) |
| 3-CF$_2$CF$_3$ | CF$_3$ | H | H | C(O)CH$_2$SCH$_3$ |
| 3-CF$_2$CF$_3$ | CF$_3$ | H | H | C(O)CH$_2$S(O)CH$_3$ |
| 3-CF$_2$CF$_3$ | CF$_3$ | H | H | C(O)CH$_2$SO$_2$CH$_3$ |
| 3-CF$_2$CF$_3$ | CF$_3$ | H | H | C(O)CH$_2$SEt |
| 3-CF$_2$CF$_3$ | CF$_3$ | H | H | C(O)CH$_2$S(O)Et |
| 3-CF$_2$CF$_3$ | CF$_3$ | H | H | C(O)CH$_2$SO$_2$Et |
| 3-OCF$_3$ | CF$_3$ | H | H | C(O)Pr-c |
| 3-OCF$_3$ | CF$_3$ | H | H | C(O)CH$_2$Pr-c |
| 3-OCF$_3$ | CF$_3$ | H | H | C(O)CH$_2$CF$_3$ |
| 3-OCF$_3$ | CF$_3$ | CH$_3$ | H | C(O)(E4-2a) |
| 3-OCF$_3$ | CF$_3$ | H | H | C(O)CH$_2$SCH$_3$ |
| 3-OCF$_3$ | CF$_3$ | H | H | C(O)CH$_2$S(O)CH$_3$ |
| 3-OCF$_3$ | CF$_3$ | H | H | C(O)CH$_2$SO$_2$CH$_3$ |
| 3-OCF$_3$ | CF$_3$ | H | H | C(O)CH$_2$SEt |
| 3-OCF$_3$ | CF$_3$ | H | H | C(O)CH$_2$S(O)Et |
| 3-OCF$_3$ | CF$_3$ | H | H | C(O)CH$_2$SO$_2$Et |
| 3-SCF$_3$ | CF$_3$ | H | H | C(O)Pr-c |
| 3-SCF$_3$ | CF$_3$ | H | H | C(O)CH$_2$Pr-c |
| 3-SCF$_3$ | CF$_3$ | H | H | C(O)CH$_2$CF$_3$ |
| 3-SCF$_3$ | CF$_3$ | CH$_3$ | H | C(O)(E4-2a) |
| 3-SCF$_3$ | CF$_3$ | H | H | C(O)CH$_2$SCH$_3$ |
| 3-SCF$_3$ | CF$_3$ | H | H | C(O)CH$_2$S(O)CH$_3$ |
| 3-SCF$_3$ | CF$_3$ | H | H | C(O)CH$_2$SO$_2$CH$_3$ |
| 3-SCF$_3$ | CF$_3$ | H | H | C(O)CH$_2$SEt |

TABLE 5-continued

| $(X)_m$ | $R^3$ | $R^{4a}$ | $R^{2a}$ | $R^{1a}$ |
|---|---|---|---|---|
| 3-SCF$_3$ | CF$_3$ | H | H | C(O)CH$_2$S(O)Et |
| 3-SCF$_3$ | CF$_3$ | H | H | C(O)CH$_2$SO$_2$Et |
| 3-SF$_5$ | CF$_3$ | H | H | C(O)Pr-c |
| 3-SF$_5$ | CF$_3$ | H | H | C(O)CH$_2$Pr-c |
| 3-SF$_5$ | CF$_3$ | H | H | C(O)CH$_2$CF$_3$ |
| 3-SF$_5$ | CF$_3$ | CH$_3$ | H | C(O)(E4-2a) |
| 3-SF$_5$ | CF$_3$ | H | H | C(O)CH$_2$SCH$_3$ |
| 3-SF$_5$ | CF$_3$ | H | H | C(O)CH$_2$S(O)CH$_3$ |
| 3-SF$_5$ | CF$_3$ | H | H | C(O)CH$_2$SO$_2$CH$_3$ |
| 3-SF$_5$ | CF$_3$ | H | H | C(O)CH$_2$SEt |
| 3-SF$_5$ | CF$_3$ | H | H | C(O)CH$_2$S(O)Et |
| 3-SF$_5$ | CF$_3$ | H | H | C(O)CH$_2$SO$_2$Et |
| 3-Cl-4-F | CF$_3$ | H | H | C(O)Et |
| 3-Cl-4-F | CF$_3$ | H | H | C(O)Pr-n |
| 3-Cl-4-F | CF$_3$ | H | H | C(O)Pr-i |
| 3-Cl-4-F | CF$_3$ | H | H | C(O)Pr-c |
| 3-Cl-4-F | CF$_3$ | CH$_3$ | H | C(O)Pr-c |
| 3-Cl-4-F | CF$_3$ | H | H | C(O)Bu-i |
| 3-Cl-4-F | CF$_3$ | H | H | C(O)CH$_2$Pr-c |
| 3-Cl-4-F | CF$_3$ | CH$_3$ | H | C(O)CH$_2$Pr-c |
| 3-Cl-4-F | CF$_3$ | H | H | C(O)CH$_2$CF$_3$ |
| 3-Cl-4-F | CF$_3$ | CH$_3$ | H | C(O)CH$_2$CF$_3$ |
| 3-Cl-4-F | CF$_3$ | CH$_3$ | H | C(O)(E4-2a) |
| 3-Cl-4-F | CF$_3$ | H | H | C(O)CH$_2$SCH$_3$ |
| 3-Cl-4-F | CF$_3$ | H | H | C(O)CH$_2$S(O)CH$_3$ |
| 3-Cl-4-F | CF$_3$ | H | H | C(O)CH$_2$SO$_2$CH$_3$ |
| 3-Cl-4-F | CF$_3$ | H | H | C(O)CH$_2$SEt |
| 3-Cl-4-F | CF$_3$ | H | H | C(O)CH$_2$S(O)Et |
| 3-Cl-4-F | CF$_3$ | H | H | C(O)CH$_2$SO$_2$Et |
| 3-Cl-4-F | CF$_3$ | H | H | C(O)NHEt |
| 3-Cl-4-F | CF$_3$ | H | H | C(O)NHPr-c |
| 3-Cl-4-F | CF$_3$ | CH$_3$ | H | C(O)NHPr-c |
| 3-F-5-Cl | CF$_3$ | H | H | C(O)Et |
| 3-F-5-Cl | CF$_3$ | H | H | C(O)Pr-n |
| 3-F-5-Cl | CF$_3$ | H | H | C(O)Pr-i |
| 3-F-5-Cl | CF$_3$ | H | H | C(O)Pr-c |
| 3-F-5-Cl | CF$_3$ | CH$_3$ | H | C(O)Pr-c |
| 3-F-5-Cl | CF$_3$ | H | H | C(O)Bu-i |
| 3-F-5-Cl | CF$_3$ | H | H | C(O)CH$_2$Pr-c |
| 3-F-5-Cl | CF$_3$ | CH$_3$ | H | C(O)CH$_2$Pr-c |
| 3-F-5-Cl | CF$_3$ | H | H | C(O)CH$_2$CF$_3$ |
| 3-F-5-Cl | CF$_3$ | CH$_3$ | H | C(O)CH$_2$CF$_3$ |
| 3-F-5-Cl | CF$_3$ | CH$_3$ | H | C(O)(E4-2a) |
| 3-F-5-Cl | CF$_3$ | H | H | C(O)CH$_2$SCH$_3$ |
| 3-F-5-Cl | CF$_3$ | H | H | C(O)CH$_2$S(O)CH$_3$ |
| 3-F-5-Cl | CF$_3$ | H | H | C(O)CH$_2$SO$_2$CH$_3$ |
| 3-F-5-Cl | CF$_3$ | H | H | C(O)CH$_2$SEt |
| 3-F-5-Cl | CF$_3$ | H | H | C(O)CH$_2$S(O)Et |
| 3-F-5-Cl | CF$_3$ | H | H | C(O)CH$_2$SO$_2$Et |
| 3-F-5-Cl | CF$_3$ | H | H | C(O)NHEt |
| 3-F-5-Cl | CF$_3$ | H | H | C(O)NHPr-c |
| 3-F-5-Cl | CF$_3$ | CH$_3$ | H | C(O)NHPr-c |
| 3,4-Cl$_2$ | CF$_3$ | H | H | C(O)Et |
| 3,4-Cl$_2$ | CF$_3$ | H | H | C(O)Pr-n |
| 3,4-Cl$_2$ | CF$_3$ | H | H | C(O)Pr-i |
| 3,4-Cl$_2$ | CF$_3$ | H | H | C(O)Pr-c |
| 3,4-Cl$_2$ | CF$_3$ | CH$_3$ | H | C(O)Pr-c |
| 3,4-Cl$_2$ | CF$_3$ | H | H | C(O)Bu-i |
| 3,4-Cl$_2$ | CF$_3$ | H | H | C(O)CH$_2$Pr-c |
| 3,4-Cl$_2$ | CF$_3$ | CH$_3$ | H | C(O)CH$_2$Pr-c |
| 3,4-Cl$_2$ | CF$_3$ | H | H | C(O)CH$_2$CF$_3$ |
| 3,4-Cl$_2$ | CF$_3$ | CH$_3$ | H | C(O)CH$_2$CF$_3$ |
| 3,4-Cl$_2$ | CF$_3$ | CH$_3$ | H | C(O)(E4-2a) |
| 3,4-Cl$_2$ | CF$_3$ | H | H | C(O)CH$_2$SCH$_3$ |
| 3,4-Cl$_2$ | CF$_3$ | H | H | C(O)CH$_2$S(O)CH$_3$ |
| 3,4-Cl$_2$ | CF$_3$ | H | H | C(O)CH$_2$SO$_2$CH$_3$ |
| 3,4-Cl$_2$ | CF$_3$ | H | H | C(O)CH$_2$SEt |
| 3,4-Cl$_2$ | CF$_3$ | H | H | C(O)CH$_2$S(O)Et |
| 3,4-Cl$_2$ | CF$_3$ | H | H | C(O)CH$_2$SO$_2$Et |
| 3,4-Cl$_2$ | CF$_3$ | H | H | C(O)NHEt |
| 3,4-Cl$_2$ | CF$_3$ | H | H | C(O)NHPr-c |
| 3,4-Cl$_2$ | CF$_3$ | CH$_3$ | H | C(O)NHPr-c |
| 3,5-Cl$_2$ | CF$_3$ | H | H | C(O)CH$_3$ |
| 3,5-Cl$_2$ | CF$_3$ | CH$_3$ | H | C(O)Et |
| 3,5-Cl$_2$ | CF$_3$ | H | Et | C(O)Et |
| 3,5-Cl$_2$ | CF$_3$ | H | CH$_2$C≡CH | C(O)Et |
| 3,5-Cl$_2$ | CF$_3$ | H | H | C(O)Pr-n |

TABLE 5-continued

| (X)$_m$ | R$^3$ | R$^{4a}$ | R$^{2a}$ | R$^{1a}$ |
|---|---|---|---|---|
| 3,5-Cl$_2$ | CF$_3$ | CH$_3$ | H | C(O)Pr-n |
| 3,5-Cl$_2$ | CF$_3$ | H | Et | C(O)Pr-n |
| 3,5-Cl$_2$ | CF$_3$ | H | H | C(O)Pr-i |
| 3,5-Cl$_2$ | CF$_3$ | CH$_3$ | H | C(O)Pr-i |
| 3,5-Cl$_2$ | CF$_3$ | H | H | C(O)Pr-c |
| 3,5-Cl$_2$ | CF$_3$ | CH$_3$ | H | C(O)Pr-c |
| 3,5-Cl$_2$ | CF$_3$ | H | Et | C(O)Pr-c |
| 3,5-Cl$_2$ | CF$_3$ | CH$_3$ | Et | C(O)Pr-c |
| 3,5-Cl$_2$ | CF$_3$ | H | CH$_2$Pr-c | C(O)Pr-c |
| 3,5-Cl$_2$ | CF$_3$ | H | CH$_2$OCH$_3$ | C(O)Pr-c |
| 3,5-Cl$_2$ | CF$_3$ | CH$_3$ | CH$_2$CN | C(O)Pr-c |
| 3,5-Cl$_2$ | CF$_3$ | H | CH$_2$C≡CH | C(O)Pr-c |
| 3,5-Cl$_2$ | CF$_3$ | CH$_3$ | CH$_2$C≡CH | C(O)Pr-c |
| 3,5-Cl$_2$ | CF$_3$ | H | H | C(O)Bu-i |
| 3,5-Cl$_2$ | CF$_3$ | CH$_3$ | H | C(O)Bu-i |
| 3,5-Cl$_2$ | CF$_3$ | H | H | C(O)CH$_2$Pr-c |
| 3,5-Cl$_2$ | CF$_3$ | CH$_3$ | H | C(O)CH$_2$Pr-c |
| 3,5-Cl$_2$ | CF$_3$ | CN | H | C(O)CH$_2$Pr-c |
| 3,5-Cl$_2$ | CF$_3$ | H | Et | C(O)CH$_2$Pr-c |
| 3,5-Cl$_2$ | CF$_3$ | H | H | C(O)CH$_2$CF$_3$ |
| 3,5-Cl$_2$ | CF$_3$ | CH$_3$ | H | C(O)CH$_2$CF$_3$ |
| 3,5-Cl$_2$ | CF$_3$ | H | H | C(O)(E4-2a) |
| 3,5-Cl$_2$ | CF$_3$ | CH$_3$ | H | C(O)(E4-2a) |
| 3,5-Cl$_2$ | CF$_3$ | H | H | C(O)CH$_2$SCH$_3$ |
| 3,5-Cl$_2$ | CF$_3$ | H | H | C(O)CH$_2$S(O)CH$_3$ |
| 3,5-Cl$_2$ | CF$_3$ | H | H | C(O)CH$_2$SO$_2$CH$_3$ |
| 3,5-Cl$_2$ | CF$_3$ | H | H | C(O)CH$_2$SEt |
| 3,5-Cl$_2$ | CF$_3$ | H | Et | C(O)CH$_2$SEt |
| 3,5-Cl$_2$ | CF$_3$ | H | H | C(O)CH$_2$S(O)Et |
| 3,5-Cl$_2$ | CF$_3$ | H | H | C(O)CH$_2$SO$_2$Et |
| 3,5-Cl$_2$ | CF$_3$ | H | CH$_3$ | C(O)CH$_2$SO$_2$Et |
| 3,5-Cl$_2$ | CF$_3$ | H | H | C(O)NHEt |
| 3,5-Cl$_2$ | CF$_3$ | CH$_3$ | H | C(O)NHEt |
| 3,5-Cl$_2$ | CF$_3$ | H | H | C(O)NHPr-c |
| 3,5-Cl$_2$ | CF$_3$ | CH$_3$ | H | C(O)NHPr-c |
| 3,5-Cl$_2$ | CF$_3$ | CH$_3$ | H | C(O)NHCH$_2$C≡CH |
| 3,5-Cl$_2$ | CF$_2$Cl | H | H | C(O)Pr-c |
| 3,5-Cl$_2$ | CF$_2$Cl | H | H | C(O)CH$_2$Pr-c |
| 3,5-Cl$_2$ | CF$_2$Cl | H | H | C(O)CH$_2$CF$_3$ |
| 3,5-Cl$_2$ | CF$_2$Cl | CH$_3$ | H | C(O)(E4-2a) |
| 3,5-Cl$_2$ | CF$_2$Cl | H | H | C(O)CH$_2$SCH$_3$ |
| 3,5-Cl$_2$ | CF$_2$Cl | H | H | C(O)CH$_2$S(O)CH$_3$ |
| 3,5-Cl$_2$ | CF$_2$Cl | H | H | C(O)CH$_2$SO$_2$CH$_3$ |
| 3,5-Cl$_2$ | CF$_2$Cl | H | H | C(O)CH$_2$SEt |
| 3,5-Cl$_2$ | CF$_2$Cl | H | H | C(O)CH$_2$S(O)Et |
| 3,5-Cl$_2$ | CF$_2$Cl | H | H | C(O)CH$_2$SO$_2$Et |
| 3-Br-4-F | CF$_3$ | H | H | C(O)Et |
| 3-Br-4-F | CF$_3$ | H | H | C(O)Pr-n |
| 3-Br-4-F | CF$_3$ | H | H | C(O)Pr-i |
| 3-Br-4-F | CF$_3$ | H | H | C(O)Pr-c |
| 3-Br-4-F | CF$_3$ | CH$_3$ | H | C(O)Pr-c |
| 3-Br-4-F | CF$_3$ | H | H | C(O)Bu-i |
| 3-Br-4-F | CF$_3$ | H | H | C(O)CH$_2$Pr-c |
| 3-Br-4-F | CF$_3$ | CH$_3$ | H | C(O)CH$_2$Pr-c |
| 3-Br-4-F | CF$_3$ | H | H | C(O)CH$_2$CF$_3$ |
| 3-Br-4-F | CF$_3$ | CH$_3$ | H | C(O)CH$_2$CF$_3$ |
| 3-Br-4-F | CF$_3$ | CH$_3$ | H | C(O)(E4-2a) |
| 3-Br-4-F | CF$_3$ | H | H | C(O)CH$_2$SCH$_3$ |
| 3-Br-4-F | CF$_3$ | H | H | C(O)CH$_2$S(O)CH$_3$ |
| 3-Br-4-F | CF$_3$ | H | H | C(O)CH$_2$SO$_2$CH$_3$ |
| 3-Br-4-F | CF$_3$ | H | H | C(O)CH$_2$SEt |
| 3-Br-4-F | CF$_3$ | H | H | C(O)CH$_2$S(O)Et |
| 3-Br-4-F | CF$_3$ | H | H | C(O)CH$_2$SO$_2$Et |
| 3-Br-4-F | CF$_3$ | H | H | C(O)NHEt |
| 3-Br-4-F | CF$_3$ | H | H | C(O)NHPr-c |
| 3-Br-4-F | CF$_3$ | CH$_3$ | H | C(O)NHPr-c |
| 3-F-5-Br | CF$_3$ | H | H | C(O)Et |
| 3-F-5-Br | CF$_3$ | H | H | C(O)Pr-n |
| 3-F-5-Br | CF$_3$ | H | H | C(O)Pr-i |
| 3-F-5-Br | CF$_3$ | H | H | C(O)Pr-c |
| 3-F-5-Br | CF$_3$ | CH$_3$ | H | C(O)Pr-c |
| 3-F-5-Br | CF$_3$ | H | H | C(O)Bu-i |
| 3-F-5-Br | CF$_3$ | H | H | C(O)CH$_2$Pr-c |
| 3-F-5-Br | CF$_3$ | CH$_3$ | H | C(O)CH$_2$Pr-c |
| 3-F-5-Br | CF$_3$ | H | H | C(O)CH$_2$CF$_3$ |
| 3-F-5-Br | CF$_3$ | CH$_3$ | H | C(O)CH$_2$CF$_3$ |
| 3-F-5-Br | CF$_3$ | CH$_3$ | H | C(O)(E4-2a) |
| 3-F-5-Br | CF$_3$ | H | H | C(O)CH$_2$SCH$_3$ |

TABLE 5-continued

| (X)$_m$ | R$^3$ | R$^{4a}$ | R$^{2a}$ | R$^{1a}$ |
|---|---|---|---|---|
| 3-F-5-Br | CF$_3$ | H | H | C(O)CH$_2$S(O)CH$_3$ |
| 3-F-5-Br | CF$_3$ | H | H | C(O)CH$_2$SO$_2$CH$_3$ |
| 3-F-5-Br | CF$_3$ | H | H | C(O)CH$_2$SEt |
| 3-F-5-Br | CF$_3$ | H | H | C(O)CH$_2$S(O)Et |
| 3-F-5-Br | CF$_3$ | H | H | C(O)CH$_2$SO$_2$Et |
| 3-F-5-Br | CF$_3$ | H | H | C(O)NHEt |
| 3-F-5-Br | CF$_3$ | H | H | C(O)NHPr-c |
| 3-F-5-Br | CF$_3$ | CH$_3$ | H | C(O)NHPr-c |
| 3-Br-4-Cl | CF$_3$ | H | H | C(O)Pr-c |
| 3-Br-4-Cl | CF$_3$ | H | H | C(O)CH$_2$Pr-c |
| 3-Br-4-Cl | CF$_3$ | H | H | C(O)CH$_2$CF$_3$ |
| 3-Br-4-Cl | CF$_3$ | CH$_3$ | H | C(O)(E4-2a) |
| 3-Br-4-Cl | CF$_3$ | H | H | C(O)CH$_2$SCH$_3$ |
| 3-Br-4-Cl | CF$_3$ | H | H | C(O)CH$_2$S(O)CH$_3$ |
| 3-Br-4-Cl | CF$_3$ | H | H | C(O)CH$_2$SO$_2$CH$_3$ |
| 3-Br-4-Cl | CF$_3$ | H | H | C(O)CH$_2$SEt |
| 3-Br-4-Cl | CF$_3$ | H | H | C(O)CH$_2$S(O)Et |
| 3-Br-4-Cl | CF$_3$ | H | H | C(O)CH$_2$SO$_2$Et |
| 3-Cl-4-Br | CF$_3$ | H | H | C(O)Pr-c |
| 3-Cl-4-Br | CF$_3$ | H | H | C(O)CH$_2$Pr-c |
| 3-Cl-4-Br | CF$_3$ | H | H | C(O)CH$_2$CF$_3$ |
| 3-Cl-4-Br | CF$_3$ | CH$_3$ | H | C(O)(E4-2a) |
| 3-Cl-4-Br | CF$_3$ | H | H | C(O)CH$_2$SCH$_3$ |
| 3-Cl-4-Br | CF$_3$ | H | H | C(O)CH$_2$S(O)CH$_3$ |
| 3-Cl-4-Br | CF$_3$ | H | H | C(O)CH$_2$SO$_2$CH$_3$ |
| 3-Cl-4-Br | CF$_3$ | H | H | C(O)CH$_2$SEt |
| 3-Cl-4-Br | CF$_3$ | H | H | C(O)CH$_2$S(O)Et |
| 3-Cl-4-Br | CF$_3$ | H | H | C(O)CH$_2$SO$_2$Et |
| 3-Cl-5-Br | CF$_3$ | H | H | C(O)CH$_3$ |
| 3-Cl-5-Br | CF$_3$ | H | H | C(O)Et |
| 3-Cl-5-Br | CF$_3$ | CH$_3$ | H | C(O)Et |
| 3-Cl-5-Br | CF$_3$ | H | Et | C(O)Et |
| 3-Cl-5-Br | CF$_3$ | H | CH$_2$C≡CH | C(O)Et |
| 3-Cl-5-Br | CF$_3$ | H | H | C(O)Pr-n |
| 3-Cl-5-Br | CF$_3$ | CH$_3$ | H | C(O)Pr-n |
| 3-Cl-5-Br | CF$_3$ | H | Et | C(O)Pr-n |
| 3-Cl-5-Br | CF$_3$ | H | H | C(O)Pr-i |
| 3-Cl-5-Br | CF$_3$ | CH$_3$ | H | C(O)Pr-i |
| 3-Cl-5-Br | CF$_3$ | H | H | C(O)Pr-c |
| 3-Cl-5-Br | CF$_3$ | CH$_3$ | H | C(O)Pr-c |
| 3-Cl-5-Br | CF$_3$ | H | Et | C(O)Pr-c |
| 3-Cl-5-Br | CF$_3$ | CH$_3$ | Et | C(O)Pr-c |
| 3-Cl-5-Br | CF$_3$ | H | CH$_2$Pr-c | C(O)Pr-c |
| 3-Cl-5-Br | CF$_3$ | H | CH$_2$OCH$_3$ | C(O)Pr-c |
| 3-Cl-5-Br | CF$_3$ | CH$_3$ | CH$_2$CN | C(O)Pr-c |
| 3-Cl-5-Br | CF$_3$ | H | CH$_2$C≡CH | C(O)Pr-c |
| 3-Cl-5-Br | CF$_3$ | CH$_3$ | CH$_2$C≡CH | C(O)Pr-c |
| 3-Cl-5-Br | CF$_3$ | H | H | C(O)Bu-i |
| 3-Cl-5-Br | CF$_3$ | CH$_3$ | H | C(O)Bu-i |
| 3-Cl-5-Br | CF$_3$ | H | H | C(O)CH$_2$Pr-c |
| 3-Cl-5-Br | CF$_3$ | CH$_3$ | H | C(O)CH$_2$Pr-c |
| 3-Cl-5-Br | CF$_3$ | CN | H | C(O)CH$_2$Pr-c |
| 3-Cl-5-Br | CF$_3$ | H | Et | C(O)CH$_2$Pr-c |
| 3-Cl-5-Br | CF$_3$ | H | H | C(O)CH$_2$CF$_3$ |
| 3-Cl-5-Br | CF$_3$ | CH$_3$ | H | C(O)CH$_2$CF$_3$ |
| 3-Cl-5-Br | CF$_3$ | H | H | C(O)(E4-2a) |
| 3-Cl-5-Br | CF$_3$ | CH$_3$ | H | C(O)(E4-2a) |
| 3-Cl-5-Br | CF$_3$ | H | H | C(O)CH$_2$SCH$_3$ |
| 3-Cl-5-Br | CF$_3$ | H | H | C(O)CH$_2$S(O)CH$_3$ |
| 3-Cl-5-Br | CF$_3$ | H | H | C(O)CH$_2$SO$_2$CH$_3$ |
| 3-Cl-5-Br | CF$_3$ | H | H | C(O)CH$_2$SEt |
| 3-Cl-5-Br | CF$_3$ | H | Et | C(O)CH$_2$SEt |
| 3-Cl-5-Br | CF$_3$ | H | H | C(O)CH$_2$S(O)Et |
| 3-Cl-5-Br | CF$_3$ | H | H | C(O)CH$_2$SO$_2$Et |
| 3-Cl-5-Br | CF$_3$ | H | CH$_3$ | C(O)CH$_2$SO$_2$Et |
| 3-Cl-5-Br | CF$_3$ | H | H | C(O)NHEt |
| 3-Cl-5-Br | CF$_3$ | CH$_3$ | H | C(O)NHEt |
| 3-Cl-5-Br | CF$_3$ | H | H | C(O)NHPr-c |
| 3-Cl-5-Br | CF$_3$ | CH$_3$ | H | C(O)NHPr-c |
| 3-Cl-5-Br | CF$_3$ | CH$_3$ | H | C(O)NHCH$_2$C≡CH |
| 3-Cl-5-Br | CF$_2$Cl | H | H | C(O)Pr-c |
| 3-Cl-5-Br | CF$_2$Cl | H | H | C(O)CH$_2$Pr-c |
| 3-Cl-5-Br | CF$_2$Cl | H | H | C(O)CH$_2$CF$_3$ |
| 3-Cl-5-Br | CF$_2$Cl | CH$_3$ | H | C(O)(E4-2a) |
| 3-Cl-5-Br | CF$_2$Cl | H | H | C(O)CH$_2$SCH$_3$ |
| 3-Cl-5-Br | CF$_2$Cl | H | H | C(O)CH$_2$S(O)CH$_3$ |
| 3-Cl-5-Br | CF$_2$Cl | H | H | C(O)CH$_2$SO$_2$CH$_3$ |
| 3-Cl-5-Br | CF$_2$Cl | H | H | C(O)CH$_2$SEt |

TABLE 5-continued

| (X)$_m$ | R$^3$ | R$^{4a}$ | R$^{2a}$ | R$^{1a}$ |
|---|---|---|---|---|
| 3-Cl-5-Br | CF$_2$Cl | H | H | C(O)CH$_2$S(O)Et |
| 3-Cl-5-Br | CF$_2$Cl | H | H | C(O)CH$_2$SO$_2$Et |
| 3,4-Br$_2$ | CF$_3$ | H | H | C(O)Pr-c |
| 3,4-Br$_2$ | CF$_3$ | H | H | C(O)CH$_2$Pr-c |
| 3,4-Br$_2$ | CF$_3$ | H | H | C(O)CH$_2$CF$_3$ |
| 3,4-Br$_2$ | CF$_3$ | CH$_3$ | H | C(O)(E4-2a) |
| 3,4-Br$_2$ | CF$_3$ | H | H | C(O)CH$_2$SCH$_3$ |
| 3,4-Br$_2$ | CF$_3$ | H | H | C(O)CH$_2$S(O)CH$_3$ |
| 3,4-Br$_2$ | CF$_3$ | H | H | C(O)CH$_2$SO$_2$CH$_3$ |
| 3,4-Br$_2$ | CF$_3$ | H | H | C(O)CH$_2$SEt |
| 3,4-Br$_2$ | CF$_3$ | H | H | C(O)CH$_2$S(O)Et |
| 3,4-Br$_2$ | CF$_3$ | H | H | C(O)CH$_2$SO$_2$Et |
| 3,5-Br$_2$ | CF$_3$ | H | H | C(O)CH$_3$ |
| 3,5-Br$_2$ | CF$_3$ | H | H | C(O)Et |
| 3,5-Br$_2$ | CF$_3$ | CH$_3$ | H | C(O)Et |
| 3,5-Br$_2$ | CF$_3$ | H | Et | C(O)Et |
| 3,5-Br$_2$ | CF$_3$ | H | CH$_2$C≡CH | C(O)Et |
| 3,5-Br$_2$ | CF$_3$ | H | H | C(O)Pr-n |
| 3,5-Br$_2$ | CF$_3$ | CH$_3$ | H | C(O)Pr-n |
| 3,5-Br$_2$ | CF$_3$ | H | Et | C(O)Pr-n |
| 3,5-Br$_2$ | CF$_3$ | H | H | C(O)Pr-i |
| 3,5-Br$_2$ | CF$_3$ | CH$_3$ | H | C(O)Pr-i |
| 3,5-Br$_2$ | CF$_3$ | H | H | C(O)Pr-c |
| 3,5-Br$_2$ | CF$_3$ | CH$_3$ | H | C(O)Pr-c |
| 3,5-Br$_2$ | CF$_3$ | H | Et | C(O)Pr-c |
| 3,5-Br$_2$ | CF$_3$ | CH$_3$ | Et | C(O)Pr-c |
| 3,5-Br$_2$ | CF$_3$ | H | CH$_2$Pr-c | C(O)Pr-c |
| 3,5-Br$_2$ | CF$_3$ | H | CH$_2$OCH$_3$ | C(O)Pr-c |
| 3,5-Br$_2$ | CF$_3$ | CH$_3$ | CH$_2$CN | C(O)Pr-c |
| 3,5-Br$_2$ | CF$_3$ | H | CH$_2$C≡H | C(O)Pr-c |
| 3,5-Br$_2$ | CF$_3$ | CH$_3$ | CH$_2$C≡CH | C(O)Pr-c |
| 3,5-Br$_2$ | CF$_3$ | H | H | C(O)Bu-i |
| 3,5-Br$_2$ | CF$_3$ | CH$_3$ | H | C(O)Bu-i |
| 3,5-Br$_2$ | CF$_3$ | H | H | C(O)CH$_2$Pr-c |
| 3,5-Br$_2$ | CF$_3$ | CH$_3$ | H | C(O)CH$_2$Pr-c |
| 3,5-Br$_2$ | CF$_3$ | CN | H | C(O)CH$_2$Pr-c |
| 3,5-Br$_2$ | CF$_3$ | H | Et | C(O)CH$_2$Pr-c |
| 3,5-Br$_2$ | CF$_3$ | H | H | C(O)CH$_2$CF$_3$ |
| 3,5-Br$_2$ | CF$_3$ | CH$_3$ | H | C(O)CH$_2$CF$_3$ |
| 3,5-Br$_2$ | CF$_3$ | H | H | C(O)(E4-2a) |
| 3,5-Br$_2$ | CF$_3$ | CH$_3$ | H | C(O)(E4-2a) |
| 3,5-Br$_2$ | CF$_3$ | H | H | C(O)CH$_2$SCH$_3$ |
| 3,5-Br$_2$ | CF$_3$ | H | H | C(O)CH$_2$S(O)CH$_3$ |
| 3,5-Br$_2$ | CF$_3$ | H | H | C(O)CH$_2$SO$_2$CH$_3$ |
| 3,5-Br$_2$ | CF$_3$ | H | H | C(O)CH$_2$SEt |
| 3,5-Br$_2$ | CF$_3$ | H | Et | C(O)CH$_2$SEt |
| 3,5-Br$_2$ | CF$_3$ | H | H | C(O)CH$_2$S(O)Et |
| 3,5-Br$_2$ | CF$_3$ | H | H | C(O)CH$_2$SO$_2$Et |
| 3,5-Br$_2$ | CF$_3$ | H | CH$_3$ | C(O)CH$_2$SO$_2$Et |
| 3,5-Br$_2$ | CF$_3$ | H | H | C(O)NHEt |
| 3,5-Br$_2$ | CF$_3$ | CH$_3$ | H | C(O)NHEt |
| 3,5-Br$_2$ | CF$_3$ | H | H | C(O)NHPr-c |
| 3,5-Br$_2$ | CF$_3$ | CH$_3$ | H | C(O)NHPr-c |
| 3,5-Br$_2$ | CF$_3$ | CH$_3$ | H | C(O)NHCH$_2$C≡CH |
| 3,5-Br$_2$ | CF$_2$Cl | H | H | C(O)Pr-c |
| 3,5-Br$_2$ | CF$_2$Cl | H | H | C(O)CH$_2$Pr-c |
| 3,5-Br$_2$ | CF$_2$Cl | H | H | C(O)CH$_2$CF$_3$ |
| 3,5-Br$_2$ | CF$_2$Cl | CH$_3$ | H | C(O)(E4-2a) |
| 3,5-Br$_2$ | CF$_2$Cl | H | H | C(O)CH$_2$SCH$_3$ |
| 3,5-Br$_2$ | CF$_2$Cl | H | H | C(O)CH$_2$S(O)CH$_3$ |
| 3,5-Br$_2$ | CF$_2$Cl | H | H | C(O)CH$_2$SO$_2$CH$_3$ |
| 3,5-Br$_2$ | CF$_2$Cl | H | H | C(O)CH$_2$SEt |
| 3,5-Br$_2$ | CF$_2$Cl | H | H | C(O)CH$_2$S(O)Et |
| 3,5-Br$_2$ | CF$_2$Cl | H | H | C(O)CH$_2$SO$_2$Et |
| 3-I-4-F | CF$_3$ | H | H | C(O)Pr-c |
| 3-I-4-F | CF$_3$ | H | H | C(O)CH$_2$Pr-c |
| 3-I-4-F | CF$_3$ | H | H | C(O)CH$_2$CF$_3$ |
| 3-I-4-F | CF$_3$ | CH$_3$ | H | C(O)(E4-2a) |
| 3-I-4-F | CF$_3$ | H | H | C(O)CH$_2$SCH$_3$ |
| 3-I-4-F | CF$_3$ | H | H | C(O)CH$_2$S(O)CH$_3$ |
| 3-I-4-F | CF$_3$ | H | H | C(O)CH$_2$SO$_2$CH$_3$ |
| 3-I-4-F | CF$_3$ | H | H | C(O)CH$_2$SEt |
| 3-I-4-F | CF$_3$ | H | H | C(O)CH$_2$S(O)Et |
| 3-I-4-F | CF$_3$ | H | H | C(O)CH$_2$SO$_2$Et |
| 3-F-5-I | CF$_3$ | H | H | C(O)Pr-c |
| 3-F-5-I | CF$_3$ | H | H | C(O)CH$_2$Pr-c |
| 3-F-5-I | CF$_3$ | H | H | C(O)CH$_2$CF$_3$ |
| 3-F-5-I | CF$_3$ | CH$_3$ | H | C(O)(E4-2a) |

TABLE 5-continued

| (X)$_m$ | R$^3$ | R$^{4a}$ | R$^{2a}$ | R$^{1a}$ |
|---|---|---|---|---|
| 3-F-5-I | CF$_3$ | H | H | C(O)CH$_2$SCH$_3$ |
| 3-F-5-I | CF$_3$ | H | H | C(O)CH$_2$S(O)CH$_3$ |
| 3-F-5-I | CF$_3$ | H | H | C(O)CH$_2$SO$_2$CH$_3$ |
| 3-F-5-I | CF$_3$ | H | H | C(O)CH$_2$SEt |
| 3-F-5-I | CF$_3$ | H | H | C(O)CH$_2$S(O)Et |
| 3-F-5-I | CF$_3$ | H | H | C(O)CH$_2$SO$_2$Et |
| 3-Cl-5-I | CF$_3$ | H | H | C(O)Et |
| 3-Cl-5-I | CF$_3$ | H | H | C(O)Pr-n |
| 3-Cl-5-I | CF$_3$ | H | H | C(O)Pr-i |
| 3-Cl-5-I | CF$_3$ | H | H | C(O)Pr-c |
| 3-Cl-5-I | CF$_3$ | CH$_3$ | H | C(O)Pr-c |
| 3-Cl-5-I | CF$_3$ | H | H | C(O)Bu-i |
| 3-Cl-5-I | CF$_3$ | H | H | C(O)CH$_2$Pr-c |
| 3-Cl-5-I | CF$_3$ | CH$_3$ | H | C(O)CH$_2$Pr-c |
| 3-Cl-5-I | CF$_3$ | H | H | C(O)CH$_2$CF$_3$ |
| 3-Cl-5-I | CF$_3$ | CH$_3$ | H | C(O)CH$_2$CF$_3$ |
| 3-Cl-5-I | CF$_3$ | CH$_3$ | H | C(O)(E4-2a) |
| 3-Cl-5-I | CF$_3$ | H | H | C(O)CH$_2$SCH$_3$ |
| 3-Cl-5-I | CF$_3$ | H | H | C(O)CH$_2$S(O)CH$_3$ |
| 3-Cl-5-I | CF$_3$ | H | H | C(O)CH$_2$SO$_2$CH$_3$ |
| 3-Cl-5-I | CF$_3$ | H | H | C(O)CH$_2$SEt |
| 3-Cl-5-I | CF$_3$ | H | H | C(O)CH$_2$S(O)Et |
| 3-Cl-5-I | CF$_3$ | H | H | C(O)CH$_2$SO$_2$Et |
| 3-Cl-5-I | CF$_3$ | H | H | C(O)NHEt |
| 3-Cl-5-I | CF$_3$ | H | H | C(O)NHPr-c |
| 3-Cl-5-I | CF$_3$ | CH$_3$ | H | C(O)NHPr-c |
| 3-CF$_3$-4-F | CF$_3$ | H | H | C(O)Et |
| 3-CF$_3$-4-F | CF$_3$ | H | H | C(O)Pr-n |
| 3-CF$_3$-4-F | CF$_3$ | H | H | C(O)Pr-i |
| 3-CF$_3$-4-F | CF$_3$ | H | H | C(O)Pr-c |
| 3-CF$_3$-4-F | CF$_3$ | CH$_3$ | H | C(O)Pr-c |
| 3-CF$_3$-4-F | CF$_3$ | H | H | C(O)Bu-i |
| 3-CF$_3$-4-F | CF$_3$ | H | H | C(O)CH$_2$Pr-c |
| 3-CF$_3$-4-F | CF$_3$ | CH$_3$ | H | C(O)CH$_2$Pr-c |
| 3-CF$_3$-4-F | CF$_3$ | H | H | C(O)CH$_2$CF$_3$ |
| 3-CF$_3$-4-F | CF$_3$ | CH$_3$ | H | C(O)CH$_2$CF$_3$ |
| 3-CF$_3$-4-F | CF$_3$ | CH$_3$ | H | C(O)(E4-2a) |
| 3-CF$_3$-4-F | CF$_3$ | H | H | C(O)CH$_2$SCH$_3$ |
| 3-CF$_3$-4-F | CF$_3$ | H | H | C(O)CH$_2$S(O)CH$_3$ |
| 3-CF$_3$-4-F | CF$_3$ | H | H | C(O)CH$_2$SO$_2$CH$_3$ |
| 3-CF$_3$-4-F | CF$_3$ | H | H | C(O)CH$_2$SEt |
| 3-CF$_3$-4-F | CF$_3$ | H | H | C(O)CH$_2$S(O)Et |
| 3-CF$_3$-4-F | CF$_3$ | H | H | C(O)CH$_2$SO$_2$Et |
| 3-CF$_3$-4-F | CF$_3$ | H | H | C(O)NHEt |
| 3-CF$_3$-4-F | CF$_3$ | H | H | C(O)NHPr-c |
| 3-CF$_3$-4-F | CF$_3$ | CH$_3$ | H | C(O)NHPr-c |
| 3-F-5-CF$_3$ | CF$_3$ | H | H | C(O)Et |
| 3-F-5-CF$_3$ | CF$_3$ | H | H | C(O)Pr-n |
| 3-F-5-CF$_3$ | CF$_3$ | H | H | C(O)Pr-i |
| 3-F-5-CF$_3$ | CF$_3$ | H | H | C(O)Pr-c |
| 3-F-5-CF$_3$ | CF$_3$ | CH$_3$ | H | C(O)Pr-c |
| 3-F-5-CF$_3$ | CF$_3$ | H | H | C(O)Bu-i |
| 3-F-5-CF$_3$ | CF$_3$ | H | H | C(O)CH$_2$Pr-c |
| 3-F-5-CF$_3$ | CF$_3$ | CH$_3$ | H | C(O)CH$_2$Pr-c |
| 3-F-5-CF$_3$ | CF$_3$ | H | H | C(O)CH$_2$CF$_3$ |
| 3-F-5-CF$_3$ | CF$_3$ | CH$_3$ | H | C(O)CH$_2$CF$_3$ |
| 3-F-5-CF$_3$ | CF$_3$ | CH$_3$ | H | C(O)(E4-2a) |
| 3-F-5-CF$_3$ | CF$_3$ | H | H | C(O)CH$_2$SCH$_3$ |
| 3-F-5-CF$_3$ | CF$_3$ | H | H | C(O)CH$_2$S(O)CH$_3$ |
| 3-F-5-CF$_3$ | CF$_3$ | H | H | C(O)CH$_2$SO$_2$CH$_3$ |
| 3-F-5-CF$_3$ | CF$_3$ | H | H | C(O)CH$_2$SEt |
| 3-F-5-CF$_3$ | CF$_3$ | H | H | C(O)CH$_2$S(O)Et |
| 3-F-5-CF$_3$ | CF$_3$ | H | H | C(O)CH$_2$SO$_2$Et |
| 3-F-5-CF$_3$ | CF$_3$ | H | H | C(O)NHEt |
| 3-F-5-CF$_3$ | CF$_3$ | H | H | C(O)NHPr-c |
| 3-F-5-CF$_3$ | CF$_3$ | CH$_3$ | H | C(O)NHPr-c |
| 3-CF$_3$-4-Cl | CF$_3$ | H | H | C(O)Et |
| 3-CF$_3$-4-Cl | CF$_3$ | H | H | C(O)Pr-n |
| 3-CF$_3$-4-Cl | CF$_3$ | H | H | C(O)Pr-i |
| 3-CF$_3$-4-Cl | CF$_3$ | H | H | C(O)Pr-c |
| 3-CF$_3$-4-Cl | CF$_3$ | CH$_3$ | H | C(O)Pr-c |
| 3-CF$_3$-4-Cl | CF$_3$ | H | H | C(O)Bu-i |
| 3-CF$_3$-4-Cl | CF$_3$ | H | H | C(O)CH$_2$Pr-c |
| 3-CF$_3$-4-Cl | CF$_3$ | CH$_3$ | H | C(O)CH$_2$Pr-c |
| 3-CF$_3$-4-Cl | CF$_3$ | H | H | C(O)CH$_2$CF$_3$ |
| 3-CF$_3$-4-Cl | CF$_3$ | CH$_3$ | H | C(O)CH$_2$CF$_3$ |
| 3-CF$_3$-4-Cl | CF$_3$ | CH$_3$ | H | C(O)(E4-2a) |
| 3-CF$_3$-4-Cl | CF$_3$ | H | H | C(O)CH$_2$SCH$_3$ |

TABLE 5-continued

| (X)$_m$ | R$^3$ | R$^{4a}$ | R$^{2a}$ | R$^{1a}$ |
|---|---|---|---|---|
| 3-CF$_3$-4-Cl | CF$_3$ | H | H | C(O)CH$_2$S(O)CH$_3$ |
| 3-CF$_3$-4-Cl | CF$_3$ | H | H | C(O)CH$_2$SO$_2$CH$_3$ |
| 3-CF$_3$-4-Cl | CF$_3$ | H | H | C(O)CH$_2$SEt |
| 3-CF$_3$-4-Cl | CF$_3$ | H | H | C(O)CH$_2$S(O)Et |
| 3-CF$_3$-4-Cl | CF$_3$ | H | H | C(O)CH$_2$SO$_2$Et |
| 3-CF$_3$-4-Cl | CF$_3$ | H | H | C(O)NHEt |
| 3-CF$_3$-4-Cl | CF$_3$ | H | H | C(O)NHPr-c |
| 3-CF$_3$-4-Cl | CF$_3$ | CH$_3$ | H | C(O)NHPr-c |
| 3-Cl-5-CF$_3$ | CF$_3$ | H | H | C(O)CH$_3$ |
| 3-Cl-5-CF$_3$ | CF$_3$ | H | H | C(O)Et |
| 3-Cl-5-CF$_3$ | CF$_3$ | CH$_3$ | H | C(O)Et |
| 3-Cl-5-CF$_3$ | CF$_3$ | H | Et | C(O)Et |
| 3-Cl-5-CF$_3$ | CF$_3$ | H | CH$_2$C≡CH | C(O)Et |
| 3-Cl-5-CF$_3$ | CF$_3$ | H | H | C(O)Pr-n |
| 3-Cl-5-CF$_3$ | CF$_3$ | CH$_3$ | H | C(O)Pr-n |
| 3-Cl-5-CF$_3$ | CF$_3$ | H | Et | C(O)Pr-n |
| 3-Cl-5-CF$_3$ | CF$_3$ | H | H | C(O)Pr-i |
| 3-Cl-5-CF$_3$ | CF$_3$ | CH$_3$ | H | C(O)Pr-i |
| 3-Cl-5-CF$_3$ | CF$_3$ | H | H | C(O)Pr-c |
| 3-Cl-5-CF$_3$ | CF$_3$ | CH$_3$ | H | C(O)Pr-c |
| 3-Cl-5-CF$_3$ | CF$_3$ | H | Et | C(O)Pr-c |
| 3-Cl-5-CF$_3$ | CF$_3$ | CH$_3$ | Et | C(O)Pr-c |
| 3-Cl-5-CF$_3$ | CF$_3$ | H | CH$_2$Pr-c | C(O)Pr-c |
| 3-Cl-5-CF$_3$ | CF$_3$ | H | CH$_2$OCH$_3$ | C(O)Pr-c |
| 3-Cl-5-CF$_3$ | CF$_3$ | CH$_3$ | CH$_2$CN | C(O)Pr-c |
| 3-Cl-5-CF$_3$ | CF$_3$ | H | CH$_2$C≡CH | C(O)Pr-c |
| 3-Cl-5-CF$_3$ | CF$_3$ | CH$_3$ | CH$_2$C≡CH | C(O)Pr-c |
| 3-Cl-5-CF$_3$ | CF$_3$ | H | H | C(O)Bu-i |
| 3-Cl-5-CF$_3$ | CF$_3$ | CH$_3$ | H | C(O)Bu-i |
| 3-Cl-5-CF$_3$ | CF$_3$ | H | H | C(O)CH$_2$Pr-c |
| 3-Cl-5-CF$_3$ | CF$_3$ | CH$_3$ | H | C(O)CH$_2$Pr-c |
| 3-Cl-5-CF$_3$ | CF$_3$ | CN | H | C(O)CH$_2$Pr-c |
| 3-Cl-5-CF$_3$ | CF$_3$ | H | Et | C(O)CH$_2$Pr-c |
| 3-Cl-5-CF$_3$ | CF$_3$ | H | H | C(O)CH$_2$CF$_3$ |
| 3-Cl-5-CF$_3$ | CF$_3$ | CH$_3$ | H | C(O)CH$_2$CF$_3$ |
| 3-Cl-5-CF$_3$ | CF$_3$ | H | H | C(O)(E4-2a) |
| 3-Cl-5-CF$_3$ | CF$_3$ | CH$_3$ | H | C(O)(E4-2a) |
| 3-Cl-5-CF$_3$ | CF$_3$ | H | H | C(O)CH$_2$SCH$_3$ |
| 3-Cl-5-CF$_3$ | CF$_3$ | H | H | C(O)CH$_2$S(O)CH$_3$ |
| 3-Cl-5-CF$_3$ | CF$_3$ | H | H | C(O)CH$_2$SO$_2$CH$_3$ |
| 3-Cl-5-CF$_3$ | CF$_3$ | H | H | C(O)CH$_2$SEt |
| 3-Cl-5-CF$_3$ | CF$_3$ | H | Et | C(O)CH$_2$SEt |
| 3-Cl-5-CF$_3$ | CF$_3$ | H | H | C(O)CH$_2$S(O)Et |
| 3-Cl-5-CF$_3$ | CF$_3$ | H | H | C(O)CH$_2$SO$_2$Et |
| 3-Cl-5-CF$_3$ | CF$_3$ | H | CH$_3$ | C(O)CH$_2$SO$_2$Et |
| 3-Cl-5-CF$_3$ | CF$_3$ | H | H | C(O)NHEt |
| 3-Cl-5-CF$_3$ | CF$_3$ | CH$_3$ | H | C(O)NHEt |
| 3-Cl-5-CF$_3$ | CF$_3$ | H | H | C(O)NHPr-c |
| 3-Cl-5-CF$_3$ | CF$_3$ | CH$_3$ | H | C(O)NHPr-c |
| 3-Cl-5-CF$_3$ | CF$_3$ | CH$_3$ | H | C(O)NHCH$_2$C≡CH |
| 3-Cl-5-CF$_3$ | CF$_2$Cl | H | H | C(O)Pr-c |
| 3-Cl-5-CF$_3$ | CF$_2$Cl | H | H | C(O)CH$_2$Pr-c |
| 3-Cl-5-CF$_3$ | CF$_2$Cl | H | H | C(O)CH$_2$CF$_3$ |
| 3-Cl-5-CF$_3$ | CF$_2$Cl | CH$_3$ | H | C(O)(E4-2a) |
| 3-Cl-5-CF$_3$ | CF$_2$Cl | H | H | C(O)CH$_2$SCH$_3$ |
| 3-Cl-5-CF$_3$ | CF$_2$Cl | H | H | C(O)CH$_2$S(O)CH$_3$ |
| 3-Cl-5-CF$_3$ | CF$_2$Cl | H | H | C(O)CH$_2$SO$_2$CH$_3$ |
| 3-Cl-5-CF$_3$ | CF$_2$Cl | H | H | C(O)CH$_2$SEt |
| 3-Cl-5-CF$_3$ | CF$_2$Cl | H | H | C(O)CH$_2$S(O)Et |
| 3-Cl-5-CF$_3$ | CF$_2$Cl | H | H | C(O)CH$_2$SO$_2$Et |
| 3-Br-5-CF$_3$ | CF$_3$ | H | H | C(O)CH$_3$ |
| 3-Br-5-CF$_3$ | CF$_3$ | H | H | C(O)Et |
| 3-Br-5-CF$_3$ | CF$_3$ | CH$_3$ | H | C(O)Et |
| 3-Br-5-CF$_3$ | CF$_3$ | H | Et | C(O)Et |
| 3-Br-5-CF$_3$ | CF$_3$ | H | CH$_2$C≡CH | C(O)Et |
| 3-Br-5-CF$_3$ | CF$_3$ | H | H | C(O)Pr-n |
| 3-Br-5-CF$_3$ | CF$_3$ | CH$_3$ | H | C(O)Pr-n |
| 3-Br-5-CF$_3$ | CF$_3$ | H | Et | C(O)Pr-n |
| 3-Br-5-CF$_3$ | CF$_3$ | H | H | C(O)Pr-i |
| 3-Br-5-CF$_3$ | CF$_3$ | CH$_3$ | H | C(O)Pr-i |
| 3-Br-5-CF$_3$ | CF$_3$ | H | H | C(O)Pr-c |
| 3-Br-5-CF$_3$ | CF$_3$ | CH$_3$ | H | C(O)Pr-c |
| 3-Br-5-CF$_3$ | CF$_3$ | H | Et | C(O)Pr-c |
| 3-Br-5-CF$_3$ | CF$_3$ | CH$_3$ | Et | C(O)Pr-c |
| 3-Br-5-CF$_3$ | CF$_3$ | H | CH$_2$Pr-c | C(O)Pr-c |
| 3-Br-5-CF$_3$ | CF$_3$ | H | CH$_2$OCH$_3$ | C(O)Pr-c |
| 3-Br-5-CF$_3$ | CF$_3$ | CH$_3$ | CH$_2$CN | C(O)Pr-c |
| 3-Br-5-CF$_3$ | CF$_3$ | H | CH$_2$C≡CH | C(O)Pr-c |

TABLE 5-continued

| (X)$_m$ | R$^3$ | R$^{4a}$ | R$^{2a}$ | R$^{1a}$ |
|---|---|---|---|---|
| 3-Br-5-CF$_3$ | CF$_3$ | CH$_3$ | CH$_2$C≡CH | C(O)Pr-c |
| 3-Br-5-CF$_3$ | CF$_3$ | H | H | C(O)Bu-i |
| 3-Br-5-CF$_3$ | CF$_3$ | CH$_3$ | H | C(O)Bu-i |
| 3-Br-5-CF$_3$ | CF$_3$ | H | H | C(O)CH$_2$Pr-c |
| 3-Br-5-CF$_3$ | CF$_3$ | CH$_3$ | H | C(O)CH$_2$Pr-c |
| 3-Br-5-CF$_3$ | CF$_3$ | CN | H | C(O)CH$_2$Pr-c |
| 3-Br-5-CF$_3$ | CF$_3$ | H | Et | C(O)CH$_2$Pr-c |
| 3-Br-5-CF$_3$ | CF$_3$ | H | H | C(O)CH$_2$CF$_3$ |
| 3-Br-5-CF$_3$ | CF$_3$ | CH$_3$ | H | C(O)CH$_2$CF$_3$ |
| 3-Br-5-CF$_3$ | CF$_3$ | H | H | C(O)(E4-2a) |
| 3-Br-5-CF$_3$ | CF$_3$ | CH$_3$ | H | C(O)(E4-2a) |
| 3-Br-5-CF$_3$ | CF$_3$ | H | H | C(O)CH$_2$SCH$_3$ |
| 3-Br-5-CF$_3$ | CF$_3$ | H | H | C(O)CH$_2$S(O)CH$_3$ |
| 3-Br-5-CF$_3$ | CF$_3$ | H | H | C(O)CH$_2$SO$_2$CH$_3$ |
| 3-Br-5-CF$_3$ | CF$_3$ | H | H | C(O)CH$_2$SEt |
| 3-Br-5-CF$_3$ | CF$_3$ | H | Et | C(O)CH$_2$SEt |
| 3-Br-5-CF$_3$ | CF$_3$ | H | H | C(O)CH$_2$S(O)Et |
| 3-Br-5-CF$_3$ | CF$_3$ | H | H | C(O)CH$_2$SO$_2$Et |
| 3-Br-5-CF$_3$ | CF$_3$ | H | CH$_3$ | C(O)CH$_2$SO$_2$Et |
| 3-Br-5-CF$_3$ | CF$_3$ | H | H | C(O)NHEt |
| 3-Br-5-CF$_3$ | CF$_3$ | CH$_3$ | H | C(O)NHEt |
| 3-Br-5-CF$_3$ | CF$_3$ | H | H | C(O)NHPr-c |
| 3-Br-5-CF$_3$ | CF$_3$ | CH$_3$ | H | C(O)NHPr-c |
| 3-Br-5-CF$_3$ | CF$_3$ | CH$_3$ | H | C(O)NHCH$_2$C≡CH |
| 3-Br-5-CF$_3$ | CF$_2$Cl | H | H | C(O)Pr-c |
| 3-Br-5-CF$_3$ | CF$_2$Cl | H | H | C(O)CH$_2$Pr-c |
| 3-Br-5-CF$_3$ | CF$_2$Cl | H | H | C(O)CH$_2$CF$_3$ |
| 3-Br-5-CF$_3$ | CF$_2$Cl | CH$_3$ | H | C(O)(E4-2a) |
| 3-Br-5-CF$_3$ | CF$_2$Cl | H | H | C(O)CH$_2$SCH$_3$ |
| 3-Br-5-CF$_3$ | CF$_2$Cl | H | H | C(O)CH$_2$S(O)CH$_3$ |
| 3-Br-5-CF$_3$ | CF$_2$Cl | H | H | C(O)CH$_2$SO$_2$CH$_3$ |
| 3-Br-5-CF$_3$ | CF$_2$Cl | H | H | C(O)CH$_2$SEt |
| 3-Br-5-CF$_3$ | CF$_2$Cl | H | H | C(O)CH$_2$S(O)Et |
| 3-Br-5-CF$_3$ | CF$_2$Cl | H | H | C(O)CH$_2$SO$_2$Et |
| 3,5-(CF$_3$)$_2$ | CF$_3$ | H | H | C(O)CH$_3$ |
| 3,5-(CF$_3$)$_2$ | CF$_3$ | H | H | C(O)Et |
| 3,5-(CF$_3$)$_2$ | CF$_3$ | CH$_3$ | H | C(O)Et |
| 3,5-(CF$_3$)$_2$ | CF$_3$ | CH$_3$(S) | H | C(O)Et |
| 3,5-(CF$_3$)$_2$ | CF$_3$ | CN | H | C(O)Et |
| 3,5-(CF$_3$)$_2$ | CF$_3$ | H | Et | C(O)Et |
| 3,5-(CF$_3$)$_2$ | CF$_3$ | H | CH$_2$CN | C(O)Et |
| 3,5-(CF$_3$)$_2$ | CF$_3$ | H | CH$_2$CH=CH$_2$ | C(O)Et |
| 3,5-(CF$_3$)$_2$ | CF$_3$ | H | CH$_2$C≡CH | C(O)Et |
| 3,5-(CF$_3$)$_2$ | CF$_3$ | H | H | C(O)Pr-n |
| 3,5-(CF$_3$)$_2$ | CF$_3$ | CH$_3$ | H | C(O)Pr-n |
| 3,5-(CF$_3$)$_2$ | CF$_3$ | CH$_3$(S) | H | C(O)Pr-n |
| 3,5-(CF$_3$)$_2$ | CF$_3$ | H | Et | C(O)Pr-n |
| 3,5-(CF$_3$)$_2$ | CF$_3$ | H | H | C(O)Pr-i |
| 3,5-(CF$_3$)$_2$ | CF$_3$ | CH$_3$ | H | C(O)Pr-i |
| 3,5-(CF$_3$)$_2$ | CF$_3$ | CH$_3$(S) | H | C(O)Pr-i |
| 3,5-(CF$_3$)$_2$ | CF$_3$ | CN | H | C(O)Pr-i |
| 3,5-(CF$_3$)$_2$ | CF$_3$ | H | H | C(O)Pr-c |
| 3,5-(CF$_3$)$_2$ | CF$_3$ | CH$_3$ | H | C(O)Pr-c |
| 3,5-(CF$_3$)$_2$ | CF$_3$ | CH$_3$(S) | H | C(O)Pr-c |
| 3,5-(CF$_3$)$_2$ | CF$_3$ | CN | H | C(O)Pr-c |
| 3,5-(CF$_3$)$_2$ | CF$_3$ | C(S)NH$_2$ | H | C(O)Pr-c |
| 3,5-(CF$_3$)$_2$ | CF$_3$ | H | Et | C(O)Pr-c |
| 3,5-(CF$_3$)$_2$ | CF$_3$ | CH$_3$ | Et | C(O)Pr-c |
| 3,5-(CF$_3$)$_2$ | CF$_3$ | CH$_3$(S) | Et | C(O)Pr-c |
| 3,5-(CF$_3$)$_2$ | CF$_3$ | H | CH$_2$Pr-c | C(O)Pr-c |
| 3,5-(CF$_3$)$_2$ | CF$_3$ | CH$_3$ | CH$_2$Pr-c | C(O)Pr-c |
| 3,5-(CF$_3$)$_2$ | CF$_3$ | H | CH$_2$OCH$_3$ | C(O)Pr-c |
| 3,5-(CF$_3$)$_2$ | CF$_3$ | CH$_3$ | CH$_2$CN | C(O)Pr-c |
| 3,5-(CF$_3$)$_2$ | CF$_3$ | CH$_3$(S) | CH$_2$CN | C(O)Pr-c |
| 3,5-(CF$_3$)$_2$ | CF$_3$ | H | CH$_2$C≡CH | C(O)Pr-c |
| 3,5-(CF$_3$)$_2$ | CF$_3$ | CH$_3$ | CH$_2$C≡CH | C(O)Pr-c |
| 3,5-(CF$_3$)$_2$ | CF$_3$ | CH$_3$(S) | CH$_2$C≡CH | C(O)Pr-c |
| 3,5-(CF$_3$)$_2$ | CF$_3$ | H | H | C(O)Bu-i |
| 3,5-(CF$_3$)$_2$ | CF$_3$ | CH$_3$ | H | C(O)Bu-i |
| 3,5-(CF$_3$)$_2$ | CF$_3$ | CH$_3$(S) | H | C(O)Bu-i |
| 3,5-(CF$_3$)$_2$ | CF$_3$ | H | H | C(O)CH$_2$Pr-c |
| 3,5-(CF$_3$)$_2$ | CF$_3$ | CH$_3$ | H | C(O)CH$_2$Pr-c |
| 3,5-(CF$_3$)$_2$ | CF$_3$ | CH$_3$(S) | H | C(O)CH$_2$Pr-c |
| 3,5-(CF$_3$)$_2$ | CF$_3$ | CN | H | C(O)CH$_2$Pr-c |
| 3,5-(CF$_3$)$_2$ | CF$_3$ | CN(S) | H | C(O)CH$_2$Pr-c |
| 3,5-(CF$_3$)$_2$ | CF$_3$ | H | CH$_3$ | C(O)CH$_2$Pr-c |
| 3,5-(CF$_3$)$_2$ | CF$_3$ | H | Et | C(O)CH$_2$Pr-c |
| 3,5-(CF$_3$)$_2$ | CF$_3$ | H | H | C(O)(T-1) |

TABLE 5-continued

| (X)$_m$ | R$^3$ | R$^{4a}$ | R$^{2a}$ | R$^{1a}$ |
|---|---|---|---|---|
| 3,5-(CF$_3$)$_2$ | CF$_3$ | H | H | C(O)Bu-c |
| 3,5-(CF$_3$)$_2$ | CF$_3$ | H | H | C(O)CF$_3$ |
| 3,5-(CF$_3$)$_2$ | CF$_3$ | H | H | C(O)CH$_2$CH$_2$Cl |
| 3,5-(CF$_3$)$_2$ | CF$_3$ | H | H | C(O)CH$_2$CF$_3$ |
| 3,5-(CF$_3$)$_2$ | CF$_3$ | CH$_3$ | H | C(O)CH$_2$CF$_3$ |
| 3,5-(CF$_3$)$_2$ | CF$_3$ | CH$_3$(S) | H | C(O)CH$_2$CF$_3$ |
| 3,5-(CF$_3$)$_2$ | CF$_3$ | CN | H | C(O)CH$_2$CF$_3$ |
| 3,5-(CF$_3$)$_2$ | CF$_3$ | H | H | C(O)CH$_2$CH$_2$CF$_3$ |
| 3,5-(CF$_3$)$_2$ | CF$_3$ | H | H | C(O)(E4-2a) |
| 3,5-(CF$_3$)$_2$ | CF$_3$ | CH$_3$ | H | C(O)(E4-2a) |
| 3,5-(CF$_3$)$_2$ | CF$_3$ | CH$_3$(S) | H | C(O)(E4-2a) |
| 3,5-(CF$_3$)$_2$ | CF$_3$ | H | CH$_3$ | C(O)(E4-2a) |
| 3,5-(CF$_3$)$_2$ | CF$_3$ | H | H | C(O)CH$_2$SCH$_3$ |
| 3,5-(CF$_3$)$_2$ | CF$_3$ | CH$_3$ | H | C(O)CH$_2$SCH$_3$ |
| 3,5-(CF$_3$)$_2$ | CF$_3$ | H | CH$_3$ | C(O)CH$_2$SCH$_3$ |
| 3,5-(CF$_3$)$_2$ | CF$_3$ | H | CH$_2$C≡CH | C(O)CH$_2$SCH$_3$ |
| 3,5-(CF$_3$)$_2$ | CF$_3$ | H | H | C(O)CH$_2$S(O)CH$_3$ |
| 3,5-(CF$_3$)$_2$ | CF$_3$ | CH$_3$ | H | C(O)CH$_2$S(O)CH$_3$ |
| 3,5-(CF$_3$)$_2$ | CF$_3$ | H | CH$_3$ | C(O)CH$_2$S(O)CH$_3$ |
| 3,5-(CF$_3$)$_2$ | CF$_3$ | H | CH$_2$C≡CH | C(O)CH$_2$S(O)CH$_3$ |
| 3,5-(CF$_3$)$_2$ | CF$_3$ | H | H | C(O)CH$_2$SO$_2$CH$_3$ |
| 3,5-(CF$_3$)$_2$ | CF$_3$ | CH$_3$ | H | C(O)CH$_2$SO$_2$CH$_3$ |
| 3,5-(CF$_3$)$_2$ | CF$_3$ | H | CH$_3$ | C(O)CH$_2$SO$_2$CH$_3$ |
| 3,5-(CF$_3$)$_2$ | CF$_3$ | H | Et | C(O)CH$_2$SO$_2$CH$_3$ |
| 3,5-(CF$_3$)$_2$ | CF$_3$ | H | CH$_2$C≡CH | C(O)CH$_2$SO$_2$CH$_3$ |
| 3,5-(CF$_3$)$_2$ | CF$_3$ | H | H | C(O)CH$_2$SEt |
| 3,5-(CF$_3$)$_2$ | CF$_3$ | CH$_3$ | H | C(O)CH$_2$SEt |
| 3,5-(CF$_3$)$_2$ | CF$_3$ | H | CH$_3$ | C(O)CH$_2$SEt |
| 3,5-(CF$_3$)$_2$ | CF$_3$ | H | Et | C(O)CH$_2$SEt |
| 3,5-(CF$_3$)$_2$ | CF$_3$ | H | H | C(O)CH$_2$S(O)Et |
| 3,5-(CF$_3$)$_2$ | CF$_3$ | CH$_3$ | H | C(O)CH$_2$S(O)Et |
| 3,5-(CF$_3$)$_2$ | CF$_3$ | H | H | C(O)CH$_2$SO$_2$Et |
| 3,5-(CF$_3$)$_2$ | CF$_3$ | CH$_3$ | H | C(O)CH$_2$SO$_2$Et |
| 3,5-(CF$_3$)$_2$ | CF$_3$ | H | CH$_3$ | C(O)CH$_2$SO$_2$Et |
| 3,5-(CF$_3$)$_2$ | CF$_3$ | H | Et | C(O)CH$_2$SO$_2$Et |
| 3,5-(CF$_3$)$_2$ | CF$_3$ | H | CH$_2$C≡CH | C(O)CH$_2$SO$_2$Et |
| 3,5-(CF$_3$)$_2$ | CF$_3$ | H | H | C(O)CH$_2$SCH$_2$CF$_3$ |
| 3,5-(CF$_3$)$_2$ | CF$_3$ | H | H | C(O)CH$_2$SCH$_2$CN |
| 3,5-(CF$_3$)$_2$ | CF$_3$ | H | H | C(O)CH(CH$_3$)SCH$_3$ |
| 3,5-(CF$_3$)$_2$ | CF$_3$ | H | H | C(O)CH(CH$_3$)S(O)CH$_3$ |
| 3,5-(CF$_3$)$_2$ | CF$_3$ | H | H | C(O)CH(CH$_3$)SO$_2$CH$_3$ |
| 3,5-(CF$_3$)$_2$ | CF$_3$ | H | H | C(O)CH(CH$_3$)SEt |
| 3,5-(CF$_3$)$_2$ | CF$_3$ | H | H | C(O)CH(CH$_3$)S(O)Et |
| 3,5-(CF$_3$)$_2$ | CF$_3$ | H | H | C(O)CH(CH$_3$)SO$_2$Et |
| 3,5-(CF$_3$)$_2$ | CF$_3$ | H | H | C(O)(E5-1a) |
| 3,5-(CF$_3$)$_2$ | CF$_3$ | H | H | C(O)(E5-1b) |
| 3,5-(CF$_3$)$_2$ | CF$_3$ | H | H | C(O)(E5-1c) |
| 3,5-(CF$_3$)$_2$ | CF$_3$ | H | H | C(O)(E5-2a) |
| 3,5-(CF$_3$)$_2$ | CF$_3$ | H | H | C(O)(E5-2b) |
| 3,5-(CF$_3$)$_2$ | CF$_3$ | H | H | C(O)(E5-2c) |
| 3,5-(CF$_3$)$_2$ | CF$_3$ | H | H | C(O)CF$_2$SCH$_3$ |
| 3,5-(CF$_3$)$_2$ | CF$_3$ | H | H | C(O)CF$_2$S(O)CH$_3$ |
| 3,5-(CF$_3$)$_2$ | CF$_3$ | H | H | C(O)CF$_2$SO$_2$CH$_3$ |
| 3,5-(CF$_3$)$_2$ | CF$_3$ | H | H | C(O)CH(SCH$_3$)$_2$ |
| 3,5-(CF$_3$)$_2$ | CF$_3$ | H | H | C(O)CH(SEt)S(O)Et |
| 3,5-(CF$_3$)$_2$ | CF$_3$ | H | H | C(O)CH[S(O)Et]$_2$ |
| 3,5-(CF$_3$)$_2$ | CF$_3$ | H | H | C(O)CH[S(O)Et]SO$_2$Et |
| 3,5-(CF$_3$)$_2$ | CF$_3$ | H | H | C(O)CH$_2$NHCH$_2$CN |
| 3,5-(CF$_3$)$_2$ | CF$_3$ | H | H | C(O)CH$_2$C(O)NHCH$_3$ |
| 3,5-(CF$_3$)$_2$ | CF$_3$ | H | H | C(O)CH=CH$_2$ |
| 3,5-(CF$_3$)$_2$ | CF$_3$ | H | H | C(O)CH$_2$CH$_2$C≡CH |
| 3,5-(CF$_3$)$_2$ | CF$_3$ | H | H | C(O)(Ph-2,4,6-F$_3$) |
| 3,5-(CF$_3$)$_2$ | CF$_3$ | CH$_3$ | H | C(O)(Ph-2,4,6-F$_3$) |
| 3,5-(CF$_3$)$_2$ | CF$_3$ | H | H | C(O)NHEt |
| 3,5-(CF$_3$)$_2$ | CF$_3$ | CH$_3$ | H | C(O)NHEt |
| 3,5-(CF$_3$)$_2$ | CF$_3$ | CH$_3$(S) | H | C(O)NHEt |
| 3,5-(CF$_3$)$_2$ | CF$_3$ | H | H | C(O)N(Et)$_2$ |
| 3,5-(CF$_3$)$_2$ | CF$_3$ | H | H | C(O)NHPr-c |
| 3,5-(CF$_3$)$_2$ | CF$_3$ | CH$_3$ | H | C(O)NHPr-c |
| 3,5-(CF$_3$)$_2$ | CF$_3$ | CH$_3$(S) | H | C(O)NHPr-c |
| 3,5-(CF$_3$)$_2$ | CF$_3$ | H | H | C(O)NHCH$_2$CF$_3$ |
| 3,5-(CF$_3$)$_2$ | CF$_3$ | CH$_3$ | H | C(O)NHCH$_2$CF$_3$ |
| 3,5-(CF$_3$)$_2$ | CF$_3$ | H | H | C(O)NHCH$_2$C≡CH |
| 3,5-(CF$_3$)$_2$ | CF$_3$ | CH$_3$ | H | C(O)NHCH$_2$C≡CH |
| 3,5-(CF$_3$)$_2$ | CF$_3$ | CH$_3$(S) | H | C(O)NHCH$_2$C≡CH |
| 3,5-(CF$_3$)$_2$ | CF$_3$ | H | H | C(S)CH$_2$SCH$_3$ |
| 3,5-(CF$_3$)$_2$ | CF$_3$ | H | H | C(S)CH$_2$SEt |
| 3,5-(CF$_3$)$_2$ | CF$_2$Cl | H | H | C(O)Et |

TABLE 5-continued

| (X)$_m$ | R$^3$ | R$^{4a}$ | R$^{2a}$ | R$^{1a}$ |
|---|---|---|---|---|
| 3,5-(CF$_3$)$_2$ | CF$_2$Cl | H | H | C(O)Pr-n |
| 3,5-(CF$_3$)$_2$ | CF$_2$Cl | H | H | C(O)Pr-i |
| 3,5-(CF$_3$)$_2$ | CF$_2$Cl | H | H | C(O)Pr-c |
| 3,5-(CF$_3$)$_2$ | CF$_2$Cl | CH$_3$ | H | C(O)Pr-c |
| 3,5-(CF$_3$)$_2$ | CF$_2$Cl | H | H | C(O)Bu-i |
| 3,5-(CF$_3$)$_2$ | CF$_2$Cl | H | H | C(O)CH$_2$Pr-c |
| 3,5-(CF$_3$)$_2$ | CF$_2$Cl | CH$_3$ | H | C(O)CH$_2$Pr-c |
| 3,5-(CF$_3$)$_2$ | CF$_2$Cl | H | H | C(O)CH$_2$CF$_3$ |
| 3,5-(CF$_3$)$_2$ | CF$_2$Cl | CH$_3$ | H | C(O)CH$_2$CF$_3$ |
| 3,5-(CF$_3$)$_2$ | CF$_2$Cl | CH$_3$ | H | C(O)(E4-2a) |
| 3,5-(CF$_3$)$_2$ | CF$_2$Cl | H | H | C(O)CH$_2$SCH$_3$ |
| 3,5-(CF$_3$)$_2$ | CF$_2$Cl | H | H | C(O)CH$_2$S(O)CH$_3$ |
| 3,5-(CF$_3$)$_2$ | CF$_2$Cl | H | H | C(O)CH$_2$SO$_2$CH$_3$ |
| 3,5-(CF$_3$)$_2$ | CF$_2$Cl | H | H | C(O)CH$_2$SEt |
| 3,5-(CF$_3$)$_2$ | CF$_2$Cl | H | H | C(O)CH$_2$S(O)Et |
| 3,5-(CF$_3$)$_2$ | CF$_2$Cl | H | H | C(O)CH$_2$SO$_2$Et |
| 3,5-(CF$_3$)$_2$ | CF$_2$Cl | H | H | C(O)NHEt |
| 3,5-(CF$_3$)$_2$ | CF$_2$Cl | H | H | C(O)NHPr-c |
| 3,5-(CF$_3$)$_2$ | CF$_2$Cl | CH$_3$ | H | C(O)NHPr-c |
| 3-Cl-5-OCHF$_2$ | CF$_3$ | H | H | C(O)Et |
| 3-Cl-5-OCHF$_2$ | CF$_3$ | H | H | C(O)Pr-n |
| 3-Cl-5-OCHF$_2$ | CF$_3$ | H | H | C(O)Pr-i |
| 3-Cl-5-OCHF$_2$ | CF$_3$ | H | H | C(O)Pr-c |
| 3-Cl-5-OCHF$_2$ | CF$_3$ | CH$_3$ | H | C(O)Pr-c |
| 3-Cl-5-OCHF$_2$ | CF$_3$ | H | H | C(O)Bu-i |
| 3-Cl-5-OCHF$_2$ | CF$_3$ | H | H | C(O)CH$_2$Pr-c |
| 3-Cl-5-OCHF$_2$ | CF$_3$ | CH$_3$ | H | C(O)CH$_2$Pr-c |
| 3-Cl-5-OCHF$_2$ | CF$_3$ | H | H | C(O)CH$_2$CF$_3$ |
| 3-Cl-5-OCHF$_2$ | CF$_3$ | CH$_3$ | H | C(O)CH$_2$CF$_3$ |
| 3-Cl-5-OCHF$_2$ | CF$_3$ | CH$_3$ | H | C(O)(E4-2a) |
| 3-Cl-5-OCHF$_2$ | CF$_3$ | H | H | C(O)CH$_2$SCH$_3$ |
| 3-Cl-5-OCHF$_2$ | CF$_3$ | H | H | C(O)CH$_2$S(O)CH$_3$ |
| 3-Cl-5-OCHF$_2$ | CF$_3$ | H | H | C(O)CH$_2$SO$_2$CH$_3$ |
| 3-Cl-5-OCHF$_2$ | CF$_3$ | H | H | C(O)CH$_2$SEt |
| 3-Cl-5-OCHF$_2$ | CF$_3$ | H | H | C(O)CH$_2$S(O)Et |
| 3-Cl-5-OCHF$_2$ | CF$_3$ | H | H | C(O)CH$_2$SO$_2$Et |
| 3-Cl-5-OCHF$_2$ | CF$_3$ | H | H | C(O)NHEt |
| 3-Cl-5-OCHF$_2$ | CF$_3$ | H | H | C(O)NHPr-c |
| 3-Cl-5-OCHF$_2$ | CF$_3$ | CH$_3$ | H | C(O)NHPr-c |
| 3-Br-5-OCHF$_2$ | CF$_3$ | H | H | C(O)Pr-c |
| 3-Br-5-OCHF$_2$ | CF$_3$ | H | H | C(O)CH$_2$Pr-c |
| 3-Br-5-OCHF$_2$ | CF$_3$ | H | H | C(O)CH$_2$CF$_3$ |
| 3-Br-5-OCHF$_2$ | CF$_3$ | CH$_3$ | H | C(O)(E4-2a) |
| 3-Br-5-OCHF$_2$ | CF$_3$ | H | H | C(O)CH$_2$SCH$_3$ |
| 3-Br-5-OCHF$_2$ | CF$_3$ | H | H | C(O)CH$_2$S(O)CH$_3$ |
| 3-Br-5-OCHF$_2$ | CF$_3$ | H | H | C(O)CH$_2$SO$_2$CH$_3$ |
| 3-Br-5-OCHF$_2$ | CF$_3$ | H | H | C(O)CH$_2$SEt |
| 3-Br-5-OCHF$_2$ | CF$_3$ | H | H | C(O)CH$_2$S(O)Et |
| 3-Br-5-OCHF$_2$ | CF$_3$ | H | H | C(O)CH$_2$SO$_2$Et |
| 3-CF$_3$-5-OCHF$_2$ | CF$_3$ | H | H | C(O)Pr-c |
| 3-CF$_3$-5-OCHF$_2$ | CF$_3$ | H | H | C(O)CH$_2$Pr-c |
| 3-CF$_3$-5-OCHF$_2$ | CF$_3$ | H | H | C(O)CH$_2$CF$_3$ |
| 3-CF$_3$-5-OCHF$_2$ | CF$_3$ | CH$_3$ | H | C(O)(E4-2a) |
| 3-CF$_3$-5-OCHF$_2$ | CF$_3$ | H | H | C(O)CH$_2$SCH$_3$ |
| 3-CF$_3$-5-OCHF$_2$ | CF$_3$ | H | H | C(O)CH$_2$S(O)CH$_3$ |
| 3-CF$_3$-5-OCHF$_2$ | CF$_3$ | H | H | C(O)CH$_2$SO$_2$CH$_3$ |
| 3-CF$_3$-5-OCHF$_2$ | CF$_3$ | H | H | C(O)CH$_2$SEt |
| 3-CF$_3$-5-OCHF$_2$ | CF$_3$ | H | H | C(O)CH$_2$S(O)Et |
| 3-CF$_3$-5-OCHF$_2$ | CF$_3$ | H | H | C(O)CH$_2$SO$_2$Et |
| 3-Cl-5-OCF$_3$ | CF$_3$ | H | H | C(O)Et |
| 3-Cl-5-OCF$_3$ | CF$_3$ | H | H | C(O)Pr-n |
| 3-Cl-5-OCF$_3$ | CF$_3$ | H | H | C(O)Pr-i |
| 3-Cl-5-OCF$_3$ | CF$_3$ | H | H | C(O)Pr-c |
| 3-Cl-5-OCF$_3$ | CF$_3$ | CH$_3$ | H | C(O)Pr-c |
| 3-Cl-5-OCF$_3$ | CF$_3$ | H | H | C(O)Bu-i |
| 3-Cl-5-OCF$_3$ | CF$_3$ | H | H | C(O)CH$_2$Pr-c |
| 3-Cl-5-OCF$_3$ | CF$_3$ | CH$_3$ | H | C(O)CH$_2$Pr-c |
| 3-Cl-5-OCF$_3$ | CF$_3$ | H | H | C(O)CH$_2$CF$_3$ |
| 3-Cl-5-OCF$_3$ | CF$_3$ | CH$_3$ | H | C(O)CH$_2$CF$_3$ |
| 3-Cl-5-OCF$_3$ | CF$_3$ | CH$_3$ | H | C(O)(E4-2a) |
| 3-Cl-5-OCF$_3$ | CF$_3$ | H | H | C(O)CH$_2$SCH$_3$ |
| 3-Cl-5-OCF$_3$ | CF$_3$ | H | H | C(O)CH$_2$S(O)CH$_3$ |
| 3-Cl-5-OCF$_3$ | CF$_3$ | H | H | C(O)CH$_2$SO$_2$CH$_3$ |
| 3-Cl-5-OCF$_3$ | CF$_3$ | H | H | C(O)CH$_2$SEt |
| 3-Cl-5-OCF$_3$ | CF$_3$ | H | H | C(O)CH$_2$S(O)Et |
| 3-Cl-5-OCF$_3$ | CF$_3$ | H | H | C(O)CH$_2$SO$_2$Et |
| 3-Cl-5-OCF$_3$ | CF$_3$ | H | H | C(O)NHEt |
| 3-Cl-5-OCF$_3$ | CF$_3$ | H | H | C(O)NHPr-c |

TABLE 5-continued

| (X)$_m$ | R$^3$ | R$^{4a}$ | R$^{2a}$ | R$^{1a}$ |
|---|---|---|---|---|
| 3-Cl-5-OCF$_3$ | CF$_3$ | CH$_3$ | H | C(O)NHPr-c |
| 3-Br-5-OCF$_3$ | CF$_3$ | H | H | C(O)Pr-c |
| 3-Br-5-OCF$_3$ | CF$_3$ | H | H | C(O)CH$_2$Pr-c |
| 3-Br-5-OCF$_3$ | CF$_3$ | H | H | C(O)CH$_2$CF$_3$ |
| 3-Br-5-OCF$_3$ | CF$_3$ | CH$_3$ | H | C(O)(E4-2a) |
| 3-Br-5-OCF$_3$ | CF$_3$ | H | H | C(O)CH$_2$SCH$_3$ |
| 3-Br-5-OCF$_3$ | CF$_3$ | H | H | C(O)CH$_2$S(O)CH$_3$ |
| 3-Br-5-OCF$_3$ | CF$_3$ | H | H | C(O)CH$_2$SO$_2$CH$_3$ |
| 3-Br-5-OCF$_3$ | CF$_3$ | H | H | C(O)CH$_2$SEt |
| 3-Br-5-OCF$_3$ | CF$_3$ | H | H | C(O)CH$_2$S(O)Et |
| 3-Br-5-OCF$_3$ | CF$_3$ | H | H | C(O)CH$_2$SO$_2$Et |
| 3-CF$_3$-5-OCF$_3$ | CF$_3$ | H | H | C(O)Pr-c |
| 3-CF$_3$-5-OCF$_3$ | CF$_3$ | H | H | C(O)CH$_2$Pr-c |
| 3-CF$_3$-5-OCF$_3$ | CF$_3$ | H | H | C(O)CH$_2$CF$_3$ |
| 3-CF$_3$-5-OCF$_3$ | CF$_3$ | CH$_3$ | H | C(O)(E4-2a) |
| 3-CF$_3$-5-OCF$_3$ | CF$_3$ | H | H | C(O)CH$_2$SCH$_3$ |
| 3-CF$_3$-5-OCF$_3$ | CF$_3$ | H | H | C(O)CH$_2$S(O)CH$_3$ |
| 3-CF$_3$-5-OCF$_3$ | CF$_3$ | H | H | C(O)CH$_2$SO$_2$CH$_3$ |
| 3-CF$_3$-5-OCF$_3$ | CF$_3$ | H | H | C(O)CH$_2$SEt |
| 3-CF$_3$-5-OCF$_3$ | CF$_3$ | H | H | C(O)CH$_2$S(O)Et |
| 3-CF$_3$-5-OCF$_3$ | CF$_3$ | H | H | C(O)CH$_2$SO$_2$Et |
| 3-Cl-5-SCF$_3$ | CF$_3$ | H | H | C(O)Et |
| 3-Cl-5-SCF$_3$ | CF$_3$ | H | H | C(O)Pr-n |
| 3-Cl-5-SCF$_3$ | CF$_3$ | H | H | C(O)Pr-i |
| 3-Cl-5-SCF$_3$ | CF$_3$ | H | H | C(O)Pr-c |
| 3-Cl-5-SCF$_3$ | CF$_3$ | CH$_3$ | H | C(O)Pr-c |
| 3-Cl-5-SCF$_3$ | CF$_3$ | H | H | C(O)Bu-i |
| 3-Cl-5-SCF$_3$ | CF$_3$ | H | H | C(O)CH$_2$Pr-c |
| 3-Cl-5-SCF$_3$ | CF$_3$ | CH$_3$ | H | C(O)CH$_2$Pr-c |
| 3-Cl-5-SCF$_3$ | CF$_3$ | H | H | C(O)CH$_2$CF$_3$ |
| 3-Cl-5-SCF$_3$ | CF$_3$ | CH$_3$ | H | C(O)CH$_2$CF$_3$ |
| 3-Cl-5-SCF$_3$ | CF$_3$ | CH$_3$ | H | C(O)(E4-2a) |
| 3-Cl-5-SCF$_3$ | CF$_3$ | H | H | C(O)CH$_2$SCH$_3$ |
| 3-Cl-5-SCF$_3$ | CF$_3$ | H | H | C(O)CH$_2$S(O)CH$_3$ |
| 3-Cl-5-SCF$_3$ | CF$_3$ | H | H | C(O)CH$_2$SO$_2$CH$_3$ |
| 3-Cl-5-SCF$_3$ | CF$_3$ | H | H | C(O)CH$_2$SEt |
| 3-Cl-5-SCF$_3$ | CF$_3$ | H | H | C(O)CH$_2$S(O)Et |
| 3-Cl-5-SCF$_3$ | CF$_3$ | H | H | C(O)CH$_2$SO$_2$Et |
| 3-Cl-5-SCF$_3$ | CF$_3$ | H | H | C(O)NHEt |
| 3-Cl-5-SCF$_3$ | CF$_3$ | H | H | C(O)NHPr-c |
| 3-Cl-5-SCF$_3$ | CF$_3$ | CH$_3$ | H | C(O)NHPr-c |
| 3-Br-5-SCF$_3$ | CF$_3$ | H | H | C(O)Pr-c |
| 3-Br-5-SCF$_3$ | CF$_3$ | H | H | C(O)CH$_2$Pr-c |
| 3-Br-5-SCF$_3$ | CF$_3$ | H | H | C(O)CH$_2$CF$_3$ |
| 3-Br-5-SCF$_3$ | CF$_3$ | CH$_3$ | H | C(O)(E4-2a) |
| 3-Br-5-SCF$_3$ | CF$_3$ | H | H | C(O)CH$_2$SCH$_3$ |
| 3-Br-5-SCF$_3$ | CF$_3$ | H | H | C(O)CH$_2$S(O)CH$_3$ |
| 3-Br-5-SCF$_3$ | CF$_3$ | H | H | C(O)CH$_2$SO$_2$CH$_3$ |
| 3-Br-5-SCF$_3$ | CF$_3$ | H | H | C(O)CH$_2$SEt |
| 3-Br-5-SCF$_3$ | CF$_3$ | H | H | C(O)CH$_2$S(O)Et |
| 3-Br-5-SCF$_3$ | CF$_3$ | H | H | C(O)CH$_2$SO$_2$Et |
| 3-CF$_3$-5-CN | CF$_3$ | H | H | C(O)Pr-c |
| 3-CF$_3$-5-CN | CF$_3$ | H | H | C(O)CH$_2$Pr-c |
| 3-CF$_3$-5-CN | CF$_3$ | H | H | C(O)CH$_2$CF$_3$ |
| 3-CF$_3$-5-CN | CF$_3$ | CH$_3$ | H | C(O)(E4-2a) |
| 3-CF$_3$-5-CN | CF$_3$ | H | H | C(O)CH$_2$SCH$_3$ |
| 3-CF$_3$-5-CN | CF$_3$ | H | H | C(O)CH$_2$S(O)CH$_3$ |
| 3-CF$_3$-5-CN | CF$_3$ | H | H | C(O)CH$_2$SO$_2$CH$_3$ |
| 3-CF$_3$-5-CN | CF$_3$ | H | H | C(O)CH$_2$SEt |
| 3-CF$_3$-5-CN | CF$_3$ | H | H | C(O)CH$_2$S(O)Et |
| 3-CF$_3$-5-CN | CF$_3$ | H | H | C(O)CH$_2$SO$_2$Et |
| 3,4,5-F$_3$ | CF$_3$ | H | H | C(O)Pr-c |
| 3,4,5-F$_3$ | CF$_3$ | H | H | C(O)CH$_2$Pr-c |
| 3,4,5-F$_3$ | CF$_3$ | H | H | C(O)CH$_2$CF$_3$ |
| 3,4,5-F$_3$ | CF$_3$ | CH$_3$ | H | C(O)(E4-2a) |
| 3,4,5-F$_3$ | CF$_3$ | H | H | C(O)CH$_2$SCH$_3$ |
| 3,4,5-F$_3$ | CF$_3$ | H | H | C(O)CH$_2$S(O)CH$_3$ |
| 3,4,5-F$_3$ | CF$_3$ | H | H | C(O)CH$_2$SO$_2$CH$_3$ |
| 3,4,5-F$_3$ | CF$_3$ | H | H | C(O)CH$_2$SEt |
| 3,4,5-F$_3$ | CF$_3$ | H | H | C(O)CH$_2$S(O)Et |
| 3,4,5-F$_3$ | CF$_3$ | H | H | C(O)CH$_2$SO$_2$Et |
| 3,5-Cl$_2$-4-F | CF$_3$ | H | H | C(O)CH$_3$ |
| 3,5-Cl$_2$-4-F | CF$_3$ | H | H | C(O)Et |
| 3,5-Cl$_2$-4-F | CF$_3$ | CH$_3$ | H | C(O)Et |
| 3,5-Cl$_2$-4-F | CF$_3$ | H | Et | C(O)Et |
| 3,5-Cl$_2$-4-F | CF$_3$ | H | CH$_2$C≡CH | C(O)Et |
| 3,5-Cl$_2$-4-F | CF$_3$ | H | H | C(O)Pr-n |
| 3,5-Cl$_2$-4-F | CF$_3$ | CH$_3$ | H | C(O)Pr-n |

TABLE 5-continued

| (X)$_m$ | R$^3$ | R$^{4a}$ | R$^{2a}$ | R$^{1a}$ |
|---|---|---|---|---|
| 3,5-Cl$_2$-4-F | CF$_3$ | H | Et | C(O)Pr-n |
| 3,5-Cl$_2$-4-F | CF$_3$ | H | H | C(O)Pr-i |
| 3,5-Cl$_2$-4-F | CF$_3$ | CH$_3$ | H | C(O)Pr-i |
| 3,5-Cl$_2$-4-F | CF$_3$ | H | H | C(O)Pr-c |
| 3,5-Cl$_2$-4-F | CF$_3$ | CH$_3$ | H | C(O)Pr-c |
| 3,5-Cl$_2$-4-F | CF$_3$ | H | Et | C(O)Pr-c |
| 3,5-Cl$_2$-4-F | CF$_3$ | CH$_3$ | Et | C(O)Pr-c |
| 3,5-Cl$_2$-4-F | CF$_3$ | H | CH$_2$Pr-c | C(O)Pr-c |
| 3,5-Cl$_2$-4-F | CF$_3$ | H | CH$_2$OCH$_3$ | C(O)Pr-c |
| 3,5-Cl$_2$-4-F | CF$_3$ | CH$_3$ | CH$_2$CN | C(O)Pr-c |
| 3,5-Cl$_2$-4-F | CF$_3$ | H | CH$_2$C≡CH | C(O)Pr-c |
| 3,5-Cl$_2$-4-F | CF$_3$ | CH$_3$ | CH$_2$C≡CH | C(O)Pr-c |
| 3,5-Cl$_2$-4-F | CF$_3$ | H | H | C(O)Bu-i |
| 3,5-Cl$_2$-4-F | CF$_3$ | CH$_3$ | H | C(O)Bu-i |
| 3,5-Cl$_2$-4-F | CF$_3$ | H | H | C(O)CH$_2$Pr-c |
| 3,5-Cl$_2$-4-F | CF$_3$ | CH$_3$ | H | C(O)CH$_2$Pr-c |
| 3,5-Cl$_2$-4-F | CF$_3$ | CN | H | C(O)CH$_2$Pr-c |
| 3,5-Cl$_2$-4-F | CF$_3$ | H | Et | C(O)CH$_2$Pr-c |
| 3,5-Cl$_2$-4-F | CF$_3$ | H | H | C(O)CH$_2$CF$_3$ |
| 3,5-Cl$_2$-4-F | CF$_3$ | CH$_3$ | H | C(O)CH$_2$CF$_3$ |
| 3,5-Cl$_2$-4-F | CF$_3$ | H | H | C(O)(E4-2a) |
| 3,5-Cl$_2$-4-F | CF$_3$ | CH$_3$ | H | C(O)(E4-2a) |
| 3,5-Cl$_2$-4-F | CF$_3$ | H | H | C(O)CH$_2$SCH$_3$ |
| 3,5-Cl$_2$-4-F | CF$_3$ | H | H | C(O)CH$_2$S(O)CH$_3$ |
| 3,5-Cl$_2$-4-F | CF$_3$ | H | H | C(O)CH$_2$SO$_2$CH$_3$ |
| 3,5-Cl$_2$-4-F | CF$_3$ | H | H | C(O)CH$_2$SEt |
| 3,5-Cl$_2$-4-F | CF$_3$ | H | Et | C(O)CH$_2$SEt |
| 3,5-Cl$_2$-4-F | CF$_3$ | H | H | C(O)CH$_2$S(O)Et |
| 3,5-Cl$_2$-4-F | CF$_3$ | H | H | C(O)CH$_2$SO$_2$Et |
| 3,5-Cl$_2$-4-F | CF$_3$ | H | CH$_3$ | C(O)CH$_2$SO$_2$Et |
| 3,5-Cl$_2$-4-F | CF$_3$ | H | H | C(O)NHEt |
| 3,5-Cl$_2$-4-F | CF$_3$ | CH$_3$ | H | C(O)NHEt |
| 3,5-Cl$_2$-4-F | CF$_3$ | H | H | C(O)NHPr-c |
| 3,5-Cl$_2$-4-F | CF$_3$ | CH$_3$ | H | C(O)NHPr-c |
| 3,5-Cl$_2$-4-F | CF$_3$ | CH$_3$ | H | C(O)NHCH$_2$C≡CH |
| 3,5-Cl$_2$-4-F | CF$_2$Cl | H | H | C(O)Pr-c |
| 3,5-Cl$_2$-4-F | CF$_2$Cl | H | H | C(O)CH$_2$Pr-c |
| 3,5-Cl$_2$-4-F | CF$_2$Cl | H | H | C(O)CH$_2$CF$_3$ |
| 3,5-Cl$_2$-4-F | CF$_2$Cl | CH$_3$ | H | C(O)(E4-2a) |
| 3,5-Cl$_2$-4-F | CF$_2$Cl | H | H | C(O)CH$_2$SCH$_3$ |
| 3,5-Cl$_2$-4-F | CF$_2$Cl | H | H | C(O)CH$_2$S(O)CH$_3$ |
| 3,5-Cl$_2$-4-F | CF$_2$Cl | H | H | C(O)CH$_2$SO$_2$CH$_3$ |
| 3,5-Cl$_2$-4-F | CF$_2$Cl | H | H | C(O)CH$_2$SEt |
| 3,5-Cl$_2$-4-F | CF$_2$Cl | H | H | C(O)CH$_2$S(O)Et |
| 3,5-Cl$_2$-4-F | CF$_2$Cl | H | H | C(O)CH$_2$SO$_2$Et |
| 3,4,5-Cl$_3$ | CF$_3$ | H | H | C(O)CH$_3$ |
| 3,4,5-Cl$_3$ | CF$_3$ | H | H | C(O)Et |
| 3,4,5-Cl$_3$ | CF$_3$ | CH$_3$ | H | C(O)Et |
| 3,4,5-Cl$_3$ | CF$_3$ | H | Et | C(O)Et |
| 3,4,5-Cl$_3$ | CF$_3$ | H | CH$_2$C≡CH | C(O)Et |
| 3,4,5-Cl$_3$ | CF$_3$ | H | H | C(O)Pr-n |
| 3,4,5-Cl$_3$ | CF$_3$ | CH$_3$ | H | C(O)Pr-n |
| 3,4,5-Cl$_3$ | CF$_3$ | H | Et | C(O)Pr-n |
| 3,4,5-Cl$_3$ | CF$_3$ | H | H | C(O)Pr-i |
| 3,4,5-Cl$_3$ | CF$_3$ | CH$_3$ | H | C(O)Pr-i |
| 3,4,5-Cl$_3$ | CF$_3$ | H | H | C(O)Pr-c |
| 3,4,5-Cl$_3$ | CF$_3$ | CH$_3$ | H | C(O)Pr-c |
| 3,4,5-Cl$_3$ | CF$_3$ | H | Et | C(O)Pr-c |
| 3,4,5-Cl$_3$ | CF$_3$ | CH$_3$ | Et | C(O)Pr-c |
| 3,4,5-Cl$_3$ | CF$_3$ | H | CH$_2$Pr-c | C(O)Pr-c |
| 3,4,5-Cl$_3$ | CF$_3$ | H | CH$_2$OCH$_3$ | C(O)Pr-c |
| 3,4,5-Cl$_3$ | CF$_3$ | CH$_3$ | CH$_2$CN | C(O)Pr-c |
| 3,4,5-Cl$_3$ | CF$_3$ | H | CH$_2$C≡CH | C(O)Pr-c |
| 3,4,5-Cl$_3$ | CF$_3$ | CH$_3$ | CH$_2$C≡CH | C(O)Pr-c |
| 3,4,5-Cl$_3$ | CF$_3$ | H | H | C(O)Bu-i |
| 3,4,5-Cl$_3$ | CF$_3$ | CH$_3$ | H | C(O)Bu-i |
| 3,4,5-Cl$_3$ | CF$_3$ | H | H | C(O)CH$_2$Pr-c |
| 3,4,5-Cl$_3$ | CF$_3$ | CH$_3$ | H | C(O)CH$_2$Pr-c |
| 3,4,5-Cl$_3$ | CF$_3$ | CN | H | C(O)CH$_2$Pr-c |
| 3,4,5-Cl$_3$ | CF$_3$ | H | Et | C(O)CH$_2$Pr-c |
| 3,4,5-Cl$_3$ | CF$_3$ | H | H | C(O)CH$_2$CF$_3$ |
| 3,4,5-Cl$_3$ | CF$_3$ | CH$_3$ | H | C(O)CH$_2$CF$_3$ |
| 3,4,5-Cl$_3$ | CF$_3$ | H | H | C(O)(E4-2a) |
| 3,4,5-Cl$_3$ | CF$_3$ | CH$_3$ | H | C(O)(E4-2a) |
| 3,4,5-Cl$_3$ | CF$_3$ | H | H | C(O)CH$_2$SCH$_3$ |
| 3,4,5-Cl$_3$ | CF$_3$ | H | H | C(O)CH$_2$S(O)CH$_3$ |
| 3,4,5-Cl$_3$ | CF$_3$ | H | H | C(O)CH$_2$SO$_2$CH$_3$ |
| 3,4,5-Cl$_3$ | CF$_3$ | H | H | C(O)CH$_2$SEt |

TABLE 5-continued

| (X)$_m$ | R$^3$ | R$^{4a}$ | R$^{2a}$ | R$^{1a}$ |
|---|---|---|---|---|
| 3,4,5-Cl$_3$ | CF$_3$ | H | Et | C(O)CH$_2$SEt |
| 3,4,5-Cl$_3$ | CF$_3$ | H | H | C(O)CH$_2$S(O)Et |
| 3,4,5-Cl$_3$ | CF$_3$ | H | H | C(O)CH$_2$SO$_2$Et |
| 3,4,5-Cl$_3$ | CF$_3$ | H | CH$_3$ | C(O)CH$_2$SO$_2$Et |
| 3,4,5-Cl$_3$ | CF$_3$ | H | H | C(O)NHEt |
| 3,4,5-Cl$_3$ | CF$_3$ | CH$_3$ | H | C(O)NHEt |
| 3,4,5-Cl$_3$ | CF$_3$ | H | H | C(O)NHPr-c |
| 3,4,5-Cl$_3$ | CF$_3$ | CH$_3$ | H | C(O)NHPr-c |
| 3,4,5-Cl$_3$ | CF$_3$ | CH$_3$ | H | C(O)NHCH$_2$C≡CH |
| 3,4,5-Cl$_3$ | CF$_2$Cl | H | H | C(O)Pr-c |
| 3,4,5-Cl$_3$ | CF$_2$Cl | H | H | C(O)CH$_2$Pr-c |
| 3,4,5-Cl$_3$ | CF$_2$Cl | H | H | C(O)CH$_2$CF$_3$ |
| 3,4,5-Cl$_3$ | CF$_2$Cl | CH$_3$ | H | C(O)(E4-2a) |
| 3,4,5-Cl$_3$ | CF$_2$Cl | H | H | C(O)CH$_2$SCH$_3$ |
| 3,4,5-Cl$_3$ | CF$_2$Cl | H | H | C(O)CH$_2$S(O)CH$_3$ |
| 3,4,5-Cl$_3$ | CF$_2$Cl | H | H | C(O)CH$_2$SO$_2$CH$_3$ |
| 3,4,5-Cl$_3$ | CF$_2$Cl | H | H | C(O)CH$_2$SEt |
| 3,4,5-Cl$_3$ | CF$_2$Cl | H | H | C(O)CH$_2$S(O)Et |
| 3,4,5-Cl$_3$ | CF$_2$Cl | H | H | C(O)CH$_2$SO$_2$Et |
| 3,5-Br$_2$-4-F | CF$_3$ | H | H | C(O)CH$_3$ |
| 3,5-Br$_2$-4-F | CF$_3$ | H | H | C(O)Et |
| 3,5-Br$_2$-4-F | CF$_3$ | CH$_3$ | H | C(O)Et |
| 3,5-Br$_2$-4-F | CF$_3$ | H | Et | C(O)Et |
| 3,5-Br$_2$-4-F | CF$_3$ | H | CH$_2$C≡CH | C(O)Et |
| 3,5-Br$_2$-4-F | CF$_3$ | H | H | C(O)Pr-n |
| 3,5-Br$_2$-4-F | CF$_3$ | CH$_3$ | H | C(O)Pr-n |
| 3,5-Br$_2$-4-F | CF$_3$ | H | Et | C(O)Pr-n |
| 3,5-Br$_2$-4-F | CF$_3$ | H | H | C(O)Pr-i |
| 3,5-Br$_2$-4-F | CF$_3$ | CH$_3$ | H | C(O)Pr-i |
| 3,5-Br$_2$-4-F | CF$_3$ | H | H | C(O)Pr-c |
| 3,5-Br$_2$-4-F | CF$_3$ | CH$_3$ | H | C(O)Pr-c |
| 3,5-Br$_2$-4-F | CF$_3$ | H | Et | C(O)Pr-c |
| 3,5-Br$_2$-4-F | CF$_3$ | CH$_3$ | Et | C(O)Pr-c |
| 3,5-Br$_2$-4-F | CF$_3$ | H | CH$_2$Pr-c | C(O)Pr-c |
| 3,5-Br$_2$-4-F | CF$_3$ | H | CH$_2$OCH$_3$ | C(O)Pr-c |
| 3,5-Br$_2$-4-F | CF$_3$ | CH$_3$ | CH$_2$CN | C(O)Pr-c |
| 3,5-Br$_2$-4-F | CF$_3$ | H | CH$_2$C≡CH | C(O)Pr-c |
| 3,5-Br$_2$-4-F | CF$_3$ | CH$_3$ | CH$_2$C≡CH | C(O)Pr-c |
| 3,5-Br$_2$-4-F | CF$_3$ | H | H | C(O)Bu-i |
| 3,5-Br$_2$-4-F | CF$_3$ | CH$_3$ | H | C(O)Bu-i |
| 3,5-Br$_2$-4-F | CF$_3$ | H | H | C(O)CH$_2$Pr-c |
| 3,5-Br$_2$-4-F | CF$_3$ | CH$_3$ | H | C(o)CH$_2$Pr-c |
| 3,5-Br$_2$-4-F | CF$_3$ | CN | H | C(O)CH$_2$Pr-c |
| 3,5-Br$_2$-4-F | CF$_3$ | H | Et | C(O)CH$_2$Pr-c |
| 3,5-Br$_2$-4-F | CF$_3$ | H | H | C(O)CH$_2$CF$_3$ |
| 3,5-Br$_2$-4-F | CF$_3$ | CH$_3$ | H | C(O)CH$_2$CF$_3$ |
| 3,5-Br$_2$-4-F | CF$_3$ | H | H | C(O)(E4-2a) |
| 3,5-Br$_2$-4-F | CF$_3$ | CH$_3$ | H | C(O)(E4-2a) |
| 3,5-Br$_2$-4-F | CF$_3$ | H | H | C(O)CH$_2$SCH$_3$ |
| 3,5-Br$_2$-4-F | CF$_3$ | H | H | C(O)CH$_2$S(O)CH$_3$ |
| 3,5-Br$_2$-4-F | CF$_3$ | H | H | C(O)CH$_2$SO$_2$CH$_3$ |
| 3,5-Br$_2$-4-F | CF$_3$ | H | H | C(O)CH$_2$SEt |
| 3,5-Br$_2$-4-F | CF$_3$ | H | Et | C(O)CH$_2$SEt |
| 3,5-Br$_2$-4-F | CF$_3$ | H | H | C(O)CH$_2$S(O)Et |
| 3,5-Br$_2$-4-F | CF$_3$ | H | H | C(O)CH$_2$SO$_2$Et |
| 3,5-Br$_2$-4-F | CF$_3$ | H | CH$_3$ | C(O)CH$_2$SO$_2$Et |
| 3,5-Br$_2$-4-F | CF$_3$ | H | H | C(O)NHEt |
| 3,5-Br$_2$-4-F | CF$_3$ | CH$_3$ | H | C(O)NHEt |
| 3,5-Br$_2$-4-F | CF$_3$ | H | H | C(O)NHPr-c |
| 3,5-Br$_2$-4-F | CF$_3$ | CH$_3$ | H | C(O)NHPr-c |
| 3,5-Br$_2$-4-F | CF$_3$ | CH$_3$ | H | C(O)NHCH$_2$C≡CH |
| 3,5-Br$_2$-4-F | CF$_2$Cl | H | H | C(O)Pr-c |
| 3,5-Br$_2$-4-F | CF$_2$Cl | H | H | C(O)CH$_2$Pr-c |
| 3,5-Br$_2$-4-F | CF$_2$Cl | H | H | C(O)CH$_2$CF$_3$ |
| 3,5-Br$_2$-4-F | CF$_2$Cl | CH$_3$ | H | C(O)(E4-2a) |
| 3,5-Br$_2$-4-F | CF$_2$Cl | H | H | C(O)CH$_2$SCH$_3$ |
| 3,5-Br$_2$-4-F | CF$_2$Cl | H | H | C(O)CH$_2$S(O)CH$_3$ |
| 3,5-Br$_2$-4-F | CF$_2$Cl | H | H | C(O)CH$_2$SO$_2$CH$_3$ |
| 3,5-Br$_2$-4-F | CF$_2$Cl | H | H | C(O)CH$_2$SEt |
| 3,5-Br$_2$-4-F | CF$_2$Cl | H | H | C(O)CH$_2$S(O)Et |
| 3,5-Br$_2$-4-F | CF$_2$Cl | H | H | C(O)CH$_2$SO$_2$Et |
| 3,4,5-Br$_3$ | CF$_3$ | H | H | C(O)Pr-c |
| 3,4,5-Br$_3$ | CF$_3$ | H | H | C(O)CH$_2$Pr-c |
| 3,4,5-Br$_3$ | CF$_3$ | H | H | C(O)CH$_2$CF$_3$ |
| 3,4,5-Br$_3$ | CF$_3$ | CH$_3$ | H | C(O)(E4-2a) |
| 3,4,5-Br$_3$ | CF$_3$ | H | H | C(O)CH$_2$SCH$_3$ |
| 3,4,5-Br$_3$ | CF$_3$ | H | H | C(O)CH$_2$S(O)CH$_3$ |
| 3,4,5-Br$_3$ | CF$_3$ | H | H | C(O)CH$_2$SO$_2$CH$_3$ |

TABLE 5-continued

| (X)$_m$ | R$^3$ | R$^{4a}$ | R$^{2a}$ | R$^{1a}$ |
|---|---|---|---|---|
| 3,4,5-Br$_3$ | CF$_3$ | H | H | C(O)CH$_2$SEt |
| 3,4,5-Br$_3$ | CF$_3$ | H | H | C(O)CH$_2$S(O)Et |
| 3,4,5-Br$_3$ | CF$_3$ | H | H | C(O)CH$_2$SO$_2$Et |
| 3,4-F$_2$-5-CF$_3$ | CF$_3$ | H | H | C(O)CH$_3$ |
| 3,4-F$_2$-5-CF$_3$ | CF$_3$ | H | H | C(O)Et |
| 3,4-F$_2$-5-CF$_3$ | CF$_3$ | CH$_3$ | H | C(O)Et |
| 3,4-F$_2$-5-CF$_3$ | CF$_3$ | H | Et | C(O)Et |
| 3,4-F$_2$-5-CF$_3$ | CF$_3$ | H | CH$_2$C≡CH | C(O)Et |
| 3,4-F$_2$-5-CF$_3$ | CF$_3$ | H | H | C(O)Pr-n |
| 3,4-F$_2$-5-CF$_3$ | CF$_3$ | CH$_3$ | H | C(O)Pr-n |
| 3,4-F$_2$-5-CF$_3$ | CF$_3$ | H | Et | C(O)Pr-n |
| 3,4-F$_2$-5-CF$_3$ | CF$_3$ | H | H | C(O)Pr-i |
| 3,4-F$_2$-5-CF$_3$ | CF$_3$ | CH$_3$ | H | C(O)Pr-i |
| 3,4-F$_2$-5-CF$_3$ | CF$_3$ | H | H | C(O)Pr-c |
| 3,4-F$_2$-5-CF$_3$ | CF$_3$ | CH$_3$ | H | C(O)Pr-c |
| 3,4-F$_2$-5-CF$_3$ | CF$_3$ | H | Et | C(O)Pr-c |
| 3,4-F$_2$-5-CF$_3$ | CF$_3$ | CH$_3$ | Et | C(O)Pr-c |
| 3,4-F$_2$-5-CF$_3$ | CF$_3$ | H | CH$_2$Pr-c | C(O)Pr-c |
| 3,4-F$_2$-5-CF$_3$ | CF$_3$ | H | CH$_2$OCH$_3$ | C(O)Pr-c |
| 3,4-F$_2$-5-CF$_3$ | CF$_3$ | CH$_3$ | CH$_2$CN | C(O)Pr-c |
| 3,4-F$_2$-5-CF$_3$ | CF$_3$ | H | CH$_2$C≡CH | C(O)Pr-c |
| 3,4-F$_2$-5-CF$_3$ | CF$_3$ | CH$_3$ | CH$_2$C≡CH | C(O)Pr-c |
| 3,4-F$_2$-5-CF$_3$ | CF$_3$ | H | H | C(O)Bu-i |
| 3,4-F$_2$-5-CF$_3$ | CF$_3$ | CH$_3$ | H | C(O)Bu-i |
| 3,4-F$_2$-5-CF$_3$ | CF$_3$ | H | H | C(O)CH$_2$Pr-c |
| 3,4-F$_2$-5-CF$_3$ | CF$_3$ | CH$_3$ | H | C(O)CH$_2$Pr-c |
| 3,4-F$_2$-5-CF$_3$ | CF$_3$ | CN | H | C(O)CH$_2$Pr-c |
| 3,4-F$_2$-5-CF$_3$ | CF$_3$ | H | Et | C(O)CH$_2$Pr-c |
| 3,4-F$_2$-5-CF$_3$ | CF$_3$ | H | H | C(O)CH$_2$CF$_3$ |
| 3,4-F$_2$-5-CF$_3$ | CF$_3$ | CH$_3$ | H | C(O)CH$_2$CF$_3$ |
| 3,4-F$_2$-5-CF$_3$ | CF$_3$ | H | H | C(O)(E4-2a) |
| 3,4-F$_2$-5-CF$_3$ | CF$_3$ | CH$_3$ | H | C(O)(E4-2a) |
| 3,4-F$_2$-5-CF$_3$ | CF$_3$ | H | H | C(O)CH$_2$SCH$_3$ |
| 3,4-F$_2$-5-CF$_3$ | CF$_3$ | H | H | C(O)CH$_2$S(O)CH$_3$ |
| 3,4-F$_2$-5-CF$_3$ | CF$_3$ | H | H | C(O)CH$_2$SO$_2$CH$_3$ |
| 3,4-F$_2$-5-CF$_3$ | CF$_3$ | H | H | C(O)CH$_2$SEt |
| 3,4-F$_2$-5-CF$_3$ | CF$_3$ | H | Et | C(O)CH$_2$SEt |
| 3,4-F$_2$-5-CF$_3$ | CF$_3$ | H | H | C(O)CH$_2$S(O)Et |
| 3,4-F$_2$-5-CF$_3$ | CF$_3$ | H | H | C(O)CH$_2$SO$_2$Et |
| 3,4-F$_2$-5-CF$_3$ | CF$_3$ | H | CH$_3$ | C(O)CH$_2$SO$_2$Et |
| 3,4-F$_2$-5-CF$_3$ | CF$_3$ | H | H | C(O)NHEt |
| 3,4-F$_2$-5-CF$_3$ | CF$_3$ | CH$_3$ | H | C(O)NHEt |
| 3,4-F$_2$-5-CF$_3$ | CF$_3$ | H | H | C(O)NHPr-c |
| 3,4-F$_2$-5-CF$_3$ | CF$_3$ | CH$_3$ | H | C(O)NHPr-c |
| 3,4-F$_2$-5-CF$_3$ | CF$_3$ | CH$_3$ | H | C(O)NHCH$_2$C≡CH |
| 3,4-F$_2$-5-CF$_3$ | CF$_2$Cl | H | H | C(O)Pr-c |
| 3,4-F$_2$-5-CF$_3$ | CF$_2$Cl | H | H | C(O)CH$_2$Pr-c |
| 3,4-F$_2$-5-CF$_3$ | CF$_2$Cl | H | H | C(O)CH$_2$CF$_3$ |
| 3,4-F$_2$-5-CF$_3$ | CF$_2$Cl | CH$_3$ | H | C(O)(E4-2a) |
| 3,4-F$_2$-5-CF$_3$ | CF$_2$Cl | H | H | C(O)CH$_2$SCH$_3$ |
| 3,4-F$_2$-5-CF$_3$ | CF$_2$Cl | H | H | C(O)CH$_2$S(O)CH$_3$ |
| 3,4-F$_2$-5-CF$_3$ | CF$_2$Cl | H | H | C(O)CH$_2$SO$_2$CH$_3$ |
| 3,4-F$_2$-5-CF$_3$ | CF$_2$Cl | H | H | C(O)CH$_2$SEt |
| 3,4-F$_2$-5-CF$_3$ | CF$_2$Cl | H | H | C(O)CH$_2$S(O)Et |
| 3,4-F$_2$-5-CF$_3$ | CF$_2$Cl | H | H | C(O)CH$_2$SO$_2$Et |
| 3-Cl-4-F-5-CF$_3$ | CF$_3$ | H | H | C(O)CH$_3$ |
| 3-Cl-4-F-5-CF$_3$ | CF$_3$ | H | H | C(O)Et |
| 3-Cl-4-F-5-CF$_3$ | CF$_3$ | CH$_3$ | H | C(O)Et |
| 3-Cl-4-F-5-CF$_3$ | CF$_3$ | H | Et | C(O)Et |
| 3-Cl-4-F-5-CF$_3$ | CF$_3$ | H | CH$_2$C≡CH | C(O)Et |
| 3-Cl-4-F-5-CF$_3$ | CF$_3$ | H | H | C(O)Pr-n |
| 3-Cl-4-F-5-CF$_3$ | CF$_3$ | CH$_3$ | H | C(O)Pr-n |
| 3-Cl-4-F-5-CF$_3$ | CF$_3$ | H | Et | C(O)Pr-n |
| 3-Cl-4-F-5-CF$_3$ | CF$_3$ | H | H | C(O)Pr-i |
| 3-Cl-4-F-5-CF$_3$ | CF$_3$ | CH$_3$ | H | C(O)Pr-i |
| 3-Cl-4-F-5-CF$_3$ | CF$_3$ | H | H | C(O)Pr-c |
| 3-Cl-4-F-5-CF$_3$ | CF$_3$ | CH$_3$ | H | C(O)Pr-c |
| 3-Cl-4-F-5-CF$_3$ | CF$_3$ | H | Et | C(O)Pr-c |
| 3-Cl-4-F-5-CF$_3$ | CF$_3$ | CH$_3$ | Et | C(O)Pr-c |
| 3-Cl-4-F-5-CF$_3$ | CF$_3$ | H | CH$_2$Pr-c | C(O)Pr-c |
| 3-Cl-4-F-5-CF$_3$ | CF$_3$ | H | CH$_2$OCH$_3$ | C(O)Pr-c |
| 3-Cl-4-F-5-CF$_3$ | CF$_3$ | CH$_3$ | CH$_2$CN | C(O)Pr-c |
| 3-Cl-4-F-5-CF$_3$ | CF$_3$ | H | CH$_2$C≡CH | C(O)Pr-c |
| 3-Cl-4-F-5-CF$_3$ | CF$_3$ | CH$_3$ | CH$_2$C≡CH | C(O)Pr-c |
| 3-Cl-4-F-5-CF$_3$ | CF$_3$ | H | H | C(O)Bu-i |
| 3-Cl-4-F-5-CF$_3$ | CF$_3$ | CH$_3$ | H | C(O)Bu-i |
| 3-Cl-4-F-5-CF$_3$ | CF$_3$ | H | H | C(O)CH$_2$Pr-c |
| 3-Cl-4-F-5-CF$_3$ | CF$_3$ | CH$_3$ | H | C(O)CH$_2$Pr-c |

TABLE 5-continued

| (X)$_m$ | R$^3$ | R$^{4a}$ | R$^{2a}$ | R$^{1a}$ |
|---|---|---|---|---|
| 3-Cl-4-F-5-CF$_3$ | CF$_3$ | CN | H | C(O)CH$_2$Pr-c |
| 3-Cl-4-F-5-CF$_3$ | CF$_3$ | H | Et | C(O)CH$_2$Pr-c |
| 3-Cl-4-F-5-CF$_3$ | CF$_3$ | H | H | C(O)CH$_2$CF$_3$ |
| 3-Cl-4-F-5-CF$_3$ | CF$_3$ | CH$_3$ | H | C(O)CH$_2$CF$_3$ |
| 3-Cl-4-F-5-CF$_3$ | CF$_3$ | H | H | C(O)(E4-2a) |
| 3-Cl-4-F-5-CF$_3$ | CF$_3$ | CH$_3$ | H | C(O)(E4-2a) |
| 3-Cl-4-F-5-CF$_3$ | CF$_3$ | H | H | C(O)CH$_2$SCH$_3$ |
| 3-Cl-4-F-5-CF$_3$ | CF$_3$ | H | H | C(O)CH$_2$S(O)CH$_3$ |
| 3-Cl-4-F-5-CF$_3$ | CF$_3$ | H | H | C(O)CH$_2$SO$_2$CH$_3$ |
| 3-Cl-4-F-5-CF$_3$ | CF$_3$ | H | H | C(O)CH$_2$SEt |
| 3-Cl-4-F-5-CF$_3$ | CF$_3$ | H | Et | C(O)CH$_2$SEt |
| 3-Cl-4-F-5-CF$_3$ | CF$_3$ | H | H | C(O)CH$_2$S(O)Et |
| 3-Cl-4-F-5-CF$_3$ | CF$_3$ | H | H | C(O)CH$_2$SO$_2$Et |
| 3-Cl-4-F-5-CF$_3$ | CF$_3$ | H | CH$_3$ | C(O)CH$_2$SO$_2$Et |
| 3-Cl-4-F-5-CF$_3$ | CF$_3$ | H | H | C(O)NHEt |
| 3-Cl-4-F-5-CF$_3$ | CF$_3$ | CH$_3$ | H | C(O)NHEt |
| 3-Cl-4-F-5-CF$_3$ | CF$_3$ | H | H | C(O)NHPr-c |
| 3-Cl-4-F-5-CF$_3$ | CF$_3$ | CH$_3$ | H | C(O)NHPr-c |
| 3-Cl-4-F-5-CF$_3$ | CF$_3$ | CH$_3$ | H | C(O)NHCH$_2$C≡CH |
| 3-Cl-4-F-5-CF$_3$ | CF$_2$Cl | H | H | C(O)Pr-c |
| 3-Cl-4-F-5-CF$_3$ | CF$_2$Cl | H | H | C(O)CH$_2$Pr-c |
| 3-Cl-4-F-5-CF$_3$ | CF$_2$Cl | H | H | C(O)CH$_2$CF$_3$ |
| 3-Cl-4-F-5-CF$_3$ | CF$_2$Cl | CH$_3$ | H | C(O)(E4-2a) |
| 3-Cl-4-F-5-CF$_3$ | CF$_2$Cl | H | H | C(O)CH$_2$SCH$_3$ |
| 3-Cl-4-F-5-CF$_3$ | CF$_2$Cl | H | H | C(O)CH$_2$S(O)CH$_3$ |
| 3-Cl-4-F-5-CF$_3$ | CF$_2$Cl | H | H | C(O)CH$_2$SO$_2$CH$_3$ |
| 3-Cl-4-F-5-CF$_3$ | CF$_2$Cl | H | H | C(O)CH$_2$SEt |
| 3-Cl-4-F-5-CF$_3$ | CF$_2$Cl | H | H | C(O)CH$_2$S(O)Et |
| 3-Cl-4-F-5-CF$_3$ | CF$_2$Cl | H | H | C(O)CH$_2$SO$_2$Et |
| 3,4-Cl$_2$-5-CF$_3$ | CF$_3$ | H | H | C(O)CH$_3$ |
| 3,4-Cl$_2$-5-CF$_3$ | CF$_3$ | H | H | C(O)Et |
| 3,4-Cl$_2$-5-CF$_3$ | CF$_3$ | CH$_3$ | H | C(O)Et |
| 3,4-Cl$_2$-5-CF$_3$ | CF$_3$ | H | Et | C(O)Et |
| 3,4-Cl$_2$-5-CF$_3$ | CF$_3$ | H | CH$_2$C≡CH | C(O)Et |
| 3,4-Cl$_2$-5-CF$_3$ | CF$_3$ | H | H | C(O)Pr-n |
| 3,4-Cl$_2$-5-CF$_3$ | CF$_3$ | CH$_3$ | H | C(O)Pr-n |
| 3,4-Cl$_2$-5-CF$_3$ | CF$_3$ | H | Et | C(O)Pr-n |
| 3,4-Cl$_2$-5-CF$_3$ | CF$_3$ | H | H | C(O)Pr-i |
| 3,4-Cl$_2$-5-CF$_3$ | CF$_3$ | CH$_3$ | H | C(O)Pr-i |
| 3,4-Cl$_2$-5-CF$_3$ | CF$_3$ | H | H | C(O)Pr-c |
| 3,4-Cl$_2$-5-CF$_3$ | CF$_3$ | CH$_3$ | H | C(O)Pr-c |
| 3,4-Cl$_2$-5-CF$_3$ | CF$_3$ | H | Et | C(O)Pr-c |
| 3,4-Cl$_2$-5-CF$_3$ | CF$_3$ | CH$_3$ | Et | C(O)Pr-c |
| 3,4-Cl$_2$-5-CF$_3$ | CF$_3$ | H | CH$_2$Pr-c | C(O)Pr-c |
| 3,4-Cl$_2$-5-CF$_3$ | CF$_3$ | H | CH$_2$OCH$_3$ | C(O)Pr-c |
| 3,4-Cl$_2$-5-CF$_3$ | CF$_3$ | CH$_3$ | CH$_2$CN | C(O)Pr-c |
| 3,4-Cl$_2$-5-CF$_3$ | CF$_3$ | H | CH$_2$C≡CH | C(O)Pr-c |
| 3,4-Cl$_2$-5-CF$_3$ | CF$_3$ | CH$_3$ | CH$_2$C≡CH | C(O)Pr-c |
| 3,4-Cl$_2$-5-CF$_3$ | CF$_3$ | H | H | C(O)Bu-i |
| 3,4-Cl$_2$-5-CF$_3$ | CF$_3$ | CH$_3$ | H | C(O)Bu-i |
| 3,4-Cl$_2$-5-CF$_3$ | CF$_3$ | H | H | C(O)CH$_2$Pr-c |
| 3,4-Cl$_2$-5-CF$_3$ | CF$_3$ | CH$_3$ | H | C(O)CH$_2$Pr-c |
| 3,4-Cl$_2$-5-CF$_3$ | CF$_3$ | CN | H | C(O)CH$_2$Pr-c |
| 3,4-Cl$_2$-5-CF$_3$ | CF$_3$ | H | Et | C(O)CH$_2$Pr-c |
| 3,4-Cl$_2$-5-CF$_3$ | CF$_3$ | H | H | C(O)CH$_2$CF$_3$ |
| 3,4-Cl$_2$-5-CF$_3$ | CF$_3$ | CH$_3$ | H | C(O)CH$_2$CF$_3$ |
| 3,4-Cl$_2$-5-CF$_3$ | CF$_3$ | H | H | C(O)(E4-2a) |
| 3,4-Cl$_2$-5-CF$_3$ | CF$_3$ | CH$_3$ | H | C(O)(E4-2a) |
| 3,4-Cl$_2$-5-CF$_3$ | CF$_3$ | H | H | C(O)CH$_2$SCH$_3$ |
| 3,4-Cl$_2$-5-CF$_3$ | CF$_3$ | H | H | C(O)CH$_2$S(O)CH$_3$ |
| 3,4-Cl$_2$-5-CF$_3$ | CF$_3$ | H | H | C(O)CH$_2$SO$_2$CH$_3$ |
| 3,4-Cl$_2$-5-CF$_3$ | CF$_3$ | H | H | C(O)CH$_2$SEt |
| 3,4-Cl$_2$-5-CF$_3$ | CF$_3$ | H | Et | C(O)CH$_2$SEt |
| 3,4-Cl$_2$-5-CF$_3$ | CF$_3$ | H | H | C(O)CH$_2$S(O)Et |
| 3,4-Cl$_2$-5-CF$_3$ | CF$_3$ | H | H | C(O)CH$_2$SO$_2$Et |
| 3,4-Cl$_2$-5-CF$_3$ | CF$_3$ | H | CH$_3$ | C(O)CH$_2$SO$_2$Et |
| 3,4-Cl$_2$-5-CF$_3$ | CF$_3$ | H | H | C(O)NHEt |
| 3,4-Cl$_2$-5-CF$_3$ | CF$_3$ | CH$_3$ | H | C(O)NHEt |
| 3,4-Cl$_2$-5-CF$_3$ | CF$_3$ | H | H | C(O)NHPr-c |
| 3,4-Cl$_2$-5-CF$_3$ | CF$_3$ | CH$_3$ | H | C(O)NHPr-c |
| 3,4-Cl$_2$-5-CF$_3$ | CF$_3$ | CH$_3$ | H | C(O)NHCH$_2$C≡CH |
| 3,4-Cl$_2$-5-CF$_3$ | CF$_2$Cl | H | H | C(O)Pr-c |
| 3,4-Cl$_2$-5-CF$_3$ | CF$_2$Cl | H | H | C(O)CH$_2$Pr-c |
| 3,4-Cl$_2$-5-CF$_3$ | CF$_2$Cl | H | H | C(O)CH$_2$CF$_3$ |
| 3,4-Cl$_2$-5-CF$_3$ | CF$_2$Cl | CH$_3$ | H | C(O)(E4-2a) |
| 3,4-Cl$_2$-5-CF$_3$ | CF$_2$Cl | H | H | C(O)CH$_2$SCH$_3$ |
| 3,4-Cl$_2$-5-CF$_3$ | CF$_2$Cl | H | H | C(O)CH$_2$S(O)CH$_3$ |
| 3,4-Cl$_2$-5-CF$_3$ | CF$_2$Cl | H | H | C(O)CH$_2$SO$_2$CH$_3$ |

TABLE 5-continued

| $(X)_m$ | $R^3$ | $R^{4a}$ | $R^{2a}$ | $R^{1a}$ |
|---|---|---|---|---|
| 3,4-Cl$_2$-5-CF$_3$ | CF$_2$Cl | H | H | C(O)CH$_2$SEt |
| 3,4-Cl$_2$-5-CF$_3$ | CF$_2$Cl | H | H | C(O)CH$_2$S(O)Et |
| 3,4-Cl$_2$-5-CF$_3$ | CF$_2$Cl | H | H | C(O)CH$_2$SO$_2$Et |
| 3,5-(CF$_3$)$_2$-4-Cl | CF$_3$ | H | H | C(O)CH$_3$ |
| 3,5-(CF$_3$)$_2$-4-Cl | CF$_3$ | H | H | C(O)Et |
| 3,5-(CF$_3$)$_2$-4-Cl | CF$_3$ | CH$_3$ | H | C(O)Et |
| 3,5-(CF$_3$)$_2$-4-Cl | CF$_3$ | H | Et | C(O)Et |
| 3,5-(CF$_3$)$_2$-4-Cl | CF$_3$ | H | CH$_2$C≡CH | C(O)Et |
| 3,5-(CF$_3$)$_2$-4-Cl | CF$_3$ | H | H | C(O)Pr-n |
| 3,5-(CF$_3$)$_2$-4-Cl | CF$_3$ | CH$_3$ | H | C(O)Pr-n |
| 3,5-(CF$_3$)$_2$-4-Cl | CF$_3$ | H | Et | C(O)Pr-n |
| 3,5-(CF$_3$)$_2$-4-Cl | CF$_3$ | H | H | C(O)Pr-i |
| 3,5-(CF$_3$)$_2$-4-Cl | CF$_3$ | CH$_3$ | H | C(O)Pr-i |
| 3,5-(CF$_3$)$_2$-4-Cl | CF$_3$ | H | H | C(O)Pr-c |
| 3,5-(CF$_3$)$_2$-4-Cl | CF$_3$ | CH$_3$ | H | C(O)Pr-c |
| 3,5-(CF$_3$)$_2$-4-Cl | CF$_3$ | H | Et | C(O)Pr-c |
| 3,5-(CF$_3$)$_2$-4-Cl | CF$_3$ | CH$_3$ | Et | C(O)Pr-c |
| 3,5-(CF$_3$)$_2$-4-Cl | CF$_3$ | H | CH$_2$Pr-c | C(O)Pr-c |
| 3,5-(CF$_3$)$_2$-4-Cl | CF$_3$ | H | CH$_2$OCH$_3$ | C(O)Pr-c |
| 3,5-(CF$_3$)$_2$-4-Cl | CF$_3$ | CH$_3$ | CH$_2$CN | C(O)Pr-c |
| 3,5-(CF$_3$)$_2$-4-Cl | CF$_3$ | H | CH$_2$C≡CH | C(O)Pr-c |
| 3,5-(CF$_3$)$_2$-4-Cl | CF$_3$ | CH$_3$ | CH$_2$C≡CH | C(O)Pr-c |
| 3,5-(CF$_3$)$_2$-4-Cl | CF$_3$ | H | H | C(O)Bu-i |
| 3,5-(CF$_3$)$_2$-4-Cl | CF$_3$ | CH$_3$ | H | C(O)Bu-i |
| 3,5-(CF$_3$)$_2$-4-Cl | CF$_3$ | H | H | C(O)CH$_2$Pr-c |
| 3,5-(CF$_3$)$_2$-4-Cl | CF$_3$ | CH$_3$ | H | C(O)CH$_2$Pr-c |
| 3,5-(CF$_3$)$_2$-4-Cl | CF$_3$ | CN | H | C(O)CH$_2$Pr-c |
| 3,5-(CF$_3$)$_2$-4-Cl | CF$_3$ | H | Et | C(O)CH$_2$Pr-c |
| 3,5-(CF$_3$)$_2$-4-Cl | CF$_3$ | H | H | C(O)CH$_2$CF$_3$ |
| 3,5-(CF$_3$)$_2$-4-Cl | CF$_3$ | CH$_3$ | H | C(O)CH$_2$CF$_3$ |
| 3,5-(CF$_3$)$_2$-4-Cl | CF$_3$ | H | H | C(O)(E4-2a) |
| 3,5-(CF$_3$)$_2$-4-Cl | CF$_3$ | CH$_3$ | H | C(O)(E4-2a) |
| 3,5-(CF$_3$)$_2$-4-Cl | CF$_3$ | H | H | C(O)CH$_2$SCH$_3$ |
| 3,5-(CF$_3$)$_2$-4-Cl | CF$_3$ | H | H | C(O)CH$_2$S(O)CH$_3$ |
| 3,5-(CF$_3$)$_2$-4-Cl | CF$_3$ | H | H | C(O)CH$_2$SO$_2$CH$_3$ |
| 3,5-(CF$_3$)$_2$-4-Cl | CF$_3$ | H | H | C(O)CH$_2$SEt |
| 3,5-(CF$_3$)$_2$-4-Cl | CF$_3$ | H | Et | C(O)CH$_2$SEt |
| 3,5-(CF$_3$)$_2$-4-Cl | CF$_3$ | H | H | C(O)CH$_2$S(O)Et |
| 3,5-(CF$_3$)$_2$-4-Cl | CF$_3$ | H | H | C(O)CH$_2$SO$_2$Et |
| 3,5-(CF$_3$)$_2$-4-Cl | CF$_3$ | H | CH$_3$ | C(O)CH$_2$SO$_2$Et |
| 3,5-(CF$_3$)$_2$-4-Cl | CF$_3$ | H | H | C(O)NHEt |
| 3,5-(CF$_3$)$_2$-4-Cl | CF$_3$ | CH$_3$ | H | C(O)NHEt |
| 3,5-(CF$_3$)$_2$-4-Cl | CF$_3$ | H | H | C(O)NHPr-c |
| 3,5-(CF$_3$)$_2$-4-Cl | CF$_3$ | CH$_3$ | H | C(O)NHPr-c |
| 3,5-(CF$_3$)$_2$-4-Cl | CF$_3$ | CH$_3$ | H | C(O)NHCH$_2$C≡CH |
| 3,5-(CF$_3$)$_2$-4-Cl | CF$_2$Cl | H | H | C(O)Pr-c |
| 3,5-(CF$_3$)$_2$-4-Cl | CF$_2$Cl | H | H | C(O)CH$_2$Pr-c |
| 3,5-(CF$_3$)$_2$-4-Cl | CF$_2$Cl | H | H | C(O)CH$_2$CF$_3$ |
| 3,5-(CF$_3$)$_2$-4-Cl | CF$_2$Cl | CH$_3$ | H | C(O)(E4-2a) |
| 3,5-(CF$_3$)$_2$-4-Cl | CF$_2$Cl | H | H | C(O)CH$_2$SCH$_3$ |
| 3,5-(CF$_3$)$_2$-4-Cl | CF$_2$Cl | H | H | C(O)CH$_2$S(O)CH$_3$ |
| 3,5-(CF$_3$)$_2$-4-Cl | CF$_2$Cl | H | H | C(O)CH$_2$SO$_2$CH$_3$ |
| 3,5-(CF$_3$)$_2$-4-Cl | CF$_2$Cl | H | H | C(O)CH$_2$SEt |
| 3,5-(CF$_3$)$_2$-4-Cl | CF$_2$Cl | H | H | C(O)CH$_2$S(O)Et |
| 3,5-(CF$_3$)$_2$-4-Cl | CF$_2$Cl | H | H | C(O)CH$_2$SO$_2$Et |
| 3,5-Cl$_2$-4-OCHF$_2$ | CF$_3$ | H | H | C(O)Pr-c |
| 3,5-Cl$_2$-4-OCHF$_2$ | CF$_3$ | H | H | C(O)CH$_2$Pr-c |
| 3,5-Cl$_2$-4-OCHF$_2$ | CF$_3$ | H | H | C(O)CH$_2$CF$_3$ |
| 3,5-Cl$_2$-4-OCHF$_2$ | CF$_3$ | CH$_3$ | H | C(O)(E4-2a) |
| 3,5-Cl$_2$-4-OCHF$_2$ | CF$_3$ | H | H | C(O)CH$_2$SCH$_3$ |
| 3,5-Cl$_2$-4-OCHF$_2$ | CF$_3$ | H | H | C(O)CH$_2$S(O)CH$_3$ |
| 3,5-Cl$_2$-4-OCHF$_2$ | CF$_3$ | H | H | C(O)CH$_2$SO$_2$CH$_3$ |
| 3,5-Cl$_2$-4-OCHF$_2$ | CF$_3$ | H | H | C(O)CH$_2$SEt |
| 3,5-Cl$_2$-4-OCHF$_2$ | CF$_3$ | H | H | C(O)CH$_2$S(O)Et |
| 3,5-Cl$_2$-4-OCHF$_2$ | CF$_3$ | H | H | C(O)CH$_2$SO$_2$Et |
| 3,5-Br$_2$-4-OCHF$_2$ | CF$_3$ | H | H | C(O)Pr-c |
| 3,5-Br$_2$-4-OCHF$_2$ | CF$_3$ | H | H | C(O)CH$_2$Pr-c |
| 3,5-Br$_2$-4-OCHF$_2$ | CF$_3$ | H | H | C(O)CH$_2$CF$_3$ |
| 3,5-Br$_2$-4-OCHF$_2$ | CF$_3$ | CH$_3$ | H | C(O)(E4-2a) |
| 3,5-Br$_2$-4-OCHF$_2$ | CF$_3$ | H | H | C(O)CH$_2$SCH$_3$ |
| 3,5-Br$_2$-4-OCHF$_2$ | CF$_3$ | H | H | C(O)CH$_2$S(O)CH$_3$ |
| 3,5-Br$_2$-4-OCHF$_2$ | CF$_3$ | H | H | C(O)CH$_2$SO$_2$CH$_3$ |
| 3,5-Br$_2$-4-OCHF$_2$ | CF$_3$ | H | H | C(O)CH$_2$SEt |
| 3,5-Br$_2$-4-OCHF$_2$ | CF$_3$ | H | H | C(O)CH$_2$S(O)Et |
| 3,5-Br$_2$-4-OCHF$_2$ | CF$_3$ | H | H | C(O)CH$_2$SO$_2$Et |

Compounds represented by Structure Formulae [1]-1 to [1]-110 and [2]-1 to [2]-75 having structures in which $G^2$ is represented by $G^2$-4 to $G^2$-11.

$G^2$-4:
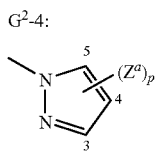

$G^2$-5:
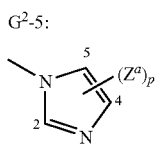

$G^2$-6:
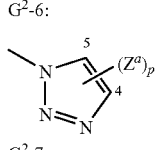

$G^2$-7:
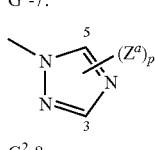

$G^2$-8:
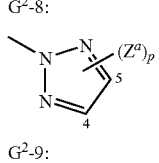

$G^2$-9:
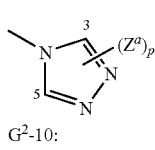

$G^2$-10:
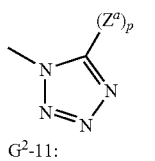

$G^2$-11:
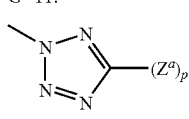

In Table, the number representing the substitution site of the substituent $(X)_m$ corresponds to the site indicated by the number in each of Structure Formulae [1]-1 to [1]-110 and [2]-1 to [2]-75, the number representing the substitution site of a substituent $(Z^a)_p$ corresponds to the site indicated by the number in $G^2$-4 to $G^2$-11, and the expression of "—" represents unsubstituted.

| $(X)_m$ | $R^3$ | $G^2$ | $(Z^a)_p$ |
|---|---|---|---|
| 3-Br | $CF_3$ | $G^2$-7 | — |
| 3-I | $CF_3$ | $G^2$-7 | — |
| 3-I | $CF_3$ | $G^2$-10 | — |
| 3-$CF_3$ | $CF_3$ | $G^2$-7 | — |

-continued

| $(X)_m$ | $R^3$ | $G^2$ | $(Z^a)_p$ |
|---|---|---|---|
| 3-$CF_3$ | $CF_3$ | $G^2$-10 | — |
| 3-$CF_2CF_3$ | $CF_3$ | $G^2$-7 | — |
| 3-$OCF_3$ | $CF_3$ | $G^2$-7 | — |
| 3-$SCF_3$ | $CF_3$ | $G^2$-7 | — |
| 3-$SF_5$ | $CF_3$ | $G^2$-7 | — |
| 3-Cl-4-F | $CF_3$ | $G^2$-7 | — |
| 3-Cl-4-F | $CF_3$ | $G^2$-10 | — |
| 3,4-$Cl_2$ | $CF_3$ | $G^2$-7 | — |
| 3,4-$Cl_2$ | $CF_3$ | $G^2$-10 | — |
| 3,5-$Cl_2$ | $CF_3$ | $G^2$-4 | 4-C(O)NHCH$_2$CF$_3$ |
| 3,5-$Cl_2$ | $CF_3$ | $G^2$-6 | — |
| 3,5-$Cl_2$ | $CF_3$ | $G^2$-7 | — |
| 3,5-$Cl_2$ | $CF_3$ | $G^2$-9 | — |
| 3,5-$Cl_2$ | $CF_3$ | $G^2$-10 | — |
| 3,5-$Cl_2$ | $CF_3$ | $G^2$-10 | $CH_3$ |
| 3,5-$Cl_2$ | $CF_2Cl$ | $G^2$-7 | — |
| 3-Br-4-F | $CF_3$ | $G^2$-7 | — |
| 3-Br-4-F | $CF_3$ | $G^2$-10 | — |
| 3-F-5-Br | $CF_3$ | $G^2$-7 | — |
| 3-F-5-Br | $CF_3$ | $G^2$-10 | — |
| 3-Br-4-Cl | $CF_3$ | $G^2$-7 | — |
| 3-Cl-4-Br | $CF_3$ | $G^2$-7 | — |
| 3-Cl-5-Br | $CF_3$ | $G^2$-4 | 4-C(O)NHCH$_2$CF$_3$ |
| 3-Cl-5-Br | $CF_3$ | $G^2$-6 | — |
| 3-Cl-5-Br | $CF_3$ | $G^2$-7 | — |
| 3-Cl-5-Br | $CF_3$ | $G^2$-9 | — |
| 3-Cl-5-Br | $CF_3$ | $G^2$-10 | — |
| 3-Cl-5-Br | $CF_3$ | $G^2$-10 | $CH_3$ |
| 3-Cl-5-Br | $CF_2Cl$ | $G^2$-7 | — |
| 3,4-$Br_2$ | $CF_3$ | $G^2$-7 | — |
| 3,5-$Br_2$ | $CF_3$ | $G^2$-4 | 4-C(O)NHCH$_2$CF$_3$ |
| 3,5-$Br_2$ | $CF_3$ | $G^2$-6 | — |
| 3,5-$Br_2$ | $CF_3$ | $G^2$-7 | — |
| 3,5-$Br_2$ | $CF_3$ | $G^2$-9 | — |
| 3,5-$Br_2$ | $CF_3$ | $G^2$-10 | — |
| 3,5-$Br_2$ | $CF_3$ | $G^2$-10 | $CH_3$ |
| 3,5-$Br_2$ | $CF_2Cl$ | $G^2$-7 | — |
| 3-I-4-F | $CF_3$ | $G^2$-7 | — |
| 3-F-5-I | $CF_3$ | $G^2$-7 | — |
| 3-Cl-5-I | $CF_3$ | $G^2$-7 | — |
| 3-Cl-5-I | $CF_3$ | $G^2$-10 | — |
| 3-$CF_3$-4-F | $CF_3$ | $G^2$-7 | — |
| 3-$CF_3$-4-F | $CF_3$ | $G^2$-10 | — |
| 3-F-5-$CF_3$ | $CF_3$ | $G^2$-7 | — |
| 3-F-5-$CF_3$ | $CF_3$ | $G^2$-10 | — |
| 3-$CF_3$-4-Cl | $CF_3$ | $G^2$-7 | — |
| 3-$CF_3$-4-Cl | $CF_3$ | $G^2$-10 | — |
| 3-Cl-5-$CF_3$ | $CF_3$ | $G^2$-4 | 4-C(O)NHCH$_2$CF$_3$ |
| 3-Cl-5-$CF_3$ | $CF_3$ | $G^2$-6 | — |
| 3-Cl-5-$CF_3$ | $CF_3$ | $G^2$-7 | — |
| 3-Cl-5-$CF_3$ | $CF_3$ | $G^2$-9 | — |
| 3-Cl-5-$CF_3$ | $CF_3$ | $G^2$-10 | — |
| 3-Cl-5-$CF_3$ | $CF_3$ | $G^2$-10 | $CH_3$ |
| 3-Cl-5-$CF_3$ | $CF_2Cl$ | $G^2$-7 | — |
| 3-Br-5-$CF_3$ | $CF_3$ | $G^2$-4 | 4-C(O)NHCH$_2$CF$_3$ |
| 3-Br-5-$CF_3$ | $CF_3$ | $G^2$-6 | — |
| 3-Br-5-$CF_3$ | $CF_3$ | $G^2$-7 | — |
| 3-Br-5-$CF_3$ | $CF_3$ | $G^2$-9 | — |
| 3-Br-5-$CF_3$ | $CF_3$ | $G^2$-10 | — |
| 3-Br-5-$CF_3$ | $CF_3$ | $G^2$-10 | $CH_3$ |
| 3-Br-5-$CF_3$ | $CF_2Cl$ | $G^2$-7 | — |
| 3,5-$(CF_3)_2$ | $CF_3$ | $G^2$-4 | — |
| 3,5-$(CF_3)_2$ | $CF_3$ | $G^2$-4 | 4-F |
| 3,5-$(CF_3)_2$ | $CF_3$ | $G^2$-4 | 4-Br |
| 3,5-$(CF_3)_2$ | $CF_3$ | $G^2$-4 | 4-C(O)NHCH$_2$CF$_3$ |
| 3,5-$(CF_3)_2$ | $CF_3$ | $G^2$-4 | 4-NO$_2$ |
| 3,5-$(CF_3)_2$ | $CF_3$ | $G^2$-5 | — |
| 3,5-$(CF_3)_2$ | $CF_3$ | $G^2$-6 | — |
| 3,5-$(CF_3)_2$ | $CF_3$ | $G^2$-7 | — |
| 3,5-$(CF_3)_2$ | $CF_3$ | $G^2$-7 | 3-Br |
| 3,5-$(CF_3)_2$ | $CF_3$ | $G^2$-7 | 5-Br |
| 3,5-$(CF_3)_2$ | $CF_3$ | $G^2$-7 | 3-NH$_2$ |
| 3,5-$(CF_3)_2$ | $CF_3$ | $G^2$-7 | 5-NH$_2$ |
| 3,5-$(CF_3)_2$ | $CF_3$ | $G^2$-8 | — |
| 3,5-$(CF_3)_2$ | $CF_3$ | $G^2$-9 | — |
| 3,5-$(CF_3)_2$ | $CF_3$ | $G^2$-10 | — |
| 3,5-$(CF_3)_2$ | $CF_3$ | $G^2$-10 | $CH_3$ |
| 3,5-$(CF_3)_2$ | $CF_3$ | $G^2$-11 | — |

-continued

| (X)$_m$ | R$^3$ | G$^2$ | (Z$^a$)$_p$ |
|---|---|---|---|
| 3,5-(CF$_3$)$_2$ | CF$_2$Cl | G$^2$-7 | — |
| 3,5-(CF$_3$)$_2$ | CF$_2$Cl | G$^2$-10 | — |
| 3-Cl-5-OCHF$_2$ | CF$_3$ | G$^2$-7 | — |
| 3-Cl-5-OCHF$_2$ | CF$_3$ | G$^2$-10 | — |
| 3-Br-5-OCHF$_2$ | CF$_3$ | G$^2$-7 | — |
| 3-CF$_3$-5-OCHF$_2$ | CF$_3$ | G$^2$-7 | — |
| 3-Cl-5-OCF$_3$ | CF$_3$ | G$^2$-7 | — |
| 3-Cl-5-OCF$_3$ | CF$_3$ | G$^2$-10 | — |
| 3-Br-5-OCF$_3$ | CF$_3$ | G$^2$-7 | — |
| 3-CF$_3$-5-OCF$_3$ | CF$_3$ | G$^2$-7 | — |
| 3-Cl-5-SCF$_3$ | CF$_3$ | G$^2$-7 | — |
| 3-Cl-5-SCF$_3$ | CF$_3$ | G$^2$-10 | — |
| 3-Br-5-SCF$_3$ | CF$_3$ | G$^2$-7 | — |
| 3-CF$_3$-5-CN | CF$_3$ | G$^2$-7 | — |
| 3,4,5-F$_3$ | CF$_3$ | G$^2$-7 | — |
| 3,5-Cl$_2$-4-F | CF$_3$ | G$^2$-4 | 4-C(O)NHCH$_2$CF$_3$ |
| 3,5-Cl$_2$-4-F | CF$_3$ | G$^2$-6 | — |
| 3,5-Cl$_2$-4-F | CF$_3$ | G$^2$-7 | — |
| 3,5-Cl$_2$-4-F | CF$_3$ | G$^2$-9 | — |
| 3,5-Cl$_2$-4-F | CF$_3$ | G$^2$-10 | — |
| 3,5-Cl$_2$-4-F | CF$_3$ | G$^2$-10 | CH$_3$ |
| 3,5-Cl$_2$-4-F | CF$_2$Cl | G$^2$-7 | — |
| 3,4,5-Cl$_3$ | CF$_3$ | G$^2$-4 | 4-C(O)NHCH$_2$CF$_3$ |
| 3,4,5-Cl$_3$ | CF$_3$ | G$^2$-6 | — |
| 3,4,5-Cl$_3$ | CF$_3$ | G$^2$-7 | — |
| 3,4,5-Cl$_3$ | CF$_3$ | G$^2$-9 | — |
| 3,4,5-Cl$_3$ | CF$_3$ | G$^2$-10 | — |
| 3,4,5-Cl$_3$ | CF$_3$ | G$^2$-10 | CH$_3$ |
| 3,4,5-Cl$_3$ | CF$_2$Cl | G$^2$-7 | — |
| 3,5-Br$_2$-4-F | CF$_3$ | G$^2$-4 | 4-C(O)NHCH$_2$CF$_3$ |
| 3,5-Br$_2$-4-F | CF$_3$ | G$^2$-6 | — |
| 3,5-Br$_2$-4-F | CF$_3$ | G$^2$-7 | — |
| 3,5-Br$_2$-4-F | CF$_3$ | G$^2$-9 | — |
| 3,5-Br$_2$-4-F | CF$_3$ | G$^2$-10 | — |
| 3,5-Br$_2$-4-F | CF$_3$ | G$^2$-10 | CH$_3$ |
| 3,5-Br$_2$-4-F | CF$_2$Cl | G$^2$-7 | — |
| 3,4,5-Br$_3$ | CF$_3$ | G$^2$-7 | — |
| 3,4-F$_2$-5-CF$_3$ | CF$_3$ | G$^2$-4 | 4-C(O)NHCH$_2$CF$_3$ |
| 3,4-F$_2$-5-CF$_3$ | CF$_3$ | G$^2$-6 | — |
| 3,4-F$_2$-5-CF$_3$ | CF$_3$ | G$^2$-7 | — |
| 3,4-F$_2$-5-CF$_3$ | CF$_3$ | G$^2$-9 | — |
| 3,4-F$_2$-5-CF$_3$ | CF$_3$ | G$^2$-10 | — |
| 3,4-F$_2$-5-CF$_3$ | CF$_3$ | G$^2$-10 | CH$_3$ |
| 3,4-F$_2$-5-CF$_3$ | CF$_2$Cl | G$^2$-7 | — |
| 3-Cl-4-F-5-CF$_3$ | CF$_3$ | G$^2$-4 | 4-C(O)NHCH$_2$CF$_3$ |
| 3-Cl-4-F-5-CF$_3$ | CF$_3$ | G$^2$-6 | — |
| 3-Cl-4-F-5-CF$_3$ | CF$_3$ | G$^2$-7 | — |
| 3-Cl-4-F-5-CF$_3$ | CF$_3$ | G$^2$-9 | — |
| 3-Cl-4-F-5-CF$_3$ | CF$_3$ | G$^2$-10 | — |
| 3-Cl-4-F-5-CF$_3$ | CF$_3$ | G$^2$-10 | CH$_3$ |
| 3-Cl-4-F-5-CF$_3$ | CF$_2$Cl | G$^2$-7 | — |
| 3,4-Cl$_2$-5-CF$_3$ | CF$_3$ | G$^2$-4 | 4-C(O)NHCH$_2$CF$_3$ |
| 3,4-Cl$_2$-5-CF$_3$ | CF$_3$ | G$^2$-6 | — |
| 3,4-Cl$_2$-5-CF$_3$ | CF$_3$ | G$^2$-7 | — |
| 3,4-Cl$_2$-5-CF$_3$ | CF$_3$ | G$^2$-9 | — |
| 3,4-Cl$_2$-5-CF$_3$ | CF$_3$ | G$^2$-10 | — |
| 3,4-Cl$_2$-5-CF$_3$ | CF$_3$ | G$^2$-10 | CH$_3$ |
| 3,4-Cl$_2$-5-CF$_3$ | CF$_2$Cl | G$^2$-7 | — |
| 3,5-(CF$_3$)$_2$-4-Cl | CF$_3$ | G$^2$-4 | 4-C(O)NHCH$_2$CF$_3$ |
| 3,5-(CF$_3$)$_2$-4-Cl | CF$_3$ | G$^2$-6 | — |
| 3,5-(CF$_3$)$_2$-4-Cl | CF$_3$ | G$^2$-7 | — |
| 3,5-(CF$_3$)$_2$-4-Cl | CF$_3$ | G$^2$-9 | — |
| 3,5-(CF$_3$)$_2$-4-Cl | CF$_3$ | G$^2$-10 | — |
| 3,5-(CF$_3$)$_2$-4-Cl | CF$_3$ | G$^2$-10 | CH$_3$ |
| 3,5-(CF$_3$)$_2$-4-Cl | CF$_2$Cl | G$^2$-7 | — |
| 3,5-Cl$_2$-4-OCHF$_2$ | CF$_3$ | G$^2$-7 | — |
| 3,5-Br$_2$-4-OCHF$_2$ | CF$_3$ | G$^2$-7 | — |

Specific examples of the production intermediates or active compounds represented by Structure Formulae [3]-1 to [3]-90 and [4]-1 to [4]-18 included in the present invention include compounds shown in Table 6. However, the compounds in Table 6 are only for exemplification and the present invention is not limited to these compounds.

TABLE 6

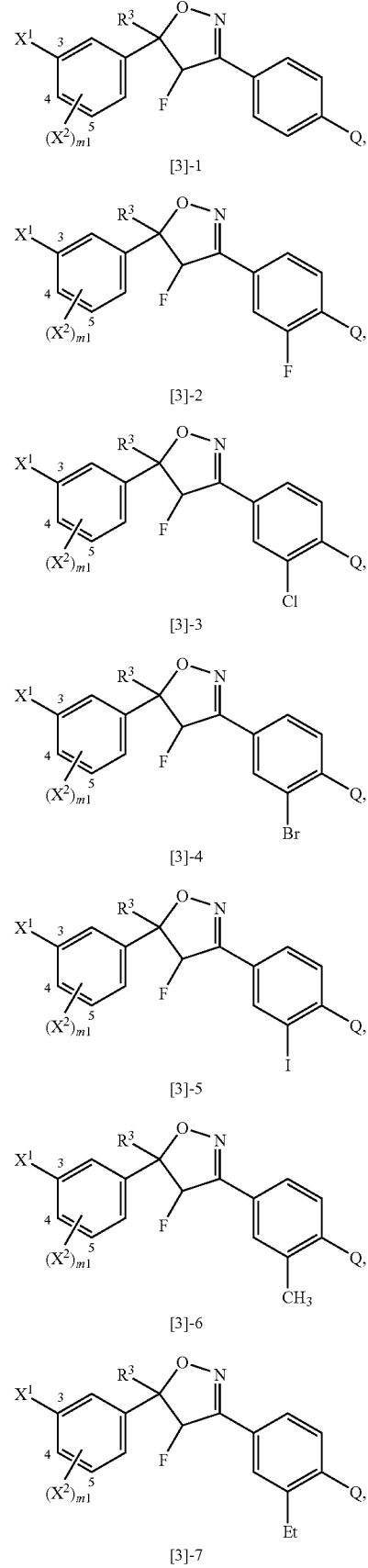

TABLE 6-continued
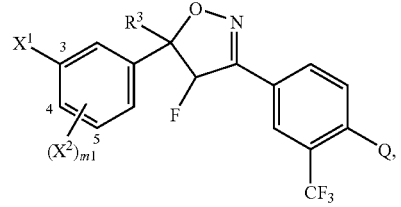
[3]-8
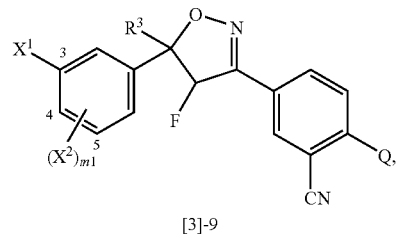
[3]-9
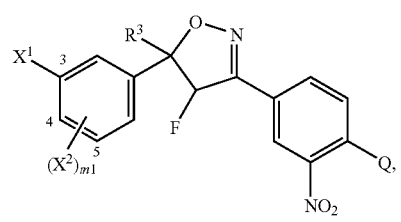
[3]-10
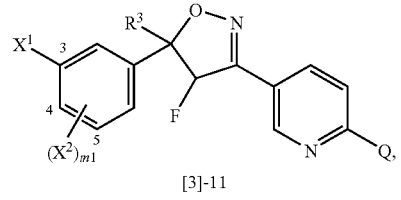
[3]-11
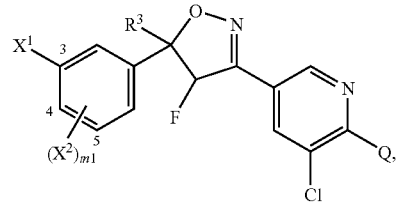
[3]-12
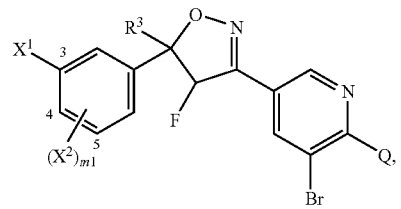
[3]-13
TABLE 6-continued
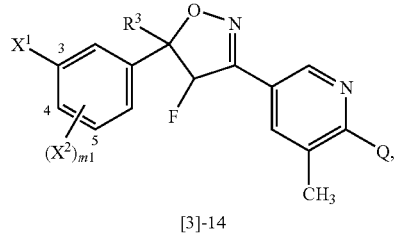
[3]-14
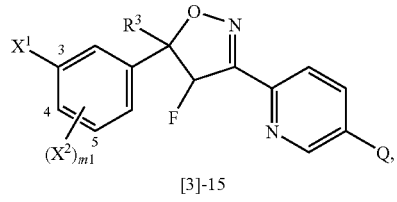
[3]-15
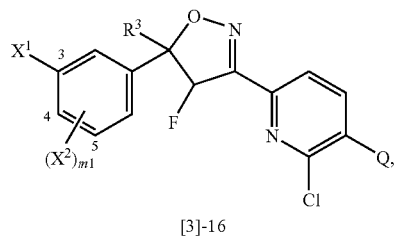
[3]-16
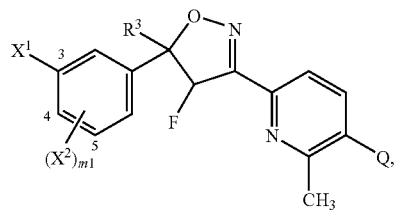
[3]-17
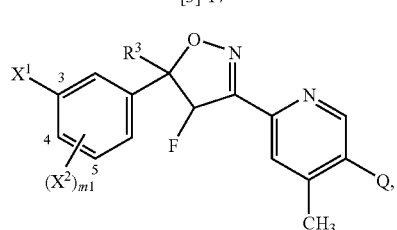
[3]-18
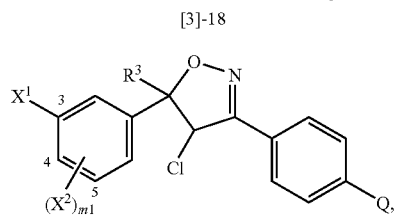
[3]-19
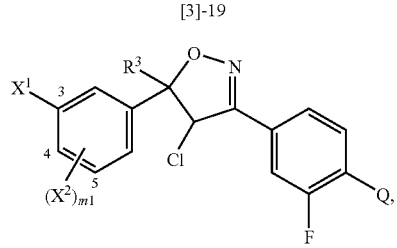
[3]-20

TABLE 6-continued
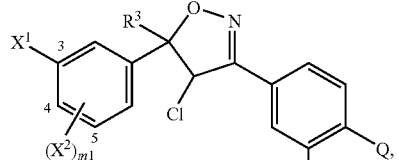
[3]-21
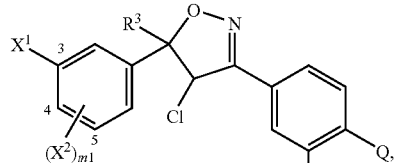
[3]-22
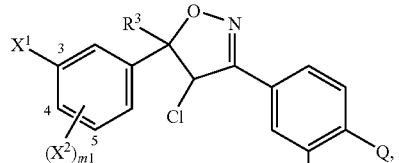
[3]-23
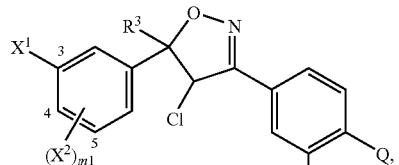
[3]-24
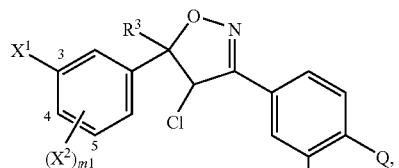
[3]-25
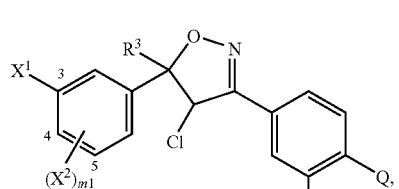
[3]-26
TABLE 6-continued
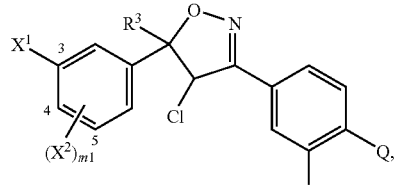
[3]-27
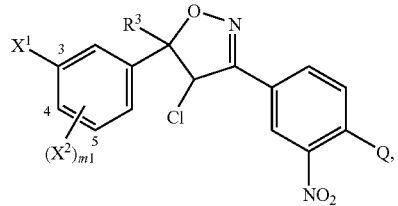
[3]-28
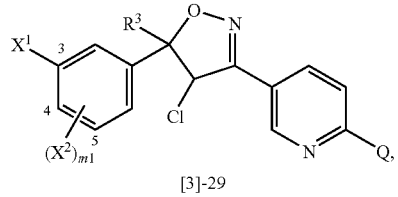
[3]-29
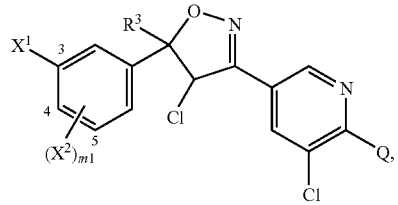
[3]-30
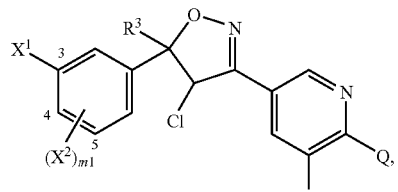
[3]-31
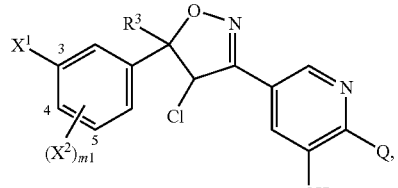
[3]-32
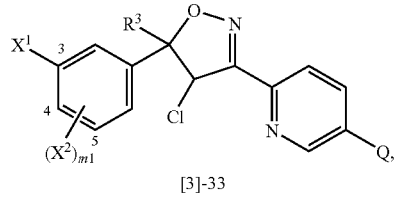
[3]-33

TABLE 6-continued
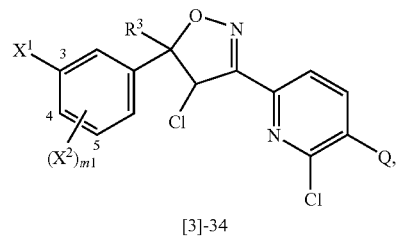
[3]-34
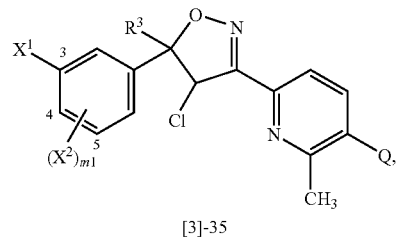
[3]-35
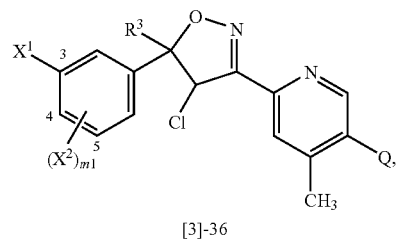
[3]-36
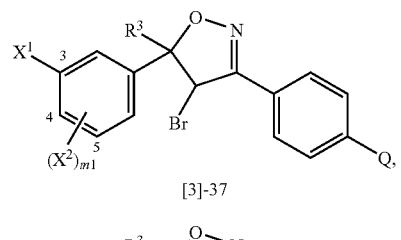
[3]-37
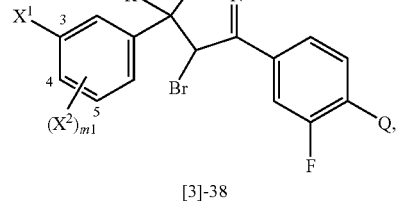
[3]-38
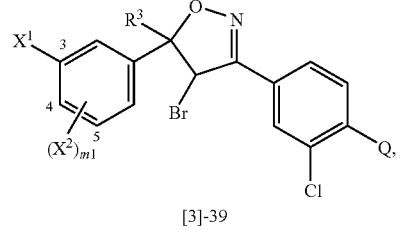
[3]-39
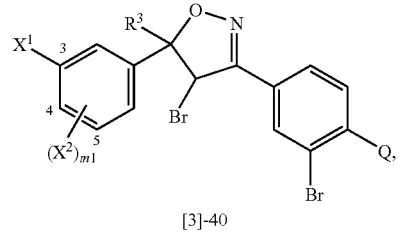
[3]-40
TABLE 6-continued
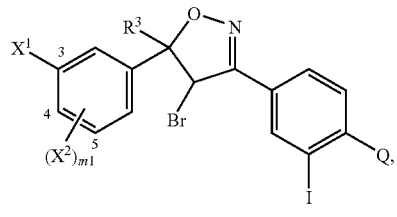
[3]-41
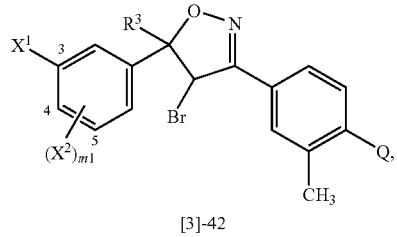
[3]-42
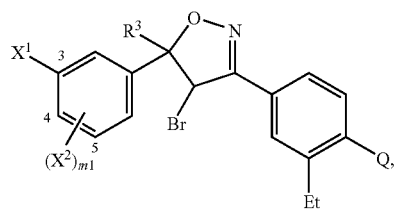
[3]-43
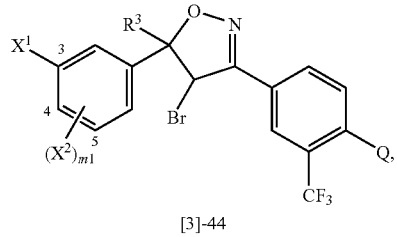
[3]-44
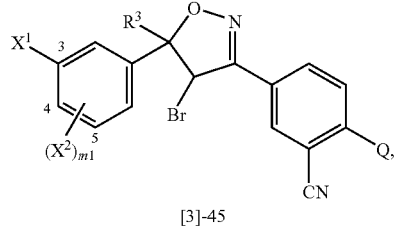
[3]-45
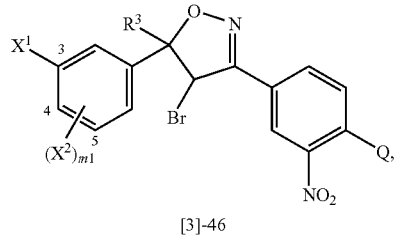
[3]-46

TABLE 6-continued
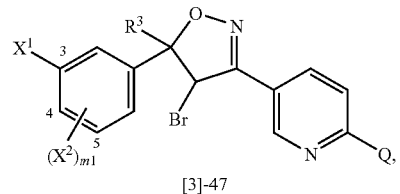
[3]-47
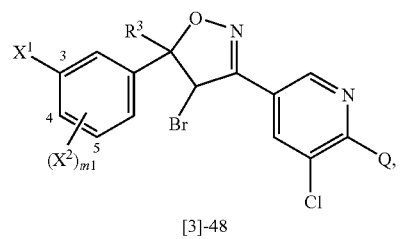
[3]-48
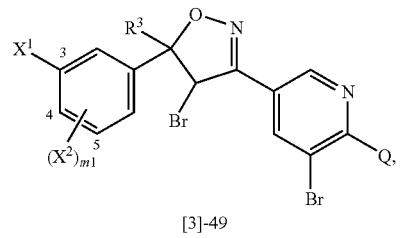
[3]-49
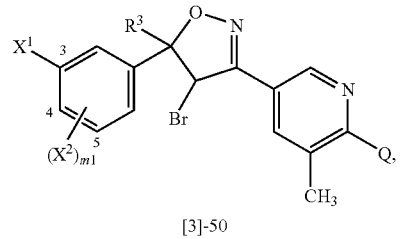
[3]-50
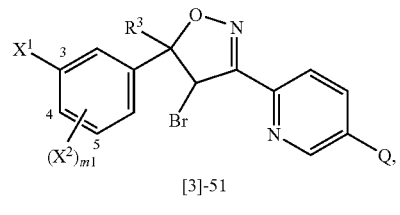
[3]-51
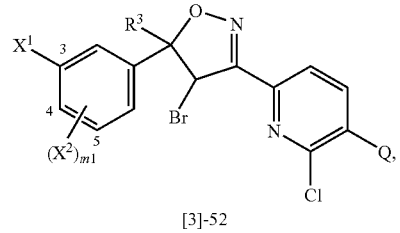
[3]-52
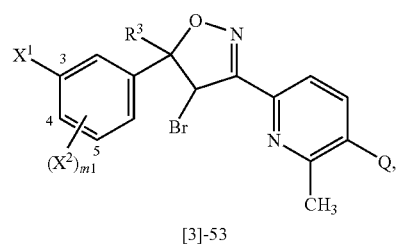
[3]-53
TABLE 6-continued
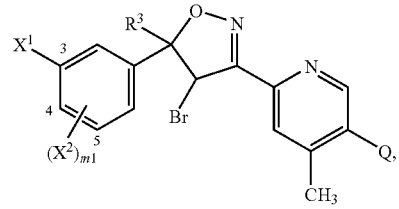
[3]-54
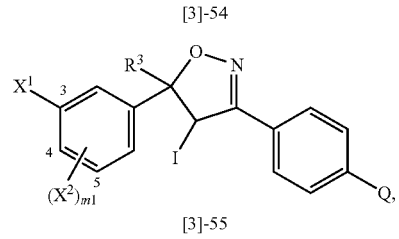
[3]-55
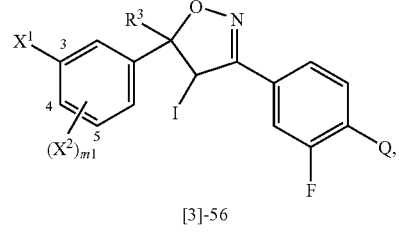
[3]-56
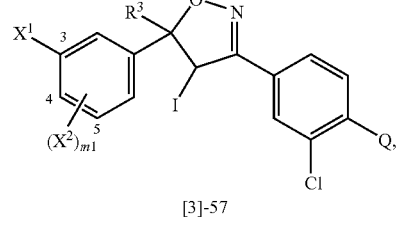
[3]-57
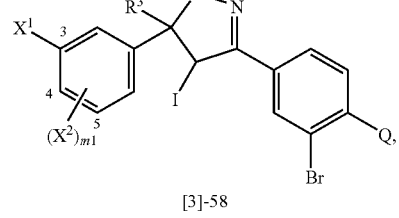
[3]-58
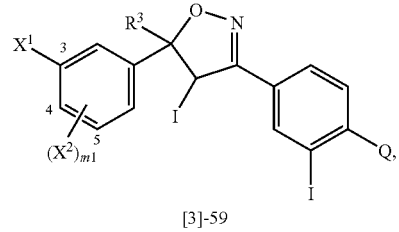
[3]-59
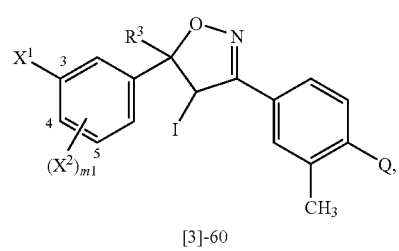
[3]-60

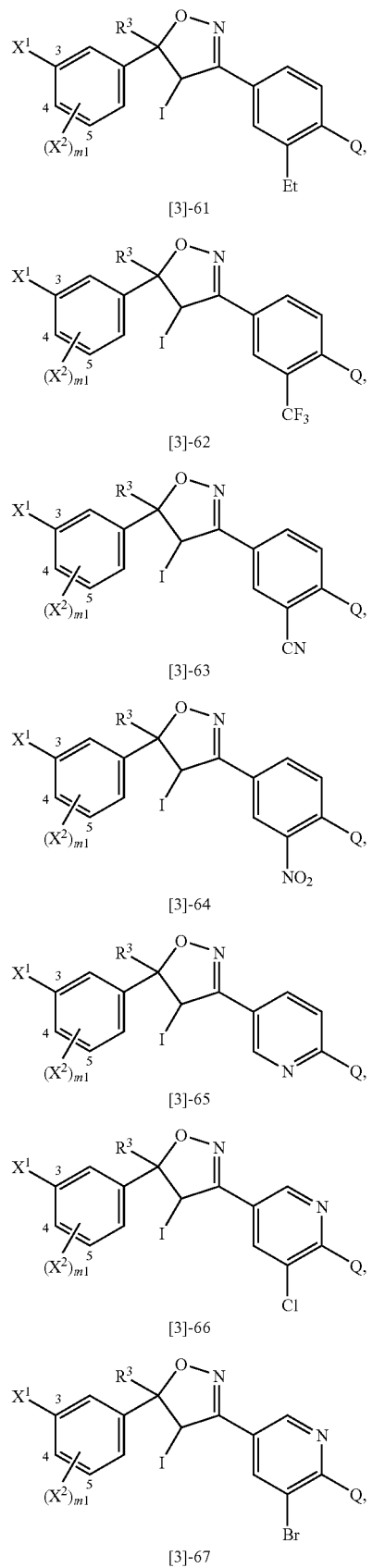
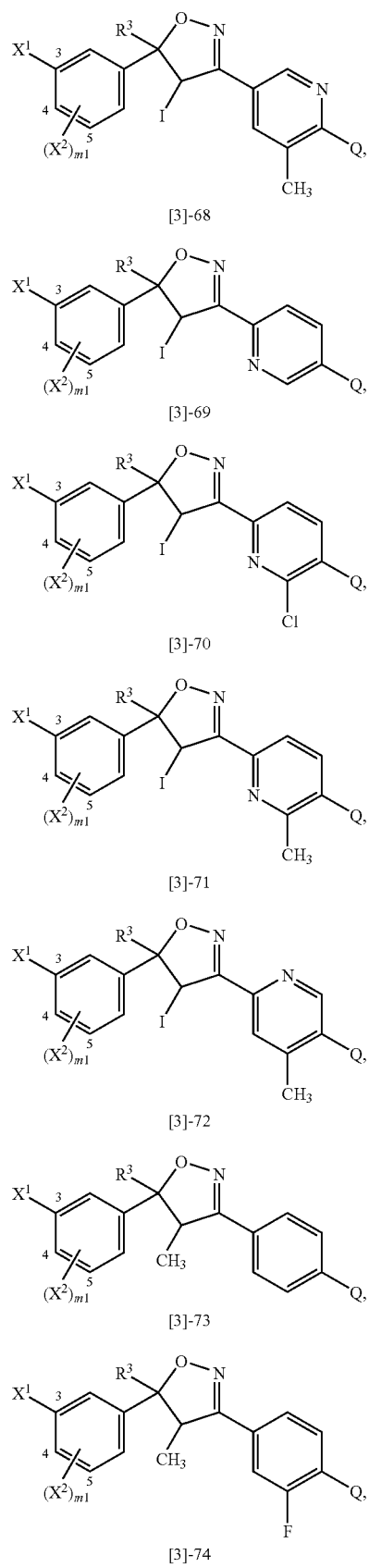

TABLE 6-continued
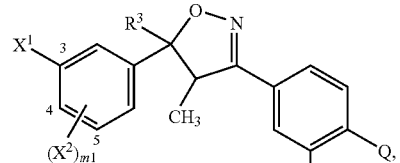
[3]-75
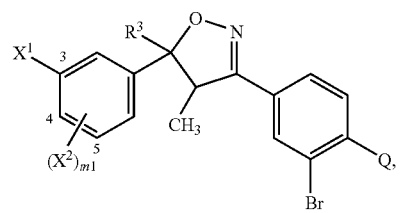
[3]-76
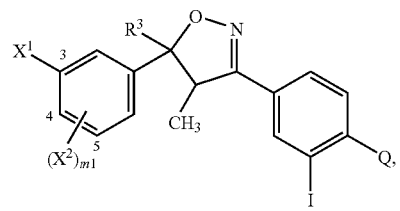
[3]-77
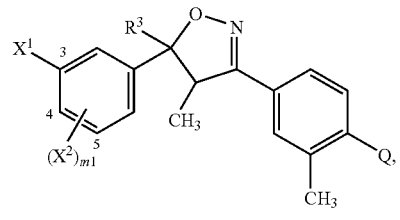
[3]-78
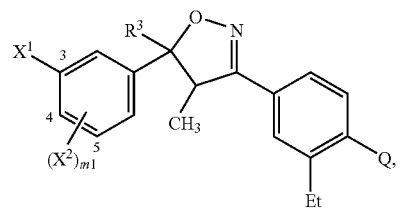
[3]-79
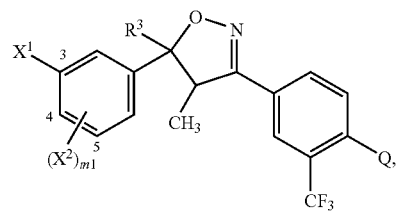
[3]-80
TABLE 6-continued
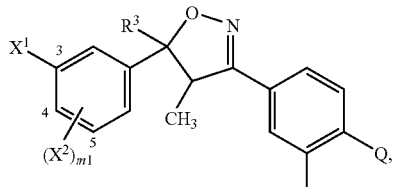
[3]-81
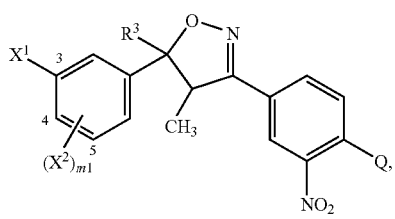
[3]-82
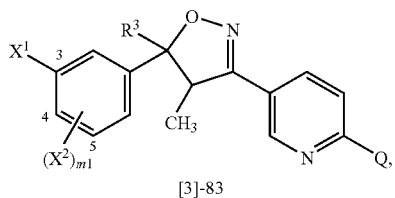
[3]-83
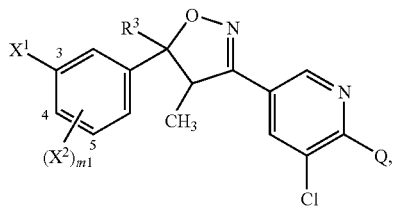
[3]-84
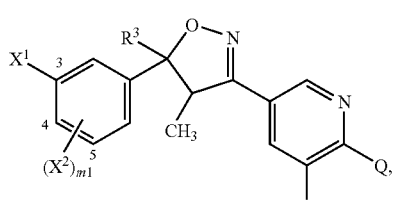
[3]-85
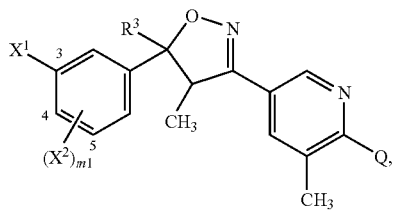
[3]-86
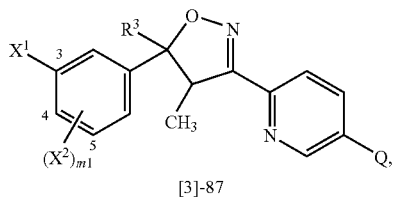
[3]-87

TABLE 6-continued
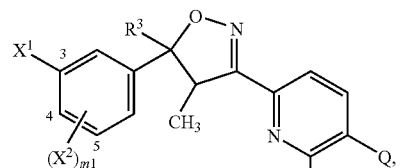
[3]-88
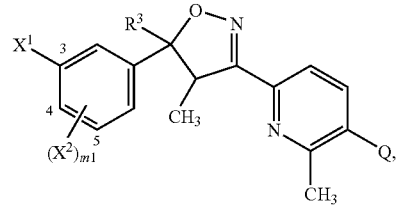
[3]-89
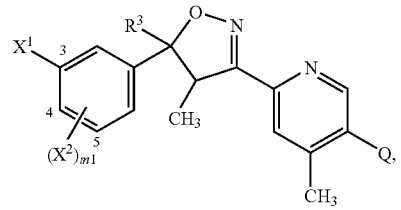
[3]-90
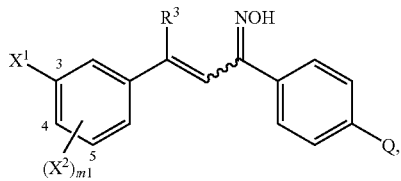
[4]-1
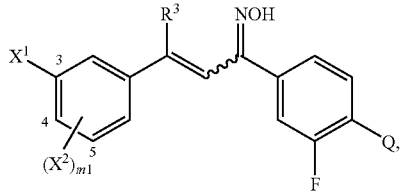
[4]-2
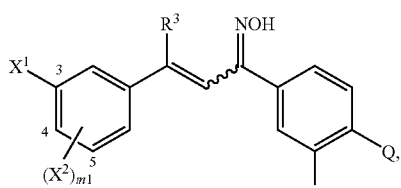
[4]-3
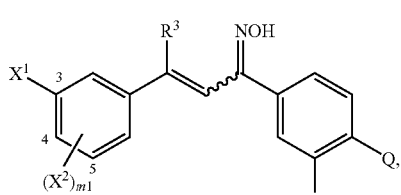
[4]-4
TABLE 6-continued
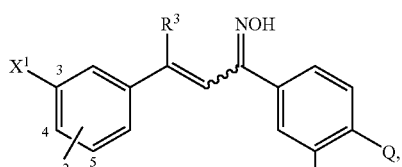
[4]-5
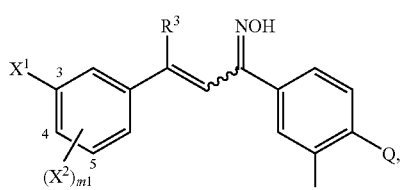
[4]-6
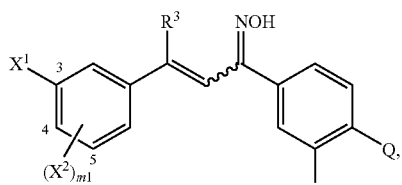
[4]-7
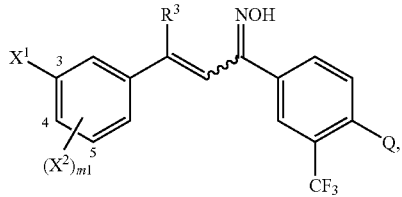
[4]-8
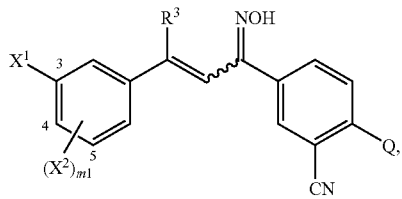
[4]-9
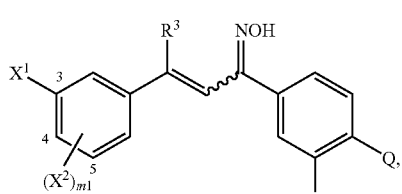
[4]-10
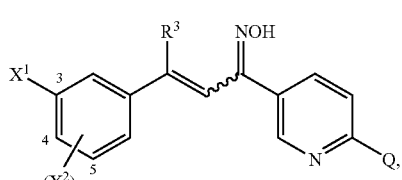
[4]-11

TABLE 6-continued

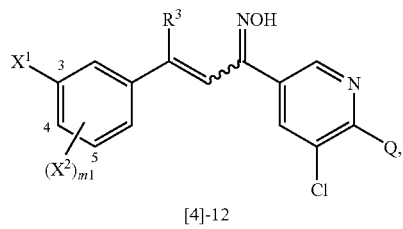

[4]-12

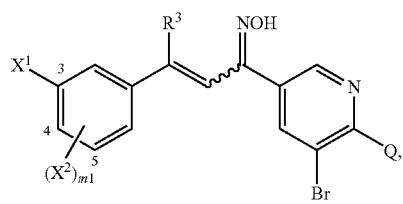

[4]-13

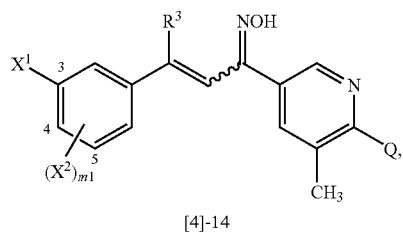

[4]-14

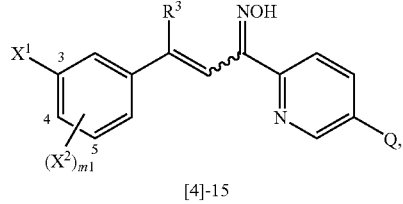

[4]-15

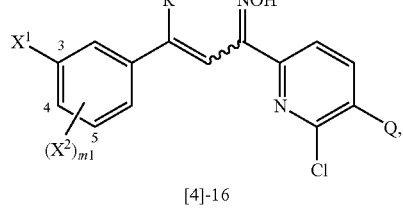

[4]-16

TABLE 6-continued

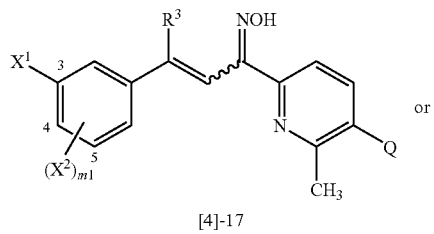

[4]-17 or

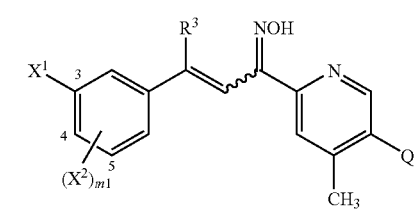

[4]-18

In Table, the number representing the substitution site of the substituent $X^1$ and $(X^2)_{m1}$ corresponds to the site indicated by the number in each of Structure Formulae [1]-1 to [1]-110 and [2]-1 to [2]-75.

Furthermore, in Table, aromatic heterocyclic rings represented by D7-1a, D11-1a and D22-1a represent the following structures.

D7-1a:

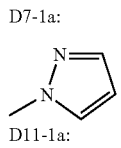

D11-1a:

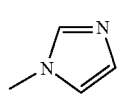

D22-1a:

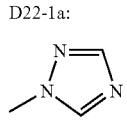

Moreover, in Table, the description of Et represents an ethyl group and t-Bu and Bu-t represent a tertiary butyl group.

| $X^1, (X^2)_{ml}$ | $R^3$ | Q | $X^1, (X^2)_{ml}$ | $R^3$ | Q |
|---|---|---|---|---|---|
| 3-Br | $CF_3$ | CN | 3,5-$(CF_3)_2$ | $CF_3$ | $CH(CH_3)NH_2$ |
| 3-Br | $CF_3$ | C(O)OH | 3,5-$(CF_3)_2$ | $CF_3$ | $CH(CN)NH_2$ |
| 3-Br | $CF_3$ | $C(O)OCH_3$ | 3,5-$(CF_3)_2$ | $CF_3$ | CHO |
| 3-Br | $CF_3$ | C(O)Cl | 3,5-$(CF_3)_2$ | $CF_3$ | $C(O)CH_3$ |
| 3-Br | $CF_3$ | $NO_2$ | 3,5-$(CF_3)_2$ | $CF_3$ | CN |
| 3-I | $CF_3$ | CN | 3,5-$(CF_3)_2$ | $CF_3$ | C(O)OH |
| 3-I | $CF_3$ | C(O)OH | 3,5-$(CF_3)_2$ | $CF_3$ | $C(O)OCH_3$ |
| 3-I | $CF_3$ | $C(O)OCH_3$ | 3,5-$(CF_3)_2$ | $CF_3$ | C(O)OEt |
| 3-I | $CF_3$ | C(O)OEt | 3,5-$(CF_3)_2$ | $CF_3$ | C(O)OBu-t |
| 3-I | $CF_3$ | C(O)Cl | 3,5-$(CF_3)_2$ | $CF_3$ | C(O)Cl |
| 3-I | $CF_3$ | $NO_2$ | 3,5-$(CF_3)_2$ | $CF_3$ | C(O)(D7-1a) |
| 3-I | $CF_3$ | $NH_2$ | 3,5-$(CF_3)_2$ | $CF_3$ | C(O)(D11-1a) |
| 3-I | $CF_3$ | $SCH_3$ | 3,5-$(CF_3)_2$ | $CF_3$ | C(O)(D22-1a) |
| 3-I | $CF_3$ | $S(O)CH_3$ | 3,5-$(CF_3)_2$ | $CF_3$ | $NO_2$ |
| 3-I | $CF_3$ | $SO_2CH_3$ | 3,5-$(CF_3)_2$ | $CF_3$ | $NH_2$ |
| 3-$CF_3$ | $CF_3$ | CN | 3,5-$(CF_3)_2$ | $CF_3$ | OH |
| 3-$CF_3$ | $CF_3$ | C(O)OH | 3,5-$(CF_3)_2$ | $CF_3$ | $OCH_3$ |
| 3-$CF_3$ | $CF_3$ | $C(O)OCH_3$ | 3,5-$(CF_3)_2$ | $CF_3$ | $OCF_3$ |

-continued

| $X^1, (X^2)_{ml}$ | $R^3$ | Q | $X^1, (X^2)_{ml}$ | $R^3$ | Q |
|---|---|---|---|---|---|
| 3-CF$_3$ | CF$_3$ | C(O)OEt | 3,5-(CF$_3$)$_2$ | CF$_3$ | OSO$_2$CH$_3$ |
| 3-CF$_3$ | CF$_3$ | C(O)Cl | 3,5-(CF$_3$)$_2$ | CF$_3$ | OSO$_2$CF$_3$ |
| 3-CF$_3$ | CF$_3$ | NO$_2$ | 3,5-(CF$_3$)$_2$ | CF$_3$ | SCH$_3$ |
| 3-CF$_3$ | CF$_3$ | NH$_2$ | 3,5-(CF$_3$)$_2$ | CF$_3$ | S(O)CH$_3$ |
| 3-CF$_3$ | CF$_3$ | SCH$_3$ | 3,5-(CF$_3$)$_2$ | CF$_3$ | SO$_2$CH$_3$ |
| 3-CF$_3$ | CF$_3$ | S(O)CH$_3$ | 3,5-(CF$_3$)$_2$ | CF$_2$Cl | CN |
| 3-CF$_3$ | CF$_3$ | SO$_2$CH$_3$ | 3,5-(CF$_3$)$_2$ | CF$_2$Cl | C(O)OH |
| 3-CF$_2$CF$_3$ | CF$_3$ | CN | 3,5-(CF$_3$)$_2$ | CF$_2$Cl | C(O)OCH$_3$ |
| 3-CF$_2$CF$_3$ | CF$_3$ | C(O)OH | 3,5-(CF$_3$)$_2$ | CF$_2$Cl | C(O)OEt |
| 3-CF$_2$CF$_3$ | CF$_3$ | C(O)OCH$_3$ | 3,5-(CF$_3$)$_2$ | CF$_2$Cl | C(O)Cl |
| 3-CF$_2$CF$_3$ | CF$_3$ | C(O)Cl | 3,5-(CF$_3$)$_2$ | CF$_2$Cl | NO$_2$ |
| 3-CF$_2$CF$_3$ | CF$_3$ | NO$_2$ | 3,5-(CF$_3$)$_2$ | CF$_2$Cl | NH$_2$ |
| 3-OCF$_3$ | CF$_3$ | CN | 3,5-(CF$_3$)$_2$ | CF$_2$Cl | SCH$_3$ |
| 3-OCF$_3$ | CF$_3$ | C(O)OH | 3,5-(CF$_3$)$_2$ | CF$_2$Cl | S(O)CH$_3$ |
| 3-OCF$_3$ | CF$_3$ | C(O)OCH$_3$ | 3,5-(CF$_3$)$_2$ | CF$_2$Cl | SO$_2$CH$_3$ |
| 3-OCF$_3$ | CF$_3$ | C(O)Cl | 3-Cl-5-OCHF$_2$ | CF$_3$ | CN |
| 3-OCF$_3$ | CF$_3$ | NO$_2$ | 3-Cl-5-OCHF$_2$ | CF$_3$ | C(O)OH |
| 3-SCF$_3$ | CF$_3$ | CN | 3-Cl-5-OCHF$_2$ | CF$_3$ | C(O)OCH$_3$ |
| 3-SCF$_3$ | CF$_3$ | C(O)OH | 3-Cl-5-OCHF$_2$ | CF$_3$ | C(O)OEt |
| 3-SCF$_3$ | CF$_3$ | C(O)OCH$_3$ | 3-Cl-5-OCHF$_2$ | CF$_3$ | C(O)Cl |
| 3-SCF$_3$ | CF$_3$ | C(O)Cl | 3-Cl-5-OCHF$_2$ | CF$_3$ | NO$_2$ |
| 3-SCF$_3$ | CF$_3$ | NO$_2$ | 3-Cl-5-OCHF$_2$ | CF$_3$ | NH$_2$ |
| 3-SF$_5$ | CF$_3$ | CN | 3-Cl-5-OCHF$_2$ | CF$_3$ | SCH$_3$ |
| 3-SF$_5$ | CF$_3$ | C(O)OH | 3-Cl-5-OCHF$_2$ | CF$_3$ | S(O)CH$_3$ |
| 3-SF$_5$ | CF$_3$ | C(O)OCH$_3$ | 3-Cl-5-OCHF$_2$ | CF$_3$ | SO$_2$CH$_3$ |
| 3-SF$_5$ | CF$_3$ | C(O)Cl | 3-Br-5-OCHF$_2$ | CF$_3$ | CN |
| 3-SF$_5$ | CF$_3$ | NO$_2$ | 3-Br-5-OCHF$_2$ | CF$_3$ | C(O)OH |
| 3-Cl-4-F | CF$_3$ | CN | 3-Br-5-OCHF$_2$ | CF$_3$ | C(O)OCH$_3$ |
| 3-Cl-4-F | CF$_3$ | C(O)OH | 3-Br-5-OCHF$_2$ | CF$_3$ | C(O)Cl |
| 3-Cl-4-F | CF$_3$ | C(O)OCH$_3$ | 3-Br-5-OCHF$_2$ | CF$_3$ | NO$_2$ |
| 3-Cl-4-F | CF$_3$ | C(O)OEt | 3-CF$_3$-5-OCHF$_2$ | CF$_3$ | CN |
| 3-Cl-4-F | CF$_3$ | C(O)Cl | 3-CF$_3$-5-OCHF$_2$ | CF$_3$ | C(O)OH |
| 3-Cl-4-F | CF$_3$ | NO$_2$ | 3-CF$_3$-5-OCHF$_2$ | CF$_3$ | C(O)OCH$_3$ |
| 3-Cl-4-F | CF$_3$ | NH$_2$ | 3-CF$_3$-5-OCHF$_2$ | CF$_3$ | C(O)Cl |
| 3-Cl-4-F | CF$_3$ | SCH$_3$ | 3-CF$_3$-5-OCHF$_2$ | CF$_3$ | NO$_2$ |
| 3-Cl-4-F | CF$_3$ | S(O)CH$_3$ | 3-Cl-5-OCF$_3$ | CF$_3$ | CN |
| 3-Cl-4-F | CF$_3$ | SO$_2$CH$_3$ | 3-Cl-5-OCF$_3$ | CF$_3$ | C(O)OH |
| 3-F-5-Cl | CF$_3$ | CN | 3-Cl-5-OCF$_3$ | CF$_3$ | C(O)OCH$_3$ |
| 3-F-5-Cl | CF$_3$ | C(O)OH | 3-Cl-5-OCF$_3$ | CF$_3$ | C(O)OEt |
| 3-F-5-Cl | CF$_3$ | C(O)OCH$_3$ | 3-Cl-5-OCF$_3$ | CF$_3$ | C(O)Cl |
| 3-F-5-Cl | CF$_3$ | C(O)OEt | 3-Cl-5-OCF$_3$ | CF$_3$ | NO$_2$ |
| 3-F-5-Cl | CF$_3$ | C(O)Cl | 3-Cl-5-OCF$_3$ | CF$_3$ | NH$_2$ |
| 3-F-5-Cl | CF$_3$ | NO$_2$ | 3-Cl-5-OCF$_3$ | CF$_3$ | SCH$_3$ |
| 3-F-5-Cl | CF$_3$ | NH$_2$ | 3-Cl-5-OCF$_3$ | CF$_3$ | S(O)CH$_3$ |
| 3-F-5-Cl | CF$_3$ | SCH$_3$ | 3-Cl-5-OCF$_3$ | CF$_3$ | SO$_2$CH$_3$ |
| 3-F-5-Cl | CF$_3$ | S(O)CH$_3$ | 3-Br-5-OCF$_3$ | CF$_3$ | CN |
| 3-F-5-Cl | CF$_3$ | SO$_2$CH$_3$ | 3-Br-5-OCF$_3$ | CF$_3$ | C(O)OH |
| 3,4-Cl$_2$ | CF$_3$ | CN | 3-Br-5-OCF$_3$ | CF$_3$ | C(O)OCH$_3$ |
| 3,4-Cl$_2$ | CF$_3$ | C(O)OH | 3-Br-5-OCF$_3$ | CF$_3$ | C(O)Cl |
| 3,4-Cl$_2$ | CF$_3$ | C(O)OCH$_3$ | 3-Br-5-OCF$_3$ | CF$_3$ | NO$_2$ |
| 3,4-Cl$_2$ | CF$_3$ | C(O)OEt | 3-CF$_3$-5-OCF$_3$ | CF$_3$ | CN |
| 3,4-Cl$_2$ | CF$_3$ | C(O)Cl | 3-CF$_3$-5-OCF$_3$ | CF$_3$ | C(O)OH |
| 3,4-Cl$_2$ | CF$_3$ | NO$_2$ | 3-CF$_3$-5-OCF$_3$ | CF$_3$ | C(O)OCH$_3$ |
| 3,4-Cl$_2$ | CF$_3$ | NH$_2$ | 3-CF$_3$-5-OCF$_3$ | CF$_3$ | C(O)Cl |
| 3,4-Cl$_2$ | CF$_3$ | SCH$_3$ | 3-CF$_3$-5-OCF$_3$ | CF$_3$ | NO$_2$ |
| 3,4-Cl$_2$ | CF$_3$ | S(O)CH$_3$ | 3-Cl-5-SCF$_3$ | CF$_3$ | CN |
| 3,4-Cl$_2$ | CF$_3$ | SO$_2$CH$_3$ | 3-Cl-5-SCF$_3$ | CF$_3$ | C(O)OH |
| 3,5-Cl$_2$ | CF$_3$ | F | 3-Cl-5-SCF$_3$ | CF$_3$ | C(O)OCH$_3$ |
| 3,5-Cl$_2$ | CF$_3$ | Cl | 3-Cl-5-SCF$_3$ | CF$_3$ | C(O)OEt |
| 3,5-Cl$_2$ | CF$_3$ | Br | 3-Cl-5-SCF$_3$ | CF$_3$ | C(O)Cl |
| 3,5-Cl$_2$ | CF$_3$ | I | 3-Cl-5-SCF$_3$ | CF$_3$ | NO$_2$ |
| 3,5-Cl$_2$ | CF$_3$ | CH$_3$ | 3-Cl-5-SCF$_3$ | CF$_3$ | NH$_2$ |
| 3,5-Cl$_2$ | CF$_3$ | CF$_3$ | 3-Cl-5-SCF$_3$ | CF$_3$ | SCH$_3$ |
| 3,5-Cl$_2$ | CF$_3$ | CH$_2$OH | 3-Cl-5-SCF$_3$ | CF$_3$ | S(O)CH$_3$ |
| 3,5-Cl$_2$ | CF$_3$ | CH$_2$OC(O)CH$_3$ | 3-Cl-5-SCF$_3$ | CF$_3$ | SO$_2$CH$_3$ |
| 3,5-Cl$_2$ | CF$_3$ | CH$_2$NH$_2$ | 3-Br-5-SCF$_3$ | CF$_3$ | CN |
| 3,5-Cl$_2$ | CF$_3$ | CH(CH$_3$)NH$_2$ | 3-Br-5-SCF$_3$ | CF$_3$ | C(O)OH |
| 3,5-Cl$_2$ | CF$_3$ | CH(CN)NH$_2$ | 3-Br-5-SCF$_3$ | CF$_3$ | C(O)OCH$_3$ |
| 3,5-Cl$_2$ | CF$_3$ | CHO | 3-Br-5-SCF$_3$ | CF$_3$ | C(O)Cl |
| 3,5-Cl$_2$ | CF$_3$ | CN | 3-Br-5-SCF$_3$ | CF$_3$ | NO$_2$ |
| 3,5-Cl$_2$ | CF$_3$ | C(O)OH | 3-CF$_3$-5-CN | CF$_3$ | CN |
| 3,5-Cl$_2$ | CF$_3$ | C(O)OCH$_3$ | 3-CF$_3$-5-CN | CF$_3$ | C(O)OH |
| 3,5-Cl$_2$ | CF$_3$ | C(O)OEt | 3-CF$_3$-5-CN | CF$_3$ | C(O)OCH$_3$ |
| 3,5-Cl$_2$ | CF$_3$ | C(O)Cl | 3-CF$_3$-5-CN | CF$_3$ | C(O)Cl |
| 3,5-Cl$_2$ | CF$_3$ | C(O)(D7-1a) | 3-CF$_3$-5-CN | CF$_3$ | NO$_2$ |
| 3,5-Cl$_2$ | CF$_3$ | C(O)(D11-1a) | 3,4,5-F$_3$ | CF$_3$ | CN |
| 3,5-Cl$_2$ | CF$_3$ | C(O)(D22-1a) | 3,4,5-F$_3$ | CF$_3$ | C(O)OH |
| 3,5-Cl$_2$ | CF$_3$ | NO$_2$ | 3,4,5-F$_3$ | CF$_3$ | C(O)OCH$_3$ |

-continued

| $X^1, (X^2)_{ml}$ | $R^3$ | Q | $X^1, (X^2)_{ml}$ | $R^3$ | Q |
|---|---|---|---|---|---|
| 3,5-Cl$_2$ | CF$_3$ | NH$_2$ | 3,4,5-F$_3$ | CF$_3$ | C(O)Cl |
| 3,5-Cl$_2$ | CF$_3$ | OCF$_3$ | 3,4,5-F$_3$ | CF$_3$ | NO$_2$ |
| 3,5-Cl$_2$ | CF$_3$ | OSO$_2$CF$_3$ | 3,5-Cl$_2$-4-F | CF$_3$ | F |
| 3,5-Cl$_2$ | CF$_3$ | SCH$_3$ | 3,5-Cl$_2$-4-F | CF$_3$ | Cl |
| 3,5-Cl$_2$ | CF$_3$ | S(O)CH$_3$ | 3,5-Cl$_2$-4-F | CF$_3$ | Br |
| 3,5-Cl$_2$ | CF$_3$ | SO$_2$CH$_3$ | 3,5-Cl$_2$-4-F | CF$_3$ | I |
| 3,5-Cl$_2$ | CF$_2$Cl | CN | 3,5-Cl$_2$-4-F | CF$_3$ | CH$_3$ |
| 3,5-Cl$_2$ | CF$_2$Cl | C(O)OH | 3,5-Cl$_2$-4-F | CF$_3$ | CF$_3$ |
| 3,5-Cl$_2$ | CF$_2$Cl | C(O)OCH$_3$ | 3,5-Cl$_2$-4-F | CF$_3$ | CH$_2$OH |
| 3,5-Cl$_2$ | CF$_2$Cl | C(O)Cl | 3,5-Cl$_2$-4-F | CF$_3$ | CH$_2$OC(O)CH$_3$ |
| 3,5-Cl$_2$ | CF$_2$Cl | NO$_2$ | 3,5-Cl$_2$-4-F | CF$_3$ | CH$_2$NH$_2$ |
| 3-Br-4-F | CF$_3$ | CN | 3,5-Cl$_2$-4-F | CF$_3$ | CH(CH$_3$)NH$_2$ |
| 3-Br-4-F | CF$_3$ | C(O)OH | 3,5-Cl$_2$-4-F | CF$_3$ | CH(CN)NH$_2$ |
| 3-Br-4-F | CF$_3$ | C(O)OCH$_3$ | 3,5-Cl$_2$-4-F | CF$_3$ | CHO |
| 3-Br-4-F | CF$_3$ | C(O)OEt | 3,5-Cl$_2$-4-F | CF$_3$ | CN |
| 3-Br-4-F | CF$_3$ | C(O)Cl | 3,5-Cl$_2$-4-F | CF$_3$ | C(O)OH |
| 3-Br-4-F | CF$_3$ | NO$_2$ | 3,5-Cl$_2$-4-F | CF$_3$ | C(O)OCH$_3$ |
| 3-Br-4-F | CF$_3$ | NH$_2$ | 3,5-Cl$_2$-4-F | CF$_3$ | C(O)OEt |
| 3-Br-4-F | CF$_3$ | SCH$_3$ | 3,5-Cl$_2$-4-F | CF$_3$ | C(O)Cl |
| 3-Br-4-F | CF$_3$ | S(O)CH$_3$ | 3,5-Cl$_2$-4-F | CF$_3$ | C(O)(D7-1a) |
| 3-Br-4-F | CF$_3$ | SO$_2$CH$_3$ | 3,5-Cl$_2$-4-F | CF$_3$ | C(O)(D11-1a) |
| 3-F-5-Br | CF$_3$ | CN | 3,5-Cl$_2$-4-F | CF$_3$ | C(O)(D22-1a) |
| 3-F-5-Br | CF$_3$ | C(O)OH | 3,5-Cl$_2$-4-F | CF$_3$ | NO$_2$ |
| 3-F-5-Br | CF$_3$ | C(O)OCH$_3$ | 3,5-Cl$_2$-4-F | CF$_3$ | NH$_2$ |
| 3-F-5-Br | CF$_3$ | C(O)OEt | 3,5-Cl$_2$-4-F | CF$_3$ | OCF$_3$ |
| 3-F-5-Br | CF$_3$ | C(O)Cl | 3,5-Cl$_2$-4-F | CF$_3$ | OSO$_2$CF$_3$ |
| 3-F-5-Br | CF$_3$ | NO$_2$ | 3,5-Cl$_2$-4-F | CF$_3$ | SCH$_3$ |
| 3-F-5-Br | CF$_3$ | NH$_2$ | 3,5-Cl$_2$-4-F | CF$_3$ | S(O)CH$_3$ |
| 3-F-5-Br | CF$_3$ | SCH$_3$ | 3,5-Cl$_2$-4-F | CF$_3$ | SO$_2$CH$_3$ |
| 3-F-5-Br | CF$_3$ | S(O)CH$_3$ | 3,5-Cl$_2$-4-F | CF$_2$Cl | CN |
| 3-F-5-Br | CF$_3$ | SO$_2$CH$_3$ | 3,5-Cl$_2$-4-F | CF$_2$Cl | C(O)OH |
| 3-Br-4-Cl | CF$_3$ | CN | 3,5-Cl$_2$-4-F | CF$_2$Cl | C(O)OCH$_3$ |
| 3-Br-4-Cl | CF$_3$ | C(O)OH | 3,5-Cl$_2$-4-F | CF$_2$Cl | C(O)Cl |
| 3-Br-4-Cl | CF$_3$ | C(O)OCH$_3$ | 3,5-Cl$_2$-4-F | CF$_2$Cl | NO$_2$ |
| 3-Br-4-Cl | CF$_3$ | C(O)Cl | 3,4,5-Cl$_3$ | CF$_3$ | F |
| 3-Br-4-Cl | CF$_3$ | NO$_2$ | 3,4,5-Cl$_3$ | CF$_3$ | Cl |
| 3-Cl-4-Br | CF$_3$ | CN | 3,4,5-Cl$_3$ | CF$_3$ | Br |
| 3-Cl-4-Br | CF$_3$ | C(O)OH | 3,4,5-Cl$_3$ | CF$_3$ | I |
| 3-Cl-4-Br | CF$_3$ | C(O)OCH$_3$ | 3,4,5-Cl$_3$ | CF$_3$ | CH$_3$ |
| 3-Cl-4-Br | CF$_3$ | C(O)Cl | 3,4,5-Cl$_3$ | CF$_3$ | CF$_3$ |
| 3-Cl-4-Br | CF$_3$ | NO$_2$ | 3,4,5-Cl$_3$ | CF$_3$ | CH$_2$OH |
| 3-Cl-5-Br | CF$_3$ | F | 3,4,5-Cl$_3$ | CF$_3$ | CH$_2$OC(O)CH$_3$ |
| 3-Cl-5-Br | CF$_3$ | Cl | 3,4,5-Cl$_3$ | CF$_3$ | CH$_2$NH$_2$ |
| 3-Cl-5-Br | CF$_3$ | Br | 3,4,5-Cl$_3$ | CF$_3$ | CH(CH$_3$)NH$_2$ |
| 3-Cl-5-Br | CF$_3$ | I | 3,4,5-Cl$_3$ | CF$_3$ | CH(CN)NH$_2$ |
| 3-Cl-5-Br | CF$_3$ | CH$_3$ | 3,4,5-Cl$_3$ | CF$_3$ | CHO |
| 3-Cl-5-Br | CF$_3$ | CF$_3$ | 3,4,5-Cl$_3$ | CF$_3$ | CN |
| 3-Cl-5-Br | CF$_3$ | CH$_2$OH | 3,4,5-Cl$_3$ | CF$_3$ | C(O)OH |
| 3-Cl-5-Br | CF$_3$ | CH$_2$OC(O)CH$_3$ | 3,4,5-Cl$_3$ | CF$_3$ | C(O)OCH$_3$ |
| 3-Cl-5-Br | CF$_3$ | CH$_2$NH$_2$ | 3,4,5-Cl$_3$ | CF$_3$ | C(O)OEt |
| 3-Cl-5-Br | CF$_3$ | CH(CH$_3$)NH$_2$ | 3,4,5-Cl$_3$ | CF$_3$ | C(O)Cl |
| 3-Cl-5-Br | CF$_3$ | CH(CN)NH$_2$ | 3,4,5-Cl$_3$ | CF$_3$ | C(O)(D7-1a) |
| 3-Cl-5-Br | CF$_3$ | CHO | 3,4,5-Cl$_3$ | CF$_3$ | C(O)(D11-1a) |
| 3-Cl-5-Br | CF$_3$ | CN | 3,4,5-Cl$_3$ | CF$_3$ | C(O)(D22-1a) |
| 3-Cl-5-Br | CF$_3$ | C(O)OH | 3,4,5-Cl$_3$ | CF$_3$ | NO$_2$ |
| 3-Cl-5-Br | CF$_3$ | C(O)OCH$_3$ | 3,4,5-Cl$_3$ | CF$_3$ | NH$_2$ |
| 3-Cl-5-Br | CF$_3$ | C(O)OEt | 3,4,5-Cl$_3$ | CF$_3$ | OCF$_3$ |
| 3-Cl-5-Br | CF$_3$ | C(O)Cl | 3,4,5-Cl$_3$ | CF$_3$ | OSO$_2$CF$_3$ |
| 3-Cl-5-Br | CF$_3$ | C(O)(D7-1a) | 3,4,5-Cl$_3$ | CF$_3$ | SCH$_3$ |
| 3-Cl-5-Br | CF$_3$ | C(O)(D11-1a) | 3,4,5-Cl$_3$ | CF$_3$ | S(O)CH$_3$ |
| 3-Cl-5-Br | CF$_3$ | C(O)(D22-1a) | 3,4,5-Cl$_3$ | CF$_3$ | SO$_2$CH$_3$ |
| 3-Cl-5-Br | CF$_3$ | NO$_2$ | 3,4,5-Cl$_3$ | CF$_2$Cl | CN |
| 3-Cl-5-Br | CF$_3$ | NH$_2$ | 3,4,5-Cl$_3$ | CF$_2$Cl | C(O)OH |
| 3-Cl-5-Br | CF$_3$ | OCF$_3$ | 3,4,5-Cl$_3$ | CF$_2$Cl | C(O)OCH$_3$ |
| 3-Cl-5-Br | CF$_3$ | OSO$_2$CF$_3$ | 3,4,5-Cl$_3$ | CF$_2$Cl | C(O)Cl |
| 3-Cl-5-Br | CF$_3$ | SCH$_3$ | 3,4,5-Cl$_3$ | CF$_2$Cl | NO$_2$ |
| 3-Cl-5-Br | CF$_3$ | S(O)CH$_3$ | 3,5-Br$_2$-4-F | CF$_3$ | F |
| 3-Cl-5-Br | CF$_3$ | SO$_2$CH$_3$ | 3,5-Br$_2$-4-F | CF$_3$ | Cl |
| 3-Cl-5-Br | CF$_2$Cl | CN | 3,5-Br$_2$-4-F | CF$_3$ | Br |
| 3-Cl-5-Br | CF$_2$Cl | C(O)OH | 3,5-Br$_2$-4-F | CF$_3$ | I |
| 3-Cl-5-Br | CF$_2$Cl | C(O)OCH$_3$ | 3,5-Br$_2$-4-F | CF$_3$ | CH$_3$ |
| 3-Cl-5-Br | CF$_2$Cl | C(O)Cl | 3,5-Br$_2$-4-F | CF$_3$ | CF$_3$ |
| 3-Cl-5-Br | CF$_2$Cl | NO$_2$ | 3,5-Br$_2$-4-F | CF$_3$ | CH$_2$OH |
| 3,4-Br$_2$ | CF$_3$ | CN | 3,5-Br$_2$-4-F | CF$_3$ | CH$_2$OC(O)CH$_3$ |
| 3,4-Br$_2$ | CF$_3$ | C(O)OH | 3,5-Br$_2$-4-F | CF$_3$ | CH$_2$NH$_2$ |
| 3,4-Br$_2$ | CF$_3$ | C(O)OCH$_3$ | 3,5-Br$_2$-4-F | CF$_3$ | CH(CH$_3$)NH$_2$ |
| 3,4-Br$_2$ | CF$_3$ | C(O)Cl | 3,5-Br$_2$-4-F | CF$_3$ | CH(CN)NH$_2$ |
| 3,4-Br$_2$ | CF$_3$ | NO$_2$ | 3,5-Br$_2$-4-F | CF$_3$ | CHO |

-continued

| $X^1, (X^2)_{ml}$ | $R^3$ | Q | $X^1, (X^2)_{ml}$ | $R^3$ | Q |
|---|---|---|---|---|---|
| 3,5-Br$_2$ | CF$_3$ | F | 3,5-Br$_2$-4-F | CF$_3$ | CN |
| 3,5-Br$_2$ | CF$_3$ | Cl | 3,5-Br$_2$-4-F | CF$_3$ | C(O)OH |
| 3,5-Br$_2$ | CF$_3$ | Br | 3,5-Br$_2$-4-F | CF$_3$ | C(O)OCH$_3$ |
| 3,5-Br$_2$ | CF$_3$ | I | 3,5-Br$_2$-4-F | CF$_3$ | C(O)OEt |
| 3,5-Br$_2$ | CF$_3$ | CH$_3$ | 3,5-Br$_2$-4-F | CF$_3$ | C(O)Cl |
| 3,5-Br$_2$ | CF$_3$ | CF$_3$ | 3,5-Br$_2$-4-F | CF$_3$ | C(O)(D7-1a) |
| 3,5-Br$_2$ | CF$_3$ | CH$_2$OH | 3,5-Br$_2$-4-F | CF$_3$ | C(O)(D11-1a) |
| 3,5-Br$_2$ | CF$_3$ | CH$_2$OC(O)CH$_3$ | 3,5-Br$_2$-4-F | CF$_3$ | C(O)(D22-1a) |
| 3,5-Br$_2$ | CF$_3$ | CH$_2$NH$_2$ | 3,5-Br$_2$-4-F | CF$_3$ | NO$_2$ |
| 3,5-Br$_2$ | CF$_3$ | CH(CH$_3$)NH$_2$ | 3,5-Br$_2$-4-F | CF$_3$ | NH$_2$ |
| 3,5-Br$_2$ | CF$_3$ | CH(CN)NH$_2$ | 3,5-Br$_2$-4-F | CF$_3$ | OCF$_3$ |
| 3,5-Br$_2$ | CF$_3$ | CHO | 3,5-Br$_2$-4-F | CF$_3$ | OSO$_2$CF$_3$ |
| 3,5-Br$_2$ | CF$_3$ | CN | 3,5-Br$_2$-4-F | CF$_3$ | SCH$_3$ |
| 3,5-Br$_2$ | CF$_3$ | C(O)OH | 3,5-Br$_2$-4-F | CF$_3$ | S(O)CH$_3$ |
| 3,5-Br$_2$ | CF$_3$ | C(O)OCH$_3$ | 3,5-Br$_2$-4-F | CF$_3$ | SO$_2$CH$_3$ |
| 3,5-Br$_2$ | CF$_3$ | C(O)OEt | 3,5-Br$_2$-4-F | CF$_2$Cl | CN |
| 3,5-Br$_2$ | CF$_3$ | C(O)Cl | 3,5-Br$_2$-4-F | CF$_2$Cl | C(O)OH |
| 3,5-Br$_2$ | CF$_3$ | C(O)(D7-1a) | 3,5-Br$_2$-4-F | CF$_2$Cl | C(O)OCH$_3$ |
| 3,5-Br$_2$ | CF$_3$ | C(O)(D11-1a) | 3,5-Br$_2$-4-F | CF$_2$Cl | C(O)Cl |
| 3,5-Br$_2$ | CF$_3$ | C(O)(D22-1a) | 3,5-Br$_2$-4-F | CF$_2$Cl | NO$_2$ |
| 3,5-Br$_2$ | CF$_3$ | NO$_2$ | 3,4,5-Br$_3$ | CF$_3$ | CN |
| 3,5-Br$_2$ | CF$_3$ | NH$_2$ | 3,4,5-Br$_3$ | CF$_3$ | C(O)OH |
| 3,5-Br$_2$ | CF$_3$ | OCF$_3$ | 3,4,5-Br$_3$ | CF$_3$ | C(O)OCH$_3$ |
| 3,5-Br$_2$ | CF$_3$ | OSO$_2$CF$_3$ | 3,4,5-Br$_3$ | CF$_3$ | C(O)Cl |
| 3,5-Br$_2$ | CF$_3$ | SCH$_3$ | 3,4,5-Br$_3$ | CF$_3$ | NO$_2$ |
| 3,5-Br$_2$ | CF$_3$ | S(O)CH$_3$ | 3,4-F$_2$-5-CF$_3$ | CF$_3$ | F |
| 3,5-Br$_2$ | CF$_3$ | SO$_2$CH$_3$ | 3,4-F$_2$-5-CF$_3$ | CF$_3$ | Cl |
| 3,5-Br$_2$ | CF$_2$Cl | CN | 3,4-F$_2$-5-CF$_3$ | CF$_3$ | Br |
| 3,5-Br$_2$ | CF$_2$Cl | C(O)OH | 3,4-F$_2$-5-CF$_3$ | CF$_3$ | I |
| 3,5-Br$_2$ | CF$_2$Cl | C(O)OCH$_3$ | 3,4-F$_2$-5-CF$_3$ | CF$_3$ | CH$_3$ |
| 3,5-Br$_2$ | CF$_2$Cl | C(O)Cl | 3,4-F$_2$-5-CF$_3$ | CF$_3$ | CF$_3$ |
| 3,5-Br$_2$ | CF$_2$Cl | NO$_2$ | 3,4-F$_2$-5-CF$_3$ | CF$_3$ | CH$_2$OH |
| 3-I-4-F | CF$_3$ | CN | 3,4-F$_2$-5-CF$_3$ | CF$_3$ | CH$_2$OC(O)CH$_3$ |
| 3-I-4-F | CF$_3$ | C(O)OH | 3,4-F$_2$-5-CF$_3$ | CF$_3$ | CH$_2$NH$_2$ |
| 3-I-4-F | CF$_3$ | C(O)OCH$_3$ | 3,4-F$_2$-5-CF$_3$ | CF$_3$ | CH(CH$_3$)NH$_2$ |
| 3-I-4-F | CF$_3$ | C(O)Cl | 3,4-F$_2$-5-CF$_3$ | CF$_3$ | CH(CN)NH$_2$ |
| 3-I-4-F | CF$_3$ | NO$_2$ | 3,4-F$_2$-5-CF$_3$ | CF$_3$ | CHO |
| 3-F-5-I | CF$_3$ | CN | 3,4-F$_2$-5-CF$_3$ | CF$_3$ | CN |
| 3-F-5-I | CF$_3$ | C(O)OH | 3,4-F$_2$-5-CF$_3$ | CF$_3$ | C(O)OH |
| 3-F-5-I | CF$_3$ | C(O)OCH$_3$ | 3,4-F$_2$-5-CF$_3$ | CF$_3$ | C(O)OCH$_3$ |
| 3-F-5-I | CF$_3$ | C(O)Cl | 3,4-F$_2$-5-CF$_3$ | CF$_3$ | C(O)OEt |
| 3-F-5-I | CF$_3$ | NO$_2$ | 3,4-F$_2$-5-CF$_3$ | CF$_3$ | C(O)Cl |
| 3-Cl-5-I | CF$_3$ | CN | 3,4-F$_2$-5-CF$_3$ | CF$_3$ | C(O)(D7-1a) |
| 3-Cl-5-I | CF$_3$ | C(O)OH | 3,4-F$_2$-5-CF$_3$ | CF$_3$ | C(O)(D11-1a) |
| 3-Cl-5-I | CF$_3$ | C(O)OCH$_3$ | 3,4-F$_2$-5-CF$_3$ | CF$_3$ | C(O)(D22-1a) |
| 3-Cl-5-I | CF$_3$ | C(O)OEt | 3,4-F$_2$-5-CF$_3$ | CF$_3$ | NO$_2$ |
| 3-Cl-5-I | CF$_3$ | C(O)Cl | 3,4-F$_2$-5-CF$_3$ | CF$_3$ | NH$_2$ |
| 3-Cl-5-I | CF$_3$ | NO$_2$ | 3,4-F$_2$-5-CF$_3$ | CF$_3$ | OCF$_3$ |
| 3-Cl-5-I | CF$_3$ | NH$_2$ | 3,4-F$_2$-5-CF$_3$ | CF$_3$ | OSO$_2$CF$_3$ |
| 3-Cl-5-I | CF$_3$ | SCH$_3$ | 3,4-F$_2$-5-CF$_3$ | CF$_3$ | SCH$_3$ |
| 3-Cl-5-I | CF$_3$ | S(O)CH$_3$ | 3,4-F$_2$-5-CF$_3$ | CF$_3$ | S(O)CH$_3$ |
| 3-Cl-5-I | CF$_3$ | SO$_2$CH$_3$ | 3,4-F$_2$-5-CF$_3$ | CF$_3$ | SO$_2$CH$_3$ |
| 3-CF$_3$-4-F | CF$_3$ | CN | 3,4-F$_2$-5-CF$_3$ | CF$_2$Cl | CN |
| 3-CF$_3$-4-F | CF$_3$ | C(O)OH | 3,4-F$_2$-5-CF$_3$ | CF$_2$Cl | C(O)OH |
| 3-CF$_3$-4-F | CF$_3$ | C(O)OCH$_3$ | 3,4-F$_2$-5-CF$_3$ | CF$_2$Cl | C(O)OCH$_3$ |
| 3-CF$_3$-4-F | CF$_3$ | C(O)OEt | 3,4-F$_2$-5-CF$_3$ | CF$_2$Cl | C(O)Cl |
| 3-CF$_3$-4-F | CF$_3$ | C(O)Cl | 3,4-F$_2$-5-CF$_3$ | CF$_2$Cl | NO$_2$ |
| 3-CF$_3$-4-F | CF$_3$ | NO$_2$ | 3-Cl-4-F-5-CF$_3$ | CF$_3$ | F |
| 3-CF$_3$-4-F | CF$_3$ | NH$_2$ | 3-Cl-4-F-5-CF$_3$ | CF$_3$ | Cl |
| 3-CF$_3$-4-F | CF$_3$ | SCH$_3$ | 3-Cl-4-F-5-CF$_3$ | CF$_3$ | Br |
| 3-CF$_3$-4-F | CF$_3$ | S(O)CH$_3$ | 3-Cl-4-F-5-CF$_3$ | CF$_3$ | I |
| 3-CF$_3$-4-F | CF$_3$ | SO$_2$CH$_3$ | 3-Cl-4-F-5-CF$_3$ | CF$_3$ | CH$_3$ |
| 3-F-5-CF$_3$ | CF$_3$ | CN | 3-Cl-4-F-5-CF$_3$ | CF$_3$ | CF$_3$ |
| 3-F-5-CF$_3$ | CF$_3$ | C(O)OH | 3-Cl-4-F-5-CF$_3$ | CF$_3$ | CH$_2$OH |
| 3-F-5-CF$_3$ | CF$_3$ | C(O)OCH$_3$ | 3-Cl-4-F-5-CF$_3$ | CF$_3$ | CH$_2$OC(O)CH$_3$ |
| 3-F-5-CF$_3$ | CF$_3$ | C(O)OEt | 3-Cl-4-F-5-CF$_3$ | CF$_3$ | CH$_2$NH$_2$ |
| 3-F-5-CF$_3$ | CF$_3$ | C(O)Cl | 3-Cl-4-F-5-CF$_3$ | CF$_3$ | CH(CH$_3$)NH$_2$ |
| 3-F-5-CF$_3$ | CF$_3$ | NO$_2$ | 3-Cl-4-F-5-CF$_3$ | CF$_3$ | CH(C)NH$_2$ |
| 3-F-5-CF$_3$ | CF$_3$ | NH$_2$ | 3-Cl-4-F-5-CF$_3$ | CF$_3$ | CHO |
| 3-F-5-CF$_3$ | CF$_3$ | SCH$_3$ | 3-Cl-4-F-5-CF$_3$ | CF$_3$ | CN |
| 3-F-5-CF$_3$ | CF$_3$ | S(O)CH$_3$ | 3-Cl-4-F-5-CF$_3$ | CF$_3$ | C(O)OH |
| 3-F-5-CF$_3$ | CF$_3$ | SO$_2$CH$_3$ | 3-Cl-4-F-5-CF$_3$ | CF$_3$ | C(O)OCH$_3$ |
| 3-CF$_3$-4-Cl | CF$_3$ | CN | 3-Cl-4-F-5-CF$_3$ | CF$_3$ | C(O)OEt |
| 3-CF$_3$-4-Cl | CF$_3$ | C(O)OH | 3-Cl-4-F-5-CF$_3$ | CF$_3$ | C(O)Cl |
| 3-CF$_3$-4-Cl | CF$_3$ | C(O)OCH$_3$ | 3-Cl-4-F-5-CF$_3$ | CF$_3$ | C(O)(D7-1a) |
| 3-CF$_3$-4-Cl | CF$_3$ | C(O)OEt | 3-Cl-4-F-5-CF$_3$ | CF$_3$ | C(O)(D11-1a) |
| 3-CF$_3$-4-Cl | CF$_3$ | C(O)Cl | 3-Cl-4-F-5-CF$_3$ | CF$_3$ | C(O)(D22-1a) |
| 3-CF$_3$-4-Cl | CF$_3$ | NO$_2$ | 3-Cl-4-F-5-CF$_3$ | CF$_3$ | NO$_2$ |

-continued

| $X^1, (X^2)_{ml}$ | $R^3$ | Q | $X^1, (X^2)_{ml}$ | $R^3$ | Q |
|---|---|---|---|---|---|
| 3-CF$_3$-4-Cl | CF$_3$ | NH$_2$ | 3-Cl-4-F-5-CF$_3$ | CF$_3$ | NH$_2$ |
| 3-CF$_3$-4-Cl | CF$_3$ | SCH$_3$ | 3-Cl-4-F-5-CF$_3$ | CF$_3$ | OCF$_3$ |
| 3-CF$_3$-4-Cl | CF$_3$ | S(O)CH$_3$ | 3-Cl-4-F-5-CF$_3$ | CF$_3$ | OSO$_2$CF$_3$ |
| 3-CF$_3$-4-Cl | CF$_3$ | SO$_2$CH$_3$ | 3-Cl-4-F-5-CF$_3$ | CF$_3$ | SCH$_3$ |
| 3-Cl-5-CF$_3$ | CF$_3$ | F | 3-Cl-4-F-5-CF$_3$ | CF$_3$ | S(O)CH$_3$ |
| 3-Cl-5-CF$_3$ | CF$_3$ | Cl | 3-Cl-4-F-5-CF$_3$ | CF$_3$ | SO$_2$CH$_3$ |
| 3-Cl-5-CF$_3$ | CF$_3$ | Br | 3-Cl-4-F-5-CF$_3$ | CF$_2$Cl | CN |
| 3-Cl-5-CF$_3$ | CF$_3$ | I | 3-Cl-4-F-5-CF$_3$ | CF$_2$Cl | C(O)OH |
| 3-Cl-5-CF$_3$ | CF$_3$ | CH$_3$ | 3-Cl-4-F-5-CF$_3$ | CF$_2$Cl | C(O)OCH$_3$ |
| 3-Cl-5-CF$_3$ | CF$_3$ | CF$_3$ | 3-Cl-4-F-5-CF$_3$ | CF$_2$Cl | C(O)Cl |
| 3-Cl-5-CF$_3$ | CF$_3$ | CH$_2$OH | 3-Cl-4-F-5-CF$_3$ | CF$_2$Cl | NO$_2$ |
| 3-Cl-5-CF$_3$ | CF$_3$ | CH$_2$OC(O)CH$_3$ | 3,4-Cl$_2$-5-CF$_3$ | CF$_3$ | F |
| 3-Cl-5-CF$_3$ | CF$_3$ | CH$_2$NH$_2$ | 3,4-Cl$_2$-5-CF$_3$ | CF$_3$ | Cl |
| 3-Cl-5-CF$_3$ | CF$_3$ | CH(CH$_3$)NH$_2$ | 3,4-Cl$_2$-5-CF$_3$ | CF$_3$ | Br |
| 3-Cl-5-CF$_3$ | CF$_3$ | CH(CN)NH$_2$ | 3,4-Cl$_2$-5-CF$_3$ | CF$_3$ | I |
| 3-Cl-5-CF$_3$ | CF$_3$ | CHO | 3,4-Cl$_2$-5-CF$_3$ | CF$_3$ | CH$_3$ |
| 3-Cl-5-CF$_3$ | CF$_3$ | CN | 3,4-Cl$_2$-5-CF$_3$ | CF$_3$ | CF$_3$ |
| 3-Cl-5-CF$_3$ | CF$_3$ | C(O)OH | 3,4-Cl$_2$-5-CF$_3$ | CF$_3$ | CH$_2$OH |
| 3-Cl-5-CF$_3$ | CF$_3$ | C(O)OCH$_3$ | 3,4-Cl$_2$-5-CF$_3$ | CF$_3$ | CH$_2$OC(O)CH$_3$ |
| 3-Cl-5-CF$_3$ | CF$_3$ | C(O)OEt | 3,4-Cl$_2$-5-CF$_3$ | CF$_3$ | CH$_2$NH$_2$ |
| 3-Cl-5-CF$_3$ | CF$_3$ | C(O)Cl | 3,4-Cl$_2$-5-CF$_3$ | CF$_3$ | CH(CH$_3$)NH$_2$ |
| 3-Cl-5-CF$_3$ | CF$_3$ | C(O)(D7-1a) | 3,4-Cl$_2$-5-CF$_3$ | CF$_3$ | CH(CN)NH$_2$ |
| 3-Cl-5-CF$_3$ | CF$_3$ | C(O)(D11-1a) | 3,4-Cl$_2$-5-CF$_3$ | CF$_3$ | CHO |
| 3-Cl-5-CF$_3$ | CF$_3$ | C(O)(D22-1a) | 3,4-Cl$_2$-5-CF$_3$ | CF$_3$ | CN |
| 3-Cl-5-CF$_3$ | CF$_3$ | NO$_2$ | 3,4-Cl$_2$-5-CF$_3$ | CF$_3$ | C(O)OH |
| 3-Cl-5-CF$_3$ | CF$_3$ | NH$_2$ | 3,4-Cl$_2$-5-CF$_3$ | CF$_3$ | C(O)OCH$_3$ |
| 3-Cl-5-CF$_3$ | CF$_3$ | OCF$_3$ | 3,4-Cl$_2$-5-CF$_3$ | CF$_3$ | C(O)OEt |
| 3-Cl-5-CF$_3$ | CF$_3$ | OSO$_2$CF$_3$ | 3,4-Cl$_2$-5-CF$_3$ | CF$_3$ | C(O)Cl |
| 3-Cl-5-CF$_3$ | CF$_3$ | SCH$_3$ | 3,4-Cl$_2$-5-CF$_3$ | CF$_3$ | C(O)(D7-1a) |
| 3-Cl-5-CF$_3$ | CF$_3$ | S(O)CH$_3$ | 3,4-Cl$_2$-5-CF$_3$ | CF$_3$ | C(O)(D11-a) |
| 3-Cl-5-CF$_3$ | CF$_3$ | SO$_2$CH$_3$ | 3,4-Cl$_2$-5-CF$_3$ | CF$_3$ | C(O)(D22-1a) |
| 3-Cl-5-CF$_3$ | CF$_2$Cl | CN | 3,4-Cl$_2$-5-CF$_3$ | CF$_3$ | NO$_2$ |
| 3-Cl-5-CF$_3$ | CF$_2$Cl | C(O)OH | 3,4-Cl$_2$-5-CF$_3$ | CF$_3$ | NH$_2$ |
| 3-Cl-5-CF$_3$ | CF$_2$Cl | C(O)OCH$_3$ | 3,4-Cl$_2$-5-CF$_3$ | CF$_3$ | OCF$_3$ |
| 3-Cl-5-CF$_3$ | CF$_2$Cl | C(O)Cl | 3,4-Cl$_2$-5-CF$_3$ | CF$_3$ | OSO$_2$CF$_3$ |
| 3-Cl-5-CF$_3$ | CF$_2$Cl | NO$_2$ | 3,4-Cl$_2$-5-CF$_3$ | CF$_3$ | SCH$_3$ |
| 3-Br-5-CF$_3$ | CF$_3$ | F | 3,4-Cl$_2$-5-CF$_3$ | CF$_3$ | S(O)CH$_3$ |
| 3-Br-5-CF$_3$ | CF$_3$ | Cl | 3,4-Cl$_2$-5-CF$_3$ | CF$_3$ | SO$_2$CH$_3$ |
| 3-Br-5-CF$_3$ | CF$_3$ | Br | 3,4-Cl$_2$-5-CF$_3$ | CF$_2$Cl | CN |
| 3-Br-5-CF$_3$ | CF$_3$ | I | 3,4-Cl$_2$-5-CF$_3$ | CF$_2$Cl | C(O)OH |
| 3-Br-5-CF$_3$ | CF$_3$ | CH$_3$ | 3,4-Cl$_2$-5-CF$_3$ | CF$_2$Cl | C(O)OCH$_3$ |
| 3-Br-5-CF$_3$ | CF$_3$ | CF$_3$ | 3,4-Cl$_2$-5-CF$_3$ | CF$_2$Cl | C(O)Cl |
| 3-Br-5-CF$_3$ | CF$_3$ | CH$_2$OH | 3,4-Cl$_2$-5-CF$_3$ | CF$_2$Cl | NO$_2$ |
| 3-Br-5-CF$_3$ | CF$_3$ | CH$_2$OC(O)CH$_3$ | 3,5-(CF$_3$)$_2$-4-Cl | CF$_3$ | F |
| 3-Br-5-CF$_3$ | CF$_3$ | CH$_2$NH$_2$ | 3,5-(CF$_3$)$_2$-4-Cl | CF$_3$ | Cl |
| 3-Br-5-CF$_3$ | CF$_3$ | CH(CH$_3$)NH$_2$ | 3,5-(CF$_3$)$_2$-4-Cl | CF$_3$ | Br |
| 3-Br-5-CF$_3$ | CF$_3$ | CH(CN)NH$_2$ | 3,5-(CF$_3$)$_2$-4-Cl | CF$_3$ | I |
| 3-Br-5-CF$_3$ | CF$_3$ | CHO | 3,5-(CF$_3$)$_2$-4-Cl | CF$_3$ | CH$_3$ |
| 3-Br-5-CF$_3$ | CF$_3$ | CN | 3,5-(CF$_3$)$_2$-4-Cl | CF$_3$ | CF$_3$ |
| 3-Br-5-CF$_3$ | CF$_3$ | C(O)OH | 3,5-(CF$_3$)$_2$-4-Cl | CF$_3$ | CH$_2$OH |
| 3-Br-5-CF$_3$ | CF$_3$ | C(O)OCH$_3$ | 3,5-(CF$_3$)$_2$-4-Cl | CF$_3$ | CH$_2$OC(O)CH$_3$ |
| 3-Br-5-CF$_3$ | CF$_3$ | C(O)OEt | 3,5-(CF$_3$)$_2$-4-Cl | CF$_3$ | CH$_2$NH$_2$ |
| 3-Br-5-CF$_3$ | CF$_3$ | C(O)Cl | 3,5-(CF$_3$)$_2$-4-Cl | CF$_3$ | CH(CH$_3$)NH$_2$ |
| 3-Br-5-CF$_3$ | CF$_3$ | C(O)(D7-1a) | 3,5-(CF$_3$)$_2$-4-Cl | CF$_3$ | CH(CN)NH$_2$ |
| 3-Br-5-CF$_3$ | CF$_3$ | C(O)(D11-1a) | 3,5-(CF$_3$)$_2$-4-Cl | CF$_3$ | CHO |
| 3-Br-5-CF$_3$ | CF$_3$ | C(O)(D22-1a) | 3,5-(CF$_3$)$_2$-4-Cl | CF$_3$ | CN |
| 3-Br-5-CF$_3$ | CF$_3$ | NO$_2$ | 3,5-(CF$_3$)$_2$-4-Cl | CF$_3$ | C(O)OH |
| 3-Br-5-CF$_3$ | CF$_3$ | NH$_2$ | 3,5-(CF$_3$)$_2$-4-Cl | CF$_3$ | C(O)OCH$_3$ |
| 3-Br-5-CF$_3$ | CF$_3$ | OCF$_3$ | 3,5-(CF$_3$)$_2$-4-Cl | CF$_3$ | C(O)OEt |
| 3-Br-5-CF$_3$ | CF$_3$ | OSO$_2$CF$_3$ | 3,5-(CF$_3$)$_2$-4-Cl | CF$_3$ | C(O)Cl |
| 3-Br-5-CF$_3$ | CF$_3$ | SCH$_3$ | 3,5-(CF$_3$)$_2$-4-Cl | CF$_3$ | C(O)(D7-1a) |
| 3-Br-5-CF$_3$ | CF$_3$ | S(O)CH$_3$ | 3,5-(CF$_3$)$_2$-4-Cl | CF$_3$ | C(O)(D11-1a) |
| 3-Br-5-CF$_3$ | CF$_3$ | SO$_2$CH$_3$ | 3,5-(CF$_3$)$_2$-4-Cl | CF$_3$ | C(O)(D22-1a) |
| 3-Br-5-CF$_3$ | CF$_2$Cl | CN | 3,5-(CF$_3$)$_2$-4-Cl | CF$_3$ | NO$_2$ |
| 3-Br-5-CF$_3$ | CF$_2$Cl | C(O)OH | 3,5-(CF$_3$)$_2$-4-Cl | CF$_3$ | NH$_2$ |
| 3-Br-5-CF$_3$ | CF$_2$Cl | C(O)OCH$_3$ | 3,5-(CF$_3$)$_2$-4-Cl | CF$_3$ | OCF$_3$ |
| 3-Br-5-CF$_3$ | CF$_2$Cl | C(O)Cl | 3,5-(CF$_3$)$_2$-4-Cl | CF$_3$ | OSO$_2$CF$_3$ |
| 3-Br-5-CF$_3$ | CF$_2$Cl | NO$_2$ | 3,5-(CF$_3$)$_2$-4-Cl | CF$_3$ | SCH$_3$ |
| 3,5-(CF$_3$)$_2$ | CF$_3$ | F | 3,5-(CF$_3$)$_2$-4-Cl | CF$_3$ | S(O)CH$_3$ |
| 3,5-(CF$_3$)$_2$ | CF$_3$ | Cl | 3,5-(CF$_3$)$_2$-4-Cl | CF$_3$ | SO$_2$CH$_3$ |
| 3,5-(CF$_3$)$_2$ | CF$_3$ | Br | 3,5-(CF$_3$)$_2$-4-Cl | CF$_2$Cl | CN |
| 3,5-(CF$_3$)$_2$ | CF$_3$ | I | 3,5-(CF$_3$)$_2$-4-Cl | CF$_2$Cl | C(O)OH |
| 3,5-(CF$_3$)$_2$ | CF$_3$ | CH$_3$ | 3,5-(CF$_3$)$_2$-4-Cl | CF$_2$Cl | C(O)OCH$_3$ |
| 3,5-(CF$_3$)$_2$ | CF$_3$ | Et | 3,5-(CF$_3$)$_2$-4-Cl | CF$_2$Cl | C(O)Cl |
| 3,5-(CF$_3$)$_2$ | CF$_3$ | CH$_2$Cl | 3,5-(CF$_3$)$_2$-4-Cl | CF$_2$Cl | NO$_2$ |
| 3,5-(CF$_3$)$_2$ | CF$_3$ | CH$_2$Br | 3,5-Cl$_2$-4-OCHF$_2$ | CF$_3$ | CN |
| 3,5-(CF$_3$)$_2$ | CF$_3$ | CF$_3$ | 3,5-Cl$_2$-4-OCHF$_2$ | CF$_3$ | C(O)OH |
| 3,5-(CF$_3$)$_2$ | CF$_3$ | CH(CH$_3$)Cl | 3,5-Cl$_2$-4-OCHF$_2$ | CF$_3$ | C(O)OCH$_3$ |

-continued

| $X^1, (X^2)_{ml}$ | $R^3$ | Q | $X^1, (X^2)_{ml}$ | $R^3$ | Q |
|---|---|---|---|---|---|
| 3,5-$(CF_3)_2$ | $CF_3$ | $CH(CH_3)Br$ | 3,5-$Cl_2$-4-$OCHF_2$ | $CF_3$ | C(O)Cl |
| 3,5-$(CF_3)_2$ | $CF_3$ | $CH_2OH$ | 3,5-$Cl_2$-4-$OCHF_2$ | $CF_3$ | $NO_2$ |
| 3,5-$(CF_3)_2$ | $CF_3$ | $CH_2OC(O)CH_3$ | 3,5-$Br_2$-4-$OCHF_2$ | $CF_3$ | CN |
| 3,5-$(CF_3)_2$ | $CF_3$ | $CH_2OSO_2CH_3$ | 3,5-$Br_2$-4-$OCHF_2$ | $CF_3$ | C(O)OH |
| 3,5-$(CF_3)_2$ | $CF_3$ | $CH_2OSO_2CF_3$ | 3,5-$Br_2$-4-$OCHF_2$ | $CF_3$ | $C(O)OCH_3$ |
| 3,5-$(CF_3)_2$ | $CF_3$ | $CH(CH_3)OH$ | 3,5-$Br_2$-4-$OCHF_2$ | $CF_3$ | C(O)Cl |
| 3,5-$(CF_3)_2$ | $CF_3$ | $CH_2NH_2$ | 3,5-$Br_2$-4-$OCHF_2$ | $CF_3$ | $NO_2$ |

The compound of the present invention can effectively control with a low concentration thereof, any pests such as insects including so-called agricultural insect pests damaging agricultural or horticultural crops and trees, so-called domestic animal insect pests being parasitic in domestic animals/fowls, so-called sanitary insects adversely affecting in various manners, the living environment of the human such as the house and so-called stored grain insect pests damaging grains and the like stored in a warehouse; and mites, Crustacea, Mollusc and Nematoda which are generated and suffer damages in a situation similar to that in the case of the insects.

Specific examples of the insects, the mites, the Crustacea, the Mollusc and the Nematoda capable of being controlled using the compound of the present invention include:

Lepidopteran insects such as *Adoxophyes honmai, Adoxophyes orana faciata, Archips breviplicanus, Archips fuscocupreanus, Grapholita molesta, Homona magnanima, Leguminivora glycinivorella, Matsumuraeses phaseoli, Pandemis heparana, Bucculatrix pyrivorella, Lyonetia clerkella, Lyonetia prunifoliella malinella, Caloptilia theivora, Phyllonorycter ringoniella, Phyllocnistis citrella, Acrolepiopsis sapporensis, Acrolepiopsis suzukiella, Plutella xylostella, Stathmopoda masinissa, Helcystogramma triannulella, Pectinophora gossypiella, Carposina sasakii, Cydla pomonella, Chilo suppressalis, Cnaphalocrocis medinalis, Conogethes punctiferalis, Diaphania indica, Etiella zinckenella, Glyphodes pyloalis, Hellula undalis, Ostrinia furnacalis, Ostrinia scapulalis, Ostrinia nubilalis, Parapediasia teterrella, Parnara guttata, Pieris brassicae, Pieris rapae crucivora, Ascotis selenaria, Pseudoplusia includens, Euproctis pseudoconspersa, Lymantria dispar, Orgyia thyellina, Hyphantria cunea, Lemyra imparilis, Adris tyrannus, Aedia leucomelas, Agrotis ipsilon, Agrotis segetum, Autographa nigrisigna, Ctenoplusia agnata, Helicoverpa armigera, Helicoverpa assulta, Helicoverpa zea, Heliothis virescens, Mamestra brassicae, Mythimna separata, Naranga aenescens, Spodoptera eridania, Spodoptera exigua, Spodoptera frugiperda, Spodoptera littoralis, Spodoptera litura, Spodoptera depravata, Trichoplusia ni, Endopiza viteana, Manduca quinquemaculata* and *Manduca sexta;*

Thysanoptera insects such as *Frankliniella intonsa, Frankliniella occidentalis, Heliothrips haemorrhoidalis, Scirtothrips dorsalis, Thrips palmi, Thrips tabaci* and *Ponticulothrips diospyrosi;*

Hemiptera insects such as *Dolycoris baccarum, Eurydema rugosum, Eysarcoris aeneus, Eysarcoris lewisi, Eysarcoris ventralis, Glaucias subpunctatus, Halyomorpha halys, Nezara antennata, Nezara viridula, Piezodorus hybneri, Plautia crossota, Scotinophora lurida, Cletus punctiger, Leptocorisa chinensis, Riptortus clavatus, Rhopalus msculatus, Cavelerius saccharivorus, Togo hemipterus, Dysdercus cingulatus, Stephanitis pyrioides, Halticus insularis, Lygus lineolaris, Stenodema sibiricum, Stenotus rubrovittatus, Trigonotylus caelestialium, Arboridia apicalis, Balclutha saltuella, Epicanthus stramineus, Empoasca fabae, Empoasca nipponica, Empoasca onukii, Empoasca sakaii, Macrosteles striifrons, Nephotettix cinctinceps, Psuedatomoscelis seriatus, Laodelphax striatella, Nilaparvata lugens, Sogatella furcifera, Diaphorina citri, Psylla pyrisuga, Aleurocanthus spiniferus, Bemisia argentifolii, Bemisia tabaci, Dialeurodes citri, Trialeurodes vaporariorum, Viteus vitifolii, Aphis gossypii, Aphis spiraecola, Myzus persicae, Toxoptera aurantii, Drosicha corpulenta, Icerya purchasi, Phenacoccus solani, Planococcus citri, Planococcus kuraunhiae, Pseudococcus comstocki, Ceroplastes ceriferus, Ceroplastes rubens, Aonidiella aurantii, Comstockaspis pemiciosa, Fiorinia theae, Pseudaonidia paeoniae, Pseudaulacaspis pentagona, Pseudaulacaspis prunicola, Unaspis euonymi, Unaspis yanonensis* and *Cimex lectularius;*

Coleoptera insects such as *Anomala cuprea, Anomala rufocuprea, Gametis jucunda, Heptophylla picea, Popillia japonica, Lepinotarsa decemlineata, Melanotus fortnumi, Melanotus tamsuyensis, Lasioderma serricome, Epuraea domina, Epilachna varivestis, Epilachna vigintioctopunctata, Tenebrio molitor, Tribolium castaneum, Anoplophora malasiaca, Monochamus alternatus, Psacothea hilaris, Xylotrechus pyrrhoderus, Callosobruchus chinensis, Aulacophora femoralis, Chaetocnema concinna, Diabrotica undecimpunctata, Diabrotica virgifera, Diabrotica barberi, Oulema oryzae, Phyllotreta striolata, Psylliodes angusticollis, Rhynchites heros, Cylas formicarius, Anthonomus grandis, Echinocnemus squameus, Euscepes postfasciatus, Hypera postica, Lissohoptrus oryzophilus, Otiorhynchus sulcatus, Sitophilus granarius, Sitophilus zeamais, Sphenophorus venatus vestitus* and *Paederus fuscipes;*

Diptera insects such as *Asphondylia yushimai, Sitodiplosis mosellana, Bactrocera cucurbitae, Bactrocera dorsalis, Ceratitis capitata, Hydrellia griseola, Drosophila suzukii, Agromyza oryzae, Chromatomyia horticola, Liriomyza bryoniae, Liriomyza chinensis, Liriomyza sativae, Liriomyza trifolii, Delia platura, Pegomya cunicularia, Rhagoletis pomonella, Mayetiola destructor, Musca domestica, Stomoxys calcitrans, Melophagus ovinus, Hypoderma bovis, Hypoderma lineatum, Oestrus ovis, Glossina palpalis (Glossina morsitans), Prosimulium yezoensis, Tabanus trigonus, Telmatoscopus albipunctatus, Leptoconops nipponensis, Culex pipiens pallens, Aedes aegypti, Aedes albopicutus* and *Anopheles hyracanus sinesis;*

Hymenoptera insects such as *Apethymus kuri, Athalia rosae, Arge pagana, Neodiprion sertifer, Dryocosmus kuriphilus, Eciton burchelli (Eciton schmitti), Camponotus japonicus, Vespa mandarina, Myrmecia* spp., *Solenopsis* spp. and *Monomorium pharaonis;*

Orthoptera insects such as *Teleogryllus emma, Gryllotalpa orientalis, Locusta migratoria, Oxya yezoensis* and *Schistocerca gregaria;*

Collembolan insects such as *Onychiurus folsomi, Onychiurus sibiricus* and *Bourletiella hortensis;*

Dictyoptera insects such as *Periplaneta fuliginosa, Periplaneta japonica* and *Blattella germanica;*

Isoptera insects such as *Coptotermes formosanus*, *Reticulitermes speratus* and *Odontotermes formosanus*;

Siphonaptera insects such as *Ctenocephalidae felis*, *Ctenocephalides canis*, *Echidnophaga gallinacea*, *Pulex irritans* and *Xenopsylla cheopis*;

Mallophaga insects such as *Menacanthus stramineus* and *Bovicola bovis*;

Anoplura insects such as *Haematopinus eurysternus*, *Haematopinus suis*, *Linognathus vituli* and *Solenopotes capillatus*;

Tarsonemidae such as *Phytonemus pallidus*, *Polyphagotarsonemus latus* and *Tarsonemus bilobatus*;

Eupodidae such as *Penthaleus erythrocephalus* and *Penthaleus major*;

Tetranychidae such as *Oligonychus shinkajii*, *Panonychus citri*, *Panonychus mori*, *Panonychus ulmi*, *Tetranychus kanzawai* and *Tetranychus urticae*;

Eriophydae such as *Acaphylla theavagrans*, *Aceria tulipae*, *Aculops lycopersici*, *Aculops pelekassi*, *Aculus schlechtendali*, *Eriophyes chibaensis* and *Phyllocoptruta oleivora*;

Acaridae such as *Rhizoglyphus robini*, *Tyrophagus putrescentiae* and *Tyrophagus similis*;

*Varroa destructor* such as *Varroa jacobsoni*;

Ixodidae such as *Boophilus microplus*, *Rhipicephalus sanguineus*, *Haemaphysalis longicornis*, *Haemophysalis flava*, *Haemophysalis campanulata*, *Ixodes ovatus*, *Ixodes persulcatus*, *Amblyomma* spp. and *Dermacentor* spp.

Cheyletidae such as *Cheyletiella yasguri* and *Cheyletiella blakei*;

Demodicidae such as *Demodex canis* and *Demodex cati*;

Psoroptidae such as *Psoroptes ovis*;

Sarcoptidae such as *Sarcoptes scabiei*, *Notoedres cati* and *Knemidocoptes* spp;

Crustacea such as *Armadillidium vulgare*;

Gastropoda such as *Pomacea canaliculata*, *Achatina fulica*, *Meghimatium bilineatum*, *Limax Valentiana*, *Acusta despecta sieboldiana* and *Euhadra peliomphala*; and Nematoda such as *Prathylenchus coffeae*, *Prathylenchus penetrans*, *Prathylenchus vulnus*, *Globodera rostochiensis*, *Heterodera glycines*, *Meloidogyne hapla*, *Meloidogyne incognita*, *Aphelenchoides besseyi* and *Bursaphelenchus xylophilus*, which should not be construed as limiting the scope of the present invention.

In addition, specific examples of the internal parasites of domestic animals, fowls, pet animals or the like capable of being controlled using the compound of the present invention include:

Nematoda such as *Haemonchus*, *Trichostrongylus*, *Ostertagia*, *Nematodirus*, *Cooperia*, *Ascaris*, *Bunostomum*, *Oesophagostomum*, *Chabertia*, *Trichuris*, *Storongylus*, *Trichonema*, *Dictyocaulus*, *Capillaria*, *Heterakis*, *Toxocara*, *Ascaridia*, *Oxyuris*, *Ancylostoma*, *Uncinaria*, *Toxascaris* and *Parascaris*;

Nematoda, Filariidae such as *Wuchereria*, *Brugia*, *Onchoceca*, *Dirofilaria* and *Loa*;

Nematoda, Dracunculidae such as *Deacunculus*;

Cestoda such as *Dipylidium caninum*, *Taenia taeniaeformis*, *Taenia solium*, *Taenia saginata*, *Hymenolepis diminuta*, *Moniezia benedeni*, *Diphyllobothrium latum*, *Diphyllobothrium erinacei*, *Echinococcus granulosus* and *Echinococcus multilocularis*;

Trematoda such as *Fasciola hepatica* and *F. gigantica*, *Paragonimus westermanii*, *Fasciolopsic bruski*, *Eurytrema pancreaticum* and *E. coelomaticum*, *Clonorchis sinensis*, *Schistosoma japonicum*, *Schistosoma haematobium* and *Schistosoma mansoni*;

*Eimeria* spp. such as *Eimeria tenella*, *Eimeria acervulina*, *Eimeria brunetti*, *Eimeria maxima*, *Eimeria necatrix*, *Eimeria bovis* and *Eimeria ovinoidalis*;

*Trypanosomsa cruzi*; *Leishmania* spp.; *Plasmodium* spp.; *Babesis* spp.; *Trichomonadidae* spp.; *Histomanas* spp.; *Giardia* spp.; *Toxoplasma* spp.; *Entamoeba histolytica* and *Theileria* spp, which should not be construed as limiting the scope of the present invention.

Furthermore, the compound of the present invention is effective against pests which have developed the resistance to the related art insecticides such as organic phosphorus-based compounds, carbamate-based compounds or pyrethroid-based compounds.

That is, the compound of the present invention can effectively control pests belonging to insects such as Collembola, Dictyoptera (Blattaria), Orthoptera, Isoptera, Thysanoptera, Hemiptera (Heteroptera and Homoptera), Lepidoptera, Coleoptera, Hymenoptera, Diptera, Isoptera (Siphonaptera) and Phthiraptera; mites; Gastropoda; and Nematoda with a low concentration. On the other hand, the compound of the present invention has an extremely useful characteristic of having substantially no adverse effect on mammals, fish, Crustacea and beneficial insects (useful insects such as Apidae and Bombus, and natural enemies such as Aphelinidae, Aphidiidae, Tachinidae, Orius and Amblyseius).

For using the compound of the present invention, the compound can be put to practical use as a preparation in any formulation such as a soluble concentrate, an emulsifiable concentrate, a wettable powder, a water soluble powder, a water dispersible granule, a water soluble granule, a suspension concentrate, a concentrated emulsion, a suspoemulsion, a microemulsion, a dustable powder, a granule, a tablet and an emulsifiable gel, typically by mixing the compound with an appropriate solid carrier or liquid carrier, further if desired by adding to the resultant mixture, a surfactant, a penetrant, a spreader, a thickener, an antifreezing agent, a binder, an anti-caking agent, a disintegrant, an antifoamer, an antiseptic or a stabilizer. In addition, from the viewpoint of laborsaving and safety-enhancing, the compound can be put to use by encapsulating the above preparation in any formulation in a water soluble packaging material such as a water soluble capsule and a bag of water soluble film.

Examples of the solid carrier include: natural mineral matters such as quartz, calcite, sepiolite, dolomite, chalk, kaolinite, pyrophyllite, sericite, halloysite, methahalloysite, kibushi clay, gairome clay, pottery stone, zeeklite, allophane, Shirasu, mica, talc, bentonite, activated clay, acid clay, pumice, attapulgite, zeolite and diatom earth; burned products of natural mineral matters such as burned clay, perlite, Shirasu balloon, vermiculite, attapulgous clay and burned diatom earth; inorganic salts such as magnesium carbonate, calcium carbonate, sodium carbonate, sodium hydrogen carbonate, ammonium sulfate, sodium sulfate, magnesium sulfate, diammonium hydrogen phosphate, ammonium dihydrogen phosphate and potassium chloride; saccharides such as glucose, fructose, sucrose and lactose; polysaccharides such as starch, powdered cellulose and dextrin; organic substances such as urea, urea derivatives, benzoic acid and salts of benzoic acid; plants such as wood flour, cork flour, corncob, walnut shell and tobacco stem; fly ash; white carbon (such as hydrous synthetic silica, anhydrous synthetic silica and hydrous synthetic silicate); and fertilizers.

Examples of the liquid carrier include: aromatic hydrocarbons such as xylene, alkyl ($C_9$, $C_{10}$, or the like) benzene, phenylxylylethane and alkyl ($C_1$, $C_3$, or the like) naphthalene; aliphatic hydrocarbons such as machine oil, n-paraffin, iso-paraffin and naphthene; a mixture of aromatic hydrocarbons and aliphatic hydrocarbons such as kerosene; alcohols such as ethanol, isopropanol, cyclohexanol, phenoxyethanol and benzyl alcohol; polyalcohols such as ethylene glycol, propylene glycol, diethylene glycol, hexylene glycol, polyethylene glycol and polypropylene glycol; ethers such as propyl cellosolve, butyl cellosolve, phenyl cellosolve, propylene glycol monomethyl ether, propylene glycol monoethyl ether, propylene glycol monopropyl ether, propylene glycol monobutyl ether and propylene glycol monophenyl ether; ketones such as acetophenone, cyclohexanone and γ-butyro lactone; esters such as aliphatic acid methyl esters, succinic acid dialkyl esters, glutamic acid dialkyl esters, dialkyl adipate esters, and dialkyl phthalate esters; acid amides such as N-alkyl ($C_1$, $C_8$, $C_{12}$, or the like) pyrrolidone; oils and fats such as soybean oil, linseed oil, rapeseed oil, coconut oil, cottonseed oil and castor oil; dimethyl sulfoxide; and water.

These solid or liquid carriers may be used individually or in combination of two or more types thereof.

Examples of the surfactant include: nonionic surfactants such as polyoxyethylene alkyl ethers, polyoxyethylene alkyl (mono- or di-)phenyl ethers, polyoxyethylene (mono-, di- or tri-)styIyl phenyl ethers, polyoxyethylene-polyoxypropylene block copolymers, polyoxyethylene aliphatic acid (mono- or di-) esters, sorbitan aliphatic acid esters, polyoxyethylene sorbitan aliphatic acid esters, castor oil ethylene-oxide adducts, acetylene glycol, acetylene alcohols, acetylene glycol ethylene-oxide adducts, acetylene alcohol ethylene-oxide adducts and alkylglucosides; anionic surfactants such as alkyl sulfate ester salts, alkylbenzene sulfonates, lignin sulfonates, alkyl sulfosuccinates, naphthalene sulfonates, alkylnaphthalene sulfonates, salts of naphthalene sulfonate formalin condensate, salts of alkylnaphthalene sulfonate formalin condensate, polyoxyethylenealkylether sulfate or phosphate esters, polyoxyethylene (mono- or di-)alkylphenyl ether sulfate or phosphate esters, polyoxyethylene (mono-, di- or tri-)stylylphenyl ether sulfate or phosphate esters, polycarboxylic acid salts (such as polyacrylic acid salts, polymaleic acid salts and maleic acid-olefin copolymer) and polystylene sulfonates; cationic surfactants such as alkylamine salts and alkyl quaternary ammonium salts; amphoteric surfactants such as amino acid-type surfactants and betaine-type surfactants; silicone-based surfactants; and fluorinated surfactants.

Although the content of these surfactants is not particularly limited, it is desirably in a range of usually 0.05 to 20 parts by weight, relative to 100 parts by weight of the preparation of the present invention. In addition, these surfactants may be used individually or in combination of two or more types thereof.

Although the application dosage of the compound of the present invention varies depending on the application situation, the application period, the application method, the cultivated crop and the like, it is generally appropriate to be around 0.005 to 50 kg per hectare (ha) as an active ingredient amount.

On the other hand, in using the compound of the present invention for controlling external or internal parasites of mammals and birds as domestic animals and pet animals, an effective amount of the compound of the present invention can be administered together with additives for the preparation by: oral administration and parenteral administration such as injections (intramuscular, subcutaneous, intravenous and intraperitoneal injections); a percutaneous administration such as immersing, spraying, bathing, cleaning, pouring-on and spotting-on, and dusting; and transnasal administration. The compound of the present invention can be administered also as a molded product using a strip, a plate, a band, a collar, an ear mark, a limb band and an indicator. For the administration of the compound of the present invention, the compound can be prepared in any formulation suitable for an administration route.

Examples of the formulation in any form to be prepared include solid preparations such as dustable powders, granules, wettable powders, pellets, tablets, boluses, capsules and molded products containing activated compounds; soluble concentrates for injection, soluble concentrates for oral administration and soluble concentrates used on the skin or in the body cavity; solution preparations such as pour-on drugs, spot-on drugs, flowable drugs and emulsifiable concentrates; and semisolid preparations such as ointments and gels.

The solid preparation can be mainly used for oral administration, percutaneous administration of the preparation diluted with water, or an environmental treatment. The solid preparation can be prepared by mixing an activated compound with an appropriate excipient, if necessary together with an adjuvant, and converting the resultant mixture into a desired form. Examples of the appropriate excipient include: inorganic substances such as carbonate salts, hydrogen carbonate salts, phosphate salts, aluminum oxide, silica and clay; and organic substances such as saccharides, celluloses, ground grains and starch.

The soluble concentrate for injection can be prepared by dissolving an activated compound capable of being administered intravenously, intramuscularly or subcutaneously in an appropriate solvent, and if necessary by adding to the resultant solution, additives such as solubilizers, acids, bases, buffering salts, antioxidants and protective agents. Examples of the appropriate solvent include water, ethanol, butanol, benzyl alcohol, glycerin, propylene glycol, polyethylene glycol, N-methylpyrrolidone, mixtures thereof, physiologically acceptable vegetable oils and synthetic oils suitable for injection. Examples of the solubilizer include polyvinylpyrrolidone, polyoxyethylated castor oil and polyoxyethylated sorbitan esters. Examples of the protective agents include benzyl alcohol, trichlorobutanol, p-hydroxybenzoic acid esters and n-butanol.

The soluble concentrate for oral administration can be administered directly or as a diluted soluble concentrate and can be prepared in substantially the same manner as that in the case of the soluble concentrate for injection.

The flowable drug, the emulsifiable concentrate and the like can be administered percutaneously directly or as a diluted drug, or through an environmental treatment.

The soluble concentrate used on the skin can be administrated by dropping, spreading, rubbing, spraying, dusting or immersing (immersing, bathing or cleaning) to apply the drug on the skin. These soluble concentrates can be prepared in substantially the same manner as that in the case of the soluble concentrate for injection.

The pour-on drug and the spot-on drug are dropped or sprayed on a limited range of the skin, so that these drugs can immerse activated compounds thereof into the skin to obtain the systemic effect. The pour-on drug and the spot-on drug can be prepared by dissolving, suspending or emulsifying an active ingredient in an appropriate skin-adaptable solvent or solvent mixture. If necessary, in these drugs, an adjuvant such as a surfactant, a colorant, an absorption-accelerating substance, an antioxidant, a light stabilizer and an adhesive can be incorporated.

Examples of the appropriate solvent include water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oils, DMF, liquid paraffin, light liquid paraffin, silicone, dimethylacetoamide, N-methylpyrrolidone or 2,2-dimethyl-4-oxy-methylene-1,3-dioxolane. Examples of the absorption accelerating substance include DMSO, isopropyl myristate, dipropylene glycol pelargonate, silicone oil, aliphatic esters, triglycerides and aliphatic alcohols. Examples of the antioxidant include sulfites, metabisulfites, ascorbic acid, butylhydroxytoluene, butylated hydroxyanisole and tocopherol.

The emulsifiable concentrate can be administered by an oral administration, a percutaneous administration or an injection. The emulsifiable concentrate can be prepared by dissolving an active ingredient in a hydrophobic phase or a hydrophilic phase and homogenizing the resultant solution with a solvent of another type of phase using an appropriate emulsifier, if necessary further together with an adjuvant such as a colorant, an absorption accelerating substance, a protective agent, an antioxidant, a sunscreen and a thickener substance.

Examples of the hydrophobic phase (oil) include paraffin oil, silicone oil, sesame oil, almond oil, castor oil, synthetic triglyceride, ethyl stearate, di-n-butyryl adipate, hexyl laurate, dipropylene glycol pelargonate, an ester of a branched aliphatic acid having a short chain length with a saturated aliphatic acid having a chain length of C16 to C18, isopropyl myristate, isopropyl palmitate, caprylate/caprate esters of a saturated aliphatic alcohol having a chain length of C12 to C18, isopropyl stearate, oleyl oleate, decyl oleate, ethyl oleate, ethyl lactate, a wax-like aliphatic acid ester, dibutyl phthalate, diisopropyl adipate, isotridecyl alcohol, 2-octyl dodecanol, cetylstearyl alcohol and oleyl alcohol.

Examples of the hydrophilic phase include water, propylene glycol, glycerin and sorbitol.

Examples of the emulsifier include: nonionic surfactants such as polyoxyethylated castor oil, polyoxyethylated monoolefin acid sorbitan, sorbitan monostearate, glycerin monostearate, polyoxyethyl stearate and alkylphenol polyglycol ether; amphoteric surfactants such as disodium N-lauryl-β-iminodipropionate and lecithin; anionic surfactants such as sodium laurylsulfate, aliphatic alcohol sulfate ether and mono-/di-alkyl polyglycol orthophosphate ester monoethanolamine salt; and cationic surfactants such as cetyltrimethylammonium chloride.

Examples of the other adjuvants include carboxymethyl cellulose, methyl cellulose, polyacrylate, alginate, gelatin, gum Arabic, polyvinylpyrrolidone, polyvinyl alcohol, methyl vinyl ether, copolymers of maleic anhydride, polyethylene glycol, wax and colloidal silica.

The semisolid preparation can be administered by applying or spreading the preparation on the skin or by introducing the preparation into a body cavity. The gel can be prepared by adding to a solution prepared as described above with respect to the soluble concentrate for injection, a thickener in an amount sufficient for generating an ointment-like transparent substance having viscosity.

Next, examples of the formulation of the preparation in the case of using the compound of the present invention are described, with the proviso that the formulation examples of the present invention are not limited to these examples. Here, in the following formulation examples, the term "part" represents a part by weight.

| (Wettable powder) | |
|---|---|
| Compound of the present invention | 0.1 to 80 parts |
| Solid carrier | 5 to 98.9 parts |
| Surfactant | 1 to 10 part(s) |
| Others | 0 to 5 parts |

Other examples include an anticaking agent and a stabilizer.

| (Emulsifiable concentrate) | |
|---|---|
| Compound of the present invention | 0.1 to 30 parts |
| Liquid carrier | 45 to 95 parts |
| Surfactant | 4.9 to 15 parts |
| Others | 0 to 10 parts |

Other examples include a spreader and a stabilizer.

| (Suspension concentrate) | |
|---|---|
| Compound of the present invention | 0.1 to 70 parts |
| Liquid carrier | 15 to 98.89 parts |
| Surfactant | 1 to 12 part(s) |
| Others | 0.01 to 30 parts |

Other examples include an antifreezing agent and a thickener.

| (Water dispersible granule) | |
|---|---|
| Compound of the present invention | 0.1 to 90 parts |
| Solid carrier | 0 to 98.9 parts |
| Surfactant | 1 to 20 part(s) |
| Others | 0 to 10 parts |

Other examples include a binder and a stabilizer.

| (Soluble concentrate) | |
|---|---|
| Compound of the present invention | 0.01 to 70 parts |
| Liquid carrier | 20 to 99.99 parts |
| Others | 0 to 10 parts |

Other examples include an antifreezing agent and a spreader.

| (Granule) | |
|---|---|
| Compound of the present invention | 0.01 to 80 parts |
| Solid carrier | 10 to 99.99 parts |
| Others | 0 to 10 parts |

Other examples include a binder and a stabilizer.

| (Dustable powder) | |
|---|---|
| Compound of the present invention | 0.01 to 30 parts |
| Solid carrier | 65 to 99.99 parts |
| Others | 0 to 5 parts |

Other examples include an antidrift agent and a stabilizer.

Next, examples of the preparation containing the compound of the present invention as an active ingredient are more specifically described, however the examples should not be construed as limiting the scope of the present invention.

Here, in the following formulation examples, the term "parts" represents parts by weight.

(Formulation example 1) Wettable powder prepared by homogeneously mixing and grinding a composition containing:

| | |
|---|---|
| compound of the present invention No. 1-003 | 20 parts; |
| pyrophyllite | 74 parts; |
| SORPOL 5039 | 4 parts |
| (trade name; manufactured by TOHO Chemical Industry Co., LTD.; mixture of nonionic surfactant and anionic surfactant); and | |
| CARPLEX #80D | 2 parts |
| (trade name; manufactured by Shionogi & Co., Ltd.; synthetic hydrous silicic acid). | |

(Formulation example 2) Emulsifiable concentrate prepared by homogeneously mixing a composition containing:

| | |
|---|---|
| compound of the present invention No. 1-003 | 5 parts; |
| xylene | 75 parts; |
| N-methylpyrrolidone | 15 parts; and |
| SORPOL 2680 | 5 parts |
| (trade name; manufactured by TOHO Chemical Industry Co., LTD.; mixture of nonionic surfactant and anionic surfactant). | |

(Formulation example 3) Suspension concentrate prepared by homogeneously mixing a composition containing:

| | |
|---|---|
| compound of the present invention No. 1-003 | 25 parts; |
| AGRISOL S-710 | 10 parts |
| (trade name; manufactured by Kao Corporation; nonionic surfactant); | |
| LUNOX 1000C | 0.5 parts |
| (trade name; manufactured by TOHO Chemical Industry Co., LTD.; anionic surfactant); | |
| xanthan gum | 0.2 parts; and |
| water | 64.3 parts, |
| and then wet-grinding the resultant mixture. | |

(Formulation example 4) Water dispersible granule prepared by homogeneously mixing and grinding a composition containing:

| | |
|---|---|
| compound of the present invention No. 1-003 | 75 parts; |
| HITENOL NE-15 | 5 parts; |
| (trade name; manufactured by Dai-ichi Kogyo Seiyaku Co., Ltd.; anionic surfactant); | |
| VANILLEX N | 10 parts |
| (trade name; manufactured by Nippon Paper Industries Co., Ltd.; anionic surfactant); and | |
| CARPLEX #80D | 10 parts |
| (trade name; manufactured by Shionogi & Co., Ltd.; synthetic hydrous silicic acid), then adding a small amount of water to the resultant mixture to stir and mix the mixture, granulating the mixture with an extrusion granulator, and drying the resultant granules. | |

(Formulation example 5) Granule prepared by homogeneously mixing and grinding a composition containing:

| | |
|---|---|
| compound of the present invention No. 1-003 | 5 parts; |
| bentonite | 50 parts; and |
| talc | 45 parts, | then adding a small amount of water to the resultant mixture to stir and mix the mixture, granulating the mixture with an extrusion granulator, and drying the resultant granules.

(Formulation example 6) Dustable powder prepared by homogeneously mixing and grinding a composition containing:

| | |
|---|---|
| compound of the present invention No. 1-003 | 3 parts; |
| CARPLEX #80D | 0.5 parts |
| (trade name; manufactured by Shionogi & Co., Ltd.; synthetic hydrous silicic acid); | |
| kaolinite | 95 parts; and |
| diisopropyl phosphate | 1.5 parts. |

For using the preparation, the preparation is diluted with water by 1 to 10,000 time(s) to be directly dusted or is directly dusted without dilution.

(Formulation example 7) Wettable powder preparation

| | |
|---|---|
| compound of the present invention No. 1-003 | 25 parts |
| sodium diisobutylnaphthalenesulfonate | 1 part |
| calcium n-dodecylbenzenesulfonate | 10 parts |
| alkylaryl polyglycol ether | 12 parts |
| sodium salt of naphthalenesulfonic acid formalin condensate | 3 parts |
| emulsion-type silicone | 1 part |
| silicon dioxide | 3 parts |
| kaolin | 45 parts |

(Formulation example 8) Water soluble thickener preparation

| | |
|---|---|
| compound of the present invention No. 1-003 | 20 parts |
| polyoxyethylene lauryl ether | 3 parts |
| sodium dioctylsulfosuccinate | 3.5 parts |
| dimethylsulfoxide | 37 parts |
| 2-propanol | 36.5 parts |

(Formulation example 9) Soluble concentrate for spraying

| | |
|---|---|
| compound of the present invention No. 1-003 | 2 parts |
| dimethylsulfoxide | 10 parts |
| 2-propanol | 35 parts |
| acetone | 53 parts |

(Formulation example 10) Soluble concentrate for percutaneous administration

| | |
|---|---|
| compound of the present invention No. 1-003 | 5 parts |
| hexylene glycol | 50 parts |
| isopropanol | 45 parts |

(Formulation example 11)
Soluble concentrate for percutaneous administration

| | |
|---|---|
| compound of the present invention No. 1-003 | 5 parts |
| propylene glycol monomethyl ether | 50 parts |
| dipropylene glycol | 45 parts |

(Formulation example 12)
Soluble concentrate for percutaneous administration
(dropping)

| | |
|---|---|
| compound of the present invention No. 1-003 | 2 parts |
| light liquid paraffin | 98 parts |

(Formulation example 13)
Soluble concentrate for percutaneous administration
(dropping)

| | |
|---|---|
| compound of the present invention No. 1-003 | 2 parts |
| light liquid paraffin | 58 parts |
| olive oil | 30 parts |
| ODO-H | 9 parts |
| Shin-Etsu silicone | 1 part |

In addition, when the compound of the present invention is used as an agricultural chemical, if necessary the compound may be mixed with another type of herbicide, various insecticides, a miticide, a nematicide, a fungicide, a plant growth regulator, a synergist, a fertilizer or a soil conditioner to be applied during the preparation or the dusting.

Particularly, by mixing the compound with other agricultural chemicals or phytohormones to be applied, a cost reduction by reducing the application dose, an enlargement of the insecticidal spectrum by a synergism of a mixed drug and a higher pest control effect can be expected. In this case, it is possible to combine simultaneously a plurality of publicly-known agricultural chemicals. Examples of types of agricultural chemicals to be mixed with the compound of the present invention to be used include compounds described in "The Pesticide Manual, vol. 14 (2006)". Specific examples of the general names include the following names, to which the examples are not limited.

Fungicides: acibenzolar-S-methyl, acylaminobenzamide, acypetacs, aldimorph, amisulbrom, amobam, ampropylos, anilazine, azaconazole, azithiram, azoxystrobin, barium polysulfide, benalaxyl, benodanil, benomyl, benquinox, bentaluron, benthiavalicarb, benthiazole, benzamacril, benzamorf, bethoxazine, binapacryl, biphenyl, bitertanol, blasticidin-S, bordeaux mixture, boscalid, bromoconazole, bupirimate, buthiobate, calcium polysulfide, captafol, captan, carpropamid, carbamorph, carbendazim, carboxin, carvone, cheshunt mixture, chinomethionat, chlobenthiazone, chloraniformethane, chloranil, chlorfenazol, chloroneb, chloropicrin, chlorothalonil, chloroquinox, chlozolinate, climbazole, clotrimazole, copper acetate, copper carbonate basic, copper hydroxide, copper naphthenate, copper oleate, copper oxychloride, copper sulfate, copper sulfate basic, copper zinc chromate, cufraneb, cuprobam, cyazofamid, cyclafuramid, cycloheximide, cyflufenamid, cymoxanil, cypendazole, cyproconazol, cyprodinil, cyprofuram, dazomet, debacarb, decafentin, dehydroacetic acid, dichlofluanid, dichlone, dichlorophen, dichlozoline, dichlobutrazol, diclocymet, diclomedine, dicloran, diethofencarb, difenoconazole, diflumetorim, dimethirimol, dimethomorph, dimoxystrobin, diniconazole, diniconazole-M, dinobuton, dinocap, dinocap-4, dinocap-6, dinocton, dinosulfon, dinoterbon, diphenylamine, dipyrithione, ditalimfos, dithianon, dodemorph, dodine, drazoxolon, edifenphos, epoxiconazole, etaconazole, etem, ethirimol, ethoxyquin, etridiazole, famoxadone, fenarimol, febuconazole, fenamidone, fenaminosulf, fenapanil, fendazosulam, fenfuram, fenhexamid, fenitropan, fenoxanil, fenpiclonil, fenpropidin, fenpropimorph, fentin, ferbam, ferimzone, fluazinam, fludioxonil, flumetover, flumorph, fluopicolide, fluoroimide, fluotrimazole, fluoxastrobin, fluquinconazole, flusilazole, flusulfamide, flutolanil, flutriafol, folpet, fosetyl-aluminium, fuberidazole, furalaxyl, furametpyr, furcarbanil, furconazole, fluconazole-cis, furmecyclox, furphanate, glyodin, griseofulvin, guazatine, halacrinate, hexachlorobenzene, hexaconazole, hexylthiofos, 8-hydroxyquinoline sulfate, hymexazol, imazalil, imibenconazole, iminoctadine, ipconazole, iprobenfos, iprodione, iprovalicarb, isoprothiolane, isovaledione, kasugamycin, kresoxim-methyl, mancopper, mancozeb, mandipropamid, maneb, mebenil, mecarbinzid, mepanipyrim, mepronil, metalaxyl, metalaxyl-M, metam, metazoxolon, metconazole, methasulfocarb, methfuroxam, methyl isothiocyanate, metiram, metominostrobin, metrafenone, metsulfovax, milneb, myclobutanil, myclozolin, nabam, natamycin, nickel bis (dimethyldithiocarbamate), nitrostyrene, nitrothal-isopropyl, nuarimol, OCH, octhilinone, ofurace, orysastrobin, oxadixyl, oxine copper, oxycarboxin, oxpoconazole fumarate, pefurzoate, penconazole, pencycuron, penthiopyrad, o-phenylphenol, phosdiphen, phthalide, picoxystrobin, piperalin, polycarbamate, polyoxins, polyoxorim, potassium azide, potassium hydrogen carbonate, proquinazid, probenazole, prochloraz, procymidone, propamocarb hydrochloride, propiconazole, propineb, prothiocarb, prothioconazole, pyracarbolid, pyraclostrobin, pyrazophos, pyridinitril, pyrifenox, pyrimethanil, pyroquilon, pyroxychlor, pyroxyfur, quinomethionate, quinoxyfen, quintozene, quinacetol-sulfate, quinazamid, quinconazole, rabenzazole, sodium azide, sodium hydrogen carbonate, sodium hypochlorite, sulfur, spiroxamine, salycylanilide, silthiofam, simeconazole, tebuconazole, tecnazene, tecoram, tetraconazole, thiabendazole, thiadifluor, thicyofen, thifluzamide, thiochlorfenphim, thiophanate, thiophanate-methyl, thioquinox, thiram, tiadinil, tioxymid, tolclofos-methyl, tolylfluanid, triadimefon, toriadimenol, triamiphos, triarimol, triazoxide, triazbutil, tributyltin oxide, trichlamide, tricyclazole, tridemorph, trifloxystrobin, triflumizole, triforine, triticonazole, validamycin, vinclozolin, zarilamide, zinc sulfate, zineb, ziram, zoxamide, siitake mushroom mycelia extract, and the like.

Bactericides: benzalkonium chloride, bithionol, bronopol, cresol, formaldehyde, nitrapyrin, oxolinic acid, oxyterracycline, streptomycin, tecloftalam, and the like.

Nematicides: aldoxycarb, cadusafos, DBCP, dichlofenthion, DSP, ethoprophos, fenamiphos, fensulfothion, fosthiazate, fosthietan, imicyafos, isamidofos, isazofos, oxamyl, thionazin, and the like.

Miticides: acequinocyl, acrinathrin, amitraz, BCI-033 (test name), bifenazate, bromopropylate, chinomethionat, chlorobenzilate, clofentezine, cyenopyrafen, cyflumetofen, cyhexatine, dicofol, dienochlor, DNOC, etoxazole, fenazaquin, fenbutatin oxide, fenothiocarb, fenpropathrin, fenpyroximate, fluacrypyrim, halfenprox, hexythiazox, milbemectin, propargite, pyridaben, pyrimidifen, S-1870 (test name), spirodiclofen, spyromesifen, tebufenpyrad, and the like.

Insecticides: abamectin, acephate, acetamipirid, alanycarb, aldicarb, allethrin, azinphos-methyl, bacillus thuring-

*iensis*, bendiocarb, benfuracarb, bensultap, bifenthrin, buprofezin, butocarboxim, carbaryl, carbofuran, carbosulfan, cartap, chlorantraniliprole, chlorfenapyr, chlorfenvinphos, chlorfluazuron, chlorpyrifos, chlorpyrifos-methyl, chlromafenozide, clothianidin, cycloprothrin, cyflumetofen, cyfluthrin, beta-cyfluthrin, cyhalothrin, lambda-cyhalothrin, cypermethrin, cyromazine, deltamethrin, diacloden, diafenthiuron, diazinon, dichlorvos, diflubenzuron, dimethylvinphos, dinotefuran, diofenolan, disulfoton, dimethoate, emamectin-benzoate, EPN, esfenvalerate, ethiofencarb, ethiprole, etofenprox, etrimfos, fenitrothion, fenobucarb, fenoxycarb, fenpropathrin, fenthion, fenvalerate, fipronil, flonicamid, flubendiamide, flucythrinate, flufenerim, flufenoxuron, flufenprox, fluvalinate, tau-fluvalinate, fonophos, formetanate, formothion, furathiocarb, halofenozide, hexaflumuron, hydramethylnon, imidacloprid, isofenphos, indoxacarb, isoprocarb, isoxathion, lepimectin, lufenuron, malathion, metaldehyde, methamidophos, methidathion, methacrifos, metaflumizone, metalcarb, methomyl, methoprene, methoxychlor, methoxyfenozide, methyl bromide, monocrotophos, muscalure, nitenpyram, novaluron, omethoate, oxamyl, oxydemeton-methyl, oxydeprofos, parathion, parathion-methyl, pentachlorophenol (PCP), permethrin, phenthoate, phoxim, phorate, phosalone, phosmet, phosphamidon, pirimicarb, pirimiphos-methyl, profenofos, prothiofos, propaphos, protrifenbute, pymetrozine, pyraclofos, pyridalyl, pyrifluquinazon, pyriproxyfen, rotenone, SI-0405 (test name), sulprofos, silafluofen, spinetoram, spinosad, spirotetramat, sulfotep, SYJ-159 (test name), tebfenozide, teflubenzuron, tefluthrin, terbufos, tetrachlorvinphos, thiacloprid, thiocyclam, thiodicarb, thiamethoxam, thiofanox, thiometon, tolfenpyrad, tralomethrin, trichlorfon, triazuron, triflumuron, vamidothion, and the like.

EXAMPLES

Hereinafter, the present invention is described more in detail referring specifically to Synthetic Examples and Test Examples of the compound of the present invention as Examples, which should not be construed as limiting the scope of the present invention.

Synthetic Examples

Synthetic Example 1

4-(4-bromo-5-(3,5-dichlorophenyl)-5-trifluoromethyl-4,5-dihydroisoxazole-3-yl)-2-methyl-N-(2,2,2-trifluoroethyl) benzoic acid amide (compound of the present invention No. 1-003 in the following Table 7).

Process 1; Production of methyl 4-(1Z,2Z)-3-(3,5-dichlorophenyl)-4,4,4-trifluoro-1-(hydroxyimino)-2-butenyl)-2-methyl benzoate (compound of the present invention No. 9-009 in the following Table 15)

In a nitrogen atmosphere, into a solution of 0.43 g of methyl 4-(5-3,5-dichlorophenyl)-5-trifluoromethyl-4,5-dihydroisoxazole-3-yl)-2-methyl benzoate (compound No. 11-054 in Patent Document 1) in 10 mL of tetrahydrofuran, 1.0 mL of a 1.0 M lithium hexamethyldisilazane tetrahydrofuran solution was dropped at room temperature with stirring and after the completion of the dropping, the resultant mixture was continuously stirred at the same temperature further for 10 minutes. After the completion of the reaction, the reaction mixture was charged into 5 mL of ice water and thereto, a 2N hydrochloric acid aqueous solution was added, followed by extracting the resultant reaction mixture with ethyl acetate (20 mL×1) under an acidic condition. The organic phase was washed with water and then dehydrated and dried over a saturated saline and anhydrous sodium sulfate in this order, and the solvent was distilled off from the organic phase under reduced pressure, followed by purifying the resultant residue by silica gel column chromatography eluting with ethyl acetate-hexane (2:3) to obtain 0.40 g of the objective substance as a light yellow resinoid.

$^1$H NMR (CDCl$_3$, Me$_4$Si, 300 MHz) δ 8.34 (s, 1H), 7.95 (d, J=10.8 Hz, 1H), 7.4-7.5 (m, 5H), 6.79 (s, 1H), 3.92 (s, 3H), 2.64 (s, 3H).

Process 2; Production of methyl 4-(4-bromo-5-(3,5-dichlorophenyl)-5-trifluoromethyl-4,5-dihydroisoxazole-3-yl)-2-methyl benzoate (compound of the present invention No. 4-005 in the following Table 10)

To a solution of 0.56 g of methyl 4-((1Z,2Z)-3-(3,5-dichlorophenyl)-4,4,4-trifluoro-1-(hydroxyimino)-2-butenyl)-2-methyl benzoate in 10 mL of benzene, 0.25 g of N-bromosuccinimide was added and the resultant mixture was stirred at room temperature for 16 hours. After the completion of the reaction, the insoluble substance was filtered off and the solvent was distilled off under reduced pressure, followed by purifying the resultant residue by silica gel column chromatography eluting with ethyl acetate to obtain 0.38 g of the objective substance as a white crystal.

Melting point: 183.0 to 185.5° C.

$^1$H NMR (CDCl$_3$, Me$_4$Si, 300 MHz) δ 8.01 (d, J=10.8 Hz, 1H), 7.65-7.75 (m, 2H), 7.45-7.6 (m, 3H), 5.88 (s, 1H), 3.93 (s, 3H), 2.67 (s, 3H)

Process 3; Production of 4-(4-bromo-5-(3,5-dichlorophenyl)-5-trifluoromethyl-4,5-dihydroisoxazole-3-yl)-2-methyl benzoic acid To a solution of 0.38 g of methyl 4-(4-bromo-5-(3,5-dichlorophenyl)-5-trifluoromethyl-4,5-dihydroisoxazole-3-yl)-2-methyl benzoate in 10 mL of methanol, a solution of 0.25 g of potassium hydroxide in 5 mL of water was added and the resultant mixture was stirred while heating the mixture to reflux for 2 hours. After the completion of the reaction, methanol was distilled off under reduced pressure and to the residual aqueous solution, a 2N hydrochloric acid aqueous solution was added to acidize the aqueous solution, followed by extracting the aqueous solution with ethyl acetate (20 mL×2). The organic phase was dehydrated and dried over a saturated saline and anhydrous sodium sulfate in this order, and the solvent was distilled off from the organic phase under reduced pressure. The resultant residue was purified by silica gel column chromatography eluting with ethyl acetate-hexane (1:1) to obtain 0.15 g of the objective substance as a colorless resinoid.

Process 4; Production of 4-(4-bromo-5-(3,5-dichlorophenyl)-5-trifluoromethyl-4,5-dihydroisoxazole-3-yl)-2-methyl-N-(2,2,2-trifluoroethyl)benzoic acid amide To a solution of 0.15 g of 4-(4-bromo-5-(3,5-dichlorophenyl)-5-trifluoromethyl-4,5-dihydroisoxazole-3-yl)-2-methyl benzoic acid, 0.06 g of 2,2,2-trifluoroethylamine and 0.09 g of triethylamine in 4 mL of dichloromethane, 0.11 g of 1-ethyl-3-(3-dimethylaminopropyl) carbodiimide hydrochloride was added and the resultant mixture was stirred at room temperature for 15 hours. After the completion of the reaction, the solvent was distilled off under reduced pressure and the resultant residue was purified by silica gel column chromatography eluting with ethyl acetate-hexane (1:1) to obtain 0.03 g of the objective substance as a light yellow resinoid.

$^1$H NMR (CDCl$_3$, Me$_4$Si, 300 MHz) δ 7.6-7.75 (m, 2H), 7.4-7.6 (m, 4H), 6.15-6.25 (m, 1H), 5.88 (s, 1H), 4.05-4.2 (m, 2H), 2.48 (s, 3H).

Synthetic Example 2

4-(5-(3,5-dichlorophenyl)-4-methylthio-5-trifluoromethyl-4,5-dihydroisoxazole-3-yl)-2-methyl-N-(2,2,2-trifluoroethyl)benzoic acid amide (compound of the present invention No. 1-005 in the following Table 7)

Process 1; Production of methyl 4-(5-(3,5-dichlorophenyl)-4-methylthio-5-trifluoromethyl-4,5-dihydroisoxazole-3-yl)-2-methyl benzoate To a solution of 0.30 g of methyl 4-(4-bromo-5-(3,5-dichlorophenyl)-5-trifluoromethyl-4,5-dihydroisoxazole-3-yl)-2-methyl benzoate synthesized in Process 2 of Synthetic Example 1 in 6 mL of N,N-dimethylformamide, a suspension of 0.04 g of sodium thiomethoxide in 1 mL of N,N-dimethylformamide was added while ice-cooling and stirring the solution and the resultant mixture was stirred at the same temperature for 2 hours. After the completion of the reaction, the reaction mixture was charged into 3 mL of ice water and the resultant reaction mixture was extracted with ethyl acetate (10 mL×2). The organic phase was washed with 5 mL of a 2N hydrochloric acid aqueous solution and then dehydrated and dried over a saturated saline and anhydrous sodium sulfate in this order, and the solvent was distilled off from the organic phase under reduced pressure. The resultant residue was purified by silica gel column chromatography eluting with ethyl acetate-hexane (1:9) to obtain 0.08 g of the objective substance as a colorless resinoid.

Process 2; Production of 4-(5-(3,5-dichlorophenyl)-4-methylthio-5-trifluoromethyl-4,5-dihydroisoxazole-3-yl)-2-methyl benzoic acid Methyl 4-(5-(3,5-dichlorophenyl)-4-methylthio-5-trifluoromethyl-4,5-dihydroisoxazole-3-yl)-2-methyl benzoate was dissolved in 10 mL of ethanol, and to the resultant solution, a solution of 5 mL of an aqueous solution containing 0.06 g of potassium hydroxide was added, followed by stirring the resultant mixture at 70° C. for 1 hour. After the completion of the reaction, ethanol was distilled off under reduced pressure and to the resultant residue, 5 mL of water was added. The resultant reaction mixture was washed with 5 mL of diethyl ether and thereto, a 2N hydrochloric acid aqueous solution was added to acidize the reaction mixture, followed by extracting the resultant reaction mixture with diethyl ether (5 mL×2). The organic phase was dehydrated and dried over a saturated saline and anhydrous sodium sulfate in this order, and then the solvent was distilled off from the organic phase under reduced pressure, followed by purifying the resultant residue by silica gel column chromatography eluting with ethyl acetate-hexane (1:1) to obtain 0.06 g of the objective substance as a colorless resinoid.

Process 3; Production of 4-(5-(3,5-dichlorophenyl)-4-methylthio-5-trifluoromethyl-4,5-dihydroisoxazole-3-yl)-2-methyl-N-(2,2,2-trifluoroethyl)benzoic acid amide 4-(5-(3,5-dichlorophenyl)-4-methylthio-5-trifluoromethyl-4,5-dihydroisoxazole-3-yl)-2-methyl benzoic acid was dissolved in 3 mL of dichloromethane, and to the resultant solution, 0.01 g of 2,2,2-trifluoroethylamine, 0.01 g of triethylamine and 0.03 g of 1-ethyl-3-(3-dimethylaminopropyl) carbodiimide hydrochloride were added, followed by stirring the resultant mixture at room temperature for 20 hours. After the completion of the reaction, to the reaction mixture, 6 mL of water was added and the resultant reaction mixture was extracted with ethyl acetate (10 mL×2). The organic phase was dehydrated and dried over a saturated saline and anhydrous sodium sulfate in this order, and then the solvent was distilled off from the organic phase under reduced pressure, followed by purifying the resultant residue by silica gel column chromatography eluting with ethyl acetate-hexane (1:1) to obtain 0.01 g of the objective substance as a colorless resinoid.

$^1$H NMR (CDCl$_3$, Me$_4$Si, 300 MHz) δ 7.7-7.85 (m, 2H), 7.56 (s, 2H), 7.4-7.5 (m, 2H), 6.0-6.15 (m, 1H), 4.96 (s, 1H), 4.05-4.2 (m, 2H), 2.50 (s, 3H), 1.43 (s, 3H).

Synthetic Example 3

4-(5-(3,5-dichlorophenyl)-4-methyl-5-trifluoromethyl-4,5-dihydroisoxazole-3-yl)-2-methyl-N-(2,2,2-trifluoroethyl)benzoic acid amide (compound of the present invention No. 1-004 in the following Table 7).

Process 1; Production of methyl 4-(5-(3,5-dichlorophenyl)-4-methyl-5-trifluoromethyl-4,5-dihydroisoxazole-3-yl)-2-methyl benzoate In a nitrogen atmosphere, into a solution of 1.30 g of methyl 4-(5-(3,5-dichlorophenyl)-5-trifluoromethyl-4,5-dihydroisoxazole-3-yl)-2-methyl benzoate (compound No. 11-054 in Patent Document 1) in 30 mL of tetrahydrofuran, 3.30 mL of a 1.0 M lithium hexamethyldisilazane tetrahydrofuran solution was dropped at −78° C. with stirring and after the completion of the dropping, the resultant mixture was continuously stirred at the same temperature further for 30 minutes. Next, to the reaction mixture, 4.26 g of methyl iodide was added and the resultant reaction mixture was heated to room temperature while continuing the stirring of the reaction mixture further for 1 hour. After the completion of the reaction, the reaction mixture was charged into 30 mL of ice water and thereto, a 2N hydrochloric acid aqueous solution was added, followed by extracting the resultant reaction mixture with ethyl acetate (50 mL×2) under an acidic condition. The organic phase was washed with water and then dehydrated and dried over a saturated saline and anhydrous sodium sulfate in this order, and the solvent was distilled off from the organic phase under reduced pressure, followed by purifying the resultant residue by silica gel column chromatography eluting with ethyl acetate-hexane (1:4) to obtain 1.65 g of the objective substance as a light yellow resinoid.

Process 2; Production of 4-(5-(3,5-dichlorophenyl)-4-methyl-5-trifluoromethyl-4,5-dihydroisoxazole-3-yl)-2-methyl benzoic acid To a solution of 1.65 g of methyl 4-(5-(3,5-dichlorophenyl)-4-methyl-5-trifluoromethyl-4,5-dihydroisoxazole-3-yl)-2-methyl benzoate in 60 mL of ethanol, a solution of 1.04 g of potassium hydroxide in 30 mL of water was added and the resultant mixture was stirred while heating the mixture to reflux for 6 hours. After the completion of the reaction, ethanol was distilled off under reduced pressure and to the residual aqueous solution, a 2N hydrochloric acid aqueous solution was added to acidize the aqueous solution, followed by extracting the aqueous solution with ethyl acetate (40 mL×2). The organic phase was dehydrated and dried over a saturated saline and anhydrous sodium sulfate in this order, and the solvent was distilled off from the organic phase under reduced pressure to obtain 0.30 g of a crude objective substance as a light yellow solid.

Process 3; Production of 4-(5-(3,5-dichlorophenyl)-4-methyl-5-trifluoromethyl-4,5-dihydroisoxazole-3-yl)-2-methyl-N-(2,2,2-trifluoroethyl)benzoic acid amide To a solution of 0.30 g of crude 4-(5-(3,5-dichlorophenyl)-4-methyl-5-trifluoromethyl-4,5-dihydroisoxazole-3-yl)-2-methyl benzoic acid, 0.14 g of 2,2,2-trifluoroethylamine and 0.21 g of triethylamine in 10 mL of dichloromethane, 0.27 g of 1-ethyl-3-(3-dimethylaminopropyl) carbodiimide hydrochloride was added and the resultant mixture was stirred at room temperature for 22 hours. After the completion of the reaction, the solvent was distilled off under reduced pressure and the resultant residue was purified by silica gel column chromatography eluting with ethyl acetate-hexane (3:7) to obtain 0.07 g of the objective substance as a light yellow resinoid.

$^1$H NMR (CDCl$_3$, Me$_4$Si, 300 MHz) δ 7.4-7.6 (m, 6H), 6.15-6.25 (m, 1H), 4.05-4.25 (m, 3H), 2.46 (m, 3H), 0.93 (d, J=10.0 Hz, 3H).

Synthetic Example 4

4-(4-chloro-5-(3,5-dichlorophenyl)-5-trifluoromethyl-4,5-dihydroisoxazole-3-yl)-2-methyl-N-(2,2,2-trifluoroethyl)benzoic acid amide (compound of the present invention No. 1-002 in the following Table 7).

Process 1; Production of methyl 4-(4-chloro-5-(3,5-dichlorophenyl)-5-trifluoromethyl-4,5-dihydroisoxazole-3-yl)-2-methyl benzoate In a nitrogen atmosphere, into a solution of 2.00 g of methyl 4-(5-3,5-dichlorophenyl)-5-trifluoromethyl-4,5-dihydroisoxazole-3-yl)-2-methyl benzoate (compound No. 11-054 in Patent Document 1) in 30 mL of tetrahydrofuran, 7.40 mL of a 1.0 M lithium hexamethyldisilazane tetrahydrofuran solution was dropped at −78° C. with stirring and thereto, 4.95 g of N-chlorosuccinimide was added, followed by continuing the stirring of the resultant mixture at the same temperature for 4 hours. After the completion of the reaction, the reaction mixture was charged into 50 mL of water and the resultant reaction mixture was extracted with ethyl acetate (40 mL×2). The organic phase was washed with water and then dehydrated and dried over a saturated saline and anhydrous sodium sulfate in this order, and the solvent was distilled off from the organic phase under reduced pressure. The resultant residue was purified by silica gel column chromatography eluting with ethyl acetate-hexane (1:5) to obtain 0.12 g of the objective substance as a light yellow resinoid.

$^1$H NMR (CDCl$_3$, Me$_4$Si, 300 MHz) δ 8.00 and 7.96 (d, J=8.1 Hz, 1H), 7.45-7.75 (m, 5H), 5.87 and 5.68 (s, 1H), 3.93 and 3.91 (s, 3H), 2.66, 2.63 (s, 3H).

Process 2; Production of 4-(4-chloro-5-(3,5-dichlorophenyl)-5-trifluoromethyl-4,5-dihydroisoxazole-3-yl)-2-methyl-N-(2,2,2-trifluoroethyl)benzoic acid amide To a solution of 0.12 g of methyl 4-(4-chloro-5-(3,5-dichlorophenyl)-5-trifluoromethyl-4,5-dihydroisoxazole-3-yl)-2-methyl benzoate in 10 mL of methanol, a solution of 0.20 g of potassium hydroxide in 5 mL of water was added and the resultant mixture was stirred at 90° C. for 6 hours. After the completion of the reaction, to the reaction mixture, 5 mL of concentrated hydrochloric acid was added to acidize the reaction mixture and then the reaction mixture was extracted with ethyl acetate (30 mL×2). The organic phase was dehydrated and dried over a saturated saline and anhydrous sodium sulfate in this order, and the solvent was distilled off from the organic phase under reduced pressure. The resultant residue was dissolved in 10 mL of dichloromethane, and to the resultant solution, 0.10 g of oxalyl chloride and 0.05 mL of N,N-dimethylformamide were added, followed by stirring the resultant mixture at room temperature for 1 hour. After the completion of the reaction, the solvent was distilled off under reduced pressure and the resultant residue was dissolved in 10 mL of dichloromethane. To the resultant solution, 0.10 g of 2,2,2-trifluoroethylamine and 0.20 g of triethylamine were added and the resultant mixture was stirred at room temperature for 1 hour. After the completion of the reaction, to the reaction mixture, 20 mL of ethyl acetate was added and an insoluble substance was filtered off, followed by distilling off the solvent under reduced pressure. The resultant residue was purified by silica gel column chromatography eluting with ethyl acetate-hexane (1:2) to obtain 0.06 g of the objective substance as a white crystal.

Melting point: 127.0 to 128.0° C.

$^1$H NMR (CDCl$_3$, Me$_4$Si, 300 MHz) δ 7.4-7.75 (m, 6H), 6.14 (bs, 1H), 5.87 (s, 1H), 3.9-4.2 (m, 2H), 2.49 (s, 3H).

Synthetic Example 5

4-(4-bromo-5-(3,5-bis(trifluoromethyl)phenyl)-5-trifluoromethyl-4,5-dihydroisoxazole-3-yl) benzoic acid amide (compound of the present invention No. 1-001 in the following Table 7).

To a solution of 0.55 g of 4-(4-bromo-5-(3,5-bis(trifluoromethyl)phenyl)-5-trifluoromethyl-4,5-dihydroisoxazole-3-yl) benzoic acid synthesized in substantially the same manner as in Processes 1 to 3 of Synthetic Example 1 in 10 mL of dichloromethane, 0.15 g of oxalyl chloride and 2 drops of N,N-dimethylformamide were added and the resultant mixture was stirred at room temperature for 20 minutes. After the completion of the reaction, the solvent was distilled off under reduced pressure and the resultant residue was dissolved in 1 mL of tetrahydrofuran, followed by dropping the resultant solution into a mixture of 2 mL of concentrated ammonia water and 2 mL of tetrahydrofuran with stirring at room temperature. After the completion of the dropping, the resultant reaction mixture was continuously stirred at the same temperature further for 10 minutes. After the completion of the reaction, to the reaction mixture, 5 mL of water was added and the resultant reaction mixture was extracted with ethyl acetate (10 mL×1). The organic phase was washed with 5 mL of a 2N hydrochloric acid aqueous solution and dehydrated and dried over a saturated saline and anhydrous sodium sulfate in this order, and the solvent was distilled off from the organic phase under reduced pressure. To the resultant residue, 2 mL of a solvent mixture of ethyl acetate-hexane (1:1) was added and the resultant mixture was stirred at room temperature for 30 minutes, followed by filtering a separated-out crystal to obtain 0.53 g of the objective substance as a white crystal.

Melting point: 190.0 to 193.0° C.

$^1$H NMR (CDCl$_3$, Me$_4$Si, 300 MHz) δ 8.07 (bs, 1H), 8.01 (s, 1H), 7.93 (s, 5H), 5.98 (s, 1H).

Synthetic Example 6

4-(4-bromo-5-(3,5-bis(trifluoromethyl)phenyl)-5-trifluoromethyl-4,5-dihydroisoxazole-3-yl)-N-(methoxyiminomethyl)benzoic acid amide (compound of the present invention No. 1-011 in the following Table 7).

A solution of 0.12 g of 4-(4-bromo-5-(3,5-bis(trifluoromethyl)phenyl)-5-trifluoromethyl-4,5-dihydroisoxazole-3-yl) benzoic acid amide synthesized in Synthetic Example 5 and 0.05 g of N,N-dimethylformamide dimethylacetal in 2 mL of tetrahydrofuran was stirred at room temperature for 15 hours. Next, to the reaction mixture, a solution of 0.04 g of methoxyamine hydrochloride in 2 mL of water was added and the resultant mixture was continuously stirred at room temperature further for 10 minutes. After the completion of the reaction, to the reaction mixture, 5 mL of water was added and the resultant mixture was extracted with ethyl acetate (10 mL×1). The organic phase was dehydrated and dried over a saturated saline and anhydrous sodium sulfate in this order, and the solvent was distilled off from the organic phase under reduced pressure. The resultant residue was purified by silica gel column chromatography eluting with ethyl acetate-hexane (1:1) to obtain 0.10 g of the objective substance as a white crystal.

Melting point: 118.0 to 122.0° C.
$^1$H NMR (CDCl$_3$, Me$_4$Si, 300 MHz) δ 8.88 and 8.63 (d, J=9.6 Hz, 1H), 7.85-8.2 (m, 6H), 7.82 (d, J=9.9 Hz, 1H), 5.98 and 5.30 (s, 1H), 3.95 and 3.82 (s, 3H).

Synthetic Example 7

4-((2Z)-3-(3,5-dichlorophenyl)-4,4,4-trifluoro-1-(hydroxyimino)-2-butenyl)-2-methyl-N-(2,2,2-trifluoroethyl) benzoic acid amide (compound of the present invention No. 5-001 in the following Table 11).

In a nitrogen atmosphere, into a solution of 0.20 g of 4-(5-3,5-dichlorophenyl)-5-trifluoromethyl-4,5-dihydroisoxazole-3-yl)-2-methyl-N-(2,2,2-trifluoroethyl)benzoic acid amide (compound No. 5-075 in Patent Document 1) in 4 mL of tetrahydrofuran, 0.8 mL of a 1.0 M lithium hexamethyldisilazane tetrahydrofuran solution was dropped at room temperature with stirring. The resultant mixture was stirred at room temperature for 3 minutes and the reaction mixture was charged into 3 mL of ice water, and thereto, a 2N hydrochloric acid aqueous solution was added and the resultant reaction mixture was extracted with diethyl ether (10 mL×2) under an acidic condition. The organic phase was washed with water and then dehydrated and dried over a saturated saline and anhydrous sodium sulfate in this order, followed by distilling off the solvent from the organic phase under reduced pressure. The resultant residue was purified by silica gel column chromatography eluting with ethyl acetate-hexane (3:7) to obtain 0.12 g of the objective substance as a white crystal.

Melting point: 133.0 to 135.0° C.
$^1$H NMR (CDCl$_3$, Me$_4$Si, 300 MHz) δ 7.97 (s, 1H), 7.4-7.55 (m, 6H), 6.76 (s, 1H), 6.0-6.1 (m, 1H), 4.05-4.2 (m, 2H), 2.48 (s, 3H).

Synthetic Example 8

4-((2E)-3-(3,5-dichlorophenyl)-4,4,4-trifluoro-1-(hydroxyimino)-2-butenyl)-2-methyl-N-(2,2,2-trifluoroethyl) benzoic acid amide (compound of the present invention No. 6-001 in the following Table 12).

In a nitrogen atmosphere, into a solution of 0.75 g of 4-(5-(3,5-dichlorophenyl)-5-trifluoromethyl-4,5-dihydroisoxazole-3-yl)-2-methyl-N-(2,2,2-trifluoroethyl)benzoic acid amide (compound No. 5-075 in Patent Document 1) in 20 mL of tetrahydrofuran, 2.24 mL of a 1.0 M lithium hexamethyldisilazane tetrahydrofuran solution was dropped at room temperature with stirring. The resultant mixture was stirred at room temperature for 1 hour and into the mixture, 3.0 mL of a 1.0 M lithium hexamethyldisilazane tetrahydrofuran solution was further dropped. After the completion of the dropping, the resultant mixture was continuously stirred at the same temperature further for 30 minutes. After the completion of the reaction, the reaction mixture was charged into 20 mL of ice water and thereto, a 2N hydrochloric acid aqueous solution was added, followed by extracting the resultant reaction mixture with ethyl acetate (40 mL×2) under an acidic condition. The organic phase was washed with water and then dehydrated and dried over a saturated saline and anhydrous sodium sulfate in this order, and the solvent was distilled off from the organic phase under reduced pressure. The resultant residue was purified by silica gel column chromatography eluting with ethyl acetate-hexane (1:1) to obtain 0.26 g of the objective substance as a colorless resinoid.

$^1$H NMR (CDCl$_3$, Me$_4$Si, 300 MHz) δ 9.77 (s, 1H), 7.39 (s, 1H), 6.9-7.25 (m, 6H), 6.25 (t, J=8.4 Hz, 1H), 3.95-4.2 (m, 2H), 2.44 (s, 3H).

Synthetic Example 9

Tert-butyl N-(2-bromo-4-((2Z)-3-(3,5-dichlorophenyl)-1-hydroxyimino-4,4,4-trifluoro-2-butenyl)phenylmethyl)-N-(cyclopropylcarbonyl) carbamate (compound of the present invention No. 7-004 in the following Table 13).

Process 1; Production of 3-bromo-4-methylbenzaldoxime

To a solution of 17.9 g of 3-bromo-4-methylbenzaldehyde in 150 mL of methanol and 100 mL of water, 7.6 g of hydroxylamine hydrochloride was added and the resultant mixture was stirred at 70° C. for 3 hours. After the completion of the reaction, the reaction mixture was left to be cooled down to room temperature and was diluted with 150 mL of ethyl acetate to be washed with water (100 mL×1). Further, the reaction mixture was dehydrated and dried over a saturated saline and anhydrous sodium sulfate in this order and the solvent was distilled off under reduced pressure to obtain 19.1 g of the objective substance as a brown crystal. This crystal was used in the next process without being further purified.

Melting point: 55.0 to 59.0° C.
$^1$H NMR (CDCl$_3$, Me$_4$Si, 300 MHz) δ 8.06 (s, 1H), 7.74 (s, 1H), 7.39 (d, J=7.5 Hz, 1H), 7.23 (d, J=7.5 Hz, 1H), 2.41 (s, 3H).

Process 2; Production of 3-(3-bromo-4-methylphenyl)-5-(3,5-dichlorophenyl)-5-trifluoromethyl-4,5-dihydroisoxazole To a solution of 19.1 g of 3-bromo-4-methylbenzaldoxime in 100 mL of 1,2-dimethoxyethane, 13.4 g of N-chlorosuccinimide was added and the resultant mixture was stirred at 70° C. for 2 hours. Next, the reaction mixture was left to be cooled down to room temperature and thereto, 16.1 g of 3,5-dichloro-1-(1-trifluoromethylethenyl)benzene, 22.2 g of potassium hydrogen carbonate and 15 mL of water were added, followed by continuing the stirring of the resultant reaction mixture at room temperature further for 20 hours. After the completion of the reaction, the reaction mixture was diluted with 100 mL of ethyl acetate and was washed with water (70 mL×1). Further, the reaction mixture was dehydrated and dried over a saturated saline and anhydrous sodium sulfate in this order and the solvent was distilled off under reduced pressure. The resultant residual solid was washed with diisopropyl ether to obtain 20.0 g of the objective substance as a white crystal.

Melting point: 119.0 to 121.0° C.
$^1$H NMR (CDCl$_3$, Me$_4$Si, 300 MHz) δ 7.80 (d, J=1.5 Hz, 1H), 7.5-7.6 (m, 3H), 7.43 (t, J=1.5 Hz, 1H), 7.28 (d, J=8.1 Hz, 1H), 4.05 (d, J=17.4 Hz, 11-1), 3.66 (d, J=17.4 Hz, 1H), 2.43 (s, 3H).

Process 3; Production of 3-(3-bromo-4-(bromomethyl) phenyl)-5-(3,5-dichlorophenyl)-5-trifluoromethyl-4,5-dihydroisoxazole To a solution of 20.0 g of 3-(3-bromo-4-methylphenyl)-5-(3,5-dichlorophenyl)-5-trifluoromethyl-4,5-dihydroisoxazole in 170 mL of 1,2-dichloroethane, 9.4 g of N-bromosuccinimide and 0.6 g of α,α'-azobisisobutylonitrile were added and the resultant mixture was stirred at 80° C. for 3 hours. After the completion of the reaction, the reaction mixture was left to be cooled down to room temperature and was washed with water (50 mL×2). Subsequently, the reaction mixture was dehydrated and dried over a saturated saline and anhydrous sodium sulfate in this order and the solvent was distilled off under reduced pressure to obtain 25.1 g of a crude objective substance as a brown oily substance. This substance was used in the next process without being further purified.

Process 4; Production of N-(2-bromo-4-(5-(3,5-dichlorophenyl)-5-trifluoromethyl-4,5-dihydroisoxazole-3-yl) phenylmethyl) phthalimide To a solution of 12.0 g of 3-(3-bromo-4-(bromomethyl) phenyl)-5-(3,5-dichlorophenyl)-5-trifluoromethyl-4,5-dihydroisoxazole in 80 mL of N,N-dimethylformamide, 4.18 g of potassium phthalimide was added and the resultant mixture was stirred at room temperature for 3 hours. After the completion of the reaction, the reaction mixture was diluted with 120 mL of ethyl acetate and was washed with water (80 mL×3). Subsequently, the reaction mixture was dehydrated and dried over a saturated saline and anhydrous sodium sulfate in this order and the solvent was distilled off under reduced pressure. The resultant residue was purified by silica gel column chromatography eluting with ethyl acetate-hexane (1:3) to obtain 7.2 g of the objective substance as a light yellow resinoid.

$^1$H NMR (CDCl$_3$, Me$_4$Si, 300 MHz) δ 7.7-8.1 (m, 4H), 7.35-7.7 (m, 4H), 7.15-7.35 (m, 2H), 4.98 (s, 2H), 4.03 (d, J=17.4 Hz, 1H), 3.65 (d, J=17.4 Hz, 1H).

Process 5; Production of 3-(4-aminomethyl-3-bromophenyl)-5-(3,5-dichlorophenyl)-5-trifluoromethyl-4,5-dihydroisoxazole To a suspension of 5.94 g of N-(2-bromo-4-(5-(3,5-dichlorophenyl)-5-trifluoromethyl-4,5-dihydroisoxazole-3-yl)phenylmethyl) phthalimide in 150 mL of ethanol, 3.0 mL of a 80% hydrazine monohydrate aqueous solution was added and the resultant mixture was stirred while heating the reaction mixture to reflux for 2 hours. After the completion of the reaction, the reaction mixture was left to be cooled down to room temperature and thereto, 100 mL of chloroform was added to filter off an insoluble substance, followed by distilling off the solvent under reduced pressure. To the resultant residue, 50 mL of chloroform was added to dissolve the residue and to filter off the resultant insoluble substance. The filtrate was washed with water (50 mL×1) and then was dehydrated and dried over a saturated saline and anhydrous sodium sulfate in this order, and the solvent was distilled off under reduced pressure to obtain 3.87 g of the objective substance as a yellow resinoid.

$^1$H NMR (CDCl$_3$, Me$_4$Si, 300 MHz) δ 7.84 (d, J=1.5 Hz, 11-1), 7.62 (dd, J=8.1, 1.5 Hz, 1H), 7.45-7.55 (m, 3H), 7.43 (t, J=1.5 Hz, 1H), 4.06 (d, J=17.4 Hz, 1H), 3.99 (s, 2H), 3.67 (d, J=17.4 Hz, 1H).

Process 6; Production of N-(2-bromo-4-(5-(3,5-dichlorophenyl)-5-trifluoromethyl-4,5-dihydroisoxazole-3-yl) phenylmethyl cyclopropanecarboxamide Into a solution of 3.87 g of 3-(4-aminomethyl-3-bromophenyl)-5-(3,5-dichlorophenyl)-5-trifluoromethyl-4,5-dihydroisoxazole and 1.25 g of triethylamine in 60 mL of dichloromethane, 0.30 g of cyclopropanecarbonyl chloride was dropped while ice-cooling and stirring the solution. After the completion of the dropping, the resultant mixture was continuously stirred at room temperature further for 10 minutes. After the completion of the reaction, the solvent was distilled off under reduced pressure and the resultant residue was dissolved in 60 mL of ethyl acetate. The resultant solution was washed with 30 mL of a 2N hydrochloric acid aqueous solution, 30 mL of water and 30 mL of a saturated sodium hydrogen carbonate aqueous solution, and then was dehydrated and dried over a saturated saline and anhydrous sodium sulfate in this order, followed by distilling off the solvent under reduced pressure. The resultant residue was purified by silica gel column chromatography eluting with ethyl acetate-hexane (1:4) to obtain 3.40 g of the objective substance as a white crystal.

Melting point: 158.0 to 162.0° C.

$^1$H NMR (CDCl$_3$, Me$_4$Si, 300 MHz) δ 7.83 (s, 1H), 7.4-7.6 (m, 5H), 6.33 (t, J=6.0 Hz, 1H), 4.51 (d, J=6.0 Hz, 2H), 4.05 (d, J=17.4 Hz, 1H), 3.67 (d, J=17.4 Hz, 1H), 1.35-1.5 (m, 1H), 0.85-1.1 (m, 4H).

Process 7; Production of tert-butyl N-(2-bromo-4-(5-(3,5-dichlorophenyl)-5-trifluoromethyl-4,5-dihydroisoxazole-3-yl) phenylmethyl)-N-(cyclopropylcarbonyl) carbamate To a solution of 0.54 g of N-(2-bromo-4-(5-(3,5-dichlorophenyl)-5-trifluoromethyl-4,5-dihydroisoxazole-3-yl) phenylmethyl)cyclopropanecarboxamide, 0.10 g of trimethylamine and 0.01 g of 4-(N,N-dimethylamino) pyridine in 20 mL of dichloromethane, 0.44 g of di-tert-butyl dicarbonate was added and the resultant mixture was stirred at room temperature for 17 hours. After the completion of the reaction, the solvent was distilled off under reduced pressure and to the resultant residue, 20 mL of diethyl ether and 5 mL of a 1N sodium hydroxide aqueous solution were added, followed by stirring the reaction mixture at room temperature for 5 minutes. Subsequently, the organic phase was separated off. The aqueous phase was extracted with diethyl ether (10 mL×2) and combined with the organic phase. The combined organic phase was washed with 10 mL of a 2N hydrochloric acid aqueous solution and then was dehydrated and dried over a saturated saline and anhydrous sodium sulfate in this order, followed by distilling off the solvent under reduced pressure. The resultant residue was purified by silica gel column chromatography eluting with ethyl acetate-hexane (1:4) to obtain 0.50 g of the objective substance as a colorless resinoid.

$^1$H NMR (CDCl$_3$, Me$_4$Si, 300 MHz) δ 7.82 (s, 1H), 7.56 (d, J=8.1 Hz, 1H), 7.49 (s, 2H), 7.42 (s, 1H), 7.05 (d, J=8.1 Hz, 1H), 4.95 (s, 2H), 4.04 (d, J=17.1 Hz, 1H), 3.65 (d, J=17.1 Hz, 1H), 2.85-2.95 (m, 1H), 1.44 (s, 9H), 1.1-1.2 (m, 2H), 0.95-1.05 (m, 2H).

Process 8: Production of tert-butyl N-(2-bromo-4-((2Z)-3-(3,5-dichlorophenyl)-1-hydroxyimino-4,4,4-trifluoro-2-butenyl)phenylmethyl)-N-(cyclopropylcarbonyl) carbamate.

Into a solution of 0.47 g of tert-butyl N-(2-bromo-4-(5-(3,5-dichlorophenyl)-5-trifluoromethyl-4,5-dihydroisoxazole-3-yl) phenylmethyl)-N-(cyclopropylcarbonyl) carbamate in 15 mL of tetrahydrofuran, 0.74 mL of a 1.0 M lithium hexamethyldisilazane tetrahydrofuran solution was dropped at room temperature with stirring. After the completion of the dropping, the resultant mixture was continuously stirred at the same temperature further for 30 minutes. After the completion of the reaction, the reaction mixture was charged into 10 mL of ice water and thereto, a 2N hydrochloric acid aqueous solution was added, followed by extracting the resultant reaction mixture with ethyl acetate (20 mL×2) under an acidic condition. The organic phase was washed with water and then dehydrated and dried over a saturated saline and anhydrous sodium sulfate in this order, followed by distilling off the solvent from the organic phase under reduced pressure. The resultant residue was purified by silica gel column chromatography eluting with ethyl acetate-hexane (2:3) to obtain 0.41 g of the objective substance as a colorless resinoid.

$^1$H NMR (CDCl$_3$, Me$_4$Si, 300 MHz) δ 8.01 (bs, 1H), 7.82 (s, 1H), 7.4-7.45 (m, 4H), 7.04 (d, J=8.1 Hz, 1H), 6.73 (s, 1H), 4.97 (s, 2H), 2.85-3.0 (m, 1H), 1.37 (s, 9H), 1.15-1.2 (m, 2H), 0.95-1.05 (m, 2H).

Synthetic Example 10

Tert-butyl N-(2-bromo-4-(4-bromo-5-(3,5-dichlorophenyl)-5-trifluoromethyl-4,5-dihydroisoxazole-3-yl) phenylmethyl)-N-(cyclopropylcarbonyl) carbamate (compound of the present invention No. 2-006 in the following Table 8).

To a solution of 0.36 g of tert-butyl N-(2-bromo-4-((2Z)-3-(3,5-dichlorophenyl)-1-hydroxyimino-4,4,4-trifluoro-2-butenyl)phenylmethyl)-N-(cyclopropylcarbonyl) carbamate synthesized in Synthetic Example 9 in 10 mL of benzene, 0.11 g of N-bromosuccinimide was added and the resultant mixture was stirred at room temperature for 16 hours. After the completion of the reaction, an insoluble substance was filtered off and the solvent was distilled off under reduced pressure. The resultant residue was purified by silica gel column chromatography eluting with ethyl acetate-hexane (2:3) to obtain 0.23 g of the objective substance as a colorless resinoid.

$^1$H NMR (CDCl$_3$, Me$_4$Si, 300 MHz) δ 8.00 (s, 1H), 7.69 (d, J=8.4 Hz, 1H), 7.4-7.55 (m, 3H), 7.10 (d, J=8.4 Hz, 1H), 5.79 (s, 1H), 4.98 (s, 2H), 2.85-2.95 (m, 1H), 1.41 (s, 9H), 1.1-1.2 (m, 2H), 0.95-1.05 (m, 2H).

Synthetic Example 11

N-(2-bromo-4-(4-bromo-5-(3,5-dichlorophenyl)-5-trifluoromethyl-4,5-dihydroisoxazole-3-yl) phenylmethyl)cyclopropylcarboxamide (compound of the present invention No. 2-002 in the following Table 8).

To 0.23 g of tert-butyl N-(2-bromo-4-(4-bromo-5-(3,5-dichlorophenyl)-5-trifluoromethyl-4,5-dihydroisoxazole-3-yl) phenylmethyl)-N-(cyclopropylcarbonyl) carbamate synthesized in Synthetic Example 10, 10 mL of trifluoroacetic acid was added and the resultant mixture was stirred at room temperature for 1 hour. After the completion of the reaction, trifluoroacetic acid was distilled off under reduced pressure and the resultant residue was purified by silica gel column chromatography eluting with ethyl acetate-hexane (1:1) to obtain 0.15 g of the objective substance as a colorless resinoid.

$^1$H NMR (CDCl$_3$, Me$_4$Si, 300 MHz) δ 8.03 (s, 1H), 7.70 (d, J=8.4 Hz, 1H), 7.4-7.55 (m, 4H), 6.14 (t, J=6.3 Hz, 1H), 5.80 (s, 1H), 4.56 (d, J=6.3 Hz, 2H), 1.35-1.45 (m, 1H), 0.95-1.05 (m, 2H), 0.75-0.85 (m, 2H).

Synthetic Example 12

N-(2-bromo-4-(5-(3,5-dichlorophenyl)-4-methyl-5-trifluoromethyl-4,5-dihydroisoxazole-3-yl) phenylmethyl)-N-(methyl)cyclopropanecarboxamide (compound of the present invention No. 2-005 in the following Table 8).

In a nitrogen atmosphere, into a solution of 0.54 g of N-(2-bromo-4-(5-(3,5-dichlorophenyl)-5-trifluoromethyl-4,5-dihydroisoxazole-3-yl) phenylmethyl)cyclopropanecarboxamide synthesized in Process 6 of Synthetic Example 9 in 5 mL of tetrahydrofuran, 2.0 mL of a 1.0 M lithium hexamethyldisilazane tetrahydrofuran solution was dropped at −78° C. with stirring. After the completion of the dropping, the resultant mixture was continuously stirred at the same temperature further for 30 minutes. Next, to the reaction mixture, 1.42 g of methyl iodide was added and the reaction mixture was heated to room temperature while continuously stirring the reaction mixture further for 15 hours. After the completion of the reaction, the reaction mixture was charged into 5 mL of ice water and thereto, a 2N hydrochloric acid aqueous solution was added, followed by extracting the resultant reaction mixture with ethyl acetate (20 mL×2) under an acidic condition. The organic phase was washed with water and then dehydrated and dried over a saturated saline and anhydrous sodium sulfate in this order, and the solvent was distilled off from the organic phase under reduced pressure, followed by purifying the resultant residue by high performance liquid chromatography eluting with acetonitrile-water (4:1) to obtain 0.19 g of the objective substance as a colorless resinoid.

$^1$H NMR (CDCl$_3$, Me$_4$Si, 300 MHz) δ 7.98, 7.90, 7.88 and 7.79 (s, 1H), 7.4-7.7 (m, 4H), 7.15-7.3 (m, 1H), 4.65-4.8 (m, 21-1), 3.95-4.1 and 4.1-4.2 (m, 1H), 3.03, 3.05, 3.17 and 3.20 (s, 3H), 1.4-1.55 and 1.8-1.9 (m, 1H), 1.0-1.1 (m, 2H), 0.9-1.05 (m, 3H), 0.65-0.8 and 0.8-0.9 (m, 2H).

Synthetic Example 13

3-(3,5-dichlorophenyl)-4,4,4-trifluoro-1-(4-(methylthio) phenyl)-2-butenone-1-oxime (compound of the present invention No. 9-004 in the following Table 15).

In a nitrogen atmosphere, into a solution of 0.41 g of 5-(3,5-dichlorophenyl)-3-(4-(methylthio) phenyl)-5-trifluoromethyl-4,5-dihydroisoxazole (compound No. 1-002 in Patent Document 5) in 10 mL of tetrahydrofuran, 1.1 mL of a 1.0 M lithium hexamethyldisilazane tetrahydrofuran solution was dropped at room temperature with stirring. After stirring the resultant mixture at room temperature for 10 minutes, the reaction mixture was charged into 5 mL of ice water and thereto, a 2N hydrochloric acid aqueous solution was added, followed by extracting the resultant reaction mixture with diethyl ether (10 mL×2) under an acidic condition. The organic phase was washed with water and then dehydrated and dried over a saturated saline and anhydrous sodium sulfate in this order, and the solvent was distilled off from the organic phase under reduced pressure. The resultant residue was purified by silica gel column chromatography eluting with ethyl acetate-hexane (1:9) to obtain 0.35 g of the objective substance as a white crystal.

Melting point: 129.0 to 131.0° C.

$^1$H NMR (CDCl$_3$, Me$_4$Si, 300 MHz) δ 7.75 (s, 1H), 7.51 (d, J=8.1 Hz, 2H), 7.43 (s, 3H), 7.2-7.3 (m, 2H), 6.74 (s, 1H), 2.51 (s, 3H).

Synthetic Example 14

4-bromo-5-(3,5-dichlorophenyl)-3-(4-(methylthio) phenyl)-5-trifluoromethyl-4,5-dihydroisoxazole (compound of the present invention No. 4-002 in the following Table 10).

To a solution of 0.18 g of 3-(3,5-dichlorophenyl)-4,4,4-trifluoro-1-(4-(methylthio) phenyl)-2-butenone-1-oxime synthesized in Synthetic Example 13 in 4 mL of benzene, 0.09 g of N-bromosuccinimide was added and the resultant mixture was stirred at room temperature for 19 hours. After the completion of the reaction, the solvent was distilled off under reduced pressure and the resultant residue was purified by silica gel column chromatography eluting with ethyl acetate-hexane (1:4) to obtain 0.07 g of the objective substance as a white crystal.

Melting point 109.0 to 112.0° C.

$^1$H NMR (CDCl$_3$, Me$_4$Si, 300 MHz) δ 7.65-7.75 (m, 2H), 7.50 (bs, 1H), 7.4-7.45 (m, 2H), 7.25-7.3 (m, 2H), 5.83 (s, 1H), 2.53 (s, 3H).

The compound of the present invention can be produced according to the above production methods and Examples. Examples of the compound of the present invention produced in substantially the same manner as those in Synthetic Example 1 to Synthetic Example 14 are shown in Table 7 to Table 17, which should not be construed as limiting the scope of the present invention.

Here, in Tables, a structure represented by $G^2$-7 represents the following structure:

$G^2$-7:

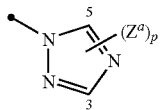

in Tables, aromatic heterocyclic rings represented by D10-2a to D34-1c individually represent the following structures:

D10-2a:

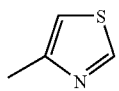

D32-1a:

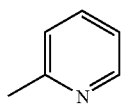

D32-1d:

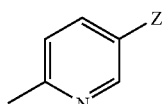

D34-1c:

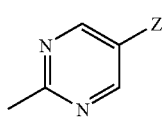

in Tables, an aliphatic heterocyclic ring represented by E4-1a represents the following structure:

E4-1a:

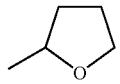

in Tables, "Et" represents an ethyl group; "c-Pr" and "Pr-c" individually represent a cyclopropyl group; "t-Bu" and "Bu-t" represent a tertiary butyl group; and a description "Ph" represents a phenyl group, in Tables, T-4 and T-5 individually represent the structures:

T-4:

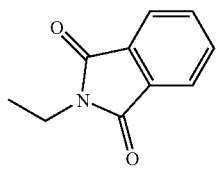

T-5:

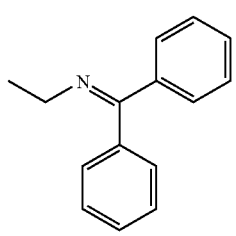

In addition, in Tables, the numbers representing substituted positions of substituents $(X)_m$ and $(Y)_n$ correspond to the positions of numbers attached to each of the following structural formulae, and an expression "-" represents "non-substituted". The number representing a substituted position of a substituent $(Z^a)_p$ corresponds to a position of a number attached to the above structural formula, and an expression "-" represents "non-substituted".

Furthermore, "*1" in Tables means "resinous".

TABLE 7

| No. | $(X)_m$ | $R^{3a}$ | $(Y)_n$ | $R^2$ | $R^1$ | m.p. (° C.) |
|---|---|---|---|---|---|---|
| 1-001 | 3,5-$(CF_3)_2$ | Br | — | H | H | 190.0-193.0 |
| 1-002 | 3,5-$Cl_2$ | Cl | 2-$CH_3$ | H | $CH_2CF_3$ | 127.0-128.0 |
| 1-003 | 3,5-$Cl_2$ | Br | 2-$CH_3$ | H | $CH_2CF_3$ | *1 |
| 1-004 | 3,5-$Cl_2$ | $CH_3$ | 2-$CH_3$ | H | $CH_2CF_3$ | *1 |
| 1-005 | 3,5-$Cl_2$ | $SCH_3$ | 2-$CH_3$ | H | $CH_2CF_3$ | *1 |
| 1-006 | 3,5-$(CF_3)_2$ | Br | — | H | E4-1a | *1 |
| 1-007 | 3,5-$(CF_3)_2$ | Br | — | H | $CH_2C(O)NHCH_2CF_3$ | *1 |
| 1-008 | 3,5-$Cl_2$ | Br | 2-$NO_2$ | H | $CH_2C(O)NHCH_2CF_3$ | *1 |
| 1-009 | 3,5-$(CF_3)_2$ | Br | — | H | $CH_2$(D10-2a) | 155.0-159.0 |
| 1-010 | 3,5-$(CF_3)_2$ | Br | — | H | $CH_2$(D32-1a) | *1 |
| 1-011 | 3,5-$(CF_3)_2$ | Br | — | H | CH=$NOCH_3$ | 118.0-122.0 |
| 1-012 | 3,5-$(CF_3)_2$ | Br | — | H | CH=NOEt | *1 |

TABLE 7-continued

| | | | | | | |
|---|---|---|---|---|---|---|
| 1-013 | 3,4-Cl$_2$-5-CF$_3$ | Br | — | H | CH=NOEt | *1 |
| 1-014 | 3,5-(CF$_3$)$_2$ | Br | — | H | C(O)OEt | 168.0-170.0 |

TABLE 8

| No. | (X)$_m$ | R$^{3a}$ | (Y)$_n$ | R$^{4a}$ | R$^{2a}$ | R$^{14}$ | m.p. (° C.) |
|---|---|---|---|---|---|---|---|
| 2-001 | 3,5-Cl$_2$ | Cl | 2-Br | H | H | c-Pr | *1 |
| 2-002 | 3,5-Cl$_2$ | Br | 2-Br | H | H | c-Pr | *1 |
| 2-003 | 3,4,5-Cl$_3$ | Br | 2-Br | H | H | c-Pr | *1 |
| 2-004 | 3,4,5-Cl$_3$ | Br | — | CH$_3$ | H | c-Pr | *1 |
| 2-005 | 3,5-Cl$_2$ | CH$_3$ | 2-Br | H | CH$_3$ | c-Pr | *1 |
| 2-006 | 3,5-Cl$_2$ | Br | 2-Br | H | C(O)OBu-t | c-Pr | *1 |

TABLE 9

| No. | (X)$_m$ | R$^{3a}$ | (Y)$_n$ | G$^2$ | (Z$^a$)$_p$ | m.p. (° C.) |
|---|---|---|---|---|---|---|
| 3-001 | 3,5-(CF$_3$)$_2$ | Br | 2-CN | G$^2$-7 | — | *1 |

TABLE 10

| No. | (X)$_m$ | R$^{3a}$ | (Y)$_n$ | Q | m.p. (° C.) |
|---|---|---|---|---|---|
| 4-001 | 3,5-Cl$_2$ | Br | — | NO$_2$ | 137.0-139.0 |
| 4-002 | 3,5-Cl$_2$ | Br | — | SCH$_3$ | 109.0-112.0 |
| 4-003 | 3,5-(CF$_3$)$_2$ | Br | — | C(O)OH | 202.0-203.0 |
| 4-004 | 3,5-(CF$_3$)$_2$ | Br | — | C(O)OCH$_3$ | 123.0-125.0 |
| 4-005 | 3,5-Cl$_2$ | Br | 2-CH$_3$ | C(O)OCH$_3$ | 183.0-185.5 |

TABLE 11

| No. | (X)$_m$ | (Y)$_n$ | R$^2$ | R$^1$ | m.p. (° C.) |
|---|---|---|---|---|---|
| 5-001 | 3,5-Cl$_2$ | 2-CH$_3$ | H | CH$_2$CF$_3$ | 133.0-135.0 |
| 5-002 | 3,5-Cl$_2$ | 2-CH$_3$ | H | E4-1a | 107.0-111.0 |
| 5-003 | 3,5-Cl$_2$ | 2-CH$_3$ | H | CH$_2$C(O)NHCH$_2$CF$_3$ | 185.0-189.0 |
| 5-004 | 3,5-Cl$_2$ | 2-CH$_3$ | H | CH=NOCH$_3$(Z) | *1 |
| 5-005 | 3,5-(CF$_3$)$_2$ | 2-CH$_3$ | H | CH=NOCH$_3$(Z) | *1 |
| 5-006 | 3,5-Cl$_2$ | 2-CH$_3$ | H | Ph | *1 |
| 5-007 | 3,5-Cl$_2$ | 2-CH$_3$ | H | Ph-4-F | 108.0-109.0 |
| 5-008 | 3,5-Cl$_2$ | 2-CH$_3$ | H | Ph-4-CN | *1 |
| 5-009 | 3,5-Cl$_2$ | 2-CH$_3$ | H | (D32-1d)Cl | 214.0-216.0 |
| 5-010 | 3,5-Cl$_2$ | 2-CH$_3$ | H | (D34-1c)Cl | 197.0-200.0 |

TABLE 12

| No. | (X)$_m$ | (Y)$_n$ | R$^2$ | R$^1$ | m.p. (° C.) |
|---|---|---|---|---|---|
| 6-001 | 3,5-Cl$_2$ | 2-CH$_3$ | H | CH$_2$CF$_3$ | *1 |
| 6-002 | 3,5-Cl$_2$ | 2-CH$_3$ | CH$_3$ | CH=C=CH$_2$ | 172.0-177.0 |

TABLE 13

| No. | (X)$_m$ | (Y)$_n$ | R$^{4a}$ | R$^{2a}$ | R$^{14}$ | m.p. (° C.) |
|---|---|---|---|---|---|---|
| 7-001 | 3,5-Cl$_2$ | 2-Br | H | H | c-Pr | *1 |
| 7-002 | 3,4,5-Cl$_3$ | 2-Br | H | H | c-Pr | *1 |
| 7-003 | 3,4,5-Cl$_3$ | — | CH$_3$ | H | c-Pr | *1 |
| 7-004 | 3,5-Cl$_2$ | 2-Br | H | C(O)OBu-t | c-Pr | *1 |

TABLE 14

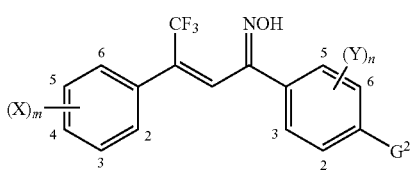

| No. | (X)$_m$ | (Y)$_n$ | G$^2$ | (Z$^a$)$_p$ | m.p. (° C.) |
|---|---|---|---|---|---|
| 8-001 | 3,5-Cl$_2$ | — | G$^2$-7 | — | *1 |
| 8-002 | 3,5-(CF$_3$)$_2$ | 2-CN | G$^2$-7 | — | 184.0-186.0 |

TABLE 15

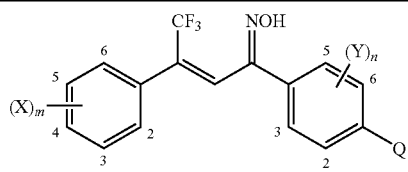

| No. | (X)$_m$ | (Y)$_n$ | Q | m.p. (° C.) |
|---|---|---|---|---|
| 9-001 | 3,4,5-Cl$_3$ | 2-Cl | T-4 | 190.0-193.0 |
| 9-002 | 3,5-Cl$_2$ | 2-Cl | T-5 | *1 |
| 9-003 | 3,5-Cl$_2$ | — | NO$_2$ | 143.0-145.0 |
| 9-004 | 3,5-Cl$_2$ | — | SCH$_3$ | 129.0-131.0 |
| 9-005 | 3,5-Cl$_2$ | — | S(O)CH$_3$ | 178.0-183.0 |
| 9-006 | 3,5-Cl$_2$ | — | SO$_2$CH$_3$ | 189.0-191.0 |
| 9-007 | 3,5-Cl$_2$ | — | C(O)OCH$_3$ | 167.0-169.0 |
| 9-008 | 3,5-(CF$_3$)$_2$ | — | C(O)OCH$_3$ | 115.0-117.0 |
| 9-009 | 3,5-Cl$_2$ | 2-CH$_3$ | C(O)OCH$_3$ | *1 |

TABLE 16

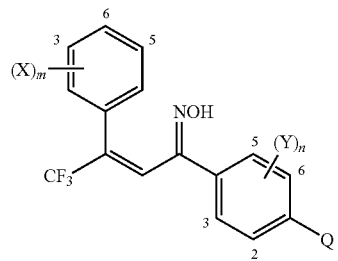

| No. | (X)$_m$ | (Y)$_n$ | Q | m.p. (° C.) |
|---|---|---|---|---|
| 10-001 | 3,5-Cl$_2$ | — | Br | 150.0-152.5 |
| 10-002 | 3,5-Cl$_2$ | 2-CH$_3$ | Br | 138.0-140.0 |

TABLE 17

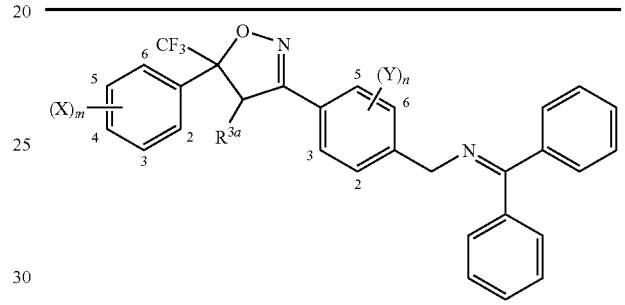

| No. | (X)$_m$ | R$^{3a}$ | (Y)$_n$ | m.p. (° C.) |
|---|---|---|---|---|
| 11-001 | 3,5-Cl$_2$ | H | 2-Cl | *1 |

$^1$H NMR data of the compound among the compounds of the present invention of which melting points or refractive indexes are not described is shown in Table 18.

TABLE 18

| No. | $^1$H NMR(CDCl$_3$, Me$_4$Si, 300 MHz) |
|---|---|
| 1-006 | δ8.0-8.15 (m, 3H), 7.89 (s, 4H), 6.58 (d, J = 7.5 Hz, 1H), 6.00 (s, 1H), 5.85-6.0 (m, 1H), 3.95-4.1 (m, 1H), 3.8-3.9 (m, 1H), 2.25-2.4 (m, 1H), 1.85-2.1 (m, 3H). |
| 1-007 | δ8.0-8.15 (m, 3H), 7.93 (s, 4H), 5.98 (s, 1H), 4.2-4.25 (m, 2H), 3.9-4.05 (m, 2H). |
| 1-008 | δ8.50 (s, 1H), 8.15-8.2 (m, 1H), 7.68 (d, J = 7.8 Hz, 1H), 7.50 (s, 3H), 6.8-7.0 (m, 2H), 5.91 (s, 1H), 4.24 (d, J = 5.4 Hz, 2H), 3.9-4.1 (m, 2H). |
| 1-010 | δ8.57 (d, J = 4.5 Hz, 1H), 7.9-8.2 (m, 7H), 7.45-7.8 (m, 2H), 7.33 (d, J = 6.9 Hz, 1H), 5.98 (s, 1H), 4.78 (d, J = 4.8 Hz, 2H). |
| 1-012 | δ8.89 and 8.63 (d, J = 9.9 Hz, 1H), 7.85-8.2 (m, 6H), 7.82 (d, J = 9.9 Hz, 1H), 5.97 and 5.30 (s, 1H), 4.19 and 4.05 (q, J = 7.2 Hz, 2H), 1.32 and 1.28 (t, J = 7.2 Hz, 3H). |
| 1-013 | δ8.90 and 8.64 (d, J = 9.9 Hz, 1H), 7.8-8.0 (m, 7H), 5.93 (s, 1H), 4.19 (q, J = 7.2 Hz, 2H), 1.33 (t, J = 7.2 Hz, 3H). |
| 2-001 | δ8.20 and 7.94 (s, 1H), 7.4-7.75 (m, 5H), 6.2-6.35 (m, 1H), 5.82 and 5.64 (s, 1H), 4.54 and 4.51 (d, J = 6.6 Hz, 2H), 1.3-1.5 (m, 1H), 0.9-1.1 (m, 2H), 0.7-0.85 (m, 2H). |
| 2-003 | δ7.9-8.1 (m, 1H), 7.25-7.8 (m, 4H), 6.20 (t, J = 6.0 Hz, 1H), 5.81 (s, 1H), 4.56 (d, J = 6.0 Hz, 2H), 1.35-1.5 (m, 1H), 0.9-1.1 (m, 2H), 0.75-0.9 (m, 2H). |
| 2-004 | δ7.78 (d, J = 8.4 Hz, 2H), 7.55-7.75 (m, 2H), 7.43 (d, J = 8.4 Hz, 2H), 5.99 (d, J = 7.2 Hz, 1H), 5.85 (s, 1H), 5.1-5.25 (m, 1H), 1.51 (d, J = 7.2 Hz, 3H), 1.3-1.45 (m, 1H), 0.9-1.05 (m, 2H), 0.65-0.8 (m, 2H). |
| 3-001 | δ8.93 (s, 1H), 8.2-8.3 (m, 3H), 7.95-8.1 (m, 4H), 5.99 (s, 1H). |
| 5-004 | δ9.49 (d, J = 2.4 Hz, 1H), 8.64 (d, J = 9.9 Hz, 1H), 7.75-7.9 (m, 1H), 7.4-7.55 (m, 6H), 6.79 (s, 1H), 3.91 (s, 3H), 2.53 (s, 3H). |
| 5-005 | δ9.07 (s, 1H), 8.61 (d, J = 9.6 Hz, 1H), 7.98 (s, 3H), 7.75-7.9 (m, 1H), 7.4-7.6 (m, 3H), 6.88 (s, 1H), 3.92 (s, 3H), 2.55 (s, 3H). |
| 5-006 | δ8.97 (s, 1H), 7.55-7.8 (m, 3H), 7.3-7.5 (m, 8H), 7.17 (t, J = 10.0 Hz, 1H), 6.76 (s, 1H), 2.51 (s, 3H), 1.81 (s, 1H). |

TABLE 18-continued

| No. | $^1$H NMR(CDCl$_3$, Me$_4$Si, 300 MHz) |
|---|---|
| 5-008 | δ8.77 (s, 1H), 8.06 (s, 1H), 7.3-7.85 (m, 10H), 6.79 (s, 1H), 2.51 (s, 3H). |
| 7-001 | δ8.34 (s, 1H), 7.81 (s, 1H), 7.35-7.55 (m, 5H), 6.71 (s, 1H), 6.15 (t, J = 6.0 Hz, 1H), 4.56 (d, J = 6.0 Hz, 2H), 1.35-1.5 (m, 1H), 1.0-1.1 (m, 2H), 0.75-0.85 (m, 2H). |
| 7-002 | δ7.75 (s, 1H), 7.55 (s, 2H), 7.3-7.45 (m, 2H), 6.74 (s, 1H), 6.64 (t, J = 6.0 Hz, 1H), 4.54 (d, J = 6.0 Hz, 2H), 1.4-1.55 (m, 1H), 1.0-1.1 (m, 2H), 0.75-0.85 (m, 2H). |
| 7-003 | δ7.55 (s, 2H), 7.52 (d, J = 8.4 Hz, 2H), 7.34 (d, J = 8.4 Hz, 2H), 6.74 (s, 1H), 6.11 (d, J = 8.1 Hz, 1H), 5.21 (qui, J = 7.2 Hz, 1H), 1.50 (d, J = 7.2 Hz, 3H), 1.3-1.45 (m, 1H), 0.95-1.1 (m, 2H), 0.7-0.85 (m, 2H). |
| 8-001 | δ8.62 (s, 1H), 8.14 (s, 1H), 7.75-7.8 (m, 5H), 7.45-7.5 (m, 3H), 6.81 (s, 1H). |
| 9-002 | δ10.0 (bs, 1H), 7.2-7.7 (m, 16H), 6.66 (s, 1H), 4.71 (s, 2H). |
| 11-001 | δ7.3-7.75 (m, 15H), 7.15-7.25 (m, 1H), 4.65 (s, 2H), 4.07 (d, J = 17.4 Hz, 1H), 3.68 (d, J = 17.4 Hz, 1H). |

Test Examples

Next, the usefulness of the compound of the present invention as a pest control agent is more specifically described in the following Test Examples which should not be construed as limiting the scope of the present invention.

Test Example 1

Mortality Test for *Plutella xylostella*

A 10% emulsifiable concentrate of the compound of the present invention (depending on the type of the compound, a 10% wettable powder was subjected to the test) was diluted with water containing a spreader to prepare a drug solution in a concentration of 10 ppm. In this drug solution, a leaf of cabbage was immersed for about 10 seconds and was air-dried and then put into a petri dish. In the petri dish, five 2 instar larvae of *Plutella xylostella* per petri dish were released and the petri dish was capped and stored in a thermostatic room of 25° C. The number of killed larvae after 6 days was counted and the mortality was calculated from the following calculation formula:

Mortality(%)=(number of killed larvae/number of released larvae)×100.

Here, the test was carried out with two replications.

As the results of the test, among the compounds subjected to the test, the following compounds exhibited the mortality of 80% or more.
The compounds of the present invention: Nos. 1-002, 1-003*, 1-004*, 1-005*, 1-006*, 1-007*, 1-008*, 1-009*, 1-010*, 1-011*, 1-012*, 1-014*, 2-001 to 2-004, 2-005**, 4-001, 4-002*, 4-004*, 5-001*, 5-002 to 5-005, 5-006*, 5-007", 5-008", 5-009, 5-010, 6-001**, 7-001*, 7-002, 7-003, 8-001, 8-002*, 9-003*, 9-004, 9-005, 9-006, and 11-001.

Here, the above mark "*" indicates that the mortality test was performed using a drug solution of 100 ppm concentration and the mark "**" indicates that the mortality test was performed using a drug solution of 500 ppm concentration.

Test Example 2

Mortality Test for *Spodoptera litura*

A 10% emulsifiable concentrate of the compound of the present invention (depending on the type of the compound, a 10% wettable powder was subjected to the test) was diluted with water containing a spreader to prepare a drug solution in a concentration of 10 ppm. In this drug solution, a leaf of cabbage was immersed for about 10 seconds and was air-dried and then put into a petri dish. In the petri dish, five 2 instar larvae of *Spodoptera litura* per petri dish were released and the petri dish was capped and stored in a thermostatic room of 25° C. The number of killed larvae after 6 days was counted and the mortality was calculated from the same calculation formula as that in Test Example 1. Here, the test was carried out with two replications.

As the results of the test, among the compounds subjected to the test, the following compounds exhibited the mortality of 80% or more.
The compounds of the present invention: Nos. 1-002, 1-003*, 1-004*, 1-005*, 1-006*, 1-007*, 1-008*, 1-009*, 1-010*, 1-011*, 1-012*, 2-001 to 2-004, 2-005", 3-001*, 4-002*, 5-001*, 5-004, 5-005, 5-006*, 5-008", 5-010, 7-001*, 7-002, 7-003, 8-002*, 9-003*, 9-004", 9-005", 9-006", and 11-001**.

Here, the above mark "*" indicates that the mortality test was performed using a drug solution of 100 ppm concentration and the mark "**" indicates that the mortality test was performed using a drug solution of 500 ppm concentration.

Test Example 3

Mortality Test for *Helicoverpa Armigera*

A 10% emulsifiable concentrate of the compound of the present invention (depending on the type of the compound, a 10% wettable powder was subjected to the test) was diluted with water containing a spreader to prepare a drug solution in a concentration of 100 ppm. In this drug solution, a leaf of cabbage was immersed for about 10 seconds and was air-dried and then put into a petri dish. In the petri dish, one 2 instar larva of *Helicoverpa armigera* per petri dish was released and the petri dish was capped and stored in a thermostatic room of 25° C. The number of killed larvae after 6 days was counted and the mortality was calculated from the same calculation formula as that in Test Example 1. Here, the test was carried out with 12 replications.

As the results of the test, among the compounds subjected to the test, the following compounds exhibited the mortality of 80% or more.
The compounds of the present invention: Nos. 1-001 to 1-012, 1-014, 2-001 to 2-004, 3-001, 4-002, 5-001 to 5-010, 7-001 to 7-004, 8-001, 9-003, and 10-002.

Test Example 4

Mortality Test for *Homona magnanima*

A 10% emulsifiable concentrate of the compound of the present invention (depending on the type of the compound, a 10% wettable powder was subjected to the test) was diluted with water containing a spreader to prepare a drug solution in a concentration of 100 ppm. In this drug solution, a leaf of cabbage was immersed for about 10 seconds and was air-dried and then put into a petri dish. In the petri dish, five 2 instar larvae of *Homona magnanima* per petri dish were released and the petri dish was capped and stored in a thermostatic room of 25° C. The number of killed larvae after 6 days was counted and the mortality was calculated from the same calculation formula as that in Test Example 1. Here, the test was carried out with two replications.

As the results of the test, among the compounds subjected to the test, the following compounds exhibited the mortality of 80% or more.

The compounds of the present invention: Nos. 1-004, 2-001, 2-004, and 5-005.

Test Example 5

Mortality Test for *Frankliniella occidentalis*

In a styrol cup having an inner diameter of 7 cm, a wet filtration paper was laid and on the paper, a leaf of kidney bean cut out so as to have the same diameter as the inner diameter of the cup was laid, followed by inoculating ten 1 instar larvae of *Frankliniella occidentalis* per leaf to the leaf. A 10% emulsifiable concentrate of the compound of the present invention (depending on the type of the compound, a 10% wettable powder was subjected to the test) was diluted with water containing a spreader to prepare a drug solution in a concentration of 500 ppm. The drug solution was dusted using a rotary dusting tower in an amount of 2.5 mL per styrol cup and the cup was capped and stored in a thermostatic room of 25° C. The number of killed larvae after 2 days was counted and the mortality was calculated from the same calculation formula as that in Test Example 1. Here, the test was carried out with two replications.

As the results of the test, among the compounds subjected to the test, the following compounds exhibited the mortality of 80% or more.

The compounds of the present invention: Nos. 1-003, 1-004, 1-011, 1-012, 2-001 to 2-004, 4-001, 4-002, and 5-005.

Test Example 6

Mortality Test for *Thrips palmi*

In a styrol cup having an inner diameter of 7 cm, a wet filtration paper was laid and on the paper, a leaf of kidney bean cut out so as to have the same diameter as the inner diameter of the cup was laid, followed by inoculating ten imagines of *Thrips palmi* per leaf to the leaf. A 10% emulsifiable concentrate of the compound of the present invention (depending on the type of the compound, a 10% wettable powder was subjected to the test) was diluted with water containing a spreader to prepare a drug solution in a concentration of 100 ppm. The drug solution was dusted using a rotary dusting tower in an amount of 2.5 mL per styrol cup and the cup was capped and stored in a thermostatic room of 25° C. The number of killed imagines after 2 days was counted and the mortality was calculated from the same calculation formula as that in Test Example 1. Here, the test was carried out with two replications.

As the results of the test, among the compounds subjected to the test, the following compounds exhibited the mortality of 80% or more.

The compounds of the present invention: Nos. 1-002 to 1-004, 1-006, 1-007, 1-009 to 1-012, 2-001 to 2-004, 3-001, 5-005, 8-002, and 11-001.

Test Example 7

Mortality Test for *Eysarcoris lewisi*

A 10% emulsifiable concentrate of the compound of the present invention (depending on the type of the compound, a 10% wettable powder was subjected to the test) was diluted with water containing a spreader to prepare a drug solution in a concentration of 500 ppm. In this drug solution, a leaf sheath of rice was immersed for about 10 seconds and was air-dried and then put into a test tube. In the test tube, five 1 instar larvae of *Eysarcoris lewisi* per test tube were released and the test tube was capped with a sponge and stored in a thermostatic room of 25° C. The number of killed larvae after 2 days was counted and the mortality was calculated from the same calculation formula as that in Test Example 1. Here, the test was carried out with two replications.

As the results of the test, among the compounds subjected to the test, the following compounds exhibited the mortality of 80% or more.

The compounds of the present invention: Nos. 1-003, 1-004, and 10-002.

Test Example 8

Mortality Test for *Nilaparvata lugens*

A 10% emulsifiable concentrate of the compound of the present invention (depending on the type of the compound, a 10% wettable powder was subjected to the test) was diluted with water containing a spreader to prepare a drug solution in a concentration of 500 ppm. In this drug solution, a leaf sheath of rice was immersed for about 10 seconds and was air-dried and then put into a test tube. In the test tube, five 2 instar larvae of *Nilaparvata lugens* per test tube were released and the test tube was capped with a sponge and stored in a thermostatic room of 25° C. The number of killed larvae after 6 days was counted and the mortality was calculated from the same calculation formula as that in Test Example 1. Here, the test was carried out with two replications.

As the results of the test, among the compounds subjected to the test, the following compounds exhibited the mortality of 80% or more.

The compounds of the present invention: Nos. 1-003, 1-007, 1-008, 1-011, 1-012, 2-001, 2-002, 4-001, 4-002, 5-004, and 5-010.

Test Example 9

Mortality Test for *Bemisia argentifolii*

In a styrol cup having an inner diameter of 7 cm, a wet filtration paper was laid and on the paper, a cut-out leaf of tomato on which *Bemisia argentifolii* laid eggs (10 eggs/leaf) was laid. A 10% emulsifiable concentrate of the compound of the present invention (depending on the type of the compound, a 10% wettable powder was subjected to the test) was diluted with water containing a spreader to prepare a drug solution in a concentration of 500 ppm. The drug solution was dusted using a rotary dusting tower in an amount of 2.5 mL per styrol cup and the cup was capped and stored in a thermostatic room of 25° C. The number of killed larvae after 6 days was counted and the mortality was calculated from the same calculation formula as that in Test Example 1. Here, the test was carried out with two replications.

As the results of the test, among the compounds subjected to the test, the following compounds exhibited the mortality of 80% or more.

The compounds of the present invention: Nos. 1-003, 1-010 to 1-012, 2-001 to 2-003, 5-004, and 5-005.

Test Example 10

Mortality Test for *Myzus persicae*

In a glass petri dish having an inner diameter of 3 cm, a wet absorbent cotton was laid and on the cotton, a leaf of cabbage cut out so as to have the same diameter as the inner diameter of the petri dish was laid, followed by releasing four apterous imagines of *Myzus persicae* on the leaf. After one day, a 10% emulsifiable concentrate of the compound of the present invention (depending on the type of the compound, a 10% wettable powder was subjected to the test) was diluted with water containing a spreader to prepare a drug solution in a concentration of 500 ppm. The drug solution was dusted using a rotary dusting tower (2.5 mg/cm$^2$) and the petri dish was capped and stored in a thermostatic room of 25° C. The number of killed imagines after 6 days was counted and the mortality was calculated from the same calculation formula as that in Test Example 1. Here, the test was carried out with two replications.

As the results of the test, among the compounds subjected to the test, the following compounds exhibited the mortality of 80% or more.

The compounds of the present invention: Nos. 1-003, 1-006 to 1-008, 1-010, 1-011, 1-012, 2-001, 2-002, 3-001, 4-001, 4-002, 5-003, 5-004, 7-002, and 7-003.

Test Example 11

Mortality Test for *Planococcus kraunhiae*

In a styrol cup having an inner diameter of 7 cm, a wet filtration paper was laid and on the paper, a leaf of kidney bean cut out so as to have the same diameter as the inner diameter of the cup was laid, followed by inoculating ten 1 instar larvae of *Planococcus kraunhiae* per leaf to the leaf. A 10% emulsifiable concentrate of the compound of the present invention (depending on the type of the compound, a 10% wettable powder was subjected to the test) was diluted with water containing a spreader to prepare a drug solution in a concentration of 500 ppm. The drug solution was dusted using a rotary dusting tower in an amount of 2.5 mL per styrol cup and the cup was capped and stored in a thermostatic room of 25° C. The number of killed larvae after 6 days was counted and the mortality was calculated from the same calculation formula as that in Test Example 1. Here, the test was carried out with two replications.

As the results of the test, among the compounds subjected to the test, the following compounds exhibited the mortality of 80% or more.

The compounds of the present invention: No. 1-003 and 1-004.

Test Example 12

Mortality Test for *Aulacophora femoralis*

A 10% emulsifiable concentrate of the compound of the present invention (depending on the type of the compound, a 10% wettable powder was subjected to the test) was diluted with water containing a spreader to prepare a drug solution in a concentration of 500 ppm. In this drug solution, a leaf of cucumber was immersed for about 10 seconds and was air-dried and then put into a petri dish. In the petri dish, five 2 instar larvae of *Aulacophora femoralis* per petri dish were released and the petri dish was capped and stored in a thermostatic room of 25° C. The number of killed larvae after 6 days was counted and the mortality was calculated from the same calculation formula as that in Test Example 1. Here, the test was carried out with two replications.

As the results of the test, among the compounds subjected to the test, the following compounds exhibited the mortality of 80% or more.

The compounds of the present invention: Nos. 1-003, 1-004, and 6-001.

Test Example 13

Mortality Test for *Liriomyza trifolii*

A 10% emulsifiable concentrate of the compound of the present invention (depending on the type of the compound, a 10% wettable powder was subjected to the test) was diluted with water containing a spreader to prepare a drug solution in a concentration of 500 ppm. In this drug solution, a leaf of kidney bean on which *Liriomyza trifolii* laid eggs (10 eggs/leaf) and which was cut out to a diameter of 7 cm was immersed for about 10 seconds and was air-dried and then laid on a wet filtration paper laid in a styrol cup having an inner diameter of 7 cm. The styrol cup was capped and stored in a thermostatic room of 25° C. The number of killed larvae after 6 days was counted and the mortality was calculated from the same calculation formula as that in Test Example 1. Here, the test was carried out with two replications.

As the results of the test, among the compounds subjected to the test, the following compounds exhibited the mortality of 80% or more.

The compounds of the present invention: Nos. 1-003 and 1-004.

Test Example 14

Mortality Test for *Tetranychus urticae*

In a styrol cup having an inner diameter of 7 cm, a wet filtration paper was laid and on the paper, a leaf of kidney bean cut out so as to have the same diameter as the inner diameter of the cup was laid, followed by inoculating ten larvae of *Tetranychus urticae* per leaf to the leaf. A 10% emulsifiable concentrate of the compound of the present invention (depending on the type of the compound, a 10% wettable powder was subjected to the test) was diluted with water containing a spreader to prepare a drug solution in a concentration of 500 ppm. The drug solution was dusted using a rotary dusting tower in an amount of 2.5 mL per styrol cup and the cup was capped and stored in a thermostatic room of 25° C. The number of killed larvae after 6 days was counted and the mortality was calculated from the same calculation formula as that in Test Example 1. Here, the test was carried out with two replications.

As the results of the test, among the compounds subjected to the test, the following compounds exhibited the mortality of 80% or more.

The compounds of the present invention: Nos. 1-003, 1-006 to 1-008, 1-011, 1-012, 2-001, 2-002, 2-003*, 2-004*, 4-002, 5-002 to 5-004, 7-001, and 7-003.

Here, the above mark "*" indicates that the mortality test was performed using a drug solution of 100 ppm concentration.

Test Example 15

Mortality Test for *Aculops pelekassi*

In a styrol cup having an inner diameter of 7 cm, a wet filtration paper was laid and on the paper, a leaf of mandarin orange cut out so as to have the same diameter as the inner diameter of the cup was laid, followed by inoculating ten larvae of *Aculops pelekassi* per leaf to the leaf. A 10% emulsifiable concentrate of the compound of the present invention (depending on the type of the compound, a 10% wettable powder was subjected to the test) was diluted with water containing a spreader to prepare a drug solution in a concentration of 100 ppm. The drug solution was dusted using a rotary dusting tower in an amount of 2.5 mL per styrol cup and the cup was capped and stored in a thermostatic room of 25° C. The number of killed larvae after 6 days was counted and the mortality was calculated from the same calculation formula as that in Test Example 1. Here, the test was carried out with two replications.

As the results of the test, among the compounds subjected to the test, the following compound has exhibited the mortality of 80% or more.

The compound of the present invention: No. 7-002.

Test Example 16

Mortality Test for *Polyphagotarsonemus latus*

In a styrol cup having an inner diameter of 7 cm, a wet filtration paper was laid and on the paper, a leaf of kidney bean cut out so as to have the same diameter as the inner diameter of the cup was laid, followed by inoculating ten imagines of *Polyphagotarsonemus latus* per leaf to the leaf. A 10% emulsifiable concentrate of the compound of the present invention (depending on the type of the compound, a 10% wettable powder was subjected to the test) was diluted with water containing a spreader to prepare a drug solution in a concentration of 100 ppm. The drug solution was dusted using a rotary dusting tower in an amount of 2.5 mL per styrol cup and the cup was capped and stored in a thermostatic room of 25° C. The number of killed imagines after 2 days was counted and the mortality was calculated from the same calculation formula as that in Test Example 1. Here, the test was carried out with two replications.

As the results of the test, among the compounds subjected to the test, the following compound has exhibited the mortality of 80% or more.

The compound of the present invention: No. 7-002.

INDUSTRIAL APPLICABILITY

The substituted isoxazoline compound or the substituted enone oxime compound according to the present invention is an extremely useful compound exhibiting excellent pest control activity, particularly excellent insecticidal and miticidal activity and having substantially no adverse effect on non-target organisms such as mammals, fish and beneficial insects.

The invention claimed is:

1. A substituted isoxazoline compound or a substituted enone oxime compound represented by General Formula (1) or General Formula (2):

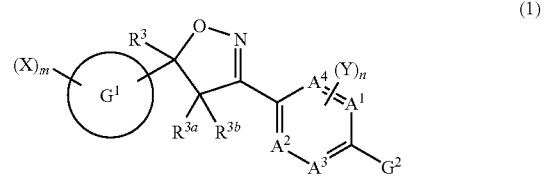

(1)

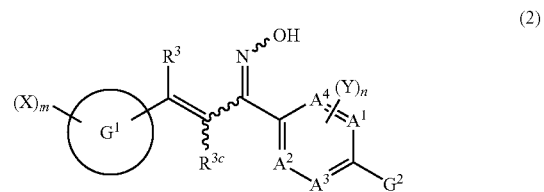

(2)

(where $A^1$, $A^2$, $A^3$ and $A^4$ independently represent a carbon atom or a nitrogen atom, $G^1$ represents a benzene ring, a nitrogen-containing 6-membered aromatic heterocyclic ring, a furan ring, a thiophehe ring or a 5-membered aromatic heterocyclic ring containing two or more heteroatoms selected from an oxygen atom, a sulfur atom and a nitrogen atom, $G^2$ represents a structure represented by $G^2$-1 to $G^2$-11:

$G^2$-1:

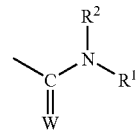

$G^2$-2:

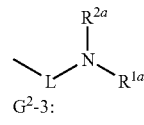

$G^2$-3:

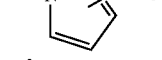

$G^2$-4:

$G^2$-5:

$G^2$-6:

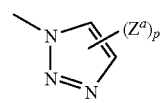

-continued

G²-7:
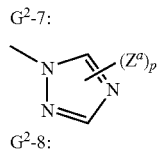

G²-8:
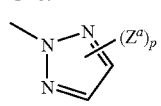

G²-9:
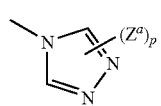

G²-10:
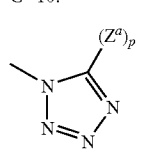

G²-11:
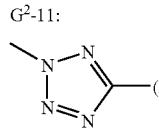

W represents an oxygen atom or a sulfur atom,

L represents —C($R^{4a}$)($R^{4b}$)—, —C($R^{4a}$)($R^{4b}$)CH$_2$—, —CH$_2$C($R^{4a}$)($R^{4b}$)—, —N($R^{4c}$)—, —C($R^{4a}$)($R^{4b}$)N($R^{4c}$)— or a single bond, X represents a halogen atom, a cyano, a nitro, an azide, —SCN, —SF$_5$, a C$_1$ to C$_6$ alkyl, a (C$_1$ to C$_6$) alkyl optionally substituted with R$^4$, a C$_3$ to C$_8$ cycloalkyl, a (C$_3$ to C$_8$) cycloalkyl optionally substituted with R$^4$, E1 to E19, a C$_2$ to C$_6$ alkenyl, a (C$_2$ to C$_6$) alkenyl optionally substituted with R$^4$, a C$_5$ to C$_{10}$ cycloalkenyl, a C$_5$ to C$_{10}$ halocycloalkenyl, a C$_2$ to C$_6$ alkynyl, a (C$_2$ to C$_6$) alkynyl optionally substituted with R$^4$, —OH, —OR$^5$, —OS(O)$_2$R$^5$, —SH, —S(O)$_r$R$^5$, —N(R$^7$)R$^6$, —N═C(R$^{7a}$) R$^{6a}$, —C(O)R$^8$, —C(R$^8$)═NOH, —C(R$^8$)═NOR$^9$, M3, M13, M30, —C(O)OR$^9$, —C(O)SR$^9$, —C(O)NH$_2$, —C(O)N(R$^{10}$)R$^9$, —C(S)OR$^9$, —C(S)SR$^9$, —C(S)NH$_2$, —C(S)N(R$^{10}$)R$^9$, M23 to M26, M28, M29, —S(O)$_2$OR$^9$, —S(O)$_2$NH$_2$, —S(O)$_2$N(R$^{10}$)R$^9$, —Si(R$^{11a}$)(R$^{11b}$)R$^{11}$, a phenyl, a phenyl substituted with (Z)$_{p1}$ or D1 to D38, where when m represents an integer of 2 or more, Xs are optionally the same as or different from each other, and further, when two Xs are adjacent to each other, the two Xs adjacent to each other optionally form —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$N(R$^{12}$)—, —CH$_2$N(R$^{12}$)CH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —CH$_2$CH═CH—, —OCH═CH—, —SCH═CH—, —N(R$^{12}$)CH═CH—, —OCH═N—, —SCH═N—, —N(R$^{12}$)CH═N—, —N(R$^{12}$)N═CH—, —CH═CHCH═CH—, —OCH$_2$CH═N—, —N═CHCH═CH—, —N═CHCH═N— or —N═CHN═CH— to form together with carbon atoms to which each of the two Xs is bonded, a 5-membered ring or a 6-membered ring, and in this case, a hydrogen atom bonded to each carbon atom forming the ring is optionally replaced by Z, further when hydrogen atoms are replaced simultaneously by 2 or more Zs, Zs are optionally the same as or different from each other, Y represents a halogen atom, a cyano, a nitro, an azide, —SCN, —SF$_5$, a C$_1$ to C$_6$ alkyl, a (C$_1$ to C$_6$) alkyl optionally substituted with R$^4$, a C$_3$ to C$_8$ cycloalkyl, a (C$_3$ to C$_8$) cycloalkyl optionally substituted with R$^4$, E1 to E18, a C$_2$ to C$_6$ alkenyl, a (C$_2$ to C$_6$) alkenyl optionally substituted with R$^4$, a C$_2$ to C$_6$ alkynyl, a (C$_2$ to C$_6$) alkynyl optionally substituted with R$^4$, —OH, —OR$^5$, —OS(O)$_2$R$^5$, —SH, —S(O)$_r$R$^5$, —NH$_2$, —N(R$^7$)R$^6$, —N(R$^7$)C(O)R$^{8a}$, —N═C(R$^{7a}$)R$^{6a}$, —C(O)NH$_2$, —C(O)N(R$^{10}$)R$^9$, —C(S)NH$_2$, —C(S)N(R$^{10}$)R$^9$, —Si(R$^{11a}$)(R$^{11b}$)R$^{11}$, a phenyl, a phenyl substituted with (Z)$_{p1}$ or D1 to D38, where when n represents an integer of 2 or more, Ys are optionally the same as or different from each other, and further, when two Ys are adjacent to each other, the two Ys adjacent to each other optionally form —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —SCH$_2$S—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —SCH$_2$CH$_2$S—, —OCH═N—, —SCH═N—, —CH═CHCH═CH—, —CH═CHCH═N—, —CH═CHN═CH—, —CH═NCH═CH— or —N═CHCH═CH— to form together with carbon atoms to which each of the two Ys is bonded, a 5-membered ring or a 6-membered ring, and in this case, a hydrogen atom bonded to each carbon atom forming the ring is optionally replaced by Z, and further when hydrogen atoms are replaced simultaneously by 2 or more Zs, Zs are optionally the same as or different from each other, Z$^a$ represents a halogen atom, a cyano, a nitro, a C$_1$ to C$_6$ alkyl, a (C$_1$ to C$_6$) alkyl optionally substituted with R$^4$, —OH, —OR$^5$, —OS(O)$_2$R$^5$, —SH, —S(O)$_r$R$^5$, —NH$_2$, —N(R$^7$)R$^6$, —C(O)R$^8$, —C(R$^8$)═NOH, —C(R$^8$)═NOR$^9$, M3, M13, M30, —C(O)OR$^9$, —C(O)SR$^9$, —C(O)N(R$^2$)R$^1$, —C(S)OR$^9$, —C(S)SR$^9$, —C(S)N(R$^2$)R$^1$, M23 to M26, M28, M29, —S(O)$_2$OR$^9$, —S(O)$_2$NH$_2$, —S(O)$_2$N(R$^{10}$)R$^9$, —Si(R$^{11a}$)(R$^{11b}$)R$^{11}$, a phenyl or a phenyl substituted with (Z)$_{p1}$, where when p represents an integer of 2 or more, Z$^a$s are optionally the same as or different from each other, and further, when two Z$^a$s are adjacent to each other, the two Z$^a$ adjacent to each other optionally form —CH═CH—CH═CH— to form a fused ring, in this case, a hydrogen atom bonded to each carbon atom forming the ring is optionally replaced by a halogen atom, a cyano group, a nitro group, a C$_1$ to C$_4$ alkyl group, a C$_1$ to C$_4$ haloalkyl group, a C$_1$ to C$_4$ alkoxy group or a C$_1$ to C$_4$ alkylthio group, R$^1$ represents a hydrogen atom, a cyano, a C$_1$ to C$_{12}$ alkyl, a (C$_1$ to C$_{12}$) alkyl optionally substituted with R$^{13}$, a C$_3$ to C$_{12}$ cycloalkyl, a (C$_3$ to C$_{12}$) cycloalkyl optionally substituted with R$^{13}$, E2 to E6, E9, E12 to E15, E18, a C$_2$ to C$_{12}$ alkenyl, a (C$_2$ to C$_{12}$) alkenyl optionally substituted with R$^{13}$, a C$_5$ to C$_{14}$ cycloalkenyl, a C$_5$ to C$_{14}$ halocycloalkenyl, a C$_3$ to C$_{12}$ alkynyl, a (C$_3$ to C$_{12}$) alkynyl optionally substituted with R$^{13}$, a C$_3$ to C$_{12}$ allenyl, —C(O)R$^{14}$, —C(R$^{14}$)═NOH, —C(R$^{14}$)═NOR$^{15}$, M3, M13, M30, —C(R$^{14}$)═NN(R$^{17}$)R$^{16}$, —C(O )OR$^{15}$, —C(O)

$-SR^{15}$, $-C(O)N(R^{17})R^{16}$, $-C(O)N(R^{17})OR^{15}$, $-C(O)N(R^{17})N(R^{17})R^{16}$, $-C(S)R^{14}$, $-C(S)OR^{15}$, $-C(S)SR^{15}$, $-C(S)N(R^{17})R^{16}$, $-C(=NR^{16})OR^{15}$, $-C(=NOR^{15})OR^{15}$, M7, M17, M23, M26, $-C(=NR^{16})SR^{15}$, M9, M19, M24, M28, $-C(=NR^{16})N(R^{17})R^{16}$, $-C(=NCN)N(R^{17})R^{16}$, $-C(=NOR^{15})N(R^{17})R^{16}$, $-C(=NNO_2)N(R^{17})R^{16}$, M11, M21, M25, M29, $-OR^{15}$, $-SR^{15}$, $-S(O)_2R^{15}$, $-S(O)_2N(R^{17})R^{16}$, $-N(R^{17})R^{16}$, $-N=C(R^{17a})R^{16a}$, $-C(O)ON=C(R^{17a})R^{16a}$, $-SN(R^{19})R^{18}$, a phenyl, a phenyl substituted with $(Z)_{p1}$, D1 to D25 or D27 to D38, $R^2$ represents a hydrogen atom, a cyano, a $C_1$ to $C_{12}$ alkyl, a ($C_1$ to $C_{12}$) alkyl optionally substituted with $R^{13a}$, a $C_3$ to $C_{12}$ cycloalkyl, a $C_3$ to $C_{12}$ alkenyl, a $C_3$ to $C_{12}$ haloalkenyl, a $C_5$ to $C_{14}$ cycloalkenyl, a $C_5$ to $C_{14}$ halocycloalkenyl, $C_3$ to $C_{12}$ alkynyl, a $C_3$ to $C_{12}$ haloalkynyl, $-C(O)R^{14a}$, $-C(O)OR^{15a}$, $-C(O)SR^{15a}$, $-C(O)N(R^{17})R^{16}$, $-C(O)C(O)OR^{15a}$, $-C(S)OR^{15a}$, $-C(S)SR^{15a}$, $-C(S)N(R^{17})R^{16}$, $-OR^{15}$, $-SR^{15}$, $-N(R^{17})R^{16}$, $-N=C(R^{17a})R^{16a}$, $-S(O)_2R^{15a}$, $-S(O)_2N(R^{17})R^{16}$, $-SN(R^{19})R^{18}$, a phenyl, a phenyl substituted with $(Z)_{p1}$, D1, D2 or D32 to D35, or $R^2$ together with $R^1$ optionally forms $=C(R^{2b})R^{1b}$ or a $C_2$ to $C_7$ alkylene chain to form together with a nitrogen atom to which $R^1$ and $R^2$ are bonded, a 3- to 8-membered ring, and in this case, the alkylene chain optionally contains one oxygen atom, sulfur atom or nitrogen atom and is optionally substituted with a halogen atom, a $C_1$ to $C_6$ alkyl group, a $C_1$ to $C_6$ haloalkyl group, a $C_1$ to $C_6$ alkoxy($C_1$ to $C_6$) alkyl group, a $C_1$ to $C_6$ alkoxy group, a —CHO group, a $C_1$ to $C_6$ alkylcarbonyl group, a $C_1$ to $C_6$ haloalkylcarbonyl group, a $C_1$ to $C_6$ alkoxycarbonyl group, a $C_1$ to $C_6$ haloalkoxycarbonyl group, a $C_1$ to $C_6$ alkylaminocarbonyl group, a $C_1$ to $C_6$ haloalkylaminocarbonyl group, a phenyl group, a phenyl substituted with $(Z)_{p1}$, a D32 group, a D33 group, a D34 group, a D35 group, an oxo group or a thioxo group, and further, when the substituent Y is present adjacent to $G^2$, $R^2$ together with Y optionally forms $-CH_2-$, $-CH_2CH_2-$, $-CH_2O-$, $-CH_2S-$, $-CH_2N(R^6)-$, $-CH=CH-$ or $-CH=N-$ to form together with atoms to which each of $R^2$ and Y is bonded, a 5-membered ring or a 6-membered ring, and in this case, a hydrogen atom bonded to each carbon atom forming the ring is optionally replaced by a halogen atom, a $C_1$ to $C_6$ alkyl group, a $C_1$ to $C_6$ haloalkyl group, a $C_1$ to $C_6$ alkylidene group, a $C_1$ to $C_6$ haloalkylidene group, an oxo group or a thioxo group, $R^{1a}$ represents $-C(O)R^{14}$, $-C(O)OR^{15}$, $-C(O)SR^{15}$, $-C(O)N(R^{17})R^{16}$, $-C(O)N(R^{17})OR^{15}$, $-C(O)N(R^{17})N(R^{17})R^{16}$, $-C(S)R^{14}$, $-C(S)OR^{15}$, $-C(S)SR^{15}$, $-C(S)N(R^{17})R^{16}$, $-C(SR^{15})=NCN$, $-C(SR^{15})=NNO_2$, $-S(O)_2R^{15}$ or $-S(O)_2N(R^{17})R^{16}$, $R^{2a}$ represents a hydrogen atom, a cyano, a $C_1$ to $C_{12}$ alkyl, a ($C_1$ to $C_{12}$) alkyl optionally substituted with $R^{13a}$, a $C_3$ to $C_{12}$ cycloalkyl, a $C_3$ to $C_{12}$ alkenyl, a $C_3$ to $C_{12}$ haloalkenyl, a $C_3$ to $C_{12}$ alkynyl, a $C_3$ to $C_{12}$ haloalkynyl, $-C(O)R^{14a}$, $-C(O)OR^{15a}$, $-C(O)SR^{15a}$, $-C(O)N(R^{17})R^{16}$, $-C(O)C(O)OR^{15a}$, $-C(S)OR^{15a}$, $-C(S)SR^{15a}$, $-C(S)N(R^{17})R^{16}$, a $C_1$ to $C_{12}$ alkoxy, a $C_1$ to $C_{12}$ haloalkoxy, $-SR^{15}$, $-S(O)_2R^{15a}$, $-SN(R^{19})R^{18}$, a phenyl, a phenyl substituted with $(Z)_{p1}$, D1, D2 or D32 to D35, or $R^{2a}$ together with $R^{1a}$ optionally forms a $C_3$ to $C_6$ alkylene chain to form together with a nitrogen atom to which $R^{1a}$ and $R^{2a}$ are bonded, a 4- to 7-membered ring, and in this case, the alkylene chain optionally contains one oxygen atom, sulfur atom or nitrogen atom and is optionally substituted with a $C_1$ to $C_6$ alkyl group, a $C_1$ to $C_6$ alkylidene group, a —CHO group, a $C_1$ to $C_6$ alkylcarbonyl group, a $C_1$ to $C_6$ haloalkylcarbonyl group, a $C_1$ to $C_6$ alkoxycarbonyl group, a $C_1$ to $C_6$ haloalkoxycarbonyl group, a $C_1$ to $C_6$ alkylaminocarbonyl group, a $C_1$ to $C_6$ haloalkylaminocarbonyl group, a di($C_1$ to $C_6$ alkyl) aminocarbonyl group, a phenyl group, a D32 group, a D34 group, an oxo group or a thioxo group, $R^{1b}$ represents a hydrogen atom, $R^{14}$, $-OR^{15}$, $-SR^{15}$, $-S(O)_2R^{15}$ or $-N(R^{17b})R^{16b}$, $R^{2b}$ represents a $C_1$ to $C_6$ alkyl, $-OR^{15a}$, $-SR^{15a}$, $-SC(O)R^{14a}$, $-SC(O)OR^{15a}$ or $-N(R^{17c})R^{16c}$, or $R^{2b}$ together with $R^{1b}$ optionally forms a $C_4$ to $C_5$ alkylene chain or a $C_4$ to $C_5$ alkenylene chain to form together with a carbon atom to which $R^{1b}$ and $R^{2b}$ are bonded, a 5-or 6-membered ring, and in this case, the alkylene chain or the alkenylene chain optionally contains one to three oxygen atom(s), sulfur atom(s) or nitrogen atom(s) and is optionally substituted with a halogen atom, a cyano group, a nitro group, a $C_1$ to $C_6$ alkyl group, a $C_1$ to $C_6$ haloalkyl group, a $C_1$ to $C_6$ alkoxy group, a $C_1$ to $C_6$ haloalkoxy group, a $C_1$ to $C_6$ alkylthio group, a $C_1$ to $C_6$ haloalkylthio group or a $R^{17c}$ group, $R^3$ represents a halogen atom, a cyano, a $C_1$ to $C_6$ alkyl, a ($C_1$ to $C_6$) alkyl optionally substituted with $R^4$, a $C_3$ to $C_8$ cycloalkyl, a ($C_3$ to $C_8$) cycloalkyl optionally substituted with $R^4$, E1 to E19, a $C_3$ to $C_6$ alkenyl, a ($C_2$ to $C_6$) alkenyl optionally substituted with $R^4$, a $C_3$ to $C_6$ alkynyl, a ($C_2$ to $C_6$) alkynyl optionally substituted with $R^4$, $-OR^5$, $-S(O)_rR^5$, $-N(R^{10})R^9$, $-C(O)R^8$, $-C(R^8)=NOH$, $-C(R^8)=NOR^9$, M3, M13, M30, $-C(O)OR^9$, $-C(O)SR^9$, $-C(O)NH_2$, $-C(O)N(R^{10})R^9$, $-C(S)OR^9$, $-C(S)SR^9$, $-C(S)NH_2$, $-C(S)N(R^{10})R^9$, $-Si(R^{11a})(R^{11b})R^{11}$, $-P(O)(OR^{20})_2$, a phenyl, a phenyl substituted with $(Z)_{p1}$ or D1 to D38, $R^{3a}$ represents a halogen atom, a cyano, a nitro, a $C_1$ to $C_6$ alkyl, a ($C_1$ to $C_6$) alkyl optionally substituted with $R^4$, a $C_3$ to $C_8$ cycloalkyl, a $C_2$ to $C_6$ alkenyl, a $C_2$ to $C_6$ alkynyl, $-C(O)OR^9$, $-C(O)SR^9$, $-C(O)NH_2$, $-C(O)N(R^{10})R^9$, $-C(S)OR^9$, $-C(S)SR^9$, $-C(S)NH_2$, $-C(S)N(R^{10})R^9$, a $C_1$ to $C_6$ alkylthio, a $C_1$ to $C_6$ haloalkylthio or a phenyl, $R^{3b}$ represents a hydrogen atom, a halogen atom, a $C_1$ to $C_6$ alkyl, a $C_1$ to $C_6$ haloalkyl, a $C_3$ to $C_6$ alkenyl or a $C_3$ to $C_6$ alkynyl, $R^{3c}$ represents a hydrogen atom or $R^{3a}$, D1 to D38 individually represent an aromatic heterocyclic ring represented by the following Structural Formulae:

D1

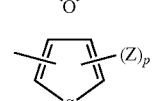

D2

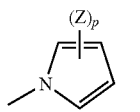
D3
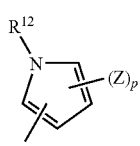
D4
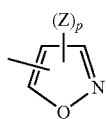
D5
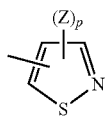
D6
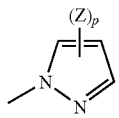
D7
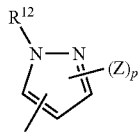
D8
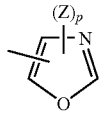
D9
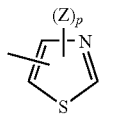
D10
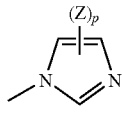
D11
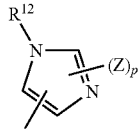
D12
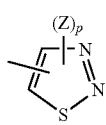
D13
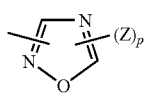
D14
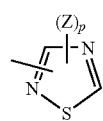
D15
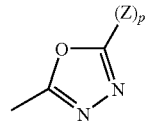
D16
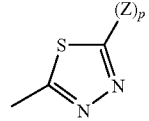
D17
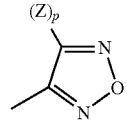
D18
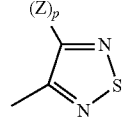
D19
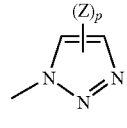
D20
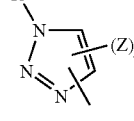
D21
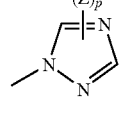
D22
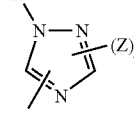
D23
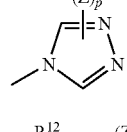
D24
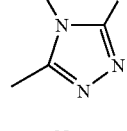
D25
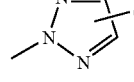
D26

-continued

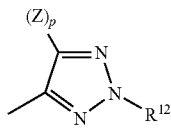
D27

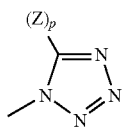
D28

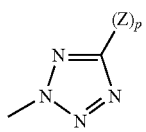
D29

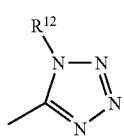
D30

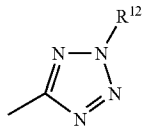
D31

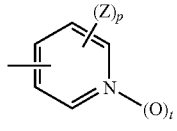
D32

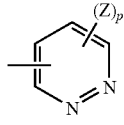
D33

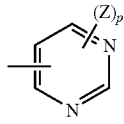
D34

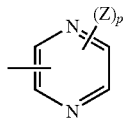
D35

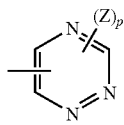
D36

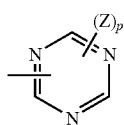
D37

-continued

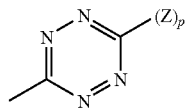
D38

Z represents a halogen atom, a cyano, a nitro, a $C_1$ to $C_6$ alkyl, a $C_1$ to $C_6$ haloalkyl, a $C_1$ to $C_4$ alkoxy($C_1$ to $C_4$) alkyl, a $C_1$ to $C_4$ haloalkoxy($C_1$ to $C_4$) alkyl, a $C_1$ to $C_4$ alkylthio($C_1$ to $C_4$) alkyl, a $C_1$ to $C_4$ haloalkylthio($C_1$ to $C_4$) alkyl, a $C_1$ to $C_4$ alkylsulfinyl($C_1$ to $C_4$) alkyl, a $C_1$ to $C_4$ haloalkylsulfinyl($C_1$ to $C_4$) alkyl, a $C_1$ to $C_4$ alkylsulfonyl($C_1$ to $C_4$) alkyl, a $C_1$ to $C_4$ haloalkylsulfonyl($C_1$ to $C_4$) alkyl, a $C_3$ to $C_6$ cycloalkyl, a $C_3$ to $C_6$ halocycloalkyl, —OH, a $C_1$ to $C_6$ alkoxy, a $C_1$ to $C_6$ haloalkoxy, a $C_1$ to $C_6$ alkyl sulfonyloxy, a $C_1$ to $C_6$ haloalkylsulfonyloxy, a $C_1$ to $C_6$ alkylthio, a $C_1$ to $C_6$ haloalkylthio, a $C_1$ to $C_6$ alkylsulfinyl, a $C_1$ to $C_6$ haloalkylsulfinyl, a $C_1$ to $C_6$ alkylsulfonyl, a $C_1$ to $C_6$ haloalkylsulfonyl, —$NH_2$, a $C_1$ to $C_6$ alkylamino, a di($C_1$ to $C_6$ alkyl) amino, a $C_1$ to $C_6$ alkoxycarbonyl, a $C_1$ to $C_6$ haloalkoxycarbonyl, —C(O)$NH_2$, a $C_1$ to $C_6$ alkylaminocarbonyl, a $C_1$ to $C_6$ haloalkylaminocarbonyl, a di($C_1$ to $C_6$ alkyl) aminocarbonyl, —C(S)$NH_2$, —S(O)$_2NH_2$, a $C_1$ to $C_6$ alkylaminosulfonyl, a di($C_1$ to $C_6$ alkyl) aminosulfonyl, a phenyl or a phenyl optionally substituted with a halogen atom, where when p and p1 individually represent an integer of 2 or more, Zs are optionally the same as or different from each other, and further, when two Zs are adjacent to each other, the two Zs adjacent to each other optionally form —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$CH_2CH_2CH_2S$—, —$OCH_2CH_2S$— or —CH=CH—CH=CH— to form together with carbon atoms to which each of the two Zs is bonded, a 5-membered ring or a 6-membered ring, and in this case, a hydrogen atom bonded to each carbon atom forming the ring is optionally replaced by a halogen atom, a cyano group, a nitro group, a $C_1$ to $C_4$ alkyl group, a $C_1$ to $C_4$ haloalkyl group, a $C_1$ to $C_4$ alkoxy group or a $C_1$ to $C_4$ alkylthio group, E1 to E19 individually represent a saturated heterocyclic ring represented by the following Structural Formulae:

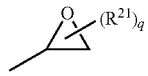
E1

E2

E3

-continued

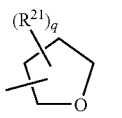 E4

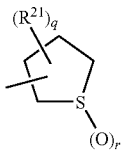 E5

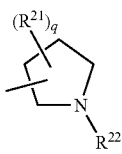 E6

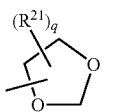 E7

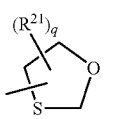 E8

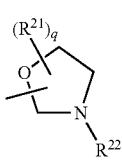 E9

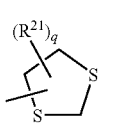 E10

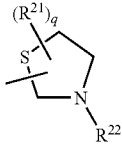 E11

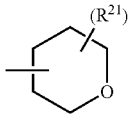 E12

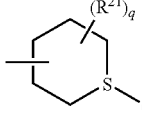 E13

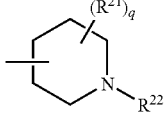 E14

-continued

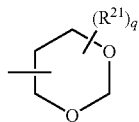 E15

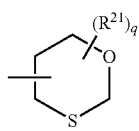 E16

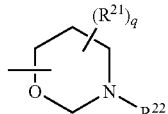 E17

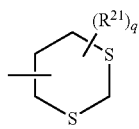 E18

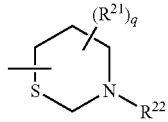 E19

$R^4$ represents a halogen atom, a cyano, a $C_3$ to $C_8$ cycloalkyl, a $C_3$ to $C_8$ halocycloalkyl, E1 to E19, —OH, —OR$^5$, —SH, —S(O)$_{rR}$R$^5$, —N(R$^7$)R$^6$, —N(R$^7$)C(O)R$^{8a}$, —C(O)OR$^9$, —C(O)N(R$^{10}$)R$^9$, —Si(R$^{11a}$)(R$^{11b}$)R$^{11}$, a phenyl, a phenyl substituted with (Z)$_{p1}$ or D1 to D38, $R^{4a}$ represents a hydrogen atom, a cyano, a $C_1$ to $C_6$ alkyl, a $C_1$ to $C_6$ haloalkyl, a $C_3$ to $C_6$ cycloalkyl, a $C_2$ to $C_6$ alkenyl, a $C_2$ to $C_4$ alkynyl, a $C_1$ to $C_6$ alkoxycarbonyl, —C(O)NH$_2$, —C(S)NH$_2$, a phenyl, a phenyl substituted with (Z)$_{p1}$, D1, D2, D9, D10 or D32, $R^{4b}$ represents a hydrogen atom or a $C_1$ to $C_6$ alkyl, or $R^{4b}$ together with $R^{4a}$ optionally forms a $C_2$ to $C_5$ alkylene chain to form together with a carbon atom to which $R^{4a}$ and $R^{4b}$ are bonded, a 3- to 6-membered ring, and in this case, the alkylene chain optionally contains one oxygen atom, sulfur atom or nitrogen atom and is optionally substituted with a $C_1$ to $C_6$ alkyl group, a —CHO group, a $C_1$ to $C_6$ alkylcarbonyl group, a $C_1$ to $C_6$ alkoxycarbonyl group, a $C_1$ to $C_6$ alkylaminocarbonyl group, a $C_1$ to $C_6$ haloalkylaminocarbonyl group or a phenyl group, $R^{4c}$ represents a hydrogen atom, a $C_1$ to $C_6$ alkyl, a $C_1$ to $C_6$ haloalkyl, a $C_1$ to $C_6$ alkylcarbonyl, a $C_1$ to $C_6$ haloalkylcarbonyl, a $C_3$ to $C_6$ cycloalkylcarbonyl, a $C_3$ to $C_6$ halocycloalkylcarbonyl, a $C_1$ to $C_6$ alkoxycarbonyl or a $C_1$ to $C_6$ haloalkoxycarbonyl, $R^5$ represents a $C_1$ to $C_6$ alkyl, a ($C_1$ to $C_6$) alkyl optionally substituted with $R^{23}$, a $C_3$ to $C_8$ cycloalkyl, a ($C_3$ to $C_8$) cycloalkyl optionally substituted with $R^{23}$, E2 to E6, E12 to E15, E18, a $C_2$ to $C_6$ alkenyl, a ($C_2$ to $C_6$) alkenyl optionally substituted with $R^{23}$, a $C_5$ to $C_{10}$ cycloalkenyl, a $C_5$ to $C_{10}$ halocycloalkenyl, a $C_3$ to $C_6$ alkynyl, a ($C_3$ to $C_6$) alkynyl optionally substituted with $R^{23}$, a $C_1$ to $C_6$ alkylcarbonyl, a $C_1$ to $C_6$ alkoxycarbonyl, a phenyl, a phenyl substituted with (Z)$_{p1}$, D1, D2, D4 to D6, D8 to D10, D12 to D19, D21, D23, D25, D27 or D30 to D38, $R^6$ represents a $C_1$ to $C_6$ alkyl, a ($C_1$ to $C_6$) alkyl optionally substituted with $R^{23}$, a $C_3$ to $C_8$ cycloalkyl, a $C_3$ to $C_8$ halocycloalkyl, a $C_3$ to $C_6$ alkenyl, a $C_3$ to $C_6$ haloalkenyl, a $C_3$ to $C_6$ alkynyl, a $C_3$ to $C_6$ haloalkynyl, —C(O)$R^8$, —C(O)$R^9$, —C(O)S$R^9$, —C(O)NH$_2$, —C(O)N($R^{10}$)$R^9$, —C(S)O$R^9$, —C(S)S$R^9$, —C(S)NH$_2$, —C(S)N($R^{10}$)$R^9$, —C(O)C(O)$R^9$, —C(O)C(O)O$R^9$, —OH, —S(O)$_2R^9$, —S(O)$_2$N($R^{10}$)$R^9$, —P(O)(O$R^{20}$)$_2$ or —P(S)(O$R^{20}$)$_2$, $R^7$ represents a hydrogen atom, a $C_1$ to $C_6$ alkyl, a ($C_1$ to $C_6$) alkyl optionally substituted with $R^{23}$, a $C_3$ to $C_8$ cycloalkyl, a $C_3$ to $C_6$ alkenyl, a $C_3$ to $C_6$ haloalkenyl, a $C_3$ to $C_6$ alkynyl, a $C_3$ to $C_6$ haloalkynyl, —CHO, a $C_1$ to $C_6$ alkylcarbonyl, a $C_1$ to $C_6$ haloalkylcarbonyl or a $C_1$ to $C_6$ alkoxycarbonyl, or $R^7$ together with $R^6$ optionally forms a $C_2$ to $C_6$ alkylene chain to form together with a nitrogen atom to which $R^6$ and $R^7$ are bonded, a 3- to 7-membered ring, and in this case, the alkylene chain optionally contains one oxygen atom, sulfur atom or nitrogen atom and is optionally substituted with a halogen atom, a $C_1$ to $C_6$ alkyl group, a $C_1$ to $C_6$ haloalkyl group, an oxo group or a thioxo group, $R^{6a}$ represents a $C_1$ to $C_6$ alkyl, a $C_1$ to $C_6$ alkoxy, a $C_1$ to $C_6$ haloalkoxy, a $C_3$ to $C_6$ alkenyloxy, a phenoxy or a phenoxy substituted with $(Z)_{p1}$, $R^{7a}$ represents a hydrogen atom, a $C_1$ to $C_6$ alkyl, a $C_1$ to $C_6$ haloalkyl, a $C_3$ to $C_6$ alkenyl, a phenyl or a phenyl substituted with $(Z)_{p1}$, or $R^{7a}$ together with $R^{6a}$ optionally forms a $C_4$ to $C_6$ alkylene chain to form together with a carbon atom to which $R^{6a}$ and $R^{7a}$ are bonded, a 5- to 7-membered ring, and in this case, the alkylene chain optionally contains one oxygen atom or sulfur atom, $R^8$ represents a hydrogen atom, a $C_1$ to $C_6$ alkyl, a ($C_1$ to $C_6$) alkyl optionally substituted with $R^{23}$, a $C_3$ to $C_8$ cycloalkyl, a $C_3$ to $C_8$ halocycloalkyl, E4 to E6, E12 to E14, a $C_3$ to $C_6$ alkenyl, a $C_3$ to $C_6$ haloalkenyl, a $C_5$ to $C_{10}$ cycloalkenyl, a $C_5$ to $C_{10}$ halocycloalkenyl, a $C_3$ to $C_6$ alkynyl or a $C_3$ to $C_6$ haloalkynyl, $R^{8a}$ represents a phenyl, a phenyl substituted with $(Z)_{p1}$, or D1 to D38, $R^9$ represents a $C_1$ to $C_6$ alkyl, a ($C_1$ to $C_6$) alkyl optionally substituted with $R^{23}$, a $C_3$ to $C_8$ cycloalkyl, a $C_3$ to $C_8$ halocycloalkyl, E2 to E6, E12 to E19, a $C_3$ to $C_6$ alkenyl, a $C_3$ to $C_6$ haloalkenyl, a $C_3$ to $C_6$ alkynyl, a $C_3$ to $C_6$ haloalkynyl, a phenyl, a phenyl substituted with $(Z)_{p1}$, D1 to D25 or D27 to D38, $R^{10}$ represents a hydrogen atom, a $C_1$ to $C_6$ alkyl, a $C_1$ to $C_6$ haloalkyl, a $C_3$ to $C_6$ cycloalkyl($C_1$ to $C_4$) alkyl, a $C_1$ to $C_6$ alkoxy($C_1$ to $C_4$) alkyl, a $C_1$ to $C_6$ alkylthio ($C_1$ to $C_4$) alkyl, a cyano($C_1$ to $C_6$) alkyl, a $C_3$ to $C_6$ alkenyl or a $C_3$ to $C_6$ alkynyl, or $R^{10}$ together with $R^9$ optionally forms a $C_2$ to $C_6$ alkylene chain to form together with a nitrogen atom to which $R^9$ and $R^{10}$ are bonded, a 3- to 7-membered ring, and in this case, the alkylene chain optionally contains one oxygen atom, sulfur atom or nitrogen atom and is optionally substituted with a halogen atom, a $C_1$ to $C_6$ alkyl group, a $C_1$ to $C_6$ alkoxy group, a —CHO group, a $C_1$ to $C_6$ alkylcarbonyl group or a $C_1$ to $C_6$ alkoxycarbonyl group, $R^{11}$ represents a $C_1$ to $C_6$ alkyl, a $C_1$ to $C_6$ haloalkyl, a $C_1$ to $C_6$ alkoxy, a phenyl or a phenyl substituted with $(Z)_{p1}$, $R^{11a}$ and $R^{11b}$ independently represent a $C_1$ to $C_6$ alkyl, a $C_1$ to $C_6$ haloalkyl or a $C_1$ to $C_6$ alkoxy, $R^{12}$ represents a hydrogen atom, a $C_1$ to $C_6$ alkyl, a $C_1$ to $C_6$ haloalkyl, a $C_1$ to $C_6$ alkoxycarbonyl($C_1$ to $C_4$) alkyl, a $C_1$ to $C_6$ haloalkoxycarbonyl($C_1$ to $C_4$) alkyl, a phenyl($C_1$ to $C_4$) alkyl, a phenyl($C_1$ to $C_4$) alkyl substituted with $(Z)_{p1}$, a $C_2$ to $C_6$ alkenyl, a $C_2$ to $C_6$ haloalkenyl, a $C_3$ to $C_6$ alkynyl, a $C_3$ to $C_6$ haloalkynyl, a $C_1$ to $C_6$ alkoxy, a $C_1$ to $C_6$ alkoxylcarbonyl, a $C_1$ to $C_6$ haloalkoxycarbonyl, a phenyl or a phenyl substituted with $(Z)_{p1}$, and further, when Z is present adjacent to $R^{12}$, $R^{12}$ and Z adjacent to each other optionally form —CH$_2$CH$_2$CH$_2$CH$_2$—, —CH=CH—CH=CH—, —N=CH—CH=CH—, —CH=N—CH=CH—, —CH=CH—N=CH— or —CH=CH—CH=N— to form together with atoms to which each of $R^{12}$ and Z is bonded, a 6-membered ring, and in this case, a hydrogen atom bonded to each carbon atom forming the ring is optionally replaced by a halogen atom, a $C_1$ to $C_4$ alkyl group or a $C_1$ to $C_4$ haloalkyl group, $R^{13}$ and $R^{13a}$ independently represent a halogen atom, a cyano, a nitro, a $C_3$ to $C_8$ cycloalkyl, a $C_3$ to $C_8$ halocycloalkyl, a hydroxy($C_3$ to $C_8$) cycloalkyl, a $C_1$ to $C_4$ alkoxy($C_3$ to $C_8$) cycloalkyl, E1 to E19, a $C_5$ to $C_{10}$ cycloalkenyl, a $C_5$ to $C_{10}$ halocycloalkenyl, —O$R^{24}$, —N($R^{25}$)$R^{24}$, —SH, —S(O)'$R^{26}$, —C(O)$R^{27}$, —C($R^{27}$)=NOH, —C($R^{27}$)=NO$R^{28}$, —C(O)OH, —C(O)O$R^{28}$, —C(O)S$R^{28}$, —C(O)NH$_2$, —C(O)N($R^{29}$)$R^{28}$, —C(O)N($R^{29}$)O$R^{28}$, —C(O)N($R^{29}$)N($R^{29}$)$R^{28}$, —C(O)C(O)O$R^{28}$, —C(S)O$R^{28}$, —C(S)S$R^{28}$, —C(S)NH$_2$, —C(S)N($R^{29}$)$R^{28}$, —C(=N$R^{29}$)O$R^{28}$, —C(=N$R^{29}$)S$R^{28}$, —C(=N$R^{29}$)N($R^{29}$)$R^{28}$, —C(=NO$R^{28}$)N($R^{29}$)$R^{28}$, —S(O)$_2$OH, —S(O)$_2$NH$_2$, —S(O)$_2$N($R^{29}$)$R^{28}$, —Si($R^{11a}$)($R^{11b}$)$R^{11}$, —P(O)(O$R^{20}$)$_2$, —P(S)(O$R^{20}$)$_2$, —P(phenyl)$_2$, —P(O)(phenyl)$_2$, M1 to M30, a phenyl, a phenyl substituted with $(Z)_{p1}$, a naphthyl or D1 to D38, M1 to M30 individually represent a partially saturated heterocyclic ring represented by the following Structural Formulae:

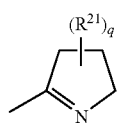

M1

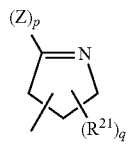

M2

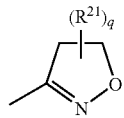

M3

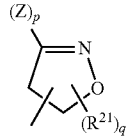

M4

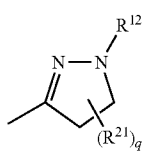 M5
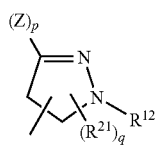 M6
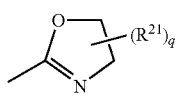 M7
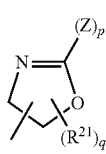 M8
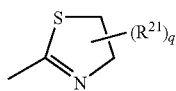 M9
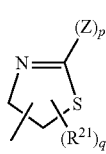 M10
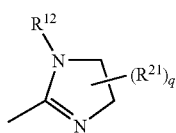 M11
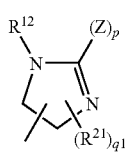 M12
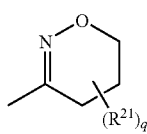 M13
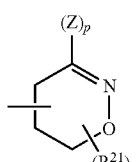 M14
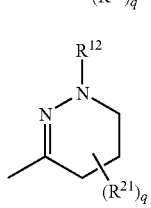 M15
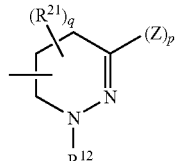 M16
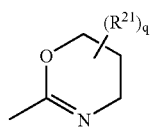 M17
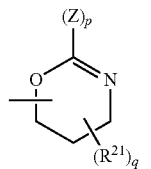 M18
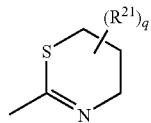 M19
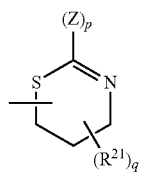 M20
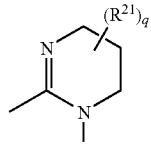 M21
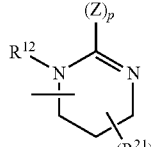 M22
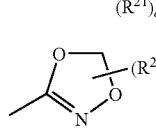 M23
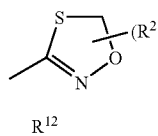 M24
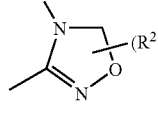 M25
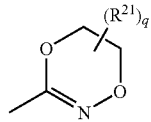 M26

-continued

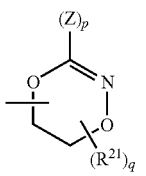
M27

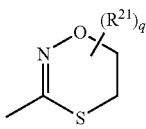
M28

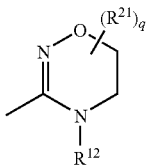
M29

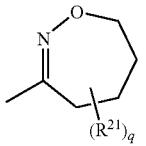
M30

$R^{14}$ and $R^{14a}$ independently represent a hydrogen atom, a $C_1$ to $C_{12}$ alkyl, a ($C_1$ to $C_{12}$) alkyl optionally substituted with $R^{30}$, a $C_3$ to $C_{12}$ cycloalkyl, a ($C_3$ to $C_{12}$) cycloalkyl optionally substituted with $R^{30}$, E1 to E19, a $C_2$ to $C_{12}$ alkenyl, a ($C_2$ to $C_{12}$) alkenyl optionally substituted with $R^{30}$, a $C_5$ to $C_{12}$ cycloalkenyl, a $C_5$ to $C_{12}$ halocycloalkenyl, a $C_2$ to $C_{12}$ alkynyl, a ($C_2$ to $C_{12}$) alkynyl optionally substituted with $R^{30}$, —C(O)$R^{27}$, —C($R^{27}$)=NOH, —C($R^{27}$)=NO$R^{28}$, —C($R^{27}$)=NN($R^{29}$)$R^{28}$, —C(O)O$R^{28}$, —C(O)N($R^{29}$)$R^{28}$, M4, a phenyl, a phenyl substituted with (Z)$_{p1}$, a naphthyl or D1 to D38, $R^{15}$ and $R^{15a}$ independently represent a $C_1$ to $C_{12}$ alkyl, a ($C_1$ to $C_{12}$) alkyl optionally substituted with $R^{30}$, a $C_3$ to $C_{12}$ cycloalkyl, a ($C_3$ to $C_{12}$) cycloalkyl optionally substituted with $R^{30}$, E2 to E6, E12 to E19, a $C_2$ to $C_{12}$ alkenyl, a $C_2$ to $C_{12}$ haloalkenyl, a $C_5$ to $C_{10}$ cycloalkenyl, a $C_5$ to $C_{10}$ halocycloalkenyl, a $C_3$ to $C_{12}$ alkynyl, a $C_2$ to $C_{12}$ haloalkynyl, a phenyl, a phenyl substituted with (Z)$_{p1}$, D1, D2, D4 to D6, D8 to D10, D12 to D19, D21, D23, D25, D27 or D30 to D38, $R^{16}$ represents a hydrogen atom, a $C_1$ to $C_{12}$ alkyl, a ($C_1$ to $C_{12}$) alkyl optionally substituted with $R^{30}$, a $C_3$ to $C_{12}$ cycloalkyl, a ($C_3$ to $C_{12}$) cycloalkyl optionally substituted with $R^{30}$, E2 to E6, E12 to E19, a $C_2$ to $C_{12}$ alkenyl, a $C_2$ to $C_{12}$ haloalkenyl, a $C_5$ to $C_{10}$ cycloalkenyl, a $C_5$ to $C_{10}$ halocycloalkenyl, a $C_3$ to $C_{12}$ alkynyl, a $C_2$ to $C_{12}$ haloalkynyl, —C(O)$R^{27}$, —C(O)O$R^{28}$, —C(O)S$R^{28}$, —C(O)NH$_2$, —C(O)N($R^{29}$)$R^{28}$, —C(S)$R^{27}$, —C(S)O$R^{28}$, —C(S)S$R^{28}$, —C(S)NH$_2$, —C(S)N($R^{29}$)$R^{28}$, M7, M9, M17, M19, —S(O)$_2$$R^{28}$, —S(O)$_2$NH$_2$, —S(O)$_2$N($R^{29}$)$R^{28}$, —P(O)(O$R^{20}$)$_2$, —P(S)(O$R^{20}$)$_2$, a phenyl, a phenyl substituted with (Z)$_{p1}$, D1 to D25 or D27 to D38, $R^{17}$ represents a hydrogen atom, a $C_1$ to $C_6$ alkyl, a $C_1$ to $C_6$ haloalkyl, a $C_3$ to $C_6$ cycloalkyl($C_1$ to $C_4$) alkyl, a $C_1$ to $C_4$ alkoxy($C_1$ to $C_4$) alkyl, a $C_1$ to $C_4$ haloalkoxy($C_1$ to $C_4$) alkyl, a $C_1$ to $C_4$ alkylthio($C_1$ to $C_4$) alkyl, a $C_1$ to $C_4$ haloalkylthio($C_1$ to $C_4$) alkyl, a $C_1$ to $C_4$ alkylsulfonyl($C_1$ to $C_4$) alkyl, a $C_1$ to $C_4$ haloalkylsulfonyl($C_1$ to $C_4$) alkyl, a cyano($C_1$ to $C_6$) alkyl, a $C_1$ to $C_4$ alkoxycarbonyl($C_1$ to $C_4$) alkyl, a phenyl($C_1$ to $C_4$) alkyl, a $C_2$ to $C_6$ alkenyl, a $C_2$ to $C_6$ haloalkenyl, a $C_3$ to $C_6$ alkynyl or a $C_3$ to $C_6$ haloalkynyl, or $R^{17}$ together with $R^{16}$ optionally forms a $C_2$ to $C_6$ alkylene chain to form together with a nitrogen atom to which $R^{16}$ and $R^{17}$ are bonded, a 3- to 7-membered ring, and in this case, the alkylene chain optionally contains one oxygen atom, sulfur atom or nitrogen atom and is optionally substituted with a halogen atom, a $C_1$ to $C_6$ alkyl group, a $C_1$ to $C_4$ alkoxy($C_1$ to $C_4$) alkyl group, a $C_1$ to $C_6$ alkoxy group, a —CHO group, a $C_1$ to $C_6$ alkylcarbonyl group, a $C_1$ to $C_6$ alkoxycarbonyl group, an oxo group or a thioxo group, $R^{16a}$ presents a hydrogen atom, a $C_1$ to $C_6$ alkyl, a $C_1$ to $C_6$ haloalkyl, a $C_1$ to $C_4$ alkoxy($C_1$ to $C_4$) alkyl, a $C_1$ to $C_4$ alkylthio($C_1$ to $C_4$) alkyl, a $C_1$ to $C_4$ alkylsulfonyl ($C_1$ to $C_4$) alkyl, a $C_1$ to $C_4$ alkoxycarbonyl($C_1$ to $C_4$) alkyl, a phenyl($C_1$ to $C_4$) alkyl, a phenyl($C_1$ to $C_4$) alkyl substituted with (Z)$_{p1}$, a $C_3$ to $C_6$ cycloalkyl, E1 to E19, a phenyl($C_2$ to $C_4$) alkenyl, a di($C_1$ to $C_6$ alkyl) amino, a phenyl, a phenyl substituted with (Z)$_{p1}$ or D1 to D38, $R^{17a}$ represents a hydrogen atom, a $C_1$ to $C_6$ alkyl, a $C_1$ to $C_6$ alkoxy, a $C_1$ to $C_6$ alkylthio or a di($C_1$ to $C_6$ alkyl) amino, or $R^{17a}$ together with $R^{16a}$ optionally forms a $C_3$ to $C_5$ alkylene chain to form together with a carbon atom to which $R^{16a}$ and $R^{17a}$ are bonded, a 4- to 6-membered ring, and in this case, the alkylene chain optionally contains one oxygen atom, sulfur atom or nitrogen atom and is optionally substituted with a halogen atom, a $C_1$ to $C_6$ alkyl group, a $C_1$ to $C_6$ haloalkyl group, a —CHO group, a $C_1$ to $C_6$ alkylcarbonyl group or a $C_1$ to $C_6$ alkoxycarbonyl group, $R^{16b}$ presents a hydrogen atom, a cyano, a nitro, a $C_1$ to $C_6$ alkyl, a $C_1$ to $C_6$ haloalkyl or a $C_1$ to $C_6$ alkoxy, $R^{17b}$ represents a hydrogen atom or a $C_1$ to $C_6$ alkyl, or $R^{17b}$ together with $R^{16b}$ optionally forms a $C_3$ to $C_5$ alkylene chain to form together with a nitrogen atom to which $R^{16b}$ and $R^{17b}$ are bonded, a 4- to 6-membered ring, and in this case, the alkylene chain optionally contains one oxygen atom, sulfur atom or nitrogen atom and is optionally substituted with a $C_1$ to $C_6$ alkyl group, a —CHO group, a $C_1$ to $C_6$ alkylcarbonyl group or a $C_1$ to $C_6$ alkoxycarbonyl group, $R^{16c}$ presents a hydrogen atom, a $C_1$ to $C_6$ alkyl, a $C_1$ to $C_6$ haloalkyl, a $C_3$ to $C_6$ alkenyl, a $C_3$ to $C_6$ alkynyl, a $C_1$ to $C_6$ alkoxy, a $C_1$ to $C_6$ haloalkoxy, —NH$_2$, a $C_1$ to $C_6$ alkylamino, a di($C_1$ to $C_6$ alkyl) amino, —NHC(O) $R^{27}$, —NHC(O)O$R^{28}$, —NHC(O)S$R^{28}$, —NHC(O) NH$_2$, —NHC(O)N($R^{29}$)$R^{28}$, —NHC(S)O$R^{28}$, —NHC(S)S$R^{28}$, —NHC(S)NH$_2$, —NHC(S)N($R^{29}$) $R^{28}$, —NHS(O)$_2$$R^{28}$, —NHS(O)$_2$NH$_2$ or —NHS(O)$_2$ N($R^{29}$)$R^{28}$, $R^{17c}$ represents a hydrogen atom or a $C_1$ to $C_6$ alkyl, or $R^{17c}$ together with $R^{16c}$ optionally forms a $C_3$ to $C_5$ alkylene chain to form together with a nitrogen atom to which $R^{16c}$ and $R^{17c}$ are bonded, a 4- to 6-membered ring, and in this case, the alkylene chain optionally contains one oxygen atom, sulfur atom or nitrogen atom and is optionally substituted with a $C_1$ to $C_6$ alkyl group, a —CHO group, a $C_1$ to $C_6$ alkylcarbonyl group or a $C_1$ to $C_6$ alkoxycarbonyl group, $R^{18}$ represents a $C_1$ to $C_{12}$ alkyl, a $C_1$ to $C_{12}$ haloalkyl, a $C_1$ to $C_{12}$ alkoxy($C_1$ to $C_{12}$) alkyl, a cyano($C_1$ to $C_{12}$)

alkyl, a $C_1$ to $C_{12}$ alkoxycarbonyl($C_1$ to $C_{12}$) alkyl, a phenyl($C_1$ to $C_4$) alkyl, a phenyl($C_1$ to $C_4$) alkyl substituted with $(Z)_{p1}$, a $C_3$ to $C_{12}$ alkenyl, a $C_3$ to $C_{12}$ haloalkenyl, a $C_3$ to $C_{12}$ alkynyl, a $C_3$ to $C_{12}$ haloalkynyl, a $C_1$ to $C_{12}$ alkylcarbonyl, a $C_1$ to $C_{12}$ alkoxycarbonyl, —C(O)ON═C(CH$_3$)SCH$_3$, —C(O)ON═C(SCH$_3$)C(O)N(CH$_3$)$_2$, a phenyl or a phenyl substituted with $(Z)_{p1}$, $R^{19}$ represents a $C_1$ to $C_{12}$ alkyl, a $C_1$ to $C_{12}$ haloalkyl, a $C_1$ to $C_{12}$ alkoxy($C_1$ to $C_{12}$) alkyl, a cyano($C_1$ to $C_{12}$) alkyl, a $C_1$ to $C_{12}$ alkoxycarbonyl($C_1$ to $C_{12}$) alkyl, a phenyl($C_1$ to $C_4$)alkyl, a phenyl($C_1$ to $C_4$) alkyl substituted with $(Z)_{p1}$, a $C_3$ to $C_{12}$ alkenyl, a $C_3$ to $C_{12}$ haloalkenyl, a $C_3$ to $C_{12}$ alkynyl, a $C_3$ to $C_{12}$ haloalkynyl, a phenyl or a phenyl substituted with $(Z)_{p1}$, or $R^{19}$ together with $R^{18}$ optionally forms a $C_4$ to $C_7$ alkylene chain to form together with a nitrogen atom to which $R^{18}$ and $R^{19}$ are bonded, a 5- to 8-membered ring, and in this case, the alkylene chain optionally contains one oxygen atom or sulfur atom and is optionally substituted with a $C_1$ to $C_4$ alkyl group or a $C_1$ to $C_4$ alkoxy group, $R^{20}$ represents a $C_1$ to $C_6$ alkyl or a $C_1$ to $C_6$ haloalkyl, $R^{21}$ represents a halogen atom, a cyano, a $C_1$ to $C_O$ alkyl, a $C_1$ to $C_6$ haloalkyl, a hydroxy($C_1$ to $C_6$) alkyl, a $C_1$ to $C_4$ alkoxy($C_1$ to $C_4$) alkyl, a $C_1$ to $C_4$ alkoxycarbonyl ($C_1$ to $C_4$)alkyl, a $C_1$ to $C_O$ alkoxy, a $C_1$ to $C_6$ alkylthio, a $C_1$ to $C_6$ alkylamino, a di($C_1$ to $C_4$ alkyl) amino, a $C_1$ to $C_6$ alkoxycarbonyl, a phenyl or a phenyl substituted with $(Z)_{p1}$, where when q represents an integer of 2 or more, $R^{21}$s are optionally the same as or different from each other, and further when two $R^{21}$s are replaced on the same carbon atom, the two $R^{21}$s together with each other optionally form an oxo, a thioxo, an imino, a $C_1$ to $C_6$ alkylimino, a $C_1$ to $C_6$ alkoxyimino or a $C_1$ to $C_6$ alkylidene, $R^{22}$ represents a hydrogen atom, a $C_1$ to $C_6$ alkyl, a ($C_1$ to $C_6$) alkyl optionally substituted with $R^{30}$, a $C_3$ to $C_6$ cycloalkyl, a $C_3$ to $C_6$ alkenyl, a $C_3$ to $C_6$ haloalkenyl, a $C_3$ to $C_6$ alkynyl, —OH, a benzyloxy, —C(O)R$^{31}$, —C(O)OR$^{32}$, —C(O)SR$^{32}$, —C(O)N(R$^{34}$)R$^{33}$, —C(S)N(R$^{34}$)R$^{33}$, —S(O)$_2$R$^{32}$, —P(O)(OR$^{20}$)$_2$, —P(S)(OR$^{20}$)$_2$, a phenyl, a phenyl substituted with $(Z)_{p1}$ or D3, $R^{23}$ represents a halogen atom, a cyano, a $C_3$ to $C_8$ cycloalkyl, a $C_3$ to $C_8$ halocycloalkyl, E1 to E19, a $C_1$ to $C_6$ alkoxy, a $C_1$ to $C_6$ haloalkoxy, a $C_1$ to $C_6$ alkylthio, a $C_1$ to $C_6$ haloalkylthio, a $C_1$ to $C_6$ alkylsulfonyl, a $C_1$ to $C_6$ haloalkylsulfonyl, a $C_1$ to $C_6$ alkylamino, a di($C_1$ to $C_6$ alkyl) amino, —CHO, a $C_1$ to $C_6$ alkylcarbonyl, a $C_1$ to $C_6$ haloalkylcarbonyl, a $C_1$ to $C_O$ alkoxycarbonyl, a $C_1$ to $C_6$ haloalkoxycarbonyl, a $C_1$ to $C_6$ alkylaminocarbonyl, a di($C_1$ to $C_6$ alkyl) aminocarbonyl, a phenyl, a phenyl substituted with $(Z)_{p1}$ or D1 to D38, $R^{24}$ represents a hydrogen atom, a $C_1$ to $C_8$ alkyl, a ($C_1$ to $C_8$) alkyl optionally substituted with $R^{30}$, a $C_3$ to $C_8$ cycloalkyl, a ($C_3$ to $C_8$) cycloalkyl optionally substituted with $R^{30}$, E2 to E6, E12 to E19, a $C_3$ to $C_8$ alkenyl, a ($C_3$ to $C_8$) alkenyl optionally substituted with $R^{30}$, a $C_3$ to $C_8$ alkynyl, a ($C_3$ to $C_8$) alkynyl optionally substituted with $R^{30}$, —C(O)R$^{31}$, —C(O)OR$^{32}$, —C(O)SR$^{32}$, —C(O)N(R$^{34}$)R$^{33}$, —C(O)C(O)OR$^{32}$, —C(S)R$^{31}$, —C(S)OR$^{32}$, —C(S)SR$^{32}$, —C(S)N(R$^{34}$)R$^{33}$, —S(O)$_2$R$^{32}$, S(O)$_2$N(R$^{34}$)R$^{33}$, —Si(R$^{11a}$)(R$^{11b}$)R$^{11}$, —P(O)(OR$^{20}$)$_2$, —P(S)(OR$^{20}$)$_2$, a phenyl, a phenyl substituted with $(Z)_{p1}$, D1, D2, D4 to D6, D8 to D10, D12 to D19, D21, D23, D25, D27 or D30 to D38, $R^{25}$ represents a hydrogen atom, a $C_1$ to $C_6$ alkyl, a $C_1$ to $C_6$ haloalkyl, a $C_1$ to $C_4$ alkoxy($C_1$ to $C_4$) alkyl, a $C_1$ to $C_4$ alkylthio($C_1$ to $C_4$) alkyl, a $C_3$ to $C_6$ cycloalkyl, a $C_3$ to $C_6$ alkenyl, a $C_3$ to $C_6$ alkynyl, a $C_1$ to $C_6$ alkoxy, a phenyl or a phenyl substituted with $(Z)_{p1}$, or $R^{25}$ together with $R^{24}$ optionally forms a $C_2$ to $C_5$ alkylene chain to form together with a nitrogen atom to which $R^{24}$ and $R^{25}$ are bonded, a 3- to 6-membered ring, and in this case, the alkylene chain optionally contains one oxygen atom, sulfur atom or nitrogen atom and is optionally substituted with a halogen atom, a $C_1$ to $C_6$ alkyl group, a $C_1$ to $C_6$ haloalkyl group, a $C_1$ to $C_6$ alkoxy group, a —CHO group, a $C_1$ to $C_6$ alkylcarbonyl group, a $C_1$ to $C_6$ alkoxycarbonyl group, a phenyl group, a phenyl group substituted with $(Z)_{p1}$, an oxo group or a thioxo group, $R^{26}$ represents a $C_1$ to $C_8$ alkyl, a ($C_1$ to $C_8$) alkyl optionally substituted with $R^{30}$, a $C_3$ to $C_8$ cycloalkyl, a ($C_3$ to $C_8$) cycloalkyl optionally substituted with $R^{30}$, E2 to E6, E12 to E19, a $C_3$ to $C_8$ alkenyl, a ($C_3$ to $C_8$) alkenyl optionally substituted with $R^{30}$, a $C_3$ to $C_8$ alkynyl, a ($C_3$ to $C_8$) alkynyl optionally substituted with $R^{30}$, —C(O)R$^{31}$, —C(O)OR$^{32}$, —C(O)SR$^{32}$, —C(O)N(R$^{34}$)R$^{33}$, —C(O)C(O)R$^{32}$, —C(O)C(O)OR$^{32}$, —C(S)R$^{31}$, —C(S)OR$^{32}$, —C(S)SR$^{32}$, —C(S)N(R$^{34}$)R$^{33}$, —SH, a $C_1$ to $C_6$ alkylthio, a $C_1$ to $C_6$ haloalkylthio, a phenylthio, a phenylthio substituted with $(Z)_{p1}$, —P(O)(OR$^{20}$)$_2$, —P(S)(OR$^{20}$)$_2$, a phenyl, a phenyl substituted with $(Z)_{p1}$, D9, D10, D12, D14 to D17, D30, D32 or D34, $R^{27}$ represents a hydrogen atom, a $C_1$ to $C_6$ alkyl, a $C_1$ to $C_6$ haloalkyl, a $C_3$ to $C_6$ cycloalkyl($C_1$ to $C_4$) alkyl, a $C_1$ to $C_6$ alkoxy($C_1$ to $C_4$) alkyl, a $C_1$ to $C_6$ haloalkoxy ($C_1$ to $C_4$) alkyl, a $C_1$ to $C_6$ alkylthio($C_1$ to $C_4$) alkyl, a $C_1$ to $C_6$ haloalkylthio($C_1$ to $C_4$) alkyl, a $C_1$ to $C_6$ alkylsulfonyl($C_1$ to $C_4$) alkyl, a $C_1$ to $C_6$ haloalkylsulfonyl($C_1$ to $C_4$) alkyl, a phenyl($C_1$ to $C_4$) alkyl, a phenyl($C_1$ to $C_4$) alkyl substituted with $(Z)_{p1}$, a $C_3$ to $C_6$ cycloalkyl, a phenyl or a phenyl substituted with $(Z)_{p1}$, $R^{28}$ represents a $C_1$ to $C_8$ alkyl, a ($C_1$ to $C_8$) alkyl optionally substituted with $R^{30}$, a $C_3$ to $C_8$ cycloalkyl, a ($C_3$ to $C_8$) cycloalkyl optionally substituted with $R^{30}$, E1 to E7, E12 to E19, a $C_2$ to $C_8$ alkenyl, a ($C_2$ to $C_8$) alkenyl optionally substituted with $R^{30}$, a $C_3$ to $C_8$ alkynyl, a ($C_3$ to $C_8$) alkynyl optionally substituted with $R^{30}$, a phenyl, a phenyl substituted with $(Z)_{p1}$, D1 to D25 or D27 to D38, $R^{29}$ represents a hydrogen atom, a $C_1$ to $C_6$ alkyl, a ($C_1$ to $C_6$) alkyl optionally substituted with $R^{30}$, a $C_3$ to $C_6$ alkenyl, a $C_3$ to $C_6$ haloalkenyl, a $C_3$ to $C_6$ alkynyl, a $C_3$ to $C_6$ haloalkynyl, a phenyl or a phenyl substituted with $(Z)_{p1}$, or $R^{29}$ together with $R^{28}$ optionally forms a $C_2$ to $C_5$ alkylene chain to form together with a nitrogen atom to which $R^{28}$ and $R^{29}$ are bonded, a 3- to 6-membered ring, and in this case, the alkylene chain optionally contains one oxygen atom, sulfur atom or nitrogen atom and is optionally substituted with a halogen atom, a $C_1$ to $C_6$ alkyl group, a $C_1$ to $C_6$ alkoxy group, a —CHO group, a $C_1$ to $C_6$ alkylcarbonyl group, a $C_1$ to $C_6$ alkoxycarbonyl group, a phenyl group or a phenyl group substituted with $(Z)_{p1}$, $R^{30}$ represents a halogen atom, a cyano, a nitro, a $C_3$ to $C_8$ cycloalkyl, a $C_3$ to $C_8$ halocycloalkyl, E4, E5, E7, E8, E10, E12, E13, E15, E16, E18, a $C_2$ to $C_6$ alkenyl, a $C_2$ to $C_6$ haloalkenyl, a $C_5$ to $C_8$ cycloalkenyl, —OH, —OR$^{32}$, —OC(O)R$^{31}$, —OC(O)OR$^{32}$, —OC(O)N(R$^{34}$)R$^{33}$, —OC(S)N(R$^{34}$)R$^{33}$, —SH, —S(O)$_r$R$^{32}$, —S(=NR$^{33}$)R$^{32}$, —S(R$^{32}$)=NC(O)R$^{31}$, —S(O)(=NR$^{33}$)R$^{32}$, —S(O)(R$^{32}$)=NC(O)R$^{31}$, —SC(O)R$^{31}$, —SC(O)OR$^{32}$, —SC(O)N(R$^{34}$)R$^{33}$, —SC(S)N(R$^{34}$)R$^{33}$, —N(R$^{34}$)R$^{33}$, —N(R$^{34}$)C(O)R$^{31}$, —N(R$^{34}$)C(O)OR$^{32}$, —N(R$^{34}$)C(O)SR$^{32}$, —N(R$^{34}$)C(O)N(R$^{34}$)R$^{33}$, —N(R$^{34}$)C(S)N(R$^{34}$)R$^{33}$, —N(R$^{34}$)S(O)$_2$R$^{32}$, —C(O)R$^{31}$, —C(O)OH, —C(O)OR$^{32}$, —C(O)SR$^{32}$, —C(O)N(R$^{34}$)R$^{33}$, —C(O)C(O)OR$^{32}$, —C(=NOR$^{32}$)N(R$^{34}$)R$^{33}$, —C(=NOR$^{32}$)NR$^{34}$)C(O)R$^{31}$, —Si(R$^{11a}$)(R$^{11b}$)R$^{11}$, —P(O)(OR$^{20}$)$_2$, —P(S)(OR$^{20}$)$_2$, —P(phenyl)$_2$, —P(O)(phenyl)$_2$, a phenyl, a phenyl substituted with (Z)$_{p1}$ or D1 to D38, R$^{31}$ represents a hydrogen atom, a $C_1$ to $C_6$ alkyl, a $C_1$ to $C_6$ haloalkyl, a ($C_1$ to $C_4$) alkyl optionally substituted with R$^{35}$, a $C_3$ to $C_6$ cycloalkyl, a $C_3$ to $C_6$ halocycloalkyl, E4, E5, E12, E13, a $C_2$ to $C_8$ alkenyl, a $C_2$ to $C_8$ haloalkenyl, a $C_5$ to $C_{10}$ cycloalkenyl, a $C_5$ to $C_{10}$ halocycloalkenyl, a $C_2$ to $C_8$ alkynyl, a $C_2$ to $C_8$ haloalkynyl, a phenyl, a phenyl substituted with (Z)$_{p1}$ or D1 to D38, R$^{32}$ represents a $C_1$ to $C_6$ alkyl, a $C_1$ to $C_6$ haloalkyl, a ($C_1$ to $C_4$) alkyl optionally substituted with R$^{35}$, a ($C_1$ to $C_4$) haloalkyl optionally substituted with R$^{35}$, a $C_3$ to $C_6$ cycloalkyl, E4, E5, a $C_2$ to $C_8$ alkenyl, a $C_2$ to $C_8$ haloalkenyl, a $C_3$ to $C_8$ alkynyl, a $C_3$ to $C_8$ haloalkynyl, a phenyl, a phenyl substituted with (Z)$_{p1}$, D12, D32 or D34, R$^{33}$ represents a hydrogen atom, a cyano, a $C_1$ to $C_6$ alkyl, a $C_1$ to $C_6$ haloalkyl, a ($C_1$ to $C_4$) alkyl optionally substituted with R$^{35}$, a $C_3$ to $C_6$ cycloalkyl, E4, E5, E12, a $C_2$ to $C_8$ alkenyl, a $C_2$ to $C_8$ haloalkenyl, a $C_3$ to $C_8$ alkynyl, a phenyl, a phenyl substituted with (Z)$_{p1}$, D1 to D25 or D27 to D38, R$^{34}$ represents a hydrogen atom, a $C_1$ to $C_6$ alkyl, a $C_1$ to $C_6$ haloalkyl, a cyano($C_1$ to $C_6$) alkyl, a $C_3$ to $C_6$ cycloalkyl($C_1$ to $C_4$) alkyl, a $C_3$ to $C_8$ cycloalkyl, a $C_3$ to $C_6$ alkenyl or a $C_3$ to $C_6$ alkynyl, or R$^{34}$ together with R$^{33}$ optionally forms a $C_2$ to $C_5$ alkylene chain to form together with a nitrogen atom to which R$^{33}$ and R$^{34}$ are bonded, a 3- to 6-membered ring, and in this case, the alkylene chain optionally contains one oxygen atom, sulfur atom or nitrogen atom and is optionally substituted with a halogen atom, a $C_1$ to $C_4$ alkyl group, a $C_1$ to $C_4$ alkoxy group, a —CHO group, a $C_1$ to $C_4$ alkylcarbonyl group, a $C_1$ to $C_4$ alkoxycarbonyl group, a phenyl group or a phenyl group substituted with (Z)$_{p1}$, R$^{35}$ represents a cyano, a $C_3$ to $C_6$ cycloalkyl, a $C_3$ to $C_6$ halocycloalkyl, E4, E5, E12, E13, a $C_1$ to $C_4$ alkoxy, a $C_1$ to $C_4$ haloalkoxy, a phenoxy, a phenoxy substituted with (Z)$_{p1}$, a $C_1$ to $C_4$ alkylthio, a $C_1$ to $C_4$ haloalkylthio, a phenylthio, a phenylthio substituted with (Z)$_{p1}$, a $C_1$ to $C_4$ alkylsulfonyl, a $C_1$ to $C_4$ haloalkylsulfonyl, a phenylsulfonyl, a phenylsulfonyl substituted with (Z)$_{p1}$, —N(R$^{37}$)R$^{36}$, a $C_1$ to $C_6$ alkylcarbonyl, a $C_1$ to $C_6$ haloalkylcarbonyl, a $C_1$ to $C_6$ alkoxycarbonyl, a $C_1$ to $C_6$ alkylaminocarbonyl, a di($C_1$ to $C_6$ alkyl) aminocarbonyl, a tri($C_1$ to $C_4$ alkyl) silyl, a phenyl, a phenyl substituted with (Z)$_{p1}$, a naphthyl or D1 to D38, R$^{36}$ represents a hydrogen atom, a $C_1$ to $C_6$ alkyl, a $C_1$ to $C_6$ alkylcarbonyl, a $C_1$ to $C_6$ haloalkylcarbonyl, a $C_1$ to $C_6$ alkoxycarbonyl, a phenylcarbonyl or a phenylcarbonyl substituted with (Z)$_{p1}$, R$^{37}$ represents a hydrogen atom or a $C_1$ to $C_6$ alkyl, m represents an integer of 0 to 5, n represents an integer of 0 to 4, p represents an integer of 0 to 4, p1 represents an integer of 1 to 5, q represents an integer of 0 to 8, r represents an integer of 0 to 2, and t represents an integer of 0 or 1), and a salt of the substituted isoxazoline compound or a salt of the substituted enone oxime compound.

2. The substituted isoxazoline compound or the substituted enone oxime compound and the salt of the substituted isoxazoline compound or the salt of the substituted enone oxime compound according to claim 1, wherein X represents a halogen atom, a cyano, a nitro, —SF$_5$, a $C_1$ to $C_6$ alkyl, a $C_1$ to $C_6$ haloalkyl, a hydroxy($C_1$ to $C_4$) haloalkyl, a $C_1$ to $C_4$ alkoxy($C_1$ to $C_4$) haloalkyl, —OR$^5$ or —S(O)$_r$R$^5$, where when m represents an integer of 2 or more, Xs are optionally the same as or different from each other, Y represents a halogen atom, a cyano, a nitro, a $C_1$ to $C_6$ alkyl, a $C_1$ to $C_6$ haloalkyl, a ($C_1$ to $C_4$) alkyl optionally substituted with R$^4$, a $C_2$ to $C_6$ alkenyl, a $C_2$ to $C_6$ alkynyl, —OR$^5$, —S(O)$_r$R$^5$, —NH$_2$, —N(R$^7$)R$^6$, —C(S)NH$_2$, D1 to D3, D7, D11 or D22, where when n represents an integer of 2 or more, Ys are optionally the same as or different from each other, Z$^a$ represents a halogen atom, a cyano, a nitro, a $C_1$ to $C_6$ alkyl, a $C_1$ to $C_6$ haloalkyl, a $C_1$ to $C_6$ alkoxy, a $C_1$ to $C_6$ haloalkoxy, a $C_1$ to $C_6$ alkylthio, a $C_1$ to $C_6$ haloalkylthio, a $C_1$ to $C_6$ alkylsulfinyl, a $C_1$ to $C_6$ haloalkylsulfinyl, a $C_1$ to $C_6$ alkylsulfonyl, a $C_1$ to $C_6$ haloalkylsulfonyl, —NH$_2$, —C(O)N(R$^2$)R$^1$ or —C(S)N(R$^2$)R$^1$, where when p represents an integer of 2 or more, Z$^a$s are optionally the same as or different from each other, R$^3$ represents a $C_1$ to $C_6$ haloalkyl or a $C_3$ to $C_8$ halocycloalkyl, R$^{3a}$ represents a halogen atom, a $C_1$ to $C_6$ alkyl or a $C_1$ to $C_6$ alkylthio, R$^{3b}$ represents a hydrogen atom or a halogen atom, R$^{3c}$ represents a hydrogen atom, a halogen atom or a $C_1$ to $C_6$ alkyl, R$^4$ represents —OH, a $C_1$ to $C_4$ alkoxy, a $C_1$ to $C_4$ haloalkoxy, a $C_1$ to $C_4$ alkylthio, a $C_1$ to $C_4$ haloalkylthio, a $C_1$ to $C_4$ alkylsulfinyl, a $C_1$ to $C_4$ haloalkylsulfinyl, a $C_1$ to $C_4$ alkylsulfonyl or a $C_1$ to $C_4$ haloalkylsulfonyl, R$^5$ represents a $C_1$ to $C_4$ alkyl, a $C_1$ to $C_4$ haloalkyl or a $C_1$ to $C_2$ haloalkoxy($C_1$ to $C_2$) haloalkyl, R$^6$ represents a $C_1$ to $C_4$ alkyl, —C(O)R$^8$, —C(O)OR$^9$, —C(O)SR$^9$, —C(S)OR$^9$, —C(S)SR$^9$ or —S(O)$_2$R$^9$, R$^7$ represents a hydrogen atom or a $C_1$ to $C_4$ alkyl, R$^8$ represents a hydrogen atom, a $C_1$ to $C_4$ alkyl, a $C_1$ to $C_4$ haloalkyl or a $C_3$ to $C_6$ cycloalkyl, and R$^9$ represents a $C_1$ to $C_4$ alkyl or a $C_1$ to $C_4$ haloalkyl.

3. The substituted isoxazoline compound or the substituted enone oxime compound and the salt of the substituted isoxazoline compound or the salt of the substituted enone oxime compound according to claim 2, wherein A$^1$ represents a carbon atom or a nitrogen atom, A$^2$, A$^3$ and A$^4$ individually represent a carbon atom, G$^1$ represents a benzene ring, G$^2$ represents a structure represented by G$^2$-1, G$^2$-2, G$^2$-4, G$^2$-6, G$^2$-7, G$^2$-9 or G$^2$-10, L represents —C(R$^{4a}$)(R$^{4b}$)—, X represents a halogen atom, a cyano, a nitro, —SF$_5$, a $C_1$ to $C_4$ alkyl, a $C_1$ to $C_4$ haloalkyl, a $C_1$ to $C_4$ alkoxy, a $C_1$ to $C_4$ haloalkoxy, a $C_1$ to $C_4$ alkylthio or a $C_1$ to $C_4$ haloalkylthio, where when m represents 2 or 3, Xs are optionally the same as or different from each other, Y represents a halogen atom, a cyano, a nitro, a $C_1$ to $C_4$ alkyl, a $C_1$ to $C_4$ haloalkyl, a $C_1$ to $C_2$ alkoxy($C_1$ to $C_2$) alkyl, a $C_2$ to $C_4$ alkynyl, a $C_1$ to $C_4$ alkoxy, a $C_1$ to $C_4$ haloalkoxy, a $C_1$ to $C_4$ alkylthio, a $C_1$ to $C_4$ haloalkylthio, —N($R^7$)$R^6$ or —C(S)NH$_2$, $Z^a$ represents a halogen atom, a cyano, a nitro, a $C_1$ to $C_4$ alkyl, —NH$_2$, —C(O)N($R^2$)$R^1$ or —C(S)N($R^2$)$R^1$, where when p represents an integer of 2 or more, $Z^a$s are optionally the same as or different from each other, $R^1$ represents a hydrogen atom, a $C_1$ to $C_6$ alkyl, a ($C_1$ to $C_6$) alkyl optionally substituted with $R^{13}$, a $C_3$ to $C_6$ cycloalkyl, a ($C_3$ to $C_6$) cycloalkyl optionally substituted with $R^{13}$, E4, E5, E12, a $C_3$ to $C_6$ alkenyl, a $C_3$ to $C_6$ haloalkenyl, a $C_3$ to $C_6$ alkynyl, a $C_1$ to $C_6$ alkylcarbonyl, —CH=NOR$^{15}$, —C(O)OR$^{15}$, —C(O)N($R^{17}$)$R^{16}$, —C(S)OR$^{15}$, —C(S)N($R^{17}$)$R^{16}$, —C(OR$^{15}$)=NOR$^{15}$, —C(NH$_2$)=NCN, —C(NH$_2$)=NOR$^{15}$, —C(NH$_2$)=NNO$_2$, —N($R^{17}$)$R^{16}$, a phenyl substituted with $(Z)_{p1}$, D1, D5 to D8, D10, D17 or D32 to D35, $R^2$ represents a hydrogen atom, a $C_1$ to $C_6$ alkyl, a ($C_1$ to $C_4$) alkyl substituted with $R^{13a}$, a $C_3$ to $C_6$ cycloalkyl, a $C_3$ to $C_6$ alkenyl, a $C_3$ to $C_6$ alkynyl, —C(O)$R^{14a}$, —C(O)OR$^{15a}$, —C(O)C(O)OR$^{15a}$ or a $C_1$ to $C_6$ haloalkylthio, or $R^2$ together with $R^1$ optionally forms =C($R^{2b}$)$R^{1b}$, $R^{1a}$ represents —C(O)$R^{14}$, —C(O)OR$^{15}$, —C(O)SR$^{15}$, —C(O)N($R^{17}$)$R^{16}$, —C(O)N($R^{17}$)N($R^{17}$)$R^{16}$ or —C(S)$R^{14}$, $R^{2a}$ represents a hydrogen atom, a $C_1$ to $C_6$ alkyl, a ($C_1$ to $C_4$) alkyl substituted with $R^{13a}$, a $C_3$ to $C_6$ alkenyl or a $C_3$ to $C_6$ alkynyl, $R^{1b}$ represents a $C_1$ to $C_6$ alkyl, a $C_1$ to $C_6$ alkoxy, a $C_1$ to $C_6$ haloalkoxy, a $C_1$ to $C_6$ alkylthio or —N($R^{17b}$)$R^{16b}$, $R^{2b}$ represents a $C_1$ to $C_6$ alkylthio or —N($R^{17c}$)$R^{16c}$, or $R^{2b}$ together with $R^{1b}$ optionally forms —N($R^{17c}$)CH=CHS— to form together with a carbon atom to which $R^{1b}$ and $R^{2b}$ are bonded, a 5-membered ring, $R^3$ represents a $C_1$ to $C_4$ haloalkyl, $R^{3a}$ represents a halogen atom or a $C_1$ to $C_2$ alkyl, $R^{3b}$ represents a hydrogen atom, $R^{3c}$ represents a hydrogen atom, a halogen atom or a $C_1$ to $C_2$ alkyl, Z represents a halogen atom, a cyano, a nitro, a $C_1$ to $C_4$ alkyl, a $C_1$ to $C_4$ haloalkyl, a $C_1$ to $C_4$ alkoxy, a $C_1$ to $C_4$ alkylsulfonyloxy or a $C_1$ to $C_4$ alkylthio, where when p and p1 individually represent an integer of 2 or more, Zs are optionally the same as or different from each other, $R^{4a}$ represents a hydrogen atom, a cyano, a $C_1$ to $C_2$ alkyl, a $C_1$ to $C_2$ haloalkyl, a $C_2$ to $C_4$ alkynyl or —C(S)NH$_2$, $R^{4b}$ represents a hydrogen atom, $R^6$ represents a hydrogen atom, a $C_1$ to $C_4$ alkyl, —CHO, a $C_1$ to $C_4$ alkylcarbonyl, a $C_1$ to $C_4$ haloalkylcarbonyl, a $C_1$ to $C_4$ alkoxycarbonyl, a $C_1$ to $C_4$ alkylthiocarbonyl, a $C_1$ to $C_4$ alkoxythiocarbonyl or a $C_1$ to $C_4$ alkyldithiocarbonyl, $R^7$ represents a hydrogen atom or a $C_1$ to $C_4$ alkyl, $R^{12}$ represents a $C_1$ to $C_4$ alkyl, $R^{13}$ represents a halogen atom, a cyano, a $C_3$ to $C_4$ cycloalkyl, E4, E7, —OR$^{24}$, —N($R^{25}$)$R^{24}$, —S(O)$_r$$R^{26}$, a $C_1$ to $C_4$ alkylcarbonyl, —C($R^{27}$)=NOR$^{28}$, —C(O)N($R^{29}$)$R^{28}$, —C(S)NH$_2$, a phenyl, a phenyl substituted with $(Z)_{p1}$, D1, D5, D7, D8, D10, D13, D16, D17, D22, D32 or D34, $R^{13a}$ represents a cyano, a $C_3$ to $C_4$ cycloalkyl, —OR$^{24}$, —S(O)$_r$$R^{26}$, a $C_1$ to $C_4$ alkoxycarbonyl or D32, $R^{14}$ represents a $C_1$ to $C_6$ alkyl, a ($C_1$ to $C_6$) alkyl optionally substituted with $R^{30}$, a $C_3$ to $C_6$ cycloalkyl, E4, E5, E10, a $C_2$ to $C_6$ alkenyl, a $C_2$ to $C_6$ haloalkenyl, a $C_2$ to $C_6$ alkynyl, a phenyl substituted with $(Z)_{p1}$ or D32, $R^{14a}$ represents a $C_1$ to $C_6$ alkyl, a $C_1$ to $C_6$ haloalkyl, a $C_1$ to $C_4$ alkoxy($C_1$ to $C_4$) alkyl, a $C_1$ to $C_4$ alkylthio($C_1$ to $C_4$) alkyl, a $C_1$ to $C_4$ alkylsulfinyl($C_1$ to $C_4$) alkyl, a $C_1$ to $C_4$ alkylsulfonyl($C_1$ to $C_4$) alkyl, a $C_3$ to $C_6$ cycloalkyl, a $C_2$ to $C_6$ alkenyl, a $C_2$ to $C_6$ alkynyl, a phenyl, a phenyl substituted with $(Z)_{p1}$ or D32, $R^{15}$ represents a $C_1$ to $C_6$ alkyl, a $C_1$ to $C_6$ haloalkyl, a $C_3$ to $C_4$ cycloalkyl($C_1$ to $C_4$) alkyl, a $C_1$ to $C_4$ alkoxycarbonyl ($C_1$ to $C_4$) alkyl or a $C_3$ to $C_6$ alkenyl, $R^{15a}$ represents a $C_1$ to $C_6$ alkyl, a $C_1$ to $C_6$ haloalkyl, a $C_1$ to $C_4$ alkoxy($C_1$ to $C_4$) alkyl, a $C_3$ to $C_6$ alkenyl, a $C_3$ to $C_6$ alkynyl or a phenyl, $R^{16}$ represents a hydrogen atom, a $C_1$ to $C_6$ alkyl, a ($C_1$ to $C_6$) alkyl optionally substituted with $R^{30}$, a $C_3$ to $C_6$ cycloalkyl, a $C_3$ to $C_6$ alkenyl, a $C_3$ to $C_6$ alkynyl, a $C_1$ to $C_6$ alkylcarbonyl, a $C_1$ to $C_6$ haloalkylcarbonyl, a $C_1$ to $C_6$ alkoxycarbonyl, a phenyl, a phenyl substituted with $(Z)_{p1}$, D32 or D34, $R^{17}$ represents a hydrogen atom, a $C_1$ to $C_6$ alkyl, a $C_3$ to $C_6$ alkenyl or a $C_3$ to $C_6$ alkynyl, or $R^{17}$ together with $R^{16}$ optionally forms a $C_3$ to $C_5$ alkylene chain to form together with a nitrogen atom to which $R^{16}$ and $R^{17}$ are bonded, a 4- to 6-membered ring, and in this case, the alkylene chain optionally contains one sulfur atom, $R^{16b}$ represents a cyano, a nitro or a $C_1$ to $C_6$ alkoxy, $R^{17b}$ represents a hydrogen atom or a $C_1$ to $C_6$ alkyl, $R^{16c}$ presents a hydrogen atom, a $C_1$ to $C_6$ alkyl, a $C_1$ to $C_6$ haloalkyl or a $C_1$ to $C_6$ alkoxy, $R^{17c}$ represents a hydrogen atom or a $C_1$ to $C_6$ alkyl, $R^{21}$ represents a $C_1$ to $C_2$ alkyl, $R^{24}$ represents a hydrogen atom, a $C_1$ to $C_4$ alkyl, a $C_1$ to $C_4$ haloalkyl, —C(O)$R^{31}$ or —C(O)OR$^{32}$, $R^{25}$ represents a hydrogen atom or a $C_1$ to $C_4$ haloalkyl, $R^{26}$ represents a $C_1$ to $C_4$ alkyl, $R^{27}$ represents a hydrogen atom or a $C_1$ to $C_4$ alkyl, $R^{28}$ represents a $C_1$ to $C_4$ alkyl, a $C_1$ to $C_4$ haloalkyl, a hydroxy($C_1$ to $C_4$) haloalkyl, a $C_3$ to $C_4$ cycloalkyl, a $C_3$ to $C_4$ alkenyl or a $C_3$ to $C_4$ alkynyl, $R^{29}$ represents a hydrogen atom or a $C_1$ to $C_4$ alkyl, $R^{30}$ represents a halogen atom, a $C_3$ to $C_6$ cycloalkyl, a $C_1$ to $C_4$ alkoxy, a $C_1$ to $C_4$ haloalkoxy, —S(O)$_r$$R^{32}$, —S($R^{32}$)=NC(O)$R^{31}$, —S(O)($R^{32}$)=NH, —N($R^{34}$)$R^{33}$, —N($R^{34}$)C(O)$R^{31}$, —N($R^{34}$)C(O)OR$^{32}$, —C(O)N($R^{34}$)$R^{33}$, a phenyl substituted with $(Z)_{p1}$ or D32, $R^{31}$ represents a $C_1$ to $C_4$ alkyl, a $C_1$ to $C_4$ haloalkyl or a $C_3$ to $C_6$ cycloalkyl, $R^{32}$ represents a $C_1$ to $C_4$ alkyl, a $C_1$ to $C_4$ haloalkyl or a cyano($C_1$ to $C_2$) alkyl, $R^{33}$ represents a hydrogen atom, a $C_1$ to $C_4$ alkyl or a cyano($C_1$ to $C_2$) alkyl, $R^{34}$ represents a hydrogen atom or a cyano($C_1$ to $C_2$) alkyl, m represents an integer of 1 to 3, n represents an integer of 0 or 1, p represents an integer of 0 to 2, p1 represents an integer of 1 to 3, q represents an integer of 0 or 1, and t represents 0.

4. The substituted isoxazoline compound or the substituted enone oxime compound and the salt of the substituted isoxazoline compound or the salt of the substituted enone oxime compound according to claim 3, wherein $G^2$ represents a structure represented by $G^2$-1, $G^2$-2, $G^2$-7 or $G^2$-10, X represents a halogen atom, a cyano, —SF$_5$, a $C_1$ to $C_2$ haloalkyl, a $C_1$ to $C_2$ haloalkoxy or a $C_1$ to $C_2$ haloalkylthio, where when m represents 2 or 3, Xs are optionally the same as or different from each other, Y represents a halogen atom, a cyano, a nitro, a $C_1$ to $C_2$ alkyl, a $C_1$ to $C_2$ haloalkyl, a $C_1$ to $C_2$ alkoxymethyl, a $C_2$ to $C_3$ alkynyl, a $C_1$ to $C_2$ haloalkoxy, a $C_1$ to $C_2$ haloalkylthio, —N($R^7$)$R^6$ or —C(S)NH$_2$, $Z^a$ represents a halogen atom, a nitro, a methyl or —NH$_2$, $R^1$ represents a $C_1$ to $C_4$ alkyl, a ($C_1$ to $C_4$) alkyl optionally substituted with $R^{13}$, a $C_3$ to $C_4$ cycloalkyl, a cyclopropyl substituted with $R^{13}$, E4, E5, a $C_3$ to $C_4$ alkenyl, a $C_3$ to $C_4$ haloalkenyl, —CH=NOR$^{15}$, —C(O)OR$^{15}$, —C(O)NHR$^{16}$, —C(S)OR$^{15}$, —N($R^{17}$)$R^{16}$, D34 or D35, $R^2$ represents a hydrogen atom, a $C_1$ to $C_4$ alkyl, a ($C_1$ to $C_2$) alkyl substituted with $R^{13a}$, a $C_3$ to $C_4$ alkynyl, —C(O)$R^{14a}$, —C(O)OR$^{15a}$ or a $C_1$ to $C_4$ haloalkylthio, or $R^2$ together with $R^1$ optionally forms =C($R^{2b}$)$R^{1b}$, $R^{1a}$ represents —C(O)$R^{14}$, —C(O)N($R^{17}$)$R^{16}$ or —C(S)$R^{14}$, $R^{2a}$ represents a hydrogen atom, a $C_1$ to $C_4$ alkyl, a ($C_1$ to $C_2$) alkyl substituted with $R^{13a}$, a $C_3$ to $C_4$ alkenyl or a $C_3$ to $C_4$ alkynyl, $R^{1b}$ represents a $C_1$ to $C_4$ alkoxy or a $C_1$ to $C_4$ alkylthio, $R^{2b}$ represents —NHR$^{16c}$, $R^3$ represents a $C_1$ to $C_2$ haloalkyl, $R^{3a}$ represents a halogen atom or a methyl, $R^{3c}$ represents a hydrogen atom, Z represents a halogen atom, a cyano or a nitro, $R^{4a}$ represents a hydrogen atom, a cyano, a methyl or —C(S)NH$_2$, $R^6$ represents a hydrogen atom, a $C_1$ to $C_2$ alkyl or a $C_1$ to $C_2$ alkylcarbonyl, $R^7$ represents a hydrogen atom or a $C_1$ to $C_2$ alkyl, $R^{13}$ represents a halogen atom, a cyano, a $C_3$ to $C_4$ cycloalkyl, E4, E7, —OR$^{24}$, —NHR$^{24}$, —C($R^{27}$)=NOR$^{28}$, —C(O)N($R^{29}$)$R^{28}$, a phenyl, a phenyl substituted with $(Z)_{p1}$, D8, D10, D13, D16, D22, D32 or D34, $R^{12}$x represents a methyl, $R^{13a}$ represents a cyano, a $C_3$ to $C_4$ cycloalkyl, —OR$^{24}$ or a $C_1$ to $C_4$ alkylthio, $R^{14}$ represents a $C_1$ to $C_4$ alkyl, a ($C_1$ to $C_4$) alkyl optionally substituted with $R^{30}$, a $C_3$ to $C_4$ cycloalkyl, E4, E5, a $C_2$ to $C_4$ alkenyl, a $C_2$ to $C_4$ alkynyl or a phenyl substituted with $(Z)_{p1}$, $R^{14a}$ represents a $C_1$ to $C_4$ alkyl, a $C_1$ to $C_2$ alkoxy($C_1$ to $C_2$) alkyl, a $C_3$ to $C_4$ cycloalkyl or a $C_2$ to $C_4$ alkenyl, $R^{15}$ represents a $C_1$ to $C_4$ alkyl, $R^{15a}$ represents a $C_1$ to $C_4$ alkyl, a $C_1$ to $C_4$ haloalkyl or a $C_1$ to $C_2$ alkoxy($C_1$ to $C_2$) alkyl, $R^{16}$ represents a hydrogen atom, a $C_1$ to $C_4$ alkyl, a $C_1$ to $C_4$ haloalkyl, a $C_3$ to $C_4$ cycloalkyl, a $C_3$ to $C_4$ alkynyl, a phenyl, D32 or D34, $R^{17}$ represents a hydrogen atom, a $C_1$ to $C_4$ alkyl, a $C_3$ to $C_4$ alkenyl or a $C_3$ to $C_4$ alkynyl, $R^{16c}$ represents a hydrogen atom or a $C_1$ to $C_4$ alkyl, $R^{21}$ represents a methyl, $R^{24}$ represents a $C_1$ to $C_4$ alkyl, a $C_1$ to $C_4$ haloalkyl, a $C_1$ to $C_4$ alkylcarbonyl or a $C_1$ to $C_4$ alkoxycarbonyl, $R^{27}$ represents a hydrogen atom or a $C_1$ to $C_2$ alkyl, $R^{28}$ represents a $C_1$ to $C_4$ alkyl, a $C_1$ to $C_4$ haloalkyl, a $C_3$ to $C_4$ alkenyl or a $C_3$ to $C_4$ alkynyl, $R^{29}$ represents a hydrogen atom or a $C_1$ to $C_2$ alkyl, $R^{30}$ represents a halogen atom, a $C_3$ to $C_4$ cycloalkyl, —S(O)$_r$$R^{32}$, —N($R^{34}$)$R^{33}$ or —C(O)N($R^{34}$)$R^{33}$, $R^{32}$ represents a $C_1$ to $C_4$ alkyl or a $C_1$ to $C_4$ haloalkyl, $R^{33}$ represents a $C_1$ to $C_4$ alkyl or a cyano($C_1$ to $C_2$) alkyl, and $R^{34}$ represents a hydrogen atom.

5. The substituted isoxazoline compound or the substituted enone oxime compound and the salt of the substituted isoxazoline compound or the salt of the substituted enone oxime compound according to claim 4, wherein $A^1$ represents a carbon atom, $G^2$ represents a structure represented by $G^2$-1, W represents an oxygen atom, X represents a halogen atom or a trifluoromethyl, where when m represents 2 or 3, Xs are optionally the same as or different from each other, Y represents a halogen atom, a methyl, an ethyl or a trifluoromethyl, $R^1$ represents a ($C_1$ to $C_2$) alkyl substituted with $R^{13}$, E4, —CH=NOR$^{15}$, —C(O)OR$^{15}$, —C(O)N11$_2$, —N($R^{17}$)$R^{16}$, D34 or D35, $R^2$ represents a hydrogen atom, a ($C_1$ to $C_2$) alkyl substituted with $R^{13a}$, a $C_1$ to $C_3$ alkylcarbonyl, a cyclopropylcarbonyl or a $C_1$ to $C_3$ alkoxycarbonyl, $R^3$ represents a trifluoromethyl or a chlorodifluoromethyl, Z represents a halogen atom or a cyano, $R^{13}$ represents a halogen atom, a $C_1$ to $C_3$ alkoxy, a $C_1$ to $C_2$ haloalkoxy, —C(O)NHR$^{28}$, D10 or D32, $R^{13a}$ represents —OR$^{24}$, $R^{15}$ represents a $C_1$ to $C_2$ alkyl, $R^{16}$ represents a phenyl or D34, $R^{17}$ represents a $C_1$ to $C_2$ alkyl, $R^{24}$ represents a $C_1$ to $C_2$ alkyl or a $C_1$ to $C_2$ alkylcarbonyl, $R^{28}$ represents a $C_1$ to $C_2$ haloalkyl, p represents an integer of 0 or 1, and q represents 0.

6. The substituted isoxazoline compound or the substituted enone oxime compound and the salt of the substituted isoxazoline compound or the salt of the substituted enone oxime compound according to claim 4, wherein $A^1$ represents a carbon atom, $G^2$ represents a structure represented by $G^2$-2, X represents a halogen atom or a trifluoromethyl, where when m represents 2 or 3, Xs are optionally the same as or different from each other, Y represents a halogen atom, a nitro or a methyl, $R^{1a}$ represents —C(O)$R^{14}$ or —C(O)NHR$^{16}$, $R^{2a}$ represents a hydrogen atom, a $C_1$ to $C_2$ alkyl, a ($C_1$ to $C_2$) alkyl substituted with $R^{13}$a or a propargyl, $R^3$ represents a trifluoromethyl or a chlorodifluoromethyl, $R^{4a}$ represents a hydrogen atom, a cyano or a methyl, $R^{13a}$ represents a cyano, a cyclopropyl or a $C_1$ to $C_2$ alkoxy, $R^{14}$ represents a $C_1$ to $C_4$ alkyl, a $C_1$ to $C_4$ haloalkyl, a ($C_1$ to $C_2$) alkyl substituted with $R^{30}$, a $C_3$ to $C_4$ cycloalkyl or E4, $R^{16}$ represents a $C_1$ to $C_2$ alkyl, a cyclopropyl or a propargyl, $R^{30}$ represents a cyclopropyl, a $C_1$ to $C_2$ alkylthio, a $C_1$ to $C_2$ alkylsulfinyl or a $C_1$ to $C_2$ alkylsulfonyl, and q represents 0.

7. The substituted isoxazoline compound or the substituted enone oxime compound and the salt of the substituted isoxazoline compound or the salt of the substituted enone oxime compound according to claim 4, wherein $A^1$ represents a carbon atom, $G^2$ represents a structure represented by $G^2$-7 or $G^2$-10, X represents a halogen atom or a trifluoromethyl, where when m represents 2 or 3, Xs are optionally the same as or different from each other, Y represents a cyano or a nitro, $R^3$ represents a trifluoromethyl or a chlorodifluoromethyl, and p represents 0.

8. A substituted isoxazoline compound or a substituted enone oxime compound represented by General Formula (3) or General Formula (4):

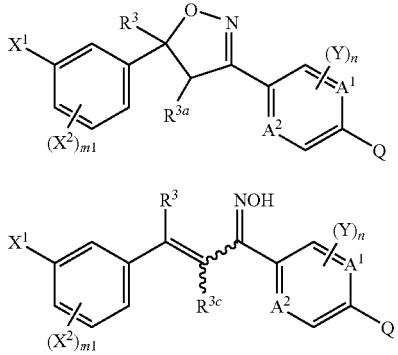

(where $A^1$ and $A^2$ independently represent a carbon atom or a nitrogen atom,
- Q represents a halogen atom, a cyano, a nitro, —CH($R^{4a}$)—$R^a$, —OH, a $C_1$ to $C_4$ alkoxy, a $C_1$ to $C_4$ haloalkoxy, a halosulfonyloxy, a $C_1$ to $C_4$ alkylsulfonyloxy, a $C_1$ to $C_4$ haloalkylsulfonyloxy, a phenylsulfonyloxy, a phenylsulfonyloxy substituted with $(Z)_{p1}$, a $C_1$ to $C_4$ alkylthio, a $C_1$ to $C_4$ alkylsulfinyl, a $C_1$ to $C_4$ alkylsulfonyl, a $C_1$ to $C_4$ haloalkylthio, a $C_1$ to $C_4$ haloalkylsulfinyl, a $C_1$ to $C_4$ haloalkylsulfonyl, —$NH_2$ or —C(O)$R^b$,
- $X^1$ represents a halogen atom, —$SF_5$, a $C_1$ to $C_4$ haloalkyl, a $C_1$ to $C_4$ haloalkoxy or a $C_1$ to $C_4$ haloalkylthio,
- $X^2$ represents a halogen atom, a cyano, a nitro, a $C_1$ to $C_4$ alkyl, a $C_1$ to $C_4$ haloalkyl, a $C_1$ to $C_4$ alkoxy, a $C_1$ to $C_4$ haloalkoxy, a $C_1$ to $C_4$ alkylthio or a $C_1$ to $C_4$ haloalkylthio, where when m1 represents 2, $X^2$s are optionally the same as or different from each other,
- Y represents a halogen atom, a cyano, a nitro, a $C_1$ to $C_4$ alkyl, a $C_1$ to $C_4$ haloalkyl, a $C_1$ to $C_2$ alkoxy($C_1$ to $C_2$) alkyl, a $C_2$ to $C_4$ alkynyl, a $C_1$ to $C_4$ alkoxy, a $C_1$ to $C_4$ haloalkoxy, a $C_1$ to $C_4$ alkylthio, a $C_1$ to $C_4$ haloalkylthio, —$N(R^7)R^6$ or —C(S)$NH_2$,
- Z represents a halogen atom or a methyl, where when p1 represents an integer of 2 or more, Zs are optionally the same as or different from each other,
- $R^a$ represents a hydrogen atom, a halogen atom, —OH, a $C_1$ to $C_2$ alkylcarbonyloxy, a $C_1$ to $C_2$ alkylsulfonyloxy, a $C_1$ to $C_2$ haloalkylsulfonyloxy or —$NH_2$,
- $R^b$ represents a hydrogen atom, a halogen atom, a $C_1$ to $C_2$ alkyl, a $C_1$ to $C_2$ haloalkyl, —OH, a $C_1$ to $C_4$ alkoxy, a 1-pyrazolyl, a 1-imidazolyl or a 1-triazolyl,
- $R^3$ represents a $C_1$ to $C_4$ haloalkyl,
- $R^{3a}$ represents a halogen atom or a $C_1$ to $C_2$ alkyl,
- $R^{3c}$ represents a hydrogen atom, a halogen atom or a $C_1$ to $C_2$ alkyl,
- $R^{4a}$ represents a hydrogen atom, a $C_1$ to $C_2$ alkyl or a $C_1$ to $C_2$ haloalkyl,
- $R^6$ represents a hydrogen atom, a $C_1$ to $C_4$ alkyl, —CHO, a $C_1$ to $C_4$ alkylcarbonyl, a $C_1$ to a $C_4$ haloalkylcarbonyl, a $C_1$ to $C_4$ alkoxycarbonyl, a $C_1$ to $C_4$ alkylthiocarbonyl, a $C_1$ to $C_4$ alkoxythiocarbonyl or a $C_1$ to $C_4$ alkyldithiocarbonyl,
- $R^7$ represents a hydrogen atom or a $C_1$ to $C_4$ alkyl,
- m1 represents an integer of 0 to 2,
- n represents an integer of 0 or 1, and
- p1 represents an integer of 1 to 5), and
- a salt of the substituted isoxazoline compound or a salt of the substituted enone oxime compound.

9. The substituted isoxazoline compound or the substituted enone oxime compound and the salt of the substituted isoxazoline compound or the salt of the substituted enone oxime compound according to claim 8, wherein
- Q represents a halogen atom, a cyano, a nitro, a $C_1$ to $C_2$ alkyl, a $C_1$ to $C_2$ haloalkyl, a hydroxy($C_1$ to $C_2$) alkyl, —OH, a $C_1$ to $C_2$ alkoxy, a $C_1$ to $C_2$ haloalkoxy, a $C_1$ to $C_2$ alkylsulfonyloxy, a $C_1$ to $C_2$ haloalkylsulfonyloxy, a $C_1$ to $C_2$ alkylthio, a $C_1$ to $C_2$ alkylsulfinyl, a $C_1$ to $C_2$ alkylsulfonyl, —$NH_2$ or —C(O)$R^b$,
- $X^1$ represents a halogen atom, —$SF_5$, a $C_1$ to $C_2$ haloalkyl, a $C_1$ to $C_2$ haloalkoxy or a $C_1$ to $C_2$ haloalkylthio,
- $X^2$ represents a halogen atom, a cyano, a $C_1$ to $C_2$ haloalkyl, a $C_1$ to $C_2$ haloalkoxy or a $C_1$ to $C_2$ haloalkylthio, where when m1 represents 2, $X^2$s are optionally the same as or different from each other,
- Y represents a halogen atom, a cyano, a nitro, a $C_1$ to $C_2$ alkyl, a $C_1$ to $C_2$ haloalkyl, a $C_1$ to $C_2$ alkoxymethyl, a $C_2$ to $C_3$ alkynyl, a $C_1$ to $C_2$ haloalkoxy, a $C_1$ to $C_2$ haloalkylthio, —$N(R^7)R^6$ or —C(S)$NH_2$,
- $R^b$ represents a hydrogen atom, a halogen atom, a methyl, —OH or a $C_1$ to $C_2$ alkoxy,
- $R^3$ represents a $C_1$ to $C_2$ haloalkyl,
- $R^{3a}$ represents a halogen atom or a methyl,
- $R^6$ represents a hydrogen atom, a $C_1$ to $C_2$ alkyl or a $C_1$ to $C_2$ alkylcarbonyl, and
- $R^7$ represents a hydrogen atom or a $C_1$ to $C_2$ alkyl.

10. The substituted isoxazoline compound or the substituted enone oxime compound and the salt of the substituted isoxazoline compound or the salt of the substituted enone oxime compound according to claim 9, wherein
- $A^1$ represents a carbon atom or a nitrogen atom,
- $A^2$ represents a carbon atom,
- Q represents a halogen atom, a cyano, a nitro, a methylthio, a methylsulfinyl or a methylsulfonyl,
- $X^1$ and $X^2$ independently represent a halogen atom or a trifluoromethyl, where when m1 represents 2, $X^2$s are optionally the same as or different from each other,
- Y represents a halogen atom, a cyano, a nitro, a methyl, an ethyl or a trifluoromethyl,
- $R^3$ represents a trifluoromethyl or a chlorodifluoromethyl, and
- $R^{3a}$ represents a halogen atom or a methyl.

11. A pest control agent containing one type or two or more types selected from the substituted isoxazoline compound or the substituted enone oxime compound and the salt of the substituted isoxazoline compound or the salt of the substituted enone oxime compound as claimed in claim 1, as active ingredient(s).

12. An agricultural chemical containing one type or two or more types selected from the substituted isoxazoline compound or the substituted enone oxime compound and the salt of the substituted isoxazoline compound or the salt of the substituted enone oxime compound as claimed in claim 1, as active ingredient(s).

13. A control agent against internal or external parasites of mammals or birds containing one type or two or more types selected from the substituted isoxazoline compound or the substituted enone oxime compound and the salt of the substituted isoxazoline compound or the salt of the substituted enone oxime compound as claimed in claim 1, as active ingredient(s).

14. An insecticide or a miticide containing one type or two or more types selected from the substituted isoxazoline compound or the substituted enone oxime compound and the salt of the substituted isoxazoline compound or the salt of the substituted enone oxime compound as claimed in claim 1, as active ingredient(s).

* * * * *

UNITED STATES PATENT AND TRADEMARK OFFICE
CERTIFICATE OF CORRECTION

PATENT NO. : 8,053,452 B2  
APPLICATION NO. : 12/452346  
DATED : November 8, 2011  
INVENTOR(S) : Takeshi Mita et al.

Page 1 of 1

It is certified that error appears in the above-identified patent and that said Letters Patent is hereby corrected as shown below:

Column 234, last line, delete "-C(O )OR15" and insert -- -C(O)OR$^{15}$--.

Column 236, line 40, delete "-Si(R$^{11\ a}$) (R$^{11b}$)R$^{11}$" and insert -- -Si(R$^{11a}$)(R$^{11b}$)R$^{11}$--.

Column 242, line 32, delete "-S(O)$_{rR}$$^{5}$" and insert -- -S(O)$_r$R$^5$--.

Column 244, line 25, delete "-S(O)$^r$R$^{26}$" and insert -- -S(O)$_r$R$^{26}$--.

Column 249, lines 24 and 27, delete "C$_0$" and insert --C$_6$--.

Column 251, line 13, delete "-Si(R$^{11a}$)(R$^{1/b}$)R$^{11}$" and insert -- -Si(R$^{11a}$)(R$^{11b}$)R$^{11}$--.

Column 252, line 24, delete "-S(O)$_r$,R$^5$" and insert -- -S(O)$_r$R$^5$--.

Column 255, line 37, delete "R$^{12}$ x represents" and insert --R$^{12}$ represents--.

Column 256, line 14, delete "-C(O)N11$_2$" and insert -- -C(O)NH$_2$--.

Column 256, line 43, delete "R$^{13}$a" and insert --R$^{13a}$--.

Signed and Sealed this  
Seventh Day of February, 2012

David J. Kappos  
*Director of the United States Patent and Trademark Office*